US008900590B2

(12) United States Patent
Olsen et al.

(10) Patent No.: US 8,900,590 B2
(45) Date of Patent: Dec. 2, 2014

(54) ANTI-HEMAGGLUTININ ANTIBODY COMPOSITIONS AND METHODS OF USE THEREOF

(75) Inventors: Ole Olsen, Everett, WA (US); Christina L. Boozer, Seattle, WA (US); Andres G. Grandea, III, Shoreline, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 96 days.

(21) Appl. No.: 13/208,754

(22) Filed: Aug. 12, 2011

(65) Prior Publication Data

US 2012/0039899 A1 Feb. 16, 2012

Related U.S. Application Data

(60) Provisional application No. 61/373,191, filed on Aug. 12, 2010, provisional application No. 61/386,235, filed on Sep. 24, 2010.

(51) Int. Cl.
| | | |
|---|---|---|
| *A61K 39/00* | (2006.01) | |
| *A61K 39/42* | (2006.01) | |
| *A61K 39/145* | (2006.01) | |
| *A61K 45/06* | (2006.01) | |
| *A61K 47/48* | (2006.01) | |
| *A61K 39/395* | (2006.01) | |
| *C07K 16/10* | (2006.01) | |
| *G01N 33/569* | (2006.01) | |

(52) U.S. Cl.
CPC ............ *A61K 39/395* (2013.01); *C07K 2317/33* (2013.01); *A61K 45/06* (2013.01); *C07K 2317/55* (2013.01); *C07K 2317/21* (2013.01); *C07K 2317/92* (2013.01); *G01N 2333/11* (2013.01); *A61K 47/4853* (2013.01); *A61K 47/48384* (2013.01); *A61K 39/42* (2013.01); *A61K 2039/505* (2013.01); *C07K 16/1018* (2013.01); *G01N 2469/10* (2013.01); *G01N 33/56983* (2013.01); *C07K 2317/76* (2013.01)
USPC .................. 424/178.1; 424/159.1; 424/206.1; 424/209.1; 530/387.1

(58) Field of Classification Search
CPC ........... C07K 2319/00; C07K 2316/96; C07K 2317/56; C07K 2317/622; C07K 2317/567; C07K 2317/55; C07K 2319/40; G01N 33/56983; G01N 2333/11; G01N 21/6428; G01N 2333/705
See application file for complete search history.

(56) References Cited

U.S. PATENT DOCUMENTS

| | | | |
|---|---|---|---|
| 3,773,919 | A | 11/1973 | Boswell et al. |
| 3,896,111 | A | 7/1975 | Kupchan et al. |
| 4,137,230 | A | 1/1979 | Hashimoto et al. |
| 4,151,042 | A | 4/1979 | Higashide et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,485,045 | A | 11/1984 | Regen |
| 4,544,545 | A | 10/1985 | Ryan et al. |
| 4,554,101 | A | 11/1985 | Hopp |
| 4,676,980 | A | 6/1987 | Segal et al. |
| 4,683,202 | A | 7/1987 | Mullis |
| 4,816,567 | A | 3/1989 | Cabilly et al. |
| 4,975,278 | A | 12/1990 | Senter et al. |
| 5,013,556 | A | 5/1991 | Woodle et al. |
| 5,053,394 | A | 10/1991 | Ellestad et al. |
| 5,208,020 | A | 5/1993 | Chari et al. |
| 5,229,275 | A | 7/1993 | Goroff |
| 5,416,064 | A | 5/1995 | Chari et al. |
| 5,500,362 | A | 3/1996 | Robinson et al. |
| 5,545,806 | A | 8/1996 | Lonberg et al. |
| 5,545,807 | A | 8/1996 | Surani et al. |
| 5,567,610 | A | 10/1996 | Borrebaeck et al. |
| 5,569,825 | A | 10/1996 | Lonberg et al. |
| 5,571,894 | A | 11/1996 | Wels et al. |

(Continued)

FOREIGN PATENT DOCUMENTS

| | | |
|---|---|---|
| DE | 266710 A | 8/1985 |
| EP | 73657 A1 | 3/1983 |

(Continued)

OTHER PUBLICATIONS

Kashyap et al. "Protection From the 1009 H1N1 Pandemic Influenza by an Antibody From Combinatorial Survivor-Based Libraries." *PLoS Pathogens.* 6.7(2010):e1000990.

(Continued)

*Primary Examiner* — Benjamin P Blumel
(74) *Attorney, Agent, or Firm* — Cooley LLP

(57) ABSTRACT

The present invention provides novel human anti-Influenza antibodies and related compositions and methods. These antibodies are used in the prevention, inhibition, neutralization, diagnosis, and treatment of influenza infection.

7 Claims, 36 Drawing Sheets

(56) References Cited

U.S. PATENT DOCUMENTS

| | | | |
|---|---|---|---|
| 5,587,458 | A | 12/1996 | King et al. |
| 5,591,669 | A | 1/1997 | Krimpenfort et al. |
| 5,627,052 | A | 5/1997 | Schrader |
| 5,641,870 | A | 6/1997 | Rinderknecht et al. |
| 5,648,237 | A | 7/1997 | Carter |
| 5,712,374 | A | 1/1998 | Kuntsmann et al. |
| 5,714,586 | A | 2/1998 | Kunstmann et al. |
| 5,731,168 | A | 3/1998 | Carter et al. |
| 5,739,116 | A | 4/1998 | Hamann et al. |
| 5,739,277 | A | 4/1998 | Presta et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,789,199 | A | 8/1998 | Joly et al. |
| 5,821,337 | A | 10/1998 | Carter et al. |
| 5,837,234 | A | 11/1998 | Gentile et al. |
| 5,840,523 | A | 11/1998 | Simmons et al. |
| 5,869,046 | A | 2/1999 | Presta et al. |
| 5,877,296 | A | 3/1999 | Hamann et al. |
| 6,331,415 | B1 | 12/2001 | Cabilly et al. |
| 6,824,780 | B1 | 11/2004 | Devaux et al. |
| 7,112,439 | B2 | 9/2006 | Johnson et al. |
| 2011/0033476 | A1 | 2/2011 | Grandea, III et al. |

FOREIGN PATENT DOCUMENTS

| | | | |
|---|---|---|---|
| EP | 183070 | A2 | 6/1986 |
| EP | 244234 | A2 | 11/1987 |
| EP | 402226 | A1 | 12/1990 |
| EP | 404097 | A2 | 12/1990 |
| EP | 0425235 | B1 | 5/1991 |
| WO | WO-8101145 | A1 | 4/1981 |
| WO | WO-8807378 | A1 | 10/1988 |
| WO | WO-9013646 | A1 | 11/1990 |
| WO | WO-9100360 | A1 | 1/1991 |
| WO | WO-9202551 | A1 | 2/1992 |
| WO | WO-9220373 | A1 | 11/1992 |
| WO | WO-9308829 | A1 | 5/1993 |
| WO | WO-9311161 | A1 | 6/1993 |
| WO | WO-9316185 | A2 | 8/1993 |
| WO | WO-9321232 | A1 | 10/1993 |
| WO | WO-9404690 | A1 | 3/1994 |
| WO | WO-9411026 | A2 | 5/1994 |
| WO | WO-9607321 | A1 | 3/1996 |
| WO | WO-9616673 | A1 | 6/1996 |
| WO | WO-9717852 | A1 | 5/1997 |
| WO | WO-9738731 | A1 | 10/1997 |
| WO | WO-9802463 | A1 | 1/1998 |

OTHER PUBLICATIONS

Krause et al. "Naturally Occuring Human Monoclonal Antibodies Neutralize Both 1918 and 200 Pandemic Influenza A (H1N1) Viruses." *J. Virology*. 84.6(2010):3127-3130.
Simmons et al. "Prophylactic and Therapeutic Efficacy of Human Monoclonal Antibodies Against H5N1 Influenza." *PLoS Med*. 4.5(2007):3178.
Throsby et al. "Heterosubtypic Neutralizing Monoclonal Antibodies Cross-Protective Against H5N1 and H1N1 Recovered From Human IgM+ Memory B Cells." *PLoS One*. 3.12(2008):e3942.
Altschul et al. "Basic Local Alignment Search Tool." *J. Mol. Biol*. 215.3(1990):403-410.
Altschul et al. "Gapped BLAST and PSI-BLAST: A New Generation of Protein Database Search Programs." *Nucl. Acids Res*. 25.17(1997):3389-3402.
ATCC Accession No. 12424, Nov. 16, 2011.
ATCC Accession No. 16045, Nov. 16, 2011.
ATCC Accession No. 24178, Nov. 16, 2011.
ATCC Accession No. 27325, Dec. 14, 2011.
ATCC Accession No. 31446, Nov. 16, 2011.
ATCC Accession No. 31537, Nov. 16, 2011.
ATCC Accession No. 36906, Nov. 16, 2011.
ATCC Accession No. 56500, Nov. 16, 2011.
ATCC Accession No. CCL10, Nov. 16, 2011.
ATCC Accession No. CCL2, Nov. 16, 2011.
ATCC Accession No. CCL34, Nov. 16, 2011.
ATCC Accession No. CCL51, Nov. 16, 2011.
ATCC Accession No. CCL70, Nov. 16, 2011.
ATCC Accession No. CCL75, Nov. 16, 2011.
ATCC Accession No. CRL1442, Nov. 16, 2011.
ATCC Accession No. CRL1587, Nov. 16, 2011.
ATCC Accession No. CRL1651, Nov. 16, 2011.
Babcock et al. "A Novel Strategy for Generating Monoclonal Antibodies from Single, Isolated Lymphocytes Producing Antibodies of Defined Specificities." *PNAS*. 93.15(1996):7843-7848.
Bird et al. "Single-Chain Antigen-Binding Proteins." *Science*. 242(1988):423-426.
Bitter et al. "Expression and Secretion Vectors for Yeast." *Meth. Enzymol*. 153(1987):516-544.
Bolton et al. "The Labelling of Proteins to High Specific Radioactives by Conjugation to a 125I-Containing Acylating Agent." *Biochem. J*. 133.3(1973):529-538.
Brennan et al. "Preparation of Bispecific Antibodies by Chemical Recombination of Monoclonal Immunoglobulin G1 Fragments." *Science*. 229(1985):81-83.
Broglie et al. "Light-Regulated Expression of a Pea Ribulose-1,5-Bisphosphate Carboxylase Small Subunit Gene in Transformed Plant Cells." *Science*. 224(1984):838-843.
Brüggermann et al. "Designer Mice: The Production of Human Antibody Repertoires in Transgenic Animals." *The Year in Immunology: Generation of Antibodies by Cell and Gene Immortalization*. Terhorst et al., eds. New York: Karger. 7(1993):33-40.
Capel et al. "Heterogeneity of Human IgC Receptors." *Immunometh*. 4.1(1994):25-34.
Carlsson et al. "Protein Thiolating and Reversible Protein-Protein Conjugation." *Biochem. J*. 173(1978):723-737.
Caron et al. "Engineered Humanized Dimeric Forms of IgG are More Effective Antibodies." *J. Exp. Med*. 176(1992):1191-1195.
Carter et al. "High Level *Escherichia coli* Espression and Production of a Bivalent Humanized Antibody Fragment." *Bio/Technology*. 10(1992):163-167.
Casadevall. "Antibodies for Defense Against Biological Attack." *Nat. Biotech*. 20(2002):114.
Chari et al. "Immunoconjugates Containing Novel Maytansinoids: Promising Anticancer Drugs." Cancer Res. 52(1992):127-131.
Chothia et al. "Canonical Structures for the Hypervariable Regions of Immunoglobulins." *J. Mol. Biol*. 196.4(1987):901-917.
Clackson et al. "Making Antibody Fragments Using Phage Display Libraries." *Nature*. 352(1991):624-628.
Clynes et al. "Fc Receptors are Required in Passive and Active Immunity to Melanoma." *PNAS*. 95.2(1998):652-656.
Colbère-Garapin et al. "A New Dominant Hybrid Selective Marker for Higher Eukoaryotic Cells." *J. Mol. Biol*. 150.1(1981):1-14.
Coruzzi et al. "Tissue-Specific and Light-Regulated Expression of a Pea Nuclear Gene Encoding the Small Subunit of Ribulose-1,5-bisphosphate Carboxylase." *EMBO J*. 3.8(1984):1671-1680.
Cunningham et al. "High-Resolution Epitope Mapping of hGH-Receptor Interactions by Alanine-Scanning Mutagenesis." *Science*. 244(1989):1081-1085.
Dayhoff et al. "A Model of Evolutionary Change in Proteins." *Atlas of Protein Sequence and Structure*. Washington, D.C.: National Biomedical Research Foundation. Dayhoff, ed. 5.S3(1978):345-358.
Daëron. "Fc Receptor Biology." *Annu. Rev. Immunol*. 15(1997):203-234.
de Haas et al. "Fc Gamma Receptors of Phagocytes." *J. Lab. Clin. Med*. 126.4(1995):330-341.
Engelhard et al. "The Insect Tracheal System: A Conduit for the Systemic Spread of *Autographa californica* M Nuclear Polyhedrosis Virus." *PNAS*. 91.8(1994):3224-3227.
Eppstein et al. "Biological Activity of Liposome-Encapsulated Murine Interferon Gamma is Mediated by a Cell Membrane Receptor." *PNAS*. 82.11(1985):3688-3692.

(56) References Cited

OTHER PUBLICATIONS

Fraker et al. "Protein and Cell Membrane Iodinations with a Sparingly Soluble Chloroadmide, 1,3,4,6-tetrachloro-3a,6a-diphenylglycoluril." *Biochem. Biophys. Res. Commun.* 80.4(1978):849-857.
Gabizon et al. "Pharmacokinetics and Tissue Distribution of Doxorubicin Encapsulated in Stable Liposome with Long Circulation Times." *J. Natl. Cancer Inst.* 81.19(1989):1484-1488.
Gazzano-Santoro et al. "A Non-Radioactive Complement-Dependent Cytotoxicity Assay for Anti-CD20 Monoclonal Antibody." *J. Immunol. Meth.* 202.2(1997):163-171.
Graham et al. "Characteristics of a Human Cell Line Transformed by DNA from Human Adenovirus Type 5." *J. gen. Virol.* 36(1977):59-72.
Gruber et al. "Efficient Tumor Cell Lysis Mediated by a Bispecific Single Chain Antibody Expressed in *Escherichia coli.*" *J. Immunol.* 152(1994):5368-5374.
Guss et al. "Structure of the IgG-Binding Regions of Streptococcal Protein G." *EMBO J.* 5.7(1986):1567-1575.
Guyer et al. "Immunoglobulin Binding by Mouse Intestinal Epithelial Cell Receptors." *J. Immunol.* 117.2(1976):587-593.
Hartman et al. "Two Dominant-Acting Selectable Markers for Gene Transfer Studies in Mammalian Cells." *PNAS.* 85.21(1988):8047-8051.
Hein. "Unified Approach to Alignment and Phylogenes." *Meth. Enzymol.* 183(1990):626-645.
Henikoff et al. "Amino Acid Substitution Matrices from Protein Blocks." *PNAS.* 89(1992):10915-10919.
Higgins et al. "Fast and Senstive Multiple Sequence Alignments on a Microcomputer." *CABIOS.* 5.2(1989):151-153.
Hobbs et al. "Genetic Engineering." McGraw Hill Yearbook of Science and Technology. New York: McGraw Hill. (1992):189-196.
Holliger et al. "Diabodies'L Small Bivalent and Bispecific Antobody Fragments." *PNAS.* 90.14(1993):6444-6448.
Honegger et al. "Yet Another Numbering Scheme for Immunoglobulin Variable Domains: An Automatic Modeling and Analysis Tool." *J. Mol. Biol.* 309.3(2001):657-670.
Hwang et al. "Hepatic Uptake and Degradation of Unilamellar Sphinogomyelin/Cholestorol Liposomes: A Kinetic Study." *PNAS.* 77.7(1980):4030-4034.
Igarashi et al. "Human Immunodeficience Virus Type 1 Neutralizing Antibodies Accelerate Clearance of Cell-Free Cirions From Blood Plasma." *Nat. Med.* 5.2(1999):211-216.
Jakobovits et al. "Analysis of Homozygous Mutant Chimeric Mice: Deletion of the Immunoglobulin Heavy-Chain Joining Region Blocks B-Cell Development and Antibody Production." *PNAS.* 90.6(1993):2551-2555.
Jakobovits et al. "Germ-Line Transmission and Expression of a Human-Derived Yeast Artificial Chromosome." *Nature.* 362(1993):255-258.
Jones et al. "Replacing the Complementarity-Determining Regions in a Human Antibody With Those From a Mouse." *Nature.* 321(1986):522-525.
Keller et al. "Passive Immunity in Prevention and Treatment of Infectious Diseases." *Clin. Microbiol. Rev.* 13.4(2000):602-614.
Kim et al. "Localization of the Site of the Murine IgG1 Molecule That is Involved in Binding to the Murine Intestinal Fc Receptor." *Eur. J. Immunol.* 24(1994):2429-2434.
Kostelny et al. "Formation of a Bispecific Antibody by the Use of Leucine Zippers." *J. Immunol.* 148.5(1992):1547-1553.
Kroll et al. "A Multifunctional Prokaryotic Protein Expression System: Overproduction, Affinity Purification and Selective Detection." *DNA Cell Biol.* 12(1993):441-453.
Kyte et al. "A Simple Method for Displaying the Hydropatric Character of a Protein." *J. Mol. Biol.* 157.1(1982):105-132.
Köhler et al. "Continuous Cultures of Fused Cells Secreting Antibody of Predefined Specificity." *Nature.* 256(1975):495-497.
Lefranc et al. "IMGT Unique Numbering for Immunoglobulin and T Cell Receptor Variable Regions and Ig Superfamily V-Like Domains." *Dev. Comp. Immunol.* 27.1(2003):55-77.

Lefranc et al. "IMGT, the International ImMunoGeneTics Database." *Nucl. Acids Red.* 27.1(1999):209-212.
Lefranc. "The IMGT Unique Numbering for Immunoglobulins, T Cell Receptors and Ig-Like Domains." *Immunologist.* 7(1999):132-136.
Lefranc. "Unique Database Numbering System for Immunogenetic Analysis." *Ummunol. Today.* 18.11(1997):509.
Lindmark et al. "Binding of Immunoglobulins to Protein A and Immunoglonulin Levels in Mammalian Sera." *J. Immunol. Meth.* 62.10(1983):1-13.
Liu et al. "Eradication of Large Colon Tumor Xenografts by Targeted Delivery of Maytansinoids." *PNAS.* 93.18(1998):8818-8623.
Logan et al. "Adenovirus Tripartite Leader Sequence Enhances Translation of mRNAs Late After Infection." *PNAS.* 81.12(1984):3655-3659.
Lowy et al. "Isolation of Transforming DNA: Cloning the Hamster Aprt Gene." *Cell.* 22.3(1980):817-823.
Macken et al. "The Value of a Database in Surveillance and Vaccine Selection." *International Congress Series.* 219(2001):103-106.
Maddox et al. "Elevated Serum Levels in Human Pregnancy of a Molecule Immunochemically Similar to Eosinophil Granule Major Basic Protein." *J. Exp. Med.* 158(1983):1211-1226.
Marks et al. "By-Passing immunization: Human Antibodies From V-Gene Libraries Displayed on Phage." *J. Mol. Biol.* 222.3(1991):581-597.
Martin et al. "Irreversible Coupling of Immunoglobulin Fragments to Preformed Vesicles." *J. Biol. Chem.* 257.1(1982)286-288.
Massey. "Catalytic Antibodies Catching On." *Nature.* 328(1987):457-458.
Mather et al. "Culture of Testicular Cells in Hormone-Supplemented Serum-Free Medium." *Ann. N.Y. Acad. Sci.* 383(1982):44-68.
Mather. "Establishment and Characterization of Two Distinct Mouse Testicular Epithelial Cell Lines," *Biol. Reprod.* 23.1(1980)243-252.
Milstein et al. "Hybrid Hybridomas and Their Use in Immunohistochemistry." *Nature.* 305(1983):537-540.
Morimoto et al. "Single-Step Purification of F(ab')2 Fragments of Mouse Monoclonal Antibodies (Immunoglobulins G1) by Hydrophobic Interaction High Performance Liquid Chromatography using TSKgel Phenyl-5PW." *J. Biochem. Biophys. Methods.* 24.1-2(1992):107-117.
Morrison et al. "Chimeric Human Antibody Molecules: Mouse Antigen-Binding Domains with Human Constant Region Domains." *PNAS.* 81.21(1984):6851-6855.
Morrison. "The Determination of the Exposed Proteins on Membranes by the Use of Lactoperoxidase." *Meth. Enzymol.* 3(1974):103-109.
Murakami et al. "Cell Cycle Regulation, Oncogenes, and Antineoplastic Drugs." The Molecular Basis of Cancer. Mendelsohn et al., eds. Philadelphia: WB Saunders. (1995)1-17.
Muster et al. "A Conserved Neutralizing Epitope on gp41 of Human Immunodeficiency Virus Type 1." *J. Virol.* 67.11(1993):6642-6647.
Myers et al. "Optimal Alignments in Linear Space." *CABIOS,* 4.1(1988)11-17.
Needleman et al. "A General Method Applicable to the Search for Similarities in the Amino Acid Sequence of Two Proteins." *J. Mol. Biol.* 48.3(1970):443-453.
Neuberger et al. "Recombinant Antibodies Possessing Novel Effctor Functions." *Nature.* 312(1984):604-608.
Pearson et al. "Improved Tools for Biological Sequence Comparison." *PNAS* 85(1988):2444-2448.
Plückthun et al. "Expression of Functional Antibody Fv and Feb Fragments in *Escherichia coli.*" *Meth. Enzymol.* 178(1989):497-515.
Plückthun. "Antibodies from *Escherichia coil.*" The Pharmacology of Monoclonal Activities. Rosenburg et al., eds. New York: Springer-Verlag. 113(1994):269-315.
Porath. "Immobilized Metal Ion Affinity Chromatography." *Prot. Exp. Purif.* 3.4(1992)263-281.
Presta. "Antibody Engineering." *Curr. Op. Struct. Biol.* 2.4(1992):263-281.
Ravetch et al. "Fc Receptors." *Annu. Rev. Immunol.* 9(1991).457-492.
Rhodes et al. "Transformation of Maize by Electroporation of Embryos." *Methods Mol. Biol.* 55(1995):121-131.

(56) References Cited

OTHER PUBLICATIONS

Riechmann el al. "Reshaping Human Antibodies for Therapy." *Nature.* 332(1988):323-327.

Robinson. "Comparison of Label Tree with Valency Three." *J. Combin. Ther. Ser. B.* 11(1971):105-119.

Ruiz et al. "IMGT, the International ImMunoGeneTics Database." *Nucl. Acids Res.* 28.1(2000):219-221.

Saitou et al. "The Neighbor-joining Method: A New Method for Reconstructing Phylogenetic Trees." *Mol. Biol. Evol.* 4.4(1987)406-425.

Sanger et al. "DNA Sequencing with Chain-Terminating Inhibitors." *PNAS.* 74.12(1977):5463-5467.

Scatchard et al. "The Attractions of Proteins for Small Molecules and Ions." *Ann. N.Y. Acad. Sci.* 51(1949):660-672.

Shalaby et al. "Development of Humanized Bispecific Antibodies Reactive with Cytotoxic Lumphocytes and Tumor Cells Overexpressing the HER2 Protooncogene." *J. Exp. Med.* 175(1992):217-225.

Shibata et al. "Neutralizing Antibody Directed Against the HIV-1 Envelope Glycoprotein Can Completely Block HIV-1/SIV Chimeric Virus Infections of Macaque Monkeys." *Nat. Med.* 5.2(1999):204-210.

Shapes, "A Genetically Engineered Human IgG Mutant with Enhanced Cytolytic Activity." *J. Immunol.* 148.9(1992)2918-2922.

Smith et al. "Comparison of Biosequences." *Adv. Appl. Math.* 2.4(1981):482-489.

Stevens et al. "Structure and Receptor Specificity of the Hemagglutinin From an H5N1 Influenza Virus." *Science.* 312(2006)404-410.

Stevenson et al. "A Chimeric Antibody with Dual Fc Receptor Regions (bisFabFc) Prepared b Manipulations at the IgG Hinge." *Anti-Cancer Drug Des.*, 1989.

Stites et al., ed. *Basic and Clinical Immunology.* Norwalk, CT: Appleton & Lange. 8(1994):71.

Suresh et al. "Bispecific Monoclonal Antibodies from Hybrid Hybridomas." *Meth. Enzymol.* 121(1986):210-228.

Syvanen et al. "Preparation of 125l-Catalytic Subunit of Aspartate Transcarbamylase and Its Use in Studies of the Regulatory Subunit." *J. Biol. Chem.* 248.11(1973):3762-3768.

Takamatsu et al. "Expression of Bacterial Chloramphenicol Acetyltransferase Gene in Tobacco Plants Mediated by TMV-RNA." *EMBO J.* 6.2(1987):307-311.

Traunecker et al. "Bispecific Single Chain Molecules (Janusins) Target Cytotoxic Lumphocytes on HIV Infected Cells." *EMBO J.* 10.12(1991):3655-3659.

Tutt et al. "Trispecific F(ab')3 Derivatives that Use Cooperative Signaling via the TCR/CD3 Complex and CD2 to Activate and Redirect Resting Cytotoxic T Cells." *J. Immunol.* 147.1(1991):60-69.

Urlaub et al. "Isolation of Chinese Hamster Cell Mutants Deficient in Dihydrofolate Reductase Activity." *PNAS.* 77.7(1980):4216-4220.

Van Heeke et al. "Expression of Human Asparagine Synthetase in *Escherichia coli.*" *J. Biol. Chem.* 264.10(1989):5503-5509.

Verhoeyen et al. "Reshaping Human Antibodies: Grafting an Antilysozyme Activity." *Science.* 239(1988):1534-1536.

Vitetta et al. "Redesigning Nature's Poisons to Create Anti-Tumor Reagents." *Science.* 238(1987):1098-1104.

Wigler at al. "Transfer of Purified Herpes Virus Thymidine Kinase Gene to Cultured Mouse Cells." *Cell.* 11.1(1977):223-232.

Wigler et al. "Transformation of Mammalian Cells with an Amplifiable Dominant-Acting Gene." *PNAS.* 77.6(1980):3567-3570.

Wilbur et al. "Rapid Similarity Searches of Nucleic Acid and Protein Data Banks." *PNAS.* 80.3(1983):726-730.

Wiley et al. "Structural Identification of the Antibody-Binding Sites of Hong Kong Influenza Haemagglutinin and Their Involvement in Antigenic Variation." *Nature.* 289(1981):373-378.

Winter et al. "The Expression of Heat Shock Protein and Cognate Genes During Plant Development." *Results Probl. Cell Differ.* 17(1991):85-105.

Wolff et al. "Monoclonal Antibody Homodimers: Enhanced Antitumor Activity in Nude Mice." *Cancer Res.* 53(1993):2560-2565.

Yaniv. "Enhancing Elements for Activation of Eukaryotic Promoters." *Nature.* 297(1982):17-18.

Yewdell et al. "The Antigenic Structure of the Influenza Virus A/PR/8/34 Hemagglutinin (H1 Subtype)." *Cell.* 31.2(1982):417-427.

Zapata et al. "Engineering Linear F(ab')$_2$ Fragments for Efficient Production in *Escherichia coli* and Enhanced Antiproliferative Activity." *Protein Eng.* 8.10(1995):1057-1062.

FIGURE 36

| mAb | | 1 | 2 | 3 | 4 | 5 | 6 | 7 | 8 | 9 | 10 | 11 | 12 |
|---|---|---|---|---|---|---|---|---|---|---|---|---|---|
| 1 | A | 100.0 | 33.3 | 11.1 | 3.7 | 1.2 | 0.4 | 0.1 | 0.1 | 0.0 | 0.0 | 0.0 | 0.0 |
|   | B | 100.0 | 33.3 | 11.1 | 3.7 | 1.2 | 0.400 | 0.080 | 0.026 | 0.003 | 0.0008 | 0.00013 | 0.00008 | 0 |
| 2 | C | 100.0 | 33.3 | 11.1 | 3.7 | 1.2 | 0.400 | 0.080 | 0.026 | 0.003 | 0.0008 | 0.00013 | 0.00008 | 0 |
|   | D | 100.0 | 33.3 | 11.1 | 3.7 | 1.2 | 0.400 | 0.080 | 0.026 | 0.003 | 0.0008 | 0.00013 | 0.00008 | 0 |
| 3 | E | 100.0 | 33.3 | 11.1 | 3.7 | 1.2 | 0.400 | 0.080 | 0.026 | 0.003 | 0.0008 | 0.00013 | 0.00008 | 0 |
|   | F | 100.0 | 33.3 | 11.1 | 3.7 | 1.2 | 0.400 | 0.080 | 0.026 | 0.003 | 0.0008 | 0.00013 | 0.00008 | 0 |
| 4 | G | 100.0 | 33.3 | 11.1 | 3.7 | 1.2 | 0.400 | 0.080 | 0.026 | 0.003 | 0.0008 | 0.00013 | 0.00008 | 0 |
|   | H | 100.0 | 33.3 | 11.1 | 3.7 | 1.2 | 0.400 | 0.080 | 0.026 | 0.003 | 0.0008 | 0.00013 | 0.00008 | 0 |
| Final [mAb] after virus addition (μg/ml) | | 100.0 | 33.3 | 11.1 | 3.7 | 1.2 | 0.411 | 0.137 | 0.046 | 0.0534 | 0.0058 | 0.00068 | 0 |

ANTI-HEMAGGLUTININ ANTIBODY COMPOSITIONS AND METHODS OF USE THEREOF

RELATED APPLICATIONS

This application claims the benefit of provisional applications U.S. Ser. No. 61/373,191, filed Aug. 12, 2010 and U.S. Ser. No. 61/386,235, filed Sep. 24, 2010, the contents which are each herein incorporated by reference in their entireties.

INCORPORATION OF SEQUENCE LISTING

The contents of the text file named "37418-515001US_ST25.txt," which was created on Aug. 12, 2011 and is 288 KB in size, are hereby incorporated by reference in their entirety.

FIELD OF THE INVENTION

The present invention relates generally to therapy, diagnosis, inhibition, and prevention of Influenza infection. The invention is more specifically related to methods of identifying influenza hemagglutinin protein-specific neutralizing antibodies as well as their manufacture and use. Such antibodies are useful in pharmaceutical compositions for the prevention and treatment of influenza, and for the diagnosis and monitoring of Influenza infection.

BACKGROUND OF THE INVENTION

Influenza virus infects 5-20% of the population and results in 30,000-50,000 deaths each year in the U.S. Although the Influenza vaccine is the primary method of infection prevention, four antiviral drugs are also available in the U.S.: amantadine, rimantadine, oseltamivir and zanamivir.

Disease caused by Influenza A viral infections is typified by its cyclical nature. Antigenic drift and shift allow for different A strains to emerge every year. Added to that, the threat of highly pathogenic strains entering into the general population has stressed the need for novel therapies for flu infections. The predominant fraction of neutralizing antibodies is directed to the polymorphic regions Influenza virus-specific proteins. Thus, such a neutralizing monoclonal antibody (MAb) would presumably target only one or a few strains.

Therefore, a long-felt need exists in the art for new antibodies that bind to an invariant Influenza protein, or domain thereof, and which neutralize a large number of Influenza strains.

SUMMARY OF THE INVENTION

The invention provides neutralizing human monoclonal antibodies that bind influenza A virus and inhibit the influenza A virus from infecting a cell. Although neutralizing human monoclonal antibodies of the invention bind epitopes within proteins that are exposed on the surface of an influenza virus, the invention focuses on the relatively invariant Influenza hemagglutinin (HA) protein. A neutralizing MAb raised against an Influenza HA protein, which is maintained in its native conformation, provides a superior therapy for all Influenza A strains because it is not dependent upon small changes to the amino acid sequence.

The Influenza hemagglutinin (HA) protein is responsible for allowing the virus to recognize target cells through binding the monosaccharide sialic acid-containing receptors on the surface of the target cell prior to infection. Moreover, the Influenza HA protein is responsible for allowing entry of the viral genome into the target cell by fusing the host endosomal membrane with the viral membrane.

The Influenza hemagglutinin (HA) protein is a homotrimeric integral membrane glycoprotein found on the surface of the Influenza virus. Using the host cell's protein synthesis machinery, the Influenza HA protein is first synthesized as a single-chain precursor polypeptide (HA0) in the endoplasmic reticulum, where it is also assembled as a homotrimer. The resulting HA homotrimer is subsequently exported to the cell surface via the Golgi network. HA homotrimers located on a cell surface are cleaved by a host-produced protease into two smaller peptide subunits: HA1 and HA2. The HA2 subunit forms a long helical chain anchored to the viral membrane whereas the HA1 subunit tops the HA2 subunit to form a large globule. The cleavage step, which converts the HA0 precursor into the mature HA protein containing HA1 and HA2 subunits, is essential for the viral pathogenicity of Influenza. Structurally, the mature HA protein contains a central α-helix coil resulting in an overall cylindrical shape with three spherical heads. The HA protein, and specifically, the HA1 subunit of the mature HA protein, binds receptors containing glycans with terminal sialic acids on host cells. The way in which sialic acid is connected to galactose, for example, α2-3 linkages as in avian serotypes versus α2-6 linkages as in human serotypes, not only determine species specificity of an Influenza virus, but also prevents cross-species infection. However, within certain serotypes of HA, such as H1 and H3, only two amino acid mutations in the framework sequence are required to convert species specificity from avian to human.

To mediate infection, the Influenza HA protein first binds sialic acid-containing receptors present on the surface of the target cell. Consequently, the target cell membrane endocytoses or engulfs the Influenza virus. Once inside the endosome, and upon the host cell's acidification of that compartment, the Influenza HA protein partially unfolds revealing a very hydrophobic fusion peptide that inserts itself into the endosomal membrane. As the rest of the Influenza HA protein refolds, the fusion protein retracts and fuses the endosomal membrane with the viral membrane. Upon fusion of the cellular and viral membranes, the contents of the virus, including the viral genome, are released in the cytoplasm of the target cell.

At least 16 different Influenza A hemagglutinin serotypes or antigens have been identified: H1-H16. Only HA serotypes H1-H3 normally mediate human Influenza infection. However, Influenza strains thought to infect only certain avian or mammalian species can mutate to infect humans. As described above, only a few amino acids need to change along the length of the entire protein to enable Influenza to cross a species barrier. For instance, a single amino acid change in the sequence of the H5 subtype allowed an avian-specific Influenza strain to become infectious in humans (H5N1). A pandemic arose when an Influenza strain common to swine species, became lethal to humans (H1N1). In contrast to Influenza A, Influenza B and C viruses each contain only one form of HA protein.

Specifically, the invention provides an isolated fully human monoclonal antibody, wherein said monoclonal antibody has the following characteristics: a) binds to an influenza A virus; b) binds to a cell contacted with influenza A; c) binds to an epitope of an influenza A viral protein; and, optionally, d) neutralizes influenza A virus infection. An antibody that does not neutralize influenza A virus infection may be used, for instance, for a conjugate therapy. In certain aspects, this antibody binds to a eukaryotic cell. Moreover, the cell is optionally a human cell.

In another aspect, this antibody is isolated from a B-cell from a human donor. Isolation of a fully human monoclonal antibody of the invention from a B-cell is performed using recombinant methods. Alternatively, or in addition, the isolated fully human monoclonal antibody of the invention is isolated from the supernatant of a plasma cell cultured either in vitro or ex vivo. Plasma cells also known as a differentiated B-cells, plasma B-cells, plasmacytes, or effector B-cells. The fully human monoclonal antibody isolated from either a B-cell or a plasma cell demonstrates neutralizing activity.

Antibodies of the invention bind to an epitope of influenza A viral hemagglutinin (HA) protein. Exemplary HA epitopes to which the antibodies of the invention bind include a hemagglutinin precursor peptide (HA0), a HA1 subunit, a HA2 subunit, a mature protein containing HA1 and HA2, and a recombinant HA polypeptide. Alternatively, antibodies of the invention bind to an epitope within a hemagglutinin precursor peptide (HA0), a HA1 subunit, a HA2 subunit, a mature protein containing HA1 and HA2, or a recombinant HA polypeptide. Recombinant HA polypeptides are encoded, for example, by the sequence of SEQ ID NO: 2, 3, 4, 5, 6, 7, 8, 9, 10, 11, 12, 13, 14, 15, 16, 17, 18, or 19.

Antibodies of the invention bind to an epitope that is linear or non-linear. In certain aspects of the invention, a non-linear epitope is a discontinuous epitope.

An antibody of the invention is TCN-522 (3212_I12), TCN-521 (3280_D18), TCN-523 (5248_A17), TCN-563 (5237_B21), TCN-526 (5084_C17), TCN-527 (5086_C06), TCN-528 (5087_P17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_O17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-564 (5256_A17b), or TCN-504 (3251_K17).

The invention further encompasses an antibody that binds the same epitope as TCN-522 (3212_I12), TCN-521 (3280_D18), TCN-523 (5248_A17), TCN-563 (5237_B21), TCN-526 (5084_C17), TCN-527 (5086_C06), TCN-528 (5087_P17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_O17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-564 (5256_A17b), or TCN-504 (3251_K17).

The invention provides an isolated fully human monoclonal anti-HA antibody or fragment thereof, wherein said antibody includes a variable heavy chain ($V_H$) region comprising CDR1 and CDR2, wherein the $V_H$ region is encoded by a human IGHV1 (or specifically, IGHV1-18, IGHV1-2, IGHV1-69, IGHV1-8), IGHV2 (or specifically, IGHV2-5), IGHV3 (or specifically, IGHV3-30, IGHV3-33, IGHV3-49, IGHV3-53, 66, IGHV3-7), IGHV4 (or specifically, IGHV4-31, IGHV4-34, IGHV4-39, IGHV4-59, IGHV4-61), or IGHV5 (or specifically, IGHV5-51) $V_H$ germline sequence or an allele thereof, or a nucleic acid sequence that is homologous to the IGHV1, IGHV2, IGHV3, IGHV4, or IGHV5 $V_H$ germline gene sequence or an allele thereof. In one aspect, the nucleic acid sequence that is homologous to the IGHV1, IGHV2, IGHV3, IGHV4, or IGHV5 $V_H$ germline sequence is at least 75% homologous to the IGHV1, IGHV2, IGHV3, IGHV4, or IGHV5 $V_H$ germline sequence or an allele thereof. Exemplary alleles include, but are not limited to, IGHV1-18*01, IGHV1-2*02, IGHV1-2*04, IGHV1-69*01, IGHV1-69*05, IGHV1-69*06, IGHV1-69*12, IGHV1-8*01, IGHV2-5*10, IGHV3-30-3*01, IGHV3-30*03, IGHV3-30*18, IGHV3-33*05, IGHV3-49*04, IGHV3-53*01, IGHV3-66*03, IGHV3-7*01, IGHV4-31*03, IGHV4-31*06, IGHV4-34*01, IGHV4-34*02, IGHV4-34*03, IGHV4-34*12, IGHV4-39*01, IGHV4-59*01, IGHV4-59*03, IGHV4-61*01, IGHV4-61*08, and IGHV5-51*01. Exemplary sequences for each allele are provided below.

```
IGHV1-18*01 nucleotide sequence
                                                          (SEQ ID NO: 457)
CAGGTTCAGCTGGTGCAGTCTGGAGCTGAGGTGAAGAAGCCTGGGGCCTCAGTGAAGGTCTCCTGCAAGGCTTCTGG

TTACACCTTTACCAGCTATGGTATCAGCTGGGTGCGACAGGCCCCTGGACAAGGGCTTGAGTGGATGGGATGGATCA

GCGCTTACAATGGTAACACAAACTATGCACAGAAGCTCCAGGGCAGAGTCACCATGACCACAGACACATCCACGAGC

ACAGCCTACATGGAGCTGAGGAGCCTGAGATCTGACGACACGGCCGTGTATTACTGTGCGAGAGA

IGHV1-2*02 nucleotide sequence
                                                          (SEQ ID NO: 458)
CAGGTGCAGCTGGTGCAGTCTGGGGCTGAGGTGAAGAAGCCTGGGGCCTCAGTGAAGGTCTCCTGCAAGGCTTCTGG

ATACACCTTCACCGGCTACTATATGCACTGGGTGCGACAGGCCCCTGGACAAGGGCTTGAGTGGATGGGATGGATCA

ACCCTAACAGTGGTGGCACAAACTATGCACAGAAGTTTCAGGGCAGGGTCACCATGACCAGGGACACGTCCATCAGC

ACAGCCTACATGGAGCTGAGCAGGCTGAGATCTGACGACACGGCCGTGTATTACTGTGCGAGAGA

IGHV1-2*04 nucleotide sequence
                                                          (SEQ ID NO: 459)
CAGGTGCAGCTGGTGCAGTCTGGGGCTGAGGTGAAGAAGCCTGGGGCCTCAGTGAAGGTCTCCTGCAAGGCTTCTGG ATACACCTTCACCGGCTACTATATGCACTGGGTGCGACAGGCCCCTGGACAAGGGCTTGAGTGGATGGGATGGATCA
```

-continued

ACCCTAACAGTGGTGGCACAAACTATGCACAGAAGTTTCAGGGCTGGGTCACCATGACCAGGGACACGTCCATCAGC

ACAGCCTACATGGAGCTGAGCAGGCTGAGATCTGACGACACGGCCGTGTATTACTGTGCGAGA

IGHV1-69*01 nucleotide sequence
(SEQ ID NO: 460)
CAGGTGCAGCTGGTGCAGTCTGGGGCTGAGGTGAAGAAGCCTGGGTCCTCGGTGAAGGTCTCCTGCAAGGCTTCTGG

AGGCACCTTCAGCAGCTATGCTATCAGCTGGGTGCGACAGGCCCCTGGACAAGGGCTTGAGTGGATGGGAGGGATCA

TCCCTATCTTTGGTACAGCAAACTACGCACAGAAGTTCCAGGGCAGAGTCACGATTACCGCGGACGAATCCACGAGC

ACAGCCTACATGGAGCTGAGCAGCCTGAGATCTGAGGACACGGCCGTGTATTACTGTGCGAGAGA

IGHV1-69*05 nucleotide sequence
(SEQ ID NO: 461)
CAGGTCCAGCTGGTGCAGTCTGGGGCTGAGGTGAAGAAGCCTGGGTCCTCGGTGAAGGTCTCCTGCAAGGCTTCTGG

AGGCACCTTCAGCAGCTATGCTATCAGCTGGGTGCGACAGGCCCCTGGACAAGGGCTTGAGTGGATGGGAGGGATCA

TCCCTATCTTTGGTACAGCAAACTACGCACAGAAGTTCCAGGGCAGAGTCACGATTACCACGGACGAATCCACGAGC

ACAGCCTACATGGAGCTGAGCAGCCTGAGATCTGAGGACACGGCCGTGTATTACTGTGCGAGA

IGHV1-69*06 nucleotide sequence
(SEQ ID NO: 462)
CAGGTGCAGCTGGTGCAGTCTGGGGCTGAGGTGAAGAAGCCTGGGTCCTCGGTGAAGGTCTCCTGCAAGGCTTCTGG

AGGCACCTTCAGCAGCTATGCTATCAGCTGGGTGCGACAGGCCCCTGGACAAGGGCTTGAGTGGATGGGAGGGATCA

TCCCTATCTTTGGTACAGCAAACTACGCACAGAAGTTCCAGGGCAGAGTCACGATTACCGCGGACAAATCCACGAGC

ACAGCCTACATGGAGCTGAGCAGCCTGAGATCTGAGGACACGGCCGTGTATTACTGTGCGAGAGA

IGHV1-69*12 nucleotide sequence
(SEQ ID NO: 463)
CAGGTCCAGCTGGTGCAGTCTGGGGCTGAGGTGAAGAAGCCTGGGTCCTCGGTGAAGGTCTCCTGCAAGGCTTCTGG

AGGCACCTTCAGCAGCTATGCTATCAGCTGGGTGCGACAGGCCCCTGGACAAGGGCTTGAGTGGATGGGAGGGATCA

TCCCTATCTTTGGTACAGCAAACTACGCACAGAAGTTCCAGGGCAGAGTCACGATTACCGCGGACGAATCCACGAGC

ACAGCCTACATGGAGCTGAGCAGCCTGAGATCTGAGGACACGGCCGTGTATTACTGTGCGAGA

IGHV1-8*01 nucleotide sequence
(SEQ ID NO: 464)
CAGGTGCAGCTGGTGCAGTCTGGGGCTGAGGTGAAGAAGCCTGGGGCCTCAGTGAAGGTCTCCTGCAAGGCTTCTGG

ATACACCTTCACCAGTTATGATATCAACTGGGTGCGACAGGCCACTGGACAAGGGCTTGAGTGGATGGGATGGATGA

ACCCTAACAGTGGTAACACAGGCTATGCACAGAAGTTCCAGGGCAGAGTCACCATGACCAGGAACACCTCCATAAGC

ACAGCCTACATGGAGCTGAGCAGCCTGAGATCTGAGGACACGGCCGTGTATTACTGTGCGAGAGG

IGHV2-5*10 nucleotide sequence
(SEQ ID NO: 465)
CAGATCACCTTGAAGGAGTCTGGTCCTACGCTGGTGAAACCCACACAGACCCTCACGCTGACCTGCACCTTCTCTGG

GTTCTCACTCAGCACTAGTGGAGTGGGTGTGGGCTGGATCCGTCAGCCCCCAGGAAAGGCCCTGGAGTGGCTTGCAC

TCATTTATTGGGATGATGATAAGCGCTACAGCCCATCTCTGAAGAGCAGGCTCACCATCACCAAGGACACCTCCAAA

AACCAGGTGGTCCTTACAATGACCAACATGGACCCTGTGGACACAGCCACATATTACTGTGCACGG

IGHV3-30-3*01 nucleotide sequence
(SEQ ID NO: 466)
CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGCTATGCACTGGGTCCGCCAGGCTCCAGGCAAGGGGCTGGAGTGGGTGGCAGTTATAT

CATATGATGGAAGCAATAAATACTACGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAGA

IGHV3-30*03 nucleotide sequence
(SEQ ID NO: 467)
CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGGCATGCACTGGGTCCGCCAGGCTCCAGGCAAGGGGCTGGAGTGGGTGGCAGTTATAT

-continued

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAGAGA

IGHV3-30*18 nucleotide sequence (SEQ ID NO: 468)

CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGGCATGCACTGGGTCCGCCAGGCTCCAGGCAAGGGGCTGGAGTGGGTGGCAGTTATAT

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAAAGA

IGHV3-33*05 nucleotide sequence (SEQ ID NO: 469)

CAGGTGCAGCTGGTGGAGTCTGGGGGAGGCGTGGTCCAGCCTGGGAGGTCCCTGAGACTCTCCTGTGCAGCGTCTGG

ATTCACCTTCAGTAGCTATGGCATGCACTGGGTCCGCCAGGCTCCAGGCAAGGGGCTGGAGTGGGTGGCAGTTATAT

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCCGAGGACACGGCTGTGTATTACTGTGCGAGAGA

IGHV3-49*04 nucleotide sequence (SEQ ID NO: 470)

GAGGTGCAGCTGGTGGAGTCTGGGGGAGGCTTGGTACAGCCAGGGCGGTCCCTGAGACTCTCCTGTACAGCTTCTGG

ATTCACCTTTGGTGATTATGCTATGAGCTGGGTCCGCCAGGCTCCAGGGAAGGGGCTGGAGTGGGTAGGTTTCATTA

GAAGCAAAGCTTATGGTGGGACAACAGAATACGCCGCGTCTGTGAAAGGCAGATTCACCATCTCAAGAGATGATTCC

AAAAGCATCGCCTATCTGCAAATGAACAGCCTGAAAACCGAGGACACAGCCGTGTATTACTGTACTAGAGA

IGHV3-53*01 nucleotide sequence (SEQ ID NO: 471)

GAGGTGCAGCTGGTGGAGTCTGGAGGAGGCTTGATCCAGCCTGGGGGGTCCCTGAGACTCTCCTGTGCAGCCTCTGG

GTTCACCGTCAGTAGCAACTACATGAGCTGGGTCCGCCAGGCTCCAGGGAAGGGGCTGGAGTGGGTCTCAGTTATTT

ATAGCGGTGGTAGCACATACTACGCAGACTCCGTGAAGGGCCGATTCACCATCTCCAGAGACAATTCCAAGAACACG

CTGTATCTTCAAATGAACAGCCTGAGAGCCGAGGACACGGCCGTGTATTACTGTGCGAGAGA

IGHV3-66*03 nucleotide sequence (SEQ ID NO: 472)

CAGGTGCAGCTGGTGCAGTCTGGCCATGAGGTGAAGCAGCCTGGGGCCTCAGTGAAGGTCTCCTGCAAGGCTTCTGG

TTACAGTTTCACCACCTATGGTATGAATTGGGTGCCACAGGCCCCTGGACAAGGGCTTGAGTGGATGGGATGGTTCA

ACACCTACACTGGGAACCCAACATATGCCCAGGGCTTCACAGGACGGTTTGTCTTCTCCATGGACACCTCTGCCAGC

ACAGCATACCTGCAGATCAGCAGCCTAAAGGCTGAGGACATGGCCATGTATTACTGTGCGAGATA

IGHV3-7*01 nucleotide sequence (SEQ ID NO: 473)

GAGGTGCAGCTGGTGGAGTCTGGGGGAGGCTTGGTCCAGCCTGGGGGGTCCCTGAGACTCTCCTGTGCAGCCTCTGG

ATTCACCTTTAGTAGCTATTGGATGAGCTGGGTCCGCCAGGCTCCAGGGAAGGGGCTGGAGTGGGTGGCCAACATAA

AGCAAGATGGAAGTGAGAAATACTATGTGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGCGAGAGA

IGHV4-31*03 nucleotide sequence (SEQ ID NO: 474)

CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTGGTTACTACTGGAGCTGGATCCGCCAGCACCCAGGGAAGGGCCTGGAGTGGATTGGGT

ACATCTATTACAGTGGGAGCACCTACTACAACCCGTCCCTCAAGAGTCGAGTTACCATATCAGTAGACACGTCTAAG

AACCAGTTCTCCCTGAAGCTGAGCTCTGTGACTGCCGCGGACACGGCCGTGTATTACTGTGCGAGAGA

IGHV4-31*06 nucleotide sequence (SEQ ID NO: 475)

CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTAGTTACTACTGGAGCTGGATCCGCCAGCACCCAGGGAAGGGCCTGGAGTGGATTGGGT

-continued

ACATCTATTACAGTGGGAGCACCTACTACAACCCGTCCCTCAAGAGTCGAGTTACCATATCAGTAGACACGTCTAAG

AACCAGTTCTCCCTGAAGCTGAGCTCTGTGACTGCCGCGGACACGGCCGTGTATTACTG

IGHV4-34*01 nucleotide sequence
(SEQ ID NO: 476)
CAGCTGCAGCTGCAGGAGTCGGGCCCAGGACTGGTGAAGCCTTCGGAGACCCTGTCCCTCACCTGCACTGTCTCTGG

TGGCTCCATCAGCAGTAGTAGTTACTACTGGGGCTGGATCCGCCAGCCCCCAGGGAAGGGGCTGGAGTGGATTGGGA

GTATCTATTATAGTGGGAGCACCTACTACAACCCGTCCCTCAAGAGTCGAGTCACCATATCCGTAGACACGTCCAAG

AACCAGTTCTCCCTGAAGCTGAGCTCTGTGACCGCCGCAGACACGGCTGTGTATTACTGTGCGAGACA

IGHV4-34*02 nucleotide sequence
(SEQ ID NO: 477)
CAGGTGCAGCTACAACAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

ATCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCTGTGTATTACTGTGCGAGAGG

IGHV4-34*03 nucleotide sequence
(SEQ ID NO: 478)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

ATCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCCGTGTATTACTG

IGHV4-34*12 nucleotide sequence
(SEQ ID NO: 479)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

TTCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCTGTGTATTACTGTGCGAGA

IGHV4-39*01 nucleotide sequence
(SEQ ID NO: 480)
CAGCTGCAGCTGCAGGAGTCGGGCCCAGGACTGGTGAAGCCTTCGGAGACCCTGTCCCTCACCTGCACTGT

CTCTGGTGGCTCCATCAGCAGTAGTAGTTACTACTGGGGCTGGATCCGCCAGCCCCCAGGGAAGGGGCTGGAGTGGA

TTGGGAGTATCTATTATAGTGGGAGCACCTACTACAACCCGTCCCTCAAGAGTCGAGTCACCATATCCGTAGACACG

TCCAAGAACCAGTTCTCCCTGAAGCTGAGCTCTGTGACCGCCGCAGACACGGCTGTGTATTACTGTGCGAGACA

IGHV4-59*01 nucleotide sequence
(SEQ ID NO: 481)
GAGGTGCAGCTGGTGGAGTCTGGGGGAGGCTTAGTAAAGACTGGAGGGGTCTCTGAGACTCTCCTGTGCAGCCTCTG

GATTCACCTTCAGTAGCTCTGCTATGCACTGGGTCCACCAGGCTCCAGGAAAGGGTTTGGAGTGGGTCTCAGTTATT

AGTACAAGTGGTGATACCGTACTCTACACAGACTCTGTGAAGGGCTGATTCACCATCTCTAGAGACAATGCCCAGAA

TTCACTGTATCTGCAAATGAACAGCCTGAGAGCCGACGACATGGCTGTGTATTACTGTGTGAAAGA

IGHV4-59*03 nucleotide sequence
(SEQ ID NO: 482)
CAGGTGCAGCTGCAGGAGTCGGGCCCAGGACTGGTGAAGCCTTCGGAGACCCTGTCCCTCACCTGCACTGTCTCTGG

TGGCTCCATCAGTAGTTACTACTGGAGCTGGATCCGGCAGCCCCCAGGGAAGGGACTGGAGTGGATTGGGTATATCT

ATTACAGTGGGAGCACCAACTACAACCCCTCCCTCAAGAGTCGAGTCACCATATCAGTAGACACGTCCAAGAACCAA

TTCTCCCTGAAGCTGAGCTCTGTGACCGCTGCGGACACGGCCGTGTATTACTGTGCG

IGHV4-61*01 nucleotide sequence
(SEQ ID NO: 483)
CAGGTGCAGCTGCAGGAGTCGGGCCCAGGACTGGTGAAGCCTTCGGAGACCCTGTCCCTCACCTGCACTGTCTCTGG

TGGCTCCGTCAGCAGTGGTAGTTACTACTGGAGCTGGATCCGGCAGCCCCCAGGGAAGGGACTGGAGTGGATTGGGT

-continued

ATATCTATTACAGTGGGAGCACCAACTACAACCCCTCCCTCAAGAGTCGAGTCACCATATCAGTAGACACGTCCAAG

AACCAGTTCTCCCTGAAGCTGAGCTCTGTGACCGCTGCGGACACGGCCGTGTATTACTGTGCGAGAGA

IGHV4-61*08 nucleotide sequence
(SEQ ID NO: 484)
CAGGTGCAGCTGGTGCAGTCTGGCCATGAGGTGAAGCAGCCTGGGGCCTCAGTGAAGGTCTCCTGCAAGGCTTCTGG

TTACAGTTTCACCACCTATGGTATGAATTGGGTGCCACAGGCCCCTGGACAAGGGCTTGAGTGGATGGGATGGTTCA

ACACCTACACTGGGAACCCAACATATGCCCAGGGCTTCACAGGACGGTTTGTCTTCTCCATGGACACCTCTGCCAGC

ACAGCATACCTGCAGATCAGCAGCCTAAAGGCTGAGGACATGGCCATGTATTACTGTGCGAGATA

IGHV5-51*01 nucleotide sequence
(SEQ ID NO: 485)
GAGGTGCAGCTGGTGCAGTCTGGAGCAGAGGTGAAAAAGCCCGGGGAGTCTCTGAAGATCTCCTGTAAGGGTTCTGG

ATACAGCTTTACCAGCTACTGGATCGGCTGGGTGCGCCAGATGCCCGGGAAAGGCCTGGAGTGGATGGGGATCATCT

ATCCTGGTGACTCTGATACCAGATACAGCCCGTCCTTCCAAGGCCAGGTCACCATCTCAGCCGACAAGTCCATCAGC

ACCGCCTACCTGCAGTGGAGCAGCCTGAAGGCCTCGGACACCGCCATGTATTACTGTGCGAGACA

In certain embodiments of the invention, the antibody further includes a variable light chain (VL) region encoded by a human IGKV1 (or specifically, IGKV1-17, IGKV1-27, IGKV1-39, IGKV1D-39, IGKV1-5), IGKV2 (or specifically, IGKV2-30), IGKV3 (or specifically, IGKV3-11, IGKV3-15, IGKV3-20), IGKV4 (or specifically, IGKV4-1, IGKV4-1), IGLV1 (or specifically, IGLV1-40, IGLV1-44, IGLV1-55), IGLV2 (or specifically, IGLV2-11, IGLV2-14, IGLV2-8), IGLV3 (or specifically, IGLV3-21 or IGLV3-25), IGLV7 (or specifically, IGLV7-43 or IGLV7-46), or IGLV9 (or specifically, IGLV9-49) or an allele thereof. $V_L$ germline gene sequence IGKV1, IGKV2, IGKV3, IGKV4, IGLV1, IGLV2, IGLV3, IGLV7, or IGLV9 or an allele thereof, or a nucleotide acid sequence that is homologous to the IGKV1, IGKV2, IGKV3, IGKV4, IGLV1, IGLV2, IGLV3, IGLV7, or IGLV9 $V_L$ germline gene sequence or an allele thereof. Furthermore, the nucleic acid sequence that is homologous to the IGKV1, IGKV2, IGKV3, IGKV4, IGLV1, IGLV2, IGLV3, IGLV7, or IGLV9 $V_L$ germline sequence or an allele thereof is at least 65% homologous to the IGKV1, IGKV2, IGKV3, IGKV4, IGLV1, IGLV2, IGLV3, IGLV7, or IGLV9 $V_L$ germline sequence or an allele thereof.

IGKV1-17*01 nucleotide sequence
(SEQ ID NO: 486)
GACATCCAGATGACCCAGTCTCCATCCTCCCTGTCTGCATCTGTAGGAGACAGAGTCACCATCACTTGCCGGGCAAG

TCAGGGCATTAGAAATGATTTAGGCTGGTATCAGCAGAAACCAGGGAAAGCCCCTAAGCGCCTGATCTATGCTGCAT

CCAGTTTGCAAAGTGGGGTCCCATCAAGGTTCAGCGGCAGTGGATCTGGGACAGAATTCACTCTCACAATCAGCAGC

CTGCAGCCTGAAGATTTTGCAACTTATTACTGTCTACAGCATAATAGTTACCCTCC

IGKV1-27*01 nucleotide sequence
(SEQ ID NO: 487)
GACATCCAGATGACCCAGTCTCCATCCTCCCTGTCTGCATCTGTAGGAGACAGAGTCACCATCACTTGCCGGGCGAG

TCAGGGCATTAGCAATTATTTAGCCTGGTATCAGCAGAAACCAGGGAAAGTTCCTAAGCTCCTGATCTATGCTGCAT

CCACTTTGCAATCAGGGGTCCCATCTCGGTTCAGTGGCAGTGGATCTGGGACAGATTTCACTCTCACCATCAGCAGC

CTGCAGCCTGAAGATGTTGCAACTTATTACTGTCAAAAGTATAACAGTGCCCCTCC

IGKV1-39*01 nucleotide sequence
(SEQ ID NO: 488)
GACATCCAGATGACCCAGTCTCCATCCTCCCTGTCTGCATCTGTAGGAGACAGAGTCACCATCACTTGCCGGGCAAG

TCAGAGCATTAGCAGCTATTTAAATTGGTATCAGCAGAAACCAGGGAAAGCCCCTAAGCTCCTGATCTATGCTGCAT

CCAGTTTGCAAAGTGGGGTCCCATCAAGGTTCAGTGGCAGTGGATCTGGGACAGATTTCACTCTCACCATCAGCAGT

CTGCAACCTGAAGATTTTGCAACTTACTACTGTCAACAGAGTTACAGTACCCCTCC

IGKV1D-39*01 nucleotide sequence
(SEQ ID NO: 489)
GACATCCAGATGACCCAGTCTCCATCCTCCCTGTCTGCATCTGTAGGAGACAGAGTCACCATCACTTGCCGGGCAAG

TCAGAGCATTAGCAGCTATTTAAATTGGTATCAGCAGAAACCAGGGAAAGCCCCTAAGCTCCTGATCTATGCTGCAT

CCAGTTTGCAAAGTGGGGTCCCATCAAGGTTCAGTGGCAGTGGATCTGGGACAGATTTCACTCTCACCATCAGCAGT

CTGCAACCTGAAGATTTTGCAACTTACTACTGTCAACAGAGTTACAGTACCCCTCC

-continued

IGKV1-5*03 nucleotide sequence
(SEQ ID NO: 490)
GACATCCAGATGACCCAGTCTCCTTCCACCCTGTCTGCATCTGTAGGAGACAGAGTCACCATCACTTGCCGGGCCAG

TCAGAGTATTAGTAGCTGGTTGGCCTGGTATCAGCAGAAACCAGGGAAAGCCCCTAAGCTCCTGATCTATAAGGCGT

CTAGTTTAGAAAGTGGGGTCCCATCAAGGTTCAGCGGCAGTGGATCTGGGACAGAATTCACTCTCACCATCAGCAGC

CTGCAGCCTGATGATTTTGCAACTTATTACTGCCAACAGTATAATAGTTATTCTCC

IGKV2-30*02 nucleotide sequence
(SEQ ID NO: 491)
GATGTTGTGATGACTCAGTCTCCACTCTCCCTGCCCGTCACCCTTGGACAGCCGGCCTCCATCTCCTGCAGGTCTAG

TCAAAGCCTCGTACACAGTGATGGAAACACCTACTTGAATTGGTTTCAGCAGAGGCCAGGCCAATCTCCAAGGCGCC

TAATTTATAAGGTTTCTAACCGGGACTCTGGGGTCCCAGACAGATTCAGCGGCAGTGGGTCAGGCACTGATTTCACA

CTGAAAATCAGCAGGGTGGAGGCTGAGGATGTTGGGGTTTATTACTGCATGCAAGGTACACACTGGCCTCC

IGKV3-11*01 nucleotide sequence
(SEQ ID NO: 492)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTGGCCTCC

IGKV3-15*01 nucleotide sequence
(SEQ ID NO: 493)
GAAATAGTGATGACGCAGTCTCCAGCCACCCTGTCTGTGTCTCCAGGGGAAAGAGCCACCCTCTCCTGCAGGGCCAG

TCAGAGTGTTAGCAGCAACTTAGCCTGGTACCAGCAGAAACCTGGCCAGGCTCCCAGGCTCCTCATCTATGGTGCAT

CCACCAGGGCCACTGGTATCCCAGCCAGGTTCAGTGGCAGTGGGTCTGGGACAGAGTTCACTCTCACCATCAGCAGC

CTGCAGTCTGAAGATTTTGCAGTTTATTACTGTCAGCAGTATAATAACTGGCCTCC

IGKV3-20*01 nucleotide sequence
(SEQ ID NO: 494)
GAAATTGTGTTGACGCAGTCTCCAGGCACCCTGTCTTTGTCTCCAGGGGAAAGAGCCACCCTCTCCTGCAGGGCCAG

TCAGAGTGTTAGCAGCAGCTACTTAGCCTGGTACCAGCAGAAACCTGGCCAGGCTCCCAGGCTCCTCATCTATGGTG

CATCCAGCAGGGCCACTGGCATCCCAGACAGGTTCAGTGGCAGTGGGTCTGGGACAGACTTCACTCTCACCATCAGC

AGACTGGAGCCTGAAGATTTTGCAGTGTATTACTGTCAGCAGTATGGTAGCTCACCTCC

IGKV4-1*01 nucleotide sequence
(SEQ ID NO: 495)
GACATCGTGATGACCCAGTCTCCAGACTCCCTGGCTGTGTCTCTGGGCGAGAGGGCCACCATCAACTGCAAGTCCAG

CCAGAGTGTTTTATACAGCTCCAACAATAAGAACTACTTAGCTTGGTACCAGCAGAAACCAGGACAGCCTCCTAAGC

TGCTCATTTACTGGGCATCTACCCGGGAATCCGGGGTCCCTGACCGATTCAGTGGCAGCGGGTCTGGGACAGATTTC

ACTCTCACCATCAGCAGCCTGCAGGCTGAAGATGTGGCAGTTTATTACTGTCAGCAATATTATAGTACTCCTCC

IGLV1-40*01 nucleotide sequence
(SEQ ID NO: 496)
CAGTCTGTGCTGACGCAGCCGCCCTCAGTGTCTGGGGCCCCAGGGCAGAGGGTCACCATCTCCTGCACTGGGAGCAG

CTCCAACATCGGGGCAGGTTATGATGTACACTGGTACCAGCAGCTTCCAGGAACAGCCCCCAAACTCCTCATCTATG

GTAACAGCAATCGGCCCTCAGGGGTCCCTGACCGATTCTCTGGCTCCAAGTCTGGCACCTCAGCCTCCCTGGCCATC

ACTGGGCTCCAGGCTGAGGATGAGGCTGATTATTACTGCCAGTCCTATGACAGCAGCCTGAGTGGTTC

IGLV1-44*01 nucleotide sequence
(SEQ ID NO: 497)
CAGTCTGTGCTGACTCAGCCACCCTCAGCGTCTGGGACCCCCGGGCAGAGGGTCACCATCTCTTGTTCTGGAAGCAG

CTCCAACATCGGAAGTAATACTGTAAACTGGTACCAGCAGCTCCCAGGAACGGCCCCCAAACTCCTCATCTATAGTA

ATAATCAGCGGCCCTCAGGGGTCCCTGACCGATTCTCTGGCTCCAAGTCTGGCACCTCAGCCTCCCTGGCCATCAGT

GGGCTCCAGTCTGAGGATGAGGCTGATTATTACTGTGCAGCATGGGATGACAGCCTGAATGGTCC

IGLV1-51*02 nucleotide sequence
(SEQ ID NO: 498)
CAGTCTGTGTTGACGCAGCCGCCCTCAGTGTCTGCGGCCCCAGGACAGAAGGTCACCATCTCCTGCTCTGGAAGCAG

CTCCAACATTGGGAATAATTATGTATCCTGGTACCAGCAGCTCCCAGGAACAGCCCCCAAACTCCTCATCTATGAAA

ATAATAAGCGACCCTCAGGGATTCCTGACCGATTCTCTGGCTCCAAGTCTGGCACGTCAGCCACCCTGGGCATCACC

GGACTCCAGACTGGGGACGAGGCCGATTATTACTGCGGAACATGGGATAGCAGCCTGAGTGCTGG

IGLV2-11*01 nucleotide sequence
(SEQ ID NO: 499)
CAGTCTGCCCTGACTCAGCCTCGCTCAGTGTCCGGGTCTCCTGGACAGTCAGTCACCATCTCCTGCACTGGAACCAG

CAGTGATGTTGGTGGTTATAACTATGTCTCCTGGTACCAACAGCACCCAGGCAAAGCCCCCAAACTCATGATTTATG

ATGTCAGTAAGCGGCCCTCAGGGGTCCCTGATCGCTTCTCTGGCTCCAAGTCTGGCAACACGGCCTCCCTGACCATC

TCTGGGCTCCAGGCTGAGGATGAGGCTGATTATTACTGCTGCTCATATGCAGGCAGCTACACTTTC

IGLV2-14*01 nucleotide sequence
(SEQ ID NO: 500)
CAGTCTGCCCTGACTCAGCCTGCCTCCGTGTCTGGGTCTCCTGGACAGTCGATCACCATCTCCTGCACTGGAACCAG

CAGTGACGTTGGTGGTTATAACTATGTCTCCTGGTACCAACAGCACCCAGGCAAAGCCCCCAAACTCATGATTTATG

AGGTCAGTAATCGGCCCTCAGGGGTTTCTAATCGCTTCTCTGGCTCCAAGTCTGGCAACACGGCCTCCCTGACCATC

TCTGGGCTCCAGGCTGAGGACGAGGCTGATTATTACTGCAGCTCATATACAAGCAGCAGCACTCTC

IGLV2-8*01 nucleotide sequence
(SEQ ID NO: 501)
CAGTCTGCCCTGACTCAGCCTCCCTCCGCGTCCGGGTCTCCTGGACAGTCAGTCACCATCTCCTGCACTGGAACCAG

CAGTGACGTTGGTGGTTATAACTATGTCTCCTGGTACCAACAGCACCCAGGCAAAGCCCCCAAACTCATGATTTATG

AGGTCAGTAAGCGGCCCTCAGGGGTCCCTGATCGCTTCTCTGGCTCCAAGTCTGGCAACACGGCCTCCCTGACCGTC

TCTGGGCTCCAGGCTGAGGATGAGGCTGATTATTACTGCAGCTCATATGCAGGCAGCAACAATTTC

IGLV3-21*02 nucleotide sequence
(SEQ ID NO: 502)
TCCTATGAGCTGACACAGCTACCCTCGGTGTCAGTGTCCCCAGGACAGACAGCCAGGATCACCTGCTCTGGAGATGT

ACTGGGGGAAAATTATGCTGACTGGTACCAGCAGAAGCCAGGCCAGGCCCCTGAGTTGGTGATATACGAAGATAGTG

AGCGGTACCCTGGAATCCCTGAACGATTCTCTGGGTCCACCTCAGGGAACACGACCACCCTGACCATCAGCAGGGTC

CTGACCGAAGACGAGGCTGACTATTACTGTTTGTCTGGGGATGAGGACAATCC

IGLV3-25*03 nucleotide sequence
(SEQ ID NO: 503)
TCCTATGAGCTGACACAGCCACCCTCGGTGTCAGTGTCCCCAGGACAGACGGCCAGGATCACCTGCTCTGGAGATGC

ATTGCCAAAGCAATATGCTTATTGGTACCAGCAGAAGCCAGGCCAGGCCCCTGTGCTGGTGATATATAAAGACAGTG

AGAGGCCCTCAGGGATCCCTGAGCGATTCTCTGGCTCCAGCTCAGGGACAACAGTCACGTTGACCATCAGTGGAGTC

CAGGCAGAAGACGAGGCTGACTATTACTGTCAATCAGCAGACAGCAGTGGT

IGLV7-43*01 nucleotide sequence
(SEQ ID NO: 504)
CAGACTGTGGTGACTCAGGAGCCCTCACTGACTGTGTCCCCAGGAGGGACAGTCACTCTCACCTGTGCTTCCAGCAC

TGGAGCAGTCACCAGTGGTTACTATCCAAACTGGTTCCAGCAGAAACCTGGACAAGCACCCAGGGCACTGATTTATA

GTACAAGCAACAAACACTCCTGGACCCCTGCCCGGTTCTCAGGCTCCCTCCTTGGGGGCAAAGCTGCCCTGACACTG

TCAGGTGTGCAGCCTGAGGACGAGGCTGAGTATTACTGCCTGCTCTACTATGGTGGTGCTCAG

IGLV7-46*01 nucleotide sequence
(SEQ ID NO: 505)
CAGGCTGTGGTGACTCAGGAGCCCTCACTGACTGTGTCCCCAGGAGGGACAGTCACTCTCACCTGTGGCTCCAGCAC

TGGAGCTGTCACCAGTGGTCATTATCCCTACTGGTTCCAGCAGAAGCCTGGCCAAGCCCCCAGGACACTGATTTATG

ATACAAGCAACAAACACTCCTGGACACCTGCCCGGTTCTCAGGCTCCCTCCTTGGGGGCAAAGCTGCCCTGACCCTT

TCGGGTGCGCAGCCTGAGGATGAGGCTGAGTATTACTGCTTGCTCTCCTATAGTGGTGCTCGG

-continued

IGLV7-46*02 nucleotide sequence
(SEQ ID NO: 506)
CAGGCTGTGGTGACTCAGGAGCCCTCACTGACTGTGTCCCCAGGAGGGACAGTCACTCTCACCTGTGGCTCCAGCAC

TGGAGCTGTCACCAGTGGTCATTATCCCTACTGGTTCCAGCAGAAGCCTGGCCAAGCCCCCAGGACACTGATTTATG

ATACAAGCAACAAACACTCCTGGACACCTGCCCGGTTCTCAGGCTCCCTCCTTGGGGGCAAAGCTGCCCTGACCCTT

TTGGGTGCGCAGCCTGAGGATGAGGCTGAGTATTACTGCTTGCTCTCCTATAGTGGTGCTCGG

IGLV9-49*01 nucleotide sequence
(SEQ ID NO: 507)
CAGCCTGTGCTGACTCAGCCACCTTCTGCATCAGCCTCCCTGGGAGCCTCGGTCACACTCACCTGCACCCTGAGCAG

CGGCTACAGTAATTATAAAGTGGACTGGTACCAGCAGAGACCAGGGAAGGGCCCCCGGTTTGTGATGCGAGTGGGCA

CTGGTGGGATTGTGGGATCCAAGGGGGATGGCATCCCTGATCGCTTCTCAGTCTTGGGCTCAGGCCTGAATCGGTAC

CTGACCATCAAGAACATCCAGGAAGAGGATGAGAGTGACTACCACTGTGGGGCAGACCATGGCAGTGGGAGCAACTT

CGTGTAACC

IGLV9-49*03 nucleotide sequence
(SEQ ID NO: 508)
CAGCCTGTGCTGACTCAGCCACCTTCTGCATCAGCCTCCCTGGGAGCCTCGGTCACACTCACCTGCACCCTGAGCAG

CGGCTACAGTAATTATAAAGTGGACTGGTACCAGCAGAGACCAGGGAAGGGCCCCCGATTTGTGATGCGAGTGGGCA

CTGGTGGGATTGTGGGATCCAAGGGGGATGGCATCCCTGATCGCTTCTCAGTCTTGGGCTCAGGCCTGAATCGGTAC

CTGACCATCAAGAACATCCAGGAAGAGGATGAGAGTGACTACCACTGTGGGGCAGACCATGGCAGTGGGAGCAACTT

CGTGTAACC

The invention provides an isolated fully human monoclonal anti-HA antibody or fragment thereof, wherein said antibody comprises a variable heavy chain ($V_H$) region comprising CDR1 and CDR2, wherein said region is encoded by a human IGHV1, IGHV2, IGHV3, IGHV4, or IGHV5 $V_H$ germline sequence, or a nucleic acid sequence that is homologous to the said IGHV1, IGHV2, IGHV3, IGHV4, or IGHV5 $V_H$ germline gene sequence. In one aspect, the nucleic acid sequence that is homologous to the IGHV1, IGHV2, IGHV3, IGHV4, or IGHV5 $V_H$ germline sequence is at least 75% homologous to said IGHV1, IGHV2, IGHV3, IGHV4, or IGHV5 $V_H$ germline sequence. Alternatively, the nucleic acid sequence that is homologous to the IGHV1, IGHV2, IGHV3, IGHV4, or IGHV5 $V_H$ germline sequence is at least 75%, 80%, 85%, 90%, 95%, 100%, or any percentage point in between homologous to said IGHV1, IGHV2, IGHV3, IGHV4, or IGHV5 $V_H$ germline sequence. The antibody further comprises a variable light chain (VL) region encoded by a human IGKV1, IGKV2, IGKV3, IGKV4, IGLV1, IGLV2, IGLV3, IGLV7, or IGLV9 $V_L$ germline gene sequence, or a nucleotide acid sequence that is homologous to the said IGKV1, IGKV2, IGKV3, IGKV4, IGLV1, IGLV2, IGLV3, IGLV7, or IGLV9 $V_L$ germline gene sequence. In another aspect, the nucleic acid sequence that is homologous to the IGKV1, IGKV2, IGKV3, IGKV4, IGLV1, IGLV2, IGLV3, IGLV7, or IGLV9 $V_L$ germline sequence is at least 65% homologous to the said IGKV1, IGKV2, IGKV3, IGKV4, IGLV1, IGLV2, IGLV3, IGLV7, or IGLV9 $V_L$ germline sequence. Alternatively, the nucleic acid sequence that is homologous to the IGKV1, IGKV2, IGKV3, IGKV4, IGLV1, IGLV2, IGLV3, IGLV7, or IGLV9 $V_L$ germline sequence is at least 65%, 70%, 75%, 80%, 85%, 90%, 95%, 100%, or any percentage point in between homologous to the said IGKV1, IGKV2, IGKV3, IGKV4, IGLV1, IGLV2, IGLV3, IGLV7, or IGLV9 $V_L$ germline sequence.

The invention provides an isolated anti-HA antibody, wherein said antibody has a heavy chain with three CDRs comprising an amino acid sequence selected from the group consisting of the amino acid sequences of SEQ ID NOs: 22, 23, 24, 25, 26, 34, 35, 36, 37, 38, 46, 47, 48, 49, 50, 62, 58, 59, 60, 61, 70, 71, 72, 73, 74, 82, 83, 84, 85, 86, 94, 95, 96, 97, 98, 106, 107, 108, 109, 110, 118, 119, 120, 121, 122, 130, 131, 132, 133, 134, 142, 143, 144, 145, 146, 154, 155, 156, 158, 162, 163, 164, 165, 166, 174, 175, 176, 177, 178, 185, 186, 187, 188, 189, 196, 197, 198, 199, 200, 208, 209, 210, 211, 212, 220, 221, 222, 223, 224, 232, 233, 234, 235, 236, 244, 245, 246, 247, 248, 256, 257, 258, 259, 260, 268, 269, 270, 271, 272, 280, 281, 282, 283, 284, 292, 293, 294, 295, 296, 303, 304, 305, 306, 307, 314, 315, 316, 317, 318, 326, 327, 328, 329, 336, 337, 338, 339, 340, 347, 348, 349, 350, 351, 359, 360, 361, 362, 363, 371, 372, 373, 374, 375, 383, 384, 385, 386, 387, 393, 394, 395, 396, 397, 409, 410, 411, 412, 413, 421, 422, 423, 424, 425, 435, 436, 437, 438, 439, 447, 448, 449, 450, 451, 511, 512, 513, 514, and 515, and a light chain with three CDRs that include an amino acid sequence selected from the group consisting of the amino acid sequences of SEQ ID NOs: 29, 30, 31, 41, 42, 43, 53, 54, 55, 65, 66, 67, 77, 78, 79, 89, 90, 91, 101, 102, 103, 113, 114, 115, 125, 126, 127, 137, 138, 139, 149, 150, 151, 169, 170, 171, 157, 181, 182, 192, 193, 203, 204, 205, 215, 216, 217, 227, 228, 229, 239, 240, 241, 251, 252, 253, 263, 264, 265, 275, 276, 277, 287, 288, 289, 299, 300, 310, 311, 321, 322, 323, 332, 333, 343, 344, 354, 355, 356, 366, 367, 368, 378, 379, 380, 390, 400, 401, 406, 416, 417, 418, 428, 429, 430, 442, 443, 444, 454, 455, 456, 517, 518, 520, 521, and 522.

The invention provides an isolated anti-hemagglutinin (HA) antibody, wherein said antibody has a heavy chain with three CDRs comprising an amino acid sequence selected from the group consisting of the amino acid sequences of SEQ ID NOs: 22, 23, 24, 25, 26, 34, 35, 36, 37, 38, 46, 47, 48, 49, 50, 62, 58, 59, 60, 61, 70, 71, 72, 73, 74, 82, 83, 84, 85, 86, 94, 95, 96, 97, 98, 106, 107, 108, 109, 110, 118, 119, 120, 121, 122, 130, 131, 132, 133, 134, 142, 143, 144, 145, 146, 154, 155, 156, 158, 162, 163, 164, 165, 166, 174, 175, 176, 177, 178, 185, 186, 187, 188, 189, 196, 197, 198, 199, 200, 208, 209, 210, 211, 212, 220, 221, 222, 223, 224, 232, 233, 234, 235, 236, 244, 245, 246, 247, 248, 256, 257, 258, 259, 260, 268, 269, 270, 271, 272, 280, 281, 282, 283, 284, 292, 293, 294, 295, 296, 303, 304, 305, 306, 307, 314, 315, 316, 317, 318, 326, 327, 328, 329, 336, 337, 338, 339, 340, 347, 348, 349, 350, 351, 359, 360, 361, 362, 363, 371, 372, 373, 374, 375, 383, 384, 385, 386, 387, 393, 394, 395, 396, 397, 409, 410, 411, 412, 413, 421, 422, 423, 424, 425, 435, 436, 437, 438, 439, 447, 448, 449, 450, 451, 511, 512, 513, 514, and 515, wherein said antibody binds HA.

The invention provides an isolated anti-hemagglutinin (HA) antibody, wherein said antibody has a light chain with three CDRs that include an amino acid sequence selected from the group consisting of the amino acid sequences of SEQ ID NOs: 29, 30, 31, 41, 42, 43, 53, 54, 55, 65, 66, 67, 77, 78, 79, 89, 90, 91, 101, 102, 103, 113, 114, 115, 125, 126, 127, 137, 138, 139, 149, 150, 151, 169, 170, 171, 157, 181, 182, 192, 193, 203, 204, 205, 215, 216, 217, 227, 228, 229, 239, 240, 241, 251, 252, 253, 263, 264, 265, 275, 276, 277, 287, 288, 289, 299, 300, 310, 311, 321, 322, 323, 332, 333, 343, 344, 354, 355, 356, 366, 367, 368, 378, 379, 380, 390, 400, 401, 406, 416, 417, 418, 428, 429, 430, 442, 443, 444, 454, 455, 456, 517, 518, 520, 521, and 522, wherein said antibody binds HA.

The invention provides an isolated anti-HA antibody, wherein said antibody has a heavy chain with three CDRs comprising an amino acid sequence selected from the group consisting of the amino acid sequences of SEQ ID NOs: 511, 512, and 513, and a light chain with three CDRs that include an amino acid sequence selected from the group consisting of the amino acid sequences of SEQ ID NOs: 517, 181, and 518.

The invention provides an isolated anti-HA antibody, wherein said antibody has a heavy chain with three CDRs comprising an amino acid sequence selected from the group consisting of the amino acid sequences of SEQ ID NOs: 514, 515, and 513, and a light chain with three CDRs that include an amino acid sequence selected from the group consisting of the amino acid sequences of SEQ ID NOs: 517, 181, and 518.

The invention provides an isolated anti-HA antibody, wherein said antibody has a heavy chain with three CDRs comprising an amino acid sequence selected from the group consisting of the amino acid sequences of SEQ ID NOs: 22, 23, and 24, and a light chain with three CDRs that include an amino acid sequence selected from the group consisting of the amino acid sequences of SEQ ID NOs: 29, 30, and 31.

The invention provides an isolated anti-HA antibody, wherein said antibody has a heavy chain with three CDRs comprising an amino acid sequence selected from the group consisting of the amino acid sequences of SEQ ID NOs: 25, 26, and 24, and a light chain with three CDRs that include an amino acid sequence selected from the group consisting of the amino acid sequences of SEQ ID NOs: 29, 30, and 31.

The invention provides an isolated anti-HA antibody, wherein said antibody has a heavy chain with three CDRs comprising an amino acid sequence selected from the group consisting of the amino acid sequences of SEQ ID NOs: 34, 35, and 36, and a light chain with three CDRs that include an amino acid sequence selected from the group consisting of the amino acid sequences of SEQ ID NOs: 41, 42, and 43.

The invention provides an isolated anti-HA antibody, wherein said antibody has a heavy chain with three CDRs comprising an amino acid sequence selected from the group consisting of the amino acid sequences of SEQ ID NOs: 37, 38, and 36, and a light chain with three CDRs that include an amino acid sequence selected from the group consisting of the amino acid sequences of SEQ ID NOs: 41, 42, and 43.

The invention provides an isolated anti-HA antibody, wherein said antibody has a heavy chain with three CDRs comprising an amino acid sequence selected from the group consisting of the amino acid sequences of SEQ ID NOs: 46, 47, and 48, and a light chain with three CDRs that include an amino acid sequence selected from the group consisting of the amino acid sequences of SEQ ID NOs: 53, 54, and 55.

The invention provides an isolated anti-HA antibody, wherein said antibody has a heavy chain with three CDRs comprising an amino acid sequence selected from the group consisting of the amino acid sequences of SEQ ID NOs: 49, 50, and 48, and a light chain with three CDRs that include an amino acid sequence selected from the group consisting of the amino acid sequences of SEQ ID NOs: 53, 54, and 55.

The invention provides an isolated anti-HA antibody, wherein said antibody has a heavy chain with three CDRs comprising an amino acid sequence selected from the group consisting of the amino acid sequences of SEQ ID NOs: 62, 58, and 59, and a light chain with three CDRs that include an amino acid sequence selected from the group consisting of the amino acid sequences of SEQ ID NOs: 65, 66, and 67.

The invention provides an isolated anti-HA antibody, wherein said antibody has a heavy chain with three CDRs comprising an amino acid sequence selected from the group consisting of the amino acid sequences of SEQ ID NOs: 60, 61, and 59, and a light chain with three CDRs that include an amino acid sequence selected from the group consisting of the amino acid sequences of SEQ ID NOs: 65, 66, and 67.

The invention provides an isolated anti-HA antibody, wherein said antibody has a heavy chain with three CDRs comprising an amino acid sequence selected from the group consisting of the amino acid sequences of SEQ ID NOs: 70, 71, and 72, and a light chain with three CDRs that include an amino acid sequence selected from the group consisting of the amino acid sequences of SEQ ID NOs: 77, 78, and 79.

The invention provides an isolated anti-HA antibody, wherein said antibody has a heavy chain with three CDRs comprising an amino acid sequence selected from the group consisting of the amino acid sequences of SEQ ID NOs: 73, 74, and 72, and a light chain with three CDRs that include an amino acid sequence selected from the group consisting of the amino acid sequences of SEQ ID NOs: 77, 78, and 79.

The invention provides an isolated anti-HA antibody, wherein said antibody has a heavy chain with three CDRs comprising an amino acid sequence selected from the group consisting of the amino acid sequences of SEQ ID NOs: 82, 83, and 84, and a light chain with three CDRs that include an amino acid sequence selected from the group consisting of the amino acid sequences of SEQ ID NOs: 89, 90, and 91.

The invention provides an isolated anti-HA antibody, wherein said antibody has a heavy chain with three CDRs comprising an amino acid sequence selected from the group consisting of the amino acid sequences of SEQ ID NOs: 85, 86, and 84, and a light chain with three CDRs that include an amino acid sequence selected from the group consisting of the amino acid sequences of SEQ ID NOs: 89, 90, and 91.

The invention provides an isolated anti-HA antibody, wherein said antibody has a heavy chain with three CDRs comprising an amino acid sequence selected from the group consisting of the amino acid sequences of SEQ ID NOs: 94, 95, and 96, and a light chain with three CDRs that include an amino acid sequence selected from the group consisting of the amino acid sequences of SEQ ID NOs: 101, 102, and 103.

The invention provides an isolated anti-HA antibody, wherein said antibody has a heavy chain with three CDRs comprising an amino acid sequence selected from the group consisting of the amino acid sequences of SEQ ID NOs: 97, 98, and 96, and a light chain with three CDRs that include an amino acid sequence selected from the group consisting of the amino acid sequences of SEQ ID NOs: 101, 102, and 103.

The invention provides an isolated anti-HA antibody, wherein said antibody has a heavy chain with three CDRs comprising an amino acid sequence selected from the group consisting of the amino acid sequences of SEQ ID NOs: 106, 107, and 108, and a light chain with three CDRs that include an amino acid sequence selected from the group consisting of the amino acid sequences of SEQ ID NOs: 113, 114, and 115.

The invention provides an isolated anti-HA antibody, wherein said antibody has a heavy chain with three CDRs comprising an amino acid sequence selected from the group consisting of the amino acid sequences of SEQ ID NOs: 109, 110, and 108, and a light chain with three CDRs that include an amino acid sequence selected from the group consisting of the amino acid sequences of SEQ ID NOs: 113, 114, and 115.

The invention provides an isolated anti-HA antibody, wherein said antibody has a heavy chain with three CDRs comprising an amino acid sequence selected from the group consisting of the amino acid sequences of SEQ ID NOs: 118, 119, and 120, and a light chain with three CDRs that include an amino acid sequence selected from the group consisting of the amino acid sequences of SEQ ID NOs: 125, 126, and 127.

The invention provides an isolated anti-HA antibody, wherein said antibody has a heavy chain with three CDRs comprising an amino acid sequence selected from the group consisting of the amino acid sequences of SEQ ID NOs: 121, 122, and 120, and a light chain with three CDRs that include an amino acid sequence selected from the group consisting of the amino acid sequences of SEQ ID NOs: 125, 126, and 127.

The invention provides an isolated anti-HA antibody, wherein said antibody has a heavy chain with three CDRs comprising an amino acid sequence selected from the group consisting of the amino acid sequences of SEQ ID NOs: 130, 131, and 132, and a light chain with three CDRs that include an amino acid sequence selected from the group consisting of the amino acid sequences of SEQ ID NOs: 137, 138, and 139.

The invention provides an isolated anti-HA antibody, wherein said antibody has a heavy chain with three CDRs comprising an amino acid sequence selected from the group consisting of the amino acid sequences of SEQ ID NOs: 133, 134, and 132, and a light chain with three CDRs that include an amino acid sequence selected from the group consisting of the amino acid sequences of SEQ ID NOs: 137, 138, and 139.

The invention provides an isolated anti-HA antibody, wherein said antibody has a heavy chain with three CDRs comprising an amino acid sequence selected from the group consisting of the amino acid sequences of SEQ ID NOs: 142, 143, and 144, and a light chain with three CDRs that include an amino acid sequence selected from the group consisting of the amino acid sequences of SEQ ID NOs: 149, 150, 151.

The invention provides an isolated anti-HA antibody, wherein said antibody has a heavy chain with three CDRs comprising an amino acid sequence selected from the group consisting of the amino acid sequences of SEQ ID NOs: 145, 146, 144, and a light chain with three CDRs that include an amino acid sequence selected from the group consisting of the amino acid sequences of SEQ ID NOs: 149, 150, 151.

The invention provides an isolated anti-HA antibody, wherein said antibody has a heavy chain with three CDRs comprising an amino acid sequence selected from the group consisting of the amino acid sequences of SEQ ID NOs: 154, 155, and 156, and a light chain with three CDRs that include an amino acid sequence selected from the group consisting of the amino acid sequences of SEQ ID NOs: 53, 54, and 55.

The invention provides an isolated anti-HA antibody, wherein said antibody has a heavy chain with three CDRs comprising an amino acid sequence selected from the group consisting of the amino acid sequences of SEQ ID NOs: 49, 158, and 156, and a light chain with three CDRs that include an amino acid sequence selected from the group consisting of the amino acid sequences of SEQ ID NOs: 53, 54, and 55.

The invention provides an isolated anti-HA antibody, wherein said antibody has a heavy chain with three CDRs comprising an amino acid sequence selected from the group consisting of the amino acid sequences of SEQ ID NOs: 162, 163, and 164, and a light chain with three CDRs that include an amino acid sequence selected from the group consisting of the amino acid sequences of SEQ ID NOs: 169, 170, and 171.

The invention provides an isolated anti-HA antibody, wherein said antibody has a heavy chain with three CDRs comprising an amino acid sequence selected from the group consisting of the amino acid sequences of SEQ ID NOs: 165, 166, and 164, and a light chain with three CDRs that include an amino acid sequence selected from the group consisting of the amino acid sequences of SEQ ID NOs: 169, 170, and 171.

The invention provides an isolated anti-HA antibody, wherein said antibody has a heavy chain with three CDRs comprising an amino acid sequence selected from the group consisting of the amino acid sequences of SEQ ID NOs: 174, 175, and 176, and a light chain with three CDRs that include an amino acid sequence selected from the group consisting of the amino acid sequences of SEQ ID NOs: 157, 181, and 182.

The invention provides an isolated anti-HA antibody, wherein said antibody has a heavy chain with three CDRs comprising an amino acid sequence selected from the group consisting of the amino acid sequences of SEQ ID NOs: 177, 178, and 176, and a light chain with three CDRs that include an amino acid sequence selected from the group consisting of the amino acid sequences of SEQ ID NOs: 157, 181, and 182.

The invention provides an isolated anti-HA antibody, wherein said antibody has a heavy chain with three CDRs comprising an amino acid sequence selected from the group consisting of the amino acid sequences of SEQ ID NOs: 185, 186, and 187, and a light chain with three CDRs that include an amino acid sequence selected from the group consisting of the amino acid sequences of SEQ ID NOs: 192, 30, and 193.

The invention provides an isolated anti-HA antibody, wherein said antibody has a heavy chain with three CDRs comprising an amino acid sequence selected from the group consisting of the amino acid sequences of SEQ ID NOs: 188, 189, and 187, and a light chain with three CDRs that include an amino acid sequence selected from the group consisting of the amino acid sequences of SEQ ID NOs: 192, 30, and 193.

The invention provides an isolated anti-HA antibody, wherein said antibody has a heavy chain with three CDRs comprising an amino acid sequence selected from the group consisting of the amino acid sequences of SEQ ID NOs: 196, 197, and 198, and a light chain with three CDRs that include an amino acid sequence selected from the group consisting of the amino acid sequences of SEQ ID NOs: 203, 204, and 205.

The invention provides an isolated anti-HA antibody, wherein said antibody has a heavy chain with three CDRs comprising an amino acid sequence selected from the group consisting of the amino acid sequences of SEQ ID NOs: 199, 200, and 198, and a light chain with three CDRs that include an amino acid sequence selected from the group consisting of the amino acid sequences of SEQ ID NOs: 203, 204, and 205.

The invention provides an isolated anti-HA antibody, wherein said antibody has a heavy chain with three CDRs comprising an amino acid sequence selected from the group consisting of the amino acid sequences of SEQ ID NOs: 208, 209, 210, and a light chain with three CDRs that include an amino acid sequence selected from the group consisting of the amino acid sequences of SEQ ID NOs: 215, 216, and 217.

The invention provides an isolated anti-HA antibody, wherein said antibody has a heavy chain with three CDRs comprising an amino acid sequence selected from the group consisting of the amino acid sequences of SEQ ID NOs: 211, 212, and 210, and a light chain with three CDRs that include an amino acid sequence selected from the group consisting of the amino acid sequences of SEQ ID NOs: 215, 216, and 217.

The invention provides an isolated anti-HA antibody, wherein said antibody has a heavy chain with three CDRs comprising an amino acid sequence selected from the group consisting of the amino acid sequences of SEQ ID NOs: 220, 221, and 222, and a light chain with three CDRs that include an amino acid sequence selected from the group consisting of the amino acid sequences of SEQ ID NOs: 227, 228, and 229.

The invention provides an isolated anti-HA antibody, wherein said antibody has a heavy chain with three CDRs comprising an amino acid sequence selected from the group consisting of the amino acid sequences of SEQ ID NOs: 223, 224, and 222, and a light chain with three CDRs that include an amino acid sequence selected from the group consisting of the amino acid sequences of SEQ ID NOs: 227, 228, and 229.

The invention provides an isolated anti-HA antibody, wherein said antibody has a heavy chain with three CDRs comprising an amino acid sequence selected from the group consisting of the amino acid sequences of SEQ ID NOs: 232, 233, and 234, and a light chain with three CDRs that include an amino acid sequence selected from the group consisting of the amino acid sequences of SEQ ID NOs: 239, 240, and 241.

The invention provides an isolated anti-HA antibody, wherein said antibody has a heavy chain with three CDRs comprising an amino acid sequence selected from the group consisting of the amino acid sequences of SEQ ID NOs: 235, 236, and 234, and a light chain with three CDRs that include an amino acid sequence selected from the group consisting of the amino acid sequences of SEQ ID NOs: 239, 240, and 241.

The invention provides an isolated anti-HA antibody, wherein said antibody has a heavy chain with three CDRs comprising an amino acid sequence selected from the group consisting of the amino acid sequences of SEQ ID NOs: 244, 245, and 246, and a light chain with three CDRs that include an amino acid sequence selected from the group consisting of the amino acid sequences of SEQ ID NOs: 251, 252, and 253.

The invention provides an isolated anti-HA antibody, wherein said antibody has a heavy chain with three CDRs comprising an amino acid sequence selected from the group consisting of the amino acid sequences of SEQ ID NOs: 247, 248, and 246, and a light chain with three CDRs that include an amino acid sequence selected from the group consisting of the amino acid sequences of SEQ ID NOs: 251, 252, and 253.

The invention provides an isolated anti-HA antibody, wherein said antibody has a heavy chain with three CDRs comprising an amino acid sequence selected from the group consisting of the amino acid sequences of SEQ ID NOs: 256, 257, and 258, and a light chain with three CDRs that include an amino acid sequence selected from the group consisting of the amino acid sequences of SEQ ID NOs: 263, 264, and 265.

The invention provides an isolated anti-HA antibody, wherein said antibody has a heavy chain with three CDRs comprising an amino acid sequence selected from the group consisting of the amino acid sequences of SEQ ID NOs: 259, 260, and 258, and a light chain with three CDRs that include an amino acid sequence selected from the group consisting of the amino acid sequences of SEQ ID NOs: 263, 264, and 265.

The invention provides an isolated anti-HA antibody, wherein said antibody has a heavy chain with three CDRs comprising an amino acid sequence selected from the group consisting of the amino acid sequences of SEQ ID NOs: 268, 269, and 270, and a light chain with three CDRs that include an amino acid sequence selected from the group consisting of the amino acid sequences of SEQ ID NOs: 275, 276, and 277.

The invention provides an isolated anti-HA antibody, wherein said antibody has a heavy chain with three CDRs comprising an amino acid sequence selected from the group consisting of the amino acid sequences of SEQ ID NOs: 271, 272, and 270, and a light chain with three CDRs that include an amino acid sequence selected from the group consisting of the amino acid sequences of SEQ ID NOs: 275, 276, and 277.

The invention provides an isolated anti-HA antibody, wherein said antibody has a heavy chain with three CDRs comprising an amino acid sequence selected from the group consisting of the amino acid sequences of SEQ ID NOs: 280, 281, and 282, and a light chain with three CDRs that include an amino acid sequence selected from the group consisting of the amino acid sequences of SEQ ID NOs: 287, 288, and 289.

The invention provides an isolated anti-HA antibody, wherein said antibody has a heavy chain with three CDRs comprising an amino acid sequence selected from the group consisting of the amino acid sequences of SEQ ID NOs: 283, 284, and 282, and a light chain with three CDRs that include an amino acid sequence selected from the group consisting of the amino acid sequences of SEQ ID NOs: 287, 288, and 289.

The invention provides an isolated anti-HA antibody, wherein said antibody has a heavy chain with three CDRs comprising an amino acid sequence selected from the group consisting of the amino acid sequences of SEQ ID NOs: 292, 293, and 294, and a light chain with three CDRs that include an amino acid sequence selected from the group consisting of the amino acid sequences of SEQ ID NOs: 299, 181, and 300.

The invention provides an isolated anti-HA antibody, wherein said antibody has a heavy chain with three CDRs comprising an amino acid sequence selected from the group consisting of the amino acid sequences of SEQ ID NOs: 295, 296, and 294, and a light chain with three CDRs that include an amino acid sequence selected from the group consisting of the amino acid sequences of SEQ ID NOs: 299, 181, and 300.

The invention provides an isolated anti-HA antibody, wherein said antibody has a heavy chain with three CDRs comprising an amino acid sequence selected from the group consisting of the amino acid sequences of SEQ ID NOs: 303, 304, and 305, and a light chain with three CDRs that include an amino acid sequence selected from the group consisting of the amino acid sequences of SEQ ID NOs: 310, 30, and 311.

The invention provides an isolated anti-HA antibody, wherein said antibody has a heavy chain with three CDRs comprising an amino acid sequence selected from the group consisting of the amino acid sequences of SEQ ID NOs: 306, 307, and 305, and a light chain with three CDRs that include an amino acid sequence selected from the group consisting of the amino acid sequences of SEQ ID NOs: SEQ ID NOs: 310, 30, and 311.

The invention provides an isolated anti-HA antibody, wherein said antibody has a heavy chain with three CDRs comprising an amino acid sequence selected from the group consisting of the amino acid sequences of SEQ ID NOs: 314, 315, and 316, and a light chain with three CDRs that include an amino acid sequence selected from the group consisting of the amino acid sequences of SEQ ID NOs: 321, 322, and 323.

The invention provides an isolated anti-HA antibody, wherein said antibody has a heavy chain with three CDRs comprising an amino acid sequence selected from the group consisting of the amino acid sequences of SEQ ID NOs: 317, 318, and 316, and a light chain with three CDRs that include an amino acid sequence selected from the group consisting of the amino acid sequences of SEQ ID NOs: 321, 322, and 323.

The invention provides an isolated anti-HA antibody, wherein said antibody has a heavy chain with three CDRs comprising an amino acid sequence selected from the group consisting of the amino acid sequences of SEQ ID NOs: 303, 326, and 327, and a light chain with three CDRs that include an amino acid sequence selected from the group consisting of the amino acid sequences of SEQ ID NOs: 332, 216, and 333.

The invention provides an isolated anti-HA antibody, wherein said antibody has a heavy chain with three CDRs comprising an amino acid sequence selected from the group consisting of the amino acid sequences of SEQ ID NOs: 328, 329, and 327, and a light chain with three CDRs that include an amino acid sequence selected from the group consisting of the amino acid sequences of SEQ ID NOs: 332, 216, and 333.

The invention provides an isolated anti-HA antibody, wherein said antibody has a heavy chain with three CDRs comprising an amino acid sequence selected from the group consisting of the amino acid sequences of SEQ ID NOs: 336, 337, and 338, and a light chain with three CDRs that include an amino acid sequence selected from the group consisting of the amino acid sequences of SEQ ID NOs: 343, 216, and 344.

The invention provides an isolated anti-HA antibody, wherein said antibody has a heavy chain with three CDRs comprising an amino acid sequence selected from the group consisting of the amino acid sequences of SEQ ID NOs: 339, 340, and 338, and a light chain with three CDRs that include an amino acid sequence selected from the group consisting of the amino acid sequences of SEQ ID NOs: SEQ ID NOs: 343, 216, and 344.

The invention provides an isolated anti-HA antibody, wherein said antibody has a heavy chain with three CDRs comprising an amino acid sequence selected from the group consisting of the amino acid sequences of SEQ ID NOs: 347, 348, and 349, and a light chain with three CDRs that include an amino acid sequence selected from the group consisting of the amino acid sequences of SEQ ID NOs: 354, 355, and 356.

The invention provides an isolated anti-HA antibody, wherein said antibody has a heavy chain with three CDRs comprising an amino acid sequence selected from the group consisting of the amino acid sequences of SEQ ID NOs: 350, 351, and 349, and a light chain with three CDRs that include an amino acid sequence selected from the group consisting of the amino acid sequences of SEQ ID NOs: 354, 355, and 356.

The invention provides an isolated anti-HA antibody, wherein said antibody has a heavy chain with three CDRs comprising an amino acid sequence selected from the group consisting of the amino acid sequences of SEQ ID NOs: 359, 360, 361, and a light chain with three CDRs that include an amino acid sequence selected from the group consisting of the amino acid sequences of SEQ ID NOs: 366, 367, and 368.

The invention provides an isolated anti-HA antibody, wherein said antibody has a heavy chain with three CDRs comprising an amino acid sequence selected from the group consisting of the amino acid sequences of SEQ ID NOs: 362, 363, and 361, and a light chain with three CDRs that include an amino acid sequence selected from the group consisting of the amino acid sequences of SEQ ID NOs: 366, 367, and 368.

The invention provides an isolated anti-HA antibody, wherein said antibody has a heavy chain with three CDRs comprising an amino acid sequence selected from the group consisting of the amino acid sequences of SEQ ID NOs: 371, 372, and 373, and a light chain with three CDRs that include an amino acid sequence selected from the group consisting of the amino acid sequences of SEQ ID NOs: 378, 379, and 380.

The invention provides an isolated anti-HA antibody, wherein said antibody has a heavy chain with three CDRs comprising an amino acid sequence selected from the group consisting of the amino acid sequences of SEQ ID NOs: 374, 375, and 373, and a light chain with three CDRs that include an amino acid sequence selected from the group consisting of the amino acid sequences of SEQ ID NOs: 378, 379, and 380.

The invention provides an isolated anti-HA antibody, wherein said antibody has a heavy chain with three CDRs comprising an amino acid sequence selected from the group consisting of the amino acid sequences of SEQ ID NOs: 383, 384, and 385, and a light chain with three CDRs that include an amino acid sequence selected from the group consisting of the amino acid sequences of SEQ ID NOs: 203, 181, and 390.

The invention provides an isolated anti-HA antibody, wherein said antibody has a heavy chain with three CDRs comprising an amino acid sequence selected from the group consisting of the amino acid sequences of SEQ ID NOs: 386, 387, and 385, and a light chain with three CDRs that include an amino acid sequence selected from the group consisting of the amino acid sequences of SEQ ID NOs: 203, 181, and 390.

The invention provides an isolated anti-HA antibody, wherein said antibody has a heavy chain with three CDRs comprising an amino acid sequence selected from the group consisting of the amino acid sequences of SEQ ID NOs: 393, 394, and 395, and a light chain with three CDRs that include an amino acid sequence selected from the group consisting of the amino acid sequences of SEQ ID NOs: 400, 216, and 401.

The invention provides an isolated anti-HA antibody, wherein said antibody has a heavy chain with three CDRs comprising an amino acid sequence selected from the group consisting of the amino acid sequences of SEQ ID NOs: 396, 397, and 395, and a light chain with three CDRs that include an amino acid sequence selected from the group consisting of the amino acid sequences of SEQ ID NOs: 400, 216, and 401.

The invention provides an isolated anti-HA antibody, wherein said antibody has a heavy chain with three CDRs comprising an amino acid sequence selected from the group consisting of the amino acid sequences of SEQ ID NOs: 62, 58, and 59, and a light chain with three CDRs that include an amino acid sequence selected from the group consisting of the amino acid sequences of SEQ ID NOs: 406, 66, and 67.

The invention provides an isolated anti-HA antibody, wherein said antibody has a heavy chain with three CDRs comprising an amino acid sequence selected from the group consisting of the amino acid sequences of SEQ ID NOs: 60, 61, and 59, and a light chain with three CDRs that include an amino acid sequence selected from the group consisting of the amino acid sequences of SEQ ID NOs: 406, 66, and 67.

The invention provides an isolated anti-HA antibody, wherein said antibody has a heavy chain with three CDRs comprising an amino acid sequence selected from the group consisting of the amino acid sequences of SEQ ID NOs: 409, 410, and 411, and a light chain with three CDRs that include an amino acid sequence selected from the group consisting of the amino acid sequences of SEQ ID NOs: 416, 417, and 418.

The invention provides an isolated anti-HA antibody, wherein said antibody has a heavy chain with three CDRs comprising an amino acid sequence selected from the group consisting of the amino acid sequences of SEQ ID NOs: 412, 413, and 411, and a light chain with three CDRs that include an amino acid sequence selected from the group consisting of the amino acid sequences of SEQ ID NOs: 416, 417, and 418.

The invention provides an isolated anti-HA antibody, wherein said antibody has a heavy chain with three CDRs comprising an amino acid sequence selected from the group consisting of the amino acid sequences of SEQ ID NOs: 421, 422, and 423, and a light chain with three CDRs that include an amino acid sequence selected from the group consisting of the amino acid sequences of SEQ ID NOs: 428, 429, and 430.

The invention provides an isolated anti-HA antibody, wherein said antibody has a heavy chain with three CDRs comprising an amino acid sequence selected from the group consisting of the amino acid sequences of SEQ ID NOs: 424, 425, and 423, and a light chain with three CDRs that include an amino acid sequence selected from the group consisting of the amino acid sequences of SEQ ID NOs: 428, 429, and 430.

The invention provides an isolated anti-HA antibody, wherein said antibody has a heavy chain with three CDRs comprising an amino acid sequence selected from the group consisting of the amino acid sequences of SEQ ID NOs: 174, 175, and 176, and a light chain with three CDRs that include an amino acid sequence selected from the group consisting of the amino acid sequences of SEQ ID NOs: 125, 126, and 127.

The invention provides an isolated anti-HA antibody, wherein said antibody has a heavy chain with three CDRs comprising an amino acid sequence selected from the group consisting of the amino acid sequences of SEQ ID NOs: 177, 178, and 176, and a light chain with three CDRs that include an amino acid sequence selected from the group consisting of the amino acid sequences of SEQ ID NOs: 125, 126, and 127.

The invention provides an isolated anti-HA antibody, wherein said antibody has a heavy chain with three CDRs comprising an amino acid sequence selected from the group consisting of the amino acid sequences of SEQ ID NOs: 435, 436, and 437, and a light chain with three CDRs that include an amino acid sequence selected from the group consisting of the amino acid sequences of SEQ ID NOs: 442, 443, and 444.

The invention provides an isolated anti-HA antibody, wherein said antibody has a heavy chain with three CDRs comprising an amino acid sequence selected from the group consisting of the amino acid sequences of SEQ ID NOs: 438, 439, and 437, and a light chain with three CDRs that include an amino acid sequence selected from the group consisting of the amino acid sequences of SEQ ID NOs: 442, 443, and 444.

The invention provides an isolated anti-HA antibody, wherein said antibody has a heavy chain with three CDRs comprising an amino acid sequence selected from the group consisting of the amino acid sequences of SEQ ID NOs: 447, 448, and 449, and a light chain with three CDRs that include an amino acid sequence selected from the group consisting of the amino acid sequences of SEQ ID NOs: 454, 455, and 456.

The invention provides an isolated anti-HA antibody, wherein said antibody has a heavy chain with three CDRs comprising an amino acid sequence selected from the group consisting of the amino acid sequences of SEQ ID NOs: 450, 451, and 449, and a light chain with three CDRs that include an amino acid sequence selected from the group consisting of the amino acid sequences of SEQ ID NOs: 454, 455, and 456.

The invention provides an isolated anti-HA antibody, wherein said antibody has a heavy chain with three CDRs comprising an amino acid sequence selected from the group consisting of the amino acid sequences of SEQ ID NOs: 154, 155, and 156, and a light chain with three CDRs that include an amino acid sequence selected from the group consisting of the amino acid sequences of SEQ ID NOs: 520, 521, and 522.

The invention provides an isolated anti-hemagglutinin (HA) antibody, wherein said antibody comprises, a VH CDR1 region comprising the amino acid sequence of SEQ ID NO: 511; a VH CDR2 region comprising the amino acid sequence of SEQ ID NO: 512, a VH CDR3 region comprising the amino acid sequence of SEQ ID NO: 513, a VL CDR1 region comprising the amino acid sequence of SEQ ID NO: 517; a VL CDR2 region comprising the amino acid sequence of SEQ ID NO: 181, and a VL CDR3 region comprising the amino acid sequence of SEQ ID NO: 518.

The invention provides an isolated anti-hemagglutinin (HA) antibody wherein said antibody comprises, a VH CDR1 region comprising the amino acid sequence of SEQ ID NO: 22; a VH CDR2 region comprising the amino acid sequence of SEQ ID NO: 23, a VH CDR3 region comprising the amino acid sequence of SEQ ID NO: 24, a VL CDR1 region comprising the amino acid sequence of SEQ ID NO: 29; a VL CDR2 region comprising the amino acid sequence of SEQ ID NO: 30, and a VL CDR3 region comprising the amino acid sequence of SEQ ID NO: 31.

The invention provides an isolated anti-hemagglutinin (HA) antibody wherein said antibody comprises, a VH CDR1 region comprising the amino acid sequence of SEQ ID NO: 34; a VH CDR2 region comprising the amino acid sequence of SEQ ID NO: 35, a VH CDR3 region comprising the amino acid sequence of SEQ ID NO: 36, a VL CDR1 region comprising the amino acid sequence of SEQ ID NO: 41; a VL CDR2 region comprising the amino acid sequence of SEQ ID NO: 42, and a VL CDR3 region comprising the amino acid sequence of SEQ ID NO: 43.

The invention provides an isolated anti-hemagglutinin (HA) antibody wherein said antibody comprises, a VH CDR1 region comprising the amino acid sequence of SEQ ID NO: 46; a VH CDR2 region comprising the amino acid sequence of SEQ ID NO: 47, a VH CDR3 region comprising the amino acid sequence of SEQ ID NO: 48, a VL CDR1 region comprising the amino acid sequence of SEQ ID NO: 53; a VL CDR2 region comprising the amino acid sequence of SEQ ID NO: 54, and a VL CDR3 region comprising the amino acid sequence of SEQ ID NO: 55.

The invention provides an isolated anti-hemagglutinin (HA) antibody wherein said antibody comprises, a VH CDR1 region comprising the amino acid sequence of SEQ ID NO: 62; a VH CDR2 region comprising the amino acid sequence of SEQ ID NO: 58, a VH CDR3 region comprising the amino acid sequence of SEQ ID NO: 59, a VL CDR1 region comprising the amino acid sequence of SEQ ID NO: 65; a VL CDR2 region comprising the amino acid sequence of SEQ ID NO: 66, and a VL CDR3 region comprising the amino acid sequence of SEQ ID NO: 67.

The invention provides an isolated anti-hemagglutinin (HA) antibody wherein said antibody comprises, a VH CDR1 region comprising the amino acid sequence of SEQ ID NO: 70; a VH CDR2 region comprising the amino acid sequence of SEQ ID NO: 71, a VH CDR3 region comprising the amino acid sequence of SEQ ID NO: 72, a VL CDR1 region comprising the amino acid sequence of SEQ ID NO: 77; a VL CDR2 region comprising the amino acid sequence of SEQ ID NO: 78, and a VL CDR3 region comprising the amino acid sequence of SEQ ID NO: 79.

The invention provides an isolated anti-hemagglutinin (HA) antibody wherein said antibody comprises, a VH CDR1 region comprising the amino acid sequence of SEQ ID NO: 82; a VH CDR2 region comprising the amino acid sequence of SEQ ID NO: 83, a VH CDR3 region comprising the amino acid sequence of SEQ ID NO: 84, a VL CDR1 region comprising the amino acid sequence of SEQ ID NO: 89; a VL CDR2 region comprising the amino acid sequence of SEQ ID NO: 90, and a VL CDR3 region comprising the amino acid sequence of SEQ ID NO: 91.

The invention provides an isolated anti-hemagglutinin (HA) antibody wherein said antibody comprises, a VH CDR1 region comprising the amino acid sequence of SEQ ID NO:

94; a VH CDR2 region comprising the amino acid sequence of SEQ ID NO: 95, a VH CDR3 region comprising the amino acid sequence of SEQ ID NO: 96, a VL CDR1 region comprising the amino acid sequence of SEQ ID NO: 101; a VL CDR2 region comprising the amino acid sequence of SEQ ID NO: 102, and a VL CDR3 region comprising the amino acid sequence of SEQ ID NO: 103.

The invention provides an isolated anti-hemagglutinin (HA) antibody wherein said antibody comprises, a VH CDR1 region comprising the amino acid sequence of SEQ ID NO: 106; a VH CDR2 region comprising the amino acid sequence of SEQ ID NO: 107, a VH CDR3 region comprising the amino acid sequence of SEQ ID NO: 108, a VL CDR1 region comprising the amino acid sequence of SEQ ID NO: 113; a VL CDR2 region comprising the amino acid sequence of SEQ ID NO: 114, and a VL CDR3 region comprising the amino acid sequence of SEQ ID NO: 115.

The invention provides an isolated anti-hemagglutinin (HA) antibody wherein said antibody comprises, a VH CDR1 region comprising the amino acid sequence of SEQ ID NO: 118; a VH CDR2 region comprising the amino acid sequence of SEQ ID NO: 119, a VH CDR3 region comprising the amino acid sequence of SEQ ID NO: 120, a VL CDR1 region comprising the amino acid sequence of SEQ ID NO: 125; a VL CDR2 region comprising the amino acid sequence of SEQ ID NO: 126, and a VL CDR3 region comprising the amino acid sequence of SEQ ID NO: 127.

The invention provides an isolated anti-hemagglutinin (HA) antibody wherein said antibody comprises, a VH CDR1 region comprising the amino acid sequence of SEQ ID NO: 130; a VH CDR2 region comprising the amino acid sequence of SEQ ID NO: 131, a VH CDR3 region comprising the amino acid sequence of SEQ ID NO: 132, a VL CDR1 region comprising the amino acid sequence of SEQ ID NO: 137; a VL CDR2 region comprising the amino acid sequence of SEQ ID NO: 138, and a VL CDR3 region comprising the amino acid sequence of SEQ ID NO: 139.

The invention provides an isolated anti-hemagglutinin (HA) antibody wherein said antibody comprises, a VH CDR1 region comprising the amino acid sequence of SEQ ID NO: 142; a VH CDR2 region comprising the amino acid sequence of SEQ ID NO: 143, a VH CDR3 region comprising the amino acid sequence of SEQ ID NO: 144, a VL CDR1 region comprising the amino acid sequence of SEQ ID NO: 149; a VL CDR2 region comprising the amino acid sequence of SEQ ID NO: 150, and a VL CDR3 region comprising the amino acid sequence of SEQ ID NO: 151.

The invention provides an isolated anti-hemagglutinin (HA) antibody wherein said antibody comprises, a VH CDR1 region comprising the amino acid sequence of SEQ ID NO: 154; a VH CDR2 region comprising the amino acid sequence of SEQ ID NO: 155, a VH CDR3 region comprising the amino acid sequence of SEQ ID NO: 156, a VL CDR1 region comprising the amino acid sequence of SEQ ID NO: 53; a VL CDR2 region comprising the amino acid sequence of SEQ ID NO: 54, and a VL CDR3 region comprising the amino acid sequence of SEQ ID NO: 55.

The invention provides an isolated anti-hemagglutinin (HA) antibody wherein said antibody comprises, a VH CDR1 region comprising the amino acid sequence of SEQ ID NO: 162; a VH CDR2 region comprising the amino acid sequence of SEQ ID NO: 163, a VH CDR3 region comprising the amino acid sequence of SEQ ID NO: 164, a VL CDR1 region comprising the amino acid sequence of SEQ ID NO: 169; a VL CDR2 region comprising the amino acid sequence of SEQ ID NO: 170, and a VL CDR3 region comprising the amino acid sequence of SEQ ID NO: 171.

The invention provides an isolated anti-hemagglutinin (HA) antibody wherein said antibody comprises, a VH CDR1 region comprising the amino acid sequence of SEQ ID NO: 174; a VH CDR2 region comprising the amino acid sequence of SEQ ID NO: 175, a VH CDR3 region comprising the amino acid sequence of SEQ ID NO: 176, a VL CDR1 region comprising the amino acid sequence of SEQ ID NO: 157; a VL CDR2 region comprising the amino acid sequence of SEQ ID NO: 181, and a VL CDR3 region comprising the amino acid sequence of SEQ ID NO: 182.

The invention provides an isolated anti-hemagglutinin (HA) antibody wherein said antibody comprises, a VH CDR1 region comprising the amino acid sequence of SEQ ID NO: 185; a VH CDR2 region comprising the amino acid sequence of SEQ ID NO: 186, a VH CDR3 region comprising the amino acid sequence of SEQ ID NO: 187, a VL CDR1 region comprising the amino acid sequence of SEQ ID NO: 192; a VL CDR2 region comprising the amino acid sequence of SEQ ID NO: 30, and a VL CDR3 region comprising the amino acid sequence of SEQ ID NO: 193.

The invention provides an isolated anti-hemagglutinin (HA) antibody wherein said antibody comprises, a VH CDR1 region comprising the amino acid sequence of SEQ ID NO: 196; a VH CDR2 region comprising the amino acid sequence of SEQ ID NO: 197, a VH CDR3 region comprising the amino acid sequence of SEQ ID NO: 198, a VL CDR1 region comprising the amino acid sequence of SEQ ID NO: 203; a VL CDR2 region comprising the amino acid sequence of SEQ ID NO: 204, and a VL CDR3 region comprising the amino acid sequence of SEQ ID NO: 205.

The invention provides an isolated anti-hemagglutinin (HA) antibody wherein said antibody comprises, a VH CDR1 region comprising the amino acid sequence of SEQ ID NO: 208; a VH CDR2 region comprising the amino acid sequence of SEQ ID NO: 209, a VH CDR3 region comprising the amino acid sequence of SEQ ID NO: 210, a VL CDR1 region comprising the amino acid sequence of SEQ ID NO: 215; a VL CDR2 region comprising the amino acid sequence of SEQ ID NO: 216, and a VL CDR3 region comprising the amino acid sequence of SEQ ID NO: 217.

The invention provides an isolated anti-hemagglutinin (HA) antibody wherein said antibody comprises, a VH CDR1 region comprising the amino acid sequence of SEQ ID NO: 220; a VH CDR2 region comprising the amino acid sequence of SEQ ID NO: 221, a VH CDR3 region comprising the amino acid sequence of SEQ ID NO: 222, a VL CDR1 region comprising the amino acid sequence of SEQ ID NO: 227; a VL CDR2 region comprising the amino acid sequence of SEQ ID NO: 228, and a VL CDR3 region comprising the amino acid sequence of SEQ ID NO: 229.

The invention provides an isolated anti-hemagglutinin (HA) antibody wherein said antibody comprises, a VH CDR1 region comprising the amino acid sequence of SEQ ID NO: 232; a VH CDR2 region comprising the amino acid sequence of SEQ ID NO: 233, a VH CDR3 region comprising the amino acid sequence of SEQ ID NO: 234; a VL CDR1 region comprising the amino acid sequence of SEQ ID NO: 239; a VL CDR2 region comprising the amino acid sequence of SEQ ID NO: 240, and a VL CDR3 region comprising the amino acid sequence of SEQ ID NO: 241.

The invention provides an isolated anti-hemagglutinin (HA) antibody wherein said antibody comprises, a VH CDR1 region comprising the amino acid sequence of SEQ ID NO: 244; a VH CDR2 region comprising the amino acid sequence of SEQ ID NO: 245, a VH CDR3 region comprising the amino acid sequence of SEQ ID NO: 246; a VL CDR1 region comprising the amino acid sequence of SEQ ID NO: 251; a VL CDR2 region comprising the amino acid sequence of SEQ ID NO: 252, and a VL CDR3 region comprising the amino acid sequence of SEQ ID NO: 253.

The invention provides an isolated anti-hemagglutinin (HA) antibody wherein said antibody comprises, a VH CDR1 region comprising the amino acid sequence of SEQ ID NO: 256; a VH CDR2 region comprising the amino acid sequence of SEQ ID NO: 257, a VH CDR3 region comprising the amino acid sequence of SEQ ID NO: 258; a VL CDR1 region comprising the amino acid sequence of SEQ ID NO: 263; a VL CDR2 region comprising the amino acid sequence of SEQ ID NO: 264, and a VL CDR3 region comprising the amino acid sequence of SEQ ID NO: 265.

The invention provides an isolated anti-hemagglutinin (HA) antibody wherein said antibody comprises, a VH CDR1 region comprising the amino acid sequence of SEQ ID NO: 268; a VH CDR2 region comprising the amino acid sequence of SEQ ID NO: 269, a VH CDR3 region comprising the amino acid sequence of SEQ ID NO: 270; a VL CDR1 region comprising the amino acid sequence of SEQ ID NO: 275; a VL CDR2 region comprising the amino acid sequence of SEQ ID NO: 276, and a VL CDR3 region comprising the amino acid sequence of SEQ ID NO: 277.

The invention provides an isolated anti-hemagglutinin (HA) antibody wherein said antibody comprises, a VH CDR1 region comprising the amino acid sequence of SEQ ID NO: 280; a VH CDR2 region comprising the amino acid sequence of SEQ ID NO: 281, a VH CDR3 region comprising the amino acid sequence of SEQ ID NO: 282; a VL CDR1 region comprising the amino acid sequence of SEQ ID NO: 287; a VL CDR2 region comprising the amino acid sequence of SEQ ID NO: 288, and a VL CDR3 region comprising the amino acid sequence of SEQ ID NO: 289.

The invention provides an isolated anti-hemagglutinin (HA) antibody wherein said antibody comprises, a VH CDR1 region comprising the amino acid sequence of SEQ ID NO: 292; a VH CDR2 region comprising the amino acid sequence of SEQ ID NO: 293, a VH CDR3 region comprising the amino acid sequence of SEQ ID NO: 294; a VL CDR1 region comprising the amino acid sequence of SEQ ID NO: 299; a VL CDR2 region comprising the amino acid sequence of SEQ ID NO: 181, and a VL CDR3 region comprising the amino acid sequence of SEQ ID NO: 300.

The invention provides an isolated anti-hemagglutinin (HA) antibody wherein said antibody comprises, a VH CDR1 region comprising the amino acid sequence of SEQ ID NO: 303; a VH CDR2 region comprising the amino acid sequence of SEQ ID NO: 304, a VH CDR3 region comprising the amino acid sequence of SEQ ID NO: 305; a VL CDR1 region comprising the amino acid sequence of SEQ ID NO: 310; a VL CDR2 region comprising the amino acid sequence of SEQ ID NO: 30, and a VL CDR3 region comprising the amino acid sequence of SEQ ID NO: 311.

The invention provides an isolated anti-hemagglutinin (HA) antibody wherein said antibody comprises, a VH CDR1 region comprising the amino acid sequence of SEQ ID NO: 314; a VH CDR2 region comprising the amino acid sequence of SEQ ID NO: 315, a VH CDR3 region comprising the amino acid sequence of SEQ ID NO: 316; a VL CDR1 region comprising the amino acid sequence of SEQ ID NO: 321; a VL CDR2 region comprising the amino acid sequence of SEQ ID NO: 322, and a VL CDR3 region comprising the amino acid sequence of SEQ ID NO: 323.

The invention provides an isolated anti-hemagglutinin (HA) antibody wherein said antibody comprises, a VH CDR1 region comprising the amino acid sequence of SEQ ID NO: 303; a VH CDR2 region comprising the amino acid sequence of SEQ ID NO: 326, a VH CDR3 region comprising the amino acid sequence of SEQ ID NO: 327; a VL CDR1 region comprising the amino acid sequence of SEQ ID NO: 332; a VL CDR2 region comprising the amino acid sequence of SEQ ID NO: 216, and a VL CDR3 region comprising the amino acid sequence of SEQ ID NO: 333.

The invention provides an isolated anti-hemagglutinin (HA) antibody wherein said antibody comprises, a VH CDR1 region comprising the amino acid sequence of SEQ ID NO: 336; a VH CDR2 region comprising the amino acid sequence of SEQ ID NO: 337, a VH CDR3 region comprising the amino acid sequence of SEQ ID NO: 338; a VL CDR1 region comprising the amino acid sequence of SEQ ID NO: 343; a VL CDR2 region comprising the amino acid sequence of SEQ ID NO: 216, and a VL CDR3 region comprising the amino acid sequence of SEQ ID NO: 344.

The invention provides an isolated anti-hemagglutinin (HA) antibody wherein said antibody comprises, a VH CDR1 region comprising the amino acid sequence of SEQ ID NO: 347; a VH CDR2 region comprising the amino acid sequence of SEQ ID NO: 348, a VH CDR3 region comprising the amino acid sequence of SEQ ID NO: 349; a VL CDR1 region comprising the amino acid sequence of SEQ ID NO: 354; a VL CDR2 region comprising the amino acid sequence of SEQ ID NO: 355, and a VL CDR3 region comprising the amino acid sequence of SEQ ID NO: 356.

The invention provides an isolated anti-hemagglutinin (HA) antibody wherein said antibody comprises, a VH CDR1 region comprising the amino acid sequence of SEQ ID NO: 359; a VH CDR2 region comprising the amino acid sequence of SEQ ID NO: 360, a VH CDR3 region comprising the amino acid sequence of SEQ ID NO: 361; a VL CDR1 region comprising the amino acid sequence of SEQ ID NO: 366; a VL CDR2 region comprising the amino acid sequence of SEQ ID NO: 367, and a VL CDR3 region comprising the amino acid sequence of SEQ ID NO: 368.

The invention provides an isolated anti-hemagglutinin (HA) antibody wherein said antibody comprises, a VH CDR1 region comprising the amino acid sequence of SEQ ID NO: 371; a VH CDR2 region comprising the amino acid sequence of SEQ ID NO: 372, a VH CDR3 region comprising the amino acid sequence of SEQ ID NO: 373; a VL CDR1 region comprising the amino acid sequence of SEQ ID NO: 378; a VL CDR2 region comprising the amino acid sequence of SEQ ID NO: 379, and a VL CDR3 region comprising the amino acid sequence of SEQ ID NO: 380.

The invention provides an isolated anti-hemagglutinin (HA) antibody wherein said antibody comprises, a VH CDR1 region comprising the amino acid sequence of SEQ ID NO: 383; a VH CDR2 region comprising the amino acid sequence of SEQ ID NO: 384, a VH CDR3 region comprising the amino acid sequence of SEQ ID NO: 385; a VL CDR1 region comprising the amino acid sequence of SEQ ID NO: 203; a VL CDR2 region comprising the amino acid sequence of SEQ ID NO: 181, and a VL CDR3 region comprising the amino acid sequence of SEQ ID NO: 390.

The invention provides an n isolated anti-hemagglutinin (HA) antibody wherein said antibody comprises, a VH CDR1 region comprising the amino acid sequence of SEQ ID NO: 393; a VH CDR2 region comprising the amino acid sequence of SEQ ID NO: 394, a VH CDR3 region comprising the amino acid sequence of SEQ ID NO: 395; a VL CDR1 region comprising the amino acid sequence of SEQ ID NO: 400; a VL CDR2 region comprising the amino acid sequence of SEQ ID NO: 216, and a VL CDR3 region comprising the amino acid sequence of SEQ ID NO: 401.

The invention provides an isolated anti-hemagglutinin (HA) antibody wherein said antibody comprises, a VH CDR1 region comprising the amino acid sequence of SEQ ID NO: 62; a VH CDR2 region comprising the amino acid sequence of SEQ ID NO: 58, a VH CDR3 region comprising the amino acid sequence of SEQ ID NO: 59; a VL CDR1 region comprising the amino acid sequence of SEQ ID NO: 406; a VL CDR2 region comprising the amino acid sequence of SEQ ID NO: 66, and a VL CDR3 region comprising the amino acid sequence of SEQ ID NO: 67.

The invention provides an isolated anti-hemagglutinin (HA) antibody wherein said antibody comprises, a VH CDR1 region comprising the amino acid sequence of SEQ ID NO: 409; a VH CDR2 region comprising the amino acid sequence of SEQ ID NO: 410, a VH CDR3 region comprising the amino acid sequence of SEQ ID NO: 411; a VL CDR1 region comprising the amino acid sequence of SEQ ID NO: 416; a VL CDR2 region comprising the amino acid sequence of SEQ ID NO: 417, and a VL CDR3 region comprising the amino acid sequence of SEQ ID NO: 418.

The invention provides an isolated anti-hemagglutinin (HA) antibody wherein said antibody comprises, a VH CDR1 region comprising the amino acid sequence of SEQ ID NO: 421; a VH CDR2 region comprising the amino acid sequence of SEQ ID NO: 422, a VH CDR3 region comprising the amino acid sequence of SEQ ID NO: 423; a VL CDR1 region comprising the amino acid sequence of SEQ ID NO: 428; a VL CDR2 region comprising the amino acid sequence of SEQ ID NO: 429, and a VL CDR3 region comprising the amino acid sequence of SEQ ID NO: 430.

The invention provides an isolated anti-hemagglutinin (HA) antibody wherein said antibody comprises, a VH CDR1 region comprising the amino acid sequence of SEQ ID NO: 174; a VH CDR2 region comprising the amino acid sequence of SEQ ID NO: 175, a VH CDR3 region comprising the amino acid sequence of SEQ ID NO: 176; a VL CDR1 region comprising the amino acid sequence of SEQ ID NO: 125; a VL CDR2 region comprising the amino acid sequence of SEQ ID NO: 126, and a VL CDR3 region comprising the amino acid sequence of SEQ ID NO: 127.

The invention provides an isolated anti-hemagglutinin (HA) antibody wherein said antibody comprises, a VH CDR1 region comprising the amino acid sequence of SEQ ID NO: 435; a VH CDR2 region comprising the amino acid sequence of SEQ ID NO: 436, a VH CDR3 region comprising the amino acid sequence of SEQ ID NO: 437; a VL CDR1 region comprising the amino acid sequence of SEQ ID NO: 442; a VL CDR2 region comprising the amino acid sequence of SEQ ID NO: 443, and a VL CDR3 region comprising the amino acid sequence of SEQ ID NO: 444.

The invention provides an isolated anti-hemagglutinin (HA) antibody wherein said antibody comprises, a VH CDR1 region comprising the amino acid sequence of SEQ ID NO: 447; a VH CDR2 region comprising the amino acid sequence of SEQ ID NO: 448, a VH CDR3 region comprising the amino acid sequence of SEQ ID NO: 449; a VL CDR1 region comprising the amino acid sequence of SEQ ID NO: 454; a VL CDR2 region comprising the amino acid sequence of SEQ ID NO: 455, and a VL CDR3 region comprising the amino acid sequence of SEQ ID NO: 456.

The invention provides an isolated anti-hemagglutinin (HA) antibody wherein said antibody comprises, a VH CDR1 region comprising the amino acid sequence of SEQ ID NO: 154; a VH CDR2 region comprising the amino acid sequence of SEQ ID NO: 155, a VH CDR3 region comprising the amino acid sequence of SEQ ID NO: 156; a VL CDR1 region comprising the amino acid sequence of SEQ ID NO: 520; a VL CDR2 region comprising the amino acid sequence of SEQ ID NO: 521, and a VL CDR3 region comprising the amino acid sequence of SEQ ID NO: 522.

The invention provides an isolated anti-hemagglutinin (HA) antibody or fragment thereof, wherein said antibody comprises: (a) a $V_H$ CDR1 region comprising the amino acid sequence of SEQ ID NO: 22, 34, 46, 62, 70, 82, 94, 106, 118, 130, 142, 151, 162, 174, 185, 196, 208, 220, 232, 244, 256, 268, 280, 292, 303, 314, 336, 347, 359, 371, 383, 393, 409, 421, 435, 447, and 511; (b) a $V_H$ CDR2 region comprising the amino acid sequence of SEQ ID NO: 23, 35, 47, 58, 71, 83, 95, 107, 119, 131, 143, 155, 163, 175, 186, 197, 209, 221, 233, 245, 257, 269, 281, 293, 304, 315, 326, 337, 348, 360, 372, 384, 394, 410, 422, 436, 448, and 512; and (c) a $V_H$ CDR3 region comprising the amino acid sequence of SEQ ID NO: 24, 36, 48, 59, 72, 84, 96, 108, 120, 132, 144, 156, 164, 176, 187, 198, 210, 222, 234, 246, 258, 270, 282, 294, 305, 316, 327, 338, 349, 361, 373, 385, 395, 411, 423, 437, 449, and 513, wherein said antibody binds HA. In one aspect, the antibody further comprises: (a) a $V_L$ CDR1 region comprising the amino acid sequence of SEQ ID NO: 29, 41, 53, 65, 77, 89, 101, 113, 125, 137, 149, 169, 157, 192, 203, 215, 227, 239, 251, 263, 275, 287, 299, 310, 321, 332, 343, 354, 366, 378, 400, 406, 416, 428, 442, 454, 517, and 520; (b) a $V_L$ CDR2 region comprising the amino acid sequence of SEQ ID NO: 30, 42, 54, 66, 78, 90, 102, 114, 126, 138, 150, 170, 181, 204, 216, 228, 240, 252, 264, 276, 288, 322, 355, 367, 379, 417, 429, 443, 455, and 521; and (c) a $V_L$ CDR3 region comprising the amino acid sequence of SEQ ID NO: 31, 43, 55, 67, 79, 91, 103, 115, 127, 139, 151, 171, 182, 193, 205, 217, 229, 241, 253, 265, 277, 289, 300, 311, 323, 333, 344, 356, 368, 380, 390, 401, 418, 430, 444, 456, 518, and 522.

The invention provides an isolated anti-hemagglutinin (HA) antibody or fragment thereof, wherein said antibody comprises: (a) a $V_H$ CDR1 region comprising the amino acid sequence of SEQ ID NO: 25, 37, 49, 60, 73, 85, 97, 109, 121, 133, 145, 165, 177, 188, 199, 211, 223, 235, 247, 259, 271, 283, 295, 306, 317, 328, 338, 350, 362, 374, 386, 396, 412, 424, 438, 450, and 514; (b) a $V_H$ CDR2 region comprising the amino acid sequence of SEQ ID NO: 26, 38, 50, 61, 74, 86, 98, 110, 122, 134, 146, 158, 166, 178, 189, 200, 212, 224, 236, 248, 260, 272, 284, 296, 307, 318, 329, 340, 351, 363, 375, 387, 397, 413, 425, 439, 451, and 515; and (c) a $V_H$ CDR3 region comprising the amino acid sequence of SEQ ID NO: 24, 36, 48, 59, 72, 84, 96, 108, 120, 132, 144, 156, 164, 176, 187, 198, 210, 222, 234, 246, 258, 270, 282, 294, 305, 316, 327, 338, 349, 361, 373, 385, 395, 411, 423, 437, 449, and 513, wherein said antibody binds HA. In one aspect, the antibody further comprises: (a) a $V_L$ CDR1 region comprising the amino acid sequence of SEQ ID NO: 29, 41, 53, 65, 77, 89, 101, 113, 125, 137, 149, 169, 157, 192, 203, 215, 227, 239, 251, 263, 275, 287, 299, 310, 321, 332, 343, 354, 366, 378, 400, 406, 416, 428, 442, 454, 517, and 520; (b) a $V_L$ CDR2 region comprising the amino acid sequence of SEQ ID NO: 30, 42, 54, 66, 78, 90, 102, 114, 126, 138, 150, 170, 181, 204, 216, 228, 240, 252, 264, 276, 288, 322, 355, 367, 379, 417, 429, 443, 455, and 521; and (c) a $V_L$ CDR3 region comprising the amino acid sequence of SEQ ID NO: 31, 43, 55, 67, 79, 91, 103, 115, 127, 139, 151, 171, 182, 193, 205, 217, 229, 241, 253, 265, 277, 289, 300, 311, 323, 333, 344, 356, 368, 380, 390, 401, 418, 430, 444, 456, 518, and 522.

The invention provides an isolated fully human monoclonal anti-hemagglutinin (HA) antibody comprising: a) a heavy chain variable sequence comprising the amino acid sequence of SEQ ID NO: 510 and a light chain variable sequence comprising amino acid sequence SEQ ID NO: 524 or b) a heavy chain variable sequence comprising the amino acid sequence of SEQ ID NO: 21 and a light chain variable sequence comprising amino acid sequence SEQ ID NO: 28 or c) a heavy chain variable sequence comprising the amino acid sequence of SEQ ID NO: 33 and a light chain variable sequence comprising amino acid sequence SEQ ID NO: 40 or d) a heavy chain variable sequence comprising the amino acid sequence of SEQ ID NO: 43 and a light chain variable sequence comprising amino acid sequence SEQ ID NO: 52 or e) a heavy chain variable sequence comprising the amino acid sequence of SEQ ID NO: 57 and a light chain variable sequence comprising amino acid sequence SEQ ID NO: 64 or f) a heavy chain variable sequence comprising the amino acid sequence of SEQ ID NO: 69 and a light chain variable sequence comprising amino acid sequence SEQ ID NO: 76 or g) a heavy chain variable sequence comprising the amino acid sequence of SEQ ID NO: 81 and a light chain variable sequence comprising amino acid sequence SEQ ID NO: 88 or h) a heavy chain variable sequence comprising the amino acid sequence of SEQ ID NO: 93 and a light chain variable sequence comprising amino acid sequence SEQ ID NO: 100 or i) a heavy chain variable sequence comprising the amino acid sequence of SEQ ID NO: 105 and a light chain variable sequence comprising amino acid sequence SEQ ID NO: 112 or j) a heavy chain variable sequence comprising the amino acid sequence of SEQ ID NO: 117 and a light chain variable sequence comprising amino acid sequence SEQ ID NO: 124 or k) a heavy chain variable sequence comprising the amino acid sequence of SEQ ID NO: 129 and a light chain variable sequence comprising amino acid sequence SEQ ID NO: 136 or l) a heavy chain variable sequence comprising the amino acid sequence of SEQ ID NO: 141 and a light chain variable sequence comprising amino acid sequence SEQ ID NO: 148 or m) a heavy chain variable sequence comprising the amino acid sequence of SEQ ID NO: 153 and a light chain variable sequence comprising amino acid sequence SEQ ID NO: 52 or n) a heavy chain variable sequence comprising the amino acid sequence of SEQ ID NO: 161 and a light chain variable sequence comprising amino acid sequence SEQ ID NO: 168 or o) a heavy chain variable sequence comprising the amino acid sequence of SEQ ID NO: 173 and a light chain variable sequence comprising amino acid sequence SEQ ID NO: 180 or p) a heavy chain variable sequence comprising the amino acid sequence of SEQ ID NO: 184 and a light chain variable sequence comprising amino acid sequence SEQ ID NO: 191 or q) a heavy chain variable sequence comprising the amino acid sequence of SEQ ID NO: 195 and a light chain variable sequence comprising amino acid sequence SEQ ID NO: 202 or r) a heavy chain variable sequence comprising the amino acid sequence of SEQ ID NO: 207 and a light chain variable sequence comprising amino acid sequence SEQ ID NO: 214 or s) a heavy chain variable sequence comprising the amino acid sequence of SEQ ID NO: 219 and a light chain variable sequence comprising amino acid sequence SEQ ID NO: 226 or t) a heavy chain variable sequence comprising the amino acid sequence of SEQ ID NO: 231 and a light chain variable sequence comprising amino acid sequence SEQ ID NO: 238 or u) a heavy chain variable sequence comprising the amino acid sequence of SEQ ID NO: 243 and a light chain variable sequence comprising amino acid sequence SEQ ID NO: 250 or v) a heavy chain variable sequence comprising the amino acid sequence of SEQ ID NO: 255 and a light chain variable sequence comprising amino acid sequence SEQ ID NO: 262 or w) a heavy chain variable sequence comprising the amino acid sequence of SEQ ID NO: 267 and a light chain variable sequence comprising amino acid sequence SEQ ID NO: 274 or x) a heavy chain variable sequence comprising the amino acid sequence of SEQ ID NO: 279 and a light chain variable sequence comprising amino acid sequence SEQ ID NO: 286 or y) a heavy chain variable sequence comprising the amino acid sequence of SEQ ID NO: 291 and a light chain variable sequence comprising amino acid sequence SEQ ID NO: 298 or z) a heavy chain variable sequence comprising the amino acid sequence of SEQ ID NO: 302 and a light chain variable sequence comprising amino acid sequence SEQ ID NO: 309 or aa) a heavy chain variable sequence comprising the amino acid sequence of SEQ ID NO: 313 and a light chain variable sequence comprising amino acid sequence SEQ ID NO: 320 or bb) a heavy chain variable sequence comprising the amino acid sequence of SEQ ID NO: 325 and a light chain variable sequence comprising amino acid sequence SEQ ID NO: 331 or cc) a heavy chain variable sequence comprising the amino acid sequence of SEQ ID NO: 335 and a light chain variable sequence comprising amino acid sequence SEQ ID NO: 342 or dd) a heavy chain variable sequence comprising the amino acid sequence of SEQ ID NO: 346 and a light chain variable sequence comprising amino acid sequence SEQ ID NO: 353 or ee) a heavy chain variable sequence comprising the amino acid sequence of SEQ ID NO: 358 and a light chain variable sequence comprising amino acid sequence SEQ ID NO: 365 or ff) a heavy chain variable sequence comprising the amino acid sequence of SEQ ID NO: 370 and a light chain variable sequence comprising amino acid sequence SEQ ID NO: 377 or gg) a heavy chain variable sequence comprising the amino acid sequence of SEQ ID NO: 382 and a light chain variable sequence comprising amino acid sequence SEQ ID NO: 389 or hh) a heavy chain variable sequence comprising the amino acid sequence of SEQ ID NO: 392 and a light chain variable sequence comprising amino acid sequence SEQ ID NO: 399 or ii) a heavy chain variable sequence comprising the amino acid sequence of SEQ ID NO: 403 and a light chain variable sequence comprising amino acid sequence SEQ ID NO: 405 or jj) a heavy chain variable sequence comprising the amino acid sequence of SEQ ID NO: 420 and a light chain variable sequence comprising amino acid sequence SEQ ID NO: 427 or kk) a heavy chain variable sequence comprising the amino acid sequence of SEQ ID NO: 173 and a light chain variable sequence comprising amino acid sequence SEQ ID NO: 124 or ll) a heavy chain variable sequence comprising the amino acid sequence of SEQ ID NO: 434 and a light chain variable sequence comprising amino acid sequence SEQ ID NO: 441 or mm) a heavy chain variable sequence comprising the amino acid sequence of SEQ ID NO: 446 and a light chain variable sequence comprising amino acid sequence SEQ ID NO: 453 or nn) a heavy chain variable sequence comprising the amino acid sequence of SEQ ID NO: 153 and a light chain variable sequence comprising amino acid sequence SEQ ID NO: 519.

An antibody of the invention, or specifically, any antibody described herein, may be operably-linked to a therapeutic agent or a detectable label.

The invention further provides a pharmaceutical composition including an antibody described herein and a pharmaceutical carrier. This composition optionally includes an anti-viral drug, a viral entry inhibitor or a viral attachment inhibitor. Exemplary anti-viral drugs include, but are not limited to, a neuraminidase inhibitor, a HA inhibitor, a sialic acid inhibitor and an M2 ion channel inhibitor. In one embodiment of the composition, the M2 ion channel inhibitor is amantadine or rimantadine. Alternatively, or in addition, the neuraminidase inhibitor zanamivir or oseltamivir phosphate. The composition may also include a second anti-Influenza A antibody. The second anti-Influenza A antibody is optionally an antibody described herein.

The invention provides a method for stimulating an immune response in a subject, including administering to the subject the pharmaceutical composition described herein.

Moreover, the invention provides a method for the treatment of an Influenza virus infection in a subject, including administering to the subject the pharmaceutical composition described herein. This method further includes administering an anti-viral drug, a viral entry inhibitor or a viral attachment inhibitor.

The invention also provides a method for the prevention of an Influenza virus infection in a subject, including administering to the subject the pharmaceutical composition described herein prior to exposure of the subject to Influenza virus or infection. This method further includes administering an anti-viral drug, a viral entry inhibitor or a viral attachment inhibitor. This method may be a method of vaccination.

The subject of these methods may have an Influenza infection or is predisposed to developing an Influenza virus infection. Subjects predisposed to developing an Influenza infection, or who may be at elevated risk for contracting an infection, are those subjects with compromised immune systems because of autoimmune disease, those persons receiving immunosuppressive therapy (for example, following organ transplant), those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subject of extreme young or old age are at increased risk. Any person who comes into physical contact or close physical proximity with an infected individual has an increased risk of developing an Influenza virus infection. Moreover, a subject is at risk of contracting an influenza infection due to proximity to an outbreak of the disease, e.g. subject resides in a densely-populated city or in close proximity to subjects having confirmed or suspected infections of Influenza virus, or choice of employment, e.g. hospital worker, pharmaceutical researcher, traveler to infected area, or frequent flier.

According to the methods described herein, exemplary anti-viral drugs include, but are not limited to, a neuraminidase inhibitor, a HA inhibitor, a sialic acid inhibitor and an M2 ion channel. In one aspect of these methods, the M2 ion channel inhibitor is amantadine or rimantadine. Alternatively, or in addition, the neuraminidase inhibitor is zanamivir or oseltamivir phosphate.

These methods optionally include administering a second anti-Influenza A antibody. For example, the antibody is administered prior to or after exposure to Influenza virus. In certain aspects of these methods, the antibody is administered at a dose sufficient to promote viral clearance or to eliminate Influenza A infected cells. The second antibody is optionally an antibody described herein The invention further provides a method for determining the presence of a Influenza virus infection in a subject, including the steps of: (a) contacting a biological sample obtained from the subject with an antibody described herein or the pharmaceutical composition described herein; (b) detecting an amount of the antibody that binds to the biological sample; and (c) comparing the amount of antibody that binds to the biological sample to a control value, and therefrom determining the presence of the Influenza virus in the subject.

The invention provides a vaccine composition including an antibody described herein. This composition optionally contains a pharmaceutical carrier.

Alternatively, the invention provides a vaccine composition including an epitope of an antibody described herein. This composition optionally contains a pharmaceutical carrier.

Vaccines of the invention are multivalent vaccines. The term "multivalent vaccine" is meant to describe a single vaccine that elicits an immune response either to more than one infectious agent, e.g. recombinant homotrimeric HA0 proteins or fragments thereof derived from multiple strains of Influenza A (see, Table 2), or to several different epitopes of a molecule, e.g. a linear and a discontinuous epitope of the same recombinant homotrimeric HA0 protein or fragment thereof derived from a single strain of Influenza A. Alternatively, or in addition, the term multivalent vaccine is meant to describe the administration of a combination of human antibodies raised against more than one infectious agent, e.g. a combination of HuMHA antibodies raised against recombinant homotrimeric HA0 proteins or fragments thereof derived from multiple strains of Influenza A (see, Table 2).

The invention provides a diagnostic kit including an antibody described herein.

The invention provides a prophylactic kit including an antibody described herein or an epitope of an antibody described herein. Alternatively, or in addition, the invention provides a prophylactic kit including a vaccine composition described herein.

In a preferred embodiment, the present invention provides fully human monoclonal antibodies specifically directed against the Influenza hemagglutinin glycoprotein, which neutralize influenza infection. Optionally, the antibody is isolated from a B-cell from a mammalian donor, and preferably, a human donor. In certain embodiments of the invention, the antibody is identified for its ability to bind an intact or whole Influenza virus. Alternatively, or in addition, the antibody is identified isolated for its ability to bind to an epitope of a recombinant homotrimeric Influenza HA0 protein or HA protein(s) isolated from multiple Influenza strains, or made as recombinant proteins such as those influenza A virus strains provided in Table 2. Alternatively, or in addition, the antibody is identified for its ability to inhibit or neutralize virus infection of susceptible eukaryotic cells. Exemplary neutralizing antibodies of this profile include, but are not limited to, those antibodies listed in Table 3. Alternatively, the monoclonal antibody is an antibody that binds to the same epitope as the antibodies provided in Table 3. In certain embodiments, neutralizing human monoclonal antibodies of the invention are anti-HA antibodies. A monoclonal anti-HA antibody of the invention has one or more of the following characteristics: a) binds to an epitope in an HA1 subunit of an Influenza hemagglutinin (HA) protein; b) binds to an epitope in the HA2 subunit of Influenza hemagglutinin (HA) protein; c) binds to an epitope in the extracellular domain of an Influenza hemagglutinin (HA) protein, consisting of an HA1 subunit and an HA2 subunit; d) binds to an epitope of a recombinant homotrimeric Influenza HA0 protein; e) binds to an epitope of an Influenza HA protein expressed on an infected cell; f) binds to an epitope of an Influenza HA protein expressed on a modified cell; g) binds to an Influenza virus; or h) inhibits virus infection of susceptible eukaryotic cells.

Modified cells of the invention are transfected or transformed with a polynucleotide that encodes an Influenza HA protein, or any fragment thereof. The term "Influenza HA protein fragment" is meant to describe any portion of the protein that is smaller or less than the entire protein. Polynucleotides and polypeptides of the invention do not always encode a functional Influenza HA protein.

Infected cells of the invention are mammalian, and preferably human in origin. Specifically, mammalian cells are infected with Influenza A virus in vivo, in vitro, in situ, ex vivo, in culture, and any combination thereof. Cells are infected with active or inactive virions. Exemplary inactive virions display the HA protein on their surfaces, however, they are replication-defective, and therefore, unable to propagate within the cell or subject.

Epitopes of the human monoclonal antibodies of the invention include a transmembrane or integral membrane Influenza A protein. Specifically, epitopes of the human monoclonal antibodies of the invention comprise Influenza hemagglutinin (HA) protein.

Epitopes of the human monoclonal antibodies of the invention include one or more subunits of an influenza hemagglutinin (HA) protein. HA proteins of the invention include hemagglutinin precursor proteins (HA0), the HA1 subunit, the HA2 subunit, the mature protein containing the HA1 and HA2 subunits, and a recombinant HA protein. Recombinant HA proteins contain SEQ ID NO: 1. Exemplary recombinant proteins include but, are not limited to, those proteins described by SEQ ID NO: 2-19.

Epitopes of the human monoclonal antibodies of the invention are linear or non-linear. For instance, a non-linear epitope is discontinuous. Discontinuous epitopes are available for antibody binding only when the Influenza HA protein is maintained in its native homotrimeric conformation. When an antibody binds to a discontinuous epitope, the antibody binds to a three-dimensional surface of the target protein, i.e. the Influenza HA protein, upon which juxtaposed amino acids are alternatively exposed or masked.

Recombinant homotrimeric HA0 proteins of the invention are encoded by, for instance, sequences described by any one of SEQ ID NO: 2-19. In certain embodiments of the invention, the human monoclonal antibodies, or monoclonal anti-HA antibodies, described herein bind membrane-bound or soluble recombinant homotrimeric Influenza HA proteins. Alternatively, the monoclonal anti-HA antibodies described herein bind membrane-bound and soluble recombinant homotrimeric Influenza HA proteins. In certain embodiments of the invention, the monoclonal anti-HA antibodies described herein bind and neutralize Influenza virus subtypes H1, H2, and H3. In other embodiments of the invention, the monoclonal anti-HA antibodies bind Influenza virus subtypes H1, H2, and H3, and neutralize one of these subtypes, such as H1, H2, or H3. In a specific embodiment, the monoclonal anti-HA antibodies bind Influenza subtypes H1N1, H2N2, and H3N2, and neutralize H1N1.

In one aspect, the HA precursor polypeptide (HA0) of the soluble and recombinant homotrimeric Influenza HA protein contains a trimerization domain (foldon) encoded in the phage T4 fibritin. An exemplary trimerization domain isolated from the phage T4 fibritin has the following sequence wherein a thrombin cleavage site is italicized and bolded, a T4 trimerization domain or sequence is underlined, a V5 tag is boxed, and a hexa-histidine (His) tag is bolded:

Other features and advantages of the invention will be apparent from and are encompassed by the following detailed description and claims.

SGR*LVPRGS*PGSGYIPEAPRDGQAYVRKDGEWVLLSTFLGKPIPNPLLGLDSTGHHHHHH(SEQ ID NO: 1).

As used herein, the term "neutralizing antibody" is meant to describe an antibody that inhibits or prevents influenza A infection, inhibits or prevents Influenza A viral entry into a cell, inhibits or prevents influenza replication, inhibits or prevents influenza egress from a host cell, or reduces the Influenza A titer in a cell, biological sample, or subject. In a preferred embodiment, neutralizing antibodies of the invention prevent viral entry into the cytoplasmic compartment of host cells.

Figure 16:
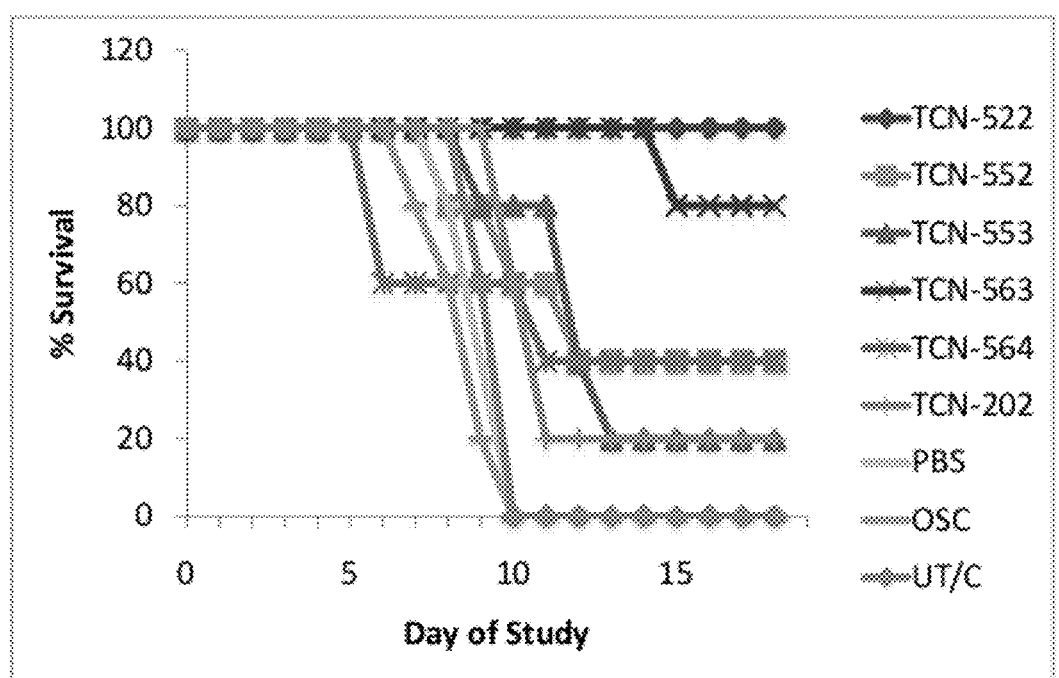

FIG. 16 is a graph depicting the survival of mice infected with 25×LD$_{50}$ of H1N1 A/California/04/09 and antibody administration at 15 mg/kg on day +3 after infection.

Figure 17:
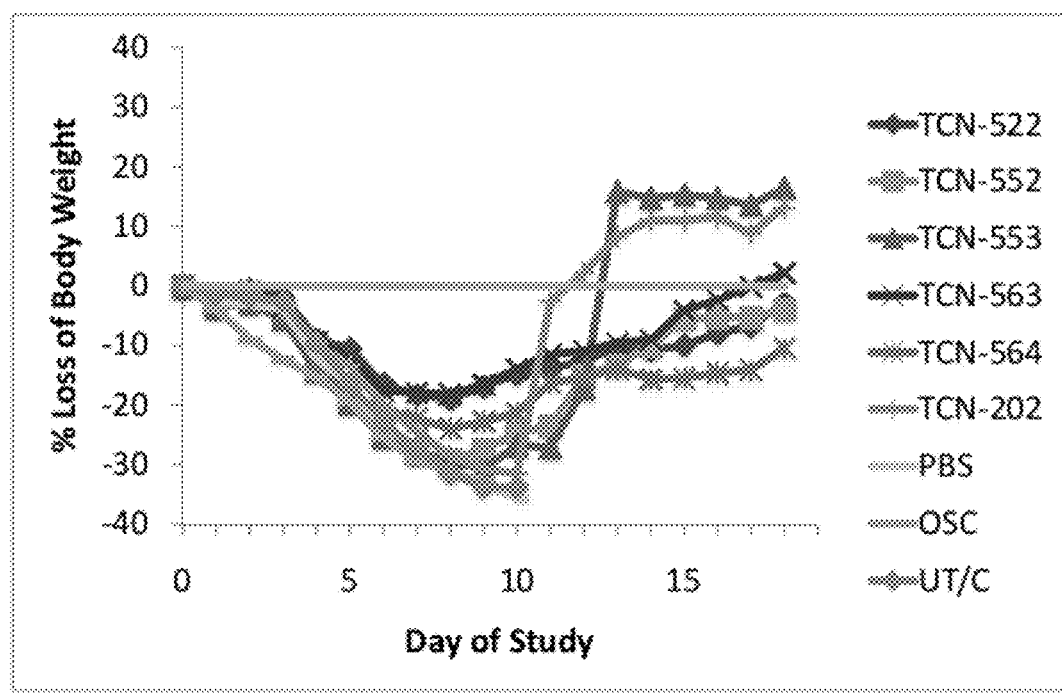

FIG. 17 is a graph depicting the percent weight loss of mice infected with 25×LD$_{50}$ of H1N1 A/California/04/09 and antibody administration at 15 mg/kg on day +3 after infection.

Figure 18:
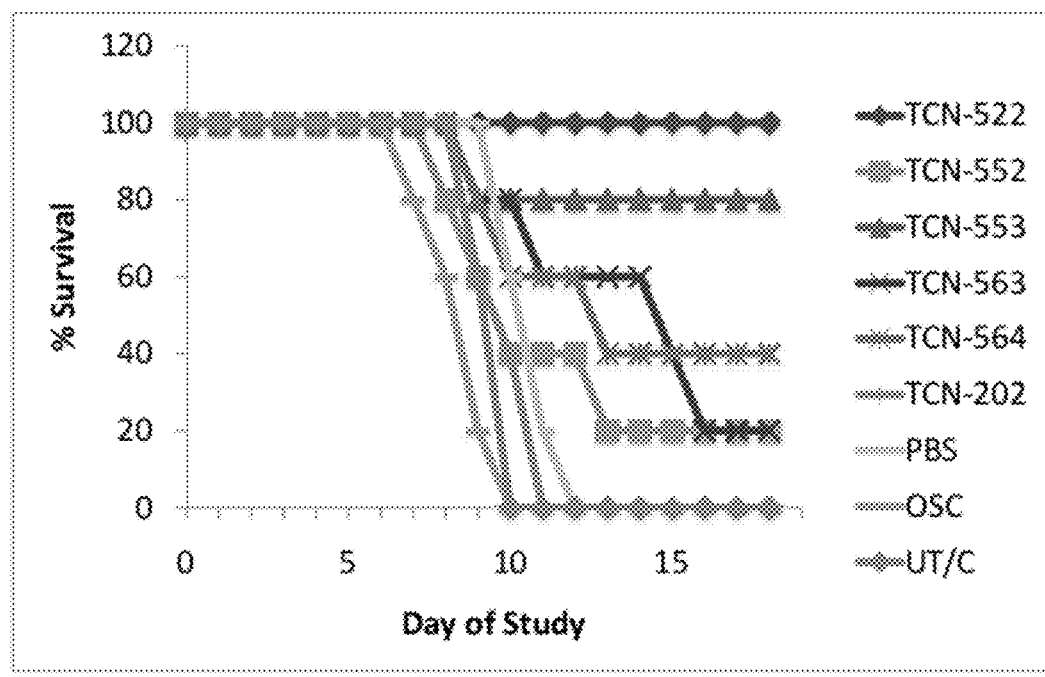

FIG. 18 is a graph depicting the survival of mice infected with 25×LD$_{50}$ of H1N1 A/California/04/09 and antibody administration at 15 mg/kg on day +5 after infection.

Figure 19:
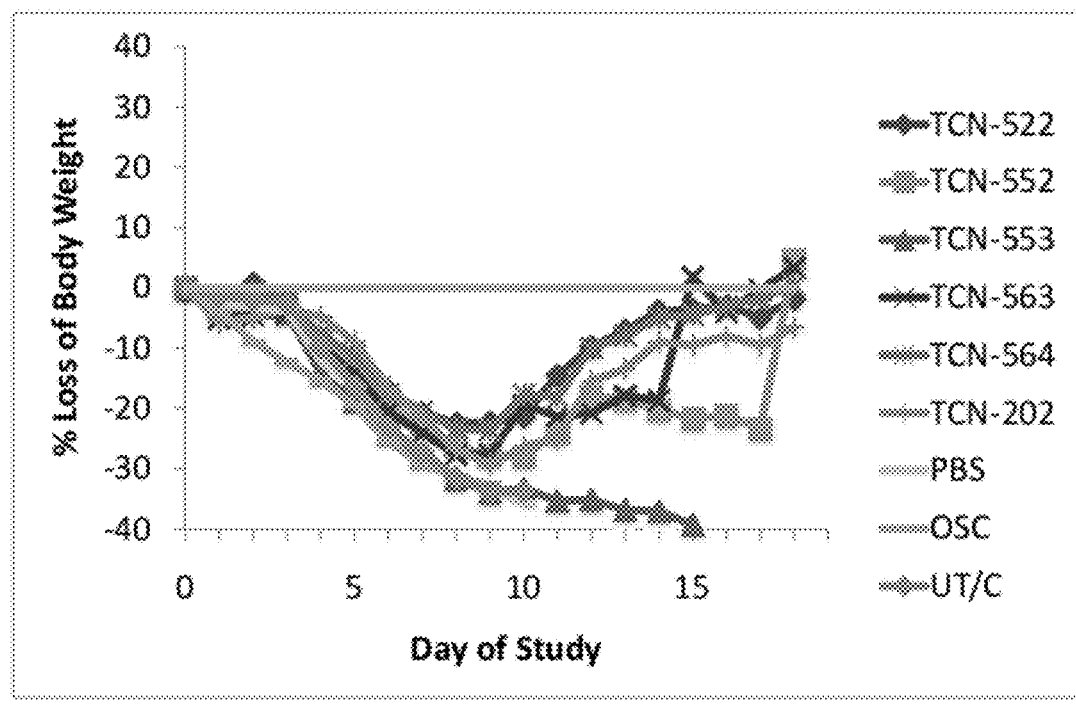

FIG. 19 is a graph depicting the percent weight loss of mice infected with 25×LD$_{50}$ of H1N1 A/California/04/09 and antibody administration at 15 mg/kg on day +5 after infection.

Figure 20:
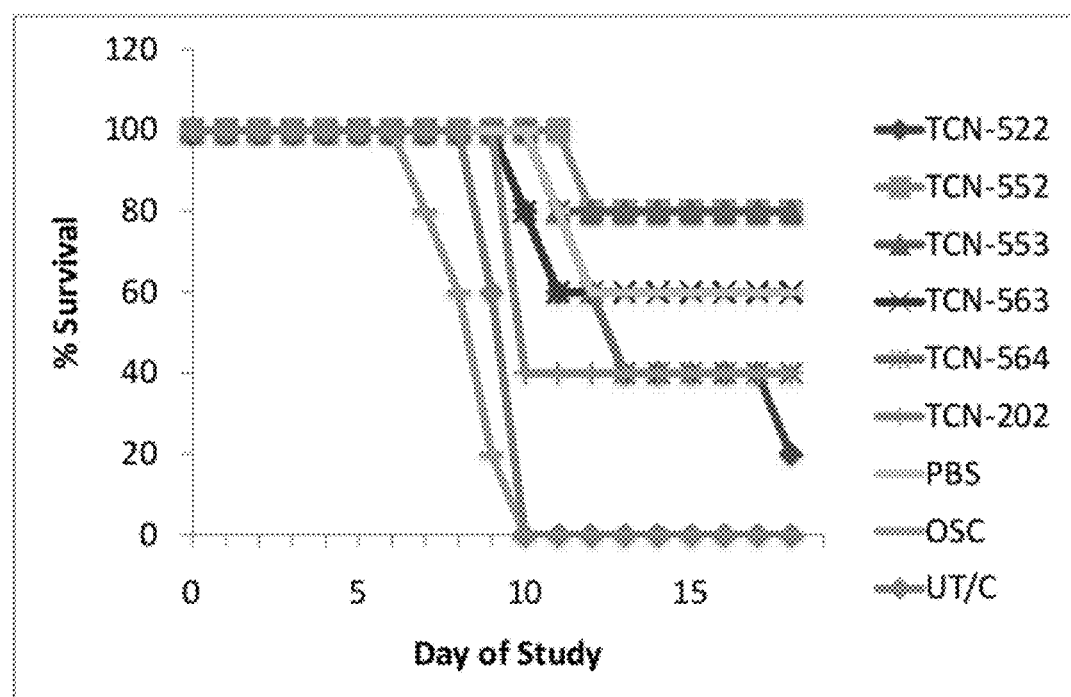

FIG. 20 is a graph depicting the survival of mice infected with 25×LD$_{50}$ of H1N1 A/California/04/09 and antibody administration at 1.5 mg/kg on day +1 after infection.

Figure 21:
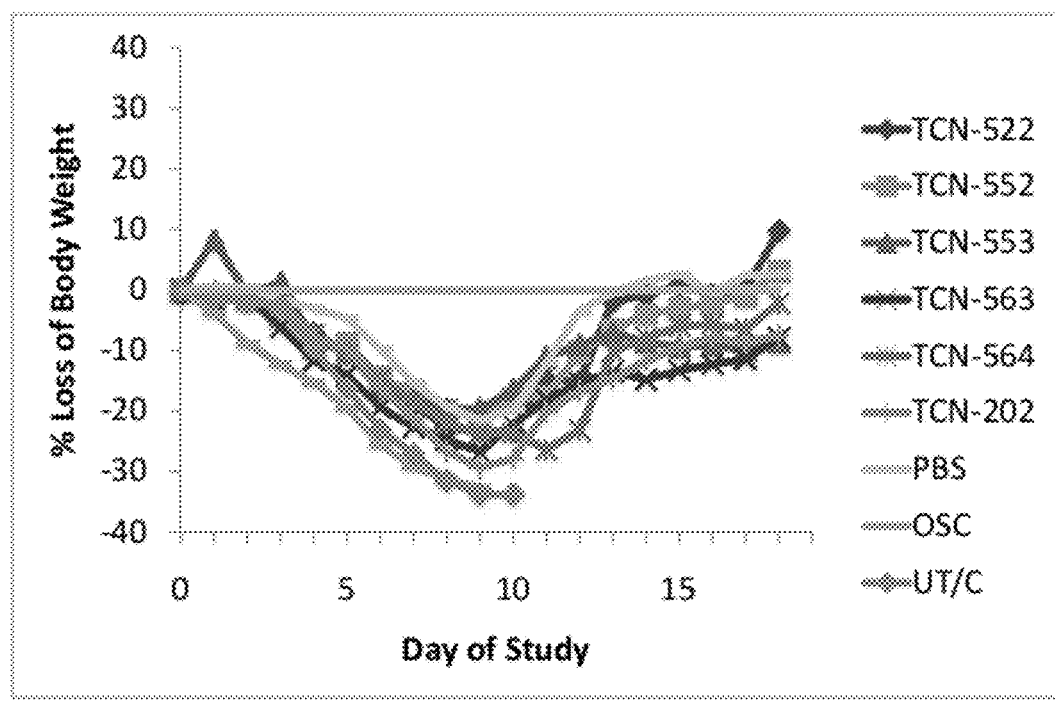

FIG. 21 is a graph depicting the percent weight loss of mice infected with 25×LD$_{50}$ of H1N1 A/California/04/09 and antibody administration at 1.5 mg/kg on day +1 after infection.

Figure 22:
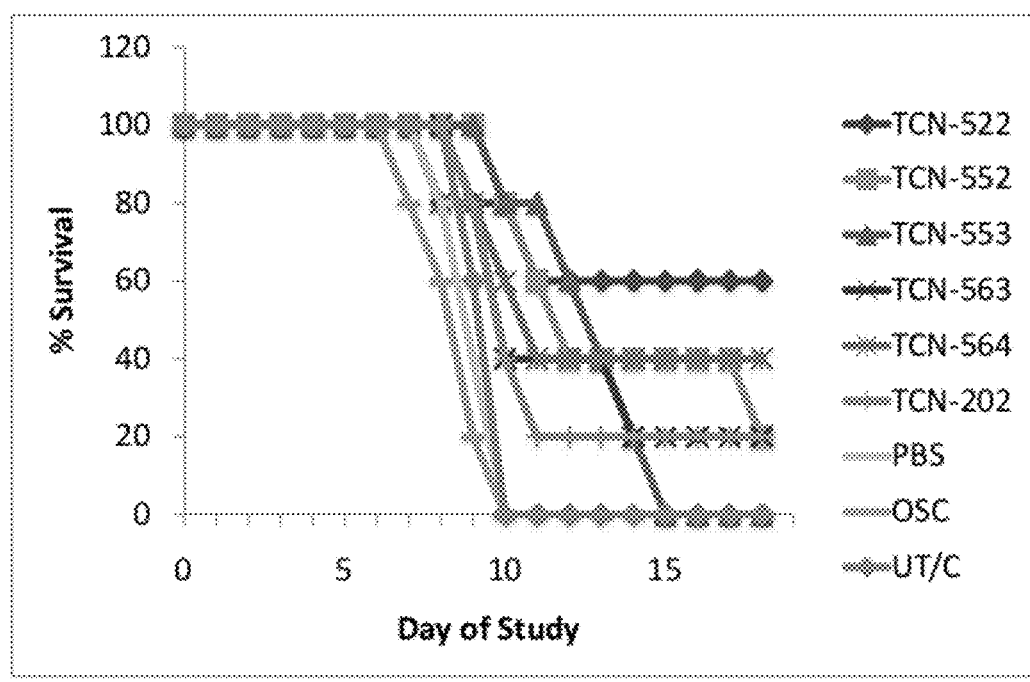

FIG. 22 is a graph depicting the percent weight loss of mice infected with 25×LD$_{50}$ of H1N1 A/California/04/09 and antibody administration at 1.5 mg/kg on day +3 after infection.

Figure 23:
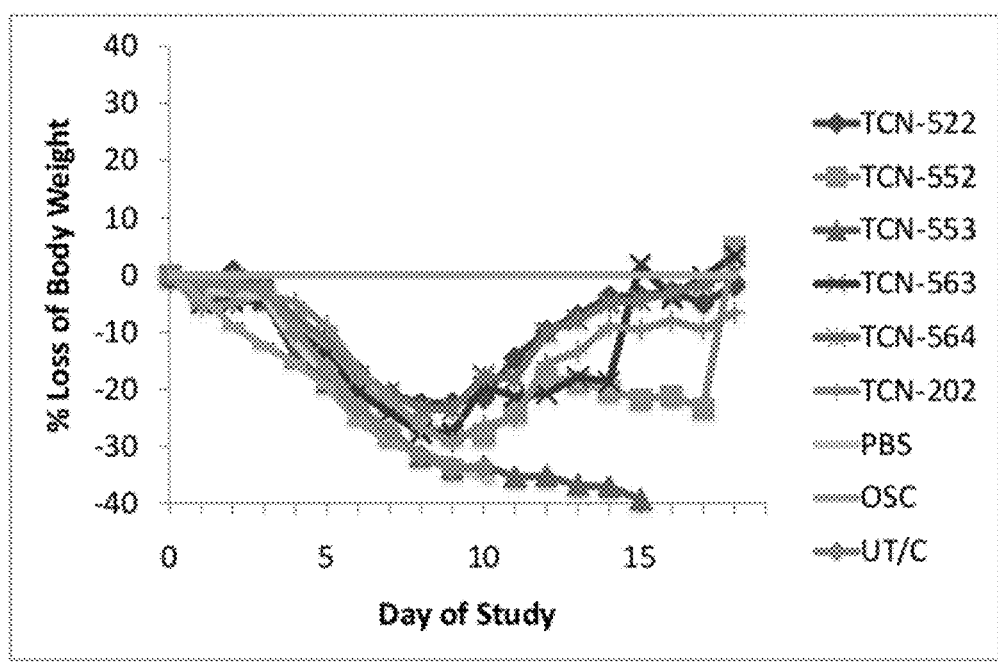

FIG. 23 is a graph depicting the survival of mice infected with 25×LD$_{50}$ of H1N1 A/California/04/09 and antibody administration at 1.5 mg/kg on day +3 after infection.

Figure 24:
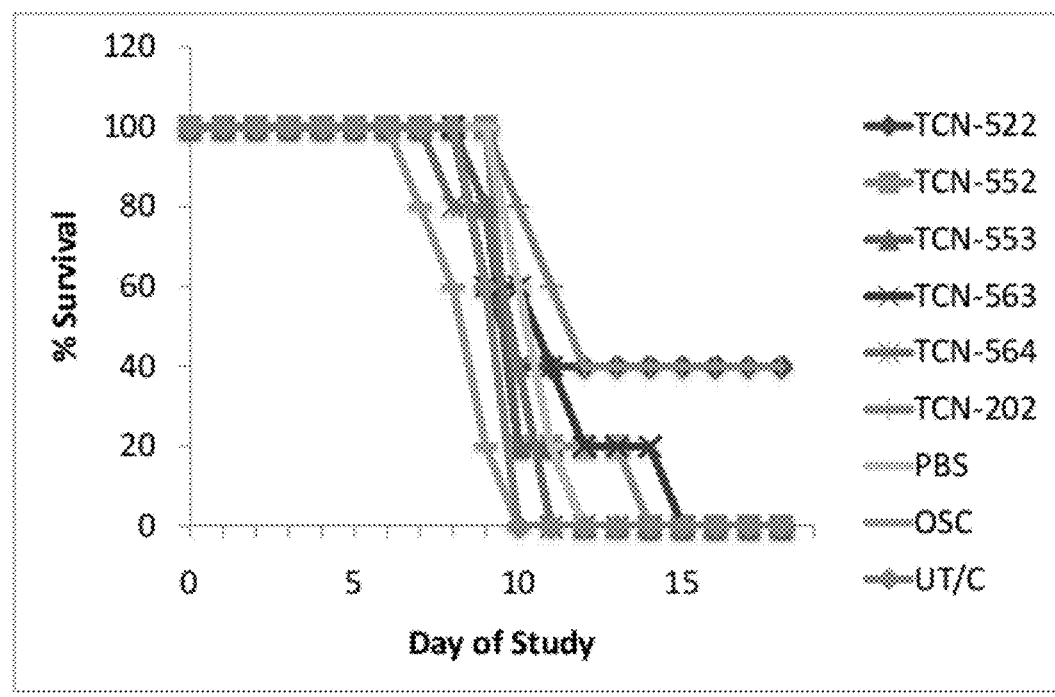

FIG. 24 is a graph depicting the survival of mice infected with 25×LD$_{50}$ of H1N1 A/California/04/09 and antibody administration at 1.5 mg/kg on day +5 after infection.

Figure 25:
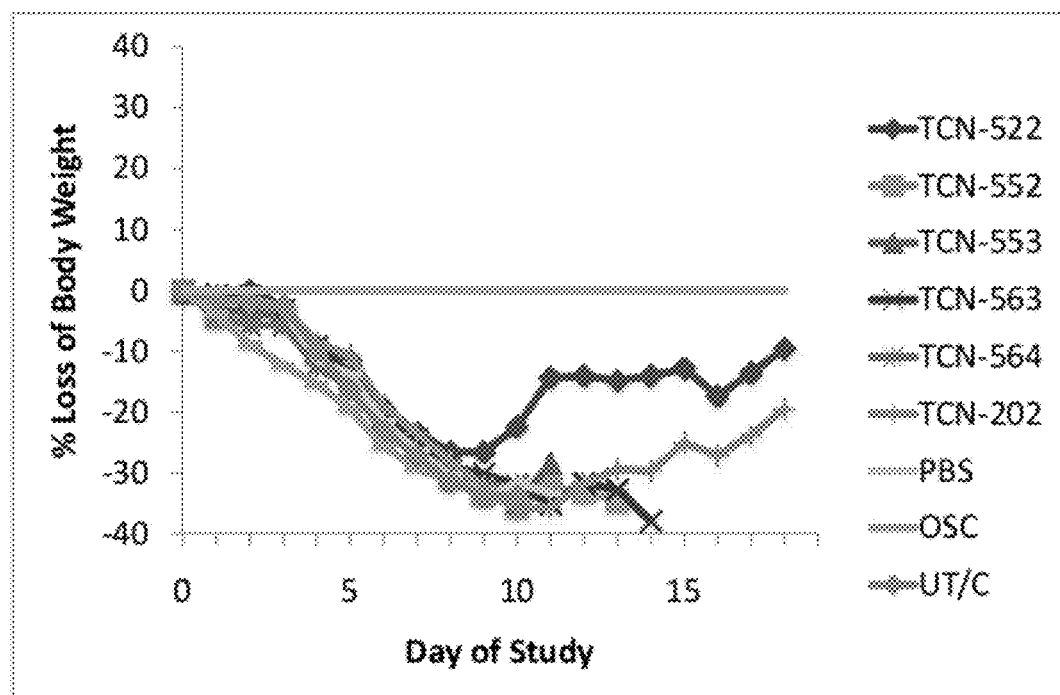

FIG. 25 is a graph depicting the percent weight loss of mice infected with 25×LD$_{50}$ of H1N1 A/California/04/09 and antibody administration at 1.5 mg/kg on day +5 after infection.

Figure 26:
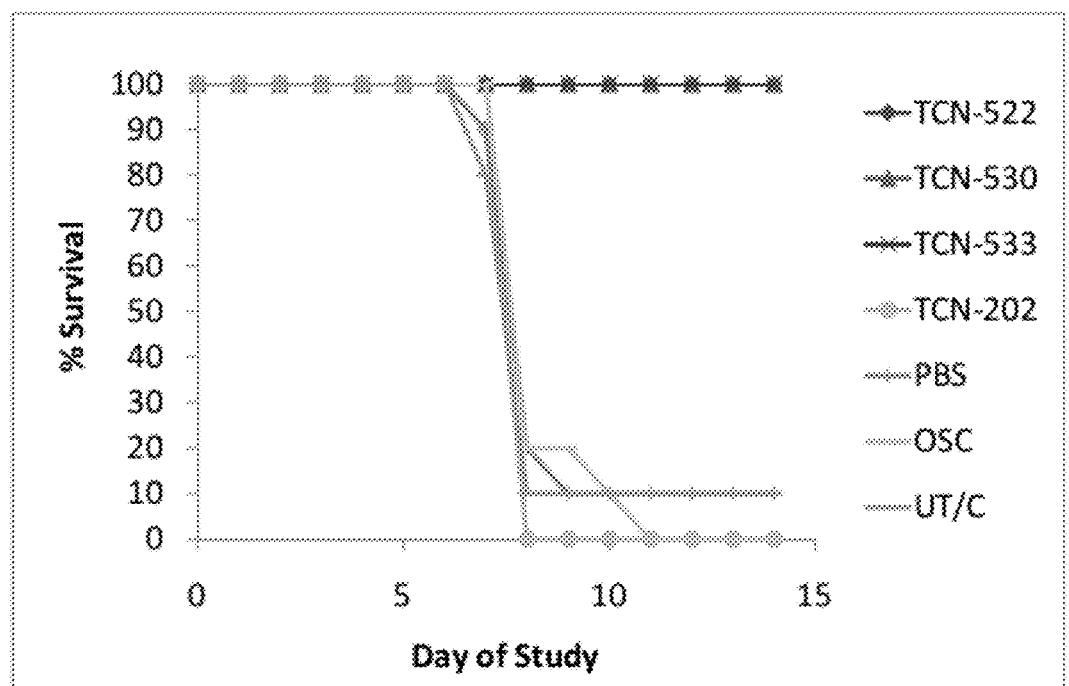

FIG. 26 is a graph depicting the survival of mice infected with 25×LD$_{50}$ of H5N1 A/Hong Kong/156/1997 and antibody administration at 15 mg/kg on day +1 after infection.

Figure 27:
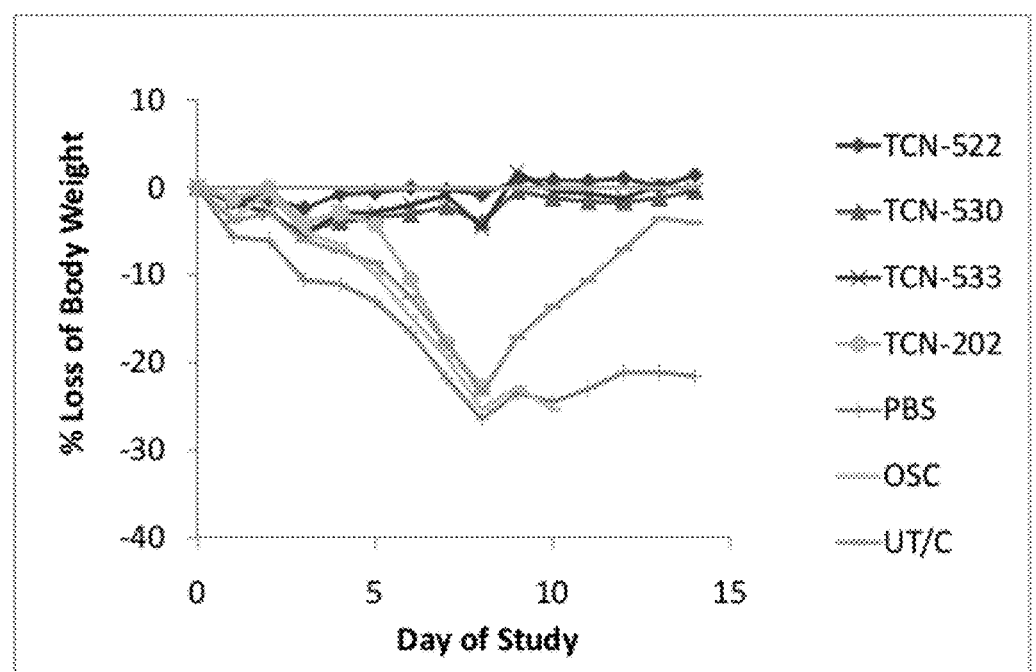

FIG. 27 is a graph depicting the percent weight loss of mice infected with 25×LD$_{50}$ of H5N1 A/Hong Kong/156/1997 and antibody administration at 15 mg/kg on day +1 after infection.

Figure 28:
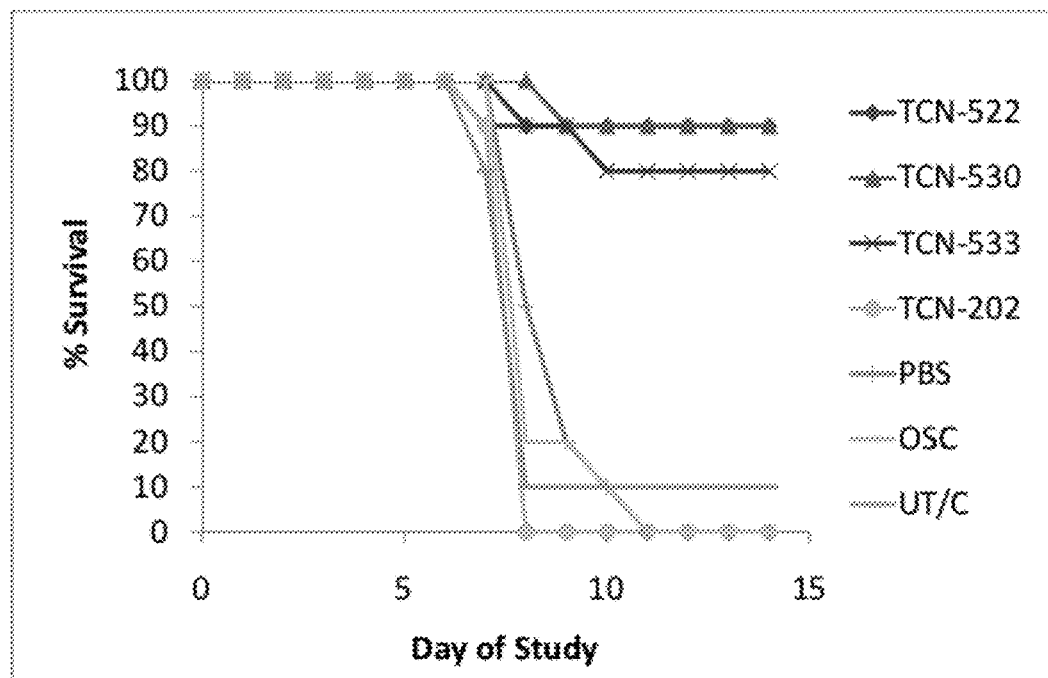

FIG. 28 is a graph depicting the survival of mice infected with 25×LD$_{50}$ of H5N1 A/Hong Kong/156/1997 and antibody administration at 15 mg/kg on day +3 after infection.

Figure 29:
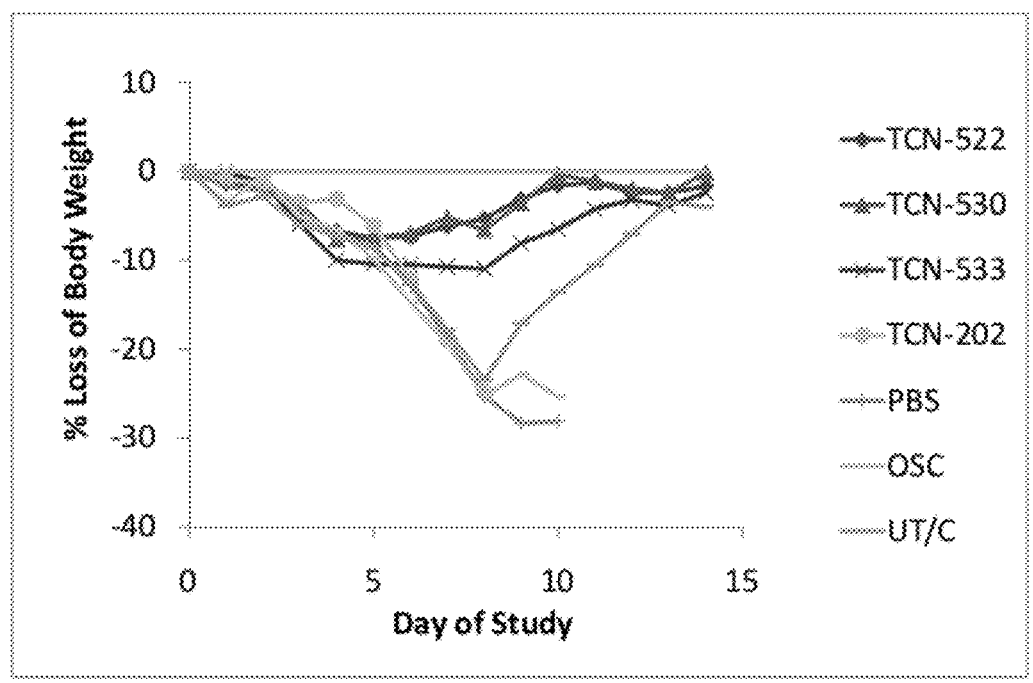

FIG. 29 is a graph depicting the percent weight loss of mice infected with 25×LD$_{50}$ of H5N1 A/Hong Kong/156/1997 and antibody administration at 15 mg/kg on day +3 after infection.

Figure 30:
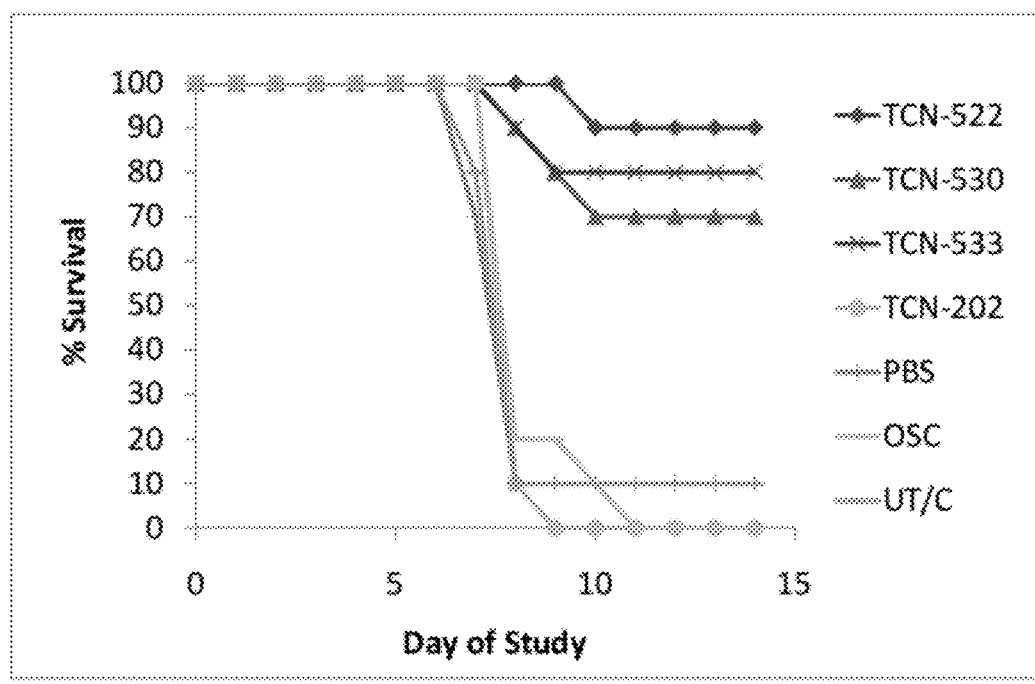

FIG. 30 is a graph depicting the survival of mice infected with 25×LD of H5N1 A/Hong Kong/156/1997 and antibody administration at 15 mg/kg on day +4 (four days) after infection.

Figure 31:
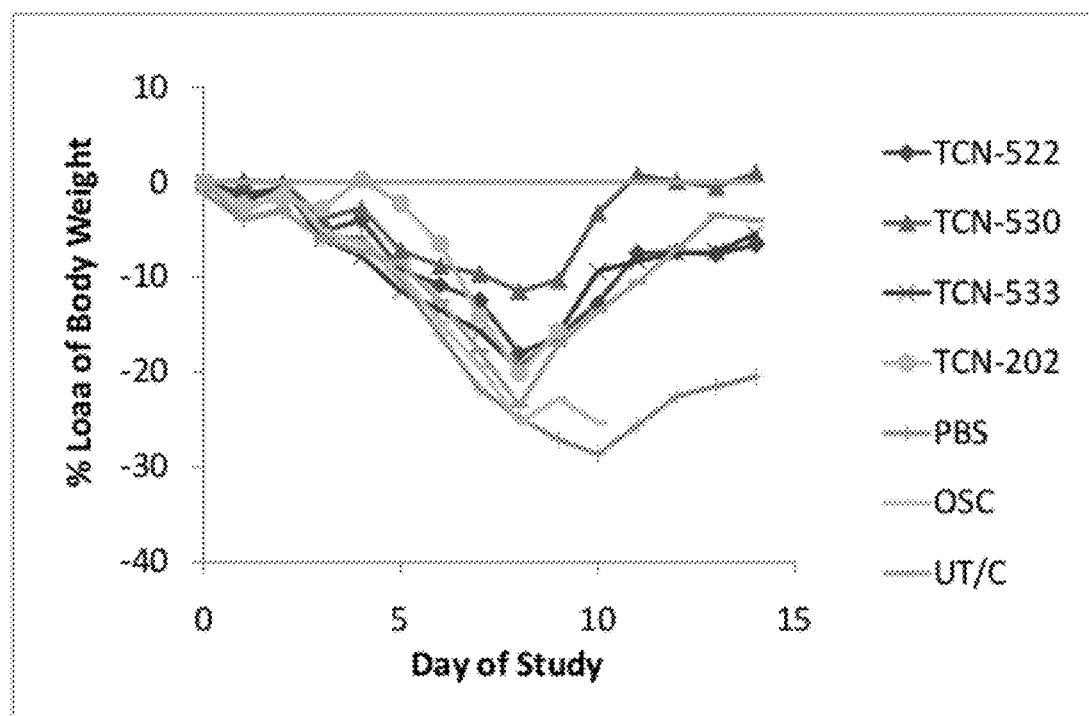

FIG. 31 is a graph depicting the percent weight loss of mice infected with 25×LD$_{50}$ of H5N1 A/Hong Kong/156/1997 and antibody administration at 15 mg/kg on day +4 after infection.

Figure 32:
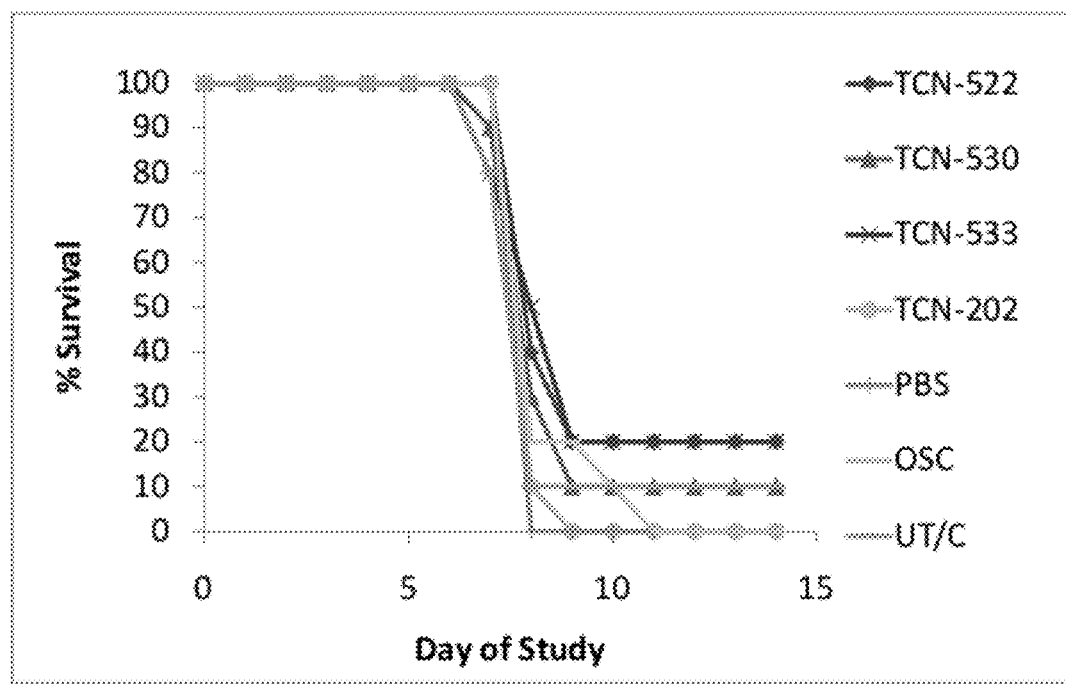

FIG. 32 is a graph depicting the survival of mice infected with 25×LD$_{50}$ of H5N1 A/Hong Kong/156/1997 and antibody administration at 15 mg/kg on day +5 after infection.

Figure 33:
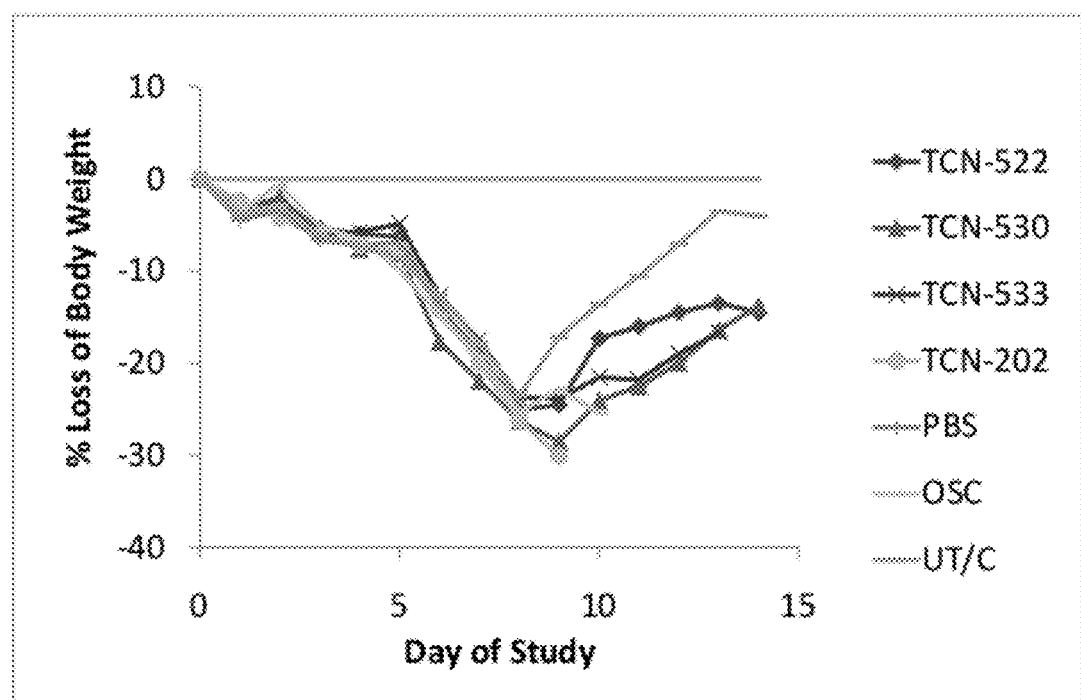

FIG. 33 is a graph depicting the percent weight loss of mice infected with 25×LD50 of H5N1 A/Hong Kong/156/1997 and antibody administration at 15 mg/kg on day +5 after infection.

Figure 34:
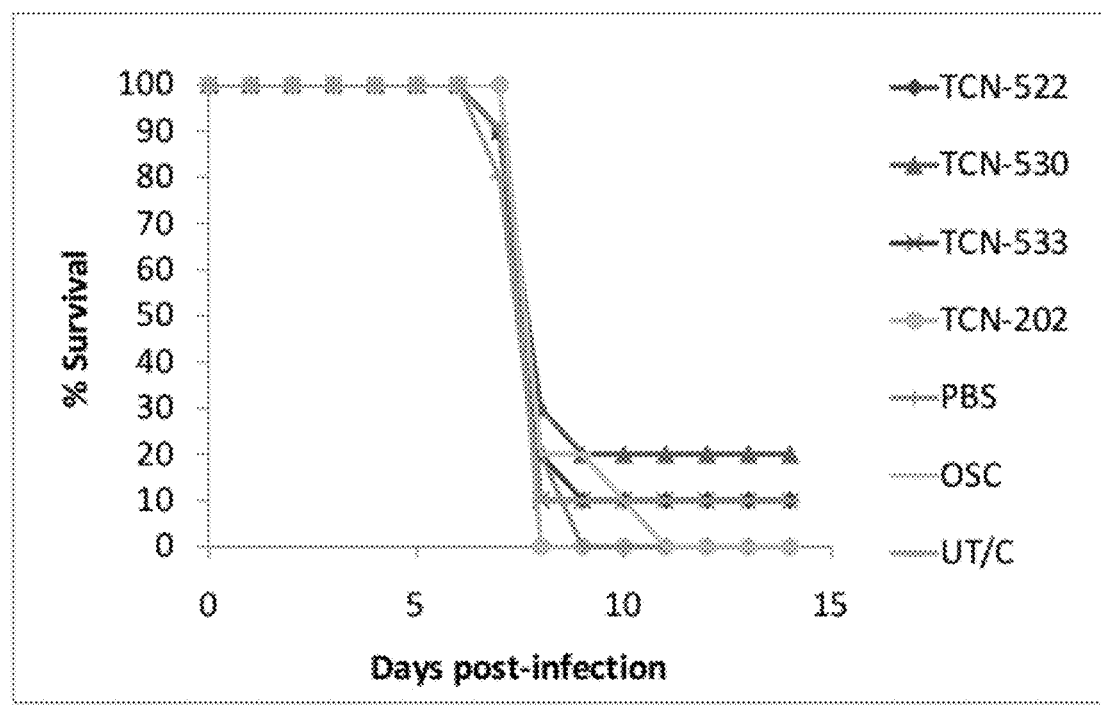

FIG. 34 is a graph depicting the percent weight loss of mice infected with 25×LD$_{50}$ of H5N1 A/Hong Kong/156/1997 and antibody administration at 15 mg/kg on day +6 (six days) after infection.

Figure 35:
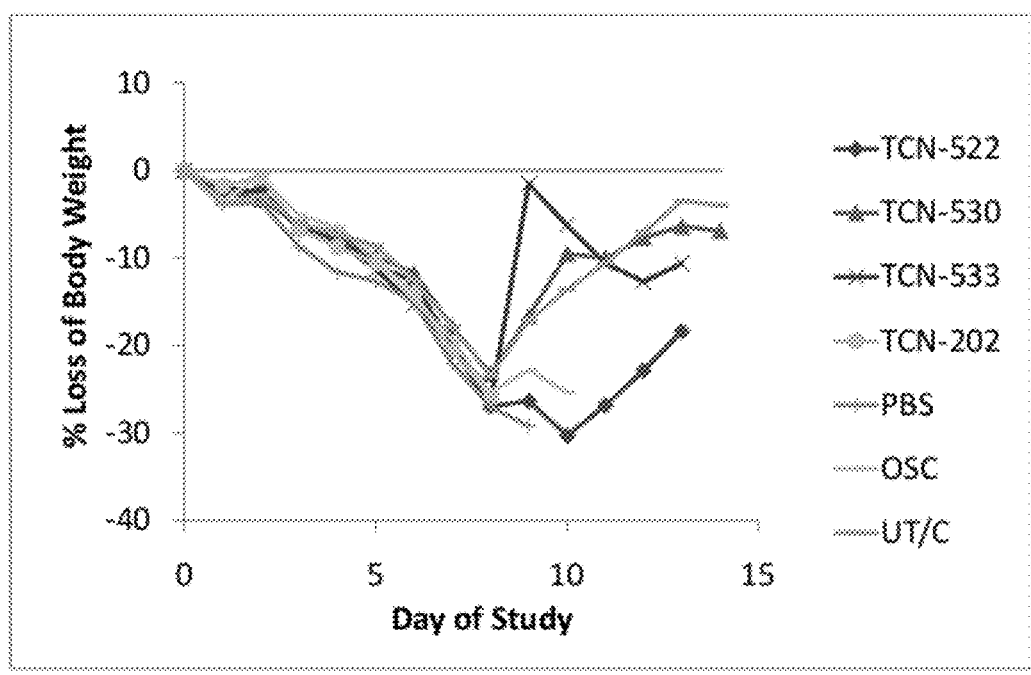

FIG. 35 is a graph depicting the survival of mice infected with 25×LD$_{50}$ of H5N1 A/Hong Kong/156/1997 and antibody administration at 15 mg/kg on day +6 after infection.

FIG. 36 is a schematic diagram of an exemplary plate depicting the experimental design of a viral microneutralization (VMN) assay.

DETAILED DESCRIPTION

The present invention provides fully human monoclonal antibodies that bind influenza virus and neutralize infection. In certain embodiments, the present invention provides fully human monoclonal neutralizing antibodies specific against the Influenza hemagglutinin protein. The antibodies are respectively referred to herein is human monoclonal anti-HA (huMHA) antibodies.

The Influenza hemagglutinin (HA) protein is a homotrimeric integral membrane glycoprotein found on the surface of the Influenza virus. To mimic the native conformation of this homotrimeric protein, the methods of the invention provide an isolated HA protein precursor that is operably-linked to a trimerization or foldon domain from the phage T4 fibritin protein (SGR*LVPRGS*PGSGYIPEAPRDGQAYVRKDGEWVLLSTFL GKPIPNPLLGLDSTG HHHHHH (SEQ ID NO: 1)).

The resultant recombinant homotrimeric foldon HA protein not only retains the native Influenza hemagglutinin homotrimeric conformation, but also becomes soluble, i.e. the protein is no longer bound to a viral or cellular membrane. Specifically, these recombinant HA homotrimeric proteins lack an integral membrane or transmembrane domain. In certain embodiments, these recombinant HA homotrimeric proteins include HA1 and HA2 subunits as well as a trimerization domain, the resultant recombinant HA homotrimeric protein containing between 1-50, 50-100, 100-150, 150-200, 200-250, 250-300, 300-350, 350-400, 400-450, 450-500, 500-550, 550-600 amino acids (aa) or any length of amino acids in between. Preferably, these recombinant HA homotrimeric proteins contain between 520-540 amino acids (aa), and preferably, about 530 amino acids. Recombinant HA homotrimeric proteins further include a signal cleavage site at the N-terminus containing between 15-25 aa. Alternatively, or in addition, recombinant HA homotrimeric proteins further include a transmembrane domain positioned between amino acids 525-535 of HA depending on the influenza A virus subtype. In a preferred embodiment, the HA protein is derived from one or more strains of an Influenza A virus. Recombinant HA homotrimeric proteins of the invention retain the native signal sequence to enable secretion from mammalian cells. Moreover, recombinant HA homotrimeric proteins of the invention contain a same signal sequence, which is not derived from HA. Furthermore, signal sequences used with recombinant HA homotrimeric proteins of the invention include those signal sequences known in the art that allow efficient secretion of proteins, such as the signal sequence of the immunoglobulin light kappa chain. Alternatively, recombinant HA homotrimeric proteins, or the HA0 precursors thereof, may have the native signal sequences in the expression constructs used by Immune Technology Corp. (http://www.immune-tech.com/). Signal sequences are retained or manipulated to allow efficient secretion from, for instance, art-recognized cell lines maintained in vitro, e.g. 293 HEK cells.

Recombinant HA homotrimeric proteins may retain a native HA1/HA2 protease cleavage site, which is critical for viral pathogenicity. In one aspect of the invention, recombinant HA homotrimeric proteins contain a substituted HA1/HA2 protease cleavage site. For example, the recombinant HA protein encoded by SEQ ID NO: 12 does not have a native cleavage site, but rather a cleavage site substituted from another HA protein. Furthermore, these proteins optionally retain sialic acid-containing receptor binding sites within the HA1 subunit.

According to the methods of the invention, human antibodies obtained from blood, serum, plasma, or cerebral spinal fluid, are contacted to recombinant and soluble HA homotrimers of the invention in vitro, wherein the recombinant and soluble HA homotrimers act as targets for human antibody binding to confirm specificity of the isolated human antibody for an Influenza HA homotrimer in its native conformation. In general, the methods include obtaining serum or plasma samples from subjects or patients that have been infected with or vaccinated against an infectious agent. These serum or plasma samples are then screened to identify those that contain antibodies specific for a particular polypeptide associated with the infectious agent, such as, e.g. a polypeptide specifically expressed on the surface of cells infected with the infectious agent, but not uninfected cells. In particular embodiments, the serum or plasma samples are screened by contacting the samples with a cell that has been transfected with an expression vector that expresses the polypeptide expressed on the surface of infected cells. In particular embodiments the serum or plasma samples are screened by contacting the samples with a recombinant protein which represents a particular protein of the infectious agent such as, e.g. hemagglutinin of the influenza A virus. In particular embodiments the serum or plasma samples are screened by contacting the samples with a purified form of the infectious agent such as, e.g. intact whole virions of the influenza A virus. In particular embodiments, the serum or plasma samples are screened by contacting the samples with a live form of the infectious agent such as, e.g. intact whole virions of the influenza A virus to determine the presence of serum antibodies that inhibit or neutralize infection of susceptible cells. Exemplary susceptible cells are eukaryotic or mammalian cells, such as MDCK cells.

Once a subject or patient is identified as having serum or plasma containing an antibody specific for the infectious agent polypeptide or virus of interest, mononuclear and/or B cells obtained from the same subject or patient are used to identify a cell or clone thereof that produces the antibody, using any of the methods described herein or available in the art. Once a B cell that produces the antibody is identified, cDNAs encoding the variable regions or fragments thereof of the antibody may be cloned using standard RT-PCR vectors and primers specific for conserved antibody sequences, and subcloned into expression vectors used for the recombinant production of monoclonal antibodies specific for the infectious agent polypeptide of interest.

More specifically, B cells are collected from a particular donor, i.e. a subject or patient is identified as having serum or plasma containing an antibody specific for HA, cultured, and antibody is secreted from these B cells into the culture medium. The culture medium is separated from these B cells, the B cells are lysed, and then frozen for storage. The culture medium is then screened for antibody binding to various HA targets and/or inhibition/neutralization of infection in vitro. When a culture well is identified as having an antibody of the desired specificity, reverse-transcriptase polymerase chain reaction (RT-PCR) is applied to the B-cell lysate to amplify the antibody variable regions and subsequently clone, express, and test for binding and function of the recombinant antibody.

Human antibodies, such as the MAbs listed in Table 3, which bind the recombinant and soluble HA homotrimer and/or bind whole virions, and optionally inhibit or neutralize infection of live virus are recombinantly reproduced and formulated into a pharmaceutical composition for administration to a subject at risk of contacting an Influenza virus. Furthermore, recombinant and soluble HA homotrimers are derived from multiple strains of Influenza viruses, including multiple strains of influenza A virus. Exemplary human antibodies specifically bind Influenza A, and may be selected for an inability to bind influenza B and C virus strains.

The invention further provides a novel process whereby full-length HA is expressed in mammalian cell lines, which allows for the identification of human antibodies that bind this cell-expressed HA. The huMHA antibodies have been shown to bind conformational determinants on the HA-transfected cells, as well as native HA, which can be isolated, or contacted to huMHA antibodies when presented either on Influenza infected cells or on Influenza A virus. Alternatively, or in addition, huMHA antibodies bind native HA, recombinant homotrimeric HA, purified virus, infected cells, linear peptide, synthetic HA peptide, HA transfected mammalian cells, and HA expressed on the surface of genetically altered bacteriophage virus, which are used for gene fragment display assays. Thus, this invention has allowed for the identification and production of human monoclonal antibodies that exhibit novel specificity for a very broad range of Influenza A virus strains. These antibodies may be used prophylactically to prevent Influenza A infection, diagnostically to identify Influenza A infection and therapeutically to treat Influenza A infection. Moreover, the epitopes to which huMHA antibodies of the invention bind are used as vaccines to prevent influenza A infection.

The huMHA antibodies of the invention has one or more of the following characteristics: a) binds to an epitope in an HA1 subunit of an Influenza hemagglutinin (HA) protein; b) binds to an epitope in the HA2 subunit of Influenza hemagglutinin (HA) protein; c) binds to an epitope in the extracellular domain of an Influenza hemagglutinin (HA) protein, consisting of an HA1 subunit and an HA2 subunit; d) binds to an epitope of a recombinant homotrimeric Influenza HA0 protein; e) binds to an epitope of an Influenza HA protein expressed on an infected cell; f) binds to an epitope of an Influenza HA protein expressed on a modified cell; g) binds to an Influenza virus; or h) inhibits virus infection of susceptible eukaryotic cells. The huMHA antibodies of the invention eliminate Influenza infected cells through immune effector mechanisms such as ADCC and/or CDC and promote direct viral clearance by binding to Influenza virions.

Exemplary Influenza A strains used for screening human plasma samples, B Cell Culture supernatants (BCC SN), and monoclonal transfection supernatants (MN are shown in Table 1 below). Live strains were used for the neutralization assays described herein. Inactivated strains were used for the virus binding assays described herein. Recombinant homotrimeric HA protein was used in the trimeric HA binding assay.

TABLE 1

| Virus | Subtype | Neutralization | Virus binding | Trimeric HA binding |
|---|---|---|---|---|
| A/California/4/09 | H1 | | | + |
| A/Solomon Islands/3/06 | H1 | + | + | + |
| A/South Carolina/1/18 | H1 | | | + |
| A/Japan/305/57 | H2 | | + | + |
| A/Wisconsin/67/05 | H3 | + | + | + |
| A/swine/Ontario/01911-2/99 | H4 | | | + |
| A/Vietnam/1203/04 | H5 | | | + |

TABLE 1-continued

| Virus | Subtype | Neutralization | Virus binding | Trimeric HA binding |
|---|---|---|---|---|
| A/Indonesia/5/05 | H5 | | | + |
| A/Egypt/3300-NAMRU3/08 | H5 | | | + |
| A/common magpie/Hong Kong/5052/07 | H5 | | | + |
| A/Anhui/1/05 | H5 | | | + |
| A/chicken/Vietnam/NCVD-016/08 | H5 | | | + |
| A/Hong Kong/156/97 | H5 | | | + |
| A/northern shoveler/California/HKWF115/07 | H6 | | | + |
| A/Netherlands/219/03 | H7 | | | + |
| A/duck/Yangzhou/02/05 | H8 | | | + |
| A/Hong Kong/2108/03 | H9 | | | + |
| A/Hong Kong/1073/99 | H9 | | | + |

Exemplary HA sequences include those sequences listed on Table 2 below.

TABLE 2

| Type | GenBank Accession No. | Subtype | HA Sequence from Strain | SEQ ID NO: |
|---|---|---|---|---|
| A | ACP41105 | H1 | A/California/04/2009(H1N1) | SEQ ID NO: 2 |
| A | ABU99109 | H1 | A/Solomon Islands/3/2006(H1N1) | SEQ ID NO: 3 |
| A | AF117241 | H1 | A/South Carolina/1/18 (H1N1) | SEQ ID NO: 4 |
| A | AAA43185 | H2 | A/Japan/305/1957(H2N2) | SEQ ID NO: 5 |
| A | ACF54576 | H3 | A/Wisconsin/67/2005(H3N2) | SEQ ID NO: 6 |
| A | AAG17427 | H4 | A/Swine/Ontario/01911-2/99 (H4N6) | SEQ ID NO: 7 |
| A | AF028709 | H5 | A/Hong Kong/156/97 (H5N1) | SEQ ID NO: 8 |
| A | AAT73274 | H5 | A/VietNam/1203/2004(H5N1) | SEQ ID NO: 9 |
| A | ABW06108 | H5 | A/Indonesia/5/2005(H5N1) | SEQ ID NO: 10 |
| A | ACI06185 | H5 | A/Egypt/3300-NAMRU3/2008(H5N1) | SEQ ID NO: 11 |
| A | ACJ26242 | H5 | A/common magpie/Hong Kong/5052/2007(H5N1) | SEQ ID NO: 12 |
| A | ABD28180 | H5 | A/Anhui/1/2005(H5N1) | SEQ ID NO: 13 |
| A | ACO07033 | H5 | A/chicken/Vietnam/NCVD-016/2008(H5N1) | SEQ ID NO: 14 |
| A | ACE81692 | H6 | A/northern shoveler/California/HKWF115/2007(H6N1) | SEQ ID NO: 15 |
| A | AAR02640 | H7 | A/Netherlands/219/03(H7N7) | SEQ ID NO: 16 |
| A | ABK32094 | H8 | A/duck/Yangzhou/02/2005(H8N4) | SEQ ID NO: 17 |
| A | ABB58945 | H15 | A/HK/2108/2003(H9N2) | SEQ ID NO: 18 |
| A | NC_004908 | H9 | A/Hong Kong/1073/99 (H9N2) | SEQ ID NO: 19 |

In one embodiment, the huMHA antibodies of the invention bind to an HA that wholly or partially includes the amino acid residues from position 1 to position 525 of Influenza hemagglutinin when numbered in accordance with SEQ ID NO: 2-19. In other embodiments, the huMHA antibodies of the invention bind to an HA that wholly or partially includes the amino acid residues from position 1 to position 566 of Influenza hemagglutinin H3, wherein the full-length protein includes amino acids 1-566, the signal peptide includes amino acids 1-16, the HA1 subunit includes amino acids 17-345 and the HA2 subunit includes amino acids 346-566 (Wiley D C, Wilson I A, Skehel J J. Nature. 1981 Jan. 29; 289(5796):373-8). Alternatively, the huMHA antibodies of the invention bind to an HA that wholly or partially includes the amino acid residues from position 1 to position 566 of Influenza hemagglutinin H1, wherein the full-length protein includes amino acids 1-566, the signal peptide includes amino acids 1-17, the HA1 subunit includes amino acids 18-344 and the HA2 subunit includes amino acids 345-566 (Caton A J, Brownlee G G, Yewdell J W, Gerhard W. Cell. 1982 December; 31(2 Pt 1):417-27).

Alternatively, the monoclonal antibody is an antibody that binds to the same epitope as the mAbs listed in Table 3.

TABLE 3

| BCC Well ID | Theraclone ID |
|---|---|
| 3251_K17 | TCN-504 |
| 3280_D18 | TCN-521 |
| 3212_I12 | TCN-522 |
| 5248_A17 | TCN-523 |
| 5084_C17 | TCN-526 |
| 5086_C06 | TCN-527 |
| 5087_P17 | TCN-528 |
| 5297_H01 | TCN-529 |
| 5248_H10a | TCN-530 |
| 5091_H13 | TCN-531 |
| 5262_H18 | TCN-532 |
| 5256_A17a | TCN-533 |
| 5249_B02 | TCN-534 |
| 5246_P19 | TCN-535 |
| 5095_N01 | TCN-536 |
| 3194_D21 | TCN-537 |
| 3206_O17 | TCN-538 |
| 5056_A08 | TCN-539 |
| 5060_F05 | TCN-540 |

TABLE 3-continued

| BCC Well ID | Theraclone ID |
|---|---|
| 5062_M11 | TCN-541 |
| 5079_A16 | TCN-542 |
| 5081_G23 | TCN-543 |
| 5082_A19 | TCN-544 |
| 5082_I15 | TCN-545 |
| 5089_L08 | TCN-546 |
| 5092_P04 | TCN-549 |
| 5096_F06 | TCN-550 |
| 5243_D01 | TCN-551 |
| 5249_I23 | TCN-552 |
| 5261_C18 | TCN-553 |
| 5277_M05 | TCN-554 |
| 5246_L16 | TCN-555 |
| 5089_K12 | TCN-556 |
| 5081_A04 | TCN-557 |
| 5248_H10 | TCN-558 |
| 5097_G08 | TCN-559 |
| 5084_P10 | TCN-560 |
| 5237_B21b | TCN-563 |
| 5256_A17b | TCN-564 |

The antibodies of the invention are able to bind, and optionally, neutralize Influenza A. Monoclonal antibodies can be produced by known procedures, e.g., as described by R. Kennet et al. in "Monoclonal Antibodies and Functional Cell Lines; Progress and Applications". Plenum Press (New York), 1984. Further materials and methods applied are based on known procedures, e.g., such as described in J. Virol. 67:6642-6647, 1993.

Isolated anti-HA monoclonal antibodies of the invention can be used as diagnostic, prophylactic, and/or therapeutic agents upon appropriate formulation.

A "neutralizing antibody" is one that can neutralize the ability of that pathogen to initiate and/or perpetuate an infection in a host and/or in target cells in vitro. The invention provides a neutralizing monoclonal human antibody, wherein the antibody recognizes an antigen from an Influenza virus, which is preferably derived from the HA protein.

Preferably an antibody according to the invention is a novel monoclonal antibody referred to herein as TCN-522 (corresponding to BCC plate and well location 3212_I12), TCN-521 (3280_D18), TCN-523 (5248_A17), TCN-563 (5237_B21), TCN-526 (5084_C17), TCN-527 (5086_C06), TCN-528 (5087_P17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_O17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-564 (5256_A17b), and TCN-504 (3251_K17). These antibodies were initially isolated from human samples and are produced by the B cell cultures referred to as 3212_I12, 3280_D18, 5248_A17, 5237_B21, 5084_C17, 5086_C06, 5087_P17, 5297_H01, 5248_H10a, 5091_H13, 5262_H18, 5256_A17a, 5249_B02, 5246_P19, 5095_N01, 3194_D21, 3206_O17, 5056_A08, 5060_F05, 5062_M11, 5079_A16, 5081_G23, 5082_A19, 5082_I15, 5089_L08, 5092_F11, 5092_P01, 5092_P04, 5096_F06, 5243_D01, 5249_I23, 5261_C18, 5277_M05, 5246_L16, 5089_K12, 5081_A04, 5248_H10b, 5097_G08, 5084_P10, 5256_A17b, and 3251_K17. These antibodies have broad neutralizing activity or broad binding activity for Influenza A in vitro.

Antibodies of the invention with broad neutralizing activity include TCN-522 (corresponding to BCC plate and well location 3212_I12), TCN-521 (3280_D18), TCN-523 (5248_A17), TCN-563 (5237_B21), TCN-526 (5084_C17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_I17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-564 (5256_A17b), and TCN-504 (3251_K17).

The CDRs of the antibody heavy chains are referred to as CDRH1, CDRH2 and CDRH3, respectively. Similarly, the CDRs of the antibody light chains are referred to as CDRL1, CDRL2 and CDRL3, respectively. The position of the CDR amino acids is defined according to the IMGT numbering system as: CDR1—IMGT positions 27 to 38, CDR2—IMGT positions 56 to 65 and CDR3—IMGT positions 105 to 117. (Lefranc, M P. et al. 2003 IMGT unique numbering for immunoglobulin and T cell receptor variable regions and Ig superfamily V-like domains. Dev Comp Immunol. 27(1):55-77; Lefranc, M P. 1997. Unique database numbering system for immunogenetic analysis. Immunology Today, 18:509; Lefranc, M P. 1999. The IMGT unique numbering for Immunoglobulins, T cell receptors and Ig-like domains. The Immunologist, 7:132-136.)

The sequences of the antibodies were determined, including the sequences of the variable regions of the Gamma heavy and Kappa or Lambda light chains of the antibodies designated. In addition, the sequence of each of the polynucleotides and polypeptides encoding the antibody sequences was determined for TCN-522 (3212_I12), TCN-521 (3280_D18), TCN-523 (5248_A17), TCN-563 (5237_B21), TCN-526 (5084_C17), TCN-527 (5086_C06), TCN-528 (5087_P17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_O17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-564 (5256_A17b), and TCN-504 (3251_K17).

Shown below are the polypeptide and polynucleotide sequences of the variable regions of the heavy and light chains.

TCN-504 (3251_K17) heavy chain variable region nucleotide sequence:

(SEQ ID NO: 509)
```
CAGGTGCAACTGCAGGAGTCGGGCCCAGGACTGGTGAAGCCCTCGGAGACCCTGTCCCTCACTTGCGCTGTCTCTGG

TGTCTCCATCAGCAATATTGATTTCTACTGGGGCTGGATCCGCCAGCCCCCAGGGAAGGGGCTAGAATGGATTGGCA

ATATCTATTATACGGGGATCACCTTCTACAACCCGTCCCTCAGCAGTCGAGTCGCCATATCCATTGACACCTCCAAG

AACCAGTTCTCCCTGACTCTGACTTCTGTGACCGCCGCAGACACGGCTATGTATTACTGTGCGAGACATTACGGTGA

CTCCGAGGCAATAAACGATGCCTTTGACATCTGGGGCCAAGGGACAATGCTCACCGTCTCGAGC
```

TCN-504 (3251_K17) gamma heavy chain variable region amino acid sequence: (Kabat CDRs in bold, Chothia CDRs underlined)

(SEQ ID NO: 510)
QVQLQESGPGLVKPSETLSLTCAVS<u>GVSISN</u>NIDFYWGWIRQPPGKGLEWI
GNIYYTGITFYNPSLSSRVAISIDTSKNQFSLTLTSVTAADTAMYYCARH
YGDSEAINDAFDIWGQGTMLTVSS

TCN-504 (3251_K17) gamma heavy chain Kabat CDRs:

```
CDR 1: NIDFYWG            (SEQ ID NO: 511)
CDR 2: NIYYTGITFYNPSLSS   (SEQ ID NO: 512)
CDR 3: HYGDSEAINDAFDI     (SEQ ID NO: 513)
```

TCN-504 (3251_K17) gamma heavy chain Chothia CDRs

```
CDR 1: GVSISN             (SEQ ID NO: 514)
CDR 2: NIYYTGITF          (SEQ ID NO: 515)
CDR 3: HYGDSEAINDAFDI     (SEQ ID NO: 513)
```

TCN-504 (3251_K17) light chain variable region nucleotide sequence:

(SEQ ID NO: 516)
GAGATAGTGATGACGCAGTCTCCAGCCACCCTGTCTGTGTCTCCAGGGGA
AAGAGCCACCCTCTCCTGCAGGGCCAGTCAGAGTGTTGGCAATAGTTTAG
CCTGGTACCAGCAGAGACCTGGCCAGGCTCCCAGGCTCCTCATCTACGGT
GCATCCACCAGGGCCACTGGTATCCCACCCAGGTTCAGTGGCAGTGGGTC
TGGGACAGAATTCACTCTCACCATCAGCAGCCTGCAGACTGAAGATTTTG
CAGTTTATTACTGTCAACAATATATTAACTGGCGTCCGCTCAGTTTTGGC
GGAGGGACCAAGGTGGAGATCAAA

TCN-504 (3251_K17) light chain variable region amino acid sequence (Kabat CDRs in bold, Chothia CDRs underlined)

(SEQ ID NO: 524)
EIVMTQSPATLSVSPGERATLSCRAS<u>QSVGNSLA</u>WYQQRPGQAPRLLIYG
<u>ASTRAT</u>GIPPRFSGSGSGTEFTLTISSLQTEDFAVYYCQQYINWRPLSFG
GGTKVEIK

TCN-504 (3251_K17) light chain Kabat CDRs:

```
CDR 1: RASQSVGNSLA        (SEQ ID NO: 517)
CDR 2: GASTRAT             (SEQ ID NO: 181)
CDR 3: QQYINWRPLS         (SEQ ID NO: 518)
```

TCN-504 (3251_K17) light chain Chothia CDRs:

```
CDR 1: RASQSVGNSLA        (SEQ ID NO: 517)
CDR 2: GASTRAT             (SEQ ID NO: 181)
CDR 3: QQYINWRPLS         (SEQ ID NO: 518)
```

TCN-521 (3280_D18) heavy chain variable region nucleotide sequence:

(SEQ ID NO: 20)
GAAGTGCAGTTGGTGCAGTCTGGAGGAGGCTTGGTCCAGCCTGGGGGGTC
CCTGAGACTCGCCTGTGTAGTCTCTGGGTTCACCGTCACCAGCAATTATA
TAACTTGGGTCCGCCAGGCTCCAGGGAAGGGGCTGGAGTGGGTCTCAGTT
ATTTATAGTCATGGTCGCGCATATTATTCAGCCTCCGTGAATGGCCGATT
CACCATCTCCAGACACACTTCCAAGAACACAGTTTATCTTGAAATGAACA
GCCTGAGACCTGAGGACACGGCCGTCTATTACTGTGCGGGCGGGGGCCTA
GTCGGTGGCTACGACGAATATTTCTTTGACTATGGGGCCAGGGAACCCT
GGCCACCGTCTCCTCA

TCN-521 (3280_D18) gamma heavy chain variable region amino acid sequence: (Kabat CDRs in bold, Chothia CDRs underlined)

(SEQ ID NO: 21)
EVQLVQSGGGLVQPGGSLRLACVVSG<u>FTVTS</u>NYITWVRQAPGKGLEWVS<u>V</u>
<u>IYSHGRAY</u>YSASVNGRFTISRHTSKNTVYLEMNSLRPEDTAVYYCAGGL
VGGYDEYFFDYWGQGTLATVSS

TCN-521 (3280_D18) gamma heavy chain Kabat CDRs:

```
CDR 1: SNYIT              (SEQ ID NO: 22)
CDR 2: VIYSHGRAYYSASVNG   (SEQ ID NO: 23)
CDR 3: GGLVGGYDEYFFDY     (SEQ ID NO: 24)
```

TCN-521 (3280_D18) gamma heavy chain Chothia CDRs:

```
CDR 1: GFTVTS             (SEQ ID NO: 25)
CDR 2: VIYSHGRAY          (SEQ ID NO: 26)
CDR 3: GGLVGGYDEYFFDY     (SEQ ID NO: 24)
```

TCN-521 (3280_D18) light chain variable region nucleotide sequence:

(SEQ ID NO: 27)
GAAACTGTCTTGACGCAATCTCCAGGCACCTTGTCTTTGACTCCAGGGGA
AAGAGCCACCCTCTCCTGCAGAGTCGGTCAGAGTGTTAGCGGCAGCCACT
TAGCCTGGTACCAACAGAAACCTGGCCAGGCTCCCAGGCTCCTCATCTAT
GGTGCATCCAGCAGGGCCACTGGCATCCCAGACAGGTTCGGTGGCAGTGT
GTCTGGGACAGACTTCACTCTCACCATCAGCAGACTGGAGCCTGAAGATT
CTGCAGTTTATTACTGTCAGCAGTATGGTGACTCACGATACACTTTTGGC
CAGGGGACCAAGCTGGAGATCAAA

TCN-521 (3280_D18) light chain variable region amino acid sequence (Kabat CDRs in bold, Chothia CDRs underlined)

(SEQ ID NO: 28)
ETVLTQSPGTLSLTPGERATLSC<u>RVGQSVSGSHLA</u>WYQQKPGQAPRLLIY
<u>GASSRAT</u>GIPDRFGGSVSGTDFTLTISRLEPEDSAVYYCQQYGDSRYTFG
QGTKLEIK

TCN-521 (3280_D18) Light chain Kabat CDRs:

```
CDR 1: RVGQSVSGSHLA      (SEQ ID NO: 29)
CDR 2: GASSRAT           (SEQ ID NO: 30)
CDR 3: QQYGDSRYT         (SEQ ID NO: 31)
```

TCN-521 (3280_D18) Light chain Chothia CDRs:

```
CDR 1: RVGQSVSGSHLA      (SEQ ID NO: 29)
CDR 2: GASSRAT           (SEQ ID NO: 30)
CDR 3: QQYGDSRYT         (SEQ ID NO: 31)
```

TCN-522 (3212_I12) heavy chain variable region nucleotide sequence:

(SEQ ID NO: 32)
CAGGTGCAGCTACAGCAGTGGGGCGCAGGACTTTTGAAACCTTCGGAGAC
CCTGTCCCTCACCTGCACTGTGTCTGGGGGGTCCCTCACTGATTACTCTT
GGAACTGGATCCGCCAGCCCCCAGGGAAGGGGCTGGAGTGGATCGGTGAC
ACCCTTCATAATGGCTACACCAACTACAACCCGTCCCTCAGGGGTCGAGT
TTCCATCTCAATAGACACGTCCAAGAACCAGGTCTCACTCAGGCTGACCT
CTGTGACCGCCGCGGACACGGCTCTTTATTACTGTGCGAGAGGCTCAGGT
GGATATGGTGGCTTCGATTATTTTGGCAAGCTCCGGACATGGGACTTCTG
GGGCCAGGGAACGCTGGTCACCGTCTCCTCA

TCN-522 (3212_I12) gamma heavy chain variable region amino acid sequence: (Kabat CDRs in bold, Chothia CDRs underlined)

(SEQ ID NO: 33)
QVQLQQWGAGLLKPSETLSLTCTVS<u>GGSLTDYSWN</u>WIRQPPGKGLEWIG<u>D</u>
<u>TLHNGYTNYNPSLRG</u>RVSISIDTSKNQVSLRLTSVTAADTALYYCAR<u>GSG</u>
<u>GYGGFDYFGKLRTWDF</u>WGQGTLVTVSS

TCN-522 (3212_I12) gamma heavy chain Kabat CDRs:

```
CDR 1: DYSWN                  (SEQ ID NO: 34)
CDR 2: DTLHNGYTNYNPSLRG       (SEQ ID NO: 35)
CDR 3: GSGGYGGFDYFGKLRTWDF    (SEQ ID NO: 36)
```

TCN-522 (3212_I12) gamma heavy chain Chothia CDRs:

```
CDR 1: GGSLTD                 (SEQ ID NO: 37)
CDR 2: DTLHNGYTN              (SEQ ID NO: 38)
CDR 3: GSGGYGGFDYFGKLRTWDF    (SEQ ID NO: 36)
```

TCN-522 (3212_I12) light chain variable region nucleotide sequence:

(SEQ ID NO: 39)
GACATTCAGTTGACCCAGTCTCCATCCTCCCTGTCTGCATCTGTGGGAGA
CAGAGTCACCATCACTTGCCGGGCAAGTCAGGGCATTAGAAATGATTTAG
GCTGGTATCAGCAAAAACCAGGGAACGCCCCTAAGCGCCTGATCTTTGGT
GCATCCAGTTTGCAAAGTGGGGTCCCATCAAGGTTCAGCGGCAGTGGATC
TGGGACAGAGTTCACTCTCACAATCAGCAGCCTGCAGCCTGAGGACTTTG
CAACTTATTACTGTCTACAGCATAATAGTTACCCGTACACTTTTGGCCAG
GGGACCAAGCTGGAGATCAAG

TCN-522 (3212_I12) light chain variable region amino acid sequence (Kabat CDRs in bold, Chothia CDRs underlined)

(SEQ ID NO: 40)
DIQLTQSPSSLSASVGDRVTITC<u>RASQGIRNDLG</u>WYQQKPGNAPKRLIF<u>G</u>
<u>ASSLQS</u>GVPSRFSGSGSGTEFTLTISSLQPEDFATYYC<u>LQHNSYPYT</u>FGQ
GTKLEIK

TCN-522 (3212_I12) Light chain Kabat CDRs:

```
CDR 1: RASQGIRNDLG            (SEQ ID NO: 41)
CDR 2: GASSLQS                (SEQ ID NO: 42)
CDR 3: LQHNSYPYT              (SEQ ID NO: 43)
```

TCN-522 (3212_I12) Light chain Chothia CDRs

```
CDR 1: RASQGIRNDLG            (SEQ ID NO: 41)
CDR 2: GASSLQS                (SEQ ID NO: 42)
CDR 3: LQHNSYPYT              (SEQ ID NO: 43)
```

TCN-523 (5248_A17) heavy chain variable region nucleotide sequence.

(SEQ ID NO: 44)
CAGGTGCAACTGGTGCAGTCTGGGGCTGAGGTGAAGAAGCCTGGGTCCTC
GGTGAAGGTCTCCTGCAAGGCTTCTGGAGGCAGCTTCAGCAACTATGCCT
TCAGCTGGGTGCGACAGGCCCCTGGACAAGGGCTTGAGTGGATGGGAGGG
ACCATCCCTCTACTTGGTACAACAAACTACGCACAGAAGTTCCAGGGCAG
AGTCACGATTTCCGCGGACCAATTCACGAGCACAGCCTACATGGAGCTGG
GCAGCCTGAGATCTGAAGACACGGCCGTGTATTACTGTACGAGACGGAAA
ATGACTACGGCTTTTGACTCCTGGGGCCAGGGAACCCTGGTCACCGTCTC
CTCA

TCN-523 (5248_A17) gamma heavy chain variable region amino acid sequence: (Kabat CDRs in bold, Chothia CDRs underlined)

(SEQ ID NO: 45)
QVQLVQSGAEVKKPGSSVKVSCKAS<u>GGSFSNYAFS</u>WVRQAPGQGLEWMG<u>G</u>
<u>TIPLLGTTNYAQKFQG</u>RVTISADQFTSTAYMELGSLRSEDTAVYYCTR<u>RK</u>
<u>MTTAFDS</u>WGQGTLVTVSS

TCN-523 (5248_A17) gamma heavy chain Kabat CDRs:

```
CDR 1:  NYAFS                (SEQ ID NO: 46)
CDR 2:  GTIPLLGTTNYAQKFQG    (SEQ ID NO: 47)
CDR 3:  RKMTTAFDS            (SEQ ID NO: 48)
```

TCN-523 (5248_A17) gamma heavy chain Chothia CDRs:

```
CDR 1:  GGSFSN               (SEQ ID NO: 49)
CDR 2:  GTIPLLGTTN           (SEQ ID NO: 50)
CDR 3:  RKMTTAFDS            (SEQ ID NO: 48)
```

TCN-523 (5248_A17) light chain variable region nucleotide sequence:

(SEQ ID NO: 51)
CAGCCTGTTCTGACTCAGCCACCTTCTGCATCAGCCTCCCTGGGAGCCTC

GGTCACACTCACCTGCACCCTGAGCAGCGCCTACAGTAATTATAAAGTGG

-continued
ACTGGTACCAGCAGAGACCAGGGAAGGGCCCCCGCTTTGTGATGCGAGTG

-continued
GGCACTGGTGGGATTGTGGGATCCAAGGGGGATGGCATCCCTGATCGCTT

CTCAGTCTTGGGCTCAGGCCTGAATCGGTACCTGACCATCAAGAACATCC

AGGAAGAGGATGAGAGTGACTACCACTGTGGGGCAGACCATGGCAGTGGG

AGCAACTTCGTGTCCCCTTACGTATTCGGCGGAGGGACCAAGCTGACCGT

TCTA

TCN-523 (5248_A17) light chain variable region amino acid sequence (Kabat CDRs in bold, Chothia CDRs underlined)

(SEQ ID NO: 52)
QPVLTQPPSASASLGASVTLTCTLSSAYSNYKVDWYQQRPGKGPRFVMRV

GTGGIVGSKGDGIPDRFSVLGSGLNRYLTIKNIQEEDESDYHCGADHGSG

SNFVSPYVFGGGTKLTVL

TCN-523 (5248_A17) Light chain Kabat CDRs:

```
CDR 1:  TLSSAYSNYKVD         (SEQ ID NO: 53)
CDR 2:  VGTGGIVGSKGD         (SEQ ID NO: 54)
CDR 3:  GADHGSGSNFVSPYV      (SEQ ID NO: 55)
```

TCN-523 (5248_A17) Light chain Chothia CDRs:

```
CDR 1:  TLSSAYSNYKVD         (SEQ ID NO: 53)
CDR 2:  VGTGGIVGSKGD         (SEQ ID NO: 54)
CDR 3:  GADHGSGSNFVSPYV      (SEQ ID NO: 55)
```

TCN-563 (5237_B21) heavy chain variable region nucleotide sequence:

(SEQ ID NO: 56)
CAGGTGCAGCTGGCGCAGTCTGGGGCTGAGGTGAAGAGGCCTGGGTCCTCGGTGAAAGTCTCATGCACGGCTTCTGG

AGGCATCTTCAGGAAGAATGCAATCAGCTGGGTGCGACAGGCCCCTGGACAAGGCCTTGAGTGGATGGGAGGGATCA

TCGCAGTCTTTAACACAGCAAATTACGCGCAGAAGTTTCAGGGCAGAGTCAAAATTACCGCAGACGAATCCGGGAAT

ACAGCCTACATGGAGCTGAGCAGCCTGAGATCTGACGACACGGCCGTGTATTACTGTGCGAGTCACCCAAAATATTT

CTATGGTTCGGGGAGTTATCCGGACTTCTGGGGCCAGGGAACCCTGGTCACCGTCTCGAGC

TCN-563 (5237_B21) gamma heavy chain variable region amino acid sequence: (Kabat CDRs in bold, Chothia CDRs underlined)

(SEQ ID NO: 57)
QVQLAQSGAEVKRPGSSVKVSCTAS<u>GGIFR</u>KNAISWVRQAPGQGLEWMG<u>G</u>IIAVFNTANYAQKFQGRVK

ITADESGNTAYMELSSLRSDDTAVYYCASHPKYFYGSGSYPDFWGQGTLVTVSS

TCN 563 (5237_B21) Mamma heavy chain Kabat CDRs:

```
CDR 1:  KNAIS                (SEQ ID NO: 62)
CDR 2:  GIIAVFNTANYAQKFQG    (SEQ ID NO: 58)
CDR 3:  HPKYFYGSGSYPDF       (SEQ ID NO: 59)
```

TCN-563 (5237_B21) Mamma heavy chain Chothia CDRs:

```
CDR 1:  GGIFRK               (SEQ ID NO: 60)
CDR 2:  GIIAVFNTAN           (SEQ ID NO: 61)
CDR 3:  HPKYFYGSGSYPDF       (SEQ ID NO: 59)
```

TCN-563 (5237_B21) light chain variable region nucleotide sequence:

(SEQ ID NO: 63)
CAATCTGCCCTGACTCAGCCTCGCTCAGTGTCCGGGTCTCCTGGACAGTCAGTCACCATCTCCTGCACTGGAAGCAG

CAGTGATGTTGGTGCTTCTAACTCTGTCTCCTGGTACCAACAACACCCAGGCAAAGCCCCCAAACTCGTTATTTATG

```
ATGTCACTGAGCGACCCTCAGGGGTCCCTCATCGCTTCTCTGGCTCCAAGTCTGGCAACACGGCCTCCCTGACCGTC

TCTGGGCTCCAGCCTGAGGACGAGGCTGATTATTTCTGCTGCGCATATGGAGGCAAATATCTTGTGGTCTTCGGCGG

AGGGACCAAGGTGACCGTCCTC
```

TCN-563 (5237_B21) light chain variable region amino acid sequence (Kabat CDRs in bold, Chothia CDRs underlined)

(SEQ ID NO: 64)
```
QSALTQPRSVSGSPGQSVTISCTGSSSDVGASNSVSWYQQHPGKAPKLVIYDVTERPSGVPHRFSGSKSGN

TASLTVSGLQPEDEADYFCCAYGGKYLVVFGGGTKVTVL
```

TCN-563 (5237_B21) light chain Kabat CDRs:

| | | |
|---|---|---|
| CDR 1: | TGSSSDVGASNSVS | (SEQ ID NO: 65) |
| CDR 2: | DVTERPS | (SEQ ID NO: 66) |
| CDR 3: | CAYGGKYLVV | (SEQ ID NO: 67) |

TCN-563 (5237_B21) light chain Chothia CDRs:

| | | |
|---|---|---|
| CDR 1: | TGSSSDVGASNSVS | (SEQ ID NO: 65) |
| CDR 2: | DVTERPS | (SEQ ID NO: 66) |
| CDR 3: | CAYGGKYLVV | (SEQ ID NO: 67) |

TCN-526 (5084_C17) heavy chain variable region nucleotide sequence:

(SEQ ID NO: 68)
```
GAGGTGCTGATGGTGGAGTCTGGGGGAGGCTTGGTCCAGCCTGGGGGGTCCGTGAGACTCTCCTGTGTAGCCTCTGG

ATTCAGTTTCAGTAGTCATTGGATGACCTGGGTCCGCCAGGCTCCAGGGAAGGGGCTGGAGTGGGTGGCCAACATAG

AGGACGATGGAGGTGACAAGTACTATGTGGACTCTGTGAAGGGCCGATTCATTATCTCCAGAGACAACGCCAAGAAT

TCAGTGTATCTGCAAATGAACAGCCTAAGAGCCGAGGACACGGCTGTGTATTTCTGTGCGAGAGGTTCGGGGAGCTC

TGATAGAAGTGATTATGACCCCCACTACTACTACTACTTGGACGTCTGGGGCAAAGGGGCCACGGTCACCGTCTCCT

CA
```

TCN-526 (5084_C17) gamma heavy chain Kabat CDRs:

| | | |
|---|---|---|
| CDR 1: | SHWMT | (SEQ ID NO: 70) |
| CDR 2: | NIEDDGGDKYYVDSVKG | (SEQ ID NO: 71) |
| CDR 3: | GSGSSDRSDYDPHYYYYLDV | (SEQ ID NO: 72) |

TCN-526 (5084_C17) gamma heavy chain Chothia CDRs:

| | | |
|---|---|---|
| CDR 1: | GFSFSS | (SEQ ID NO: 73) |
| CDR 2: | NIEDDGGDKY | (SEQ ID NO: 74) |
| CDR 3: | GSGSSDRSDYDPHYYYYLDV | (SEQ ID NO: 72) |

TCN-526 (5084_C17) gamma heavy chain variable region amino acid sequence: (Kabat CDRs in bold, Chothia CDRs underlined)

(SEQ ID NO: 69)
```
EVLMVESGGGLVQPGGSVRLSCVASGFSFSSHWMTWVRQAPGKGLEWVANIEDDGGDKYYVDSVKGR

FIISRDNAKNSVYLQMNSLRAEDTAVYFCARGSGSSDRSDYDPHYYYYLDVWGKGATVTVSS
```

TCN-526 (5084_C17) light chain variable region nucleotide sequence:

(SEQ ID NO: 75)
GACATCCAGCTGACCCAGTCTCCATCTTCCCTGTCTGCATCTGTAGGAGACAGAGTCACCATCACTTGCCGGGCAAG

TCAGAGCATTAGTAGGTATTTAAATTGGTATCAGCAAAAACCAGGGAAAGCCCCTAAGCTCCTGCTGTTTGCTGCTT

CTACTTTGCTAGATGGGGTCCCATCAAGATTCAGTGGCAGTGGATCTGGGACAGATTTCACTCTCACCATCAGCAGT

CTGCAACCTGAAGATTTTGCAACTTACTACTGTCAACGGAATCACAGTCCCTCGTGGACGTTCGGCCAAGGGACCAG

GGTGGAAATCAAA

TCN-526 (5084_C17) light chain variable region amino acid sequence (Kabat CDRs in bold, Chothia CDRs underlined)

(SEQ ID NO: 76)
DIQLTQSPSSLSASVGDRVTITCRAS<u>QSISRYLN</u>WYQQKPGKAPKLLLFAASTLLDGVPSRFSGSGSGTDFT

LTISSLQPEDFATYYCQRNHSPSWTFGQGTRVEIK

TCN-526 (5084_C17) Light chain Kabat CDRs:

```
CDR 1:  RASQSISRYLN      (SEQ ID NO: 77)
CDR 2:  AASTLLD          (SEQ ID NO: 78)
CDR 3:  QRNHSPSWT        (SEQ ID NO: 79)
```

TCN-526 (5084_C17) Light chain Chothia CDRs:

```
CDR 1:  RASQSISRYLN      (SEQ ID NO: 77)
CDR 2:  AASTLLD          (SEQ ID NO: 78)
CDR 3:  QRNHSPSWT        (SEQ ID NO: 79)
```

TCN-527 (5086_C06) heavy chain variable region nucleotide sequence:

(SEQ ID NO: 80)
CAGGTGCAGCTGCAAGAGTCGGGCCCGGGACTGGTGAAGCCTTCGGAGAC

CCTGTCCCTCAACTGCGCTGTCTCTGGAGGCTCCATCAGTAATTACTACT

GGAGCTGGATCCGGCAGCCCCCCGGGAAGGGACTGGAGTGGATTGGCTAT

ATCTCTTACAATGGGAGGCCCAAGTACAACCCCTCCCTCACGAGTCGAGT

CACCATATCCGTCGACACGTCCAAGGACCAGTTCTCCCTGGAGCTGCGCT

CTGTGACCGCTGCGGACACGGCCCTTTATTACTGTGCGAGAGAAACGCGG

TTCGGGGAGTTATTATCTCCCTATGATGCTTTTGAAATCTGGGGCCAAGG

GACAATGGTCACCGTCTCCTCA

TCN-527 (5086_C06) gamma heavy chain variable region amino acid sequence: (Kabat CDRs in bold, Chothia CDRs underlined)

(SEQ ID NO: 81)
QVQLQESGPGLVKPSETLSLNCAVS<u>GGSIS</u>NYYWSWIRQPPGKGLEWIGY

<u>ISYNGRPKYNPSLTS</u>RVTISVDTSKDQFSLELRSVTAADTALYYCAR<u>ETR</u>

<u>FGELLSPYDAFEI</u>WGQGTMVTVSS

TCN-527 (5086_C06) gamma heavy chain Kabat CDRs:

```
CDR 1:  NYYWS                 (SEQ ID NO: 82)
CDR 2:  YISYNGRPKYNPSLTS      (SEQ ID NO: 83)
CDR 3:  ETRFGELLSPYDAFEI      (SEQ ID NO: 84)
```

TCN-527 (5086_C06) gamma heavy chain Chothia CDRs:

```
CDR 1:  GGSISN                (SEQ ID NO: 85)
CDR 2:  YISYNGRPK             (SEQ ID NO: 86)
CDR 3:  ETRFGELLSPYDAFEI      (SEQ ID NO: 84)
```

TCN-527 (5086_C06) light chain variable region nucleotide sequence:

(SEQ ID NO: 87)
GACATCCAGATGACCCAGTCTCCATCCTCCCTGTCTGCATCTGTAGGAGA

CAGAGTCACCATGACTTGCCGGGCAAGTCAGAACATTAGAAGCTATTTAA

ATTGGTATCAGCAGAGACCAGGGACAGCCCCTAAACTCCTGATCTATGCT

GCATCCACTTTACACAGTGGGGTCCCATCAAGGTTCAGTGGCGGTGGGTC

TGGGACAGATTTCACTCTCACCATCAATAATCTGCAACCTGAAGATTTTG

CATCTTACTACTGTCAACAGAGTTACGATAACCCTCAGACGTTCGGCCAA

GGGACCAAGGTGGAAATCAAA

TCN-527 (5086_C06) light chain variable region amino acid sequence (Kabat CDRs in bold, Chothia CDRs underlined)

(SEQ ID NO: 88)
DIQMTQSPSSLSASVGDRVTMTCRAS<u>QNIRSYLN</u>WYQQRPGTAPKLLIYA

ASTLHSGVPSRFSGGGSGTDFTLTINNLQPEDFASYYCQQSYDNPQTFGQ

GTKVEIK

TCN-527 (5086_C61 Light chain Kabat CDRs:

```
CDR 1:  RASQNIRSYLN      (SEQ ID NO: 89)
CDR 2:  AASTLHS          (SEQ ID NO: 90)
CDR 3:  QQSYDNPQT        (SEQ ID NO: 91)
```

TCN-527 (5086_C06) Light chain Kabat CDRs:

CDR 1: RASQNIRSYLN         (SEQ ID NO: 89)
    CDR 2: AASTLHS             (SEQ ID NO: 90)
    CDR 3: QQSYDNPQT           (SEQ ID NO: 91)

TCN-528 (5087_P17) heavy chain variable region nucleotide sequence:

(SEQ ID NO: 92)
CAGGTGCAGCTGGTGCAGTCTGGGTCTGAGGTGAAGAAGCCTGGGGCCTC
AGTGAAGGTCTCCTGCAAGGCTTCTGGATACACCTTCACCAATTATGACA
TCAACTGGATTCGACAGGCCCCTGGTCAAGGACTTGAGTGGATGGGCTGG
ATAAATCCCAACAGTGGAACCACGGGCTCTGCACAGAGGTTCCAGGGCAG
AGTCACCATAACCGTGGACACCTCCATAACCACAGTCTACATGGAACTGA
GCAGCCTGAGATCTGACGACACGGCCATTTACTACTGCGCGAGAGGCCGT

-continued
GAGCTCCTCCGGCTTCAACATTTTTTGACTGACTCCCAGTCCGAGAGGAG
GGACTGCTTCGACCCCTGGGGCCAGGGAACCCTGGTCACCGTCTCCTCA TCN-528 (5087_P17) gamma heavy chain variable region amino acid sequence: (Kabat CDRs in bold, Chothia CDRs underlined)

(SEQ ID NO: 93)
QVQLVQSGSEVKKPGASVKVSCKASGYTFT<ins>NYDIN</ins>WIRQAPGQGLEWMG<ins>W
INPNSGTTG</ins>SAQRFQGRVTITVDTSITTVYMELSSLRSDDTAIYYCAR<ins>GR
ELLRLQHFLTDSQSERRDCFDP</ins>WGQGTLVTVSS TCN-528 (5087_P17) gamma heavy chain Kabat CDRs:

CDR 1: NYDIN                       (SEQ ID NO: 94)
CDR 2: WINPNSGTTGSAQRFQG           (SEQ ID NO: 95)
CDR 3: GRELLRLQHFLTDSQSERRDCFDP    (SEQ ID NO: 96)

TCN-528 (5087_P17) gamma heavy chain Chothia CDRs:

CDR 1: GYTFTN                      (SEQ ID NO: 97)
CDR 2: WINPNSGTTG                  (SEQ ID NO: 98)
CDR 3: GRELLRLQHFLTDSQSERRDCFDP    (SEQ ID NO: 96)

TCN-528 (5087_P17) light chain variable region nucleotide sequence:

(SEQ ID NO: 99)
GATATCCAGATGACCCAGTCTCCTTCCTCCCTGTCTGCATCTGTAGGAGA
CAGAGTCACCATCACTTGCCGGGCAAATCAAGACATTGGCATTTATTTAA
ATTGGTATCAACAGAATCCAGGGAAAGTCCCTAAACTCCTGCTCCATGGT
GCGTCCAGTTTGCAGGGCGGGGTCCCATCAAGGTTCAGTGCCAGTGGATC
TGGGACAGATTTCACTCTCACCATTCACAGTCTACAACCTGAAGATTTAG
CAACCTACTACTGTCAACAGAGTCGCCGTCTACCGTACACTTTTGGCCAG
GGGACCAGGGTGGAACTCAAA

TCN-528 (5087_P17) light chain variable region amino acid sequence (Kabat CDRs in bold, Chothia CDRs underlined)

(SEQ ID NO: 100)
DIQMTQSPSSLSASVGDRVTITC<ins>RANQDIGIYLN</ins>WYQQNPGKVPKLLLH<ins>GASSLQG</ins>GVPSRFSASGSGTDF
TLTIHSLQPEDLATYYCQQSRRLPYTFGQGTRVELK TCN-528 (5087_P17) Light chain Kabat CDRs:

(SEQ ID NO: 101)
    CDR 1: RANQDIGIYLN
                                    (SEQ ID NO: 102)
    CDR 2: GASSLQG
                                    (SEQ ID NO: 103)
    CDR 3: QQSRRLPYT

TCN-528 (5087_P17) Light chain Chothia CDRs:

(SEQ ID NO: 101)
    CDR 1: RANQDIGIYLN
                                    (SEQ ID NO: 102)
    CDR 2: GASSLQG
                                    (SEQ ID NO: 103)
    CDR 3: QQSRRLPYT

TCN-529 (5297_H011 heavy chain variable region nucleotide sequence:

(SEQ ID NO: 104)
CAGATCACCTTGAGGGAGTCTGGTCCTACGCTGGTGAAACCCACACAGACCCTCACGCTGACCTGCACCTTCTCTGG
GTTTTCACTCAGCACTAATGGAGTGAATGTGGGCTGGATCCGTCAGCCCCCAGGAAAGGCCCTGGAGTGGCTTGCAC
TCATTTACTGGGATGATGATAAGCGCTACAGTCCGTCTCTGAAGAGAAGGCTCACCATCACCAAGGACACCTCCAAA
AACCAAGTGGTCCTTACACTGACCAACATGGACCCTGTAGATACAGCCACATATTACTGTGCACACAGACCCGACTT
CTATGGTGACTTCGAGTACTGGGGCCCGGGAACCCTGGTCACCGTCTCCTCA

TCN-529 (5297_H01) gamma heavy chain variable region amino acid sequence: (Kabat CDRs in bold, Chothia CDRs underlined)

(SEQ ID NO: 105)
QITLRESGPTLVKPTQTLTLTCTFS<u>GFSLS</u>TNGVNVGWIRQPPGKALEWLA<u>LIYWDDDKRYSPSLKR</u>RLTI

TKDTSKNQVVLTLTNMDPVDTATYYCAH<u>RPDFYGDFEY</u>WGPGTLVTVSS

TCN-529 (5297_H01) gamma heavy chain Kabat CDRs:

```
                                    (SEQ ID NO: 106)
        CDR 1: TNGVNVG (SEQ ID NO: 107)
        CDR 2: LIYWDDDKRYSPSLKR (SEQ ID NO: 108)
        CDR 3: RPDFYGDFEY
```

TCN-529 (5297_H01) gamma heavy chain Chothia CDRs:

```
                                    (SEQ ID NO: 109)
        CDR 1: GFSLSTNG (SEQ ID NO: 110)
        CDR 2: LIYWDDDKR (SEQ ID NO: 108)
        CDR 3: RPDFYGDFEY
```

TCN-529 (5297_H01) light chain variable region nucleotide sequence.

(SEQ ID NO: 111)
CAGTCTGCACTGACTCAGCCTGCCTCCGTGTCTGGGTCTCCCGGACAGTCGATCACCATCTCCTGCACTGGAAGCAG

CAGTGACATTGGTGGTTATAACTATGTCTCCTGGTACCAACAACACCCAGGCAAGGCCCCCAAACTCATGATTTACG

ATGTCAATAATCGGCCCTCAGGGGTTTCTAATCGCTTCTCTGGCTCCAAGTCTGGCAACACGGCCTCCCTGACTATC

TCTGGGCTCCAGACTGACGACGAGGCTGATTATTACTGCGGCTCATATACAGGCAGTCCTCATTATGTCTTCGGAAC

TGGGACCAAGGTCACCGTCCTA

TCN-529 (5297_H01) light chain variable region amino acid sequence (Kabat CDRs in bold, Chothia CDRs underlined)

(SEQ ID NO: 112)
QSALTQPASVSGSPGQSITISC<u>TGSSSDIGGYNYVS</u>WYQQHPGKAPKLMIYDVNNRPSGVSNRFSGSKSGN

TASLTISGLQTDDEADYYC<u>GSYTGSPHYV</u>FGTGTKVTVL

TCN-529 (5297_H01) Light chain Kabat CDRs:

```
                                    (SEQ ID NO: 113)
        CDR 1: TGSSSDIGGYNYVS (SEQ ID NO: 114)
        CDR 2: DVNNRPS (SEQ ID NO: 115)
        CDR 3: GSYTGSPHYV
```

TCN-529 (5297_H01) Light chain Chothia CDRs:

```
                                    (SEQ ID NO: 113)
        CDR 1: TGSSSDIGGYNYVS (SEQ ID NO: 114)
        CDR 2: DVNNRPS (SEQ ID NO: 115)
        CDR 3: GSYTGSPHYV
```

TCN-530 (5248_H10a) heavy chain variable region nucleotide sequence:

(SEQ ID NO: 116)
CAGGTCCAACTGGTGCAATCTGGGGCTGAGGTGAGGAAGCCTGGGTCCTCGGTGAAGGTCTCCTGCAAGGCTTCTGG

AGGCCCCTTCATGAGTTATGCTATCGGCTGGGTGCGACAGGCCCCTGGACAAGGGCTTGAGTGGATGGGAGGGATCA

-continued

```
ACCCTGTGTTTGGTAGACCGCACTACGCACAGAAGTTCCAGGGCAGAGTCACCATCGCCACGGACGACTCCACGAAG

ACATCGTACATGGAACTGAGTAGCCTGACGTCTGAGGACACGGGCATGTATTACTGTGCGAGTAGGTATAGTAGGTC

GTCCCCAGGGACCTTTGAGTCCTGGGGCCAGGGAACCCTGGTCACCGTCTCGAGC
```

TCN-530 (5248_H10a) gamma heavy chain variable region amino acid sequence: (Kabat CDRs in bold, Chothia CDRs underlined)

(SEQ ID NO: 117)
QVQLVQSGAEVRKPGSSVKVSCKAS<u>GGPFMSYAIG</u>WVRQAPGQGLEWMG<u>GINPVFGRPHYAQKFQG</u>R
VTIATDDSTKTSYMELSSLTSEDTGMYYCAS<u>RYSRSSPGTFES</u>WGQGTLVTVSS

TCN-530 (5248_H10a) gamma heavy chain Kabat CDRs:

(SEQ ID NO: 118)
CDR 1: SYAIG
(SEQ ID NO: 119)
CDR 2: GINPVFGRPHYAQKFQG
(SEQ ID NO: 120)
CDR 3: RYSRSSPGTFES

TCN-530 (5248_H10a) gamma heavy chain Chothia CDRs:

(SEQ ID NO: 121)
CDR 1: GGPFMS
(SEQ ID NO: 122)
CDR 2: GINPVFGRPH
(SEQ ID NO: 120)
CDR 3: RYSRSSPGTFES

TCN-530 (5248_H10a) light chain variable region nucleotide sequence:

(SEQ ID NO: 123)
```
GAAATAGTGATGACGCAGTTTCCAGCCACCCTGTCTGTGTCTCCCGGGGAACGAGTCACCCTCTCCTGTAGGGCCAG

TCAGAGTGTTAGCAACAATTTAGCCTGGTACCAGCAAAAACCTGGCCAGCCTCCCAGGCTCCTCATCTATGATGCAT

CTACCAGGGCCACGGGTGTCCCAGCCAAGTTCAGTGGCACTGGGTCTGGCACAGAGTTCACTCTCAGCATCAGCAGC

CTGCAGTCCGAAGATTTTGCAGTTTATTACTGTCAGCAGTATCACAACTGGCCTCCCTCGTACAGTTTTGGCCTGGG

GACCAAGCTGGAGATCAAA
```

TCN-530 (5248_H10a) light chain variable region amino acid sequence (Kabat CDRs in bold, Chothia CDRs underlined)

(SEQ ID NO: 124)
EIVMTQFPATLSVSPGERVTLSC<u>RASQSVSNNLA</u>WYQQKPGQPPRLLIY<u>DASTRAT</u>GVPAKFSGTGSGTEF
TLSISSLQSEDFAVYYC<u>QQYHNWPPSYS</u>FGLGTKLEIK

TCN-530 (5248_H10a) Light chain Kabat CDRs:

(SEQ ID NO: 125)
CDR 1: RASQSVSNNLA
(SEQ ID NO: 126)
CDR 2: DASTRAT
(SEQ ID NO: 127)
CDR 3: QQYHNWPPSYS

TCN-530 (5248_H10a) Light chain Chothia CDRs:

(SEQ ID NO: 125)
CDR 1: RASQSVSNNLA
(SEQ ID NO: 126)
CDR 2: DASTRAT
(SEQ ID NO: 127)
CDR 3: QQYHNWPPSYS

TCN-531 (5091_H13) heavy chain variable region nucleotide sequence:

(SEQ ID NO: 128)
GAGGTGCAGCTGGTGGAGTCTGGGGGAGACTTGGTACAGCCAGGGCGGTCCCTGAAACTCTCCTGCACAGGTTCTGG
ATTCACCTTTGGTGATTATGGTGTGACCTGGGTCCGCCAGGCTCCAGGGAAGGGGCTGGAGTGGGTAGGTTTCATTA
GAACCAGACCTTGGGGTGGGACAGCAGATACCGCCGCGTCTGTGAAAGGCAGATTCACTATTTCAAGAGATGATTCC
AAAAGTCTCGCCTATCTGCAAATGAACAGCCTGAAAACCGAGGACACAGCCGTGTATTACTGTTGTAGAGATGCCCC
TCCAAATGTGGAAGTGGCTTCTATGACCAACTGGTACTTCGATCTCTGGGGCCGTGGCACCCTGGTCACCGTCTCCT
CA

TCN-531 (5091_H13) gamma heavy chain variable region amino acid sequence: (Kabat CDRs in bold, Chothia CDRs underlined)

(SEQ ID NO: 129)
EVQLVESGGDLVQPGRSLKLSCTGS<u>GFTFGDYGVT</u>WVRQAPGKGLEWVG<u>FIRTRPWGGTAD</u>TAASVKG
RFTISRDDSKSLAYLQMNSLKTEDTAVYYCCR<u>DAPPNVEVASMTNWYFDL</u>WGRGTLVTVSS

TCN-531 (5091_H13) gamma heavy chain Kabat CDRs:

```
                        (SEQ ID NO: 130)
    CDR 1: DYGVT
                        (SEQ ID NO: 131)
    CDR 2: FIRTRPWGGTADTAASVKG
                        (SEQ ID NO: 132)
    CDR 3: DAPPNVEVASMTNWYFDL
```

TCN-531 (5091_H13) gamma heavy chain Chothia CDRs:

```
                        (SEQ ID NO: 133)
    CDR 1: GFTFGD
                        (SEQ ID NO: 134)
    CDR 2: FIRTRPWGGTAD
                        (SEQ ID NO: 132)
    CDR 3: DAPPNVEVASMTNWYFDL
```

TCN-531 (5091_H13) light chain variable region nucleotide sequence:

(SEQ ID NO: 135)
GACATCCAGCTGACCCAGTCTCCATCCTCCCTGTCTGCATCTGTGGGAGACAGAGTCACCATCACTTGCCGGGCGAG
TCAGGGCATTCTCAATTGTTTAGCCTGGTATCAGCAGAAACCGGGGAAAGTTCCTAACCTCCTGATGTATGCTGCAT
CCACATTGCAGTCAGGGGTCCCATCTCGGTTCAGCGGCAGTGGATTTGGGACAGATTTCACTCTCACCATCAGCAGC
CTGCAGCCTGAAGATGTTGCAACTTATTACTGTCAAACGTATGGCGGTGTCTCTACTTTCGGCGGAGGGACCAAGGT
GGAGATCAGA

TCN-531 (5091_H13) light chain variable region amino acid sequence (Kabat CDRs in bold, Chothia CDRs underlined)

(SEQ ID NO: 136)
DIQLTQSPSSLSASVGDRVTITC<u>RASQGILNCLA</u>WYQQKPGKVPNLLMY<u>AASTLQS</u>GVPSRFSGSGFGTDF
TLTISSLQPEDVATYYC<u>QTYGGVST</u>FGGGTKVEIR

TCN-531 (5091_H13) Light chain Kabat CDRs:

```
                        (SEQ ID NO: 137)
    CDR 1: RASQGILNCLA
                        (SEQ ID NO: 138)
    CDR 2: AASTLQS
                        (SEQ ID NO: 139)
    CDR 3: QTYGGVST
```

TCN-531 (5091_H13) Light chain Chothia CDRs:

```
                        (SEQ ID NO: 137)
    CDR 1: RASQGILNCLA
                        (SEQ ID NO: 138)
    CDR 2: AASTLQS
                        (SEQ ID NO: 139)
    CDR 3: QTYGGVST
```

TCN-532 (5262_H18) heavy chain variable region nucleotide sequence.

(SEQ ID NO: 140)
```
CAGGTGCAGCTGCAGGAGTCGGGCCCAGGACTGGTGAAGCCTTCGGAGACCTTGTCCCTCACCTGCACTGTCTCTGG
TGGCTCCGTCAGCAGTGAGACTTACTACTGGAGCTGGATCCGGCAGCCCCCAGGGAAGGGACTAGAGTGGATTGGAT
ATATCTATTACATTGGGAACACCGACTACAGGCCCTCCCTCAAGAGTCGAGTCACCATATCACTGGACACGTCCAAG
AACCAGTTCTCCCTGAAGCTGAGCTCTGTGACCGCTGCGGACACGGCCGTTTATTACTGTGCGAGAGGCGCTTATTA
TGATAGTAGTGGTTACCCGGCTTTTTATATCTGGGGCCAAGGGACAATGGTCACCGTCTCCTCA
```

TCN-532 (5262_H18) gamma heavy chain variable region amino acid sequence: (Kabat CDRs in bold, Chothia CDRs underlined)

(SEQ ID NO: 141)
```
QVQLQESGPGLVKPSETLSLTCTVSGGSVSSETYYWSWIRQPPGKGLEWIGYIYYIGNTDYRPSLKSRVTIS
LDTSKNQFSLKLSSVTAADTAVYYCARGAYYDSSGYPAFYIWGQGTMVTVSS
```

TCN-532 (5262_H18) gamma heavy chain Kabat CDRs:

CDR 1: SETYYWS                (SEQ ID NO: 142)

CDR 2: YIYYIGNTDYRPSLKS       (SEQ ID NO: 143)

CDR 3: GAYYDSSGYPAFYI         (SEQ ID NO: 144)

TCN-532 (5262_H18) gamma heavy chain Chothia CDRs:

CDR 1:
    GGSVSSET                      (SEQ ID NO: 145)

CDR 2:
    YIYYIGNTD                     (SEQ ID NO: 146)

CDR 3:
    GAYYDSSGYPAFYI                (SEQ ID NO: 144)

TCN-532 (5262_H18) light chain variable region nucleotide sequence:

(SEQ ID NO: 147)
```
CAGTCTGTGCTGACGCAGCCGCCCTCAGTGTCTGGGGCCCCAGGGCAG
AGGGTCACCATCTCCTGCACTGGGAGCAGCTCCAACATCGGGTCAGAT
TATGATGTGCACTGGTACAAGCAACTTCCAGGAACAGCCCCCAAACTC
CTCATCTTTGGTAACAGCAATCGGCCCTCAGGGGTCCCTGACCGATTC
TCTGGCTCCAAGTCTGGCACCTCAGCCTCCCTGGCCATCACTGGGCTC
CAGGCTGAGGATGAGGCTGATTATTACTGCCAATCCTATGACAGCAGC
CTGAGTGGTTTTCATGTCTTCGGAAGTGGGACCAAGGTCACCGTCCTA
```

TCN-532 (5262_H18) light chain variable region amino acid sequence (Kabat CDRs in bold, Chothia CDRs underlined)

(SEQ ID NO: 148)
```
QSVLTQPPSVSGAPGQRVTISCTGSSSNIGSDYDVHWYKQLPGTAPKL
LIFGNSNRPSGVPDRFSGSKSGTSASLAITGLQAEDEADYYCQSYDSS
LSGFHVFGSGTKVTVL
```

TCN-532 (5262_H18) Light chain Kabat CDRs:

CDR 1:
    TGSSSNIGSDYDVH                (SEQ ID NO: 149)

CDR 2:
    GNSNRPS                       (SEQ ID NO: 150)

CDR 3:
    QSYDSSLSGFHV                  (SEQ ID NO: 151)

TCN-532 (5262_H18) Light chain Chothia CDRs:

CDR 1:
    TGSSSNIGSDYDVH                (SEQ ID NO: 149)

CDR 2:
    GNSNRPS                       (SEQ ID NO: 150)

CDR 3:
    QSYDSSLSGFHV                  (SEQ ID NO: 151)

TCN-533 (5256_A17a) heavy chain variable region nucleotide sequence:

(SEQ ID NO: 152)
```
CAGGTGCAGCTGGTGCAGTCTGGGGCTGACGTGAAGAAGCCTGGGTCC
TCGGTGACGGTCTCCTGCAAGGCTTCTGGAGGCAGCTTCAGCAACTAT
GGAATCAACTGGGTGCGACAGGCCCCTGGACAAGGGCTTGAGTGGATG
GGGGGAATCATCCCTCTCATTAATGCACCGAACTACGCACCGAAGTTC
CAGGGCAGAGTGACGATTACCGCGGACATGTTCTCGAATATAGTCTCC
TTGCAGTTGACCAGCCTGAGAACTGACGACACGGCCGTGTATTATTGT
GCGAGACGAAAAATGACTACGGCTATTGACTATTGGGGCCAGGGAACC
CTGGTCACCGTCTCCTCA
```

TCN-533 (5256_A17a) gamma heavy chain variable region amino acid sequence: (Kabat CDRs in bold, Chothia CDRs underlined)

(SEQ ID NO: 153)
QVQLVQSGADVKKPGSSVTVSCKAS<u>GGSFS</u>NYGINWVRQAPGQGLEWM
GG<u>IIPLINAPN</u>YAPKFQGRVTITADMFSNIVSLQLTSLRTDDTAVYYC
AR<u>RKMTTAIDY</u>WGQGTLVTVSS

TCN-533 (5256_A17a) gamma heavy chain Kabat CDRs:

```
CDR 1:
NYGIN                       (SEQ ID NO: 154)

CDR 2:
GIIPLINAPNYAPKFQG           (SEQ ID NO: 155)

CDR 3:
RKMTTAIDY                   (SEQ ID NO: 156)
```

TCN-533 (5256_A17a) gamma heavy chain Chothia CDRs:

```
CDR 1:
GGSFSN                      (SEQ ID NO: 49)

CDR 2:
GIIPLINAPN                  (SEQ ID NO: 158)

CDR 3:
RKMTTAIDY                   (SEQ ID NO: 156)
```

TCN-533 (5256_A17a) light chain variable region nucleotide sequence:

(SEQ ID NO: 159)
CAGCCTGTTCTGACTCAGCCACCTTCTGCATCAGCCTCCCTGGGAGCC
TCGGTCACACTCACCTGCACCCTGAGCAGCGCCTACAGTAATTATAAA
GTGGACTGGTACCAGCAGAGACCAGGGAAGGGCCCCCGCTTTGTGATG
CGAGTGGGCACTGGTGGGATTGTGGGATCCAAGGGGGATGGCATCCCT
GATCGCTTCTCAGTCTTGGGCTCAGGCCTGAATCGGTACCTGACCATC
AAGAACATCCAGGAAGAGGATGAGAGTGACTACCACTGTGGGGCAGAC
CATGGCAGTGGGAGCAACTTCGTGTCCCCTTACGTATTCGGCGGAGGG
ACCAAGCTGACCGTCCTA

TCN-533 (5256_A17a) light chain variable region amino acid sequence (Kabat CDRs in bold. Chothia CDRs underlined)

(SEQ ID NO: 52)
QPVLTQPPSASASLGASVTLTC<u>TLSSAYSNYKVD</u>WYQQRPGKGPRFVM
RVGTGGIVGSKGDGIPDRFSVLGSGLNRYLTIKNIQEEDESDYHCGAD
HGSGSNFVSPYVFGGGTKLTVL

TCN-533 (5256_A17a) Light chain Kabat CDRs:

```
CDR 1:
TLSSAYSNYKVD                (SEQ ID NO: 53)

CDR 2:
VGTGGIVGSKGD                (SEQ ID NO: 54)

CDR 3:
GADHGSGSNFVSPYV             (SEQ ID NO: 55)
```

TCN-533 (5256_A17a) Light chain Chothia CDRs:

```
CDR 1:
TLSSAYSNYKVD                (SEQ ID NO: 53)

CDR 2:
VGTGGIVGSKGD                (SEQ ID NO: 54)

CDR 3:
GADHGSGSNFVSPYV             (SEQ ID NO: 55)
```

TCN-534 (5249_B02) heavy chain variable region nucleotide sequence:

(SEQ ID NO: 160)
CAGGTCCAGCTGGTGCAGTCTGGGGCTGAGGTGAAGAAGCCAGGGTCC
TCGGTGAAGGTCTCCTGCAGGGAATCTGGAGGCACCTTCAACGGCTAC
ACTATCACCTGGGTGCGACAGGCCCCTGGGCAAGGCCTTGAGTGGATG
GGAGGGATCATCCCTATGATGGGGACAGTCAACTACGCACAGAAGTTG
CAGGGCAGAGTCACCATTACCACGGACTATTTCACGAAAACAGCCTAC
ATGGATCTGAACAATTTAAGATCTGAAGACACGGCCATGTATTATTGT
GTGAAAATCAGATATACTGGGCAGCAGCTGCTCTGGGGCCAGGGAACC
CTGGTCACCGTCTCCTCA

TCN-534 (5249_B02) gamma heavy chain variable region amino acid sequence: (Kabat CDRs in bold, Chothia CDRs underlined)

(SEQ ID NO: 161)
QVQLVQSGAEVKKPGSSVKVSCRES<u>GGTFN</u>GYTITWVRQAPGQGLEWM
GG<u>IIPMMGTVN</u>YAQKLQGRVTITTDYFTKTAYMDLNNLRSEDTAMYYC
VK<u>IRYTGQQLL</u>WGQGTLVTVSS

TCN-534 (5249_B02) gamma heavy chain Kabat CDRs:

```
CDR 1: GYTIT                (SEQ ID NO: 162)

CDR 2: GIIPMMGTVNYAQKLQG     (SEQ ID NO: 163)

CDR 3: IRYTGQQLL             (SEQ ID NO: 164)
```

TCN-534 (5249_B02) gamma heavy chain Chothia CDRs:

```
CDR 1: GGTFNG                (SEQ ID NO: 165)

CDR 2: GIIPMMGTVN            (SEQ ID NO: 166)

CDR 3: IRYTGQQLL             (SEQ ID NO: 164)
```

TCN-534 (5249_B02) Light chain variable region nucleotide sequence:

(SEQ ID NO: 167)
GACATCCAGATGACCCAGTCTCCTTCCACCCTGTCGGCATCTATAGGAGA
CAGAGTCACCATCACTTGCCGGGCCAGTCAGAGTATTGCAAGTTGGTTGG
CCTGGTATCAGCAAAAACCAGGGAAAGCCCCTAAGCTCCTGATCTATGAG

-continued

```
GCAGTTAATTTAGAAAGTGGGGTCCCATCAAGGTTCAGCGGCAGTGGATC
TGGGACAGATTTCACTCTCACCATCAGCAGCCTGCAGCCCGATGATTTTG
CAACTTATTTCTGCCAACATTATGGTACTATTTCTCAGACCTTCGGCGGA
GGGACCAAGGTGGAGATCAAA
```

TCN-534 (5249_B02) light chain variable region amino acid sequence (Kabat CDRs in bold, Chothia CDRs underlined)

(SEQ ID NO: 168)
DIQMTQSPSTLSASIGDRVTITCRASQSIASWLAWYQQKPGKAPKLLIYEAVNLESGVPSRFSGSGSGTDFTLTISSLQPDDFATYFCQHYGTISQTFGG GTKVEIK

TCN-534 (5249_B02) Light chain Kabat CDRs:

```
    CDR 1: RASQSIASWLA      (SEQ ID NO: 169)
    CDR 2: EAVNLES          (SEQ ID NO: 170)
    CDR 3: QHYGTISQT        (SEQ ID NO: 171)
```

TCN-534 (5249_B02) Light chain Chothia CDRs:

```
    CDR 1: RASQSIASWLA      (SEQ ID NO: 169)
    CDR 2: EAVNLES          (SEQ ID NO: 170)
    CDR 3: QHYGTISQT        (SEQ ID NO: 171)
```

TCN-535 (5246_P19) heavy chain variable region nucleotide sequence:

(SEQ ID NO: 172)
```
CAGGTCCAGCTGGTGCAATCTGGGAGTGAGGTGAAGAAGCCTGGGACCTC
GGTGAAGGTCTCCTGCACGGCCTCTGGAAGTGTCTTCACCAATTATGGAA
TTAGTTGGGTGCGACAGGCCCCTGGACAAGGGCTTGAGTGGATGGGAGGG
ATCATCCCTCTCTTTGGCGCAGCCAAGTACGCACAGAAATTCCAGGGCAG
AGTCACCATCACAGCGGACGAATCCACGAAGACAGTCTACATGGAGCTGA
GCAGGCTGACATCTAAAGACACGGCCATATATTTCTGTGCGAAGGCCCCC
CGTGTCTACGAGTACTACTTTGATCAGTGGGGCCAGGGAACCCCAGTCAC
CGTCTCCTCA
```

TCN-535 (5246_P19) gamma heavy chain variable region amino acid sequence: (Kabat CDRs in bold, Chothia CDRs underlined)

(SEQ ID NO: 173)
QVQLVQSGSEVKKPGTSVKVSCTAS_GSVFT_NYGISWVRQAPGQGLEWMGGIIPLFGAAKYAQKFQGRVTITADESTKTVYMELSRLTSKDTAIYFCAKAPRVYEYYFDQWGQGTPVTVSS

TCN-535 (5246_P191 gamma heavy chain Kabat CDRs:

```
    CDR 1: NYGIS            (SEQ ID NO: 174)
    CDR 2: GIIPLFGAAKYAQKFQG (SEQ ID NO: 175)
    CDR 3: APRVYEYYFDQ      (SEQ ID NO: 176)
```

TCN-535 (5246_P19) gamma heavy chain Chothia CDRs:

```
    CDR 1: GSVFTN           (SEQ ID NO: 177)
    CDR 2: GIIPLFGAAK       (SEQ ID NO: 178)
    CDR 3: APRVYEYYFDQ      (SEQ ID NO: 176)
```

TCN-535 (5246_P19) light chain variable region nucleotide sequence:

(SEQ ID NO: 179)
```
GAAATTGTGTTGACGCAGTCTCCAGGCACCCTGTCTTTGTCTCCAGGGGA
AAGAGCCACCCTCTCCTGCAGGGCCAGTCAGAGTGTTAGCAGCAGTCAAT
TAGCCTGGTACCAGCAAAAACCTGGCCAGGCTCCCAGGCTCATCATCTAT
GGTGCGTCCACCAGGGCCACTGGCATCCCAGACAGGTTCAGTGGAAGTGG
GTCTGGGACAGACTTCACTCTCACCATCGGCAGACTGGAGCCTGAAGATT
TTGCAGTGTTTTTCTGTCAGCAGTATAGTACCTCACCTCCGACGTTCGGC
CAAGGGACCAAGGTGGATTTCAAA
```

TCN-535 (5246_P19) light chain variable region amino acid sequence (Kabat CDRs in bold, Chothia CDRs underlined)

(SEQ ID NO: 180)
EIVLTQSPGTLSLSPGERATLSCRASQSVSSSQLAWYQQKPGQAPRLIIYGASTRATGIPDRFSGSGSGTDFTLTIGRLEPEDFAVEECQQYSTSPPTFG QGTKVDFK

TCN-535 (5246_P19) Light chain Kabat CDRs:

```
    CDR 1: RASQSVSSSQLA     (SEQ ID NO: 157)
    CDR 2: GASTRAT          (SEQ ID NO: 181)
    CDR 3: QQYSTSPPT        (SEQ ID NO: 182)
```

TCN-535 (5246_P19) Light chain Chothia CDRs:

```
    CDR 1: RASQSVSSSQLA     (SEQ ID NO: 157)
    CDR 2: GASTRAT          (SEQ ID NO: 181)
    CDR 3: QQYSTSPPT        (SEQ ID NO: 182)
```

TCN-536 (5095_N01) heavy chain variable region nucleotide sequence:

(SEQ ID NO: 183)
```
CAGGTGCAGCTGCAGCAGTGGGGCGCAGGACTGTTGAAGCCTTCGGAGAC
CCTGTCCCTCACCTGCGCTGTCTATGGTGGGTCCTTCAGTGTCAGTGGTT
ACTACTGGAGCTGGATCCGCCAGCCCCCAGGGAGGGGGCTGGAGTGGATT
GGGGAAATCAGTCATGGTGGAAGCACCAACTACAACCCGTCCCTCAAGAG
TCGAGTCACCATATCAGTGGACACGACCAAGAACCAGTTCTCCCTGAGAC
TGAGCTCTGTGACCGCCGCGGACACGGCCGTCTATTACTGTGCGAGAGGG
ACAGACCCTGACACGGAAGTATATTGTCGTGTTGGTAACTGCGCGGCCTT
TGACTACTGGGGCCAGGGAAGCCTGGTCACCGTCTCCTCA
```

TCN-536 (5095_N01) gamma heavy chain variable region amino acid sequence: (Kabat CDRs in bold, Chothia CDRs underlined)

(SEQ ID NO: 184)
QVQLQQWGAGLLKPSETLSLTCAVY<u>GGSFSVSGYYWS</u>WIRQPPGRGLEWIGEISHGGSTNYNPSLKSRVT
ISVDTTKNQFSLRLSSVTAADTAVYYCARGTDPDTEVYCRVGNCAAFDYWGQGSLVTVSS

TCN-536 (5095_N01) gamma heavy chain Kabat CDRs:

CDR 1: VSGYYWS (SEQ ID NO: 185)
CDR 2: EISHGGSTNYNPSLKS (SEQ ID NO: 186)
CDR 3: GTDPDTEVYCRVGNCAAFDY (SEQ ID NO: 187)

TCN-536 (5095_N01) gamma heavy chain Chothia CDRs:

CDR 1: GGSFSVSG (SEQ ID NO: 188)
CDR 2: EISHGGSTN (SEQ ID NO: 189)
CDR 3: GTDPDTEVYCRVGNCAAFDY (SEQ ID NO: 187)

TCN-536 (5095_N01) light chain variable region nucleotide sequence:

(SEQ ID NO: 190)
GAAATTATATTGGCGCAGTCTCCAGGCACCCTGTCTTTGTCTCCAGGGGAGAGAGCCACCCTCTCCTGCAGGGCCAG
CCAGTTTGTTAGCACCAGATCCCTGGCCTGGTACCAGCAGAGACCTGGCCAGGCTCCCAGACTCCTCATCTATGGTG
CATCCAGCAGGGCCACTGGCATCCCAGACAGGTTCAGTGGCAGTGGGTCTGGGACAGACTTCACGCTCACCATCAGC
AGACTGGAGCCTGAAGATTTTGCAGTGTATTACTGTCAGCACTATGGTTACTCACCTAGGTACGCTTTTGGCCAGGG
GTCCAAGGTTGAGATCAAA

TCN-536 (5095_N01) light chain variable region amino acid sequence (Kabat CDRs in bold, Chothia CDRs underlined)

(SEQ ID NO: 191)
EIILAQSPGTLSLSPGERATLSC<u>RASQFVSTRSLA</u>WYQQRPGQAPRLLIY<u>GASSRAT</u>GIPDRFSGSGSGTDFT
LTISRLEPEDFAVYYC<u>QHYGYSPRYA</u>FGQGSKVEIK

TCN-536 (5095_N01) Light chain Kabat CDRs:

CDR 1: RASQFVSTRSLA (SEQ ID NO: 192)
CDR 2: GASSRAT (SEQ ID NO: 30)
CDR 3: QHYGYSPRYA (SEQ ID NO: 193)

TCN-536 (5095_N01) Light chain Chothia CDRs:

CDR 1: RASQFVSTRSLA (SEQ ID NO: 192)
CDR 2: GASSRAT (SEQ ID NO: 30)
CDR 3: QHYGYSPRYA (SEQ ID NO: 193)

TCN-537 (3194_D21) heavy chain variable region nucleotide sequence:

(SEQ ID NO: 194)
CAGGTGCAGCTCCAACAGTGGGGCTCAGGACTGTTGAAGCCTTCGGAGACCCTGTCCCTCACCTGCGCTGTCTATGG
TGGGTCCTTCAGAGATGACTACTGGACCTGGATTCGCCAGCCCCCAGGCAAGGGGCTGGAGTGGATTGGGGAAATCA
ATCATAGTGGAAGAACCAACTACAACCCGTCCCTCAAGAGTCGAGTCACCATATCAGTAGACACGTCCCTGAAACAG

-continued
```
TTCTCCTTGAAGGTGATTTCTGTGACCGCCGCGGACACGGCTGTTTATTACTGTGCGAGAGGGACGAGCCATGTTTC

CCGGTATTTTGATTGGTTACCACCCACCAACTGGTTCGACCCCTGGGGCCAGGGAACCCAGGTCACCGTCTCGAGC
```

TCN-537 (3194_D21) gamma heavy chain variable region amino acid sequence: (Kabat CDRs in bold, Chothia CDRs underlined)

```
                                                              (SEQ ID NO: 195)
QVQLQQWGSGLLKPSETLSLTCAVYGGSFRDDYWTWIRQPPGKGLEWIGEINHSGRTNYNPSLKSRVTIS

VDTSLKQFSLKVISVTAADTAVYYCARGTSHVSRYFDWLPPTNWFDPWGQGTQVTVSS
```

TCN-537 (3194_D21) gamma heavy chain Kabat CDRs:

```
CDR 1: DDYWT                      (SEQ ID NO: 196)

CDR 2: EINHSGRTNYNPSLKS           (SEQ ID NO: 197)

CDR 3: GTSHVSRYFDWLPPTNWFDP       (SEQ ID NO: 198)
```

TCN-537 (3194_D21) gamma heavy chain Chothia CDRs:

```
CDR 1: GGSFRD                     (SEQ ID NO: 199)

CDR 2: EINHSGRTN                  (SEQ ID NO: 200)

CDR 3: GTSHVSRYFDWLPPTNWFDP       (SEQ ID NO: 198)
```

TCN-537 (3194_D21) light chain variable region nucleotide sequence:

```
                                                              (SEQ ID NO: 201)
GACATTGTGTTGACGCAGTCTCCAGGCACCCTGTCTTTGTCTCCAGGGGAAAGAGCCACCCTCTCCTGCAGGGCCAG

TCAGAGTGTTAGCAGCAGCTACTTAGCCTGGTACCAGCAGAAACCTGGCCAGGCTCCCAGGCTCGTCATGTATGGTG

CAGCCACCAGGGCCACTGGCATCCCAGACAGGTTCAGTGGCAGTGGGTCTGGGCCAGACTTCACTCTCACCATCAGC

AGACTGGAGCCTGAAGATTTTGCAATGTATTACTGTCAGCAGTATGGTAACTCACCGATCACCTTCGGCCAAGGGAC

ACGACTGGAGATCAAA
```

TCN-537 (3194_D21) light chain variable region amino acid sequence (Kabat CDRs in bold, Chothia CDRs underlined)

```
                                                              (SEQ ID NO: 202)
DIVLTQSPGTLSLSPGERATLSCRASQSVSSSYLAWYQQKPGQAPRLVMYGAATRATGIPDRFSGSGSGPD

FTLTISRLEPEDFAMYYCQQYGNSPITFGQGTRLEIK
```

TCN-537 (3194_D21) light chain Kabat CDRs:

```
CDR 1: RASQSVSSSYLA               (SEQ ID NO: 203)

CDR 2: GAATRAT                    (SEQ ID NO: 204)

CDR 3: QQYGNSPIT                  (SEQ ID NO: 205)
```

TCN-537 (3194_D21) Light chain Chothia CDRs:

```
CDR 1: RASQSVSSSYLA               (SEQ ID NO: 203)

CDR 2: GAATRAT                    (SEQ ID NO: 204)

CDR 3: QQYGNSPIT                  (SEQ ID NO: 205)
```

TCN-538 (3206_O17) heavy chain variable region nucleotide sequence:

```
                                                              (SEQ ID NO: 206)
CAGATCACCTTGAAGGAGTCTGGTCCTACACTGGTGAAACCCACACAGACCCTCACACTGACCTGCGTCTTCTCTGG

GTTCTCACTCAGCATTACTGGAGTGCGTGTGGGCTGGATCCGTCAGCCCCCAGGAAAGGCCCTGGAGTGGCTTGCAC

TCATTTCTTGGGATGATGAAAAGCACTACAGCCCATCTCTGCAGAGTAGGCTCACCATCACCAAGGACACCTCCAAA
```

```
AACCAGGTGGTCCTTACAATGACCAACCTGGACCCTGTCGACACAGCCACATATTACTGTGCACGGTCAACCGACAG

GGGCCACGTCTTACGATATTTTGGCTGGATGTTACCGGGTGATGCATTTGATGTCTGGGGCCAAGGGACAATGGTCA

CCGTCTCGAGC
```

TCN-538 (3206_O17) gamma heavy chain variable region amino acid sequence: (Kabat CDRs in bold, Chothia CDRs underlined)

(SEQ ID NO: 207)
```
QITLKESGPTLVKPTQTLTLTCVFSGFSLSITGVRVGWIRQPPGKALEWLALISWDDEKHYSPSLQSRLTIT

KDTSKNQVVLTMTNLDPVDTATYYCARSTDRGHVLRYFGWMLPGDAFDVWGQGTMVTVSS
```

TCN-538 (3206_O17) gamma heavy chain Kabat CDRs:

```
CDR 1: ITGVRVG              (SEQ ID NO: 208)

CDR 2: LISWDDEKHYSPSLQS     (SEQ ID NO: 209)

CDR 3: STDRGHVLRYFGWMLPGDAFDV (SEQ ID NO: 210)
```

TCN-538 (3206_O17) gamma heavy chain Chothia CDRs:

```
CDR 1: GFSLSITG              (SEQ ID NO: 211)

CDR 2: LISWDDEKH             (SEQ ID NO: 212)

CDR 3: STDRGHVLRYFGWMLPGDAFDV (SEQ ID NO: 210)
```

TCN-538 (3206_O17) light chain variable region nucleotide sequence:

(SEQ ID NO: 213)
```
GACATCGTGATGACCCAGTCTCCAGACTTCCTGCCTGTGTCTCTGGGCGAGAGGGCCACCATCAACTGCAAGTCCAG

CCAGAGAGTTTTATACAGCTCCAACAATAAAAACTACTTAGCTTGGTACCAGCTGAAACCAGGGCAGCCTCCTAAGT

TGATCATTTATTGGGCATCTACCCGGGAATCCGGGGTCCCTGACCGATTCAGTGGCAGCGGGTCTGGGACAGAATTC

ACTCTCACCATCAGCAGCCTGCAGGCTGAAGATGTGGCAGTTTATTACTGTCAACAATATTATAGTCGTCCGTACAC

TTTTGGCCAGGGGACCAAGCTCGAGATCAAA
```

TCN-538 (3206_O17) light chain variable region amino acid sequence (Kabat CDRs in bold, Chothia CDRs underlined)

(SEQ ID NO: 214)
```
DIVMTQSPDFLPVSLGERATINCKSSQRVLYSSNNKNYLAWYQLKPGQPPKLIIYWASTRESGVPDRFSGS

GSGTEFTLTISSLQAEDVAVYYCQQYYSRPYTFGQGTKLEIK
```

TCN-538 (3206_O17) Light chain Kabat CDRs:

```
CDR 1: KSSQRVLYSSNNKNYLA    (SEQ ID NO: 215)

CDR 2: WASTRES              (SEQ ID NO: 216)

CDR 3: QQYYSRPYT            (SEQ ID NO: 217)
```

TCN-538 (3206_O17) Light chain Chothia CDRs:

```
CDR 1: KSSQRVLYSSNNKNYLA    (SEQ ID NO: 215)

CDR 2: WASTRES              (SEQ ID NO: 216)

CDR 3: QQYYSRPYT            (SEQ ID NO: 217)
```

TCN-539 (5056_A08) heavy chain variable region nucleotide sequence:

```
                                                         (SEQ ID NO: 218)
CAGGTGCAGCTGGTGGAGTCTGGGGGAGGCGTGGTCCAGCCTGGGAGGTCCCTGAGACTCTCCTGTGCAGCCTCTGA

AATCACCTTCATTACCTATGCTATGCACTGGGTCCGCCAGGCCCCAGGCAAGGGGCTGGAGTGGGTGGCACTTATAT

CAGATGATGGAAGCAATAAATTCTACGCAGACTCCGTGAAGGGCCGATTCACCATCTCCAGAGACAATTCCAAGAAC

ACGCTGTATCTGCAAATGAACAGCCTGAGAGCTGAGGACACGGCTGCTTATTACTGTGCGAGAGAAGGGGTTTACTT

TGATTCGGGGACTTATAGGGGCTACTTTGACTACTGGGGCCAGGAAACCCTGGTCACCGTCTCGAGC
```

TCN-539 (5056_A08) gamma heavy chain variable region amino acid sequence: (Kabat CDRs in bold, Chothia CDRs underlined)

```
                                                         (SEQ ID NO: 219)
QVQLVESGGGVVQPGRSLRLSCAASEITFITYAMHWVRQAPGKGLEWVALISDDGSNKFYADSVKGRFTI

SRDNSKNTLYLQMNSLRAEDTAAYYCAREGVYFDSGTYRGYFDYWGQETLVTVSS
```

TCN-539 (5056_A08) gamma heavy chain Kabat CDRs:

```
CDR 1: TYAMH                (SEQ ID NO: 220)

CDR 2: LISDDGSNKFYADSVKG    (SEQ ID NO: 221)

CDR 3: EGVYFDSGTYRGYFDY     (SEQ ID NO: 222)
```

TCN-539 (5056_A08) gamma heavy chain Chothia CDRs:

```
CDR 1: EITFIT               (SEQ ID NO: 223)

CDR 2: LISDDGSNKF           (SEQ ID NO: 224)

CDR 3: EGVYFDSGTYRGYFDY     (SEQ ID NO: 222)
```

TCN-539 (5056_A08) light chain variable region nucleotide sequence:

```
                                                         (SEQ ID NO: 225)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCCACTGGCCTCCGATCACCTTCGGCCAAGGGAC

ACGACTGGAGATCAAA
```

TCN-539 (5056_A08) light chain variable region amino acid sequence (Kabat CDRs in bold, Chothia CDRs underlined)

(SEQ ID NO: 226)
EIVLTQSPATLSLSPGERATLSCRASQSVSSYLAWYQQKPGQAPRLLIYDASNRATGIPARFSGSGSGTDFTL
TISSLEPEDFAVYYCQQRSHWPPITFGQGTRLEIK

TCN-539 (5056_A08) Light chain Kabat CDRs:

CDR 1: RASQSVSSYLA (SEQ ID NO: 227)
CDR 2: DASNRAT (SEQ ID NO: 228)
CDR 3: QQRSHWPPIT (SEQ ID NO: 229)

TCN-539 (5056_A08) Light chain Chothia CDRs:

CDR 1: RASQSVSSYLA (SEQ ID NO: 227)
CDR 2: DASNRAT (SEQ ID NO: 228)
CDR 3: QQRSHWPPIT (SEQ ID NO: 229)

TCN-540 (5060_F05) heavy chain variable region nucleotide sequence:

(SEQ ID NO: 230)
CAGGTGCAGCTGGTACAATCTGGGGGAGGCGTGGTCCAGCCTGGGAGGTCCCTGAGACTCTCCTGTGCAGCCTCTGG
ATTCACCTTCAGTAGCTACGCCATGCACTGGGTCCGCCAGGCTCCAGGCAAGGGGCTGGAGTGGGTGGCTATTATAT
CATACGACGGAAATGATCAATACTATACAGACTCCGTGAAGGGCCGATTCACCATCTCCAGAGACAGCTCCAAGTG
TATCTCCAAATGCACAGGCTGAGACCTGAGGACACGGCTGTTTATTACTGTGCGAAAGAATTTGAAACTAGTGGTTA
TTTTCATGGGAGTTTTGACTACTGGGGCCAGGGAATCCTGGTCACCGTCTCGAGC

TCN-540 (5060_F05) gamma heavy chain variable region amino acid sequence: (Kabat CDRs in bold, Chothia CDRs underlined)

(SEQ ID NO: 231)
QVQLVQSGGGVVQPGRSLRLSCAAS<u>GFTFSS</u>SYAMHWVRQAPGKGLEWVAI<u>ISYDGNDQY</u>YTDSVKGRF
TISRDSSKVYLQMHRLRPEDTAVYYCAKEFETSGYFHGSFDYWGQGILVTVSS

TCN-540 (5060_F05) gamma heavy chain Kabat CDRs:

CDR 1: SYAMH (SEQ ID NO: 232)
CDR 2: IISYDGNDQYYTDSVKG (SEQ ID NO: 233)
CDR 3: EFETSGYFHGSFDY (SEQ ID NO: 234)

TCN-540 (5060_F05) gamma heavy chain Chothia CDRs:

CDR 1: GFTFSS (SEQ ID NO: 235)
CDR 2: IISYDGNDQY (SEQ ID NO: 236)
CDR 3: EFETSGYFHGSFDY (SEQ ID NO: 234)

TCN-540 (5060_F05) light chain variable region nucleotide sequence:

(SEQ ID NO: 237)
CAGTCTGCCCTGACTCAGCCTGCCTCCGTGTCTGGGTCTCCTGGACAGTCGATCACCATCTCCTGCACTGGAACCAG
CAGTGACGTTGGTGGTTATAACTATGTCTCCTGGTACCAACAACACCCAGGCAAAGCCCCCAAACTCTTGATTTATG
AGGTCACTAATTGGCCCTCAGGGGTTTCTAATCGCTTCTCTGGCTCCAAGTCTGGCAACACGGCCTCCCTGACAATC
TCTGGGCTCCAGGCTGAGGACGAGGCTGACTATTACTGCAGCTCATATGCGGGCAGCAGCACTTGGGTGTTCGGCGG
AGGGACCAGGGTGACCGTTCTA

TCN-540 (5060_F05) light chain variable region amino acid sequence (Kabat CDRs in bold, Chothia CDRs underlined)

(SEQ ID NO: 238)
QSALTQPASVSGSPGQSITISCTGTSSDVGGYNYVSWYQQHPGKAPKLLIYEVTNWPSGVSNRFSGSKSGN
TASLTISGLQAEDEADYYCSSYAGSSTWVFGGGTRVTVL

TCN-540 (5060_F05) Light chain Kabat CDRs:

```
CDR 1: TGTSSDVGGYNYVS    (SEQ ID NO: 239)
CDR 2: EVTNWPS           (SEQ ID NO: 240)
CDR 3: SSYAGSSTWV        (SEQ ID NO: 241)
```

TCN-540 (5060_F05) Light chain Chothia CDRs:

```
CDR 1: TGTSSDVGGYNYVS    (SEQ ID NO: 239)
CDR 2: EVTNWPS           (SEQ ID NO: 240)
CDR 3: SSYAGSSTWV        (SEQ ID NO: 241)
```

TCN-541 (5062_M11) heavy chain variable region nucleotide sequence:

(SEQ ID NO: 242)
CAGGTGCAGCTGCAGGAGTCGGGCCCAGGACTGGTGAAGCCTTCGGAGACCCTGTCCCTCACCTGCACTGTCTCTGG
TGGCTCCATCAATAGTTACTACTGGAACTGGATCCGGCAGCCCCCAGGGAAGGGACTGGAGTGGATTGGCTATATCT
ATCACAGTGGGAGCACCAACTACAACCCCTCCCTCAAGAGTCGAGTCACCATTTCGGTAGACACGTCCAAGAACCAG
TTCTCCCTGCAGCTGAGCTCTGTGACCGCCGCAGACACGGCCGTGTATTACTGTGCGAGACTCCGGACGGACTACGG
TGACCCCGACTCGGTATACTACTACGGTATGGACGTCTGGGGCCAAGGGACCACGGTCACCGTCTCGAGC

TCN-541 (5062_M11) gamma heavy chain variable region amino acid sequence: (Kabat CDRs in bold, Chothia CDRs underlined)

(SEQ ID NO: 243)
QVQLQESGPGLVKPSETLSLTCTVS<u>GGSINS</u>YYWNWIRQPPGKGLEWIGYIYHSGSTNYNPSLKSRVTISVD
TSKNQFSLQLSSVTAADTAVYYCARLRTDYGDPDSVYYYGMDVWGQGTTVTVSS

TCN-541 (5062_M11) gamma heavy chain Kabat CDRs:

```
CDR 1: SYYWN                (SEQ ID NO: 244)
CDR 2: YIYHSGSTNYNPSLKS     (SEQ ID NO: 245)
CDR 3: LRTDYGDPDSVYYYGMDV   (SEQ ID NO: 246)
```

TCN-541 (5062_M11) gamma heavy chain Chothia CDRs:

```
CDR 1: GGSINS               (SEQ ID NO: 247)
CDR 2: YIYHSGSTN            (SEQ ID NO: 248)
CDR 3: LRTDYGDPDSVYYYGMDV   (SEQ ID NO: 246)
```

TCN-541 (5062_M11) light chain variable region nucleotide sequence:

(SEQ ID NO: 249)
TCCTATGAGCTGACACAGCCACCCTCGGTGTCAGTGTCCCCAGGACAGACGGCCAGGATCACCTGCTCTGGAGATGC
ATTGCCAAAGCAAAATGCTTATTGGTACCAGCAGAAGCCAGGCCAGGCCCCTGTGCTGCTGATATATAAAGACAGTG
AGAGGCCCTCAGGGATCCCTGAGCGATTCTCTGGCTCCAGCTCAGGGACAACAGTCACGTTGACCATCAGTGGAGTC
CAGGCAGAGGACGAGGCTGACTATTACTGTCAATCAGCAGACAGCAGTGGTACTTCTTGGGTGTTCGGCGGAGGGAC
CAAACTGACCGTTCTA

TCN-541 (5062_M11) light chain variable region amino acid sequence (Kabat CDRs in bold, Chothia CDRs underlined)

(SEQ ID NO: 250)
SYELTQPPSVSVSPGQTARITCSGDALPKQNAYWYQQKPGQAPVLLIYKDSERPSGIPERFSGSSSGTTVTL

TISGVQAEDEADYYCQSADSSGTSWVFGGGTKLTVL

TCN-541 (5062_M11) light chain Kabat CDRs:

```
CDR 1:   SGDALPKQNAY       (SEQ ID NO: 251)
CDR 2:   KDSERPS           (SEQ ID NO: 252)
CDR 3:   QSADSSGTSWV       (SEQ ID NO: 253)
```

TCN-541 (5062_M11) Light chain Chothia CDRs:

```
CDR 1:   SGDALPKQNAY       (SEQ ID NO: 251)
CDR 2:   KDSERPS           (SEQ ID NO: 252)
CDR 3:   QSADSSGTSWV       (SEQ ID NO: 253)
```

TCN-542 (5079_A16) heavy chain variable region nucleotide sequence:

(SEQ ID NO: 254)
CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTAATTACTACTGGAACTGGGTCCGCCAGCACCCAGGGAAGGGCCTGGAGTGGATTGGGT

ACATCTATTACAGAGGGAGCACCTTCTACAACCCGTCCCTCAAGAGTCGAGTGACCATATCAATAGACACGTCTAAG

AACCAGTTCTCCCTGAGGCTGAGCTCTGTGACGGCCGCGGACACGGCCGTGTATTACTGTGCGAAGGATACAAGGTC

GAGCCTAGACAATTACCAGTACGGTATGGACGTCTGGGGCCAAGGGACCACGGTCACCGTCTCGAGC

TCN-542 (5079_A16) gamma heavy chain variable region amino acid sequence: (Kabat CDRs in bold, Chothia CDRs underlined)

(SEQ ID NO: 255)
QVQLQESGPGLVKPSQTLSLTCTVS<u>GGSIS</u>SGNYYWNWVRQHPGKGLEWIGYIYYRGSTFYNPSLKSRVTI

SIDTSKNQFSLRLSSVTAADTAVYYCAKDTRSSLDNYQYGMDVWGQGTTVTVSS

TCN-542 (5079_A16) gamma heavy chain Kabat CDRs:

```
CDR 1:   SGNYYWN           (SEQ ID NO: 256)
CDR 2:   YIYYRGSTFYNPSLKS  (SEQ ID NO: 257)
CDR 3:   DTRSSLDNYQYGMDV   (SEQ ID NO: 258)
```

TCN-542 (5079_A16) gamma heavy chain Chothia CDRs:

```
CDR 1:   GGSISSGN          (SEQ ID NO: 259)
CDR 2:   YIYYRGSTF         (SEQ ID NO: 260)
CDR 3:   DTRSSLDNYQYGMDV   (SEQ ID NO: 258)
```

TCN-542 (5079_A16) light chain variable region nucleotide sequence:

(SEQ ID NO: 261)
CAGACTGTGGTGACTCAGGAGCCCTCACTGACTGTGTCCCCAGGAGGGACAGTCACTCTCACCTGTGCTTCCAGCAC

TGGAGCAGTCACCAGTAGTTACTTTCCAAACTGGTTCCAGCAGAAACCTGGACAAGCGCCCAGGCCACTGATTTATA

GTACAACTATCAGACACTCCTGGACCCCGGCCCGATTCTCAGGCTCCCTCCTTGGGGGCAAAGCTGCCCTGACACTG

TCAGGTGTGCAGCCTGAGGACGAGGCTGACTATTACTGCCTGCTCTACTCTGGTGGTGATCCAGTGGCTTTCGGCGG

AGGGACCAAACTGACCGTTCTA

TCN-542 (5079_A16) light chain variable region amino acid sequence (Kabat CDRs in bold, Chothia CDRs underlined)

(SEQ ID NO: 262)
QTVVTQEPSLTVSPGGTVTLTCASSTGAVTSSYFPNWFQQKPGQAPRPLIYSTTIRHSWTPARFSGSLLGGK

AALTLSGVQPEDEADYYCLLYSGGDPVAFGGGTKLTVL

TCN-542 (5079_A16) Light chain Kabat CDRs:

```
CDR 1:    ASSTGAVTSSYFPN    (SEQ ID NO: 263)

CDR 2:    STTIRHS           (SEQ ID NO: 264)

CDR 3:    LLYSGGDPVA        (SEQ ID NO: 265)
```

TCN-542 (5079_A16) Light chain Chothia CDRs:

```
CDR 1:    ASSTGAVTSSYFPN    (SEQ ID NO: 263)

CDR 2:    STTIRHS           (SEQ ID NO: 264)

CDR 3:    LLYSGGDPVA        (SEQ ID NO: 265)
```

TCN-543 (5081_G23) heavy chain variable region nucleotide sequence:

(SEQ ID NO: 266)
```
CAGGTTCATCTGGTGCAGTCTGGAGCTGAGGTGAGGAAGCCTGGGGACTCAGTGAAGGTCTCCTGTAAGACTTCTGG

TTACACCTTTTCCACCTATCCTGTCGCCTGGGTGCGACAGGTCCCCGGACAAGGGCTTGAGTGGATGGGATGGATCA

GCACTTACAATGGAAACACAAACTTTGCACAGAACTTCCAGGGCAGAGTCACCCTGACCACAGACACAACCACGAAC

ACAGCCTACATGGAAGTGAGGAGCCTGAAATTTGACGACACGGCCGTCTATTACTGTGCGAGAGTGGAAGGCTCGTA

CAGGGATTTTTGGAATAATCAAAACAGATTCGACCCCTGGGGCCAGGGAACCCTGGTCACCGTCTCGAGC
```

TCN-543 (5081_G23) gamma heavy chain variable region amino acid sequence: (Kabat CDRs in bold, Chothia CDRs underlined)

(SEQ ID NO: 267)
QVHLVQSGAEVRKPGDSVKVSCKTSGYTFSTYPVAWVRQVPGQGLEWMGWISTYNGNTNFAQNFQGR

VTLTTDTTTNTAYMEVRSLKFDDTAVYYCARVEGSYRDFWNNQNRFDPWGQGTLVTVSS

TCN-543 (5081_G23) gamma heavy chain Kabat CDRs:

```
CDR 1:    TYPVA                (SEQ ID NO: 268)

CDR 2:    WISTYNGNTNFAQNFQG    (SEQ ID NO: 269)

CDR 3:    VEGSYRDFWNNQNRFDP    (SEQ ID NO: 270)
```

TCN-543 (5081_G23) gamma heavy chain Chothia CDRs:

```
CDR 1:    GYTFST               (SEQ ID NO: 271)

CDR 2:    WISTYNGNTN           (SEQ ID NO: 272)

CDR 3:    VEGSYRDFWNNQNRFDP    (SEQ ID NO: 270)
```

TCN-543 (5081_G23) light chain variable region nucleotide sequence:

(SEQ ID NO: 273)
```
TCCTATGTACTGACTCAGCCACCCTCGGTGTCAGTGGCCCCAGGACAGACGGCCAGGATTTCCTGTGGGGGAAGCAA

CATTGGAGGGAAAAGTGTGCACTGGTACCAGCAGAAGCCAGGCCAGGCCCCTGTGCTGGTCGTCTATGATGATAGCG

GCCGGCCCTCAGGGATCCCTGAGCGATTCTCTGGCTCCAACTCTGGGGACACGGCCACCCTGACCATCAGCAGGGTC

GAAGCCGGGGATGAGGCCGACTATTTCTGTCAGGTGTGGGATAATTTCGGGGGAGTCTTCGGAACTGGGACCAAGGT

CACCGTTCTA
```

TCN-543 (5081_G23) light chain variable region amino acid sequence (Kabat CDRs in bold, Chothia CDRs underlined)

(SEQ ID NO: 274)
SYVLTQPPSVSVAPGQTARISCGGSNIGGKSVHWYQQKPGQAPVLVVYDDSGRPSGIPERFSGSNSGDTAT

LTISRVEAGDEADYFCQVWDNFGGVFGTGTKVTVL

TCN-543 (5081_G23) Light chain Kabat CDRs:

```
                         (SEQ ID NO: 275)
    CDR 1: GGSNIGGKSVH
                         (SEQ ID NO: 276)
    CDR 2: DDSGRPS
                         (SEQ ID NO: 277)
    CDR 3: QVWDNFGGV
```

TCN-543 (5081_G23) Light chain Chothia CDRs:

```
                         (SEQ ID NO: 275)
    CDR 1: GGSNIGGKSVH
                         (SEQ ID NO: 276)
    CDR 2: DDSGRPS
                         (SEQ ID NO: 277)
    CDR 3: QVWDNFGGV
```

TCN-544 (5082_A19) heavy chain variable region nucleotide sequence:

(SEQ ID NO: 278)
CAGGTGCAGCTGCAGGAGTCGGGCCCAGGGCTGGTGAAGCCTTCGGAGACCCTGTCCCTCACCTGCACTGTCTCTCG

TGGCTCCATCGGTCATTACTTCTGGAGCTGGATCCGGCAGCCCCCAGGGAAGGGACTGGAGTGGATTGGTTATATCT

CTTACAGTGGGAGCACCAAGTACAACCCCTCCCTCAGGAGTCGAGTCACCATATCAGTAGACACGTCCAAGAACCAG

TTCTCCCTGAATCTGAACTCTGTCACCGCTACGGACACGGCCCTATATTACTGTGCGAGAGAGGATTACGATATTTT

GACTGGGGCGGGACCCGGTATGGAGGTCTGGGGCCAAGGGACCACGGTCACCGTCTCGAGC

TCN-544 (5082_A19) gamma heavy chain variable region amino acid sequence: (Kabat CDRs in bold, Chothia CDRs underlined)

(SEQ ID NO: 279)
QVQLQESGPGLVKPSETLSLTCTVS<u>RGSIG</u>HYFWSWIRQPPGKGLEWIG<u>YISYSGSTK</u>YNPSLRSRVTISVD

TSKNQFSLNLNSVTATDTALYYCAREDYDILTGAGPGMEVWGQGTTVTVSS

TCN-544 (5082_A19) gamma heavy chain Kabat CDRs:

```
                         (SEQ ID NO: 280)
    CDR 1: HYFWS
                         (SEQ ID NO: 281)
    CDR 2: YISYSGSTKYNPSLRS
                         (SEQ ID NO: 282)
    CDR 3: EDYDILTGAGPGMEV
```

TCN-544 (5082_A19) gamma heavy chain Chothia CDRs:

```
                         (SEQ ID No: 283)
    CDR 1: RGSIGH
                         (SEQ ID NO: 284)
    CDR 2: YISYSGSTK
                         (SEQ ID NO: 282)
    CDR 3: EDYDILTGAGPGMEV
```

TCN-544 (5082_A19) light chain variable region nucleotide sequence:

(SEQ ID NO: 285)
CAGTCTATGTTGACTCAGCCACCCTCAGCGTCTGGGACCCCCGGGCAGAGGGTCACCATCTCTTGTTCTGGGAGCAG

CTCCAACATCGGAAGTAATACTGTCAACTGGTTCAAACATCTCCCAGGAACGGCCCCCAAACTCCTCATCTACAGAA

-continued

```
ATGATCTGCGGCCCTCAGGGGTCCCTGACCGATTCTCTGGCTCCAAGTCTGGCACCTCAGCCTCCCTGGCCATCAGT
GGGCTCCAGTCTGAGGATGAGGCTGATTATTACTGTGCAACATGGGATGACAGCCTGAATGGTTTTTATGTCTTCGG
AACTGGGACCAAAGTCACCGTTCTA
```

TCN-544 (5082_A19) light chain variable region amino acid sequence (Kabat CDRs in bold, Chothia CDRs underlined)

(SEQ ID NO: 286)
QSMLTQPPSASGTPGQRVTISCSGSSSNIGSNTVNWFKHLPGTAPKLLIYRNDLRPSGVPDRFSGSKSGTSA
SLAISGLQSEDEADYYCATWDDSLNGFYVFGTGTKVTVL

TCN-544 (5082_A19) Light chain Kabat CDRs:

```
                              (SEQ ID NO: 287)
         CDR 1: SGSSSNIGSNTVN (SEQ ID NO: 288)
         CDR 2: RNDLRPS (SEQ ID NO: 289)
         CDR 3: ATWDDSLNGFYV
```

TCN-544 (5089_A19) Light chain Chothia CDRs:

```
                              (SEQ ID NO: 287)
         CDR 1: SGSSSNIGSNTVN (SEQ ID NO: 288)
         CDR 2: RNDLRPS (SEQ ID NO: 289)
         CDR 3: ATWDDSLNGFYV
```

TCN-545 (5082_I15) heavy chain variable region nucleotide sequence:

(SEQ ID NO: 290)
```
CAGGTGCAGCTACAGCAGTGGGGCGCAGGACTGTTGAAGCCTTCGGAGACCCTGTCCCTCTCCTGCGCTGTCTTTGG
TGGGTCCTTCAGTGATTACTACTGGACCTGGATACGCCAGCCCCCAGGGAAGGGGCTGGAGTGGATTGGCGAAATCA
ACATAGTGGAAGAACCAACTACAACCCGTCCCTTGAGAGTCGAGTCACCATATCAGTGGACACGTCCAAGAACCAG
TTTTCCCTGAAACTGAGTTCTGTGACCGCCGCGGACACGGCTATATATTATTGTGCGAGAGGGACAGACCCTGACAC
GGAGGGATATTGTCGTAGTGGTAGCTGCTCGGCCTTTGACTTCTGGGGCCAGGGAACCCTGGTCACCGTCTCGAGC
```

TCN-545 (5082_I15) gamma heavy chain variable region amino acid sequence: (Kabat CDRs in bold, Chothia CDRs underlined)

(SEQ ID NO: 291)
QVQLQQWGAGLLKPSETLSLSCAVF<u>GGSFS</u>DYYWTWIRQPPGKGLEWIGEIKHSGRTNYNPSLESRVTIS
VDTSKNQFSLKLSSVTAADTAIYYCARGTDPDTEGYCRSGSCSAFDFWGQGTLVTVSS

TCN-545 (5082_I15) gamma heavy chain Kabat CDRs:

```
                              (SEQ ID NO: 292)
         CDR 1: DYYWT (SEQ ID NO: 293)
         CDR 2: EIKHSGRTNYNPSLES (SEQ ID NO: 294)
         CDR 3: GTDPDTEGYCRSGSCSAFDF
```

TCN-545 (5082_I15) gamma heavy chain Chothia CDRs:

```
                              (SEQ ID NO: 295)
         CDR 1: GGSFSD (SEQ ID NO: 296)
         CDR 2: EIKHSGRTN (SEQ ID NO: 294)
         CDR 3: GTDPDTEGYCRSGSCSAFDF
```

TCN-545 (5082_I15) light chain variable region nucleotide sequence:

(SEQ ID NO: 297)
GAAATTGTGTTGACGCAGTCTCCAGGCACCCTGTCTTTGTCTCCAGGGG

AAAGAGCCACCCTCTCCTGCAGGGCCAGTCACTTTGTGAACTACAGGTC

CTTAGCCTGGTACCAGCAGACACCTGGCCAGGTTCCCAGGCTCCTCATC

TATGGTGCGTCCACCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTTCTGTCAGCAGTATGGTGGCTCACCTAGGTAC

ACTTTTGGCCAGGGGACCAGGCTGGAGATCAAA

TCN-545 (5082_I15) light chain variable region amino acid sequence (Kabat CDRs in bold, Chothia CDRs underlined)

(SEQ ID NO: 298)
EIVLTQSPGTLSLSPGERATLSCRASHFVNYRSLAWYQQTPGQVPRLLI

YGASTRATGIPDRFSGSGSGTDFTLTISRLEPEDFAVYFCQQYGGSPRY

TFGQGTRLEIK

TCN-545 (5082_I15) Light chain Kabat CDRs:

(SEQ ID NO: 299)
CDR 1: RASHFVNYRSLA (SEQ ID NO: 181)
CDR 2: GASTRAT (SEQ ID NO: 300)
CDR 3: QQYGGSPRYT

TCN-545 (5082_I15) Light chain Chothia CDRs:

(SEQ ID NO: 299)
CDR 1: RASHFVNYRSLA (SEQ ID NO: 181)
CDR 2: GASTRAT (SEQ ID NO: 300)
CDR 3: QQYGGSPRYT

TCN-546 (5089_L08) heavy chain variable region nucleotide sequence:

(SEQ ID NO: 301)
CAGGTGCAGCTACAGCAGTGGGGCGCAGGACTGTTGAAGCCTTCGGAGA

CCCTGTCCCTCACCTGCGGTGTCTATGGTGGGTCCCTCAGTGATTACTA

CTGGAGCTGGATCCGCCAGCCCCCAGGGAAGGGGCTGGAGTGGATTGGA

GAAATCAATCATAGTGGAGGCACCAACTACAATCCGTCCCTCAAGAGAC

GAGTCACCATATCAGTAGACACGTCAAAGAAGCAATTCTCCCTGAAGAT

GAACTCTGTGACCGCCGCGGACACGGCTGTATATTACTGTGCGAGAGGG

ACAGACCCTGACACGGAAGTATATTGTCGTGCTGGTAACTGCGCGGCCT

TTGACTTCTGGGGCCAGGGAACCCTGGTCACCGTCTCGAGC

TCN-546 (5089_L08) gamma heavy chain variable region amino acid sequence: (Kabat CDRs in bold, Chothia CDRs underlined)

(SEQ ID NO: 302)
QVQLQQWGAGLLKPSETLSLTCGVY<u>GGSLS</u>DYYWSWIRQPPGKGLEWIG

EINHSGGTNYNPSLKRRVTISVDTSKKQFSLKMNSVTAADTAVYYCARG

TDPDTEVYCRAGNCAAFDFWGQGTLVTVSS

TCN-546 (5089_L08) gamma heavy chain Kabat CDRs:

(SEQ ID NO: 303)
CDR 1: DYYWS (SEQ ID NO: 304)
CDR 2: EINHSGGTNYNPSLKR (SEQ ID NO: 305)
CDR 3: GTDPDTEVYCRAGNCAAFDF

TCN-546 (5089_L081 gamma heavy chain Chothia CDRs:

(SEQ ID NO: 306)
CDR 1: GGSLSD (SEQ ID NO: 307)
CDR 2: EINHSGGTN (SEQ ID NO: 305)
CDR 3: GTDPDTEVYCRAGNCAAFDF

TCN-546 (5089_L08) light chain variable region nucleotide sequence:

(SEQ ID NO: 308)
GAAATTGTGTTGACGCAGTCTCCAGGCACCCTGTCTTTGTCTCCAGGGG

AGAGAGCCACCCTCTCCTGCCGGGCCAGTCACTTTGTTATAGGCAGGGC

TGTAGCCTGGTACCAGCAGAAACCTGGCCAGGCTCCCAGGCTCCTCATC

TACGGTGCATCCAGCAGGGCCACTGGCATCCCGGACAGGTTCAGTGGCA

GTGGGTCTGGGACAGACTTCACTCTCACCATCAGCAGACTGGAGACTGA

AGATTTTGCTGTGTTTTACTGTCAGCACTATGGTAGCTCACCTAGGTAC

GCTTTTGGCCAGGGGACCAAGCTGGAGATCAAA

TCN-546 (5089_L08) light chain variable region amino acid sequence (Kabat CDRs in bold, Chothia CDRs underlined)

(SEQ ID NO: 309)
EIVLTQSPGTLSLSPGERATLSCRASHFVIGRAVAWYQQKPGQAPRLLI

YGASSRATGIPDRFSGSGSGTDFTLTISRLETEDFAVYCQHYGSSPRY

AFGQGTKLEIK

TCN-546 (5089_L08) Light chain Kabat CDRs:

(SEQ ID NO: 310)
CDR 1: RASHFVIGRAVA (SEQ ID NO: 30)
CDR 2: GASSRAT (SEQ ID NO: 311)
CDR 3: QHYGSSPRYAF

TCN-546 (5089_L081 Light chain Chothia CDRs:

CDR 1: RASHFVIGRAVA (SEQ ID NO: 310)

CDR 2: GASSRAT (SEQ ID NO: 30)

CDR 3: QHYGSSPRYAF (SEQ ID NO: 311)

TCN-547 (5092_F11) heavy chain variable region nucleotide sequence:

(SEQ ID NO: 312)
CAGGTGCAGCTGCAGGAGTCGGGCCCAGGACTGGTGAAGCCTTCACAGA
CCCTGTCCCTCACCTGCACTGTCTCTGGTGACTCCATTAGTAGTGTTGA
TCACTACTGGAGCTGGATCCGCCAACACCCAGTGAAGGGCCTGGAGTGG
ATTGGGTTCATGTATTACAGTGCGAGCACCTATTACAACCCGTCCCTCA
AGAGTCGAGTTACCATATCAACGGACACGTCTAAGAACCAGTTCTCCCT
GAGGCTGAGTTCTGTGACTGCCGCGGACACGGCCGTATATTACTGTGCG
AGAGGCACTTGTGCTGGTGACTGCTCCCTTCACTACTACTACTACGGTT
TGGACGTCTGGGGCCAAGGGAGGACGGTCACCGTCTCGAGC

TCN-547 (5092_F11) gamma heavy chain variable region amino acid sequence: (Kabat CDRs in bold, Chothia CDRs underlined)

(SEQ ID NO: 313)
QVQLQESGPGLVKPSQTLSLTCTVS<u>GDSIS</u>SVDHYWSWIRQHPVKGLEW
IGFMYYSASTYYNPSLKSRVTISTDTSKNQFSLRLSSVTAADTAVYYCA
RGTCAGDCSLHYYYYGLDVWGQGRTVTVSS

TCN-547 (5092_F11) gamma heavy chain Kabat CDRs:

CDR 1: SVDHYWS (SEQ ID NO: 314)

CDR 2: FMYYSASTYYNPSLKS (SEQ ID NO: 315)

CDR 3: GTCAGDCSLHYYYYGLDV (SEQ ID NO: 316)

TCN-547 (5092_F11) gamma heavy chain Chothia CDRs:

CDR 1: GDSISSVD (SEQ ID NO: 317)

CDR 2: FMYYSASTY (SEQ ID NO: 318)

CDR 3: GTCAGDCSLHYYYYGLDV (SEQ ID NO: 316)

TCN-547 (5092_F111 light chain variable region nucleotide sequence:

(SEQ ID NO: 319)
GACATCCAGATGACCCAGTCTCCATCCTCCCTGTCTGCATCTGTAGGAGACAGAGTCACCATCACTTGCCGGGCAAG

TCAGAGCATTAGCAGCTATTTAAATTGGTATCAGCACAAACCAGGGAAAGCCCCTAAGGTCCTGATGTATGCTGTAT

CCATTTTGCAAAGTGGGGTCCCATCAAGGTTCAGTGGCAGTGGATCTGGGGCAGATTTCACTCTCACCATCAGCAGT

CTGCAACCTGAAGATTTTGCAACTTACTACTGTCAACAGAGTTACAGTTCCCCGCTCACTTTCGGCGGAGGGACCAA

GGTGGAGATCAAA

TCN-547 (5092_F11) light chain variable region amino acid sequence (Kabat CDRs in bold, Chothia CDRs underlined)

(SEQ ID NO: 320)
DIQMTQSPSSLSASVGDRVTITCRASQSISSYLNWYQHKPGKAPKVLMYAVSILQSGVPSRFSGSGSGADFT
LTISSLQPEDFATYYCQQSYSSPLTFGGGTKVEIK

TCN-547 (5092_F11) Light chain Kabat CDRs:

CDR 1: RASQSISSYLN (SEQ ID NO: 321)

CDR 2: AVSILQS (SEQ ID NO: 322)

CDR 3: QQSYSSPLT (SEQ ID NO: 323)

TCN-547 (5092_F11) Light chain Chothia CDRs:

CDR 1: RASQSISSYLN (SEQ ID NO: 321)

CDR 2: AVSILQS (SEQ ID NO: 322)

CDR 3: QQSYSSPLT (SEQ ID NO: 323)

TCN-548 (5092_P01) heavy chain variable region nucleotide sequence:

(SEQ ID NO: 324)
```
CAGGTGCAGCTGCAGGAGTCGGGCCCAGGACTGGTGAAGCCTTCGGAGACCCTGTCCCTCACCTGCACTGTCTCTAG
TGGCCCCATGAGTGATTATTACTGGAGCTGGATCCGGCAGCCCCCAGGGAAGGGACTGGAGTGGATTGGGCATGTCT
CTGTCTCTCACGGAGGGAGGACCAAATCCAATCCCTCCGTCATGAGTCGAGTCACCATTTCAGTAGAAACGTCCAAG
AACCAATTCTCCCTGAAACTGACCTCCGTGACCGCTGCGGACACGGCCGTTTATTACTGTGCGAGATTAAATTACTA
TGATAGAAGTGGTTATCATTCGCCTGACGGCCCCTCGAACAACTGGTTCGACCCCTGGGGCCAGGGAACCCTGGTCA
CCGTCTCGAGC
```

TCN-548 (5092_P01) gamma heavy chain variable region amino acid sequence: (Kabat CDRs in bold, Chothia CDRs underlined)

(SEQ ID NO: 325)
QVQLQESGPGLVKPSETLSLTCTVS<u>SGPMSDYYWS</u>WIRQPPGRGLEWIG<u>HVSVSHGGRTK</u>SNPSVMSRVT ISVETSKNQFSLKLTSVTAADTAVYYCAR<u>LNYYDRSGYHSPDGPSNNWFDP</u>WGQGTLVTVSS

TCN-548 (5092_P01) gamma heavy chain Kabat CDRs:

CDR 1: DYYWS (SEQ ID NO: 303)

CDR 2: HVSVSHGGRTKSNPSVMS (SEQ ID NO: 326)

CDR 3: LNYYDRSGYHSPDGPSNNWFDP (SEQ ID NO: 327)

TCN-548 (5092_P01) gamma heavy chain Chothia CDRs:

CDR 1: SGPMSD (SEQ ID NO: 328)

CDR 2: HVSVSHGGRTK (SEQ ID NO: 329)

CDR 3: LNYYDRSGYHSPDGPSNNWFDP (SEQ ID NO: 327)

TCN-548 (5092_P01) light chain variable region nucleotide sequence:

(SEQ ID NO: 330)
```
GACATCGTGATGACCCAGTCTCCAGACTCCCTGGCTGTGTCTCTGGGCGAGAGGGCCACCATCAACTGCAAGTCCAG
CCAGAGTGTTTTATACAGCTCCAACAATAAGAACTACTTAGCTTGGTACCAGCAGAAACCAGGACAGCCTCCTAAGC
TGCTCATTTACTGGGCATCTACCCGGGAATCCGGGGTCCCTGACCGAATCAGCGGCAGCGGGTCTGGGGCAGATTTC
ACTCTCACCATCAGCAGCCTGCAGGCTGAAGATGTGGCAGTTTATTACTGTCAGCAGTATTTTGCTACTCCTCGGAC
GTTCGGCCAAGGGACCAAGGTGGAAATCAAA
```

TCN-548 (5092_P01) light chain variable region amino acid sequence (Kabat CDRs in bold, Chothia CDRs underlined)

(SEQ ID NO: 331)
DIVMTQSPDSLAVSLGERATINCKSSQSVLYSSNNKNYLAWYQQKPGQPPKLLIYWASTRESGVPDRISGS

GSGADFTLTISSLQAEDVAVYYCQQYFATPRTFGQGTKVEIK

TCN-548 (5092_P01) Light chain Kabat CDRs:

```
                              (SEQ ID NO: 332)
CDR 1: KSSQSVLYSSNNKNYLA (SEQ ID NO: 216)
CDR 2: WASTRES (SEQ ID NO: 333)
CDR 3: QQYFATPRT
```

TCN-548 (5092_P01) Light chain Chothia CDRs:

```
                              (SEQ ID NO: 332)
CDR 1: KSSQSVLYSSNNKNYLA (SEQ ID NO: 216)
CDR 2: WASTRES (SEQ ID NO: 333)
CDR 3: QQYFATPRT
```

TCN-549 (5097_P04) heavy chain variable region nucleotide sequence.

(SEQ ID NO: 334)
CAGGTACAGCTGGTGCAGTCTGGGGCTGAGGTGAAGAAGCCTGGGGCCTCAGTGAAGGTCTCCTGCAAGGCTTCTGG

ATACACCTTCACCGGCTACTATATGCACTGGGTGCGACAGGCCCCTGGACAAGGGCTTGAGTGGATGGGATGGATCA

ACCCTAACAGTGGTGACACAAACTATGCACAGAAGTTTCAGGGCAGGGTCACCATGACCAGGGACACGTCCATCACC

ACAGCCTACATGGAGCTGAGCAGCCTGAGATCTGACGACACGGCCGTGTATTACTGTGCGAGAGATTCCCCCTATAG

CAGCAGCTGGTCCTTCTTTGACTACTGGGGCCAGGGAACCCCTGGTCACCGTCTCGAGC

TCN-549 (5092_P04) gamma heavy chain variable region amino acid sequence: (Kabat CDRs in bold, Chothia CDRs underlined)

(SEQ ID NO: 335)
QVQLVQSGAEVKKPGASVKVSCKAS<u>GYTFT</u>GYYMHWVRQAPGQGLEWMG<u>WINPNSGDTNYAQKFQG</u>

RVTMTRDTSITTAYMELSSLRSDDTAVYYCAR<u>DSPYSSSWSFFDY</u>WGQGPLVTVSS

TCN-549 (5092_P04) gamma heavy chain Kabat CDRs:

```
CDR 1:                        (SEQ ID NO: 336)
GYYMH

CDR 2:                        (SEQ ID NO: 337)
WINPNSGDTNYAQKFQG

CDR 3:                        (SEQ ID NO: 338)
DSPYSSSWSFFDY
```

TCN-549 (5092_P04) gamma heavy chain Chothia CDRs:

```
CDR 1:                        (SEQ ID NO: 339)
GYTFTG

CDR 2:                        (SEQ ID NO: 340)
WINPNSGDTN

CDR 3:                        (SEQ ID NO: 338)
DSPYSSSWSFFDY
```

TCN-549 (5092_P04) light chain variable region nucleotide sequence:

(SEQ ID NO: 341)
GACATCGTGATGACCCAGTCTCCAGACTCCCTGGCTGTGTCTCTGGGCG

AGAGGGCCACCATCAACTGCAAGTCCAGCCAGAGTGTTTTATACAGCTC

CAACAATAAGAGCCACTTAGCTTGGTACCAGCAGAAACCAGGACAGCCT

CCTAAGTTGCTCATTTACTGGGCATCTACCCGGGAATCCGGGGTCCCTG

ACCGATTCAGTGGCAGCGGGTCTGGGACAGATTTCACCCTCATCATCAG

CAGCCTGCAGGCTGAGGATGTGGCAGTTTATTACTGTCAGCAATATTAT

TTTTCTCCCCTCACTTTCGGCGGAGGGACCAAGGTGGAGATCAAA

TCN-549 (5092_P04) light chain variable region amino acid sequence (Kabat CDRs in bold, Chothia CDRs underlined)

(SEQ ID NO: 342)
DIVMTQSPDSLAVSLGERATINCKSSQSVLYSSNNKSHLAWYQQKPGQP

PKLLIYWASTRESGVPDRFSGSGSGTDFTLIISSLQAEDVAVYYCQQYY

FSPLTFGGGTKVEIK

TCN-549 (5092_P04) Light chain Kabat CDRs:

```
CDR 1:                                  (SEQ ID NO: 343)
KSSQSVLYSSNNKSHLA

CDR 2:                                  (SEQ ID NO: 216)
WASTRES

CDR 3:                                  (SEQ ID NO: 344)
QQYYFSPLT
```

TCN-549 (5092_P04) Light chain Chothia CDRs:

```
CDR 1:                                  (SEQ ID NO: 343)
KSSQSVLYSSNNKSHLA

CDR 2:                                  (SEQ ID NO: 216)
WASTRES

CDR 3:                                  (SEQ ID NO: 344)
QQYYFSPLT
```

TCN-550 (5096_F06) heavy chain variable region nucleotide sequence:

```
                                        (SEQ ID NO: 345)
CAGGTGCAGCTGCAGGAGTCGGGCCCAGGACTGGTGAAGCCTTCGGAGA

CCCTGTCCCTCACCTGCACTGTCTCTGGTGCCTCCATCAATAGTCACTA

CTGGAGCTGGATCCGGCAGCCCCCAGGGAAGGGACTGGAGTGGATTGGG

TATGTCTATTACAGTGGGAGCACCACCTACAACCCCTCCCTCAAGAGTC

GAGTCACCTTATCAGTAGATACGTCCAAGAACCAGTTCTCCCTGAACCT

GAGCTCTGTGACCGCCGCAGACACGGCCTTCTATTACTGTGCGAGACAT

CCCTACGATGTTTTGACTGGTTCCGGGGACTGGTTCGACCCCTGGGGCC

AGGGAACCCTGGTCACCGTCTCGAGC
```

TCN-550 (5096_F06) gamma heavy chain variable region amino acid sequence: (Kabat CDRs in bold, Chothia CDRs underlined)

```
                                        (SEQ ID NO: 346)
QVQLQESGPGLVKPSETLSLTCTVSGASINSHYWSWIRQPPGKGLEWIG

YVYYSGSTTYNPSLKSRVTLSVDTSKNQFSLNLSSVTAADTAFYYCARH

PYDVLTGSGDWFDPWGQGTLVTVSS
```

TCN-550 (5096_F06) gamma heavy chain Kabat CDRs:

```
CDR 1:                                  (SEQ ID NO: 347)
SHYWS

CDR 2:                                  (SEQ ID NO: 348)
YVYYSGSTTYNPSLKS

CDR 3:                                  (SEQ ID NO: 349)
HPYDVLTGSGDWFDP
```

TCN-550 (5096_F06) gamma heavy chain Chothia CDRs:

```
CDR 1:                                  (SEQ ID NO: 350)
GASINSH

CDR 2:                                  (SEQ ID NO: 351)
YVYYSGSTT

CDR 3:                                  (SEQ ID NO: 349)
HPYDVLTGSGDWFDP
```

TCN-550 (5096_F06) light chain variable region nucleotide sequence:

```
                                        (SEQ ID NO: 352)
TCCTATGTTCTGACTCAGGCACCCTCGGTGTCAGTGGCCCCAGGACAGA

CGGCCAGGATTACCTGTGGGGGAAATGCCATTGGAAGTAAAAAAGTTCA

CTGGTACCAGCACAAGGCAGGCCAGGCCCCTGTACTCGTCGTCTATGAT

GATACAGACCGGCCCTCAGGGATCCCTGAGCGATTCTCTGGCTCCAACT

CTTGGAGCACGGCCACCCTGACCATCAACAGGGTCGAAGCCGGGGATGA

GGCCGACTATTACTGTCAGGTGTGGGATTTTACCATTGATCATGTGGTC

TTCGGCGGAGGGACCAAGCTGACCGTTCTA
```

TCN-550 (5096_F06) light chain variable region amino acid sequence (Kabat CDRs in bold, Chothia CDRs underlined)

```
                                        (SEQ ID NO: 353)
SYVLTQAPSVSVAPGQTARITCGGNAIGSKKVHWYQHKAGQAPVLVVYD

DTDRPSGIPERFSGSNSWSTATLTINRVEAGDEADYYCQVWDFTIDHVV

FGGGTKLTVL
```

TCN-550 (5096_F06) Light chain Kabat CDRs:

```
CDR 1:                                  (SEQ ID NO: 354)
GGNAIGSKKVH

CDR 2:                                  (SEQ ID NO: 355)
DDTDRPS

CDR 3:                                  (SEQ ID NO: 356)
QVWDFTIDHVV
```

TCN-550 (5096_F06) Light chain Chothia CDRs:

```
CDR 1:                                  (SEQ ID NO: 354)
GGNAIGSKKVH

CDR 2:                                  (SEQ ID NO: 355)
DDTDRPS

CDR 3:                                  (SEQ ID NO: 356)
QVWDFTIDHVV
```

TCN-551 (5243_D01) heavy chain variable region nucleotide sequence:

```
                                        (SEQ ID NO: 357)
GAGGTGCAACTGGTTCAGTCTGGATCAGAGGTGAAAAAGCCCGGGGAGT

CTCTGAAGATCTCCTGTAAGGGTTCTGGCTACAGCTTTAGCAACTACTG

GATCGGCTGGGTGCGCCACATGCCCGGGAAAGGCCTGGAATGGATGGGG

ATCATTTATCCTGGTGACTCTGATACCAGATACAGCCCGTCCTTCCAAG

GCCAGGTCACCATGTCAGCCGACAAGTCCAGCAGCACCGTCTACCTGCA

GTGGAGCAGCCTGAAGGCCTCGGACACCGCCATTTATTATTGTGCGAGA

CGGGGCGGACATAGTTTTGGATATGGGTCGGGGGGGACACGCACAGTG

AATTCGACTCCTGGGGCCAGGGAACCCTGGTCACCGTCTCGAGC
```

TCN-551 (5243_D01) gamma heavy chain variable region amino acid sequence: (Kabat CDRs in bold, Chothia CDRs underlined)

(SEQ ID NO: 358)
EVQLVQSGSEVKKPGESLKISCKGS<u>GYSFS</u>NYWIGWVRHMPGKGLEWMGIIYPGDSDTRYSPSFQGQVT
MSADKSSSTVYLQWSSLKASDTAIYYCARRGGHSFGYGSGGDTHSEFDSWGQGTLVTVSS

TCN-551 (5243_D01) gamma heavy chain Kabat CDRs:

CDR 1: NYWIG (SEQ ID NO: 359)
CDR 2: IIYPGDSDTRYSPSFQG (SEQ ID NO: 360)
CDR 3: RGGHSFGYGSGGDTHSEFDS (SEQ ID NO: 361)

TCN-551 (5243_D01) gamma heavy chain Chothia CDRs:

CDR 1: GYSFSN (SEQ ID NO: 362)
CDR 2: IIYPGDSDTR (SEQ ID NO: 363)
CDR 3: RGGHSFGYGSGGDTHSEFDS (SEQ ID NO: 361)

TCN-551 (5243_D01) light chain variable region nucleotide sequence:

(SEQ ID NO: 364)
CAGTCTGTATTGACGCAGTCGCCCTCAGTGTCTGCGGCCCCAGGACAGAAGGTCACCATCTCCTGCTCTGGAAGCGA
CTCCAACATTGGTGATTATTTTGTATGTTGGTACCAGCACCTCCCAGGAAAACCCCCCAACTCCTCATCTATGAAA
ATAATAAGCGACCCTCAGGGATTCCTGACCGATTCTCTGGCTCCAAGTCTGGCACGTCAGCCACCCTGGGCATCACC
GGAATCCAGACCGGGGACGAGGCCGATTACTACTGCGCAACTTGGGATGGCAGCCTGAGTGCTTGGGTGTTCGGCGG
AGGGACCAAGCTGACCGTTCTA

TCN-551 (5243_D01) light chain variable region amino acid sequence (Kabat CDRs in bold, Chothia CDRs underlined)

(SEQ ID NO: 365)
QSVLTQSPSVSAAPGQKVTISC<u>SGSDSNIGDYFVC</u>WYQHLPGKPPQLLIY<u>ENNKRPS</u>GIPDRFSGSKSGTSA
TLGITGIQTGDEADYYC<u>ATWDGSLSAWV</u>FGGGTKLTVL

TCN-551 (5243_D01) Light chain Kabat CDRs:

CDR 1: SGSDSNIGDYFVC (SEQ ID NO: 366)
CDR 2: ENNKRPS (SEQ ID NO: 367)
CDR 3: ATWDGSLSAWV (SEQ ID NO: 368)

TCN-551 (5243_D01) Light chain Chothia CDRs:

CDR 1: SGSDSNIGDYFVC (SEQ ID NO: 366)
CDR 2: ENNKRPS (SEQ ID NO: 367)
CDR 3: ATWDGSLSAWV (SEQ ID NO: 368)

TCN-552 (5249_I23) heavy chain variable region nucleotide sequence:

(SEQ ID NO: 369)
CAGGTCCAAGTGGTGCAGTCTGGGGCTGAGGTGAAGAAGCCTGGGTCCTCGGTGAGGGTCTCCTGCCAGGCTTCTGG
AGGCACCTTCATGAATTATGCTATCATTTGGGTGCGACGGGCCCCTGGACAAGGCCTTGAGTGGATGGGAGGGATCA
TCCCTGTCTTTCCTACACCAAACTACGCACAGATGTTCCAGGGCAGAGTCACGATTTCCACGGACGAATCCAGGAGC
ACATCCTTCTTGGAACTGACCAACCTGAGATATGAGGACACGGCCGTTTATTACTGTGCGAGGCGAATTTATCACGG
TGGTAACTCCGGCTTTGACTTCTGGGGCCAGGGAACCCTGGTCACCGTCTCGAGC

TCN-552 (5249_I23) gamma heavy chain variable region amino acid sequence: (Kabat CDRs in bold, Chothia CDRs underlined)

(SEQ ID NO: 370)
QVQVVQSGAEVKKPGSSVRVSCQAS<u>GGTFM</u>NYAIIWVRRAPGQGLEWMG<u>GIIPVFPTPN</u>YAQMFQGRV

TISTDESRSTSFLELTNLRYEDTAVYYCAR<u>RIYHGGNSGFDF</u>WGQGTLVTVSS

TCN-552 (5249_I23) gamma heavy chain Kabat CDRs:

```
CDR 1: NYAII              (SEQ ID NO: 371)
CDR 2: GIIPVFPTPNYAQMFQG  (SEQ ID NO: 372)
CDR 3: RIYHGGNSGFDF       (SEQ ID NO: 373)
```

TCN-552 (5249_I23) gamma heavy chain Chothia CDRs:

```
CDR 1: GGTFMN             (SEQ ID NO: 374)
CDR 2: GIIPVFPTPN         (SEQ ID NO: 375)
CDR 3: RIYHGGNSGFDF       (SEQ ID NO: 373)
```

TCN-552 (5249_I23) light chain variable region nucleotide sequence:

(SEQ ID NO: 376)
GAAATTGTGTTGACACAGTCTCCAGCCACCCTGTCTTTGTCTCCAGGGGAAAGAGCCACCCTCTCCTGCAGGGCCAG

TCAGAGTGTTGGCAACTACTTAGCCTGGTACCAACAGAAACCTGGCCAGGCTCCCAGGCTCCTCATCTATGATTCAT

CCAACAGGGCCCCTGGCATCCCAGCCAGGTTCAGTGGCAGTGGGTCTGGGACAGACTTCACTCTCACCATCAGCAGC

CTCGCGCCTGAAGATTTTGCAGTTTATTACTGTCAGCAGCGTAGCAAGTGGCCTCCCATGTACAGTTTTGGCCATGG

GACCAAGCTGGAGATCAAA

TCN-552 (5249_I23) light chain variable region amino acid sequence (Kabat CDRs in bold, Chothia CDRs underlined)

(SEQ ID NO: 377)
EIVLTQSPATLSLSPGERATLSC<u>RASQSVGNYLA</u>WYQQKPGQAPRLLIY<u>DSSNRAP</u>GIPARFSGSGSGTDFT

LTISSLAPEDFAVYYC<u>QQRSKWPPMYS</u>FGHGTKLEIK

TCN-552 (5249_I23) Light chain Kabat CDRs:

```
CDR 1: RASQSVGNYLA   (SEQ ID NO: 378)
CDR 2: DSSNRAP       (SEQ ID NO: 379)
CDR 3: QQRSKWPPMYS   (SEQ ID NO: 380)
```

TCN-552 (5249_I23) Light chain Chothia CDRs:

```
CDR 1: RASQSVGNYLA   (SEQ ID NO: 378)
CDR 2: DSSNRAP       (SEQ ID NO: 379)
CDR 3: QQRSKWPPMYS   (SEQ ID NO: 380)
```

TCN-553 (5261_C18) heavy chain variable region nucleotide sequence:

(SEQ ID NO: 381)
CAGGTCCAGGTGGTGCAGTCTGGGACTGAGGTGAAGAAGCCTGGGTCCTCGGTGAAGGTCTCCTGCCAGACTTCTGG

AGGCAGGTTCATGAGTTATGCTATCACCTGGGTGCGACAGGCCCCTGGACAAGGGCTTGAGTGGATGGGAGGCATCG

TCCCTGTCTTCGGAACAGCAAACTACGCTCAGAAGTTCCAGGGCAGAGTCACGATCACCACGGACGATTCCACGCGC

ACAGCCTATATGGAGTTGAGCAGCCTGAGAAGTGAGGACACGGCCGTTTATTACTGTGGGTTCCGATACGGCTCTGG

TTACGGGTTTGACTCCTGGGGCCAGGGAACCCTGGTCACCGTCTCGAGC

TCN-553 (5261_C18) gamma heavy chain variable region amino acid sequence: (Kabat CDRs in bold, Chothia CDRs underlined)

(SEQ ID NO: 382)
QVQVVQSGTEVKKPGSSVKVSCQTS<u>GGRFMSYAIT</u>WVRQAPGQGLEWMG<u>GIVPVFGTAN</u>YAQKFQGR

VTITTDDSTRTAYMELSSLRSEDTAVYYCGF<u>RYGSGYGFDS</u>WGQGTLVTVSS

TCN-553 (5261_C18) gamma heavy chain Kabat CDRs:

CDR 1: SYAIT (SEQ ID NO: 383)

CDR 2: GIVPVFGTANYAQKFQG (SEQ ID NO: 384)

CDR 3: RYGSGYGFDS (SEQ ID NO: 385)

TCN-553 (5261_C18) gamma heavy chain Chothia CDRs:

CDR 1: GGRFMS (SEQ ID NO: 386)

CDR 2: GIVPVFGTAN (SEQ ID NO: 387)

CDR 3: RYGSGYGFDS (SEQ ID NO: 385)

TCN-553 (5261_C18) light chain variable region nucleotide sequence:

(SEQ ID NO: 388)
GAAATTGTATTGACGCAGTCTCCAGGCACCCTGTCTTTGTCTCCAGGGGAAAGAGCCACCCTCTCCTGCAGGGCCAG

TCAGAGTGTTAGTAGCAGCTACTTAGCCTGGTATCAGAAGAAACCTGGCCAGGCTCCCAGGCTCCTCATCTATGGTG

CTTCCACTAGGGCCACTGGCATCCCGGACCGGTTCACTGGCAGTGGGTCTGGGACAGACTTCACTCTCAGCATCAGT

AGACTGGAGCCTGAAGATTTTGCAGTGTATTACTGTCAGCACTTTGGTACCTCAGTCTTCACTTTCGGCGGAGGGAC

CAAGGTTGAGATCAAA

TCN-553 (5261_C18) light chain variable region amino acid sequence (Kabat CDRs in bold, Chothia CDRs underlined)

(SEQ ID NO: 389)
EIVLTQSPGTLSLSPGERATLSC<u>RASQSVSSSYLA</u>WYQKKPGQAPRLLIY<u>GASTRAT</u>GIPDRFTGSGSGTDFT

LSISRLEPEDFAVYYC<u>QHFGTSVFT</u>FGGGTKVEIK

TCN-553 (5261_C18) Light chain Kabat CDRs:

CDR 1: RASQSVSSSYLA (SEQ ID NO: 203)

CDR 2: GASTRAT (SEQ ID NO: 181)

CDR 3: QHFGTSVFT (SEQ ID NO: 390)

TCN-553 (5261_C18) Light chain Chothia CDRs:

CDR 1: RASQSVSSSYLA (SEQ ID NO: 203)

CDR 2: GASTRAT (SEQ ID NO: 181)

CDR 3: QHFGTSVFT (SEQ ID NO: 390)

TCN-554 (5277_M05) heavy chain variable region nucleotide sequence:

(SEQ ID NO: 391)
CAGGTGCAGCTGGTGCAGTCTGGGGCTGATCTGAAGAAGCCTGGGGCCTCAGTGAAGGTCTCCTGCAAGG

CTTCTGGATACACCTTCACCGACTACTATATTCACTGGGTGCGACAGGCCCCTGGACAAGGGCTTGAGTG

GATGGGATGGATCAACCCTGAAAGTGGTGACACAAAGTATGCACAGAAGTTTCAGGGCAGGGTCACCATG

ACCAGGGACACGTCCATCACCACAGCCTACATGGAGCTGGGTAGGCTGAGATCCGACGACACGGCCGTGT

ATTACTGTGCGAGAGATGTAAGTACGACCTGGAGCTGGTTCGCCCCCTGGGGCCAGGGAACCCTGGTCAC

CGTCTCGAGC

TCN-554 (5277_M05) gamma heavy chain variable region amino acid sequence: (Kabat CDRs in bold, Chothia CDRs underlined)

(SEQ ID NO: 392)
QVQLVQSGADLKKPGASVKVSCKAS<u>GYTFTDYYIH</u>WVRQAPGQGLEWMG<u>WINPESGDTKYAQKFQG</u>R

VTMTRDTSITTAYMELGRLRSDDTAVYYCAR<u>DVSTTWSWFAP</u>WGQGTLVTVSS

TCN-554 (5277_M05) gamma heavy chain Kabat CDRs:

CDR 1: DYYIH (SEQ ID NO: 393)

CDR 2: WINPESGDTKYAQKFQG (SEQ ID NO: 394)

CDR 3: DVSTTWSWFAP (SEQ ID NO: 395)

TCN-554 (5277_M05) gamma heavy chain Chothia CDRs:

CDR 1: GYTFTD (SEQ ID NO: 396)

CDR 2: WINPESGDTK (SEQ ID NO: 397)

CDR 3: DVSTTWSWFAP (SEQ ID NO: 395)

TCN-554 (5277_M05) light chain variable region nucleotide sequence:

(SEQ ID NO: 398)
GACATCGTGATGACCCAGTCTCCAGACTCCCTGGCAGTGTCTCTGGGCGAGAGGGCCACCATCAACTGCAGGTCCAG

CCAGAGTATTTTCCACAACTCCAACAATGAGAACTACTTAGCTTGGTACCAGCAGAAACCAGGACAGCCTCCTAAGC

TGCTCATTTACTGGGCATCTACCCGGGAATCCGGGGTCCCTGACCGATTCAGTGGCAGCGGGTCTGGGACAGATTTC

ACTCTCACCATCAGCAGCCTGCAGGCTGAAGATGTGGCGGTTTATTTCTGTCAGCAATATTATAATGCTCCGCTCAC

TTTCGGCGGAGGGACCAAGGTGGAGATCAAA

TCN-554 (5277_M05) light chain variable region amino acid sequence (Kabat CDRs in bold, Chothia CDRs underlined)

(SEQ ID NO: 399)
DIVMTQSPDSLAVSLGERATINC<u>RSSQSIFHNSNNENYLA</u>WYQQKPGQPPKLLIY<u>WASTRES</u>GVPDRFSGS

GSGTDFTLTISSLQAEDVAVYFC<u>QQYYNAPLT</u>FGGGTKVEIK

TCN-554 (5277_M05) Light chain Kabat CDRs:

CDR 1: RSSQSIFHNSNNENYLA (SEQ ID NO: 400)

CDR 2: WASTRES (SEQ ID NO: 216)

CDR 3: QQYYNAPLT (SEQ ID NO: 401)

TCN-554 (5277_M05) Light chain Chothia CDRs:

CDR 1: RSSQSIFHNSNNENYLA (SEQ ID NO: 400)

CDR 2: WASTRES (SEQ ID NO: 216)

CDR 3: QQYYNAPLT (SEQ ID NO: 401)

TCN-555 (5246_L16) heavy chain variable region nucleotide sequence:

(SEQ ID NO: 402)
CAGGTGCAGCTGGTGCAGTCTGGGGCTGAGGTGAAGAGGCCTGGGTCCTCGGTGAAGGTCTCATGCACGGCTTCTGG

AGGCATCTTCAGGAAGAATGCAATCAGCTGGGTGCGACAGGCCCCTGGACAAGGCCTTGAGTGGATGGGAGGGATCA

TCGCAGTCTTTAACACAGCAAATTACGCGCAGAAGTTCCAGAACAGAGTCAAAATTACCGCAGACGAGTCAGGCAAT

ACGGCCTACATGGAGCTGAGCAGCCTGACATCTGACGACACGGCCGTGTATTACTGTGCGAGTCACCCAAAATATTT

CTATGGTTCGGGGAGTTATCCGGACTTCTGGGGCCAGGGAACCCTGGTCACCGTCTCGAGC

TCN-555 (5246_L16) gamma heavy chain variable region amino acid sequence: (Kabat CDRs in bold, Chothia CDRs underlined)

(SEQ ID NO: 403)
QVQLVQSGAEVKRPGSSVKVSCTAS<u>GGIFRK</u>KNAISWVRQAPGQGLEWMG<u>GIIAVFNTAN</u>YAQKFQNRVK

ITADESGNTAYMELSSLTSDDTAVYYCAS<u>HPKYFYGSGSYPDF</u>WGQGTLVTVSS

TCN-555 (5246_L16) gamma heavy chain Kabat CDRs:

```
CDR 1:    KNAIS              (SEQ ID NO: 62)

CDR 2:    GIIAVFNTANYAQKFQN  (SEQ ID NO: 58)

CDR 3:    HPKYFYGSGSYPDF     (SEQ ID NO: 59)
```

TCN-555 (5246_L16) gamma heavy chain Chothia CDRs:

```
CDR 1:    GGIFRK             (SEQ ID NO: 60)

CDR 2:    GIIAVFNTAN         (SEQ ID NO: 61)

CDR 3:    HPKYFYGSGSYPDF     (SEQ ID NO: 59)
```

TCN-555 (5246_L161 light chain variable region nucleotide sequence:

(SEQ ID NO: 404)
CAATCTGCCCTGACTCAGCCTCGCTCAGTGTCCGGGTCTCCTGGACAGTCAATCACCATCTCCTGTACTGGTGGCAG

CAGTGATATTGGTGCTTCTAACTCTGTCTCCTGGTACCAACAACACCCAGGCAAAGCCCCCAAACTCGTTATTTTTG

ATGTCACTGAGCGACCCTCAGGGGTCCCGCATCGGTTCTCTGGCTCCAAGTCTGGCAACACGGCCTCCCTGACCGTC

TCTGGGCTCCAGCCTGACGACGAGGCTGATTATTTCTGCTGCGCATATGGAGGCAAATATCTTGTGGTCTTCGGCGG

AGGGACCAAGGTGACCGTTCTA

TCN-555 (5246_L16) light chain variable region amino acid sequence (Kabat CDRs in bold, Chothia CDRs underlined)

(SEQ ID NO: 405)
QSALTQPRSVSGSPGQSITISC<u>TGGSSDIGASNSVS</u>WYQQHPGKAPKLVIF<u>DVTERPS</u>GVPHRFSGSKSGNT

ASLTVSGLQPDDEADYFC<u>CAYGGKYLVV</u>FGGGTKVTVL

TCN-555 (5246_L16) Light chain Kabat CDRs:

```
CDR 1:    TGGSSDIGASNSVS     (SEQ ID NO: 406)

CDR 2:    DVTERPS            (SEQ ID NO: 66)

CDR 3:    CAYGGKYLVV         (SEQ ID NO: 67)
```

TCN-555 (5246_L16) Light chain Chothia CDRs:

```
CDR 1:    TGGSSDIGASNSVS     (SEQ ID NO: 406)

CDR 2:    DVTERPS            (SEQ ID NO: 66)

CDR 3:    CAYGGKYLVV         (SEQ ID NO: 67)
```

TCN-556 (5089_K12) heavy chain variable region nucleotide sequence:

(SEQ ID NO: 407)
CAGGTGCAGCTGGTGCAGTCTGGGGCTGAGGTGAAGAAACCTGGGGCCTCAGTGAAGGTCTCCTGCAAGG

CTTCTGGATACACCTTCATCGGCTATGATATGCACTGGGTGCGACAGGCCCCTGGACAAGGGCTTGAGTG

GATGGGATGGATCAACGCTAAAAGAGGTGGCACAAACTATGCACAAAAGTTTCAGGGCAGGGTCACCATG

ACCAGGGACACGTCTATCAGCACAGCCTACATGGAGCTGAACAGCCTGAGATCTGACGACACGGCCGTGT

ATTACTGTGCGAGAGGGGTGGGGTCACGAACTACGATTTTTGGAGTTCTCAACCCGGAATTTGACTACTG

GGGCCAGGGAACCCTGGTCACCGTCTCGAGC

TCN-556 (5089_K12) gamma heavy chain variable region amino acid sequence: (Kabat CDRs in bold, Chothia CDRs underlined)

(SEQ ID NO: 408)
QVQLVQSGAEVKKPGASVKVSCKAS<u>GYTFIG</u>YDMHWVRQAPGQGLEWMG<u>WINAKRGGTN</u>YAQKFQG

RVTMTRDTSISTAYMELNSLRSDDTAVYYCAR<u>GVGSRTTIFGVLNPEFDY</u>WGQGTLVTVSS

TCN-556 (5089_K12) gamma heavy chain Kabat CDRs:

CDR 1: GYDMH (SEQ ID NO: 409)

CDR 2: WINAKRGGTNYAQKFQG (SEQ ID NO: 410)

CDR 3: GVGSRTTIFGVLNPEFDY (SEQ ID NO: 411)

TCN-556 (5089_K12) gamma heavy chain Chothia CDRs:

CDR 1: GYTFIG (SEQ ID NO: 412)

CDR 2: WINAKRGGTN (SEQ ID NO: 413)

CDR 3: GVGSRTTIFGVLNPEFDY (SEQ ID NO: 411)

TCN-556 (5089_K12) light chain variable region nucleotide sequence:

(SEQ ID NO: 414)
CAGTCTGCCCTGACTCAGCCTCCCTCCGCGTCCGGGTCTCCTGGACAGTCAGTCACCATCTCCTGCACTGGATCCAG

CAGTGACGTTGGTGGTTATGACTATGTCTCCTGGTACCAACAACACCCAGGCAAAGCCCCCAAACTCCTGATTTATG

AGGTCACTAAGCGGCCCTCAGGGGTCCCTGATCGCTTCTCTGGCTCCAAGTCTGGCAACACGGCCTCCCTGACCGTC

TCTGGGCTCCAGGCTGAGGATGAGGCTGATTATTACTGCAGCTCATATGCGGGCAACTACAATCATGTCTTCGGACC

TGGGACCAAGGTCACCGTTCTA

TCN-556 (5089_K12) light chain variable region amino acid sequence (Kabat CDRs in bold, Chothia CDRs underlined)

(SEQ ID NO: 415)
QSALTQPPSASGSPGQSVTISC<u>TGSSSDVGGYDYVS</u>WYQQHPGKAPKLLIY<u>EVTKRPS</u>GVPDRFSGSKSGN

TASLTVSGLQAEDEADYYC<u>SSYAGNYNHV</u>FGPGTKVTVL

TCN-556 (5089_K12) Light chain Kabat CDRs:

CDR 1: TGSSSDVGGYDYVS (SEQ ID NO: 416)

CDR 2: EVTKRPS (SEQ ID NO: 417)

CDR 3: SSYAGNYNHV (SEQ ID NO: 418)

TCN-556 (5089_K12) Light chain Chothia CDRs:

CDR 1: TGSSSDVGGYDYVS (SEQ ID NO: 416)

CDR 2: EVTKRPS (SEQ ID NO: 417)

CDR 3: SSYAGNYNHV (SEQ ID NO: 418)

TCN-557 (5081_A04) heavy chain variable region nucleotide sequence:

(SEQ ID NO: 419)
CAGGTGCAGCTGGTGCAGTCTGGGGCTGAGGTGAAGAAGCCTGGGGCCTCAGTGAAGGTCTCCTGCAAGGCTTCTGG

ACACACCTTCACCGGCTACTACATACACTGGGTGCGACAGGCCCCTGGACAAGGGCTTGAGTGGATGGGATGGATCA

ACCCTGACAGTGGTGCCACCAGTTCTGCACAGAACTTTCAGGGCAGGGTCACCATGACCGGGGACACGTCCTCTAGC

ACAGCCTACATGGAGCTGAGTAGGCTGAGTTTTGACGACACGGCCGTCTATTACTGTGCGAGAGTACTGTTTACCAG

TCCTTTTGACTTCTGGGGTGAGGGAACCCTGGTCACCGTCTCGAGC

TCN-557 (5081_A04) gamma heavy chain variable region amino acid sequence: (Kabat CDRs in bold, Chothia CDRs underlined)

(SEQ ID NO: 420)
QVQLVQSGAEVKKPGASVKVSCKAS<u>GHTFT</u>GYYIHWVRQAPGQGLEWMGWINPDSGATS<u>SAQNFQG</u>R

VTMTGDTSSSTAYMELSRLSFDDTAVYYCAR<u>VLFTSPFDF</u>WGEGTLVTVSS

TCN-557 (5081_A04) gamma heavy chain Kabat CDRs:

| CDR 1: | GYYIH | (SEQ ID NO: 421) |
| CDR 2: | WINPDSGATSSAQNFQG | (SEQ ID NO: 422) |
| CDR 3: | VLFTSPFDF | (SEQ ID NO: 423) |

TCN-557 (5081_A04) gamma heavy chain Chothia CDRs:

| CDR 1: | GHTFTG | (SEQ ID NO: 424) |
| CDR 2: | WINPDSGATS | (SEQ ID NO: 425) |
| CDR 3: | VLFTSPFDF | (SEQ ID NO: 423) |

TCN-557 (5081_A04) light chain variable region nucleotide sequence:

(SEQ ID NO: 426)
CAGGCTGTGGTGACTCAGGAGCCCTCACTGGCTGTGTCCCCAGGAGGGACAGTCACTCTCACCTGTGGCTCCAGCAC

TGGAGCTGTCACCAGGGGTCATTATCCCTATTGGTTCCAGCAGAAGCCTGGCCAAGCCCCCAGGGCACTCATTTATG

ATAGTGCAGGCAACAGACACTCCTGGACTCCCGCCCGATTCTCAGGCTCCCTCCTTGGGGGCAAAGCTGCCCTGACC

CTTTCGGGTGCGCAGCCTGAGGATGAGGCTGAGTATTACTGCTTGCTCTCCTATAGTGGTGTCTGGGTGTTCGGCGG

AGGGACGAAGCTGACCGTTCTA

TCN-557 (5081_A04) light chain variable region amino acid sequence (Kabat CDRs in bold, Chothia CDRs underlined)

(SEQ ID NO: 427)
QAVVTQEPSLAVSPGGTVTLTC<u>GSSTGAVTRGHYPY</u>WFQQKPGQAPRALIY<u>DSAGNRHS</u>WTPARFSGSL

LGGKAALTLSGAQPEDEAEYYC<u>LLSYSGVWV</u>FGGGTKLTVL

TCN-557 (5081_A04) Light chain Kabat CDRs:

| CDR 1: | GSSTGAVTRGHYPY | (SEQ ID NO: 428) |
| CDR 2: | DSAGNRHS | (SEQ ID NO: 429) |
| CDR 3: | LLSYSGVWV | (SEQ ID NO: 430) |

TCN-557 (5081_A04) Light chain Chothia CDRs:

| CDR 1: | GSSTGAVTRGHYPY | (SEQ ID NO: 428) |
| CDR 2: | DSAGNRHS | (SEQ ID NO: 429) |
| CDR 3: | LLSYSGVWV | (SEQ ID NO: 430) |

TCN-558 (5248_H10b) heavy chain variable region nucleotide sequence:

(SEQ ID NO: 431)
CAGGTCCAGCTGGTGCAATCTGGGAGTGAGGTGAAGAAGCCTGGGACCTCGGTGAAGGTCTCCTGCACGGCCTCTGG

AAGTGTCTTCACCAATTATGGAATTAGTTGGGTGCGACAGGCCCCTGGACAAGGGCTTGAGTGGATGGGAGGGATCA

TCCCTCTCTTTGGCGCAGCCAAGTACGCACAGAAATTCCAGGGCAGAGTCACCATCACAGCGGACGAATCCACGAAG

ACAGTCTACATGGAGCTGAGCAGGCTGACATCTAAAGACACGGCCATATATTTCTGTGCGAAGGCCCCCCGTGTCTA

CGAGTACTACTTTGATCAGTGGGGCCAGGGAACCCCAGTCACCGTCTCCTCA

TCN-558 (5248_H10b) gamma heavy chain variable region amino acid sequence: (Kabat CDRs in bold, Chothia CDRs underlined)

(SEQ ID NO: 173)
QVQLVQSGSEVKKPGTSVKVSCTAS<u>GSVFT</u>NYGISWVRQAPGQGLEWMG<u>GIIPLFGAAK</u>YAQKFQGRVT
ITADESTKTVYMELSRLTSKDTAIYFCAKAPRVYEYYFDQWGQGTPVTVSS

TCN-558 (5248_H10b) gamma heavy chain Kabat CDRs:

| | | |
|---|---|---|
| CDR 1: | NYGIS | (SEQ ID NO: 174) |
| CDR 2: | GIIPLFGAAKYAQKFQG | (SEQ ID NO: 175) |
| CDR 3: | APRVYEYYFDQ | (SEQ ID NO: 176) |

TCN-558 (5248_H10b) gamma heavy chain Chothia CDRs:

| | | |
|---|---|---|
| CDR 1: | GSVFTN | (SEQ ID NO: 177) |
| CDR 2: | GIIPLFGAAK | (SEQ ID NO: 178) |
| CDR 3: | APRVYEYYFDQ | (SEQ ID NO: 176) |

TCN-558 (5248_H10b) light chain variable region nucleotide sequence:

(SEQ ID NO: 432)
GAAATAGTGATGACGCAGTTTCCAGCCACCCTGTCTGTGTCTCCCGGGGAACGAGTCACCCTCTCCTGTAGGGCCAG
TCAGAGTGTTAGCAACAATTTAGCCTGGTACCAGCAAAAACCTGGCCAGCCTCCCAGGCTCCTCATCTATGATGCAT
CTACCAGGGCCACGGGTGTCCCAGCCAAGTTCAGTGGCACTGGGTCTGGCACAGAGTTCACTCTCAGCATCAGCAGC
CTGCAGTCCGAAGATTTTGCAGTTTATTACTGTCAGCAGTATCACAACTGGCCTCCCTCGTACAGTTTTGGCCTGGG
GACCAAGCTGGAGATCAAA

TCN-558 (5248_H10b) light chain variable region amino acid sequence (Kabat CDRs in bold, Chothia CDRs underlined)

(SEQ ID NO: 124)
EIVMTQFPATLSVSPGERVTLSC<u>RASQSVSNNLA</u>WYQQKPGQPPRLLIY<u>DASTRAT</u>GVPAKFSGTGSGTEF
TLSISSLQSEDFAVYYCQQYHNWPPSYSFGLGTKLEIK

TCN-558 (5248_H10b) Light chain Kabat CDRs:

| | | |
|---|---|---|
| CDR 1: | RASQSVSNNLA | (SEQ ID NO: 125) |
| CDR 2: | DASTRAT | (SEQ ID NO: 126) |
| CDR 3: | QQYHNWPPSYS | (SEQ ID NO: 127) |

TCN-558 (5248_H10b) Light chain Chothia CDRs:

| | | |
|---|---|---|
| CDR 1: | RASQSVSNNLA | (SEQ ID NO: 125) |
| CDR 2: | DASTRAT | (SEQ ID NO: 126) |
| CDR 3: | QQYHNWPPSYS | (SEQ ID NO: 127) |

TCN-559 (5097_G08) heavy chain variable region nucleotide sequence:

(SEQ ID NO: 433)
CAAGAGCAGCTGGTGCAGTCTGGGGCTGAGGTGAAGAAGCCTGGGGCCTCAGTGAAGGTCTCCTGCAAGGCTTCTAG
AAAGTCCTTCATTGGCTACTATGTACACTGGGTGCGACAGGCCCCTGGACAAGGGCTTGAGTGGATGGGATGGATCA
GCCCTGACAGTGATGCCACAAAGTACGCACAGAAGTTTCAGGGCTCCGTCATCATGACCAGGGACACGTCCGTCAGC
ACAGTGTACATGGAGCTGAGTAGGCTGACATCTGACGACACGGCCCTTTATTACTGTCTCCTTTTTCGAGGTGGAAA
CTCCCTCTCCTGGGGCCAGGGAACCCTGGTCACCGTCTCGAGC

TCN-559 (5097_G08) gamma heavy chain variable region amino acid sequence: (Kabat CDRs in bold, Chothia CDRs underlined)

(SEQ ID NO: 434)
QEQLVQSGAEVKKPGASVKVSCKAS<u>RKSFIGYYVH</u>WVRQAPGQGLEWMGWISPDSDATKYAQKFQGS

VIMTRDTSVSTVYMELSRLTSDDTALYYCLL<u>FRGGNSLS</u>WGQGTLVTVSS

TCN-559 (5097_G08) gamma heavy chain Kabat CDRs:

| CDR 1: | GYYVH | (SEQ ID NO: 435) |
| CDR 2: | WISPDSDATKYAQKFQG | (SEQ ID NO: 436) |
| CDR 3: | FRGGNSLS | (SEQ ID NO: 437) |

TCN-559 (5097_G08) gamma heavy chain Chothia CDRs:

| CDR 1: | RKSFIG | (SEQ ID NO: 438) |
| CDR 2: | WISPDSDATK | (SEQ ID NO: 439) |
| CDR 3: | FRGGNSLS | (SEQ ID NO: 437) |

TCN-559 (5097_G08) light chain variable region nucleotide sequence:

(SEQ ID NO: 440)
CAGGCTGTGGTGACTCAGGAGCCCTCACTGACTGTGTCCCCAGGAGGGACAGTCACCCTCACCTGTGGCTCCAGCAC

TGGACCTGTCACCAGTGGTCATTATCCCTACTGGTTCCAGCAGAAGCCTGGCCAAGCCCCCAGGACATTGATTTCTG

CTACATCCAACACACACTCCTGGACACCTGCCCGCTTCTCAGGCTCCCTCCTTGGGGGCAGAGCTGCCCTGACCCTT

TCGGGTGCGCAGCCTGAGGATGAGGCTGACTATTATTGCTTTCTCTCCTACAGTGGTGCTTGGGTGTTCGGCGGAGG

GACCACGCTGACCGTTCTA

TCN-559 (5097_G08) light chain variable region amino acid sequence (Kabat CDRs in bold, Chothia CDRs underlined)

(SEQ ID NO: 441)
QAVVTQEPSLTVSPGGTVTLTC<u>GSSTGPVTSGHYPY</u>WFQQKPGQAPRTLIS<u>ATSNTHS</u>WTPARFSGSLLGG

RAALTLSGAQPEDEADYYC<u>FLSYSGAWV</u>FGGGTTLTVL

TCN-559 (5097_G08) Light chain Kabat CDRs:

| CDR 1: | GSSTGPVTSGHYPY | (SEQ ID NO: 442) |
| CDR 2: | ATSNTHS | (SEQ ID NO: 443) |
| CDR 3: | FLSYSGAWV | (SEQ ID NO: 444) |

TCN-559 (5097_G08) Light chain Chothia CDRs:

| CDR 1: | GSSTGPVTSGHYPY | (SEQ ID NO: 442) |
| CDR 2: | ATSNTHS | (SEQ ID NO: 443) |
| CDR 3: | FLSYSGAWV | (SEQ ID NO: 444) |

TCN-560 (5084_P10) heavy chain variable region nucleotide sequence:

(SEQ ID NO: 445)
GAGGTGCAGCTGGTGGAATCTGGGGGAGGCTTGGTCCAGCCGGGGGGGTCCCTGAGACTCTCCTGTGCAGCCTCTGG

ATTTATCTTTAGAAATTACTGGATGAGCTGGGTCCGGCAGGCTCCAGGGAAGGGGCTGGAGTGGGTGGCCAACATAA

AACAAGATGGAAGAGAGAAGTACTATGTGGACTCTCTGAGGGGCCGAGTCAACATCTCCAGAGACAACGCCGAGAAC

TCATTGTATCTGCACATGAACAGCCTGAGAGTCGAGGACACGGCTGTTTATTTCTGTGCGAGAGCTCGGATGGTGGT

GGTTACTGGCGATGGTTTTGATGTCTGGGGCCATGGGACAATGGTCACCGTCTCGAGC

TCN-560 (5084_P10) gamma heavy chain variable region amino acid sequence: (Kabat CDRs in bold, Chothia CDRs underlined)

(SEQ ID NO: 446)
EVQLVESGGGLVQPGGSLRLSCAAS<u>GFIFR</u>NYWMSWVRQAPGKGLEWVANI<u>KQDGREKY</u>YVDSLRGRV

NISRDNAENSLYLHMNSLRVEDTAVYFCAR<u>ARMVVVTGDGFDV</u>WGHGTMVTVSS

TCN-560 (5084_P10) gamma heavy chain Kabat CDRs:

| CDR 1: | NYWMS | (SEQ ID NO: 447) |
| --- | --- | --- |
| CDR 2: | NIKQDGREKYYVDSLRG | (SEQ ID NO: 448) |
| CDR 3: | ARMVVVTGDGFDV | (SEQ ID NO: 449) |

TCN-560 (5084_P10) gamma heavy chain Chothia CDRs:

| CDR 1: | GFIFRN | (SEQ ID N6: 450) |
| --- | --- | --- |
| CDR 2: | NIKQDGREKY | (SEQ ID NO: 451) |
| CDR 3: | ARMVVVTGDGFDV | (SEQ ID NO: 449) |

TCN-560 (5084_P10) light chain variable region nucleotide sequence:

(SEQ ID NO: 452)
GACATCCAGATGACCCAGTCTCCATCCTCCCTGTCTGCATCTGTGGGAGACAGAGTCACCATCACTTGCCGGGCAAG

TCAGAATATTAAGAGGTATTTCAATTGGTATCAGCAGAAACCAGGGAAAGCCCCTAAGCTCCTGATCTATGCTGCAT

CCAATTTAGAAAATGGGGTCCCATCAAGGTTCAGTGGCAGTGGATCTGGGACAGATTTCACTCTCACCATCAGCAGT

CTGCAACCTGAGGATTTTGCGACTTATTACTGTCAGCAGAGTTTCAGTAAATCGTGGACATTCGGCCAAGGGACCAA

CGTGGACATCAAA

TCN-560 (5084_P10) light chain variable region amino acid sequence (Kabat CDRs in bold, Chothia CDRs underlined)

(SEQ ID NO: 453)
DIQMTQSPSSLSASVGDRVTITC<u>RASQNIKRYFN</u>WYQQKPGKAPKLLIY<u>AASNLEN</u>GVPSRFSGSGSGTDF

TLTISSLQPEDFATYYC<u>QQSFSKSWT</u>FGQGTNVDIK

TCN-560 (5084_P10) Light chain Kabat CDRs:

| CDR 1: | RASQNIKRYFN | (SEQ ID NO: 454) |
| --- | --- | --- |
| CDR 2: | AASNLEN | (SEQ ID NO: 455) |
| CDR 3: | QQSFSKSWT | (SEQ ID NO: 456) |

TCN-560 (5084_P10) Light chain Chothia CDRs:

| CDR 1: | RASQNIKRYFN | (SEQ ID NO: 454) |
| --- | --- | --- |
| CDR 2: | AASNLEN | (SEQ ID NO: 455) |
| CDR 3: | QQSFSKSWT | (SEQ ID NO: 456) |

TCN-564 (5256_A17b) heavy chain variable region nucleotide sequence:

(SEQ ID NO: 152)
CAGGTGCAGCTGGTGCAGTCTGGGGCTGACGTGAAGAAGCCTGGGTCCTCGGTGACGGTCTCCTGCAAGGCTTCTGG

AGGCAGCTTCAGCAACTATGGAATCAACTGGGTGCGACAGGCCCCTGGACAAGGGCTTGAGTGGATGGGGGGAATCA

TCCCTCTCATTAATGCACCGAACTACGCACCGAAGTTCCAGGGCAGAGTGACGATTACCGCGGACATGTTCTCGAAT

ATAGTCTCCTTGCAGTTGACCAGCCTGAGAACTGACGACACGGCCGTGTATTATTGTGCGAGACGAAAAATGACTAC

GGCTATTGACTATTGGGGCCAGGGAACCCTGGTCACCGTCTCCTCA

TCN-564 (5256_A17b) gamma heavy chain variable region amino acid sequence: (Kabat CDRs in bold, Chothia CDRs underlined)

(SEQ ID NO: 153)

```
QVQLVQSGADVKKPGSSVTVSCKASGGSFSNYGINWVRQAPGQGLEWMGGIIPLINAPNYAPKFQGRVT

ITADMFSNIVSLQLTSLRTDDTAVYYCARRKMTTAIDYWGQGTLVTVSS
```

TCN-564 (5256_A17b) gamma heavy chain Kabat CDRs:

```
CDR 1:     NYGIN                 (SEQ ID NO: 154)
CDR 2:     GIIPLINAPNYAPKFQG     (SEQ ID NO: 155)
CDR 3:     RKMTTAIDY             (SEQ ID NO: 156)
```

TCN-564 (5256_A17b) gamma heavy chain Chothia CDRs:

```
CDR 1:     GGSFSN                (SEQ ID NO: 49)
CDR 2:     GIIPLINAPN            (SEQ ID NO: 158)
CDR 3:     RKMTTAIDY             (SEQ ID NO: 156)
```

TCN-564 (5256_A17b) light chain variable region nucleotide sequence:

(SEQ ID NO: 523)

```
CAGCCTGTGTTGAGTCAGCCACCTTCTGCATCGGCCTCCCTGGGAGCCTCCGTCACACTCACCTGCACCCTGAGTAG

CGGCTTCGATAATTATCAAGTGGCCTGGTACCAGCAGAGACCAGGGAAGGGCCCCCGCTTTGTGATGCGGGTGGGCA

ATGGTGGGAATGTGGCTTCCAAGGGGATGGCATTCCTGATCGTTTCTCAGTCTCGGGCTCAGGCCTGAATCGGTAC

CTGACCATCAAGAACATCCAGGAAGACGATGAGAGTGACTATTATTGTGGGGCAGACCATGGCAGTGGGAACAACTT

CGTGTCCCCTTATGTGTTTGGCGGAGGGACCAAGCTGACCGTTCTA
```

TCN-564 (5256_A17b) light chain variable region amino acid sequence (Kabat CDRs in bold, Chothia CDRs underlined)

(SEQ ID NO: 519)

```
QPVLSQPPSASASLGASVTLTCTLSSGFDNYQVAWYQQRPGKGPRFVMRVGNGGNVASKGDGIPDRFSV

SGSGLNRYLTIKNIQEDDESDYYCGADHGSGNNFVSPYVFGGGTKLTVL
```

TCN-564 (5256_A17b) Light chain Kabat CDRs:

```
CDR 1:     TLSSGFDNYQVA          (SEQ ID NO: 520)
CDR 2:     VGNGGNVASKGD          (SEQ ID NO: 521)
CDR 3:     GADHGSGNNFVSPYV       (SEQ ID NO: 522)
```

TCN-564 (5256_A17b) Light chain Chothia CDRs:

```
CDR 1:     TLSSGFDNYQVA          (SEQ ID NO: 520)
CDR 2:     VGNGGNVASKGD          (SEQ ID NO: 521)
CDR 3:     GADHGSGNNFVSPYV       (SEQ ID NO: 522)
```

The invention provides an isolated fully human monoclonal anti-HA antibody or fragment thereof, wherein said antibody includes a variable heavy chain ($V_H$) region comprising CDR1 and CDR2, wherein the $V_H$ region is encoded by a human IGHV1 (or specifically, IGHV1-18, IGHV1-2, IGHV1-69, IGHV1-8), IGHV2 (or specifically, IGHV2-5), IGHV3 (or specifically, IGHV3-30, IGHV3-33, IGHV3-49, IGHV3-53, 66, IGHV3-7), IGHV4 (or specifically, IGHV4-31, IGHV4-34, IGHV4-39, IGHV4-59, IGHV4-61), or IGHV5 (or specifically, IGHV5-51) $V_H$ germline sequence or an allele thereof, or a nucleic acid sequence that is homologous to the IGHV1, IGHV2, IGHV3, IGHV4, or IGHV5 $V_H$ germline gene sequence or an allele thereof. In one aspect, the nucleic acid sequence that is homologous to the IGHV1, IGHV2, IGHV3, IGHV4, or IGHV5 $V_H$ germline sequence is at least 75% homologous to the IGHV1, IGHV2, IGHV3, IGHV4, or IGHV5 $V_H$ germline sequence or an allele thereof.

Exemplary alleles include, but are not limited to, IGHV1-18*01, IGHV1-2*02, IGHV1-2*04, IGHV1-69*01, IGHV1-69*05, IGHV1-69*06, IGHV1-69*12, IGHV1-8*01, IGHV2-5*10, IGHV3-30-3*01, IGHV3-30*03, IGHV3-30*18, IGHV3-33*05, IGHV3-49*04, IGHV3-53*01, IGHV3-66*03, IGHV3-7*01, IGHV4-31*03, IGHV4-31*06, IGHV4-34*01, IGHV4-34*02, IGHV4-34*03, IGHV4-34*12, IGHV4-39*01, IGHV4-59*01, IGHV4-59*03, IGHV4-61*01, IGHV4-61*08, and IGHV5-51*01. Exemplary sequences for each allele are provided below.

IGHV1-18*01 nucleotide sequence
(SEQ ID NO: 457)
CAGGTTCAGCTGGTGCAGTCTGGAGCTGAGGTGAAGAAGCCTGGGGCCTCAGTGAAGGTCTCCTGCAAGGCTTCTGG
TTACACCTTTACCAGCTATGGTATCAGCTGGGTGCGACAGGCCCCTGGACAAGGGCTTGAGTGGATGGGATGGATCA
GCGCTTACAATGGTAACACAAACTATGCACAGAAGCTCCAGGGCAGAGTCACCATGACCACAGACACATCCACGAGC
ACAGCCTACATGGAGCTGAGGAGCCTGAGATCTGACGACACGGCCGTGTATTACTGTGCGAGAGA IGHV1-2*02 nucleotide sequence
(SEQ ID NO: 458)
CAGGTGCAGCTGGTGCAGTCTGGGGCTGAGGTGAAGAAGCCTGGGGCCTCAGTGAAGGTCTCCTGCAAGGCTTCTGG
ATACACCTTCACCGGCTACTATATGCACTGGGTGCGACAGGCCCCTGGACAAGGGCTTGAGTGGATGGGATGGATCA
ACCCTAACAGTGGTGGCACAAACTATGCACAGAAGTTTCAGGGCAGGGTCACCATGACCAGGGACACGTCCATCAGC
ACAGCCTACATGGAGCTGAGCAGGCTGAGATCTGACGACACGGCCGTGTATTACTGTGCGAGAGA IGHV1-2*04 nucleotide sequence
(SEQ ID NO: 459)
CAGGTGCAGCTGGTGCAGTCTGGGGCTGAGGTGAAGAAGCCTGGGGCCTCAGTGAAGGTCTCCTGCAAGGCTTCTGG
ATACACCTTCACCGGCTACTATATGCACTGGGTGCGACAGGCCCCTGGACAAGGGCTTGAGTGGATGGGATGGATCA
ACCCTAACAGTGGTGGCACAAACTATGCACAGAAGTTTCAGGGCTGGGTCACCATGACCAGGGACACGTCCATCAGC
ACAGCCTACATGGAGCTGAGCAGGCTGAGATCTGACGACACGGCCGTGTATTACTGTGCGAGA IGHV1-69*01 nucleotide sequence
(SEQ ID NO: 460)
CAGGTGCAGCTGGTGCAGTCTGGGGCTGAGGTGAAGAAGCCTGGGTCCTCGGTGAAGGTCTCCTGCAAGGCTTCTGG
AGGCACCTTCAGCAGCTATGCTATCAGCTGGGTGCGACAGGCCCCTGGACAAGGGCTTGAGTGGATGGGAGGGATCA
TCCCTATCTTTGGTACAGCAAACTACGCACAGAAGTTCCAGGGCAGAGTCACGATTACCGCGGACGAATCCACGAGC
ACAGCCTACATGGAGCTGAGCAGCCTGAGATCTGAGGACACGGCCGTGTATTACTGTGCGAGAGA IGHV1-69*05 nucleotide sequence
(SEQ ID NO: 461)
CAGGTCCAGCTGGTGCAGTCTGGGGCTGAGGTGAAGAAGCCTGGGTCCTCGGTGAAGGTCTCCTGCAAGGCTTCTGG
AGGCACCTTCAGCAGCTATGCTATCAGCTGGGTGCGACAGGCCCCTGGACAAGGGCTTGAGTGGATGGGAGGGATCA
TCCCTATCTTTGGTACAGCAAACTACGCACAGAAGTTCCAGGGCAGAGTCACGATTACCACGGACGAATCCACGAGC
ACAGCCTACATGGAGCTGAGCAGCCTGAGATCTGAGGACACGGCCGTGTATTACTGTGCGAGA IGHV1-69*06 nucleotide sequence
(SEQ ID NO: 462)
CAGGTGCAGCTGGTGCAGTCTGGGGCTGAGGTGAAGAAGCCTGGGTCCTCGGTGAAGGTCTCCTGCAAGGCTTCTGG
AGGCACCTTCAGCAGCTATGCTATCAGCTGGGTGCGACAGGCCCCTGGACAAGGGCTTGAGTGGATGGGAGGGATCA
TCCCTATCTTTGGTACAGCAAACTACGCACAGAAGTTCCAGGGCAGAGTCACGATTACCGCGGACAAATCCACGAGC
ACAGCCTACATGGAGCTGAGCAGCCTGAGATCTGAGGACACGGCCGTGTATTACTGTGCGAGAGA IGHV1-69*12 nucleotide sequence
(SEQ ID NO: 463)
CAGGTCCAGCTGGTGCAGTCTGGGGCTGAGGTGAAGAAGCCTGGGTCCTCGGTGAAGGTCTCCTGCAAGGCTTCTGG
AGGCACCTTCAGCAGCTATGCTATCAGCTGGGTGCGACAGGCCCCTGGACAAGGGCTTGAGTGGATGGGAGGGATCA
TCCCTATCTTTGGTACAGCAAACTACGCACAGAAGTTCCAGGGCAGAGTCACGATTACCGCGGACGAATCCACGAGC
ACAGCCTACATGGAGCTGAGCAGCCTGAGATCTGAGGACACGGCCGTGTATTACTGTGCGAGAGA IGHV1-8*01 nucleotide sequence
(SEQ ID NO: 464)
CAGGTGCAGCTGGTGCAGTCTGGGGCTGAGGTGAAGAAGCCTGGGGCCTCAGTGAAGGTCTCCTGCAAGGCTTCTGG
ATACACCTTCACCAGTTATGATATCAACTGGGTGCGACAGGCCACTGGACAAGGGCTTGAGTGGATGGGATGGATGA
ACCCTAACAGTGGTAACACAGGCTATGCACAGAAGTTCCAGGGCAGAGTCACCATGACCAGGAACACCTCCATAAGC
ACAGCCTACATGGAGCTGAGCAGCCTGAGATCTGAGGACACGGCCGTGTATTACTGTGCGAGAGG -continued IGHV2-5*10 nucleotide sequence
(SEQ ID NO: 465)
CAGATCACCTTGAAGGAGTCTGGTCCTACGCTGGTGAAACCCACACAGACCCTCACGCTGACCTGCACCTTCTCTGG

GTTCTCACTCAGCACTAGTGGAGTGGGTGTGGGCTGGATCCGTCAGCCCCCAGGAAAGGCCCTGGAGTGGCTTGCAC

TCATTTATTGGGATGATGATAAGCGCTACAGCCCATCTCTGAAGAGCAGGCTCACCATCACCAAGGACACCTCCAAA

AACCAGGTGGTCCTTACAATGACCAACATGGACCCTGTGGACACAGCCACATATTACTGTGCACGG

IGHV3-30-3*01 nucleotide sequence
(SEQ ID NO: 466)
CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGCTATGCACTGGGTCCGCCAGGCTCCAGGCAAGGGGCTGGAGTGGGTGGCAGTTATAT

CATATGATGGAAGCAATAAATACTACGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAGA

IGHV3-30*03 nucleotide sequence
(SEQ ID NO: 467)
CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGGCATGCACTGGGTCCGCCAGGCTCCAGGCAAGGGGCTGGAGTGGGTGGCAGTTATAT

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAGAGA

IGHV3-30*18 nucleotide sequence
(SEQ ID NO: 468)
CAGGTGCAGCTGGTGGAGTCTGGGGGAGGCGTGGTCCAGCCTGGGAGGTCCCTGAGACTCTCCTGTGCAGCCTCTGG

ATTCACCTTCAGTAGCTATGGCATGCACTGGGTCCGCCAGGCTCCAGGCAAGGGGCTGGAGTGGGTGGCAGTTATAT

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCTGAGGACACGGCTGTGTATTACTGTGCGAAAGA

IGHV3-33*05 nucleotide sequence
(SEQ ID NO: 469)
CAGGTGCAGCTGGTGGAGTCTGGGGGAGGCGTGGTCCAGCCTGGGAGGTCCCTGAGACTCTCCTGTGCAGCGTCTGG

ATTCACCTTCAGTAGCTATGGCATGCACTGGGTCCGCCAGGCTCCAGGCAAGGGGCTGGAGTGGGTGGCAGTTATAT

CATATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCCGAGGACACGGCTGTGTATTACTGTGCGAGAGA

IGHV3-49*04 nucleotide sequence
(SEQ ID NO: 470)
GAGGTGCAGCTGGTGGAGTCTGGGGGAGGCTTGGTACAGCCAGGGCGGTCCCTGAGACTCTCCTGTACAGCTTCTGG

ATTCACCTTTGGTGATTATGCTATGAGCTGGGTCCGCCAGGCTCCAGGGAAGGGGCTGGAGTGGGTAGGTTTCATTA

GAAGCAAAGCTTATGGTGGGACAACAGAATACGCCGCGTCTGTGAAAGGCAGATTCACCATCTCAAGAGATGATTCC

AAAAGCATCGCCTATCTGCAAATGAACAGCCTGAAAACCGAGGACACAGCCGTGTATTACTGTACTAGAGA

IGHV3-53*01 nucleotide sequence
(SEQ ID NO: 471)
GAGGTGCAGCTGGTGGAGTCTGGAGGAGGCTTGATCCAGCCTGGGGGGTCCCTGAGACTCTCCTGTGCAGCCTCTGG

GTTCACCGTCAGTAGCAACTACATGAGCTGGGTCCGCCAGGCTCCAGGGAAGGGGCTGGAGTGGGTCTCAGTTATTT

ATAGCGGTGGTAGCACATACTACGCAGACTCCGTGAAGGGCCGATTCACCATCTCCAGAGACAATTCCAAGAACACG

CTGTATCTTCAAATGAACAGCCTGAGAGCCGAGGACACGGCCGTGTATTACTGTGCGAGAGA

IGHV3-66*03 nucleotide sequence
(SEQ ID NO: 472)
CAGGTGCAGCTGGTGCAGTCTGGCCATGAGGTGAAGCAGCCTGGGGCCTCAGTGAAGGTCTCCTGCAAGGCTTCTGG

TTACAGTTTCACCACCTATGGTATGAATTGGGTGCCACAGGCCCCTGGACAAGGGCTTGAGTGGATGGGATGGTTCA

ACACCTACACTGGGAACCCAACATATGCCCAGGGCTTCACAGGACGGTTTGTCTTCTCCATGGACACCTCTGCCAGC

ACAGCATACCTGCAGATCAGCAGCCTAAAGGCTGAGGACATGGCCATGTATTACTGTGCGAGATA

IGHV3-7*01 nucleotide sequence
(SEQ ID NO: 473)
GAGGTGCAGCTGGTGGAGTCTGGGGGAGGCTTGGTCCAGCCTGGGGGGTCCCTGAGACTCTCCTGTGCAGCCTCTGG

ATTCACCTTTAGTAGCTATTGGATGAGCTGGGTCCGCCAGGCTCCAGGGAAGGGGCTGGAGTGGGTGGCCAACATAA

AGCAAGATGGAAGTGAGAAATACTATGTGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGCGAGAGA

IGHV4-31*03 nucleotide sequence
(SEQ ID NO: 474)
CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTGGTTACTACTGGAGCTGGATCCGCCAGCACCCAGGGAAGGGCCTGGAGTGGATTGGGT

ACATCTATTACAGTGGGAGCACCTACTACAACCCGTCCCTCAAGAGTCGAGTTACCATATCAGTAGACACGTCTAAG

AACCAGTTCTCCCTGAAGCTGAGCTCTGTGACTGCCGCGGACACGGCCGTGTATTACTGTGCGAGAGA

IGHV4-31*06 nucleotide sequence
(SEQ ID NO: 475)
CAGGTGCAGCTGCAGGAGTCGGGCCCAGGACTGGTGAAGCCTTCACAGACCCTGTCCCTCACCTGCACTGTCTCTGG

TGGCTCCATCAGCAGTGGTAGTTACTACTGGAGCTGGATCCGCCAGCACCCAGGGAAGGGCCTGGAGTGGATTGGGT

ACATCTATTACAGTGGGAGCACCTACTACAACCCGTCCCTCAAGAGTCGAGTTACCATATCAGTAGACACGTCTAAG

AACCAGTTCTCCCTGAAGCTGAGCTCTGTGACTGCCGCGGACACGGCCGTGTATTACTG

IGHV4-34*01 nucleotide sequence
(SEQ ID NO: 476)
CAGCTGCAGCTGCAGGAGTCGGGCCCAGGACTGGTGAAGCCTTCGGAGACCCTGTCCCTCACCTGCACTGTCTCTGG

TGGCTCCATCAGCAGTAGTAGTTACTACTGGGGCTGGATCCGCCAGCCCCCAGGGAAGGGGCTGGAGTGGATTGGGA

GTATCTATTATAGTGGGAGCACCTACTACAACCCGTCCCTCAAGAGTCGAGTCACCATATCCGTAGACACGTCCAAG

AACCAGTTCTCCCTGAAGCTGAGCTCTGTGACCGCCGCAGACACGGCTGTGTATTACTGTGCGAGACA

IGHV4-34*02 nucleotide sequence
(SEQ ID NO: 477)
CAGGTGCAGCTACAACAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

ATCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCTGTGTATTACTGTGCGAGAGG

IGHV4-34*03 nucleotide sequence
(SEQ ID NO: 478)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

ATCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCCGTGTATTACTG

IGHV4-34*12 nucleotide sequence
(SEQ ID NO: 479)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAGCTGGATCCGCCAGCCCCCAGGGAAGGGGCTGGAGTGGATTGGGGAAATCA

TTCATAGTGGAAGCACCAACTACAACCCGTCCCTCAAGAGTCGAGTCACCATATCAGTAGACACGTCCAAGAACCAG

TTCTCCCTGAAGCTGAGCTCTGTGACCGCCGCGGACACGGCTGTGTATTACTGTGCGAGA

IGHV4-39*01 nucleotide sequence
(SEQ ID NO: 480)
CAGCTGCAGCTGCAGGAGTCGGGCCCAGGACTGGTGAAGCCTTCGGAGACCCTGTCCCTCACCTGCACTGTCTCTGG

TGGCTCCATCAGCAGTAGTAGTTACTACTGGGGCTGGATCCGCCAGCCCCCAGGGAAGGGGCTGGAGTGGATTGGGA

GTATCTATTATAGTGGGAGCACCTACTACAACCCGTCCCTCAAGAGTCGAGTCACCATATCCGTAGACACGTCCAAG

AACCAGTTCTCCCTGAAGCTGAGCTCTGTGACCGCCGCAGACACGGCTGTGTATTACTGTGCGAGACA

IGHV4-59*01 nucleotide sequence
(SEQ ID NO: 481)
GAGGTGCAGCTGGTGGAGTCTGGGGGAGGCTTAGTAAAGACTGGAGGGGTCTCTGAGACTCTCCTGTGCAGCCTCTG

GATTCACCTTCAGTAGCTCTGCTATGCACTGGGTCCACCAGGCTCCAGGAAAGGGTTTGGAGTGGGTCTCAGTTATT

AGTACAAGTGGTGATACCGTACTCTACACAGACTCTGTGAAGGGCTGATTCACCATCTCTAGAGACAATGCCCAGAA

TTCACTGTATCTGCAAATGAACAGCCTGAGAGCCGACGACATGGCTGTGTATTACTGTGTGAAAGA

IGHV4-59*03 nucleotide sequence
(SEQ ID NO: 482)
CAGGTGCAGCTGCAGGAGTCGGGCCCAGGACTGGTGAAGCCTTCGGAGACCCTGTCCCTCACCTGCACTGTCTCTGG

TGGCTCCATCAGTAGTTACTACTGGAGCTGGATCCGGCAGCCCCCAGGGAAGGGACTGGAGTGGATTGGGTATATCT

ATTACAGTGGGAGCACCAACTACAACCCCTCCCTCAAGAGTCGAGTCACCATATCAGTAGACACGTCCAAGAACCAA

TTCTCCCTGAAGCTGAGCTCTGTGACCGCTGCGGACACGGCCGTGTATTACTGTGCG

IGHV4-61*01 nucleotide sequence
(SEQ ID NO: 483)
CAGGTGCAGCTGCAGGAGTCGGGCCCAGGACTGGTGAAGCCTTCGGAGACCCTGTCCCTCACCTGCACTGTCTCTGG

TGGCTCCGTCAGCAGTGGTAGTTACTACTGGAGCTGGATCCGGCAGCCCCCAGGGAAGGGACTGGAGTGGATTGGGT

ATATCTATTACAGTGGGAGCACCAACTACAACCCCTCCCTCAAGAGTCGAGTCACCATATCAGTAGACACGTCCAAG

AACCAGTTCTCCCTGAAGCTGAGCTCTGTGACCGCTGCGGACACGGCCGTGTATTACTGTGCGAGAGA

IGHV4-61*08 nucleotide sequence
(SEQ ID NO: 484)
CAGGTGCAGCTGGTGCAGTCTGGCCATGAGGTGAAGCAGCCTGGGGCCTCAGTGAAGGTCTCCTGCAAGGCTTCTGG

TTACAGTTTCACCACCTATGGTATGAATTGGGTGCCACAGGCCCCTGGACAAGGGCTTGAGTGGATGGGATGGTTCA

ACACCTACACTGGGAACCCAACATATGCCCAGGGCTTCACAGGACGGTTTGTCTTCTCCATGGACACCTCTGCCAGC

ACAGCATACCTGCAGATCAGCAGCCTAAAGGCTGAGGACATGGCCATGTATTACTGTGCGAGATA

IGHV5-51*01 nucleotide sequence
(SEQ ID NO: 485)
GAGGTGCAGCTGGTGCAGTCTGGAGCAGAGGTGAAAAAGCCCGGGGAGTCTCTGAAGATCTCCTGTAAGGGTTCTGG

ATACAGCTTTACCAGCTACTGGATCGGCTGGGTGCGCCAGATGCCCGGGAAAGGCCTGGAGTGGATGGGGATCATCT

ATCCTGGTGACTCTGATACCAGATACAGCCCGTCCTTCCAAGGCCAGGTCACCATCTCAGCCGACAAGTCCATCAGC

ACCGCCTACCTGCAGTGGAGCAGCCTGAAGGCCTCGGACACCGCCATGTATTACTGTGCGAGACA

In certain embodiments of the invention, the antibody further includes a variable light chain (VL) region encoded by a human IGKV1 (or specifically, IGKV1-17, IGKV1-27, IGKV1-39, IGKV1D-39, IGKV1-5), IGKV2 (or specifically, IGKV2-30), IGKV3 (or specifically, IGKV3-11, IGKV3-15, IGKV3-20), IGKV4 (or specifically, IGKV4-1, IGKV4-1), IGLV1 (or specifically, IGLV1-40, IGLV1-44, IGLV1-55), IGLV2 (or specifically, IGLV2-11, IGLV2-14, IGLV2-8), IGLV3 (or specifically, IGLV3-21 or IGLV3-25), IGLV7 (or specifically, IGLV7-43 or IGLV7-46), or IGLV9 (or specifically, IGLV9-49) or an allele thereof. $V_L$ germline gene sequence IGKV1, IGKV2, IGKV3, IGKV4, IGLV1, IGLV2, IGLV3, IGLV7, or IGLV9 or an allele thereof, or a nucleotide acid sequence that is homologous to the IGKV1, IGKV2, IGKV3, IGKV4, IGLV1, IGLV2, IGLV3, IGLV7, or IGLV9 $V_L$ germline gene sequence or an allele thereof. Furthermore, the nucleic acid sequence that is homologous to the IGKV1, IGKV2, IGKV3, IGKV4, IGLV1, IGLV2, IGLV3, IGLV7, or IGLV9 $V_L$ germline sequence or an allele thereof is at least 65% homologous to the IGKV1, IGKV2, IGKV3, IGKV4, IGLV1, IGLV2, IGLV3, IGLV7, or IGLV9 $V_L$ germline sequence or an allele thereof.

IGKV1-17*01 nucleotide sequence
(SEQ ID NO: 486)
GACATCCAGATGACCCAGTCTCCATCCTCCCTGTCTGCATCTGTAGGAGACAGAGTCACCATCACTTGCCGGGCAAG

TCAGGGCATTAGAAATGATTTAGGCTGGTATCAGCAGAAACCAGGGAAAGCCCCTAAGCGCCTGATCTATGCTGCAT

CCAGTTTGCAAAGTGGGGTCCCATCAAGGTTCAGCGGCAGTGGATCTGGGACAGAATTCACTCTCACAATCAGCAGC

CTGCAGCCTGAAGATTTTGCAACTTATTACTGTCTACAGCATAATAGTTACCCTCC

IGKV1-27*01 nucleotide sequence
(SEQ ID NO: 487)
GACATCCAGATGACCCAGTCTCCATCCTCCCTGTCTGCATCTGTAGGAGACAGAGTCACCATCACTTGCCGGGCGAG

TCAGGGCATTAGCAATTATTTAGCCTGGTATCAGCAGAAACCAGGGAAAGTTCCTAAGCTCCTGATCTATGCTGCAT

-continued

CCACTTTGCAATCAGGGGTCCCATCTCGGTTCAGTGGCAGTGGATCTGGGACAGATTTCACTCTCACCATCAGCAGC

CTGCAGCCTGAAGATGTTGCAACTTATTACTGTCAAAAGTATAACAGTGCCCCTCC

IGKV1-39*01 nucleotide sequence (SEQ ID NO: 488)

GACATCCAGATGACCCAGTCTCCATCCTCCCTGTCTGCATCTGTAGGAGACAGAGTCACCATCACTTGCCGGGCAAG

TCAGAGCATTAGCAGCTATTTAAATTGGTATCAGCAGAAACCAGGGAAAGCCCCTAAGCTCCTGATCTATGCTGCAT

CCAGTTTGCAAAGTGGGGTCCCATCAAGGTTCAGTGGCAGTGGATCTGGGACAGATTTCACTCTCACCATCAGCAGT

CTGCAACCTGAAGATTTTGCAACTTACTACTGTCAACAGAGTTACAGTACCCCTCC

IGKV1D-39*01 nucleotide sequence (SEQ ID NO: 489)

GACATCCAGATGACCCAGTCTCCATCCTCCCTGTCTGCATCTGTAGGAGACAGAGTCACCATCACTTGCCGGGCAAG

TCAGAGCATTAGCAGCTATTTAAATTGGTATCAGCAGAAACCAGGGAAAGCCCCTAAGCTCCTGATCTATGCTGCAT

CCAGTTTGCAAAGTGGGGTCCCATCAAGGTTCAGTGGCAGTGGATCTGGGACAGATTTCACTCTCACCATCAGCAGT

CTGCAACCTGAAGATTTTGCAACTTACTACTGTCAACAGAGTTACAGTACCCCTCC

IGKV1-5*03 nucleotide sequence (SEQ ID NO: 490)

GACATCCAGATGACCCAGTCTCCTTCCACCCTGTCTGCATCTGTAGGAGACAGAGTCACCATCACTTGCCGGGCCAG

TCAGAGTATTAGTAGCTGGTTGGCCTGGTATCAGCAGAAACCAGGGAAAGCCCCTAAGCTCCTGATCTATAAGGCGT

CTAGTTTAGAAAGTGGGGTCCCATCAAGGTTCAGCGGCAGTGGATCTGGGACAGAATTCACTCTCACCATCAGCAGC

CTGCAGCCTGATGATTTTGCAACTTATTACTGCCAACAGTATAATAGTTATTCTCC

IGKV2-30*02 nucleotide sequence (SEQ ID NO: 491)

GATGTTGTGATGACTCAGTCTCCACTCTCCCTGCCCGTCACCCTTGGACAGCCGGCCTCCATCTCCTGCAGGTCTAG

TCAAAGCCTCGTACACAGTGATGGAAACACCTACTTGAATTGGTTTCAGCAGAGGCCAGGCCAATCTCCAAGGCGCC

TAATTTATAAGGTTTCTAACCGGGACTCTGGGGTCCCAGACAGATTCAGCGGCAGTGGGTCAGGCACTGATTTCACA

CTGAAAATCAGCAGGGTGGAGGCTGAGGATGTTGGGGTTTATTACTGCATGCAAGGTACACACTGGCCTCC

IGKV3-11*01 nucleotide sequence (SEQ ID NO: 492)

GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTGGCCTCC

IGKV3-15*01 nucleotide sequence (SEQ ID NO: 493)

GAAATAGTGATGACGCAGTCTCCAGCCACCCTGTCTGTGTCTCCAGGGGAAAGAGCCACCCTCTCCTGCAGGGCCAG

TCAGAGTGTTAGCAGCAACTTAGCCTGGTACCAGCAGAAACCTGGCCAGGCTCCCAGGCTCCTCATCTATGGTGCAT

CCACCAGGGCCACTGGTATCCCAGCCAGGTTCAGTGGCAGTGGGTCTGGGACAGAGTTCACTCTCACCATCAGCAGC

CTGCAGTCTGAAGATTTTGCAGTTTATTACTGTCAGCAGTATAATAACTGGCCTCC

IGKV3-20*01 nucleotide sequence (SEQ ID NO: 494)

GAAATTGTGTTGACGCAGTCTCCAGGCACCCTGTCTTTGTCTCCAGGGGAAAGAGCCACCCTCTCCTGCAGGGCCAG

TCAGAGTGTTAGCAGCAGCTACTTAGCCTGGTACCAGCAGAAACCTGGCCAGGCTCCCAGGCTCCTCATCTATGGTG

CATCCAGCAGGGCCACTGGCATCCCAGACAGGTTCAGTGGCAGTGGGTCTGGGACAGACTTCACTCTCACCATCAGC

AGACTGGAGCCTGAAGATTTTGCAGTGTATTACTGTCAGCAGTATGGTAGCTCACCTCC

IGKV4-1*01 nucleotide sequence (SEQ ID NO: 495)

GACATCGTGATGACCCAGTCTCCAGACTCCCTGGCTGTGTCTCTGGGCGAGAGGGCCACCATCAACTGCAAGTCCAG

CCAGAGTGTTTTATACAGCTCCAACAATAAGAACTACTTAGCTTGGTACCAGCAGAAACCAGGACAGCCTCCTAAGC

-continued

TGCTCATTTACTGGGCATCTACCCGGGAATCCGGGGTCCCTGACCGATTCAGTGGCAGCGGGTCTGGGACAGATTTC

ACTCTCACCATCAGCAGCCTGCAGGCTGAAGATGTGGCAGTTTATTACTGTCAGCAATATTATAGTACTCCTCC

IGLV1-40*01 nucleotide sequence (SEQ ID NO: 496)
CAGTCTGTGCTGACGCAGCCGCCCTCAGTGTCTGGGGCCCCAGGGCAGAGGGTCACCATCTCCTGCACTGGGAGCAG

CTCCAACATCGGGGCAGGTTATGATGTACACTGGTACCAGCAGCTTCCAGGAACAGCCCCCAAACTCCTCATCTATG

GTAACAGCAATCGGCCCTCAGGGGTCCCTGACCGATTCTCTGGCTCCAAGTCTGGCACCTCAGCCTCCCTGGCCATC

ACTGGGCTCCAGGCTGAGGATGAGGCTGATTATTACTGCCAGTCCTATGACAGCAGCCTGAGTGGTTC

IGLV1-44*01 nucleotide sequence (SEQ ID NO: 497)
CAGTCTGTGCTGACTCAGCCACCCTCAGCGTCTGGGACCCCCGGGCAGAGGGTCACCATCTCTTGTTCTGGAAGCAG

CTCCAACATCGGAAGTAATACTGTAAACTGGTACCAGCAGCTCCCAGGAACGGCCCCCAAACTCCTCATCTATAGTA

ATAATCAGCGGCCCTCAGGGGTCCCTGACCGATTCTCTGGCTCCAAGTCTGGCACCTCAGCCTCCCTGGCCATCAGT

GGGCTCCAGTCTGAGGATGAGGCTGATTATTACTGTGCAGCATGGGATGACAGCCTGAATGGTCC

IGLV1-51*02 nucleotide sequence (SEQ ID NO: 498)
CAGTCTGTGTTGACGCAGCCGCCCTCAGTGTCTGCGGCCCCAGGACAGAAGGTCACCATCTCCTGCTCTGGAAGCAG

CTCCAACATTGGGAATAATTATGTATCCTGGTACCAGCAGCTCCCAGGAACAGCCCCCAAACTCCTCATCTATGAAA

ATAATAAGCGACCCTCAGGGATTCCTGACCGATTCTCTGGCTCCAAGTCTGGCACGTCAGCCACCCTGGGCATCACC

GGACTCCAGACTGGGGACGAGGCCGATTATTACTGCGGAACATGGGATAGCAGCCTGAGTGCTGG

IGLV2-11*01 nucleotide sequence (SEQ ID NO: 499)
CAGTCTGCCCTGACTCAGCCTCGCTCAGTGTCCGGGTCTCCTGGACAGTCAGTCACCATCTCCTGCACTGGAACCAG

CAGTGATGTTGGTGGTTATAACTATGTCTCCTGGTACCAACAGCACCCAGGCAAAGCCCCCAAACTCATGATTTATG

ATGTCAGTAAGCGGCCCTCAGGGGTCCCTGATCGCTTCTCTGGCTCCAAGTCTGGCAACACGGCCTCCCTGACCATC

TCTGGGCTCCAGGCTGAGGATGAGGCTGATTATTACTGCTGCTCATATGCAGGCAGCTACACTTTC

IGLV2-14*01 nucleotide sequence (SEQ ID NO: 500)
CAGTCTGCCCTGACTCAGCCTGCCTCCGTGTCTGGGTCTCCTGGACAGTCGATCACCATCTCCTGCACTGGAACCAG

CAGTGACGTTGGTGGTTATAACTATGTCTCCTGGTACCAACAGCACCCAGGCAAAGCCCCCAAACTCATGATTTATG

AGGTCAGTAATCGGCCCTCAGGGGTTTCTAATCGCTTCTCTGGCTCCAAGTCTGGCAACACGGCCTCCCTGACCATC

TCTGGGCTCCAGGCTGAGGACGAGGCTGATTATTACTGCAGCTCATATACAAGCAGCAGCACTCTC

IGLV2-8*01 nucleotide sequence (SEQ ID NO: 501)
CAGTCTGCCCTGACTCAGCCTCCCTCCGCGTCCGGGTCTCCTGGACAGTCAGTCACCATCTCCTGCACTGGAACCAG

CAGTGACGTTGGTGGTTATAACTATGTCTCCTGGTACCAACAGCACCCAGGCAAAGCCCCCAAACTCATGATTTATG

AGGTCAGTAAGCGGCCCTCAGGGGTCCCTGATCGCTTCTCTGGCTCCAAGTCTGGCAACACGGCCTCCCTGACCGTC

TCTGGGCTCCAGGCTGAGGATGAGGCTGATTATTACTGCAGCTCATATGCAGGCAGCAACAATTTC

IGLV3-21*02 nucleotide sequence (SEQ ID NO: 502)
TCCTATGAGCTGACACAGCTACCCTCGGTGTCAGTGTCCCCAGGACAGACAGCCAGGATCACCTGCTCTGGAGATGT

ACTGGGGGAAAATTATGCTGACTGGTACCAGCAGAAGCCAGGCCAGGCCCCTGAGTTGGTGATATACGAAGATAGTG

AGCGGTACCCTGGAATCCCTGAACGATTCTCTGGGTCCACCTCAGGGAACACGACCACCCTGACCATCAGCAGGGTC

CTGACCGAAGACGAGGCTGACTATTACTGTTTGTCTGGGGATGAGGACAATCC

IGLV3-25*03 nucleotide sequence (SEQ ID NO: 503)
TCCTATGAGCTGACACAGCCACCCTCGGTGTCAGTGTCCCCAGGACAGACGGCCAGGATCACCTGCTCTGGAGATGC

ATTGCCAAAGCAATATGCTTATTGGTACCAGCAGAAGCCAGGCCAGGCCCCTGTGCTGGTGATATATAAAGACAGTG

```
AGAGGCCCTCAGGGATCCCTGAGCGATTCTCTGGCTCCAGCTCAGGGACAACAGTCACGTTGACCATCAGTGGAGTC

CAGGCAGAAGACGAGGCTGACTATTACTGTCAATCAGCAGACAGCAGTGGT

IGLV7-43*01 nucleotide sequence
                                                                  (SEQ ID NO: 504)
CAGACTGTGGTGACTCAGGAGCCCTCACTGACTGTGTCCCCAGGAGGGACAGTCACTCTCACCTGTGCTTCCAGCAC

TGGAGCAGTCACCAGTGGTTACTATCCAAACTGGTTCCAGCAGAAACCTGGACAAGCACCCAGGGCACTGATTTATA

GTACAAGCAACAAACACTCCTGGACCCCTGCCCGGTTCTCAGGCTCCCTCCTTGGGGGCAAAGCTGCCCTGACACTG

TCAGGTGTGCAGCCTGAGGACGAGGCTGAGTATTACTGCCTGCTCTACTATGGTGGTGCTCAG

IGLV7-46*01 nucleotide sequence
                                                                  (SEQ ID NO: 505)
CAGGCTGTGGTGACTCAGGAGCCCTCACTGACTGTGTCCCCAGGAGGGACAGTCACTCTCACCTGTGGCTCCAGCAC

TGGAGCTGTCACCAGTGGTCATTATCCCTACTGGTTCCAGCAGAAGCCTGGCCAAGCCCCCAGGACACTGATTTATG

ATACAAGCAACAAACACTCCTGGACACCTGCCCGGTTCTCAGGCTCCCTCCTTGGGGGCAAAGCTGCCCTGACCCTT

TCGGGTGCGCAGCCTGAGGATGAGGCTGAGTATTACTGCTTGCTCTCCTATAGTGGTGCTCGG

IGLV7-46*02 nucleotide sequence
                                                                  (SEQ ID NO: 506)
CAGGCTGTGGTGACTCAGGAGCCCTCACTGACTGTGTCCCCAGGAGGGACAGTCACTCTCACCTGTGGCTCCAGCAC

TGGAGCTGTCACCAGTGGTCATTATCCCTACTGGTTCCAGCAGAAGCCTGGCCAAGCCCCCAGGACACTGATTTATG

ATACAAGCAACAAACACTCCTGGACACCTGCCCGGTTCTCAGGCTCCCTCCTTGGGGGCAAAGCTGCCCTGACCCTT

TTGGGTGCGCAGCCTGAGGATGAGGCTGAGTATTACTGCTTGCTCTCCTATAGTGGTGCTCGG

IGLV9-49*01 nucleotide sequence
                                                                  (SEQ ID NO: 507)
CAGCCTGTGCTGACTCAGCCACCTTCTGCATCAGCCTCCCTGGGAGCCTCGGTCACACTCACCTGCACCCTGAGCAG

CGGCTACAGTAATTATAAAGTGGACTGGTACCAGCAGAGACCAGGGAAGGGCCCCCGGTTTGTGATGCGAGTGGGCA

CTGGTGGGATTGTGGGATCCAAGGGGATGGCATCCCTGATCGCTTCTCAGTCTTGGGCTCAGGCCTGAATCGGTAC

CTGACCATCAAGAACATCCAGGAAGAGGATGAGAGTGACTACCACTGTGGGGCAGACCATGGCAGTGGGAGCAACTT

CGTGTAACC

IGLV9-49*03 nucleotide sequence
                                                                  (SEQ ID NO: 508)
CAGCCTGTGCTGACTCAGCCACCTTCTGCATCAGCCTCCCTGGGAGCCTCGGTCACACTCACCTGCACCCTGAGCAG

CGGCTACAGTAATTATAAAGTGGACTGGTACCAGCAGAGACCAGGGAAGGGCCCCCGATTTGTGATGCGAGTGGGCA

CTGGTGGGATTGTGGGATCCAAGGGGATGGCATCCCTGATCGCTTCTCAGTCTTGGGCTCAGGCCTGAATCGGTAC

CTGACCATCAAGAACATCCAGGAAGAGGATGAGAGTGACTACCACTGTGGGGCAGACCATGGCAGTGGGAGCAACTT

CGTGTAACC
```

The heavy chain of an isolated monoclonal anti-hemagglutinin (HA) antibody (i.e., anti-hemagglutinin antibody of the invention) is derived from a germ line V (variable) gene such as, for example, the IGHV1, IGHV2, IGHV3, IGHV4, or IGHV5 germline gene or an allele thereof.

The HA antibodies of the invention include a variable heavy chain ($V_H$) region encoded by a human IGHV1, IGHV2, IGHV3, IGHV4, or IGHV5 germline gene sequence or an allele thereof. A IGHV1, IGHV2, IGHV3, IGHV4, or IGHV5 germline gene sequence is shown, e.g., in SEQ ID NOs: 457 to 485. The HA antibodies of the invention include a $V_H$ region that is encoded by a nucleic acid sequence that is at least 75% homologous to the IGHV1, IGHV2, IGHV3, IGHV4, or IGHV5 germline gene sequence or an allele thereof. Preferably, the nucleic acid sequence is at least 75%, 80%, 85%, 90%, 95%, 96%, 97% homologous to the IGHV1, IGHV2, IGHV3, IGHV4, or IGHV5 germline gene sequence or an allele thereof, and more preferably, at least 98%, 99% homologous to the IGHV1, IGHV2, IGHV3, IGHV4, or IGHV5 germline gene sequence or an allele thereof. The $V_H$ region of the HA antibody is at least 75% homologous to the amino acid sequence of the $V_H$ region encoded by the IGHV1, IGHV2, IGHV3, IGHV4, or IGHV5 $V_H$ germline gene sequence or an allele thereof. Preferably, the amino acid sequence of $V_H$ region of the HA antibody is at least 75%, 80%, 85%, 90%, 95%, 96%, 97% homologous to the amino acid sequence encoded by the 75%, 80%, 85%, 90%, 95%, 96%, 97% germline gene sequence or an allele thereof, and more preferably, at least 98%, 99% homologous to the sequence encoded by the 75%, 80%, 85%, 90%, 95%, 96%, 97% germline gene sequence or an allele thereof.

The HA antibodies of the invention also include a variable light chain ($V_L$) region encoded by a human IGKV1, IGKV2, IGKV3, IGKV4, IGLV1, IGLV2, IGLV3, IGLV7, or IGLV9 germline gene sequence or an allele thereof. A human IGKV1, IGKV2, IGKV3, IGKV4, IGLV1, IGLV2, IGLV3, IGLV7, or IGLV9 $V_L$ germline gene sequence, or an allele thereof is shown, e.g., at SEQ ID NOs: 486 to 508. Alternatively, the HA antibodies include a IGKV1, IGKV2, IGKV3, IGKV4, IGLV1, IGLV2, IGLV3, IGLV7, or IGLV9 $V_L$ region that is encoded by a nucleic acid sequence that is at least 65% homologous to the IGKV1, IGKV2, IGKV3, IGKV4, IGLV1, IGLV2, IGLV3, IGLV7, or IGLV9 germline gene sequence or an allele thereof. Preferably, the nucleic acid sequence is at least 65%, 70%, 75%, 80%, 85%, 90%, 95%, 96%, 97% homologous to the IGKV1, IGKV2, IGKV3, IGKV4, IGLV1, IGLV2, IGLV3, IGLV7, or IGLV9 germline gene sequence or an allele thereof, and more preferably, at least 98%, 99% homologous to the IGKV1, IGKV2, IGKV3, IGKV4, IGLV1, IGLV2, IGLV3, IGLV7, or IGLV9 germline gene sequence or an allele thereof. The $V_L$ region of the HA antibody is at least 65% homologous to the amino acid sequence of the $V_L$ region encoded the IGKV1, IGKV2, IGKV3, IGKV4, IGLV1, IGLV2, IGLV3, IGLV7, or IGLV9 germline gene sequence or an allele thereof. Preferably, the amino acid sequence of $V_L$ region of the HA antibody is at least 65%, 70%, 75%, 80%, 85%, 90%, 95%, 96%, 97% homologous to the amino acid sequence encoded by the IGKV1, IGKV2, IGKV3, IGKV4, IGLV1, IGLV2, IGLV3, IGLV7, or IGLV9 germline gene sequence or an allele thereof, and more preferably, at least 98%, 99% homologous to the sequence encoded by the IGKV1, IGKV2, IGKV3, IGKV4, IGLV1, IGLV2, IGLV3, IGLV7, or IGLV9 germline gene sequence or an allele thereof.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called a J chain, and therefore contains 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the $\alpha$ and $\gamma$ chains and four $C_H$ domains for $\mu$ and $\epsilon$ isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may include residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_\epsilon RI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

As used herein, an antibody that "internalizes" is one that is taken up by (i.e., enters) the cell upon binding to an antigen on a mammalian cell (e.g., a cell surface polypeptide or receptor). The internalizing antibody includes antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuMHA antibody specifically binds to HA if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (*Ann. N.Y. Acad. Sci. USA* 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, virus, or cell that it specifically binds. Methods for identifying antagonist antibodies may comprise contacting a polypeptide, virus, or cell specifically bound by a candidate antagonist antibody with the candidate antagonist antibody and measuring a detectable change in one or more biological activities normally associated with the polypeptide, virus, or cell.

An "antibody that inhibits the growth of infected cells" or a "growth inhibitory" antibody is one that binds to and results in measurable growth inhibition of infected cells expressing or capable of expressing an HA epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 μg/ml or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 μg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), may be performed.

The terms "Influenza A" and "Influenza virus A" refer to a genus of the Orthomyxoviridae family of viruses. Influenza virus A includes only one species: Influenza A virus which causes Influenza in birds, humans, pigs, and horses. Strains of all subtypes of Influenza A virus have been isolated from wild birds, although disease is uncommon. Some isolates of Influenza A virus cause severe disease both in domestic poultry and, rarely, in humans.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The term "epitope tagged" as used herein refers to a chimeric polypeptide comprising a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen, an Influenza virus, or an Influenza-infected cell, preferably, an Influenza A virus or an Influenza-A-infected virus.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions, inversions, and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions, inversions, and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences that encode said peptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region. Specifically, the poly-His tail of SEQ ID NO: 1 is bound to a solid support when this sequence is incorporated into a soluble and recombinant Influenza HA protein of the invention, such that this homotrimeric protein is used as a target for trapping human antibodies that bind a conformational epitope of this antigenic and homotrimeric Influenza protein.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

The present invention includes human monoclonal anti-influenza A antibodies. In one embodiment, the antibody is an antibody designated herein as TCN-522 (3212_I12), TCN-521 (3280_D18), TCN-523 (5248_A17), TCN-563 (5237_B21), TCN-526 (5084_C17), TCN-527 (5086_C06), TCN-528 (5087_P17), TCN-529 (5297_H01), TCN-530 (5248_H10), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_I07), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_L16), TCN-556 (5089_$K_{12}$), TCN-557 (5081_A04), TCN 558 (5248_H10b), TCN-559 (5097_G08), TCN-560 (5084_P10), TCN-564 (5256_A17b), or TCN-504 (3251_K17). These antibodies bind to an epitope of an Influenza protein on multiple Influenza subtypes and inhibit influenza A infection.

In particular embodiments, the antibodies of the present invention bind to the HA protein. In certain embodiments, the present invention provides HuMHA antibodies that bind to epitopes within HA protein that are only present in the native conformation, i.e., as expressed on the surface of the Influenza virus. It is understood that these antibodies recognize non-linear (i.e. conformational) epitope(s) of the HA protein, particularly in its homotrimeric conformation.

These specific conformational epitopes within the HA protein may be used as vaccines to prevent the development of Influenza infection within a subject.

As will be understood by the skilled artisan, general description of antibodies herein and methods of preparing and using the same also apply to individual antibody polypeptide constituents and antibody fragments.

The antibodies of the present invention may be polyclonal or monoclonal antibodies. However, in preferred embodiments, they are monoclonal. In particular embodiments, antibodies of the present invention are fully human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include fully human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils an mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, comprise a variable light chain that is either kappa or lambda. The lambda chain may be any of subtype, including, e.g., lambda 1, lambda 2, lambda 3, and lambda 4.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, a human MAb arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an HA-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H 3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain.

Antibodies of the present invention further include single chain antibodies.

In particular embodiments, antibodies of the present invention are internalizing antibodies.

Amino acid sequence modification(s) of the antibodies described herein are contemplated. For example, it may be desirable to improve the binding affinity and/or other biological properties of the antibody. Amino acid sequence variants of the antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention may be included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum or plasma half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and an antigen or infected cell. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-

2922 (1992). Homodimeric antibodies with enhanced anti-infection activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989).

To increase the serum or plasma half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention may also be modified to include an epitope tag or label, e.g., for use in purification or diagnostic applications. The invention also pertains to therapy with immunoconjugates comprising an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Examples of other agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof that can be used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232.

The present invention further includes an immunoconjugate formed between an antibody and a compound with nucleolytic activity (e.g., a ribonuclease or a DNA endonuclease such as a deoxyribonuclease; DNase).

For selective destruction of infected cells, the antibody includes a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al. (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Alternatively, a fusion protein comprising the antibody and cytotoxic agent is made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibodies of the present invention are also used in antibody dependent enzyme mediated prodrug therapy (ADET) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention can be covalently bound to the antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein are also formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989).

Antibodies of the present invention, or fragments thereof, may possess any of a variety of biological or functional characteristics. In certain embodiments, these antibodies are Influenza A specific or HA protein specific antibodies, indicating that they specifically bind to or preferentially bind to Influenza A or the HA protein thereof, respectively, as compared to a normal control cell. In particular embodiments, the antibodies are HuMHA antibodies, indicating that they specifically bind to an Influenza HA protein, preferably to an epitope of an HA1 or HA2 domain that is only present when the HA protein is expressed as a soluble recombinant Influenza HA protein or in its native confirmation on the surface of an Influenza virus.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Methods of Identifying and Producing Antibodies Specific for Influenza Virus

The present invention provides novel methods for the identification of HuMHA antibodies, as exemplified in Example 3. These methods may be readily adapted to identify antibodies specific for other polypeptides expressed on a viral surface.

In general, the methods include obtaining serum or plasma samples from patients that have been infected with or vaccinated against an infectious agent. These serum or plasma samples are then screened to identify those that contain antibodies specific for a particular polypeptide associated with the infectious agent, such as, e.g., a polypeptide specifically expressed on the surface of cells infected with the infectious agent, but not uninfected cells. In particular embodiments, the serum or plasma samples are screened by contacting the samples with a cell that has been transfected with an expression vector that expresses the polypeptide expressed on the surface of infected cells. In particular embodiments the serum or plasma samples are screened by contacting the samples with a recombinant protein which represents a particular protein of the infectious agent such as, e.g. hemagglutinin of the influenza A virus. In particular embodiments the serum or plasma samples are screened by contacting the samples with a purified form of the infectious agent such as, e.g. intact whole virions of the influenza A virus. In particular embodiments the serum or plasma samples are screened by contacting the samples with a live form of the infectious agent such as, e.g. intact whole virions of the influenza A virus to determine the presence of serum antibodies that inhibit or neutralize infection of susceptible cells e.g MDCK cells.

Once a patient is identified as having serum or plasma containing an antibody specific for the infectious agent polypeptide of interest, mononuclear and/or B cells obtained from the same patient are used to identify a cell or clone thereof that produces the antibody, using any of the methods described herein or available in the art. Once a B cell that produces the antibody is identified, cDNAs encoding the variable regions or fragments thereof of the antibody may be cloned using standard RT-PCR vectors and primers specific for conserved antibody sequences, and subcloned into expression vectors used for the recombinant production of monoclonal antibodies specific for the infectious agent polypeptide of interest.

In one embodiment, the present invention provides a method of identifying an antibody that specifically binds Influenza A-infected cells, comprising: contacting an Influenza A virus or a cell expressing the HA protein with a biological sample obtained from a patient having been infected by Influenza A; determining an amount of antibody in the biological sample that binds to the cell; and comparing the amount determined with a control value, wherein if the value determined is at least two-fold greater than the control value, an antibody that specifically binds Influenza A-infected cells is indicated.

In various embodiments, the cells expressing an HA protein are cells infected with an Influenza virus, preferably an Influenza A virus, or cells that have been transfected with a polynucleotide that expressed the HA protein. Alternatively, the cells may express a portion of the HA protein and a trimerization domain wherein the soluble recombinant homotrimeric HA protein is presented in the same conformation as when present on the viral surface. Methods of preparing an HA expression vector and transfecting an appropriate cell, including those described herein, may be readily accomplished, in view of many HA sequences being publicly available. See, for example, the Influenza Sequence Database (ISD) (flu.Ian1.gov on the World Wide Web, described in Macken et al., 2001, "The value of a database in surveillance and vaccine selection" in Options for the Control of Influenza IV. A.D.M.E., Osterhaus & Hampson (Eds.), Elsevier Science, Amsterdam, pp. 103-106) and the Microbial Sequencing Center (MSC) at The Institute for Genomic Research (TIGR) (tigr.org/msc/infl_a_virus.shtml on the World Wide Web).

The HA-expressing cells or virus described above are used to screen the biological sample obtained from a patient infected with Influenza A for the presence of antibodies that preferentially bind to the cell expressing the HA polypeptide using standard biological techniques. For example, in certain embodiments, the antibodies may be labeled, and the presence of label associated with the cell detected, e.g., using FMAT or FACs analysis. In particular embodiments, the biological sample is blood, serum, plasma, bronchial lavage, or saliva. Methods of the present invention may be practiced using high throughput techniques.

Identified human antibodies may then be characterized further. For example the particular conformational epitopes with in the HA protein that are necessary or sufficient for binding of the antibody may be determined, e.g., using site-directed mutagenesis of expressed HA polypeptides. These methods may be readily adapted to identify human antibodies that bind any protein expressed on a cell surface. Furthermore, these methods may be adapted to determine binding of the antibody to the virus itself, as opposed to a cell expressing recombinant HA or infected with the virus.

Polynucleotide sequences encoding the antibodies, variable regions thereof, or antigen-binding fragments thereof may be subcloned into expression vectors for the recombinant production of HuMHA antibodies. In one embodiment, this is accomplished by obtaining mononuclear cells from the patient from the serum or plasma containing the identified HuMHA antibody was obtained; producing B cell clones from the mononuclear cells; inducing the B cells to become antibody-producing plasma cells; and screening the supernatants produced by the plasma cells to determine if it contains the HuMHA antibody. Once a B cell clone that produces an HuMHA antibody is identified, reverse-transcription polymerase chain reaction (RT-PCR) is performed to clone the DNAs encoding the variable regions or portions thereof of the HuMHA antibody. These sequences are then subcloned into expression vectors suitable for the recombinant production of human HuMHA antibodies. The binding specificity may be confirmed by determining the recombinant antibody's ability to bind cells expressing HA polypeptide.

In particular embodiments of the methods described herein, B cells isolated from peripheral blood or lymph nodes are sorted, e.g., based on their being CD19 positive, and plated, e.g., as low as a single cell specificity per well, e.g., in 96, 384, or 1536 well configurations. The cells are induced to differentiate into antibody-producing cells, e.g., plasma cells, and the culture supernatants are harvested and tested for 1) binding to cells expressing the infectious agent polypeptide on their surface using, e.g., FMAT or FACS analysis; and/or 2) binding to intact virions coated onto plastic plates, e.g., ELISA; and/or 3) binding to soluble recombinant homotrimeric HA protein in microarray format e.g., Aushon microarrayer; and/or 4) inhibition or neutralization of virus infection of susceptible cells e.g., MDCK cells. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and may be further tested for pan-specificity across various strains of isolates of the infectious agent.

Thus, in one embodiment, a method of identifying HuMHA antibodies is practiced as follows. First, full length or approximately full length HA cDNAs are transfected into a cell line for expression of HA protein. Secondly, individual human plasma or sera samples are tested for antibodies that bind the cell-expressed HA. And lastly, MAbs derived from plasma- or serum-positive individuals are characterized for binding to the same cell-expressed HA. Further definition of the fine specificities of the MAbs can be performed at this point.

These methods may be practiced to identify a variety of different HuMHA antibodies, including antibodies specific for (a) epitopes in a linear HA peptide, (b) common epitopes in multiple variants of an HA peptide or protein, (c) conformational determinants of an HA homotrimer, and (d) common conformational determinants of multiple variants of the HA homotrimer. The last category is particularly desirable, as this specificity is perhaps specific for all strains of influenza, particularly A strains of influenza.

Polynucleotides that encode the HuMHA antibodies or portions thereof of the present invention may be isolated from cells expressing HuMHA antibodies, according to methods available in the art and described herein, including amplification by polymerase chain reaction using primers specific for conserved regions of human antibody polypeptides. For example, light chain and heavy chain variable regions may be cloned from the B cell according to molecular biology techniques described in WO 92/02551; U.S. Pat. No. 5,627,052; or Babcook et al., *Proc. Natl. Acad. Sci. USA* 93:7843-48 (1996). In certain embodiments, polynucleotides encoding all or a region of both the heavy and light chain variable regions of the IgG molecule expressed by the clonal daughter plasma cells expressing the HuMHA antibody are subcloned and sequenced. The sequence of the encoded polypeptide may be readily determined from the polynucleotide sequence.

Isolated polynucleotides encoding a polypeptide of the present invention may be subcloned into an expression vector to recombinantly produce antibodies and polypeptides of the present invention, using procedures known in the art and described herein.

Binding properties of an antibody (or fragment thereof) to HA, soluble recombinant HA, or infected cells or tissues may generally be determined and assessed using immunodetection methods including, for example, immunofluorescence-based assays, such as immuno-histochemistry (IHC) and/or fluorescence-activated cell sorting (FACS). Immunoassay methods may include controls and procedures to determine whether antibodies bind specifically to HA from one or more specific strains of Influenza A, and do not recognize or cross-react with normal control cells.

Following pre-screening of serum or plasma to identify patients that produce antibodies to an infectious agent or polypeptide thereof, e.g., HA, the methods of the present invention typically include the isolation or purification of B cells from a biological sample previously obtained from a patient or subject. The patient or subject may be currently or previously diagnosed with or suspect or having a particular disease or infection, or the patient or subject may be considered free or a particular disease or infection. Typically, the patient or subject is a mammal and, in particular embodiments, a human. The biological sample may be any sample that contains B cells, including but not limited to, lymph node or lymph node tissue, pleural effusions, peripheral blood, ascites, tumor tissue, or cerebrospinal fluid (CSF). In various embodiments, B cells are isolated from different types of biological samples, such as a biological sample affected by a particular disease or infection. However, it is understood that any biological sample comprising B cells may be used for any of the embodiments of the present invention.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, infectious agent, or polypeptide. In certain embodiments, the specific antigen, e.g., cell surface polypeptide bound by the antibody is not known, while in other embodiments, the antigen specifically bound by the antibody is known.

According to the present invention, B cells may be isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art may be employed, such as, e.g., column purification using CD19 magnetic beads or IgG-specific magnetic beads, followed by elution from the column. However, magnetic isolation of B cells utilizing any marker may result in loss of certain B cells. Therefore, in certain embodiments, the isolated cells are not sorted but, instead, ficolll-purified mononuclear cells isolated from tumor are directly plated to the appropriate or desired number of specificities per well.

In order to identify B cells that produce an infectious agent-specific antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtitre plates, e.g., in 96, 384, or 1536 well configurations. When the B cells are initially plated at a density greater than one cell per well, then the methods of the present invention may include the step of subsequently diluting cells in a well identified as producing an antigen-specific antibody, until a single cell specificity per well is achieved, thereby facilitating the identification of the B cell that produces the antigen-specific antibody. Cell supernatants or a portion thereof and/or cells may be frozen and stored for future testing and later recovery of antibody polynucleotides.

In certain embodiments, the B cells are cultured under conditions that favor the production of antibodies by the B cells. For example, the B cells may be cultured under conditions favorable for B cell proliferation and differentiation to yield antibody-producing plasmablast, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feeder cells and/or other B cell activators, such as CD40 ligand.

Cell culture supernatants or antibodies obtained therefrom may be tested for their ability to bind to a target antigen, using routine methods available in the art, including those described herein. In particular embodiments, culture supernatants are tested for the presence of antibodies that bind to a target antigen using high-throughput methods. For example, B cells may be cultured in multi-well microtitre dishes, such that robotic plate handlers may be used to simultaneously sample multiple cell supernatants and test for the presence of antibodies that bind to a target antigen. In particular embodiments, antigens are bound to beads, e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT™ is a fluorescence macro-confocal platform for high-throughput screening, which mix-and-read, non-radioactive assays using live cells or beads.

In the context of comparing the binding of an antibody to a particular target antigen (e.g., a biological sample such as infected tissue or cells, or infectious agents) as compared to a control sample (e.g., a biological sample such as uninfected cells, or a different infectious agent), in various embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, may be isolated from cells utilizing any means available in the art. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products may be sequenced.

The resulting PCR products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a tumor-specific antibody or fragment thereof, as described herein, may be propagated and expressed according to any of a variety of well-known procedures for nucleic acid excision, ligation, transformation, and transfection. Thus, in certain embodiments expression of an antibody fragment may be preferred in a prokaryotic host cell, such as *Escherichia coli* (see, e.g., Pluckthun et al., *Methods Enzymol.* 178:497-515 (1989)). In certain other embodiments, expression of the antibody or an antigen-binding fragment thereof may be preferred in a eukaryotic host cell, including yeast (e.g., *Saccharomyces cerevisiae, Schizosaccharomyces pombe,* and *Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector may be designed for expressing foreign sequences in a particular host system, and then polynucleotide sequences encoding the tumor-specific antibody (or fragment thereof) may be inserted. The regulatory elements will vary according to the particular host.

One or more replicable expression vectors containing a polynucleotide encoding a variable and/or constant region may be prepared and used to transform an appropriate cell line, for example, a non-producing myeloma cell line, such as a mouse NSO line or a bacterium, such as *E. coli*, in which production of the antibody will occur. In order to obtain efficient transcription and translation, the polynucleotide sequence in each vector should include appropriate regulatory sequences, particularly a promoter and leader sequence operatively linked to the variable domain sequence. Particular methods for producing antibodies in this way are generally well known and routinely used. For example, molecular biology procedures are described by Sambrook et al. (*Molecular Cloning, A Laboratory Manual,* 2nd ed., Cold Spring Harbor Laboratory, New York, 1989; see also Sambrook et al., 3rd ed., Cold Spring Harbor Laboratory, New York, (2001)). While not required, in certain embodiments, regions of polynucleotides encoding the recombinant antibodies may be sequenced. DNA sequencing can be performed as described in Sanger et al. (*Proc. Natl. Acad. Sci. USA* 74:5463 (1977)) and the Amersham International plc sequencing handbook and including improvements thereto.

In particular embodiments, the resulting recombinant antibodies or fragments thereof are then tested to confirm their original specificity and may be further tested for pan-specificity, e.g., with related infectious agents. In particular embodiments, an antibody identified or produced according to methods described herein is tested for cell killing via antibody dependent cellular cytotoxicity (ADCC) or apoptosis, and/or well as its ability to internalize.

Polynucleotides

The present invention, in other aspects, provides polynucleotide compositions. In preferred embodiments, these polynucleotides encode a polypeptide of the invention, e.g., a region of a variable chain of an antibody that binds to Influenza virus (Influenza A, B, or C), HA, or soluble and recombinant HA. Polynucleotides of the invention are single-stranded (coding or antisense) or double-stranded DNA (genomic, cDNA or synthetic) or RNA molecules. RNA molecules include, but are not limited to, HnRNA molecules, which contain introns and correspond to a DNA molecule in a one-to-one manner, and mRNA molecules, which do not contain introns. Alternatively, or in addition, coding or non-coding sequences are present within a polynucleotide of the present invention. Also alternatively, or in addition, a polynucleotide is linked to other molecules and/or support materials of the invention. Polynucleotides of the invention are used, e.g., in hybridization assays to detect the presence of an Influenza Antibody (preferably an Influenza A antibody) in a biological sample, and in the recombinant production of polypeptides of the invention.

In certain preferred embodiments, the polynucleotide sequences set forth herein encode polypeptides capable of preferentially binding an Influenza virus (preferably, an Influenza A virus) as compared to a non-Influenza virus, an Influenza A-infected cell as compared to a normal control uninfected cell, or a soluble and recombinant Influenza HA protein in a native homotrimeric conformation compared to a linear peptide from an Influenza HA protein, including a polypeptide having a sequence of, for instance, SEQ ID NOs: 2-19. Furthermore, the invention includes all polynucleotides that encode any polypeptide of the present invention.

In other related embodiments, the invention provides polynucleotide variants having substantial identity, for example those comprising at least 70% sequence identity, preferably at least 75%, 80%, 85%, 90%, 95%, 96%, 97%, 98%, or 99% or higher, sequence identity compared to a polynucleotide sequence of this invention, as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions, inversions, and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. As used herein, the term "intermediate lengths" is meant to describe any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to the same epitope or Influenza A strain) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are included in many implementations of this invention.

It will be appreciated by those of ordinary skill in the art that, as a result of the degeneracy of the genetic code, there are multiple nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the invention. Further, alleles of the genes including the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

In certain embodiments of the present invention, mutagenesis of the disclosed polynucleotide sequences is performed in order to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest enables them to detect the presence of complementary sequences in a given sample. However, other uses are also encompassed by the invention, such as the use of the sequence information for the preparation of mutant species primers, or primers for use in preparing other genetic constructions. As such, nucleic acid segments of the invention that include a sequence region of at least about 15 nucleotide long contiguous sequence that has the same sequence as, or is complementary to, a 15 nucleotide long contiguous sequence disclosed herein is particularly useful. Longer contiguous identical or complementary sequences, e.g., those of about 20, 30, 40, 50, 100, 200, 500, 1000 (including all intermediate lengths) including full length sequences, and all lengths in between, are also used in certain embodiments.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch(es), ultimately depends on the intended use or application of the particular nucleic acid segment. Smaller fragments are generally used in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer where desired, are generally preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences is governed by various factors. For example, one may wish to employ primers from towards the termini of the total sequence.

Polynucleotide of the present invention, or fragments or variants thereof, are readily prepared by, for example, directly synthesizing the fragment by chemical means, as is commonly practiced using an automated oligonucleotide synthesizer. Also, fragments are obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

Vectors, Host Cells and Recombinant Methods

The invention provides vectors and host cells comprising a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors comprising a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention are amplified by polymerase chain reaction using oligonucleotide primers complementary to each strand of the polynucleotide. These primers also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers are synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the $V_H$ and $V_L$ domains are produced using these methods (see Bird et al., Science 242:423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. Such elements may vary in their strength and specificity. Depending on the vector system and host utilized, any number of suitable transcription and translation elements, including constitutive and inducible promoters, is used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like are used.

A variety of promoter sequences are known for eukaryotes and any are used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells are controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA-3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264:5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) *EMBO J.* 6:307-311. Alternatively, plant promoters such as the small subunit of RUBISCO or heat shock promoters are used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs can be introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide are cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses are then used to infect, for example, *S. frugiperda* cells or *Trichoplusia larvae*, in which the polypeptide of interest is expressed (Engelhard, E. K. et al. (1994) Proc. Natl. Acad. Sci. 91:3224-3227).

Specific initiation signals are also used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons are of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer is spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and used herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris*. (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein is also used to facilitate correct insertion, folding and/or function. Different host cells such as CHO, COS, HeLa, MDCK, HEK293, and WI38, which have specific cellular machinery and characteristic mechanisms for such post-translational activities, are chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins are produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and can be purified through, e.g., a protein A or G column depending on the isotype. Final purification can be carried out using a process similar to that used for purifying antibody expressed e.g., in CHO cells.

Suitable host cells for the expression of glycosylated polypeptides and antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses are used as the virus herein according to the present invention, particularly for transfection of *Spodoptera frugiperda* cells. Plant cell cultures of cotton, corn, potato, soybean, petunia, tomato, and tobacco are also utilized as hosts.

Methods of propagation of antibody polypeptides and fragments thereof in vertebrate cells in culture (tissue culture) are encompassed by the invention. Examples of mammalian host cell lines used in the methods of the invention are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest are transformed using expression vectors that contain viral origins of replication and/or endogenous expression elements and a selectable marker gene on the same or on a separate vector. Following the introduction of the vector, cells are allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells are proliferated using tissue culture techniques appropriate to the cell type.

A plurality of selection systems are used to recover transformed cell lines. These include, but are not limited to, the herpes simplex virus thymidine kinase (Wigler, M. et al. (1977) Cell 11:223-32) and adenine phosphoribosyltransferase (Lowy, I. et al. (1990) Cell 22:817-23) genes that are employed in tk⁻ or aprt⁻ cells, respectively. Also, antimetabolite, antibiotic or herbicide resistance is used as the basis for selection; for example, dhfr, which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al. (1981) J. Mol. Biol. 150:1-14); and also or pat, which confer resistance to chlorsulfuron and phosphinotricin acetyltransferase, respectively (Murry, supra). Additional selectable genes have been described. For example, trpB allows cells to utilize indole in place of tryptophan, and hisD allows cells to utilize histinol in place of histidine (Hartman, S. C. and R. C. Mulligan (1988) Proc. Natl. Acad. Sci. 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression is confirmed. For example, if the sequence encoding a polypeptide is inserted within a marker gene sequence, recombinant cells containing sequences are identified by the absence of marker gene function. Alternatively, a marker gene is placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Nonlimiting examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide is preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and are used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof are cloned into a vector for the production of an mRNA probe. Such vectors are known in the art, are commercially available, and are used to synthesize RNA probes in vitro by addition of an appropriate RNA polymerase such as T7, T3, or SP6 and labeled nucleotides. These procedures are conducted using a variety of commercially available kits. Suitable reporter molecules or labels, which are used include, but are not limited to, radionuclides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. Expression vectors containing polynucleotides of the invention are designed to contain signal sequences that direct secretion of the encoded polypeptide through a prokaryotic or eukaryotic cell membrane.

In certain embodiments, a polypeptide of the invention is produced as a fusion polypeptide further including a polypeptide domain that facilitates purification of soluble proteins. Such purification-facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide are used to facilitate purification. An exemplary expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors used for producing fusion proteins is provided in Kroll, D. J. et al. (1993; DNA Cell Biol. 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence is selected, for example, from the group of the alkaline phosphatase, penicillinase, 1 pp, or heat-stable enterotoxin II leaders. For yeast secretion, the signal sequence is selected from, e.g., the yeast invertase leader, α factor leader (including Saccharomyces and Kluyveromyces α factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody is produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasmic space of E. coli. Briefly, cell paste is thawed in the presence of sodium acetate (pH 3.5), EDTA, and phenylmethylsulfonylfluoride (PMSF) over about 30 min. Cell debris is removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. Optionally, a protease inhibitor such as PMSF is included in any of the foregoing steps to inhibit proteolysis and antibiotics is included to prevent the growth of adventitious contaminants.

The polypeptide or antibody composition prepared from the cells are purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A is used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody comprises a $C_H 3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered. Following any preliminary purification step(s), the mixture comprising the polypeptide or antibody of interest and contaminants are subjected to low pH hydrophobic interaction chromatography using an elution buffer at a pH between about 2.5-4.5, preferably performed at low salt concentrations (e.g., from about 0-0.25M salt).

Pharmaceutical Compositions

The invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions. Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably comprises the polypeptide or antibody at a concentration of between 5-200 mg/ml, preferably between 10-100 mg/ml.

The formulations herein also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the invention, an additional or second antibody, anti-viral agent, anti-infective agent and/or cardioprotectant is added to the formulation. Such molecules are suitably present in the pharmaceutical formulation in amounts that are effective for the purpose intended.

The active ingredients, e.g., polypeptides and antibodies of the invention and other therapeutic agents, are also entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations are prepared. Suitable examples of sustained-release preparations include, but are not limited to, semi-permeable matrices of solid hydrophobic polymers containing the antibody, which matrices are in the form of shaped articles, e.g., films, or microcapsules. Non-limiting examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxyburyric acid.

Formulations to be used for in vivo administration are preferably sterile. This is readily accomplished by filtration through sterile filtration membranes.

Diagnostic Uses

Antibodies and fragments thereof, and therapeutic compositions, of the invention specifically bind or preferentially bind to an Influenza virus, Influenza virus-infected cells or Influenzavirus-infected tissue, as compared to a unrelated virus, normal control cells and normal control tissue. Thus, these Influenza Antibodies are used to detect an Influenza virus, preferably Influenza A, as well as infected cells or tissues in a patient, biological sample, or cell population, using any of a variety of diagnostic and prognostic methods, including those described herein. The ability of a human anti-HA specific antibody to detect an Influenza virus or an infected cell depends upon its binding specificity, which is readily determined by testing its ability to bind to an Influenza virus, an Influenza virus-infected cell or an Influenza virus-infected tissue obtained from different patients, and/or from patients infected with different strains of an Influenza virus, preferably, Influenza A.

Diagnostic methods also generally involve contacting an Influenza virus, preferably an Influenza A virus, with an Influenza Antibody, and determining whether the antibody preferentially binds to the Influenza virus as compared to a control virus (e.g. unrelated virus or dissociated virus) or predetermined cut-off value, thereby indicating the presence of an Influenza virus. In particular embodiments, at least two-fold, three-fold, or five-fold more HuMHA antibody binds to an Influenza virus as compared to an appropriate control virus or predetermined cut-off value. A pre-determined cut-off value is determined, e.g., by averaging the amount of HuMHA antibody that binds to several different appropriate control viruses under the same conditions used to perform the diagnostic assay of the biological sample being tested. Alternatively or in addition, a hemagglutinin (HA) protein is substituted for an Influenza virus in the above method. The HA protein is presented on the surface of a virus, host cell (e.g. any mammalian cell), or in a recombinant and soluble form. In the HA version of this above diagnostic method, the control protein is a denatured HA protein, a linear HA peptide, an unrelated protein of similar size and shape, but dissimilar sequence, or a pre-determined cut-off value.

Diagnostic methods also generally involve contacting a biological sample obtained from a patient, such as, e.g., blood, serum, plasma, cerebral spinal fluid, saliva, urine, sputum, a cell swab sample, or a tissue biopsy, with an Influenza, preferably Influenza A, antibody, e.g., HuMHA, and determining whether the antibody preferentially binds to the sample as compared to a control sample or predetermined cut-off value, thereby indicating the presence of infected cells. In particular embodiments, at least two-fold, three-fold, or five-fold more HuMHA antibody binds to an infected cell as compared to an appropriate control normal cell or tissue sample. A pre-determined cut-off value is determined, e.g., by averaging the amount of HuMHA antibody that binds to several different appropriate control samples under the same conditions used to perform the diagnostic assay of the biological sample being tested.

Bound antibody is detected using procedures described herein and known in the art. In certain embodiments, diagnostic methods of the invention are practiced using HuMHA antibodies that are conjugated to a detectable label, e.g., a fluorophore, to facilitate detection of bound antibody. However, they are also practiced using methods of secondary detection of the HuMHA antibody. These include, for example, RIA, ELISA, precipitation, agglutination, complement fixation and immuno-fluorescence.

In certain procedures, the HuMHA antibodies are labeled. The label is detected directly. Exemplary labels that are detected directly include, but are not limited to, radiolabels and fluorochromes. Alternatively, or in addition, labels are moieties, such as enzymes, that must be reacted or derivatized to be detected. Nonlimiting examples of isotope labels are $^{99}$Tc, $^{14}$C, $^{131}$I, $^{125}$I, $^{3}$H, $^{32}$P and $^{35}$S. Fluorescent materials that are used include, but are not limited to, for example, fluorescein and its derivatives, rhodamine and its derivatives, auramine, dansyl, umbelliferone, luciferia, 2,3-dihydro-phthalazinediones, horseradish peroxidase, alkaline phosphatase, lysozyme, and glucose-6-phosphate dehydrogenase.

An enzyme label is detected by any of the currently utilized colorimetric, spectrophotometric, fluorospectro-photometric or gasometric techniques. Many enzymes which are used in these procedures are known and utilized by the methods of the invention. Nonlimiting examples are peroxidase, alkaline phosphatase, β-glucuronidase, β-D-glucosidase, β-D-galactosidase, urease, glucose oxidase plus peroxidase, galactose oxidase plus peroxidase and acid phosphatase.

The antibodies are tagged with such labels by known methods. For instance, coupling agents such as aldehydes, carbodiimides, dimaleimide, imidates, succinimides, bid-diazotized benzandine and the like are used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529 (1973).

HuMHA antibodies of the present invention are capable of differentiating between patients with and patients without an Influenzainfection, preferably an Influenza A infection, and determining whether or not a patient has an infection, using the representative assays provided herein.

According to one method, a biological sample is obtained from a patient suspected of having or known to have an Influenza infection. The sample is blood, serum, plasma, cerebral spinal fluid, saliva, urine, sputum, a cell swab sample, or a tissue biopsy. In certain embodiments, the biological sample is cell free, i.e. the sample is a fluid containing an intact or whole Influenza virus. In other embodiments, the biological sample includes cells from the patient. The sample is contacted with an HuMHA antibody, e.g., for a time and under conditions sufficient to allow the HuMHA antibody to bind to either the Influenza virus or to an infected cell present in the sample. For instance, the sample is contacted with an HuMHA antibody for 10 seconds, 30 seconds, 1 minute, 5 minutes, 10 minutes, 30 minutes, 1 hour, 6 hours, 12 hours, 24 hours, 3 days or any point in between. The amount of bound HuMHA antibody is determined and compared to a control value, which may be, e.g., a pre-determined value or a value determined from performing this procedure with an unrelated virus or a normal (uninfected) tissue sample. An increased amount of antibody bound to the patient sample as compared to the control sample is indicative of the presence of an Influenza virus or an infected cell in the patient sample.

In a related method, a biological sample obtained from a patient is contacted with an HuMHA antibody for a time and under conditions sufficient to allow the antibody to bind to an Influenza virus or to an infected cell. Bound antibody is then detected, and the presence of bound antibody indicates that the sample contains an Influenza virus or an infected cell. This embodiment is particularly useful when the HuMHA antibody does not bind unrelated viruses or normal cells at a detectable level. Different HuMHA antibodies possess different binding and specificity characteristics. Depending upon these characteristics, particular HuMHA antibodies are used to detect the presence of one or more strains of an Influenza virus, which are preferably strains of Influenza A. For example, certain antibodies bind specifically to only one or several strains of an Influenza virus, whereas others bind to all or a majority of different strains of Influenza virus. Antibodies specific for only one strain of Influenza A are used to identify the strain of an infection.

In certain embodiments, antibodies that bind to an Influenza virus or to an infected cell preferably generate a signal indicating the presence of an infection in at least about 20% of patients with the infection being detected, more preferably at least about 30% of patients. Alternatively, or in addition, the antibody generates a negative signal indicating the absence of the infection in at least about 90% of individuals without the infection being detected. Each antibody satisfies the above criteria; however, antibodies of the present invention are used in combination to improve sensitivity.

The present invention also includes kits useful in performing diagnostic and prognostic assays using the antibodies of the present invention. Kits of the invention include a suitable container comprising a HuMHA antibody of the invention in either labeled or unlabeled form. In addition, when the antibody is supplied in a labeled form suitable for an indirect binding assay, the kit further includes reagents for performing the appropriate indirect assay. For example, the kit includes one or more suitable containers including enzyme substrates or derivatizing agents, depending on the nature of the label. Control samples and/or instructions are also included.

Therapeutic/Prophylactic Uses

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using human monoclonal antibodies provide an immediate treatment strategy for emergency prophylaxis and treatment of Influenza.

HuMHA antibodies and fragments thereof, and therapeutic compositions, of the invention specifically bind or preferentially bind to an Influenza virus and/or an infected cell, as compared to an unrelated, non-Influenza virus, or a normal control uninfected cell or tissue. Thus, these HuMHA antibodies are used to selectively target Influenza viruses, infected cells, or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods include contacting an infected cell with a HuMHA antibody of the invention. These methods are practiced in vitro, ex vivo, and in vivo.

In various embodiments, antibodies of the invention are intrinsically therapeutically active. Alternatively, or in addition, antibodies of the invention are conjugated to a cytotoxic agent or growth inhibitory agent, e.g., a radioisotope or toxin, that is used in treating infected cells bound or contacted by the antibody.

In one embodiment, the invention provides methods of treating or preventing infection in a patient, including the steps of providing an HuMHA antibody of the invention to a patient diagnosed with, at risk of developing, or suspected of having an Influenza infection, preferably an Influenza A infection. The methods of the invention are used in the first-line treatment of the infection, follow-on treatment, or in the treatment of a relapsed or refractory infection.

Treatment with an antibody of the invention is a stand-alone treatment. Alternatively, treatment with an antibody of the invention is one component or phase of a combination therapy regime, in which one or more additional therapeutic agents are also used to treat the patient.

Subjects at risk for an Influenza virus-related diseases or disorders include patients who have come into contact with an infected person or who have been exposed to the Influenza virus in some other way. Administration of a prophylactic agent can occur prior to the manifestation of symptoms characteristic of the Influenza virus-related disease or disorder, such that a disease or disorder is prevented or, alternatively, delayed in its progression.

In various aspects, the huMHA is administered substantially contemporaneously with or following infection of the subject, i.e., therapeutic treatment. In another aspect, the antibody provides a therapeutic benefit. In various aspects, a therapeutic benefit includes reducing or decreasing progression, severity, frequency, duration or probability of one or more symptoms or complications of Influenza infection, virus titer, virus replication or an amount of a viral protein of one or more Influenza strains. still another aspect, a therapeutic benefit includes hastening or accelerating a subject's recovery from Influenza infection.

Methods for preventing an increase in Influenza virus titer, virus replication, virus proliferation or an amount of an Influenza viral protein in a subject are further provided. In one embodiment, a method includes administering to the subject an amount of a huMHA antibody effective to prevent an increase in Influenza virus titer, virus replication or an amount of an Influenza viral protein of one or more Influenza strains or isolates in the subject.

Methods for protecting a subject from infection or decreasing susceptibility of a subject to infection by one or more Influenza strains/isolates or subtypes, i.e., prophylactic methods, are additionally provided. In one embodiment, a method includes administering to the subject an effective amount of huMHA antibody that specifically binds Influenza HA to protect the subject from infection, or to decrease susceptibility of the subject to infection, by one or more Influenza strains/isolates or subtypes.

Optionally, the subject is further administered with a second agent such as, but not limited to, an Influenza virus antibody, an anti-viral drug such as a neuraminidase inhibitor, a HA inhibitor, a sialic acid inhibitor or an M2 ion channel inhibitor, a viral entry inhibitor or a viral attachment inhibitor. The M2 ion channel inhibitor is for example amantadine or rimantadine. The neuraminidase inhibitor for example zanamivir, or oseltamivir phosphate.

Symptoms or complications of Influenza infection that can be reduced or decreased include, for example, chills, fever, cough, sore throat, nasal congestion, sinus congestion, nasal infection, sinus infection, body ache, head ache, fatigue, pneumonia, bronchitis, ear infection, ear ache or death.

For in vivo treatment of human and non-human patients, the patient is usually administered or provided a pharmaceutical formulation including a HuMHA antibody of the invention. When used for in vivo therapy, the antibodies of the invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the site of infection, target cell site, or intravenously. Intravenous or subcutaneous administration of the antibody is preferred in certain embodiments. Therapeutic compositions of the invention are administered to a patient or subject systemically, parenterally, or locally.

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/ml to 10 mg/ml.

The dose and dosage regimen depends upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered is in the range of about 0.1 mg/kg to about 50 mg/kg of patient body weight. Depending on the type and severity of the infection, about 0.1 mg/kg to about 50 mg/kg body weight (e.g., about 0.1-15 mg/kg/dose) of antibody is an initial candidate dosage for administration to the patient, whether, for example, by one or more separate administrations, or by continuous infusion. The progress of this therapy is readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include, but are not limited to, maytansinoids, calicheamicins, ribonucleases and DNA endonucleases.

Other therapeutic regimens are combined with the administration of the HuM2e antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the invention with another antibody directed against another antigen associated with the infectious agent.

Aside from administration of the antibody protein to the patient, the invention provides methods of administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

In another embodiment, anti-HA antibodies of the invention are used to determine the structure of bound antigen, e.g., conformational epitopes, the structure of which is then used to develop a vaccine having or mimicking this structure, e.g., through chemical modeling and SAR methods. Such a vaccine could then be used to prevent Influenza A infection.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

EXAMPLES

Example 1

Screening and Characterization of HA-Specific Antibodies Present in Human Plasma that Bind Purified Whole Inactivated Influenza A Virions, Bind Recombinant Homotrimeric HA Proteins, and Neutralize Infectious Influenza A Fully human monoclonal antibodies specific for HA and capable of binding purified whole inactivated Influenza A Virions, binding recombinant homotrimeric HA proteins, and neutralizing live influenza A were identified in patient plasma, as described below.

Expression of Recombinant Soluble HA

An expression construct was generated containing a cDNA encoding an HA precursor (HA0) polypeptide corresponding to the derived HA sequence found in the Influenza subtypes, for example, as listed in Table 2. Recombinant HA0 precursor polypeptides of the invention lack an integral membrane or transmembrane domain, and contain additional amino acids at the C-terminus of the HA0 ectodomain, for instance, corresponding to the sequence:

```
SGRLVPRGSPGSGYIPEAPRDGQAYVRKDGEWVLLSTFLGKPIPNPLLGLDSTGHHHHHH (SEQ ID NO: 1),
``` wherein the thrombin cleavage site is bolded and italicized, the bacteriophage T4 fibritin "foldon" or trimerization domain is underlined, the last amino acid of the trimerization domain, "G", is the start of the boxed "V5" epitope tag, which is followed by the hexa histidine (HIS) epitope tag in bold. The hexa-HIS tag within the preceding C-terminal region is used for purification of recombinant HA proteins of the invention. Thus, recombinant HA0 precursor proteins that contain a trimerization domain are considered recombinant HA homotrimeric proteins of the invention.

Recombinant HA homotrimeric proteins of the invention retain the native signal sequence to allow efficient secretion from art-recognized cell lines maintained in vitro, e.g. 293 HEK cells as done by Immune Technology Corp. (http://www.immune-tech.com/). Moreover, within these recombinant HA homotrimeric proteins, or the HA0 precursors thereof, the native HA1/HA2 viral protease cleavage site was maintained, for instance, in all of the sequences provided in Table 2, except SEQ ID NO: 12, in which the native cleavage site positioned at amino acids 337-347 and consisting of the sequence "PQREGGRRRKR" (SEQ ID NO: 525) was substituted with the sequence "PQTETR" (SEQ ID NO: 526).

Furthermore, exemplary receptor binding domains of recombinant HA homotrimeric proteins, or the HA0 precursors thereof, include the following structural elements: a 190 α-helix, a 130-loop, and a 220-loop (see, sequence of Influenza A strain A/Vietnam/1203/2004) (or equivalent HA structures in other Influenza A strains that the ordinarily skilled artisan could readily obtain by accessing public databases, including GenBank, http://www.ncbi.nlm.nih.gov, and The Influenza Sequence Database, www.flu.lan1.gov, and downloading sequences) (Stevens et al. 2006. Science 312: 404-410). In other embodiments of the invention, in which the recombinant HA homotrimeric protein, or HA0 precursor thereof, encoded by this expression construct is partially or entirely expressed and administered to a subject, these receptor binding domains may be modified. The term "modified" is meant to describe the removal of one or more structural elements. Alternatively, or in addition, "modified" is meant to describe the addition, deletion, substitution, inversion, or translocation of one or more amino acids within a structural element of a receptor-binding domain of HA. For instance, a linear or discontinuous epitope to which a HuMHA antibody of the invention binds is administered to a subject at risk of contracting an influenza infection to prevent the infection. Alternatively or in addition, a linear or discontinuous epitope to which a HuMHA antibody of the invention binds is administered to a subject prior to exposure to an influenza virus to prevent influenza infection. In other embodiments a structural mimic of the conformational or discontinuous epitope is administered to a subject. When the above proteins are used for prophylactic purposes, for instance, as a vaccine, it may be advantageous to modify one or more receptor binding domains to control the resultant immune response in the subject. Exemplary structural elements of HA that are optionally modified include, but are not limited to, the 190 α-helix, the 130-loop, and the 220-loop of HA.

Recombinant homotrimeric HA proteins of the invention are encoded by the following amino acid sequences, wherein the native sequence is bolded and the sequence of SEQ ID NO: 1 is normal (see also, Table 2):

```
A/California/4/09
                                                              (SEQ ID NO: 2)
DTLCIGYHANNSTDTVDTVLEKNVTVTHSVNLLEDKHNGKLCKLRGVAPLHLGKCNIAGWILGNPECESLSTASSWSY

IVETPSSDNGTCYPGDFIDYEELREQLSSVSSFERFEIFPKTSSWPNHDSNKGVTAACPHAGAKSFYKNLIWLVKKGNS

YPKLSKSYINDKGKEVLVLWGIHHPSTSADQQSLYQNADTYVFVGSSRYSKKFKPEIAIRPKVRDQEGRMNYYWTLV

EPGDKITFEATGNLVVPRYAFAMERNAGSGIIISDTPVHDCNTTCQTPKGAINTSLPFQNIHPITIGKCPKYVKSTKLRL

ATGLRNIPSIQSRGLFGAIAGFIEGGWTGMVDGWYHHQNEQGSGYAADLKSTQNAIDEITNKVNSVIEKMNTQ

FTAVGKEFNHLEKRIENLNKKVDDGFLDIWTYNAELLVLLENERTLDYHDSNVKNLYEKVRSQLKNNAKEIGNGCFEF

YHKCDNTCMESVKNGTYDYPKYSEEAKLNREEIDGVKLESTRIYQSGRLVPRGSPGSGYIPEAPRDGQAYVRKDGEW

VLLSTFLGKPIPNPLLGLDSTGHHHHHH

A/Solomon Islands/3/06 - H1N1
                                                              (SEQ ID NO: 3)
DTICIGYHANNSTDTVDTVLEKNVTVTHSVNLLEDSHNGKLCLLKGIAPLQLGNCSVAGWILGNPECELLISRESWSYI

VEKPNPENGTCYPGHFADYEELREQLSSVSSFERFEIFPKESSWPNHTTTGVSASCSHNGESSFYKNLLWLTGKNGLY

PNLSKSYANNKEKEVLVLWGVHHPPNIGDQRALYHKENAYVSVVSSHYSRKFTPEIAKRPKVRDQEGRINYYWTLLE

PGDTIIFEANGNLIAPRYAFALSRGFGSGIINSNAPMDECDAKCQTPQGAINSSLPFQNVHPVTIGECPKYVRSAKLR

MVTGLRNIPSIQSRGLFGAIAGFIEGGWTGMVDGWYGYHHQNEQGSGYAADQKSTQNAINGITNKVNSVIEKMN

TQFTAVGKEFNKLERRMENLNKKVDDGFIDIWTYNAELLVLLENERTLDFHDSNVKNLYEKVKSQLKNNAKEIGNGC

FEFYHKCNDECMESVKNGTYDYPKYSEESKLNREKIDGVKLESMGVYQSGRLVPRGSPGSGYIPEAPRDGQAYVRKD

GEWVLLSTFLGKPIPNPLLGLDSTGHHHHHH

A/South Carolina/1/18 -
                                                              (SEQ ID NO: 4)
MEARLLVLLCAFAATNADTICIGYHANNSTDTVDTVLEKNVTVTHSVNLLEDSHNGKLCKLKGIAPLQLGKCNIAGWL

LGNPECDLLLTASSWSYIVETSNSENGTCYPGDFIDYEELREQLSSVSSFEKFEIFPKTSSWPNHETTKGVTAACSYAGA

SSFYRNLLWLTKKGSSYPKLSKSYVNNKGKEVLVLWGVHHPPTGTDQQSLYQNADAYVSVGSSKYNRRFTPEIAARP

KVRDQAGRMNYYWTLLEPGDTITFEATGNLIAPWYAFALNRGSGSGIITSDAPVHDCNTKCQTPHGAINSSLPFQNI

HPVTIGECPKYVRSTKLRMATGLRNIPSIQSRGLFGAIAGFIEGGWTGMIDGWYGYHHQNEQGSGYAADQKSTQN

AIDGITNKVNSVIEKMNTQFTAVGKEFNNLERRIENLNKKVDDGFLDIWTYNAELLVLLENERTLDFHDSNVRNLYEK

VKSQLKNNAKEIGNGCFEFYHKCDDACMESVRNGTYDYPKYSEESKLNREEIDGVKLESMGVYQSGRLVPRGSPGSG

YIPEAPRDGQAYVRKDGEWVLLSTFLGKPIPNPLLGLDSTGHHHHHH
```

-continued

A/Japan/305/57 - H2N2
(SEQ ID NO: 5)

DQICIGYHANNSTEKVDTNLERNVTVTHAKDILEKTHNGKLCKLNGIPPLELGDCSIAGWLLGNPECDRLLSVPEWSYI

MEKENPRDGLCYPGSFNDYEELKHLLSSVKHFEKVKILPKDRWTQHTTTGGSRACAVSGNPSFFRNMVWLTKEGSD

YPVAKGSYNNTSGEQMLIIWGVHHPIDETEQRTLYQNVGTYVSVGTSTLNKRSTPEIATRPKVNGQGGRMEFSWTL

LDMWDTINFESTGNLIAPEYGFKISKRGSSGIMKTEGTLENCETKCQTPLGAINTTLPFHNVHPLTIGECPKYVKSEKLV

LATGLRNVPQIESRGLFGAIAGFIEGGWQGMVDGWYGYHHSNDQGSGYAADKESTQKAFDGITNKVNSVIEKMN

TQFEAVGKEFGNLERRLENLNKRMEDGFLDVWTYNAELLVLMENERTLDFHDSNVKNLYDKVRMQLRDNVKELGN

GCFEFYHKCDDECMNSVKNGTYDYPKYEEESKLNRNEIKGVKLSSMGVYQSGR*LVPRGS*PGSGYIPEAPRDGQAYVR

KDGEWVLLSTFLGKPIPNPLLGLDSTGHHHHHH

A/Wisconsin/67/05 - H3N2

(SEQ ID NO: 6)

QKLPGNDNSTATLCLGHHAVPNGTIVKTITNDQIEVTNATELVQSSSTGGICDSPHQILDGENCTLIDALLGDPQCDG

FQNKKWDLFVERSKAYSNCYPYDVPDYASLRSLVASSGTLEFNDESFNWTGVTQNGTSSSCKRRSNNSFFSRLNWL

TQLKFKYPALNVTMPNNEKFDKLYIWGVHHPVTDNDQIFLYAQASGRITVSTKRSQQTVIPNIGSRPRIRNIPSRISIY

WTIVKPGDILLINSTGNLIAPRGYFKIRSGKSSIMRSDAPIGKCNSECITPNGSIPNDKPFQNVNRITYGACPRYVKQNT

LKLATGMRNVPEKQTRGIFGAIAGFIENGWEGMVDGWYGFRHQNSEGIGQAADLKSTQAAINQINGKLNRLIGKT

NEKFHQIEKEFSEVEGRIQDLEKYVEDTKIDLWSYNAELLVALENQHTIDLTDSEMNKLFERTKKQLRENAEDMGNG

CFKIYHKCDNACIGSIRNGTYDHDVYRDEALNNRFQIKGVELKSGSGR*LVPRGS*PGSGYIPEAPRDGQAYVRKDGEWV

LLSTFLGKPIPNPLLGLDSTGHHHHHH

A/swine/Ontario/01911-2/99 - H4N6

(SEQ ID NO: 7)

QNYTGNPVICLGHHAVSNGTMVKTLTDDQIEVVTAQELVESQHLPELCPSPLRLVDGQTCDIVNGALGSPGCDHLN

GAEWDVFIERPTAVDTCYPFDVPDYQSLRSILANNGKFEFIAEEFQWNTVKQNGKSGACKRANVNDFFNRLNWLT

KSDGNAYPLQNLTKVNNGDYARLYIWGVHHPSTDTEQTNLYKNNPGRVTVSTQTSQTSVVPNIGSRPWVRGLSSRI

SFYWTIVEPGDLIVFNTIGNLIAPRGHYKLNSQKKSTILNTAVPIGSCVSKCHTDKGSISTTKPFQNISRISIGDCPKYVK

QGSLKLATGMRSILEKATRGLFGAIAGFIENGWQGLIDGWYGFRHQNAEGTGTAADLKSTQAAIDQINGKLNRLIGK

PNEKYHQIEKEFEQVEGRIQDLEKYVEDTKIDLWSYNAELLVALENQHTIDVTDSEMNKLFERVRHQLRENAEDKGN

GCFEIFHQCDNSCIESIRNGTYDHDIYRDEAINNRFQIQGVKLIQGYKDSGR*LVPRGS*PGSGYIPEAPRDGQAYVRKDG

EWVLLSTFLGKPIPNPLLGLDSTGHHHHHH

A/Hong Kong/156/97 - H5N1

(SEQ ID NO: 8)

MERTVLLLATVSLVKSDQICIGYHANNSTEQVDTIMEKNVTVTHAQDILERTHNGKLCDLNGVKPLILRDCSVAGWL

LGNPMCDEFINVPEWSYIVEKASPANDLCYPGNFNDYEELKHLLSRINHFEKIQIIPKSSWSNHDASSGVSSACPYLGR

SSFFRNVVWLIKKNSAYPTIKRSYNNTNQEDLLVLWGVHHPNDAAEQTKLYQNPTTYISVGTSTLNQRLVPEIATRPK

VNGQSGRMEFFWTILKPNDAINFESNGNFIAPEYAYKIVKKGDSTIMKSELEYGNCNTKCQTPMGAINSSMPFHNIH

PLTIGECPKYVKSNRLVLATGLRNTPQRERRRKKRGLFGAIAGFIEGGWQGMVDGWYGYHHSNEQGSCYSADKEST

QKAIDGVTNKVNSIINKMNTQFEAVGREFNNLERRIENLNKKMEDGFLDVWTYNAELLVLMENERTLDFHDSNVK

NLYDKVRLQLRDNAKELGNGCFEFYHKCDNECMESVKNGTYDYPQYSEEARLNREEISGVKLESMGTYQSGR*LVPR*

*GS*PGSGYIPEAPRDGQAYVRKDGEWVLLSTFLGKPIPNPLLGLDSTGHHHHHH

A/Vietnam/1203/04 - H5N1

(SEQ ID NO: 9)

DQICIGYHANNSTEQVDTIMEKNVTVTHAQDILEKKHNGKLCDLDGVKPLILRDCSVAGWLLGNPMCDEFINVPEW

SYIVEKANPVNDLCYPGDFNDYEELKHLLSRINHFEKIQIIPKSSWSSHEASLGVSSACPYQGKSSFFRNVVWLIKKNST

YPTIKRSYNNTNQEDLLVLWGIHHPNDAAEQTKLYQNPTTYISVGTSTLNQRLVPRIATRSKVNGQSGRMEFFWTIL

-continued

KPNDAINFESNGNFIAPEYAYKIVKKGDSTIMKSELEYGNCNTKCQTPMGAINSSMPFHNIHPLTIGECPKYVKSNRL

VLATGLRNSPQRERRRKKRGLFGAIAGFIEGGWQGMVDGWYGYHHSNEQGSYAADKESTQKAIDGVTNKVNSII

DKMNTQFEAVGREFNNLERRIENLNKKMEDGFLDVWTYNAELLVLMENERTLDFHDSNVKNLYDKVRLQLRDNAK

ELGNGCFEFYHKCDNECMESVRNGTYDYPQYSEEARLKREEISGVKLESIGIYQSGR*LVPRGS*PGSGYIPEAPRDGQAY

VRKDGEWVLLSTFLGKPIPNPLLGLDSTGHHHHHH

A/Indonesia/5/05 - H5N1

(SEQ ID NO: 10)

DQICIGYHANNSTEQVDTIMEKNVTVTHAQDILEKTHNGKLCDLDGVKPLILRDCSVAGWLLGNPMCDEFINVPEW

SYIVEKANPTNDLCYPGSFNDYEELKHLLSRINHFEKIQIIPKSSWSDHEASSGVSSACPYLGSPSFFRNVVWLIKKNST

YPTIKKSYNNTNQEDLLVLWGIHHPNDAAEQTRLYQNPTTYISIGTSTLNQRLVPKIATRSKVNGQSGRMEFFWTILK

PNDAINFESNGNFIAPEYAYKIVKKGDSAIMKSELEYGNCNTKCQTPMGAINSSMPFHNIHPLTIGECPKYVKSNRLV

LATGLRNSPQRESRRKKRGLFGAIAGFIEGGWQGMVDGWYGYHHSNEQGSYAADKESTQKAIDGVTNKVNSIID

KMNTQFEAVGREFNNLERRIENLNKKMEDGFLDVWTYNAELLVLMENERTLDFHDSNVKNLYDKVRLQLRDNAKE

LGNGCFEFYHKCDNECMESIRNGTYNYPQYSEEARLKREEISGVKLESIGTYQSGR*LVPRGS*PGSGYIPEAPRDGQAYV

RKDGEWVLLSTFLGKPIPNPLLGLDSTGHHHHHH

A/Egypt/3300-NAMRU3/08 - H5N1

(SEQ ID NO: 11)

DQICIGYHANNSTEQVDTIMEKNVTVTHAQDILEKTHNGKLCDLDGVKPLILRDCSVAGWLLGNPMCDEFLNVSEW

SYIVEKINPANDLCYPGNFNNYEELKHLLSRINRFEKIQIIPKSSWPDHEASLGVSSACPYQGGPSFYRNVVWLIKKNN

TYPTIKKSYHNTNQEDLLVLWGIHHPNDEAEQTRIYKNPTTYISVGTSTLNQRLVPKIATRSKVNGQSGRVEFFWTILK

SNDTINFESNGNFIAPENAYKIVKKGDSTIMKSELEYGNCNTKCQTPIGAINSSMPFHNIHPLTIGECPKYVKSNRLVL

ATGLRNSPQGERRRKKRGLFGAIAGFIEGGWQGMVDGWYGYHHSNEQGSYAADKESTQKAIDGVTNKVNSIID

KMNTQFEAVGREFNNLERRIENLNKKMEDGFLDVWTYNAELLVLMENERTLDFHDSNVKNLYDKVRLQLRDNAKE

LGNGCFEFYHRCDNECMESVRNGTYDYPQYSEEARLKREEISGVKLESIGTYQSGR*LVPRGS*PGSGYIPEAPRDGQAY

VRKDGEWVLLSTFLGKPIPNPLLGLDSTGHHHHHH

A/Common magpie/Hong Kong/5052/07 - H5N1

(SEQ ID NO: 12)

DHICIGYHANNSTEQVDTIMEKNVTVTHAQDILEKTHNGKLCDLNGVKPLILKDCSVAGWLLGNPMCDEFINVPEW

SYIVEKANPANDLCYPGNFNDYEELKHLLSRINHFEKIQIIPKDSWSDHEASLGVSSACPYQGNSSFFRNVVWLIKKGN

AYPTIKKSYNNTNQEDLLVLWGIHHPNDEAEQTRLYQNPTTYISIGTSTLNQRLVPKIATRSKVNGQSGRIDFFWTILK

PNDAINFESNGNFIAPEYAYKIVKKGDSTIMKSEVEYGNCNTRCQTPMGAINSSMPFHNIHPLTIGECPKYVKSNKLV

LATGLRNSPQRERRRKKRGLFGAIAGFIEGGWQGMVDGWYGYHHSNEQGSYAADKESTQKAIDGVTNKVNSIIDK

MNTQFEAVGREFNNLERRIENLNKKMEDGFLDVWTYNAELLVLMENERTLDFHDSNVKNLYDKVRLQLRDNAKEL

GNGCFEFYHKCDNECMESVRNGTYDYPQYSEEARLKREEISGVKLESIGTYQSGR*LVPRGS*PGSGYIPEAPRDGQAYV

RKDGEWVLLSTFLGKPIPNPLLGLDSTGHHHHHH

A/Anhui/1/05 - H5N1

(SEQ ID NO: 13)

DQICIGYHANNSTEQVDTIMEKNVTVTHAQDILEKTHNGKLCDLDGVKPLILRDCSVAGWLLGNPMCDEFINVPEW

SYIVEKANPANDLCYPGNFNDYEELKHLLSRINHFEKIQIIPKSSWSDHEASSGVSSACPYQGTPSFFRNVVWLIKKNN

TYPTIKRSYNNTNQEDLLILWGIHHSNDAAEQTKLYQNPTTYISVGTSTLNQRLVPKIATRSKVNGQSGRMDFFWTIL

KPNDAINFESNGNFIAPEYAYKIVKKGDSAIVKSEVEYGNCNTKCQTPIGAINSSMPFHNIHPLTIGECPKYVKSNKLVL

ATGLRNSPLRERRRKRGLFGAIAGFIEGGWQGMVDGWYGYHHSNEQGSYAADKESTQKAIDGVTNKVNSIIDK

MNTQFEAVGREFNNLERRIENLNKKMEDGFLDVWTYNAELLVLMENERTLDFHDSNVKNLYDKVRLQLRDNAKEL

GNGCFEFYHKCDNECMESVRNGTYDYPQYSEEARLKREEISGVKLESIGTYQSGR*LVPRGS*PGSGYIPEAPRDGQAYV

RKDGEWVLLSTFLGKPIPNPLLGLDSTGHHHHHH

-continued

A/chicken/Vietnam/NCVD-016/08 - H5N1
(SEQ ID NO: 14)
DQICIGYHANNSTEQVDTIMEKNVTVTHAQDILEKTHNGKLCNLDGVKPLILKDCSVAGWLLGNPMCDEFLNVSEW

SYIVEKASPANGLCYPGDFNDYEELKHLLSRINHLKKIKIIPKSYWSNHEASSGVSAACSYLGEPSFFRNVVWLIKKNNT

YPPIKVNYTNTNQEDLLVLWGIHHPNDEKEQIRIYQNPNTSISVGTSTLNQRLVPKIATRPKVNGQSGRMEFFWTILK

PNDSINFDSNGNFIAPEYAYKIAKKGDSVIMKSELEYGNCNTKCQTPMGAINSSMPFHNIHPLTIGECPKYVKSNRLV

LATGLRNAPQTETRGLFGAIAGFIEGGWQGMVDGWYGYHHSNEQGSGYAADKESTQKAIDGITNKVNSIIDKMNT

QFEIVGREFNNLERRIENLNKKMEDGFLDVWTYNAELLVLMENERTLDFHDSNVKNLYEKVRLQLRDNAKELGNGC

FEFYHKCDNECMESVRNGTYDYPQYSEEARLSREEISGVKMESMVTYQSGR*LVPRGS*PGSGYIPEAPRDGQAYVRKD

GEWVLLSTFLGKPIPNPLLGLDSTGHHHHHH

A/northern shoveler/California/HKWF115/2007 - H6N1
(SEQ ID NO: 15)
DKICIGYHANNSTTQVDTILEKNVTVTHSVELLENQKEERFCKILNKAPLDLRGCTIEGWILGNPQCDLLLGDQSWSYI

VERPTAQNGICYPGALNEVEELKALIGSGERVERFEMFPKSTWTGVDTSSGVTKACPYNSGSSFYRNLLWIIKTKSAA

YPVIKGTYNNTGSQPILYFWGVHHPPDTNEQNTLYGSGDRYVRMGTESMNFAKSPEIAARPAVNGQRGRIDYYWS

VLKPGETLNVESNGNLIAPWYAYKFVSTNNKGAIFKSNLPIENCDATCQTIAGVLRTNKTFQNVSPLWIGECPKYVKS

ESLRLATGLRNVPQIETRGLFGAIAGFIEGGWTGMIDGWYGYHHENSQGSGYAADKESTQKAIDGITNKVNSIIDKM

NTQFEAVDHEFSNLERRIDNLNKRMEDGFLDVWTYNAELLVLLENERTLDLHDANVKNLYEKVKSQLRDNANDLGN

GCFEFWHKCDNECIESVKNGTYDYPKYQDESKLNRQEIESVKLDNLGVYQSGR*LVPRGS*PGSGYIPEAPRDGQAYVRK

DGEWVLLSTFLGKPIPNPLLGLDSTGHHHHHH

A/Netherlands/219/03 - H7N7
(SEQ ID NO: 16)
DKICLGHHAVSNGTKVNTLTERGVEVVNATETVERTNVPRICSKGKRTVDLGQCGLLGTITGPPQCDQFLEFSADLIIE

RREGSDVCYPGKFVNEEALRQILRESGGIDKETMGFTYSGIRTNGTTSACRRSGSSFYAEMKWLLSNTDNAAFPQMT

KSYKNTRKDPALIIWGIHHSGSTTEQTKLYGSGNKLITVGSSNYQQSFVPSPGARPQVNGQSGRIDFHWLILNPNDT

VTFSFNGAFIAPDRASFLRGKSMGIQSEVQVDANCEGDCYHSGGTIISNLPFQNINSRAVGKCPRYVKQESLLLATG

MKNVPEIPKRRRRGLFGAIAGFIENGWEGLIDGWYGFRHQNAQGEGTAADYKSTQSAIDQITGKLNRLIEKTNQQF

ELIDNEFTEVERQIGNVINWTRDSMTEVWSYNAELLVAMENQHTIDLADSEMNKLYERVKRQLRENAEEDGTGCFE

IFHKCDDDCMASIRNNTYDHSKYREEAIQNRIQIDPVKLSSGYKDSGR*LVPRGS*PGSGYIPEAPRDGQAYVRKDGEWV

LLSTFLGKPIPNPLLGLDSTGHHHHHH

H8N4 - A/duck/Yangzhou/02/2005
(SEQ ID NO: 17)
DRICIGYQSNNSTDTVNTLIEQKVPVTQTMELVETEKHPAYCNTDLGAPLELRDCKIEAVIYGNPKCDIHLKDQGWSY

IVERPSAPEGMCYPGSVENLEELRFVFSSAASYKRIRLFDYSRWNVTSSGTSKACNASTGGQSFYRSINWLTKKKPDT

YDFNEGTYVNNEDGDIIFLWGIHHPPDTKEQTTLYKNANTLSSVTTNTINRSFQPNIGPRPLVRGQQGRMDYYWGIL

KRGETLKIRTNGNLIAPEFGYLLKGESHGRTIQNEDIPIGNCYTKCQTYAGAINSSKPFQNASRHYMGECPKYVKKASL

RLAVGLRNTPSVEPRGLFGAIAGFIEGGWSGMIDGWYGFHHSNSEGTGMAADQKSTQEAIDKITNKVNNIVDKM

NREFEVVNHEFSEVEKRINMINDKIDDQIEDLWAYNAELLVLLENQKTLDEHDSNVKNLFDEVKRRLSANAIDAGNG

CFDILHKCDNECMETIKNGTYDHKEYEEEAKLERSKINGVKLEENTTYKSGR*LVPRGS*PGSGYIPEAPRDGQAYVRKDG

EWVLLSTFLGKPIPNPLLGLDSTGHHHHHH

A/Hong Kong/2108/03 - H9N2
(SEQ ID NO: 18)
DKICIGYQSTNSTETVDTLTKTNVPVTQAKELLHTEHNGMLCATNLGHPLILDTCTIEGLIYGNPSCDLLLGGREWSYIV

ERPSAVNGMCYPGNVENLEELRLLFSSASSYQRVQIFPDTIWNVTYSGTSSACSNSFYRSMRWLTQKDNTYPVDA

QYTNNRGKSILFMWGINHPPTDTVQTNLYTRTDTTTSVTTEDINRAFKPVIGPRPLVNGLQGRIDYYWSVLKPGQTL

-continued

RVRSNGNLIAPWYGHILSGESHGRILKSDLNSGNCVVQCQTERGGLNTTLPFHNVSKYAFGNCPKYVGVKSLKLAVG

MRNVPARSSRGLFGAIAGFIEGGWPGLVAGWYGFQHSNDQGVGMAADRDSTQKAIDKITSKVNNIVDKMNKQY

EIIDHEFSEIETRLNMINNKIDDQIQDIWAYNAELLVLLENQKTLDEHDANVNNLYNKVKRALGSNAMEDGKGCFEL

YHKCDDRCMETIRNGTYNRGKYKEESRLERQKIEGVKLESEGTYKSGRLVPRGSPGSGYIPEAPRDGQAYVRKDGEW

VLLSTFLGKPIPNPLLGLDSTGHHHHHH

A/Hong Kong/1073/99 - H9N2

(SEQ ID NO: 19)

METISLITILLVVTASNADKICIGHQSTNSTETVDTLTETNVPVTHAKELLHTEHNGMLCATSLGHPLILDTCTIEGLVYG

NPSCDLLLGGREWSYIVERSSAVNGTCYPGNVENLEELRTLFSSASSYQRIQIFPDTTWNVTYTGTSRACSGSFYRSM

RWLTQKSGFYPVQDAQYTNNRGKSILFVWGIHHPPTYTEQTNLYIRNDTTTSVTTEDLNRTFKPVIGPRPLVNGLQG

RIDYYWSVLKPGQTLRVRSNGNLIAPWYGHVLSGGSHGRILKTDLKGGNCVVQCQTEKGGLNSTLPFHNISKYAFGT

CPKYVRVNSLKLAVGLRNVPARSSRGLFGAIAGFIEGGWPGLVAGWYGFQHSNDQGVGMAADRDSTQKAIDKITS

KVNNIVDKMNKQYEIIDHEFSEVETRLNMINNKIDDQIQDVWAYNAELLVLLENQKTLDEHDANVNNLYNKVKRAL

GSNAMEDGKGCFELYHKCDDQCMETIRNGTYNRRKYREESRLERQKIEGVKLESEGTYKSGRLVPRGSPGSGYIPEAP

RDGQAYVRKDGEWVLLSTFLGKPIPNPLLGLDSTGHHHHHH

The recombinant and soluble HA expression constructs of SEQ ID NO: 2-19 were transfected into 293 HEK cells. Recombinant HA0 protein or HA cleaved into its respective subunits HA1 and HA2 and disulphide linked was purified from culture supernatant by standard procedures using the hexa-HIS tag at the C-terminal. The purified protein was analyzed by size exclusion chromatography and/or denaturing coomasie gel to confirm a recombinant protein of the expected size was present.

Example 2

Screening of Antibodies in Peripheral Blood

One hundred and twenty-six individual serum or plasma samples were screened for the presence of IgG antibody that bound to recombinant soluble homotrimeric HA proteins (Table 2) using a micro-array scanning system, bind to whole inactivated Influenza A virions (Table 3) using standard ELISA techniques, and inhibits or neutralizes virus infection of MDCK cells with Influenza A H1N1 A/Solomon Islands/3/06 or H3N2 A/Wisconsin/67/05. A portion of the plasma samples contained IgG antibodies that bound specifically to the recombinant soluble HA homotrimeric protein, bound to inactivated virions, and neutralized virus infectivity. This indicates that the antibodies could be binding linear or discontinuous epitopes in the HA homotrimer, as well as binding to conformational determinants of multiple variants of the HA homotrimer. Soluble targets include, but are not limited to, exemplary recombinant HA proteins derived from the influenza virus strains listed enable 2 and the inactivated virus strains listed in Table 4.

TABLE 4

Inactivated whole virions used in ELISA binding assays.

| Influenza A Subtype | Strain designation |
|---|---|
| H1N1 | A/Solomon Islands/3/06 |
| H2N2 | A/Japan/305/57 |
| H3N2 | A/Wisconsin/67/05 |

Example 3

Identification and rescue of HA-Specific Antibodies

IgG+ memory B cells purified from a human blood sample were cultured for 9 days in order to activate, proliferate, and differentiate these memory B cells into IgG secreting plasma cells. The B cell culture media containing the IgG was screened for the presence of IgG antibody that bound to recombinant soluble homotrimeric HA proteins (Table 2) using a micro-array scanning system, bind to whole Influenza A virus (Table 3) using standard ELISA techniques, and inhibits or neutralizes virus infection of MDCK cells with Influenza A H1N1 A/Solomon Islands/3/06 or H3N2 A/Wisconsin/67/05. As shown in Tables 5, 6, and 7, thirty-nine BCC wells were identified that contained an IgG antibody with several virus, HA, or neutralizing profiles and the variable regions of the antibody were then cloned from the corresponding B cell cultures.

Transient transfections with monoclonal heavy and light chain pairs from each BCC well were performed in 293 6E cells to reconstitute and produce the antibody. Reconstituted antibody supernatants were then screened for IgG that binds to recombinant soluble homotrimeric HA proteins (Table 2) using a micro-array scanning system, bind to whole Influenza A virus (Table 4) using standard ELISA techniques, and inhibits or neutralizes virus infection of MDCK cells with Influenza A H1N1 A/Solomon Islands/3/06, and/or H1N1 A/California/04/09, and/or H3N2 A/Wisconsin/67/05 to identify the rescued anti-HA antibody. Binding and neutralization of the human IgG antibodies to the preceding targets is compared to the binding of the proprietary positive control antibody TCN-032 (specific for the N-terminal of the matrix 2 protein of influenza A, U.S. patent application Ser. No. 12/795,618) or to the binding of the broadly HA specific, non-neutralizing mAb TCN-504 (also known as 3251K17, and described herein), and the proprietary negative control antibody TCN-202 (specific for the AD2 site I epitope on human cytomegalovirus gB) to these same targets.

The sequences of the rescued antibodies are determined. In addition, the sequence of each of the polynucleotides encoding the antibody sequences is determined.

Example 4

Binding Profiles of IgG in B Cell Culture Supernatant or Monoclonal Transfection Supernatant Using Inactivated Whole Influenza A Virions To determine whether the human mAbs in BCC SN or monoclonal transfection supernatant bind to purified virus, Enzyme-Linked ImmunoSorbent Assays (ELISAs) were performed according to the following methods. Briefly, various purified Influenza A virus subtype strains were coated directly onto an ELISA plate. A single dilution of BCC supernatant of the mAbs shown in Table 5 or of the monoclonal transfection supernatant shown in Table 8 and various dilutions of a positive control antibody (TCN-032) were then added to the virus coated wells. Unbound antibody was washed away and the bound antibody was detected with an anti-human antibody conjugated to HRP. The presence of anti-influenza antibodies was detected when the chromogen (TMB) is oxidized by the HRP conjugate, resulting in a blue color. The reaction is stopped by the addition of HCl, turning antibody positive wells yellow. The yellow color has a maximal absorbance at 450 nm.

Methods:

The following protocol was used:

1) Coat Microlon™ plates with 25 ul/well of 3 ug/ml inactivated influenza A virions.

2) Incubate plates overnight at 4° C.

3) Remove plates from 4° C. and wash four times with phosphate buffered saline with Calicum and Magnesium (PBS w/$Ca^{2+}$, $Mg^{2+}$), using EL405x (Wash program: ELISA_4x_wash).

4) Add 20 μl/well of 1% milk/PBS to plates.

5) Prepare control mAb curves by 1:3 dilutions of 6 ug/ml 6) 5 ul of each BCC SN or monoclonal transient transfection supernatant and control mAb curves are stamped onto the plate according to the plate map.

7) Incubate 2 hour (hr) at room temperature (RT).

8) Wash plates four times with PBS w/$Ca^{2+}$, $Mg^{2+}$, using EL405x (Wash program: ELISA_4x_wash)

9) Add 25 μl/well of polyclonal antibody (pAb) goat anti-human (aHuman) IgG Fc horseradish peroxidase (HRP) at a dilution of 1:5000.

10) Incubate 1 hr at RT.

11) Wash plates four times with PBS w/$Ca^{2+}$, $Mg^{2+}$, using EL405x (Wash program: ELISA_4x_wash)

12) Add 25 μl/well of Ultra-TMB (3,3',5,5'-tetramethylbenzidine) at Neat.

13) Develop 30 minutes (min) at RT.

14) Stop by adding 25 μl/well of hydrochloric acid (HCl) at a concentration of 0.3M.

15) Read the plate at 450 nm with the Spectromax.

One or more of the following control antibodies were used in these experiments: TCN-504 (also known as 3251_K17, and described herein) TCN-032 (also known as 8110, specific for the influenza A M2 protein), and TCN-202 (also known as 2N9, specific for the AD2 site I epitope on human cytomegalovirus gB protein).

The following purified viruses were used in these experiments: A/Solomon Islands/3/2006(H1N1) (SEQ ID NO: 3), A/Japan/305/1957(H2N2) (SEQ ID NO: 4), A/Wisconsin/67/2005(H3N2) (SEQ ID NO: 5). As shown in table 8 the human monoclonal antibodies in the transient transfection supernatant bind strongly to one or more of the H1N1, H2N2, and/or H3N2 viruses reproducing the virus binding profile of the IgG antibody in the original BCC SN (Table 5).

Example 5

Binding Profiles of IgG in B Cell Culture Supernatant or Monoclonal Transfection Supernatant Using Trimeric HA To determine whether the human mAbs in BCC SN or monoclonal transfection supernatant bind to one or more of the recombinant homotrimeric HA proteins, a micro-array scanning system was used according to the following methods. Twenty Nexterion P (Schott) glass slides are incubated overnight in a humid chamber with 3 mg/ml goat anti-human, Fc-specific antibody. Nexterion P slides contain a hydrogel that terminates in an NHS ester reactive group that binds the capture antibody. The reaction is then quenched using 50 mM ethanolamine in 50 mM NaBorate (pH 8.0) buffer for 1 hour with agitation followed by 3 washes with ultrapure water. Transfection supernatants are transferred to 384-well array source plates. Control array source plates are made in 8-point, 3-fold serial dilutions of antibody starting at 3 ug/ml and ending 0 ug/ml in BCC or mock transfection media. Both BCC or transfection supernatant array source plates and control plates are loaded onto an Aushon 2470 microarray printer along with the 20 prepared slides.

Microarrays are printed in 48 subarray blocks with variable number of features and replicates depending on number of transfection supernatants are being printed. Printed microarrays are allowed to sit for at least 1 hour after printing (to overnight) in the printer's humidity controlled chamber (80%). They are then quickly removed from the printer, washed, and spun dry to prepare the slides for sample incubations. A LifterSlip is placed on each slide and 90 μl of sample is added to each. Each slide receives either one of 18 V5-tagged HA trimerics at predetermined concentrations, a horseradish peroxidase goat anti-human H+ L specific antibody at a 1 ug/ml, or a blank for a total of 20 slides. The slides are then incubated overnight in a humid chamber at room temperature. After washing, spin drying, and new LifterSlip application, 19 slides, excluding slide incubated with anti-human IgG, are incubated with anti-V5 conjugated to biotin at a 1:1000 dilution for 1 hour. Subsequently the slides are again washed, dried and prepared for an 1-hour incubation with a 1:300 dilution of NeutrAvidin-HRP. After further washing, drying and preparation all 20 slides are incubated for 1 hour with a Tyramide-AlexaFluor reagent according to kit instructions. After final washing and drying the slides are scanned on an Axon Genepix 4300A at an excitation wavelength of 594 nm and with an emission band ranging from 619 nm to 641 nm. Data is recovered using the Axon Genepix software and is then analyzed for binding profiles.

Methods:

The following protocol was used:

1. Dilute goat anti-human, FC-specific antibody (JacksonImmuno, 10 mg/ml) to 3 mg/ml in PBS 0.05&Tween and apply to 20 Nexterion P Slides (Schott) using 90 μl under lifterslips (Thermo).

2. Incubate in a humid chamber overnight at room temperature

3. Removing the lifterslip quench all slides in 50 mM ethanolamine (Fisher)) in 50 mM Sodium tetraborate decahydrate (Fisher, S248-500) at a pH of 8.0

4. Quench for 1 hour with incubation at room temperature

5. Wash all slides (3×2 min MilliQ water washes with agitation).

6. Load all slides onto Aushon 2470 MicroArray printer.
7. Prepare control plates using by spiking control antibodies into transfection media to form an 8 point 3-fold serial dilution starting at 3 µg/ml and ending in 0 µg/ml. Transfer control dilutions to 4 array source plates (Thermo).
8. Load all array source plates, control and sample, onto Aushon 2470 microarray printer and begin deposition after checking all required fluid levels. Number of replicates is based on number of transfection supernatants being printed. Typically 1 to 10 replicates.
9. Allow slides to sit at 80% humidity for at least an hour, to overnight, after deposition.
10. Immediately wash (PBS with 2% tween 20, 5 min; MilliQ water, 2 min, 3×) and spin dry (2000 RPM for 1 minute)
11. Using lifterslips and apply 90 µl of HA at the following concentration:

| Homotrimeric HA - strain | [ug/ml] |
|---|---|
| A/California/4/09 - H1N1 | 5 |
| A/Solomon Islands/3/06 - H1N1 | 5 |
| A/Japan/305/57 - H2N2 | 5 |
| A/Wisconsin/67/05 - H3N2 | 20 |
| A/swine/Ontario/01911-2/99 - H4N6 | 5 |
| A/Vietnam/1203/04 - H5N1 | 20 |
| A/Indonesia/5/05 - H5N1 | 0.5 |
| A/Egypt/3300-NAMRU3/08 - H5N1 | 0.5 |
| A/Common magpie/Hong Kong/5052/07 - H5N1 | 0.5 |
| A/Anhui/1/05 - H5N1 | 0.5 |
| A/chicken/Vietnam/NCVD-016/08 - H5N1 | 0.5 |
| A/northern shoveler/California/HKWF115/2007 - H6N1 | 0.5 |
| A/Netherlands/219/03 - H7N7 | 0.5 |
| A/duck/Yangzhou/02/2005 - H8N4 | 5 |
| A/Hong Kong/2108/03 - H9N2 | 5 |
| A/South Carolina/1/18 - H1N1 | 20 |
| A/Hong Kong/1073/99 | 20 |
| A/Hong Kong/156/97 - H5N1 | 5 |

12. Use 1×PBS, 0.05% Tween 20, 10% Blocker Casein (Thermo, #37528) to bring the homotrimeric HA to the desired concentration.
13. Incubate overnight in a humid chamber at room temperature
14. Immediately wash (PBS with 2% tween 20, 5 min; MilliQ water, 2 min, 3×) and spin dry (2000 RPM for 1 minute)
15. Using lifterslips incubate all but slide previously incubated with anti-human IgG(H&L)-HRP with 90 µl of anti-V5-biotin (AbD Serotec, MCA1360B) at 1 µg/ml in 1×PBS 0.05% Tween 20 for 1 hour at room temperature in a humid chamber.
16. Immediately wash (PBS with 2% tween 20, 5 min; MilliQ water, 2 min, 3×) and spin dry (2000 RPM for 1 minute)
17. Using lifterslips incubate with 90 µl of horseradish peroxidase conjugated NeutrAvidin (Pierce #31030) for 1 hour at room temperature in a humid chamber.
18. Immediately wash (PBS with 2% tween 20, 5 min; MilliQ water, 2 min, 3×) and spin dry (2000 RPM for 1 minute)
19. Prepare Tyramide Signal Amplification reagent according to kit instructions (TSA Kit #25, Invitrogen, T20935). Briefly dilute 1 µl of hydrogen peroxide solution into 200 µl of amplification buffer. Take 20 µl of hydrogen peroxide/amplification buffer solution and add to 1940 µl of fresh amplification buffer. Then add 40 µl of tyramide-Alexa Fluor resulting in a total of 2 ml of amplification reagent
20. Incubate all 20 slides with amplification reagent for 1 hour at room temperature in a humid chamber.
21. Immediately wash (PBS with 2% tween 20, 5 min; MilliQ water, 2 min, 3×) and spin dry (2000 RPM for 1 minute)
22. Scan all slides on an Axon Genepix 4300A at an excitation wavelength of 594 nm and with an emission band ranging from 619 nm to 641 nm or optical scanner with similar capabilities.
23. Lay templates on each slide using GenePix Pro 7 or similar software to recover feature data.
24. Analyze feature data for binding profiles to each HA trimeric.

As shown in Table 9, the human monoclonal antibodies in the transient transfection supernatant bind strongly to one or more of the recombinant homotrimeric HA proteins reproducing the virus binding profile of the IgG antibody in the original BCC SN (Table 5).

Example 6

Neutralization Profiles of IgG in B Cell Culture Supernatant or Monoclonal Transfection Supernatant MDCK cells were plated at $3 \times 10^3$ cells/well in a 384-well plate in complete DMEM media (supplemented with 10% FBS, 1× penicillin/streptomycin, 1× Glutamax™, and 1× Sodium Pyruvate) and incubated at 37° C. overnight.

Influenza A virus was preincubated with either BCC supernatant or monoclonal transfection supernatant or a positive control neutralizing monoclonal antibody (MAb), which was diluted in pooled BCC supernatant or in mock transfection supernatant at the desired concentrations and incubated overnight (~16 hours) at 37° C. Void volumes and dilutions were made in PBS with $Mg^{2+}$, $Ca^{2+}$, 200 mM Mannose, and 1% BSA at 37° C. with a total volume of 30 µl/well.

Each sample well contained:
(a) 20 µl/well BCC supernatant; or
(b) 20 ul/well of monoclonal transfection
(c) 3000 IU/well A/Solomon Islands/03/2006 (H1N1) in 10 µl/well; or
(e) 3000 IU/well A/California/04/2009 (H1N1) in 10 ul/well; or
(f) 3000 IU/well A/Wisconsin/67/05 (H3N2) in 10 ul/well Prior to infection, the MDCK cells were washed once with a solution containing PBS, $Mg^{2+}$, and $Ca^{2+}$ at 60 µl/well. After the wash, 25 ul of the virus/mAb mixture was transferred and the infection proceeded for 4 hours at 37° C.

After 4 hours of infection, the MDCK cells are washed twice with complete DMEM. After the last wash, 25 µl/well of complete DMEM remained, and the plates were incubated overnight at 37° C.

After the overnight incubation the culture media was removed and 20 µl of BD Cytofix/Cytoperm™ (cat#51-2090KZ) was added to each well and incubated at room temperature (RT) for 30 minutes. Next, the wells were washed three times using the M384 Atlas plate washer.

After the final wash, 15 µl/well of 100 µg/ml Rabbit IgG (Sigma) in PBS with $Mg^{2+}$, $Ca^{2+}$, and 1% BSA, was added and incubated for at least 5 minutes at RT. Twenty µl/well of anti-M2e mAb TCN-032 at 2 µg/ml in PBS with $Mg^{2+}$, $Ca^{2+}$, and 1% BSA, were added to each well and incubated for at least 30 mins at room temperature. The wells are washed one time using the Atlas plate washer with PBS with $Mg^{2+}$, $Ca^{2+}$ Twenty µl/well of 2 µg/ml Alexa Fluor® 647 anti-Human IgG H+ L (Invitrogen™) and 20 µg/ml Hoechst 33342 (Invitrogen™) was added and incubated in the dark for 45 mins at room temperature. Wells were washed three times using the Atlas plate washer with PBS with $Mg^{2+}$, $Ca^{2+}$. Twenty microliters of PBS with $Mg^{2+}$, $Ca^{2+}$, and 1% BSA was added to each well, and plates were sealed with black sealing tape. Plates were analyzed by scanning using an IN Cell analyzer.

Specifically, the scan was performed using the IN Cell Developer Software, Protocol "384 GG Hoechst AF647 4x." Analysis of the scan was performed using the Developer Tool Box software, Protocol "Cellular Binding Nuclei GG Density 4."

The assay was able to detect well supernatants that individually neutralized the Influenza A infection. If an arbitrary cutoff was established at <150 nucleoprotein (NP)+ cells and the wells with a disrupted cell monolayer were subtracted, a total of 122 wells scored as positive.

Exemplary influenza neutralizing antibodies that were identified using this method are TCN-522 (3212_I12), TCN-521 (3280_D18), TCN-523 (5248_A17), TCN-526 (5084_C17), TCN-527 (5086_C06), TCN-528 (5087_P17), TCN-529 (5297_H01), TCN-530 (5248_H10a), TCN-531 (5091_H13), TCN-532 (5262_H18), TCN-533 (5256_A17a), TCN-534 (5249_B02), TCN-535 (5246_P19), TCN-536 (5095_N01), TCN-537 (3194_D21), TCN-538 (3206_O17), TCN-539 (5056_A08), TCN-540 (5060_F05), TCN-541 (5062_M11), TCN-542 (5079_A16), TCN-543 (5081_G23), TCN-544 (5082_A19), TCN-545 (5082_I15), TCN-546 (5089_L08), TCN-547 (5092_F11), TCN-548 (5092_P01), TCN-549 (5092_P04), TCN-550 (5096_F06), TCN-551 (5243_D01), TCN-552 (5249_I23), TCN-553 (5261_C18), TCN-554 (5277_M05), TCN-555 (5246_I16), TCN-556 (5089_K12), TCN-557 (5081_A04), TCN-558 (5248_H10b), TCN-559 (5097_G08), TCN-560 (5084_P10), TCN-563 (5237_B21), TCN-564 (5256_A17b), and TCN-504 (3251_K17). The individual neutralization activities of some of these antibodies are provided in Table 10.

Several antibodies were identified that may be non-neutralizing, including, TCN-504 (3251_K17), TCN-556 (5089_K12), TCN-557 (5081_A04), TCN-559 (5097_G08), and TCN-560 (5084_P10). These antibodies, similar to the neutralizing antibodies of the invention, bind to a broad range of HA proteins, including sequence and conformational variants. In certain embodiments of the invention, non-neutralizing antibodies, including TCN-504 (3251_K17), TCN-556 (5089_K12), TCN-557 (5081_A04), TCN-559 (5097_G08), and TCN-560 (5084_P10) may be used as antibody-drug conjugates.

TABLE 5

Summary of BCC SN screening by ELISA for virus binding.

| Theraclone mAb ID | BCC well ID | ELISA: Virus Binding ($OD_{450}$) | | |
|---|---|---|---|---|
| | | A/Solomon Islands/ 3/06 H1N1 | A/Japan/ 305/57 H2N2 | A/Wisconsin/ 67/05 H3N2 |
| TCN-521 | 3280_D18 | 3.70 | 3.10 | 1.10 |
| TCN-522 | 3212_I12 | 2.12 | ND | 0.07 |
| TCN-523 | 5248_A17 | 3.47 | 1.62 | 0.08 |
| TCN-526 | 5084_C17 | 0.06 | 0.07 | 3.65 |
| TCN-527 | 5086_C06 | 3.03 | 1.48 | 0.07 |
| TCN-528 | 5087_P17 | 3.62 | 2.82 | 0.24 |
| TCN-529 | 5297_H01 | 0.07 | ND | 3.62 |
| TCN-530 | 5248_H10 | 3.52 | 1.73 | 0.06 |
| TCN-531 | 5091_H13 | 3.23 | 0.67 | 3.45 |
| TCN-532 | 5262_H18 | 0.06 | 0.07 | 3.67 |
| TCN-533 | 5256_A17 | 3.54 | 1.10 | 0.10 |
| TCN-534 | 5249_B02 | 3.55 | 2.56 | 0.07 |
| TCN-535 | 5246_P19 | 3.43 | 1.46 | 0.08 |
| TCN-536 | 5095_N01 | 3.63 | 0.08 | 3.66 |
| TCN-537 | 3194_D21 | 3.24 | ND | 0.06 |
| TCN-538 | 3206_O17 | 3.47 | ND | 0.07 |
| TCN-539 | 5056_A08 | 0.06 | 0.06 | 2.85 |
| TCN-540 | 5060_F05 | 0.07 | 3.62 | 3.65 |
| TCN-541 | 5062_M11 | 3.44 | 0.06 | 0.25 |
| TCN-542 | 5079_A16 | 3.66 | 0.08 | 3.13 |
| TCN-543 | 5081_G23 | 3.63 | 3.62 | 0.07 |
| TCN-544 | 5082_A19 | 0.32 | 0.07 | 2.71 |
| TCN-545 | 5082_I15 | 3.32 | 0.06 | 0.47 |
| TCN-546 | 5089_L08 | 1.95 | 0.06 | 3.69 |
| TCN-547 | 5092_F11 | 0.06 | 0.07 | 3.68 |
| TCN-548 | 5092_P01 | 0.09 | 0.09 | 3.62 |
| TCN-549 | 5092_P04 | 0.09 | 0.08 | 3.58 |
| TCN-550 | 5096_F06 | 0.06 | 0.06 | 3.65 |
| TCN-551 | 5243_D01 | 3.35 | 0.19 | 0.07 |
| TCN-552 | 5249_I23 | 3.57 | 0.71 | 0.06 |
| TCN-553 | 5261_C18 | 3.60 | 2.54 | 0.07 |
| TCN-554 | 5277_M05 | 0.06 | ND | 1.09 |
| TCN-555 | 5246_L16 | 2.89 | 0.60 | 0.06 |
| TCN-556 | 5089_K12 | 2.70 | 2.41 | 0.06 |
| TCN-557 | 5081_A04 | 2.32 | 2.70 | 0.07 |
| TCN-559 | 5097_G08 | 3.68 | 1.25 | 0.70 |
| TCN-560 | 5084_P10 | 3.63 | 2.07 | 0.07 |
| TCN-563 | 5237_B21 | 3.62 | 1.23 | 0.07 |
| TCN-564 | 5256_A17 | 3.54 | 1.10 | 0.10 |
| TCN-202 | 2N9 | ND | ND | ND |
| TCN-504 | 3251_K17 | ND | ND | ND |
| TCN-032 | 8I10 | 3.61 | 3.61 | 3.62 |

TABLE 6

Summary of BCC SN screening for virus binding to recombinant homotrimeric HA.

| Theraclone mAb ID | BCC well ID | Trimeric HA Binding: RLU | | | | | | | | |
|---|---|---|---|---|---|---|---|---|---|---|
| | | A/California/ 4/09 H1N1 | A/Solomon Islands/ 3/06 H1N1 | A/South Carolina/ 1/18 H1N1 | A/Japan/ 305/57 H2N2 | A/Wisconsin/67/ 05 H3N2 | A/swine/ Ontario/ 01911-2/ 99 H4N6 | A/Vietnam/ 1203/04 H5N1 | A/Indonesia/ 5/05 H5N1 | A/Egypt/ 3300-NAMRU3/ 08 H5N1 |
| TCN-521 | 3280_D18 | 25726 | 39644 | ND | 6732 | 2298 | 210 | 196 | 31473 | 47871 |
| TCN-522 | 3212_I12 | 5019 | 38914 | ND | 989 | 302 | 156 | 145 | 67 | ND |
| TCN-523 | 5248_A17 | 34721 | 37916 | ND | 5111 | 22568 | 1288 | 3383 | 45815 | 36471 |
| TCN-526 | 5084_C17 | 203 | 341 | ND | 246 | 49312 | 253 | 372 | 46027 | ND |
| TCN-527 | 5086_C06 | 27991 | 16507 | ND | 19261 | 5715 | 7686 | 21264 | 23838 | ND |

TABLE 6-continued

Summary of BCC SN screening for virus binding to recombinant homotrimeric HA.

| TCN-528 | 5087_P17 | 48845 | 44804 | ND | 46393 | 48795 | 47500 | 45577 | 42801 | ND |
|---|---|---|---|---|---|---|---|---|---|---|
| TCN-529 | 5297_H01 | 434 | 179 | ND | 435 | 51631 | 235 | 101 | 44085 | 53394 |
| TCN-530 | 5248_H10 | 46600 | 32801 | ND | 47049 | 36846 | 2743 | 7152 | 39774 | 30430 |
| TCN-531 | 5091_H13 | 22207 | 51663 | ND | 410 | 7094 | 408 | 357 | 37443 | ND |
| TCN-532 | 5262_H18 | 135 | 327 | ND | 176 | 18046 | 119 | 440 | 27992 | 24500 |
| TCN-533 | 5256_A17 | 29280 | 39186 | ND | 10806 | 13823 | 1582 | 5677 | 44063 | 34299 |
| TCN-534 | 5249_B02 | 30109 | 44185 | ND | 50626 | 7978 | 683 | 3435 | 46352 | 41381 |
| TCN-535 | 5246_P19 | 48576 | 39442 | ND | 26068 | 34320 | 5950 | 4740 | 45592 | 39412 |
| TCN-536 | 5095_N01 | 151 | 150 | ND | 121 | 34996 | 79 | 146 | 3969 | ND |
| TCN-537 | 3194_D21 | 21918 | 44264 | ND | 44685 | 549 | 19 | 80 | 14858 | 38168 |
| TCN-538 | 3206_O17 | 13808 | 33228 | ND | 43002 | 6900 | 406 | 60 | 26421 | 23553 |
| TCN-539 | 5056_A08 | 1803 | 239 | ND | 468 | 715 | 1579 | 545 | 49 | 11420 |
| TCN-540 | 5060_F05 | 57 | 64 | ND | 2969 | 728 | 178 | 63 | 31 | 1968 |
| TCN-541 | 5062_M11 | 34 | 51 | ND | 83 | 2923 | 102 | 43 | 30 | 1162 |
| TCN-542 | 5079_A16 | 3108 | 132 | ND | 142 | 1940 | 350 | 306 | ND | ND |
| TCN-543 | 5081_G23 | 13080 | 511 | ND | 197 | 1358 | 428 | 488 | ND | ND |
| TCN-544 | 5082_A19 | 281 | 179 | ND | 187 | 2090 | 316 | 349 | 3052 | ND |
| TCN-545 | 5082_I15 | 365 | 266 | ND | 157 | 575 | 289 | 235 | ND | ND |
| TCN-546 | 5089_L08 | 350 | 256 | ND | 520 | 30209 | 587 | 349 | 18432 | ND |
| TCN-547 | 5092_F11 | 170 | 155 | ND | 40 | 16932 | 252 | 308 | 6986 | ND |
| TCN-548 | 5092_P01 | 234 | 283 | ND | 416 | 48600 | 240 | 270 | 17626 | ND |
| TCN-549 | 5092_P04 | 338 | 284 | ND | 387 | 30912 | 421 | 312 | 11445 | ND |
| TCN-550 | 5096_F06 | 454 | 204 | ND | 201 | 26315 | 195 | 277 | 9100 | ND |
| TCN-551 | 5243_D01 | 53362 | 53821 | ND | 22633 | 6840 | 733 | 4152 | 53543 | 47183 |
| TCN-552 | 5249_I23 | 35312 | 39314 | ND | 23832 | 14769 | 493 | 2728 | 43559 | 39971 |
| TCN-553 | 5261_C18 | 20281 | 16271 | ND | 25509 | 20043 | 2583 | 6560 | 24406 | 18828 |
| TCN-554 | 5277_M05 | 173 | 115 | ND | 328 | 46531 | 78 | 113 | 32348 | 36126 |
| TCN-555 | 5246_L16 | 44903 | 26404 | ND | 2131 | 9800 | 1953 | 876 | 34539 | 42676 |
| TCN-556 | 5089_K12 | 14640 | 2846 | ND | 5611 | 9323 | 5604 | 13823 | 8454 | ND |
| TCN-557 | 5081_A04 | 17603 | 40699 | ND | 43367 | 10218 | 26967 | 47282 | 45165 | ND |
| TCN-559 | 5097_G08 | 539 | 7376 | ND | 16332 | 2402 | 1658 | 21670 | 18295 | ND |
| TCN-560 | 5084_P10 | 49166 | 38758 | ND | 46720 | 49078 | 41599 | 43990 | 35864 | ND |
| TCN-563 | 5237_B21 | 45157 | 30005 | ND | 6612 | 40848 | 4501 | 4836 | 39533 | 27514 |
| TCN-564 | 5256_A17 | 29280 | 39186 | ND | 10806 | 13823 | 1582 | 5677 | 44063 | 34299 |
| TCN-202 | 2N9 | 39 | 46 | ND | 85 | 252 | 75 | 53 | 24 | 1275 |
| TCN-504 | 3251_K17 | 3326 | 24140 | ND | 4091 | 40516 | 14669 | 196 | 43259 | 44352 |
| TCN-032 | 8I10 | ND | ND | ND | ND | ND | ND | ND | ND | ND |

Trimeric HA Binding: RLU

| Theraclone mAb ID | A/common magpie/Hong Kong/5052/ 07 H5N1 | A/Anhui/ 1/05 H5N1 | A/chicken/ Vietnam/ NCVD-016/ 08 H5N1 | A/Hong Kong/156/ 97 H5N1 | A/northern shoveler/ California/ HKWF115/07 H6N4 | A/Nether- lands/219/ 03 H7N7 | A/duck/ Yangzhou/ 02/05 H8N4 | A/Hong Kong/2108/ 03 H9N2 | A/Hong Kong/1073/ 99 H9N2 |
|---|---|---|---|---|---|---|---|---|---|
| TCN-521 | 13528 | 487 | 32390 | ND | 47991 | 2496 | 11659 | 93 | ND |
| TCN-522 | ND | ND | ND | ND | ND | ND | 502 | 639 | ND |
| TCN-523 | 45837 | 5705 | 48880 | ND | 46908 | 2336 | 28949 | 189 | ND |
| TCN-526 | ND | 20916 | 179 | ND | 2100 | 1338 | 596 | 36629 | ND |
| TCN-527 | ND | 21369 | 27047 | ND | 30323 | 8892 | 28803 | 15956 | ND |
| TCN-528 | ND | 49772 | 38191 | ND | 46781 | 49251 | 38362 | 41966 | ND |
| TCN-529 | 302 | 39376 | 410 | ND | 533 | 1165 | 771 | 42271 | ND |
| TCN-530 | 42460 | 11874 | 48341 | ND | 45339 | 2896 | 41661 | 486 | ND |
| TCN-531 | ND | 3606 | 20840 | ND | 43874 | 1969 | 3117 | 745 | ND |
| TCN-532 | 134 | 25219 | 46 | ND | 511 | 327 | 785 | 29816 | ND |
| TCN-533 | 44511 | 8065 | 47704 | ND | 41449 | 2473 | 24745 | 172 | ND |
| TCN-534 | 32514 | 6861 | 56642 | ND | 52429 | 4340 | 46537 | 165 | ND |
| TCN-535 | 45937 | 6875 | 49961 | ND | 48192 | 4757 | 36650 | 861 | ND |
| TCN-536 | ND | 543 | 287 | ND | 2210 | 976 | 436 | 1566 | ND |
| TCN-537 | 18702 | 335 | 8617 | ND | 5206 | 1052 | 7826 | 147 | ND |
| TCN-538 | 18746 | 689 | 37312 | ND | 17448 | 6531 | 6123 | 109 | ND |
| TCN-539 | 3957 | 91 | 100 | ND | 814 | 1698 | 1488 | 292 | ND |
| TCN-540 | 113 | 25 | 70 | ND | 131 | 381 | 117 | 22 | ND |
| TCN-541 | 71 | 17 | 40 | ND | 106 | 381 | 131 | 29 | ND |
| TCN-542 | ND | ND | 375 | ND | 900 | 909 | 332 | 1907 | ND |
| TCN-543 | ND | 325 | 347 | ND | 2128 | 661 | 737 | 131 | ND |
| TCN-544 | ND | ND | 272 | ND | 1690 | 1618 | 464 | 296 | ND |
| TCN-545 | ND | ND | 392 | ND | 1167 | 1182 | 656 | 227 | ND |
| TCN-546 | ND | 2037 | 421 | ND | 1354 | 1451 | 487 | 12983 | ND |
| TCN-547 | ND | 1476 | 198 | ND | 1005 | 401 | 278 | 3986 | ND |
| TCN-548 | ND | 5381 | 254 | ND | 314 | 758 | 184 | 3424 | ND |
| TCN-549 | ND | 1793 | 498 | ND | 1103 | 1134 | 844 | 5037 | ND |
| TCN-550 | ND | 1206 | 361 | ND | 964 | 939 | 407 | 2279 | ND |
| TCN-551 | 45688 | 4187 | 42301 | ND | 52491 | 786 | 9817 | 224 | ND |
| TCN-552 | 42201 | 4156 | 46249 | ND | 38413 | 1241 | 13115 | 171 | ND |
| TCN-553 | 25979 | 12610 | 24158 | ND | 21732 | 1838 | 27998 | 273 | ND |
| TCN-554 | 224 | 10851 | 250 | ND | 296 | 610 | 583 | 28594 | ND |
| TCN-555 | 16060 | 1497 | 22302 | ND | 49507 | 3399 | 18390 | 262 | ND |

TABLE 6-continued

Summary of BCC SN screening for virus binding to recombinant homotrimeric H

TABLE 8-continued

Summary of monoclonal antibody transfection supernatant screening by ELISA for virus binding.

|  |  |  | ELISA: Virus Binding (OD$_{450}$) | | |
|---|---|---|---|---|---|
|  | Theraclone mAb ID | BCC well ID | A/Solomon Islands/3/06 H1N1 | A/Japan/305/57 H2N2 | A/Wisconsin/67/05 H3N2 |
| Monoclonal transfection set 4 | TCN-535 | 5246_P19 | 3.52 | 2

TABLE 9-continued

Summary of monoclonal antibody transfection supernatant screening for virus binding to recombinant homotrimeric HA.

| | | | | | | | | | | | | |
|---|---|---|---|---|---|---|---|---|---|---|---|---|
| Monoclonal transfection set 5 | TCN-537 | 3194_D21 | 33793 | 760 | 46

TABLE 9-continued

Summary of monoclonal antibody transfection supernatant screening for virus binding to recombinant homotrimeric HA.

| | | | | | | | |
|---|---|---|---|---|---|---|---|
| TCN-554 | 1734 | 42805 | 2708 | 1441 | 3352 | 4522 | 5808 |
| TCN-555 | 33642 | 12236 | 35215 | 36302 | 28717 | 12656 | 8544 |
| TCN-556 | 20140 | 13795 | 22676 | 24620 | 34817 | 43640 | 22400 |
| TCN-557 | 54874 | 19980 | 23323 | 27061 | 49611 | 53747 | 24015 |
| TCN-558 | 49655 | 9783 | 33423 | 47113 | 29396 | 5841 | 19531 |
| TCN-559 | 12900 | 41835 | 33850 | 28953 | 6632 | 4852 | 42614 |
| TCN-560 | 30485 | 18628 | 18174 | 29287 | 35866 | 32120 | 27927 |
| TCN-504 | 37328 | 37168 | 34166 | 26597 | 39179 | 30626 | 35074 |
| TCN-523 | 33905 | 6079 | 51296 | 28380 | 46941 | 6750 | 25599 |
| TCN-202 | 1366 | 10033 | 2570 | 945 | 3036 | 18026 | 13796 |

TABLE 10

Summary of monoclonal antibody transfection supernatant screening for virus neutralization.

| | | | % Neutralization | | |
|---|---|---|---|---|---|
| | Theraclone mAb ID | BCC well ID | A/Solomon Islands/3/06 H1N1 | A/California/4/09 H1N1 | A/Wisconsin/67/05 H3N2 |
| Monoclonal transfection set 1 | TCN-523 | 5248_A17 | 82.71 | ND | ND |
| | TCN-504 | 3251_K17 | 0.00 | ND | 0.00 |
| | TCN-202 | 2N9 | 0.00 | ND | 0.00 |
| Monoclonal transfection set 2 | TCN-522 | 3212_I12 | 39.46 | ND | 0.84 |
| | TCN-526 | 5084_C17 | 10.58 | ND | 94.26 |
| | TCN-527 | 5086_C06 | 17.55 | ND | 0.00 |
| | TCN-528 | 5087_P17 | 23.92 | ND | 0.00 |
| | TCN-563 | 5237_B21 | 88.85 | ND | 0.00 |
| | TCN-504 | 3251_K17 | 7.19 | ND | 0.00 |
| | TCN-523 | 5248_A17 | 80.68 | ND | 0.00 |
| | TCN-202 | 2N9 | 7.00 | ND | 0.00 |
| Monoclonal transfection set 3 | TCN-531 | 5091_H13 | 0.00 | ND | 97.30 |
| | TCN-530 | 5248_H10 | 96.95 | ND | 34.54 |
| | TCN-529 | 5297_H01 | 0.00 | ND | 99.59 |
| | TCN-533 | 5256_A17 | 96.12 | ND | 32.51 |
| | TCN-532 | 5262_H18 | 0.00 | ND | 99.73 |
| | TCN-504 | 3251_K17 | 0.00 | ND | 10.74 |
| | TCN-523 | 5248_A17 | 62.19 | ND | 34.00 |
| | TCN-202 | 2N9 | 0.00 | ND | 17.77 |
| Monoclonal transfection set 4 | TCN-535 | 5246_P19 | 88.60 | 97.28 | 0.00 |
| | TCN-534 | 5249_B02 | 65.66 | 96.37 | 0.00 |
| | TCN-536 | 5095_N01 | 81.63 | 18.76 | 99.88 |
| | TCN-504 | 3251_K17 | 29.68 | 0.00 | 0.00 |
| | TCN-523 | 5248_A17 | 65.54 | 93.19 | 0.00 |
| | TCN-202 | 2N9 | ND | ND | ND |
| Monoclonal transfection set 5 | TCN-537 | 3194_D21 | 0 | 71 | 0 |
| | TCN-538 | 3206_O17 | 21 | 66 | 0 |
| | TCN-539 | 5056_A08 | 0 | 0 | 99 |
| | TCN-540 | 5060_F05 | 3 | 0 | 98 |
| | TCN-541 | 5062_M11 | 88 | 0 | 4 |
| | TCN-542 | 5079_A16 | 99 | 15 | 8 |
| | TCN-543 | 5081_G23 | 98 | 0 | 73 |
| | TCN-544 | 5082_A19 | 0 | 0 | 97 |
| | TCN-545 | 5082_I15 | 88 | 0 | 99 |
| | TCN-546 | 5089_L08 | 98 | 0 | 100 |
| | TCN-547 | 5092_F11 | 0 | 0 | 88 |
| | TCN-548 | 5092_P01 | 0 | 0 | 96 |
| | TCN-549 | 5092_P04 | 0 | 0 | 100 |
| | TCN-550 | 5096_F06 | 0 | 0 | 100 |
| | TCN-551 | 5243_D01 | 99 | 74 | 6 |
| | TCN-552 | 5249_I23 | 0 | 81 | 14 |
| | TCN-553 | 5261_C18 | 44 | 83 | 5 |
| | TCN-554 | 5277_M05 | 0 | 0 | 100 |
| | TCN-555 | 5246_L16 | 49 | 89 | 5 |
| | TCN-556 | 5089_K12 | 0 | 0 | 15 |
| | TCN-557 | 5081_A04 | 7 | 10 | 0 |
| | TCN-558 | 5248_H10 | 84 | 96 | 7 |
| | TCN-559 | 5097_G08 | 7 | 10 | 12 |
| | TCN-560 | 5084_P10 | 0 | 0 | 4 |
| | TCN-504 | 3251_K17 | 0 | 0 | 0 |
| | TCN-523 | 5248_A17 | 39 | 86 | 7 |
| | TCN-202 | 2N9 | 0 | 0 | 0 |

Example 7

Binding Profiles of Purified IgGs Using Inactivated Whole Influenza A Virions For the antibodies listed in Table 11, milligram quantities of purified monoclonal IgG antibodies were made by transient transfection of 293 E cells with monoclonal heavy and light chain pairs followed by protein A purification to reconstitute and produce the antibody. To determine whether the purified mAbs bind to purified virus, Enzyme-Linked ImmunoSorbent Assays (ELISAs) were performed as described in Example 4 using an 8-point dilution series of test mAb. As shown in Table 11, at approximately 1.0 μg/ml, the purified mAbs bind strongly to one or more of the H1N1, H2N2, and/or H3N2 viruses reproducing the virus binding profile of the IgG antibody in the original BCC SN (Table 5) or monoclonal transfection SN (Table 8).

TABLE 11

Summary of screening purified IgG by ELISA for virus binding.

| | ELISA: Virus Binding ($OD_{450}$) | | |
|---|---|---|---|
| Theraclone mAb ID | A/Solomon Islands/3/06 H1N1 | A/Japan/305/57 H2N2 | A/Wisconsin/67/05 H3N2 |
| TCN-522 | 3.64 | 3.48 | 0.12 |
| TCN-523 | 3.64 | 3.55 | 0.13 |
| TCN-526 | 0.07 | 0.07 | 2.84 |
| TCN-527 | 3.63 | 3.62 | 0.22 |
| TCN-528 | 3.63 | 3.61 | 0.46 |
| TCN-529 | 0.07 | 0.07 | 3.60 |
| TCN-530 | 3.62 | 3.43 | 0.13 |
| TCN-531 | 0.08 | 0.07 | 3.61 |
| TCN-532 | 0.07 | 0.07 | 2.36 |
| TCN-533 | 3.62 | 3.56 | 0.16 |
| TCN-534 | 3.62 | 3.56 | 0.13 |
| TCN-535 | 3.63 | 3.35 | 0.12 |
| TCN-536 | 3.61 | 0.07 | 3.60 |
| TCN-537 | 3.63 | 3.59 | 0.09 |
| TCN-538 | 3.64 | 3.60 | 0.11 |
| TCN-539 | 0.07 | 0.06 | 0.13 |
| TCN-540 | 0.07 | 3.63 | 3.64 |
| TCN-541 | 3.63 | 0.06 | 0.07 |
| TCN-543 | 3.64 | 3.64 | 3.63 |
| TCN-544 | 0.08 | 0.07 | 3.60 |
| TCN-545 | 3.43 | 0.06 | 3.64 |
| TCN-546 | ND | ND | ND |
| TCN-549 | ND | ND | ND |
| TCN-550 | 0.06 | 0.17 | 3.63 |
| TCN-551 | 3.63 | 0.06 | 0.26 |
| TCN-552 | 3.61 | 3.41 | 0.12 |
| TCN-553 | 3.59 | 3.49 | 0.16 |
| TCN-554 | 0.86 | 0.07 | 3.57 |
| TCN-555 | 3.63 | 3.40 | 0.11 |
| TCN-556 | ND | ND | ND |
| TCN-557 | ND | ND | ND |
| TCN-558 | 3.59 | 3.45 | 0.13 |

TABLE 11-continued

Summary of screening purified IgG by ELISA for virus binding.

| Theraclone mAb ID | ELISA: Virus Binding (OD$_{450}$) | | |
|---|---|---|---|
| | A/Solomon Islands/ 3/06 H1N1 | A/Japan/ 305/57 H2N2 | A/Wisconsin/ 67/05 H3N2 |
| TCN-559 | ND | ND | ND |
| TCN-560 | ND | ND | ND |
| TCN-563 | 3.58 | 3.16 | 0.12 |
| TCN-564 | ND | ND | ND |
| TCN-202 | 0.07 | 0.06 | 0.07 |

Example 8

Binding Profiles of Purified IgGs Using Trimeric HA

To determine whether the purified human mAbs bind to one or more of the recombinant homotrimeric HA proteins, a micro-array scanning system was used as described in Example 5 using an 8-point dilution series of test mAb. As shown in Table 12, the human mAbs bind strongly to one or more of the recombinant homotrimeric HA proteins. The binding profile shown in Table 12 substantially reproduces the virus binding profile of the IgG antibody in the original BCC SN (Table 5).

TABLE 12

Summary of screening purified IgG for virus binding to recombinant homotrimeric HA.

| Theraclone mAb ID | Trimeric HA Binding: RLU | | | | | | | | |
|---|---|---|---|---|---|---|---|---|---|
| | A/California/ 4/09 H1N1 | A/Solomon Islands/ 3/06 H1N1 | A/South Carolina/ 1/18 H1N1 | A/Japan/ 305/57 H2N2 | A/Wisconsin/ 67/05 H3N2 | A/swine/ Ontario/ 01911-2/99 H4N6 | A/Vietnam/ 1203/04 H5N1 | A/Indonesia/ 5/05 H5N1 | A/Egypt/ 3300-NAMRU3/ 08 H5N1 |
| TCN-522 | 13871 | 19146 | 4500 | 9744 | 108 | 73 | 11308 | 12511 | 11341 |
| TCN-523 | 19546 | 5131 | 9722 | 15313 | 245 | 85 | 20045 | 16864 | 21334 |
| TCN-526 | 620 | 804 | 87 | 642 | 26620 | 140 | 1164 | 140 | 11543 |
| TCN-527 | 18648 | 22893 | 314 | 26976 | 600 | 11118 | 19760 | 29601 | 23888 |
| TCN-528 | 6812 | 25431 | 16882 | 30119 | 1064 | 9488 | 24554 | 26986 | 25584 |
| TCN-529 | 977 | 2822 | 243 | 1558 | 25597 | 311 | 1505 | 234 | 17970 |
| TCN-530 | 14159 | 8574 | 7362 | 9039 | 132 | 139 | 19052 | 10919 | 12270 |
| TCN-531 | 114 | 769 | 56 | 441 | 20642 | 84 | 488 | 84 | 2811 |
| TCN-532 | 238 | 571 | 149 | 764 | 25228 | 122 | 765 | 146 | 14164 |
| TCN-533 | 24019 | 12022 | 8670 | 23364 | 308 | 384 | 26885 | 23135 | 20622 |
| TCN-534 | 20653 | 11397 | 9242 | 29122 | 230 | 220 | 25938 | 19460 | 18205 |
| TCN-535 | 17196 | 11329 | 5662 | 13037 | 148 | 118 | 20823 | 17932 | 18056 |
| TCN-536 | 298 | 830 | 160 | 771 | 24726 | 126 | 749 | 152 | 4707 |
| TCN-537 | 10197 | 9351 | 2840 | 19487 | 154 | 368 | 5689 | 265 | 3189 |
| TCN-538 | 4814 | 9739 | 6768 | 20493 | 122 | 235 | 14014 | 7451 | 7290 |
| TCN-539 | 129 | 1065 | 60 | 544 | 8847 | 138 | 636 | 85 | 651 |
| TCN-540 | 266 | 9361 | 139 | 28961 | 6905 | 138 | 830 | 139 | 860 |
| TCN-541 | 343 | 3766 | 192 | 934 | 296 | 261 | 1154 | 160 | 791 |
| TCN-542 | 238 | 23353 | 117 | 502 | 151 | 473 | 1062 | 108 | 730 |
| TCN-543 | 162 | 18316 | 259 | 13952 | 302 | 169 | 640 | 91 | 580 |
| TCN-544 | 285 | 1006 | 148 | 450 | 22600 | 154 | 773 | 117 | 2145 |
| TCN-545 | 672 | 3161 | 289 | 1398 | 23667 | 362 | 1704 | 193 | 1412 |
| TCN-546 | 277 | 1756 | 88 | 503 | 25548 | 271 | 1202 | 147 | 11208 |
| TCN-549 | 196 | 1396 | 72 | 413 | 27206 | 237 | 763 | 116 | 6919 |
| TCN-550 | 238 | 752 | 104 | 499 | 21266 | 203 | 829 | 107 | 3526 |
| TCN-551 | 19381 | 24996 | 10275 | 1595 | 267 | 415 | 2950 | 296 | 907 |
| TCN-552 | 23876 | 19410 | 14175 | 24666 | 123 | 268 | 26982 | 23591 | 20345 |
| TCN-553 | 25056 | 24601 | 20646 | 25681 | 197 | 271 | 27176 | 25968 | 24612 |
| TCN-554 | 357 | 1537 | 166 | 705 | 27125 | 253 | 1206 | 147 | 11894 |
| TCN-555 | 25456 | 17902 | 13665 | 10711 | 369 | 333 | 26476 | 15633 | 20186 |
| TCN-556 | 25782 | 24255 | 21025 | 25802 | 2362 | 24103 | 21517 | 23036 | 24803 |
| TCN-557 | 1172 | 22686 | 3592 | 28896 | 327 | 19168 | 25389 | 23316 | 23634 |
| TCN-558 | 24695 | 21965 | 13577 | 27206 | 320 | 342 | 27714 | 26156 | 25503 |
| TCN-559 | 274 | 26114 | 427 | 9163 | 2110 | 295 | 3362 | 173 | 1239 |
| TCN-560 | 24138 | 18490 | 20086 | 20524 | 11202 | 23015 | 14383 | 18049 | 21897 |
| TCN-563 | 25894 | 20971 | 16342 | 12379 | 314 | 376 | 27651 | 23202 | 21590 |
| TCN-564 | 27463 | 8568 | 15127 | 20218 | 339 | 251 | 25423 | 26345 | 19871 |
| TCN-202 | 104 | 667 | 203 | 779 | 314 | 96 | 851 | 138 | 450 |

| Theraclone mAb ID | Trimeric HA Binding: RLU | | | | | | | | |
|---|---|---|---|---|---|---|---|---|---|
| | A/common magpie/Hong Kong/ 5052/07 H5N1 | A/Anhui/ 1/05 H5N1 | A/chicken/ Vietnam/ NCVD-016/08 H5N1 | A/Hong Kong/ 156/97 H5N1 | A/northern shoveler/ California/ HKWF115/ 07 H6N4 | A/Netherlands/ 219/03 H7N7 | A/duck/ Yangzhou/ 02/05 H8N4 | A/Hong Kong/ 2108/03 H9N2 | A/Hong Kong/ 1073/99 H9N2 |
| TCN-522 | 15056 | 5265 | 1964 | 14838 | 3180 | 223 | 182 | 152 | 5049 |
| TCN-523 | 20890 | 7242 | 4961 | 5807 | 3371 | 306 | 303 | 163 | 2128 |
| TCN-526 | 713 | 18734 | 167 | 471 | 223 | 413 | 174 | 378 | 449 |
| TCN-527 | 24560 | 24663 | 25231 | 28619 | 13241 | 15182 | 25977 | 18727 | 366 |
| TCN-528 | 25491 | 28848 | 22749 | 25660 | 17960 | 16710 | 24106 | 23625 | 512 |

TABLE 12-continued

Summary of screening purified IgG for virus binding to recombinant homotrimeric HA.

| TCN-529 | 841 | 25090 | 681 | 1499 | 184 | 1306 | 737 | 295 | 966 |
| TCN-530 | 10264 | 1837 | 2046 | 14031 | 9013 | 402 | 158 | 169 | 874 |
| TCN-531 | 674 | 4963 | 124 | 259 | 45 | 170 | 112 | 142 | 350 |
| TCN-532 | 770 | 23198 | 487 | 609 | 117 | 129 | 176 | 399 | 729 |
| TCN-533 | 19005 | 5651 | 5466 | 13200 | 20390 | 712 | 365 | 164 | 5807 |
| TCN-534 | 16536 | 1896 | 5169 | 13236 | 21667 | 3418 | 173 | 172 | 918 |
| TCN-535 | 20436 | 6697 | 2626 | 13154 | 5878 | 339 | 121 | 161 | 3466 |
| TCN-536 | 794 | 8856 | 419 | 732 | 114 | 186 | 251 | 225 | 984 |
| TCN-537 | 810 | 934 | 352 | 862 | 202 | 729 | 459 | 171 | 662 |
| TCN-538 | 5142 | 667 | 1061 | 7075 | 11365 | 446 | 162 | 172 | 1272 |
| TCN-539 | 717 | 570 | 144 | 103 | 124 | 161 | 124 | 140 | 416 |
| TCN-540 | 799 | 769 | 338 | 465 | 76 | 191 | 318 | 164 | 721 |
| TCN-541 | 728 | 970 | 444 | 1223 | 187 | 929 | 352 | 175 | 805 |
| TCN-542 | 1540 | 10471 | 259 | 894 | 185 | 1126 | 182 | 2554 | 588 |
| TCN-543 | 679 | 601 | 119 | 112 | 101 | 162 | 119 | 135 | 9158 |
| TCN-544 | 723 | 2329 | 402 | 362 | 82 | 203 | 380 | 145 | 534 |
| TCN-545 | 804 | 1902 | 679 | 1676 | 316 | 1487 | 396 | 262 | 987 |
| TCN-546 | 810 | 21361 | 207 | 890 | 161 | 386 | 211 | 307 | 505 |
| TCN-549 | 781 | 13032 | 177 | 410 | 112 | 193 | 166 | 161 | 450 |
| TCN-550 | 753 | 4778 | 295 | 304 | 106 | 223 | 256 | 150 | 413 |
| TCN-551 | 907 | 6639 | 794 | 824 | 401 | 1667 | 345 | 422 | 685 |
| TCN-552 | 19414 | 4520 | 4305 | 16161 | 8973 | 470 | 232 | 161 | 1876 |
| TCN-553 | 22807 | 9027 | 12357 | 23958 | 20151 | 499 | 204 | 172 | 6691 |
| TCN-554 | 889 | 16489 | 544 | 652 | 159 | 342 | 386 | 235 | 539 |
| TCN-555 | 16958 | 6626 | 4422 | 13058 | 15555 | 1329 | 375 | 302 | 3440 |
| TCN-556 | 25559 | 26898 | 22386 | 18559 | 25020 | 20960 | 18337 | 25639 | 995 |
| TCN-557 | 23720 | 21987 | 25368 | 22765 | 12550 | 7253 | 27223 | 7659 | 440 |
| TCN-558 | 21582 | 7294 | 9731 | 20115 | 12342 | 623 | 363 | 257 | 4382 |
| TCN-559 | 1599 | 1342 | 711 | 460 | 378 | 1152 | 309 | 371 | 740 |
| TCN-560 | 17892 | 16770 | 12635 | 13519 | 22167 | 19922 | 17760 | 24259 | 1109 |
| TCN-563 | 19979 | 7517 | 8581 | 17691 | 21407 | 1691 | 327 | 314 | 4601 |
| TCN-564 | 20785 | 4261 | 5862 | 18128 | 15957 | 1413 | 369 | 272 | 9473 |
| TCN-202 | 726 | 969 | 478 | 551 | 69 | 381 | 562 | 209 | 320 |

Example 9

Neutralization Profiles of Purified IgGs

To determine whether the purified human mAbs inhibit or neutralize one or more strains of influenza virus, the assay described in Example 6 was performed with 11 H1N1 and 12 H3N2 strains (Table 13) using an 8-point dilution series of test mAb. The neutralization profile (% neutralization) of the tested mAbs is shown in table 13 when tested at 20,000 or 2,000 ng/ml. The neutralization profiles of the tested mAbs demonstrate that TCN-526, 529, 531, 532, 539, 540, 544, 549, 550, and 554 only neutralize H3N2 strains of influenza A. However, these data also show that TCN-536, 545, and 546 neutralize at least 1 strain of subtype H1 and H3. In addition, one mAb, TCN-543, neutralizes at least one stain of H1 and H3 influenza A (Table 13) and binds inactivated H1, H2, and H3 influenza A (Table 11) as well as the corresponding trimeric HA (Table 12). Therefore, it is expected that TCN-543 should also neutralize influenza A of the H2 subtype.

TCN-522, 523, 530, 533, 534, 535, 552, 553, 555, 558, 563, and 564 neutralize all of the H1N1 strains tested but do not neutralize any of the H3N2 strains tested. These data, combined with the trimeric HA and virus binding data shown in tables 12 and 13, indicate that these mAbs broadly neutralize influenza A subtypes H1, H2, H5, and H9.

TABLE 13

Summary of screening purified IgG for virus neutralization.

| | | % Neutralization H1N1 | | | | | | | | | |
|---|---|---|---|---|---|---|---|---|---|---|---|
| mAb | ng/ml IgG | A/California/ 07/2009 | A/Brisbane/ 59/2007 | A/Solomon Islands/ 3/2006 | A/New Caledonia/ 20/1999 | A/Beijing/ 262/1995 | A/Singapore/ 06/1986 | A/Taiwan/1/ 1986 | A/USSR/ 90/1977 | A/Puerto Rico/ 8/1934 | A/ NWS/33 | A/ WSN/33 |
| TCN-522 | 20,000 | 96 | 63 | 80 | 52 | 94 | 83 | 39 | 83 | 82 | 85 | 93 |
| | 2,000 | 96 | 22 | 28 | 16 | 97 | 32 | 11 | 17 | 55 | 61 | 70 |
| TCN-523 | 20,000 | 77 | 60 | 49 | 32 | 77 | 86 | 36 | 72 | 39 | 36 | 72 |
| | 2,000 | 100 | 19 | 25 | 7 | 100 | 50 | 12 | 15 | 46 | 63 | 62 |
| TCN-526 | 20,000 | 0 | 0 | 0 | 0 | 0 | 0 | 7 | 0 | 0 | 0 | 6 |
| | 2,000 | 3 | 0 | 5 | 0 | 0 | 0 | 0 | 0 | 7 | 2 | 2 |
| TCN-529 | 20,000 | 0 | 0 | 0 | 0 | 0 | 0 | 0 | 0 | 0 | 0 | 0 |
| | 2,000 | 0 | 0 | 0 | 0 | 0 | 0 | 0 | 0 | 0 | 0 | 0 |
| TCN-530 | 20,000 | 57 | 87 | 49 | 85 | 53 | 91 | 76 | 97 | 30 | 0 | 71 |
| | 2,000 | 100 | 39 | 62 | 40 | 101 | 81 | 43 | 74 | 87 | 82 | 85 |
| TCN-531 | 20,000 | 1 | 0 | 0 | 0 | 0 | 0 | 0 | 0 | 4 | 0 | 1 |
| | 2,000 | 9 | 0 | 0 | 0 | 5 | 0 | 0 | 0 | 2 | 3 | 8 |
| TCN-532 | 20,000 | 0 | 0 | 0 | 0 | 0 | 0 | 0 | 0 | 0 | 0 | 0 |
| | 2,000 | 14 | 0 | 0 | 0 | 9 | 0 | 4 | 0 | 5 | 3 | 8 |

TABLE 13-continued

Summary of screening purified IgG for virus neutralization.

| mAb | ng/ml IgG | | | | | | | | | | | |
|---|---|---|---|---|---|---|---|---|---|---|---|---|
| TCN-533 | 20,000 | 90 | 91 | 87 | 92 | 91 | 94 | 80 | 100 | 68 | 60 | 93 |
|  | 2,000 | 100 | 47 | 70 | 36 | 101 | 71 | 36 | 68 | 83 | 91 | 90 |
| TCN-534 | 20,000 | 93 | 77 | 81 | 66 | 92 | 87 | 54 | 86 | 80 | 74 | 88 |
|  | 2,000 | 100 | 24 | 36 | 8 | 100 | 44 | 21 | 43 | 68 | 78 | 73 |
| TCN-535 | 20,000 | 69 | 88 | 71 | 85 | 65 | 95 | 72 | 94 | 64 | 28 | 76 |
|  | 2,000 | 100 | 41 | 69 | 41 | 100 | 73 | 30 | 58 | 83 | 84 | 84 |
| TCN-536 | 20,000 | 0 | 9 | 87 | 10 | 0 | 0 | 0 | 0 | 8 | 0 | 0 |
|  | 2,000 | 2 | 0 | 98 | 0 | 0 | 0 | 0 | 0 | 12 | 1 | 0 |
| TCN-539 | 20,000 | 0 | 0 | 0 | 0 | 0 | 0 | 5 | 0 | 7 | 0 | 3 |
|  | 2,000 | 0 | 0 | 0 | 0 | 0 | 0 | 0 | 9 | 8 | 6 | 5 |
| TCN-540 | 20,000 | 0 | 0 | 0 | 6 | 0 | 7 | 10 | 16 | 14 | 1 | 3 |
|  | 2,000 | 0 | 0 | 0 | 6 | 0 | 0 | 17 | 10 | 16 | 2 | 5 |
| TCN-543 | 20,000 | 7 | 102 | 99 | 101 | 4 | 0 | 0 | 0 | 97 | 98 | 98 |
|  | 2,000 | 5 | 102 | 101 | 101 | 2 | 0 | 0 | 0 | 100 | 100 | 61 |
| TCN-544 | 20,000 | 3 | 0 | 0 | 0 | 2 | 0 | 3 | 0 | 0 | 0 | 10 |
|  | 2,000 | 0 | 0 | 0 | 0 | 0 | 0 | 0 | 0 | 2 | 8 | 3 |
| TCN-545 | 20,000 | 0 | 0 | 97 | 0 | 0 | 0 | 0 | 7 | 5 | 9 | 0 |
|  | 2,000 | 0 | 0 | 93 | 0 | 0 | 0 | 0 | 0 | 11 | 6 | 1 |
| TCN-546 | 20,000 | 0 | 0 | 94 | 7 | 0 | 0 | 15 | 7 | 22 | 5 | 0 |
|  | 2,000 | 0 | 0 | 98 | 3 | 0 | 16 | 0 | 12 | 17 | 0 | 1 |
| TCN-549 | 20,000 | 0 | 0 | 0 | 0 | 0 | 0 | 0 | 0 | 12 | 3 | 0 |
|  | 2,000 | 0 | 0 | 0 | 0 | 0 | 5 | 0 | 0 | 0 | 5 | 0 |
| TCN-550 | 20,000 | 0 | 0 | 2 | 0 | 0 | 13 | 2 | 0 | 0 | 0 | 11 |
|  | 2,000 | 0 | 0 | 3 | 0 | 0 | 0 | 0 | 0 | 12 | 3 | 0 |
| TCN-552 | 20,000 | 77 | 78 | 70 | 83 | 77 | 92 | 69 | 93 | 59 | 1 | 79 |
|  | 2,000 | 100 | 27 | 42 | 36 | 101 | 71 | 34 | 50 | 80 | 79 | 75 |
| TCN-553 | 20,000 | 80 | 74 | 63 | 70 | 81 | 89 | 61 | 85 | 64 | 33 | 80 |
|  | 2,000 | 100 | 29 | 40 | 23 | 101 | 58 | 14 | 30 | 69 | 70 | 75 |
| TCN-554 | 20,000 | 0 | 0 | 4 | 0 | 0 | 0 | 0 | 0 | 5 | 7 | 0 |
|  | 2,000 | 0 | 0 | 2 | 3 | 0 | 12 | 0 | 0 | 13 | 9 | 0 |
| TCN-555 | 20,000 | 55 | 69 | 65 | 68 | 52 | 82 | 55 | 80 | 64 | 4 | 65 |
|  | 2,000 | 99 | 24 | 41 | 9 | 97 | 41 | 23 | 28 | 79 | 77 | 67 |
| TCN-558 | 20,000 | 69 | 78 | 18 | 73 | 70 | 86 | 60 | 80 | 0 | 0 | 64 |
|  | 2,000 | 99 | 19 | 37 | 22 | 100 | 45 | 14 | 39 | 73 | 71 | 76 |
| TCN-563 | 20,000 | 87 | 76 | 68 | 70 | 86 | 88 | 56 | 87 | 60 | 39 | 87 |
|  | 2,000 | 100 | 18 | 41 | 12 | 101 | 45 | 23 | 25 | 51 | 74 | 67 |
| TCN-564 | 20,000 | ND | 69 | ND | 63 | ND | 67 | 38 | 67 | ND | ND | ND |
|  | 2,000 | ND | 27 | ND | 9 | ND | 40 | 0 | 23 | ND | ND | ND |
| TCN-202 | 20,000 | 1 | 0 | 0 | 0 | 0 | 0 | 0 | 0 | 5 | 0 | 3 |
|  | 2,000 | 6 | 0 | 3 | 0 | 5 | 0 | 0 | 0 | 0 | 0 | 8 |

| | | % Neutralization H3N2 | | | | | | | | | | | |
|---|---|---|---|---|---|---|---|---|---|---|---|---|---|
| mAb | ng/ml IgG | A/Perth/ 16/ 2009 | A/Hiroshima/ 52/2005 | A/Wisconsin/ 67/2005 | A/Beijing/ 353/1989 | A/Shanghai/ 11/1987 | A/Mississippi/ 1/1985 | A/Victoria/ 3/1975 | A/Scotland/ 840/1974 | A/Port Chalmers/ 1/1973 | A/England/ 42/1972 | A/Aichi/ 2/1968 | A/Hong Kong/ 8/1968 |
| TCN-522 | 20,000 | 4 | 0 | 0 | 0 | 0 | 0 | 5 | 0 | 7 | 0 | 0 | 0 |
|  | 2,000 | 2 | 18 | 0 | 0 | 0 | 0 | 3 | 0 | 2 | 0 | 17 | 14 |
| TCN-523 | 20,000 | 0 | 0 | 0 | 0 | 0 | 0 | 0 | 0 | 0 | 0 | 0 | 0 |
|  | 2,000 | 3 | 0 | 0 | 0 | 0 | 0 | 8 | 0 | 6 | 0 | 8 | 2 |
| TCN-526 | 20,000 | 101 | 114 | 97 | 85 | 8 | 0 | 3 | 0 | 0 | 0 | 0 | 0 |
|  | 2,000 | 99 | 116 | 101 | 98 | 0 | 0 | 8 | 0 | 0 | 0 | 0 | 0 |
| TCN-529 | 20,000 | 100 | 120 | 100 | 1 | 0 | 0 | 7 | 0 | 0 | 0 | 0 | 0 |
|  | 2,000 | 59 | 102 | 102 | 0 | 0 | 0 | 4 | 0 | 0 | 0 | 0 | 0 |
| TCN-530 | 20,000 | 3 | 0 | 0 | 0 | 0 | 0 | 0 | 0 | 0 | 0 | 0 | 0 |
|  | 2,000 | 0 | 0 | 0 | 0 | 0 | 0 | 12 | 0 | 0 | 0 | 0 | 0 |
| TCN-531 | 20,000 | 101 | 117 | 98 | 89 | 100 | 7 | 0 | 15 | 2 | 0 | 14 | 0 |
|  | 2,000 | 101 | 122 | 101 | 101 | 101 | 4 | 1 | 0 | 0 | 0 | 0 | 0 |
| TCN-532 | 20,000 | 100 | 106 | 100 | 0 | 0 | 0 | 4 | 0 | 0 | 0 | 0 | 0 |
|  | 2,000 | 100 | 117 | 100 | 0 | 0 | 0 | 2 | 0 | 12 | 0 | 10 | 0 |
| TCN-533 | 20,000 | 0 | 0 | 0 | 0 | 0 | 0 | 2 | 0 | 0 | 0 | 0 | 0 |
|  | 2,000 | 0 | 0 | 0 | 0 | 0 | 0 | 5 | 0 | 0 | 0 | 0 | 0 |
| TCN-534 | 20,000 | 14 | 0 | 0 | 0 | 0 | 0 | 5 | 0 | 0 | 0 | 0 | 0 |
|  | 2,000 | 12 | 0 | 0 | 0 | 0 | 0 | 7 | 0 | 0 | 0 | 0 | 0 |
| TCN-535 | 20,000 | 6 | 0 | 0 | 0 | 0 | 0 | 9 | 0 | 0 | 0 | 0 | 0 |
|  | 2,000 | 11 | 0 | 3 | 3 | 0 | 0 | 10 | 0 | 9 | 0 | 3 | 0 |
| TCN-536 | 20,000 | 101 | 50 | 86 | 0 | 15 | 0 | 0 | 35 | 5 | 0 | 0 | 0 |
|  | 2,000 | 100 | 91 | 99 | 7 | 4 | 0 | 7 | 17 | 6 | 0 | 8 | 0 |
| TCN-539 | 20,000 | 42 | 114 | 97 | 0 | 0 | 0 | 7 | 0 | 0 | 0 | 0 | 0 |
|  | 2,000 | 9 | 119 | 100 | 0 | 0 | 0 | 2 | 0 | 0 | 0 | 6 | 0 |
| TCN-540 | 20,000 | 12 | 111 | 99 | 0 | 0 | 0 | 96 | 103 | 97 | 101 | 97 | 98 |
|  | 2,000 | 14 | 124 | 99 | 0 | 1 | 0 | 100 | 103 | 101 | 100 | 98 | 100 |
| TCN-543 | 20,000 | 8 | 100 | 99 | 0 | 0 | 0 | 1 | 0 | 2 | 0 | 100 | 99 |
|  | 2,000 | 2 | 119 | 101 | 6 | 0 | 0 | 0 | 0 | 0 | 0 | 101 | 100 |
| TCN-544 | 20,000 | 42 | 109 | 98 | 0 | 0 | 1 | 6 | 0 | 5 | 0 | 3 | 0 |
|  | 2,000 | 12 | 125 | 101 | 3 | 0 | 0 | 5 | 0 | 3 | 0 | 6 | 0 |

TABLE 13-continued

Summary of screening purified IgG for virus neutralization.

| | | | | | | | | | | | | | | |
|---|---|---|---|---|---|---|---|---|---|---|---|---|---|---|
| TCN-545 | 20,000 | 100 | 122 | 99 | 26 | 0 | 4 | 0 | 12 | 6 | 0 | 0 | 0 |
| | 2,000 | 71 | 127 | 102 | 28 | 0 | 2 | 6 | 0 | 25 | 0 | 5 | 0 |
| TCN-546 | 20,000 | 99 | 121 | 95 | 71 | 100 | 10 | 0 | 8 | 0 | 0 | 2 | 2 |
| | 2,000 | 101 | 128 | 101 | 39 | 54 | 0 | 0 | 0 | 3 | 2 | 5 | 0 |
| TCN-549 | 20,000 | 18 | 109 | 97 | 0 | 0 | 0 | 5 | 0 | 1 | 0 | 5 | 3 |
| | 2,000 | 6 | 132 | 101 | 0 | 2 | 2 | 6 | 0 | 4 | 1 | 0 | 0 |
| TCN-550 | 20,000 | 99 | 98 | 96 | 0 | 0 | 0 | 6 | 0 | 2 | 0 | 5 | 16 |
| | 2,000 | 100 | 122 | 0 | 0 | 13 | 0 | 5 | 0 | 3 | 1 | 17 | 12 |
| TCN-552 | 20,000 | 0 | 0 | 0 | 0 | 6 | 0 | 7 | 0 | 0 | 0 | 3 | 0 |
| | 2,000 | 12 | 10 | 0 | 8 | 7 | 12 | 9 | 0 | 6 | 1 | 2 | 0 |
| TCN-553 | 20,000 | 5 | 0 | 0 | 0 | 0 | 0 | 12 | 0 | 0 | 0 | 6 | 0 |
| | 2,000 | 8 | 2 | 7 | 4 | 13 | 16 | 15 | 2 | 11 | 0 | 20 | 11 |
| TCN-554 | 20,000 | 80 | 74 | 96 | 0 | 0 | 12 | 7 | 4 | 15 | 0 | 0 | 46 |
| | 2,000 | 13 | 103 | 101 | 10 | 5 | 27 | 8 | 0 | 7 | 5 | 1 | 51 |
| TCN-555 | 20,000 | 0 | 0 | 0 | 0 | 0 | 0 | 2 | 0 | 0 | 0 | 0 | 0 |
| | 2,000 | 3 | 0 | 0 | 0 | 0 | 0 | 5 | 0 | 0 | 0 | 0 | 0 |
| TCN-558 | 20,000 | 0 | 0 | 0 | 0 | 0 | 0 | 0 | 0 | 0 | 0 | 0 | 0 |
| | 2,000 | 1 | 7 | 0 | 0 | 0 | 3 | 0 | 0 | 0 | 0 | 0 | 0 |
| TCN-563 | 20,000 | 5 | 0 | 0 | 0 | 0 | 0 | 0 | 0 | 0 | 0 | 0 | 0 |
| | 2,000 | 0 | 11 | 0 | 6 | 0 | 0 | 0 | 0 | 0 | 0 | 5 | 7 |
| TCN-564 | 20,000 | 0 | ND | ND | ND | 0 | 0 | ND | 0 | ND | 0 | 0 | 0 |
| | 2,000 | 13 | ND | ND | ND | 0 | 0 | ND | 2 | ND | 0 | 10 | 0 |
| TCN-202 | 20,000 | 2 | 0 | 3 | 0 | 0 | 0 | 9 | 0 | 0 | 0 | 0 | 0 |
| | 2,000 | 6 | 0 | 0 | 0 | 0 | 0 | 0 | 0 | 1 | 1 | 10 | 0 |

Example 10

Neutralization of H1N1, H2N2, H3N2, H5N1, H7N7, or H9N2 Influenza A Virus by Purified IgGs TCN-522, 523, 530, 533, 534, 535, 552, 553, 555, 558, 563, and 564 were tested for neutralization of H1N1, H2N2, H3N2, H5N1, H7N7, and H9N2 strains at Midwest Research Institute (MRI) (www.mriglobal.org/lifesciences/Pages/default.aspx) by the method described infra.

Study Design

Influenza virus strains used in viral microneutralization (VMN) assays are shown in Table 14. Madin Darby canine kidney (MDCK) cells were used for the VMN assays. Purified anti-HA monoclonal antibodies TCN-522, 523, 529, 530, 533, 534, 535 and 202 were included in the study.

TABLE 14

| Subtype | Virus strain |
|---|---|
| H1N1 | A/Solomon Islands/03/2006 |
| H1N1 | A/California/07/2009 |
| H2N2 | A2/Japan/305/1957 |
| H3N2 | A/Wisconsin/67/2005 |
| H3N2 | A/Perth/16/2009 |
| H5N1 | A/Anhui/01/2005 (H5N1)-PR8-IBCDC-RG |
| H5N1 | A/Vietnam/1203/2004 |
| H5N1 | A/Human/Iraq/207-NAMRU3/2006 |
| H5N1 | A/Human/Hong Kong/156/1997 |
| H7N7 | A/Netherlands/219/2003 |
| H9N2 | A/Hong Kong/1073/1999 |

Viral Microneutralization Assay

Purified anti-HA monoclonal antibodies TCN-522, 523, 529, 530, 533, 534, 535 and 202 were included in the study as well as the negative control mAb TSN-202. Eleven (11) viruses, including, three belonging to the H1N1 subtype, one belonging to the H2N2 subtype, one belonging to the H3N2 subtype, four belonging to the H5N1 subtype, one belonging to the H7N7 subtype, and one belonging to the H9N2 subtype. Each antibody was tested against each of the eleven (11) antibodies listed in Table 14. All work was performed using aseptic technique.

Viral microneutralization (VMN) assays were performed using the Medical Research Institute (MRI) method described below, with a direct end-point read (presence of influenza virus-specific cytopathic effects) 5 days post inoculation of the cells with antibody-virus mixtures.

Although this study utilized the MRI method, alternative detection methods include, but are not limited to, ELISA detection of CPE using a colorimetric or an immunofluorescent readout and immunofluorescence for visual imaging (using, for example, GE InCell technology).

All viruses were grown in MDCK cells. During cell propagation, MDCK cells were fed Minimal Essential Medium with Earle's salts (EMEM) supplemented with 10% gamma-irradiated fetal bovine serum (FBS) with alanyl-glutamine (glutamax), antibiotics, and pyruvate. FBS was not added to EMEM during the propagation of viruses in MDCK cells. TPCK-treated trypsin was added to serum-free EMEM that was used to feed MDCK cells for the propagation of influenza A viruses.

Viruses were diluted in serum-free EMEM plus trypsin ("EMEM virus diluent"). The viruses were incubated with an anti-HA mAb of the invention (i.e., TCN-522, 523, 529, 530, 533, 534, 535 or 202) or the negative control Ab for 18 hrs prior to addition to MDCK cells.

Antibody diluent included trypsin-free EMEM+1% BSA (purified fraction V).

Experimental Procedure

Serial Dilution of Antibody.

The concentration of monoclonal antibody (mAb) was adjusted to 150.0 µg/ml in EMEM diluent w/1% BSA. To the plate in FIG. 36, 100 µl of antibody diluents was added to all wells in columns 2-12. MAb was serially diluted by ⅓ (i.e., 50 µl aliquots were serially transferred) across the plate to column 11. Fifty µl of mAb was discarded from column 11 and no mAb/virus mix was transferred to column 12.

Preparation of Ab/Virus Incubation Plate.

Virus (with known titer) was diluted to 5,000 TCID 50 units/mL in serum-free EMEM without trypsin. Eighty µl of serially-diluted mAb was transferred to a new U-Bottom plate. Twenty µL of 1.2 M Mannose was added to the plate [1.2 M mannose (Sigma M-6020) made in H2O]. Twenty µL (100 TCID50 units) of virus prep were added to the plate except for control wells in column 12 (plate having the same geometry as the plate shown FIG. 36). The mAb and viral preps were mixed by gentle pipetting. The plate was sealed and incubated overnight at 37° C. (i.e., 18 hrs). The time of incubation was recorded.

Addition of the mAb/Virus Mixture to MDCK Cells.

The same day the mAb/virus incubation plate was prepared, MDCK cells were plated at a density of $1.25 \times 10^4$ cells/well (in a 96-well plate) with complete EMEM media. MDCK cells were incubated at 37° C. overnight (i.e., 18 hrs). Prior to infection, the cells were washed twice (2×) with 200 µl EMEM without serum.

One hundred µl from the mAb/virus incubation plate was transferred to the washed MDCK cell plate and incubate 4 hours at 37° C. for H5N1 and CA/07 H1N1, and at 35° C. for all other subtypes. Thus, approximately 83.3% of the antibody-virus mix was added to the MDCK cells.

After infection, the mAb/virus mixture was removed and the cells were washed twice (2×) with 200 µl EMEM. After the last wash, 100-200 µl of EMEM with TPCK-treated trypsin was added. Infected and washed MDCK cells were incubated at 37° C. for those infected with H5N1 and CA/07 (H1N1), and at 35° C. for those infected with all other subtypes. The plates were incubated for 5 days for those infected with all viruses except CA/07 (H1N1). Plates infected with CA/07 (H1N1) were incubated for 7 days. The wells were re-fed every 3 days during the incubation period.

Figure 1:
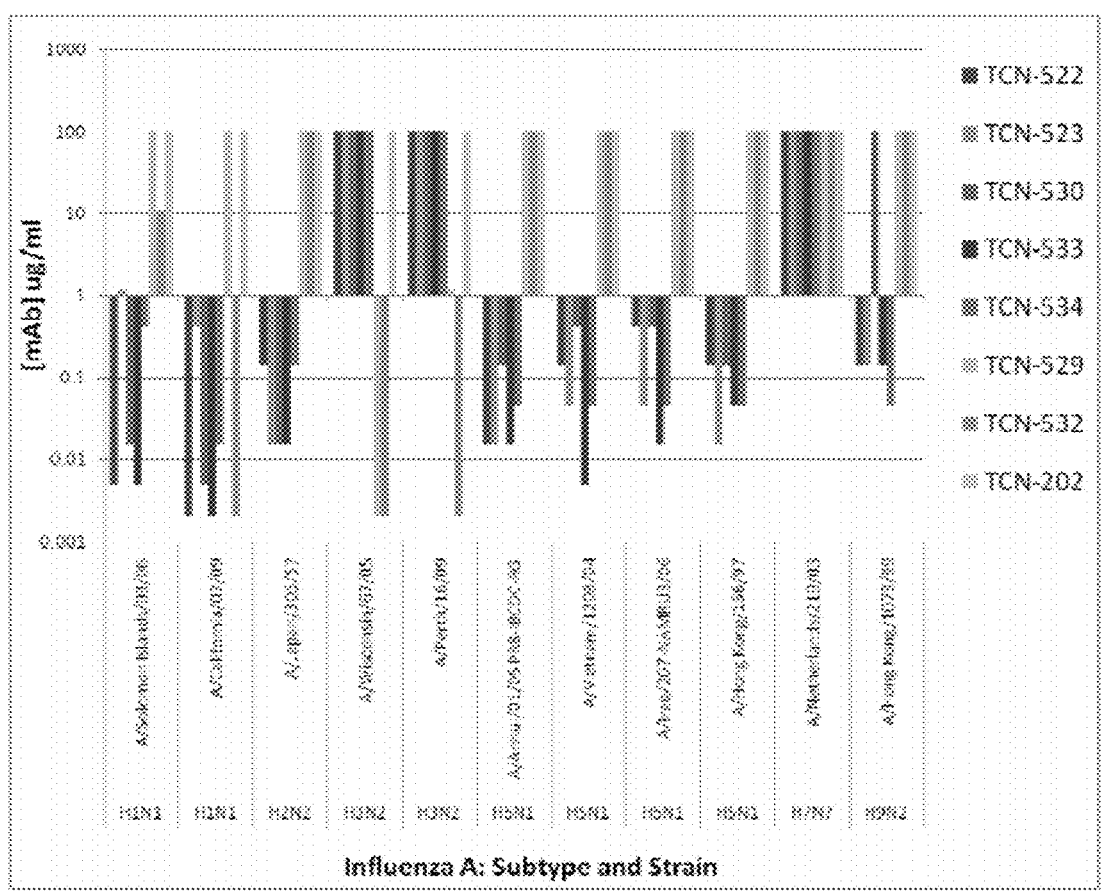
FIG. 1 is a graph depicting the minimum concentration of monoclonal antibody (mAb) that neutralized 100% of input virus, comprising H1, H2, H3, H5, H7 and H9 subtypes of influenza A.

FIG. 1 shows the minimum concentration of mAb that neutralized 100% of input virus. TCN-522, 523, 530, 533, and 534 neutralized all H1, H2, and H5 strains tested and 4 of these 5 mAbs, TCN-522, 523, 533, and 534 neutralized the H9N2 strain whereas TCN-530 did not.

TCN-529 only neutralized H3N2 strains whereas TCN-532 neutralized all of the H1N1 and H3N2 strains tested. However, this contradicts the results shown in Table 13, in which TCN-532 only neutralized H3N2 strains and bound only H3N2 virus by ELISA (Table 11) and trimeric HA for H3 (A/Wisconsin/67/05) (Table 12).

Example 11

Analysis of Purified IgGs for Inhibition of Influenza A Induced Hemagglutination or Lysis of Chicken Red Blood Cells (CRBC)

Influenza A virus causes agglutination of chicken red blood cells (CRBC) when mixed together. Thus, the inhibition of agglutination by a molecule, such as an antibody binding to the receptor binding domain (RBD) on the hemagglutinin molecule on the influenza A virus, is indicative of the specificity of the test antibody for the RBD. If the test antibody does not inhibit agglutination of the CRBC, the specificity of the test antibody is for a region of the hemagglutinin molecule at some point distant from the RBD. Therefore, TCN-522, 523, 528, 530, 533, and 202 were tested for hemagglutination inhibition (HAI).

MAbs were serially diluted 1:3 from 30 ug/ml to 0.5 ng/ml, mixed with a set concentration of live H1N1 A/Solomon Island/3/06 and incubated overnight at 37° C. (i.e., 18 hours) prior to the addition of CRBC. The CRBC were allowed to pellet for 1 hr, and scored for antibody-mediated inhibition of hemagglutination. None of the tested mAbs inhibited CRBC agglutination which indicates the specificity of these mAbs is at some point distant from the RBD (Table 14).

The hemagglutinin molecule of influenza A mediates fusion of the viral membrane with the host cell membrane once exposed to a drop in pH in the endosome upon internalization. Therefore, TCN-522, 523, 528, 530, 533, and 202 were tested for the capacity to inhibit virus-induced membrane fusion. A set concentration of CRBC was mixed with a set concentration of live H1N1 A/Solomon Island/3/06 and incubated for 1 hour at 37° C. MAbs that were serially diluted 1:3 from 30 ug/ml to 0.5 ng/ml were then added to the virus/CRBC mix and incubated overnight at 37° C. The mix was subsequently treated with acid (pH 5.0) and hemolysis was ascertained by hemoglobin release into the supernatant, as measured by A540. TCN-522, 523, 530, 533, and 534 inhibited fusion, but the non-neutralizing mAb TCN-528 and the negative control mAb TCN-202 did not (Table 14). These results demonstrate that mAbs TCN-522, 523, 530, 533, and 534 likely bind to the region of the hemagglutinin molecule known to mediate fusion by undergoing a conformational shift at low pH, and, thus, block this event. By inhibiting hemagglutinin-mediated fusion, these mAbs neutralize infection.

TABLE 15

Summary of screening purified IgG for inhibition of virus-induced agglutination of chicken erythrocytes or inhibition of virus-induced membrane fusion.

|  | HAI (ug/ml) | Fusion Inhibition EC50 (ng/ml) |
| --- | --- | --- |
| TCN-522 | >30,000 | 2,876 |
| TCN-523 | >30,000 | 2,295 |
| TCN-528 | >30,000 | >30,000 |
| TCN-530 | >30,000 | 1,626 |
| TCN-533 | >30,000 | 943 |
| TCN-534 | >30,000 | 1,280 |
| TCN-202 | >30,000 | >30,000 |

Example 12

Affinity of Antibody Fab Fragments of Purified IgGs for Recombinant Trimeric HA A/California/04/09

To determine the affinity of several broadly neutralizing mAbs, Fab fragments of mAbs TCN-522, 523, 530, 534, and 535 were made by standard techniques and then tested against the recombinant trimeric HA of H1N1 A/California/04/09 (HA-CA) described in Table 2, SEQ ID NO: 2. A Fab fragment of the influenza strain-specific mAb TCN-536 was included as a negative control (a Fab fragment which neither binds recombinant trimeric HA nor neutralizes H1N1 A/California/04/09, Tables 12 and 13).

These experiments were performed using a ProteOn biosensor with a GLM sensor chip (BioRad). HA-CA was captured onto an anti-V5 surface at 5 different densities from 20 to 500 RU. The running buffer contained 10 mM HEPES pH 7.5, 150 mM NaCl, 0.01% tween-20 and 0.1 mg/ml BSA. Data were collected at 25° C. Fabs were tested at 50 nM as the highest concentration in a 3-fold dilution series using 5 total concentrations. Surfaces were regenerated with a 20 second injection of 1 to 100 dilution of phosphoric acid. The data from the 5 different density antigen surfaces were globally fit to a 1:1 interaction binding model (using Scrubber2, Biologic Software Ptd Ltd) to extract a binding constant for each interaction. The results are provided in Table 16.

TABLE 16

Affinity analysis of HA-specific Fabs for recombinant trimeric HA (H1N1 A/California/04/09). The number in parentheses represents the statistical standard error in the last reported digit.

|     | $k_a$ (M−1s−1) | $k_d$ (s−1)    | $K_D$ (pM) |
| --- | -------------- | -------------- | ---------- |
| 522 | 6.98(6)e4      | 3.8(6)e−5      | 550(90)    |
| 523 | 5.40(2)e5      | 5.1(6)e−5      | 90(10)     |
| 530 | 5.11(1)e5      | 2.87(4)e−4     | 562(8)     |
| 533 | 6.35(2)e5      | 8.2(4)e−5      | 129(7)     |
| 534 | 5.73(2)e5      | 5.96(4)e−5     | 104.0(4)   |
| 535 | 9.87(3)e5      | 1.63(6)e−4     | 165(7)     |
| 536 |                | No binding detected |       |

All of the TCN Fabs, except TCN-522 and the negative control TCN-536, have a similar rate of association (ka) or "on-rate" for binding to HA-CA (Table 16). The on-rate for TCN-522 is 5-8 times slower than for the other Fabs (Table 16). However, the rate of dissociation or "off-rate" of TCN-522 is the slowest, and, therefore, most preferred rate of dissociation, of all of the Fabs tested with the corresponding affinity ($K_D$) of 550 μM.

Example 13

Therapeutic Activity of Purified IgGs Against a Lethal Dose of Pandemic H1N1 Influenza A In-Vivo To determine the therapeutic efficacy of several broadly neutralizing monoclonal antibodies, a study was performed in a post-infection therapeutic model against a lethal H1N1 A/California/04/09 virus challenge in-vivo, according to the study design shown in Table 17.

TABLE 17

Study design for testing therapeutic efficacy of 11 Bin 1 mAbs against lethal infection of DBA/2 mice with H1N1 A/California/04/09.

| mAb Dose (mg/kg) | Day of mAb Administration |   |   |
| ---------------- | --- | --- | --- |
|                  | 1   | 3   | 5   |
| 15               | X   |     |     |
|                  |     | X   |     |
|                  |     |     | X   |
| 1.5              | X   |     |     |
|                  |     | X   |     |
|                  |     |     | X   |

Each group of mice included 4 or 5 mice (DBA/2), which were infected intra-nasally on day 0 with 25×LD$_{50}$ of wild-type H1N1 A/California/04/09 (in a separate study the LD$_{50}$ in DBA/2 mice was determined to be approximately 1 plaque forming unit of infectious virus). A single dose of mAb (15.0 or 1.5 mg/kg) was administered by intra-peritoneal injection in 200 ul of phosphate buffered saline (PBS) on day +1, or +3, or +5 post-infection. Weight loss and survival were monitored for 18 days. The same regimen was used for the negative control mAb TCN-202 (specific for human cytomegalovirus). Oseltamivir (OSC) was dosed at 10 mg/kg twice daily on days +1-5. Vehicle control alone was 200 ul of PBS. Untreated animals challenged with virus (UT/C) were included as a positive infection control. In vivo experiments were conducted in 2 separate studies with 6 mAbs in study A and 5 mAbs in study B, respectively. Values shown for loss of body weight were the average for all surviving animals in a treatment group.

Study A

Figure 2:
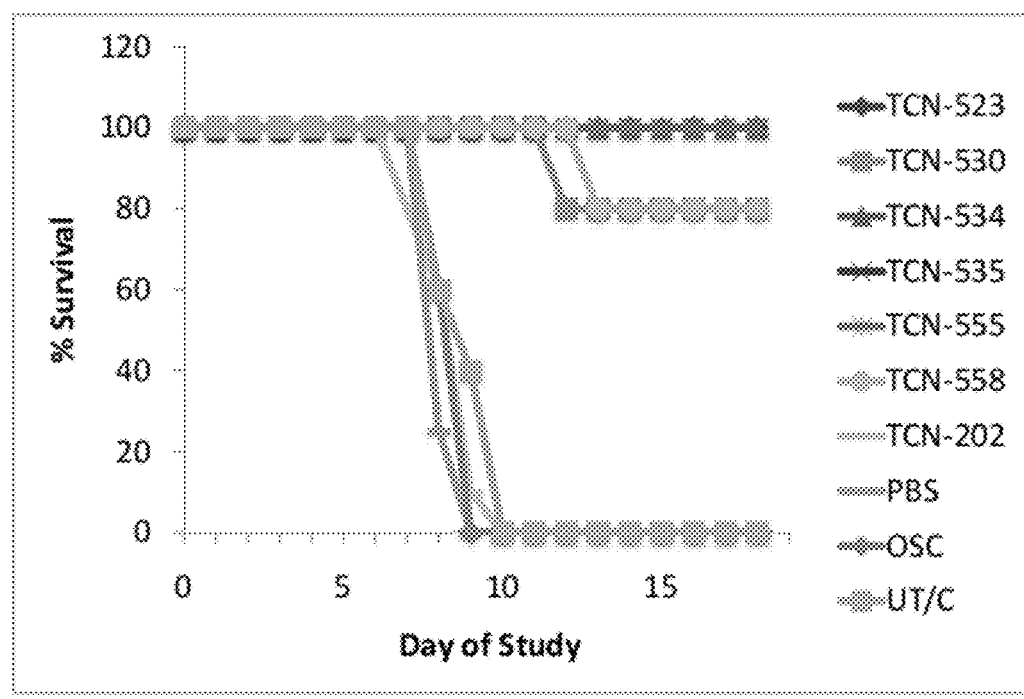
FIG. 2 is a graph depicting the survival of mice infected with 25×LD50 of H1N1 A/California/04/09 and antibody administration at 15 mg/kg on day +1 (one day) after infection.
Figure 3:
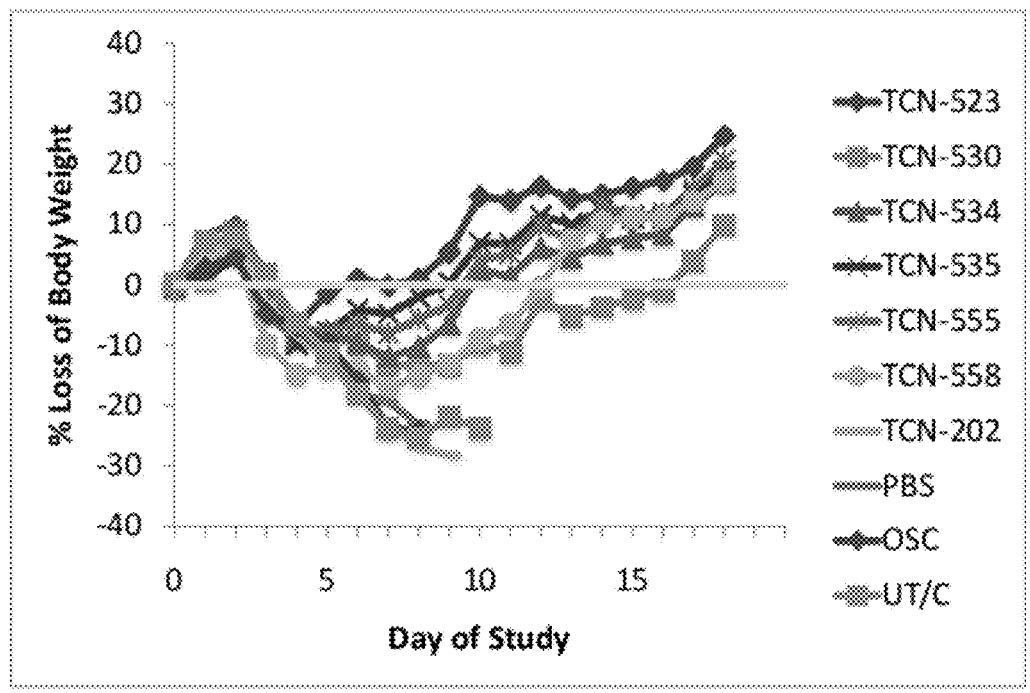
FIG. 3 is a graph depicting the percent weight loss of mice infected with 25×LD$_{50}$ of H1N1 A/California/04/09 and antibody administration at 15.0 mg/kg on day +1 after infection.

Study A, 15 mg/kg, mAb Administration Day 1 Post Infection:

80-100% of the animals survived when treated with TCN-523, 530, 534, 535, 555, and 558. There was no survival in the control groups or oseltamivir treated animals (FIG. 2). Weight loss was recorded as loss of 20-30% of body weight by day 8-10 of infection followed by onset of recovery in all infected animals (FIG. 3).

Figure 4:
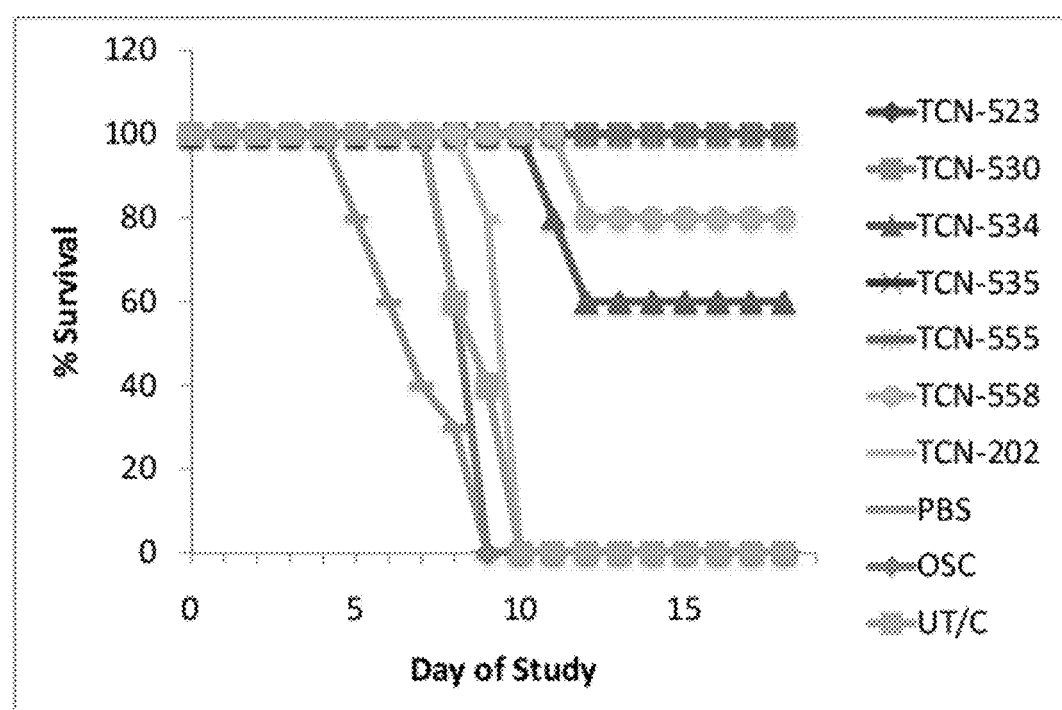
FIG. 4 is a graph depicting the survival of mice infected with 25×LD$_{50}$ of H1N1 A/California/04/09 and antibody administration at 15 mg/kg on day +3 (three days) after infection.
Figure 5:
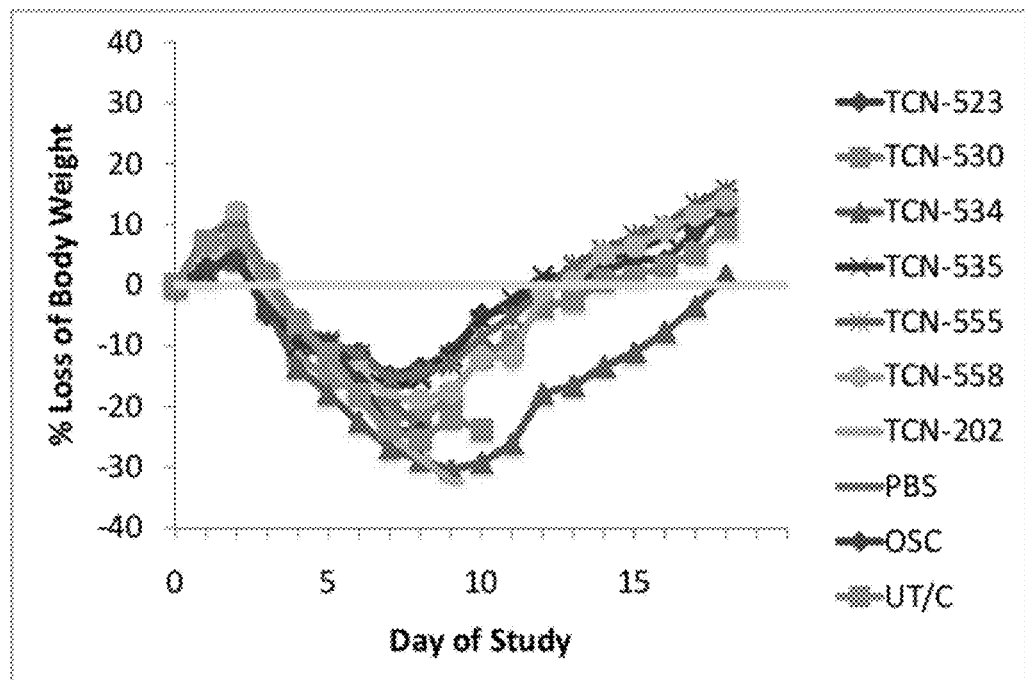
FIG. 5 is a graph depicting the percent weight loss of mice infected with 25×LD$_{50}$ of H1N1 A/California/04/09 and antibody administration at 15.0 mg/kg on day +3 after infection.

Study A, 15 mg/kg, mAb Administration Day 3 Post Infection:

60-100% of the animals survived when treated with TCN-523, 530, 534, 535, 555, and 558. There was no survival in the control groups or oseltamivir treated animals (FIG. 4). Weight loss was recorded as loss of 15-25% of body weight by day 7-8 of infection followed by onset of recovery in all infected animals (FIG. 5).

Figure 6:
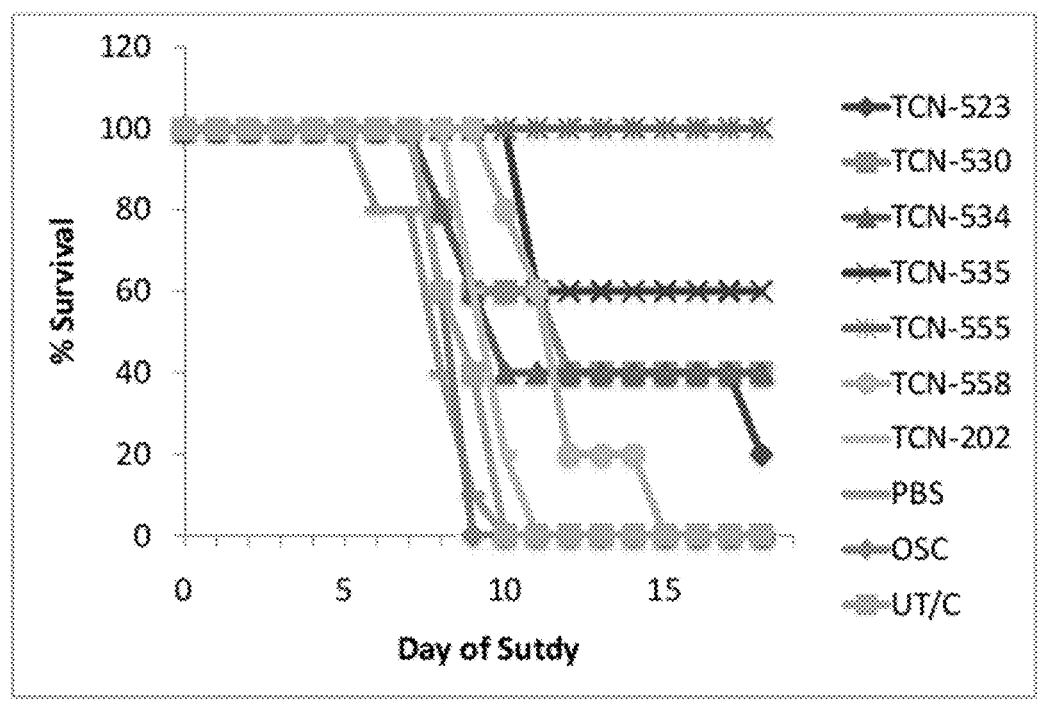
FIG. 6 is a graph depicting the survival of mice infected with 25×LD$_{50}$ of H1N1 A/California/04/09 and antibody administration at 15 mg/kg on day +5 (five days) after infection.
Figure 7:
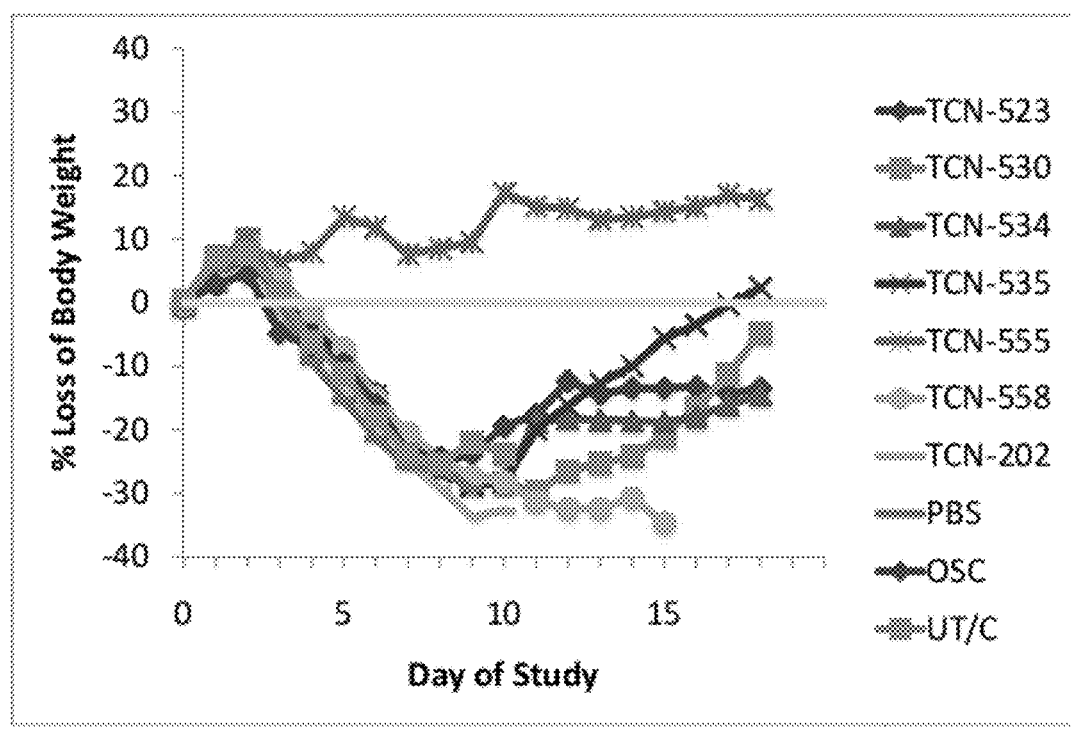
FIG. 7 is a graph depicting the percent weight loss of mice infected with 25×LD$_{50}$ of H1N1 A/California/04/09 and antibody administration at 15.0 mg/kg on day +5 after infection.

Study A, 15 mg/kg, mAb Administration Day 5 Post Infection:

60% of the animals survived when treated with TCN-535, 40% survived when treated with TCN-530 and 534, and 20% survived when treated with TCN-523. There was no survival in the TCN-558 treated group, the control groups, or oseltamivir treated animals (FIG. 6). Weight loss was recorded as loss of 20-30% of body weight by day 8 of infection followed by onset of recovery in all infected animals (FIG. 7). For TCN-555, none of the animals lost weight during the study period, indicating that they were likely not infected with virus and, consequently, resulting in 100% survival.

Figure 8:
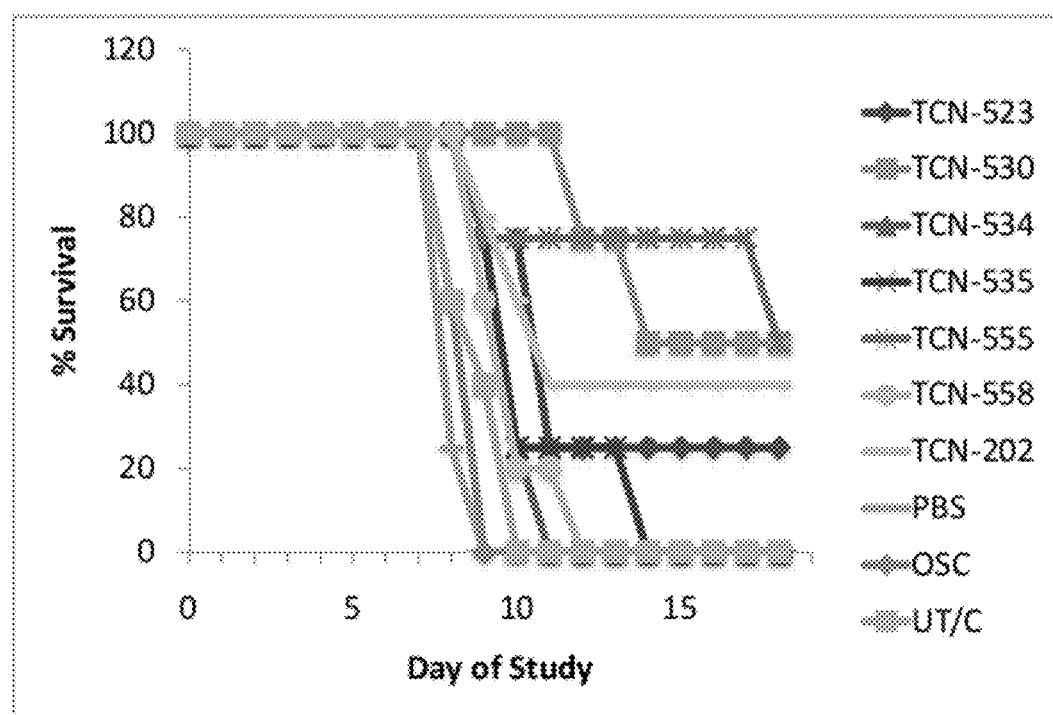
FIG. 8 is a graph depicting the survival of mice infected with 25×LD$_{50}$ of H1N1 A/California/04/09 and antibody administration at 1.5 mg/kg on day +1 after infection.
Figure 9:
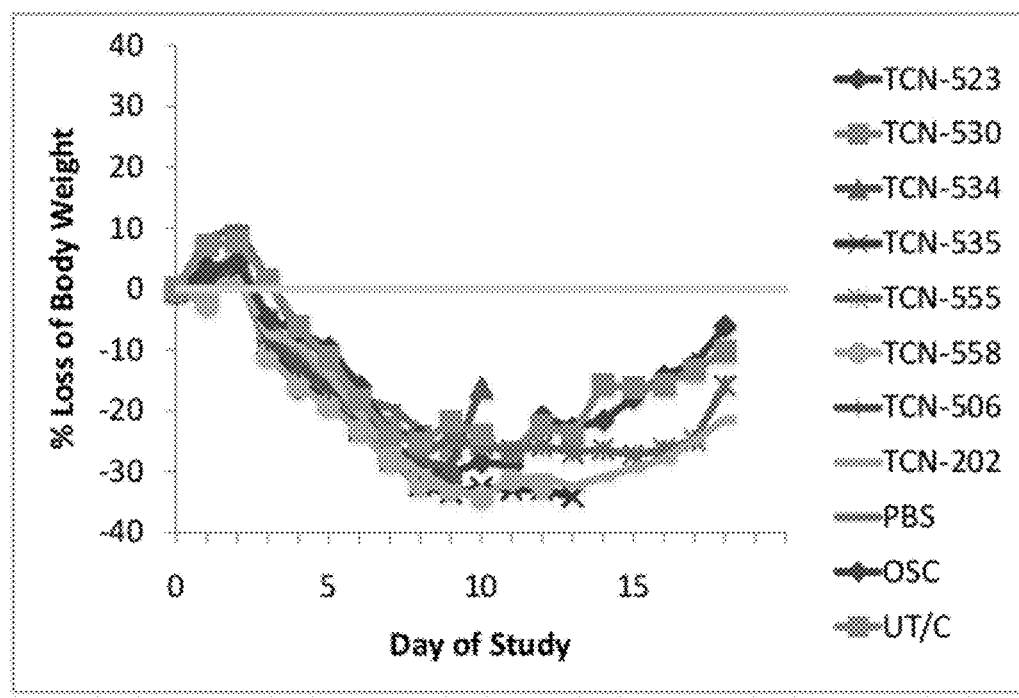
FIG. 9 is a graph depicting the percent weight loss of mice infected with 25×LD$_{50}$ of H1N1 A/California/04/09 and antibody administration at 1.5 mg/kg on day +1 after infection.

Study A, 1.5 mg/kg, mAb Administration Day 1 Post Infection:

50% of the animals survived when treated with TCN-530 and 555, 40% survived in the TCN-202 treated group, and 25% survived in the TCN-523 treated group. There was no survival in the TCN-534, 535 and 558 treated groups or in the control groups or oseltamivir treated animals (FIG. 8). Weight loss was recorded as loss of 25-35% of body weight by day 8-10 of infection followed by onset of recovery in all infected animals (FIG. 9).

Figure 10:
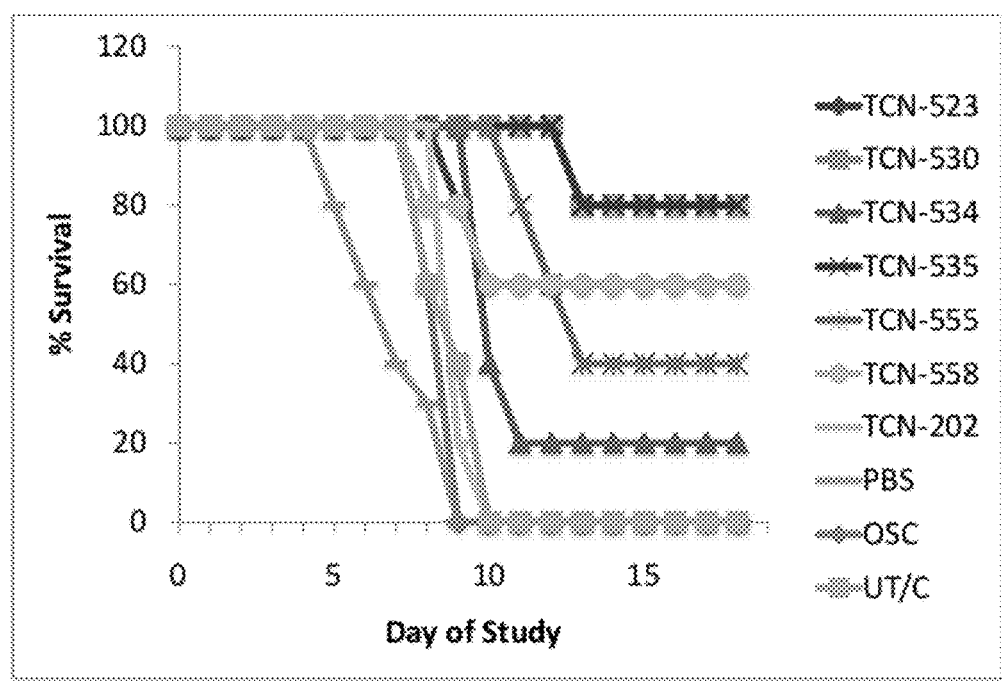
FIG. 10 is a graph depicting the survival of mice infected with 25×LD50 of H1N1 A/California/04/09 and antibody administration at 1.5 mg/kg on day +3 after infection.
Figure 11:
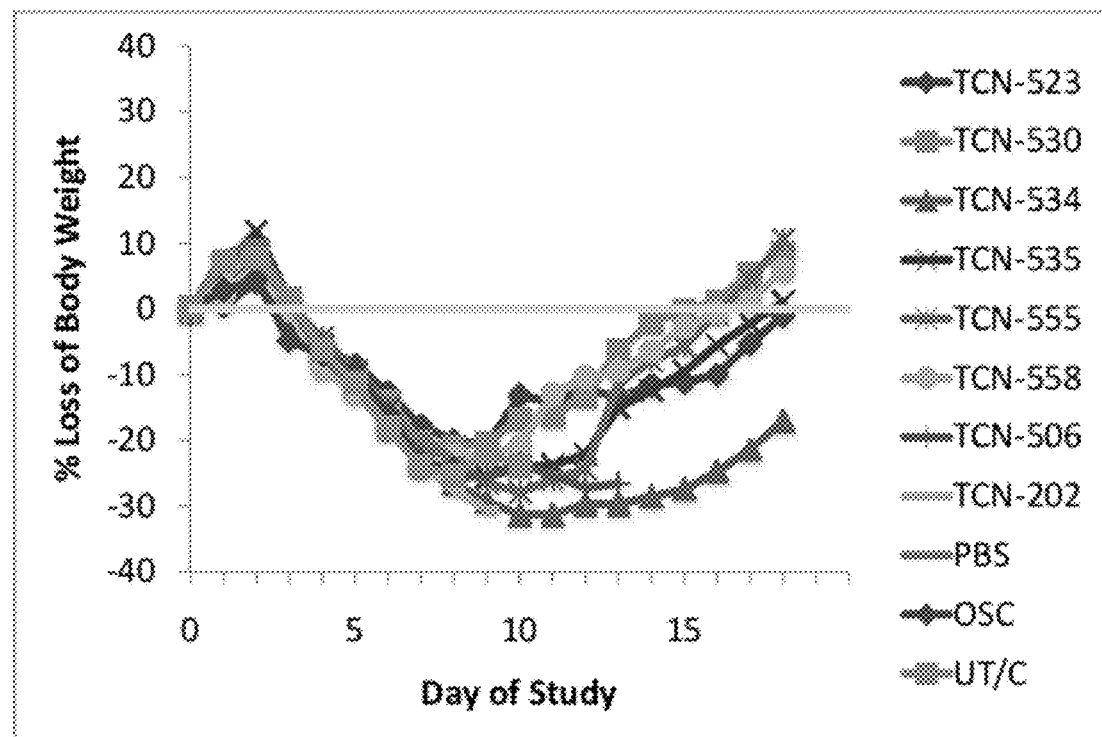
FIG. 11 is a graph depicting the percent weight loss of mice infected with 25×LD$_{50}$ of H1N1 A/California/04/09 and antibody administration at 1.5 mg/kg on day +3 after infection.

Study A, 1.5 mg/kg, mAb Administration Day 3 Post Infection:

80% of the animals survived when treated with TCN-530 and 535, 60% survived in the TCN-523 and 558 treated groups, 40% survived in the TCN-555 treated group, and 20% survived in the TCN-534 treated group. There was no survival in the control groups or oseltamivir treated animals (FIG. 10). Weight loss was recorded as loss of 20-30% of body weight by day 8-9 of infection followed by onset of recovery in all infected animals (FIG. 11).

Figure 12:
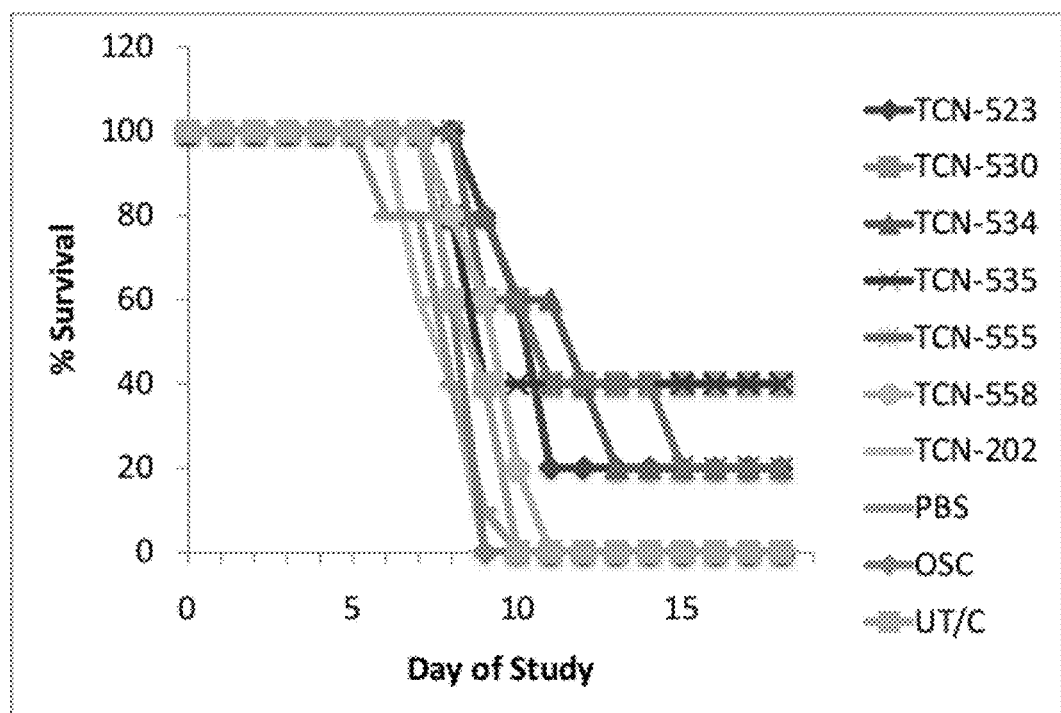
FIG. 12 is a graph depicting the survival of mice infected with 25×LD$_{50}$ of H1N1 A/California/04/09 and antibody administration at 1.5 mg/kg on day +5 after infection.
Figure 13:
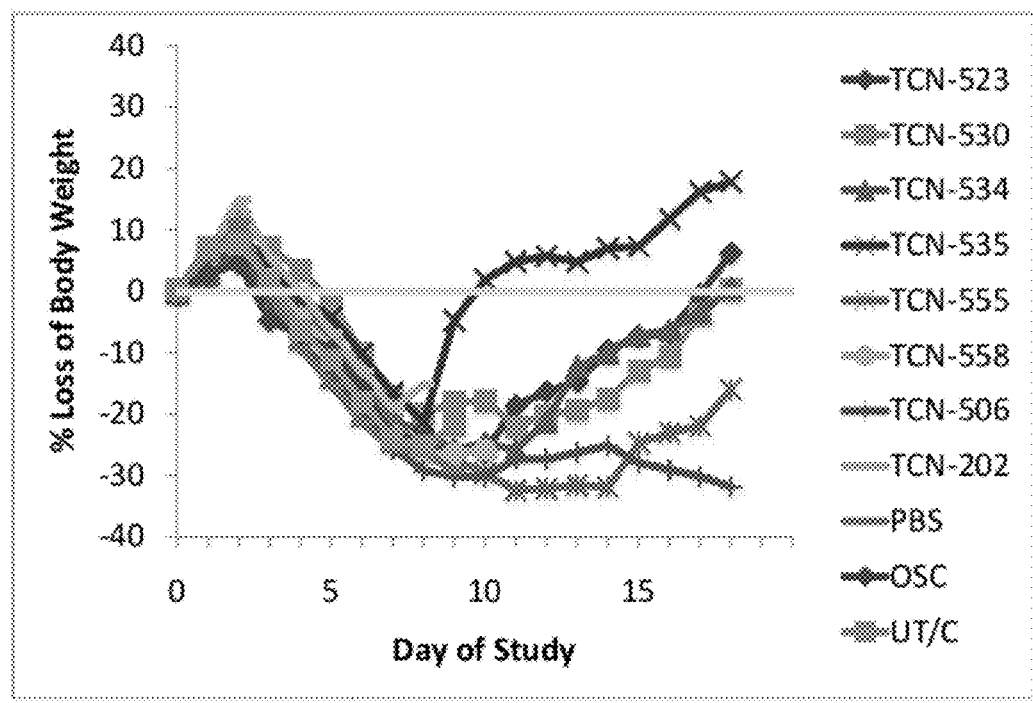
FIG. 13 is a graph depicting the percent weight loss of mice infected with 25×LD$_{50}$ of H1N1 A/California/04/09 and antibody administration at 1.5 mg/kg on day +5 after infection.
Figure 14:
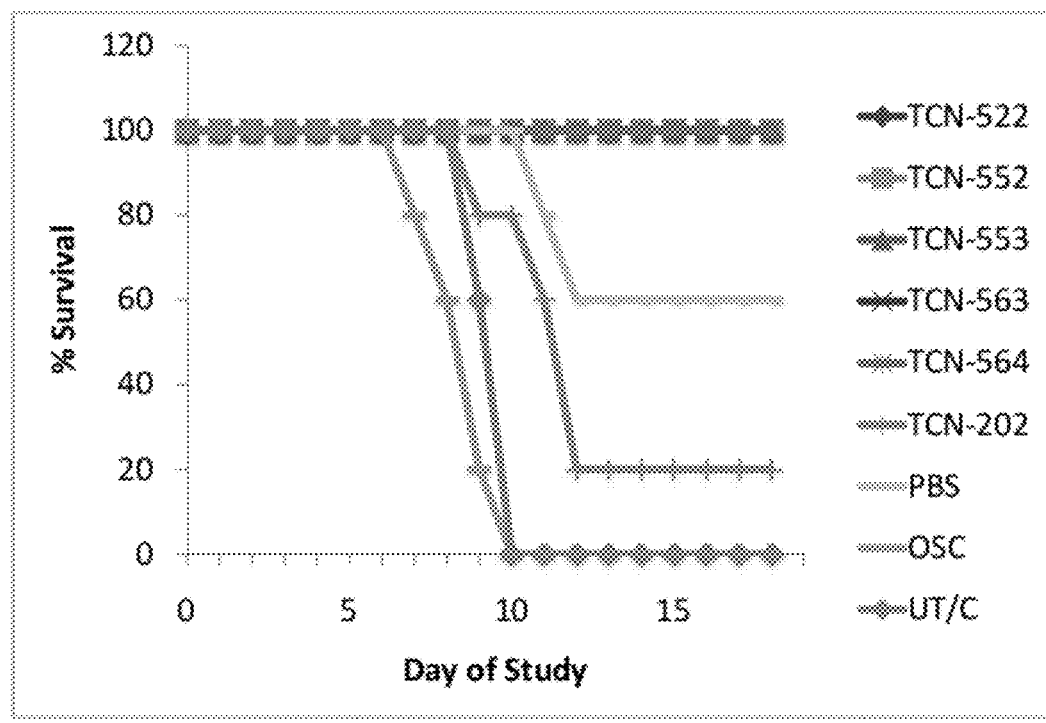
FIG. 14 is a graph depicting the survival of mice infected with 25×LD$_{50}$ of H1N1 A/California/04/09 and antibody administration at 15 mg/kg on day +1 after infection.

Study A, 1.5 mg/kg, mAb Administration Day 5 Post Infection:

40% of the animals survived when treated with TCN-530 or 535, 20% survived when treated with TCN-523, 534, or 555. There was no survival in the TCN-558 treated group, the control groups, or oseltamivir treated animals (FIG. 12). Weight loss was recorded as loss of 20-30% of body weight by day 8 of infection followed by onset of recovery in all infected animals (FIG. 13). For TCN-555, none of the animals lost weight during the study period which indicates they were likely not infected with virus resulting in 100% survival.

Study B

Study B, 15 mg/kg, mAb Administration Day 1 Post Infection:

100% of the animals survived when treated with TCN-522, 552, 553, 563, and 564, 60% survived in the PBS treated group, and 20% survived in the TCN-202 treated group. There was no survival in the oseltamivir treated animals (FIG.

Figure 15:
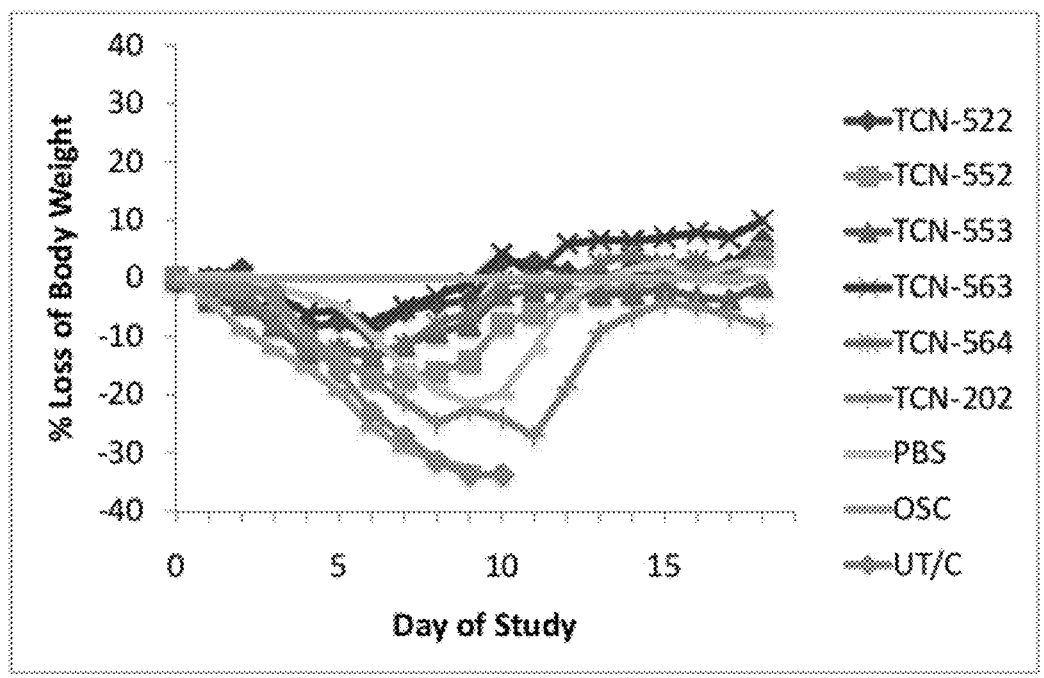
FIG. 15 is a graph depicting the percent weight loss of mice infected with 25×LD$_{50}$ of H1N1 A/California/04/09 and antibody administration at 15 mg/kg on day +1 after infection.

14). Weight loss was recorded as loss of 5-20% of body weight by day 6 of infection followed by onset of recovery in all infected animals (FIG. 15). However, the weight loss in the PBS treated group and the TCN-202 treated group was delayed by several days and did not reach a maximum until day 9 or 10 of the study, respectively.

Study B, 15 mg/kg, mAb Administration Day 3 Post Infection:

100% of the animals survived when treated with TCN-522, 80% survived in the TCN-563 treated group, 40% survived in the TCN-552 and 564 treated groups, and 20% survived in the TCN-553 and 202 treated groups. There was no survival in the PBS control group or in the oseltamivir treated animals (FIG. 16). Weight loss was recorded as loss of 20-30% of body weight by day 7-9 of infection followed by onset of recovery in all infected animals (FIG. 17).

Study B, 15 mg/kg, mAb Administration Day 5 Post Infection:

100% of the animals survived when treated with TCN-522, 80% survived in the TCN-553 treated group, 40% survived in the TCN-564 treated group, and 20% survived in the TCN-552 and 563 treated groups. There was no survival in the control groups, or oseltamivir treated animals (FIG. 18). Weight loss was recorded as loss of 25-35% of body weight by day 9 of infection followed by onset of recovery in all infected animals (FIG. 19).

Study B, 1.5 mg/kg, mAb Administration Day 1 Post Infection:

80% of the animals survived when treated with TCN-552 and 553, 60% survived in the TCN-563 and 202 treated groups, 40% survived in the TCN 564 and 202 treated groups, and 20% survived in the TCN-522 treated group. There was no survival in the oseltamivir treated animals (FIG. 20). Weight loss was recorded as loss of 20-30% of body weight by day 9 of infection followed by onset of recovery in all infected animals (FIG. 21).

Study B, 1.5 mg/kg, mAb Administration Day 3 Post Infection:

60% of the animals survived when treated with TCN-522, 40% survived in the TCN-564 treated group, and 20% survived in the TCN-552, 563, and 202 treated groups. There was no survival in the PBS control group or in the oseltamivir treated animals (FIG. 22). Weight loss was recorded as loss of 20-30% of body weight by day 8 of infection followed by onset of recovery in all infected animals (FIG. 23).

Study B, 1.5 mg/kg, mAb Administration Day 5 Post Infection:

40% of the animals survived when treated with TCN-522 or 202. There was no survival in any of the other mAb or control treated groups (FIG. 24). Weight loss was recorded as loss of 25-35% of body weight by day 8-9 of infection followed by onset of recovery in all infected animals (FIG. 25).

Example 14

Therapeutic Activity of Purified IgGs Against a Lethal Dose of H5N1 Influenza A In-Vivo MAbs TCN-522, TCN-530, and TCN-533 were tested to determine the therapeutic window of treatment in murine model of lethal infection with the highly pathogenic H5N1 A/Hong Kong/156/1997 (HK156). Each group of mice consisted of 10 BALB/C mice (except the untreated/unchallenged group: 7 mice) which were infected intra-nasally on day 0 with 25×$LD_{50}$ of HK156. A single dose of mAb of 15.0 mg/kg was administered by intra-peritoneal injection in 200 ul of phosphate buffered saline (PBS) on day +1, or +3, or +4, or day +5, or day +6 post-infection. Weight loss and survival were monitored for 15 days. The same regimen was used for the negative control mAb TCN-202 (specific for human cytomegalovirus). Oseltamivir (OSC) was dosed at 10 mg/kg twice daily on days +1-5. Vehicle control alone is 200 ul of PBS. Untreated animals challenged with virus (UT/C) were included as a positive infection control.

All of the mice survived challenge when antibodies TCN-522, TCN-530, or TCN-533 were administered on day +1 post-infection (FIG. 26) and weight loss did not exceed 10% for any of the animals that were treated with TCN-522, TCN-530, or TCN-533 at this time point (FIG. 27).

As shown in FIGS. 28 and 29, 90% and 80% of the mice survived infection with 25×$LD_{50}$ of H5N1 A/Hong Kong/156/97 (HK156), respectively, when mAb TCN-522 and TCN-530, or TCN-533 were administered on day 3 post-infection and weight loss did not exceed 15% in any of the mAb treatment groups except for the control TCN-202 group.

As shown in FIGS. 30 and 31, the 90%, 80%, and 70% of the mice survived infection with 25×$LD_{50}$ of H5N1 A/Hong Kong/156/97 (HK156) when mAb TCN-522, TCN-530, or TCN-533, respectively, were administered on day 4 post-infection and weight loss did not exceed 20% in any of the mAb treatment groups except for the control TCN-202 group.

As shown in FIGS. 32 and 33, 20% and 10% of the mice survived infection with 25×$LD_{50}$ of H5N1 A/Hong Kong/156/97 (HK156) when mAb TCN-522 and TCN-533, or TCN-530, respectively, were administered on day 5 post-infection and weight loss ranged from 20-30% in the surviving mice.

As shown in FIGS. 34 and 35, 20% and 10% of the mice survived infection with 25×$LD_{50}$ of H5N1 A/Hong Kong/156/97 (HK156) when mAb TCN-530 or mAbs TCN-522 and TCN-533, respectively, were administered on day 6 post-infection and weight loss ranged from 20-30% in the surviving mice.

These data demonstrate that mAbs TCN-522, 530, and 533 can prevent mortality in mice due to a lethal infection with a highly pathogenic H5N1 influenza virus. Moreover, these results demonstrate that even 4 days post-infection the treatment with these mAbs prevented mortality in the majority of the treated mice.

Other Embodiments

Although specific embodiments of the invention have been described herein for purposes of illustration, various modifications may be made without deviating from the spirit and scope of the invention. Accordingly, the invention is not limited except as by the appended claims.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising:
   a) an isolated human monoclonal antibody, wherein said antibody comprises a VH CDR1 region comprising the amino acid sequence of DYSWN (SEQ ID NO: 34), a VH CDR2 region comprising the amino acid sequence of DTLHNGYTNYNPSLRG (SEQ ID NO: 35), a VH CDR3 region comprising the amino acid sequence of GSGGYGGFDYFGKLRTWDF (SEQ ID NO: 36), a VL CDR1 region comprising the amino acid sequence of RASQGIRNDLG (SEQ ID NO: 41), a VL CDR2 region comprising the amino acid sequence of GASSLQS (SEQ ID NO: 42), and a VL CDR3 region comprising the amino acid sequence of LQHNSYPYT (SEQ ID NO: 43), and
   b) an isolated human monoclonal antibody, wherein said antibody comprises a VH CDR1 region comprising the amino acid sequence of NYGIS (SEQ ID NO: 174), a VH CDR2 region comprising the amino acid sequence of GIIPLFGAAKYAQKFQG (SEQ ID NO: 175), a VH CDR3 region comprising the amino acid sequence of APRVYEYYFDQ (SEQ ID NO: 176), a VL CDR1 region comprising the amino acid sequence of RASQSVSSSQLA (SEQ ID NO: 157), a VL CDR2 region comprising the amino acid sequence of GASTRAT (SEQ ID NO: 181), and a VL CDR3 region comprising the amino acid sequence of QQYSTSPPT (SEQ ID NO: 182), wherein at least one of the antibodies is directly conjugated to either a detectable label or therapeutic agent.

2. A composition comprising:
   a) an isolated human monoclonal antibody comprising a heavy chain variable sequence comprising the amino acid sequence of SEQ ID NO: 33 and a light chain variable sequence comprising the amino acid sequence of SEQ ID NO: 40; and
   b) an isolated human monoclonal antibody comprising a heavy chain variable sequence comprising the amino acid sequence of SEQ ID NO: 173 and a light chain variable sequence comprising the amino acid sequence of SEQ ID NO: 180, wherein at least one of the antibodies is directly conjugated to either a detectable label or therapeutic agent.

3. A pharmaceutical composition comprising the composition of any one of claims 1 or 2 and a pharmaceutical carrier.

4. The pharmaceutical composition of claim 3, further comprising an anti-viral drug, a viral entry inhibitor or a viral attachment inhibitor.

5. The pharmaceutical composition of claim 4, wherein said anti-viral drug is a neuraminidase inhibitor, a HA inhibitor, a sialic acid inhibitor or an M2 ion channel inhibitor.

6. The pharmaceutical composition of claim 5, wherein said neuraminidase inhibitor is zanamivir or oseltamivir phosphate.

7. A passive immunization composition comprising the composition of any one of claims 1 or 2.

* * * * *

```
                              SEQUENCE LISTING

<160> NUMBER OF SEQ ID NOS: 526

<210> SEQ ID NO 1
<211> LENGTH: 60
<212> TYPE: PRT
<213> ORGANISM: Artificial Sequence
<220> FEATURE:
<223> OTHER INFORMATION: recombinant trimerization domain

<400> SEQUENCE: 1

Ser Gly Arg Leu Val Pro Arg Gly Ser Pro Gly Ser Gly Tyr Ile Pro
1               5                   10                  15

Glu Ala Pro Arg Asp Gly Gln Ala Tyr Val Arg Lys Asp Gly Glu Trp
            20                  25                  30

Val Leu Leu Ser Thr Phe Leu Gly Lys Pro Ile Pro Asn Pro Leu Leu
        35                  40                  45

Gly Leu Asp Ser Thr Gly His His His His His His
    50                  55                  60

<210> SEQ ID NO 2
<211> LENGTH: 572
<212> TYPE: PRT
<213> ORGANISM: Influenza A virus

<400> SEQUENCE: 2

Asp Thr Leu Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Thr Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220
```

-continued

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
            245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
            275                 280                 285

Ser Leu Pro Phe Gln Asn Ile His Pro Ile Thr Ile Gly Lys Cys Pro
            290                 295                 300

Lys Tyr Val Lys Ser Thr Lys Leu Arg Leu Ala Thr Gly Leu Arg Asn
305                 310                 315                 320

Ile Pro Ser Ile Gln Ser Arg Gly Leu Phe Gly Ala Ile Ala Gly Phe
            325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Leu Lys Ser Thr
            355                 360                 365

Gln Asn Ala Ile Asp Glu Ile Thr Asn Lys Val Asn Ser Val Ile Glu
370                 375                 380

Lys Met Asn Thr Gln Phe Thr Ala Val Gly Lys Glu Phe Asn His Leu
385                 390                 395                 400

Glu Lys Arg Ile Glu Asn Leu Asn Lys Lys Val Asp Asp Gly Phe Leu
            405                 410                 415

Asp Ile Trp Thr Tyr Asn Ala Glu Leu Leu Val Leu Leu Glu Asn Glu
            420                 425                 430

Arg Thr Leu Asp Tyr His Asp Ser Asn Val Lys Asn Leu Tyr Glu Lys
            435                 440                 445

Val Arg Ser Gln Leu Lys Asn Asn Ala Lys Glu Ile Gly Asn Gly Cys
450                 455                 460

Phe Glu Phe Tyr His Lys Cys Asp Asn Thr Cys Met Glu Ser Val Lys
465                 470                 475                 480

Asn Gly Thr Tyr Asp Tyr Pro Lys Tyr Ser Glu Glu Ala Lys Leu Asn
            485                 490                 495

Arg Glu Glu Ile Asp Gly Val Lys Leu Glu Ser Thr Arg Ile Tyr Gln
            500                 505                 510

Ser Gly Arg Leu Val Pro Arg Gly Ser Pro Gly Ser Gly Tyr Ile Pro
            515                 520                 525

Glu Ala Pro Arg Asp Gly Gln Ala Tyr Val Arg Lys Asp Gly Glu Trp
            530                 535                 540

Val Leu Leu Ser Thr Phe Leu Gly Lys Pro Ile Pro Asn Pro Leu Leu
545                 550                 555                 560

Gly Leu Asp Ser Thr Gly His His His His His
            565                 570

<210> SEQ ID NO 3
<211> LENGTH: 571
<212> TYPE: PRT
<213> ORGANISM: Influenza A virus

<400> SEQUENCE: 3

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

```
Leu Glu Asp Ser His Asn Gly Lys Leu Cys Leu Lys Gly Ile Ala
         35                  40                  45

Pro Leu Gln Leu Gly Asn Cys Ser Val Ala Gly Trp Ile Leu Gly Asn
 50                  55                  60

Pro Glu Cys Glu Leu Leu Ile Ser Arg Glu Ser Trp Ser Tyr Ile Val
 65                  70                  75                  80

Glu Lys Pro Asn Pro Glu Asn Gly Thr Cys Tyr Pro Gly His Phe Ala
                 85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Asn His Thr Thr
         115                 120                 125

Thr Gly Val Ser Ala Ser Cys Ser His Asn Gly Glu Ser Ser Phe Tyr
         130                 135                 140

Lys Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                 165                 170                 175

Gly Val His His Pro Pro Asn Ile Gly Asp Gln Arg Ala Leu Tyr His
                 180                 185                 190

Lys Glu Asn Ala Tyr Val Ser Val Val Ser Ser His Tyr Ser Arg Lys
         195                 200                 205

Phe Thr Pro Glu Ile Ala Lys Arg Pro Lys Val Arg Asp Gln Glu Gly
         210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                 245                 250                 255

Ser Arg Gly Phe Gly Ser Gly Ile Ile Asn Ser Asn Ala Pro Met Asp
                 260                 265                 270

Glu Cys Asp Ala Lys Cys Gln Thr Pro Gln Gly Ala Ile Asn Ser Ser
         275                 280                 285

Leu Pro Phe Gln Asn Val His Pro Val Thr Ile Gly Glu Cys Pro Lys
         290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                 325                 330                 335

Glu Gly Gly Trp Thr Gly Met Val Asp Gly Trp Tyr Gly Tyr His His
                 340                 345                 350

Gln Asn Glu Gln Gly Ser Gly Tyr Ala Ala Asp Gln Lys Ser Thr Gln
         355                 360                 365

Asn Ala Ile Asn Gly Ile Thr Asn Lys Val Asn Ser Val Ile Glu Lys
         370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Ile Asp
                 405                 410                 415

Ile Trp Thr Tyr Asn Ala Glu Leu Leu Val Leu Leu Glu Asn Glu Arg
                 420                 425                 430

Thr Leu Asp Phe His Asp Ser Asn Val Lys Asn Leu Tyr Glu Lys Val
         435                 440                 445
```

-continued

```
Lys Ser Gln Leu Lys Asn Asn Ala Lys Glu Ile Gly Asn Gly Cys Phe
    450                 455                 460

Glu Phe Tyr His Lys Cys Asn Asp Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ser
            500                 505                 510

Gly Arg Leu Val Pro Arg Gly Ser Pro Gly Ser Gly Tyr Ile Pro Glu
        515                 520                 525

Ala Pro Arg Asp Gly Gln Ala Tyr Val Arg Lys Asp Gly Glu Trp Val
530                 535                 540

Leu Leu Ser Thr Phe Leu Gly Lys Pro Ile Pro Asn Pro Leu Leu Gly
545                 550                 555                 560

Leu Asp Ser Thr Gly His His His His His His
                565                 570

<210> SEQ ID NO 4
<211> LENGTH: 589
<212> TYPE: PRT
<213> ORGANISM: Influenza A virus

<400> SEQUENCE: 4

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255
```

```
Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ser Gly Arg Leu Val Pro Arg Gly Ser Pro Gly Ser Gly Tyr Ile
    530                 535                 540

Pro Glu Ala Pro Arg Asp Gly Gln Ala Tyr Val Arg Lys Asp Gly Glu
545                 550                 555                 560

Trp Val Leu Leu Ser Thr Phe Leu Gly Lys Pro Ile Pro Asn Pro Leu
                565                 570                 575

Leu Gly Leu Asp Ser Thr Gly His His His His His His
            580                 585

<210> SEQ ID NO 5
<211> LENGTH: 570
<212> TYPE: PRT
<213> ORGANISM: Influenza A virus

<400> SEQUENCE: 5

Asp Gln Ile Cys Ile Gly Tyr His Ala Asn Asn Ser Thr Glu Lys Val
1               5                   10                  15

Asp Thr Asn Leu Glu Arg Asn Val Thr Val Thr His Ala Lys Asp Ile
            20                  25                  30

Leu Glu Lys Thr His Asn Gly Lys Leu Cys Lys Leu Asn Gly Ile Pro
```

```
                35                  40                  45
Pro Leu Glu Leu Gly Asp Cys Ser Ile Ala Gly Trp Leu Leu Gly Asn
 50                  55                  60
Pro Glu Cys Asp Arg Leu Leu Ser Val Pro Glu Trp Ser Tyr Ile Met
 65                  70                  75                  80
Glu Lys Glu Asn Pro Arg Asp Gly Leu Cys Tyr Pro Gly Ser Phe Asn
                 85                  90                  95
Asp Tyr Glu Glu Leu Lys His Leu Leu Ser Ser Val Lys His Phe Glu
                100                 105                 110
Lys Val Lys Ile Leu Pro Lys Asp Arg Trp Thr Gln His Thr Thr Thr
                115                 120                 125
Gly Gly Ser Arg Ala Cys Ala Val Ser Gly Asn Pro Ser Phe Phe Arg
                130                 135                 140
Asn Met Val Trp Leu Thr Lys Glu Gly Ser Asp Tyr Pro Val Ala Lys
145                 150                 155                 160
Gly Ser Tyr Asn Asn Thr Ser Gly Glu Gln Met Leu Ile Ile Trp Gly
                165                 170                 175
Val His His Pro Ile Asp Glu Thr Glu Gln Arg Thr Leu Tyr Gln Asn
                180                 185                 190
Val Gly Thr Tyr Val Ser Val Gly Thr Ser Thr Leu Asn Lys Arg Ser
                195                 200                 205
Thr Pro Glu Ile Ala Thr Arg Pro Lys Val Asn Gly Gln Gly Gly Arg
                210                 215                 220
Met Glu Phe Ser Trp Thr Leu Leu Asp Met Trp Asp Thr Ile Asn Phe
225                 230                 235                 240
Glu Ser Thr Gly Asn Leu Ile Ala Pro Glu Tyr Gly Phe Lys Ile Ser
                245                 250                 255
Lys Arg Gly Ser Ser Gly Ile Met Lys Thr Glu Gly Thr Leu Glu Asn
                260                 265                 270
Cys Glu Thr Lys Cys Gln Thr Pro Leu Gly Ala Ile Asn Thr Thr Leu
                275                 280                 285
Pro Phe His Asn Val His Pro Leu Thr Ile Gly Glu Cys Pro Lys Tyr
                290                 295                 300
Val Lys Ser Glu Lys Leu Val Leu Ala Thr Gly Leu Arg Asn Val Pro
305                 310                 315                 320
Gln Ile Glu Ser Arg Gly Leu Phe Gly Ala Ile Ala Gly Phe Ile Glu
                325                 330                 335
Gly Gly Trp Gln Gly Met Val Asp Gly Trp Tyr Gly Tyr His His Ser
                340                 345                 350
Asn Asp Gln Gly Ser Gly Tyr Ala Ala Asp Lys Glu Ser Thr Gln Lys
                355                 360                 365
Ala Phe Asp Gly Ile Thr Asn Lys Val Asn Ser Val Ile Glu Lys Met
                370                 375                 380
Asn Thr Gln Phe Glu Ala Val Gly Lys Glu Phe Gly Asn Leu Glu Arg
385                 390                 395                 400
Arg Leu Glu Asn Leu Asn Lys Arg Met Glu Asp Gly Phe Leu Asp Val
                405                 410                 415
Trp Thr Tyr Asn Ala Glu Leu Leu Val Leu Met Glu Asn Glu Arg Thr
                420                 425                 430
Leu Asp Phe His Asp Ser Asn Val Lys Asn Leu Tyr Asp Lys Val Arg
                435                 440                 445
Met Gln Leu Arg Asp Asn Val Lys Glu Leu Gly Asn Gly Cys Phe Glu
                450                 455                 460
```

```
Phe Tyr His Lys Cys Asp Asp Glu Cys Met Asn Ser Val Lys Asn Gly
465                 470                 475                 480

Thr Tyr Asp Tyr Pro Lys Tyr Glu Glu Ser Lys Leu Asn Arg Asn
            485                 490                 495

Glu Ile Lys Gly Val Lys Leu Ser Ser Met Gly Val Tyr Gln Ser Gly
                500                 505                 510

Arg Leu Val Pro Arg Gly Ser Pro Gly Ser Gly Tyr Ile Pro Glu Ala
                515                 520                 525

Pro Arg Asp Gly Gln Ala Tyr Val Arg Lys Asp Gly Glu Trp Val Leu
                530                 535                 540

Leu Ser Thr Phe Leu Gly Lys Pro Ile Pro Asn Pro Leu Leu Gly Leu
545                 550                 555                 560

Asp Ser Thr Gly His His His His His His
                565                 570

<210> SEQ ID NO 6
<211> LENGTH: 570
<212> TYPE: PRT
<213> ORGANISM: Influenza A virus

<400> SEQUENCE: 6

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Gln Ile Glu Val Thr Asn Ala Thr Glu Leu Val Gln Ser Ser Ser Thr
            35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
                100                 105                 110

Ala Ser Ser Gly Thr Leu Glu Phe Asn Asp Glu Ser Phe Asn Trp Thr
            115                 120                 125

Gly Val Thr Gln Asn Gly Thr Ser Ser Ser Cys Lys Arg Arg Ser Asn
    130                 135                 140

Asn Ser Phe Phe Ser Arg Leu Asn Trp Leu Thr Gln Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Val Thr Asp Asn Asp Gln Ile
                180                 185                 190

Phe Leu Tyr Ala Gln Ala Ser Gly Arg Ile Thr Val Ser Thr Lys Arg
            195                 200                 205

Ser Gln Gln Thr Val Ile Pro Asn Ile Gly Ser Arg Pro Arg Ile Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
```

```
                   260                 265                 270
Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
        290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Ile Gly Gln Ala Ala Asp Leu Lys
        355                 360                 365

Ser Thr Gln Ala Ala Ile Asn Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys Gly Val Glu Leu Lys Ser Gly Ser Gly
            500                 505                 510

Arg Leu Val Pro Arg Gly Ser Pro Gly Ser Gly Tyr Ile Pro Glu Ala
        515                 520                 525

Pro Arg Asp Gly Gln Ala Tyr Val Arg Lys Asp Gly Glu Trp Val Leu
    530                 535                 540

Leu Ser Thr Phe Leu Gly Lys Pro Ile Pro Asn Pro Leu Leu Gly Leu
545                 550                 555                 560

Asp Ser Thr Gly His His His His His His
                565                 570

<210> SEQ ID NO 7
<211> LENGTH: 571
<212> TYPE: PRT
<213> ORGANISM: Influenza A virus

<400> SEQUENCE: 7

Gln Asn Tyr Thr Gly Asn Pro Val Ile Cys Leu Gly His His Ala Val
1               5                  10                  15

Ser Asn Gly Thr Met Val Lys Thr Leu Thr Asp Asp Gln Ile Glu Val
            20                  25                  30

Val Thr Ala Gln Glu Leu Val Glu Ser Gln His Leu Pro Glu Leu Cys
        35                  40                  45

Pro Ser Pro Leu Arg Leu Val Asp Gly Gln Thr Cys Asp Ile Val Asn
    50                  55                  60
```

```
Gly Ala Leu Gly Ser Pro Gly Cys Asp His Leu Asn Gly Ala Glu Trp
 65                  70                  75                  80

Asp Val Phe Ile Glu Arg Pro Thr Ala Val Asp Thr Cys Tyr Pro Phe
                 85                  90                  95

Asp Val Pro Asp Tyr Gln Ser Leu Arg Ser Ile Leu Ala Asn Asn Gly
            100                 105                 110

Lys Phe Glu Phe Ile Ala Glu Phe Gln Trp Asn Thr Val Lys Gln
        115                 120                 125

Asn Gly Lys Ser Gly Ala Cys Lys Arg Ala Asn Val Asn Asp Phe Phe
    130                 135                 140

Asn Arg Leu Asn Trp Leu Thr Lys Ser Asp Gly Asn Ala Tyr Pro Leu
145                 150                 155                 160

Gln Asn Leu Thr Lys Val Asn Asn Gly Asp Tyr Ala Arg Leu Tyr Ile
                165                 170                 175

Trp Gly Val His His Pro Ser Thr Asp Thr Glu Gln Thr Asn Leu Tyr
            180                 185                 190

Lys Asn Asn Pro Gly Arg Val Thr Val Ser Thr Gln Thr Ser Gln Thr
        195                 200                 205

Ser Val Val Pro Asn Ile Gly Ser Arg Pro Trp Val Arg Gly Leu Ser
210                 215                 220

Ser Arg Ile Ser Phe Tyr Trp Thr Ile Val Glu Pro Gly Asp Leu Ile
225                 230                 235                 240

Val Phe Asn Thr Ile Gly Asn Leu Ile Ala Pro Arg Gly His Tyr Lys
                245                 250                 255

Leu Asn Ser Gln Lys Lys Ser Thr Ile Leu Asn Thr Ala Val Pro Ile
            260                 265                 270

Gly Ser Cys Val Ser Lys Cys His Thr Asp Lys Gly Ser Ile Ser Thr
        275                 280                 285

Thr Lys Pro Phe Gln Asn Ile Ser Arg Ile Ser Ile Gly Asp Cys Pro
    290                 295                 300

Lys Tyr Val Lys Gln Gly Ser Leu Lys Leu Ala Thr Gly Met Arg Ser
305                 310                 315                 320

Ile Leu Glu Lys Ala Thr Arg Gly Leu Phe Gly Ala Ile Ala Gly Phe
                325                 330                 335

Ile Glu Asn Gly Trp Gln Gly Leu Ile Asp Gly Trp Tyr Gly Phe Arg
            340                 345                 350

His Gln Asn Ala Glu Gly Thr Gly Thr Ala Ala Asp Leu Lys Ser Thr
        355                 360                 365

Gln Ala Ala Ile Asp Gln Ile Asn Gly Lys Leu Asn Arg Leu Ile Gly
    370                 375                 380

Lys Pro Asn Glu Lys Tyr His Gln Ile Glu Lys Glu Phe Glu Gln Val
385                 390                 395                 400

Glu Gly Arg Ile Gln Asp Leu Glu Lys Tyr Val Glu Asp Thr Lys Ile
                405                 410                 415

Asp Leu Trp Ser Tyr Asn Ala Glu Leu Leu Val Ala Leu Glu Asn Gln
            420                 425                 430

His Thr Ile Asp Val Thr Asp Ser Glu Met Asn Lys Leu Phe Glu Arg
        435                 440                 445

Val Arg His Gln Leu Arg Glu Asn Ala Glu Asp Lys Gly Asn Gly Cys
    450                 455                 460

Phe Glu Ile Phe His Gln Cys Asp Asn Ser Cys Ile Glu Ser Ile Arg
465                 470                 475                 480

Asn Gly Thr Tyr Asp His Asp Ile Tyr Arg Asp Glu Ala Ile Asn Asn
```

```
                        485                 490                 495
Arg Phe Gln Ile Gln Gly Val Lys Leu Ile Gln Gly Tyr Lys Asp Ser
                500                 505                 510

Gly Arg Leu Val Pro Arg Gly Ser Pro Gly Ser Gly Tyr Ile Pro Glu
                515                 520                 525

Ala Pro Arg Asp Gly Gln Ala Tyr Val Arg Lys Asp Gly Glu Trp Val
                530                 535                 540

Leu Leu Ser Thr Phe Leu Gly Lys Pro Ile Pro Asn Pro Leu Leu Gly
545                 550                 555                 560

Leu Asp Ser Thr Gly His His His His His His
                565                 570

<210> SEQ ID NO 8
<211> LENGTH: 591
<212> TYPE: PRT
<213> ORGANISM: Influenza A virus

<400> SEQUENCE: 8

Met Glu Arg Thr Val Leu Leu Ala Thr Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Arg Thr His Asn Gly Lys Leu Cys Asp Leu Asn Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asn Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asn His Asp Ala Ser
        130                 135                 140

Ser Gly Val Ser Ser Ala Cys Pro Tyr Leu Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
                180                 185                 190

Gly Val His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
        210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285
```

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Cys Tyr Ser Ala Asp Lys
    370                 375                 380

Glu Ser Thr Gln Lys Ala Ile Asp Gly Val Thr Asn Lys Val Asn Ser
385                 390                 395                 400

Ile Ile Asn Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Lys Asn Gly Thr Tyr Asp Tyr Pro Gln Tyr Ser Glu Glu Ala
            500                 505                 510

Arg Leu Asn Arg Glu Glu Ile Ser Gly Val Lys Leu Glu Ser Met Gly
        515                 520                 525

Thr Tyr Gln Ser Gly Arg Leu Val Pro Arg Gly Ser Pro Gly Ser Gly
    530                 535                 540

Tyr Ile Pro Glu Ala Pro Arg Asp Gly Gln Ala Tyr Val Arg Lys Asp
545                 550                 555                 560

Gly Glu Trp Val Leu Leu Ser Thr Phe Leu Gly Lys Pro Ile Pro Asn
                565                 570                 575

Pro Leu Leu Gly Leu Asp Ser Thr Gly His His His His His
            580                 585                 590

<210> SEQ ID NO 9
<211> LENGTH: 575
<212> T

```
Glu Lys Ala Asn Pro Val Asn Asp Leu Cys Tyr Pro Gly Asp Phe Asn
                85                  90                  95
Asp Tyr Glu Glu Leu Lys His Leu Leu Ser Arg Ile Asn His Phe Glu
            100                 105                 110
Lys Ile Gln Ile Ile Pro Lys Ser Ser Trp Ser Ser His Glu Ala Ser
        115                 120                 125
Leu Gly Val Ser Ser Ala Cys Pro Tyr Gln Gly Lys Ser Ser Phe Phe
    130                 135                 140
Arg Asn Val Val Trp Leu Ile Lys Lys Asn Ser Thr Tyr Pro Thr Ile
145                 150                 155                 160
Lys Arg Ser Tyr Asn Asn Thr Asn Gln Glu Asp Leu Leu Val Leu Trp
                165                 170                 175
Gly Ile His His Pro Asn Asp Ala Ala Glu Gln Thr Lys Leu Tyr Gln
            180                 185                 190
Asn Pro Thr Thr Tyr Ile Ser Val Gly Thr Ser Thr Leu Asn Gln Arg
        195                 200                 205
Leu Val Pro Arg Ile Ala Thr Arg Ser Lys Val Asn Gly Gln Ser Gly
    210                 215                 220
Arg Met Glu Phe Phe Trp Thr Ile Leu Lys Pro Asn Asp Ala Ile Asn
225                 230                 235                 240
Phe Glu Ser Asn Gly Asn Phe Ile Ala Pro Glu Tyr Ala Tyr Lys Ile
                245                 250                 255
Val Lys Lys Gly Asp Ser Thr Ile Met Lys Ser Glu Leu Glu Tyr Gly
            260                 265                 270
Asn Cys Asn Thr Lys Cys Gln Thr Pro Met Gly Ala Ile Asn Ser Ser
        275                 280                 285
Met Pro Phe His Asn Ile His Pro Leu Thr Ile Gly Glu Cys Pro Lys
    290                 295                 300
Tyr Val Lys Ser Asn Arg Leu Val Leu Ala Thr Gly Leu Arg Asn Ser
305                 310                 315                 320
Pro Gln Arg Glu Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
            340                 345                 350
Gly Tyr His His Ser Asn Glu Gln Gly Ser Gly Tyr Ala Ala Asp Lys
        355                 360                 365
Glu Ser Thr Gln Lys Ala Ile Asp Gly Val Thr Asn Lys Val Asn Ser
    370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
            420                 425                 430
Glu Asn Glu Arg Thr Leu Asp Phe His Asp Ser Asn Val Lys Asn Leu
        435                 440                 445
Tyr Asp Lys Val Arg Leu Gln Leu Arg Asp Asn Ala Lys Glu Leu Gly
    450                 455                 460
Asn Gly Cys Phe Glu Phe Tyr His Lys Cys Asp Asn Glu Cys Met Glu
465                 470                 475                 480
Ser Val Arg Asn Gly Thr Tyr Asp Tyr Pro Gln Tyr Ser Glu Glu Ala
                485                 490                 495
```

```
Arg Leu Lys Arg Glu Glu Ile Ser Gly Val Lys Leu Glu Ser Ile Gly
                500                 505                 510

Ile Tyr Gln Ser Gly Arg Leu Val Pro Arg Gly Ser Pro Gly Ser Gly
            515                 520                 525

Tyr Ile Pro Glu Ala Pro Arg Asp Gly Gln Ala Tyr Val Arg Lys Asp
        530                 535                 540

Gly Glu Trp Val Leu Leu Ser Thr Phe Leu Gly Lys Pro Ile Pro Asn
545                 550                 555                 560

Pro Leu Leu Gly Leu Asp Ser Thr Gly His His His His His His
                565                 570                 575

<210> SEQ ID NO 10
<211> LENGTH: 575
<212> TYPE: PRT
<213> ORGANISM: Influenza A virus

<400> SEQUENCE: 10

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300
```

```
Tyr Val Lys Ser Asn Arg Leu Val Leu Ala Thr Gly Leu Arg Asn Ser
305                 310                 315                 320

Pro Gln Arg Glu Ser Arg Lys Lys Arg Gly Leu Phe Gly Ala Ile
            325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
            355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ser Gly Arg Leu Val Pro Arg Gly Ser Pro Gly Ser Gly
            515                 520                 525

Tyr Ile Pro Glu Ala Pro Arg Asp Gly Gln Ala Tyr Val Arg Lys Asp
    530                 535                 540

Gly Glu Trp Val Leu Leu Ser Thr Phe Leu Gly Lys Pro Ile Pro Asn
545                 550                 555                 560

Pro Leu Leu Gly Leu Asp Ser Thr Gly His His His His His
                565                 570                 575

<210> SEQ ID NO 11
<211> LENGTH: 575
<212> TYPE: PRT
<213> ORGANISM: Influenza A virus

<400> SEQUENCE: 11

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Leu Asn Val Ser Glu Trp Ser Tyr Ile Val
65                  70                  75                  80

Glu Lys Ile Asn Pro Ala Asn Asp Leu Cys Tyr Pro Gly Asn Phe Asn
                85                  90                  95

Asn Tyr Glu Glu Leu Lys His Leu Leu Ser Arg Ile Asn Arg Phe Glu
```

-continued

```
                100                 105                 110
Lys Ile Gln Ile Ile Pro Lys Ser Ser Trp Pro Asp His Glu Ala Ser
            115                 120                 125
Leu Gly Val Ser Ser Ala Cys Pro Tyr Gln Gly Gly Pro Ser Phe Tyr
        130                 135                 140
Arg Asn Val Val Trp Leu Ile Lys Lys Asn Asn Thr Tyr Pro Thr Ile
145                 150                 155                 160
Lys Lys Ser Tyr His Asn Thr Asn Gln Glu Asp Leu Leu Val Leu Trp
                165                 170                 175
Gly Ile His His Pro Asn Asp Glu Ala Glu Gln Thr Arg Ile Tyr Lys
            180                 185                 190
Asn Pro Thr Thr Tyr Ile Ser Val Gly Thr Ser Thr Leu Asn Gln Arg
        195                 200                 205
Leu Val Pro Lys Ile Ala Thr Arg Ser Lys Val Asn Gly Gln Ser Gly
    210                 215                 220
Arg Val Glu Phe Phe Trp Thr Ile Leu Lys Ser Asn Asp Thr Ile Asn
225                 230                 235                 240
Phe Glu Ser Asn Gly Asn Phe Ile Ala Pro Glu Asn Ala Tyr Lys Ile
                245                 250                 255
Val Lys Lys Gly Asp Ser Thr Ile Met Lys Ser Glu Leu Glu Tyr Gly
            260                 265                 270
Asn Cys Asn Thr Lys Cys Gln Thr Pro Ile Gly Ala Ile Asn Ser Ser
        275                 280                 285
Met Pro Phe His Asn Ile His Pro Leu Thr Ile Gly Glu Cys Pro Lys
    290                 295                 300
Tyr Val Lys Ser Asn Arg Leu Val Leu Ala Thr Gly Leu Arg Asn Ser
305                 310                 315                 320
Pro Gln Gly Glu Arg Arg Lys Lys Arg Gly Leu Phe Gly Ala Ile
                325                 330                 335
Ala Gly Phe Ile Glu Gly Gly Trp Gln Gly Met Val Asp Gly Trp Tyr
            340                 345                 350
Gly Tyr His His Ser Asn Glu Gln Gly Ser Gly Tyr Ala Ala Asp Lys
        355                 360                 365
Glu Ser Thr Gln Lys Ala Ile Asp Gly Val Thr Asn Lys Val Asn Ser
    370                 375                 380
Ile Ile Asp Lys Met Asn Thr Gln Phe Glu Ala Val Gly Arg Glu Phe
385                 390                 395                 400
Asn Asn Leu Glu Arg Arg Ile Glu Asn Leu Asn Lys Lys Met Glu Asp
                405                 410                 415
Gly Phe Leu Asp Val Trp Thr Tyr Asn Ala Glu Leu Leu Val Leu Met
            420                 425                 430
Glu Asn Glu Arg Thr Leu Asp Phe His Asp Ser Asn Val Lys Asn Leu
        435                 440                 445
Tyr Asp Lys Val Arg Leu Gln Leu Arg Asp Asn Ala Lys Glu Leu Gly
    450                 455                 460
Asn Gly Cys Phe Glu Phe Tyr His Arg Cys Asp Asn Glu Cys Met Glu
465                 470                 475                 480
Ser Val Arg Asn Gly Thr Tyr Asp Tyr Pro Gln Tyr Ser Glu Glu Ala
                485                 490                 495
Arg Leu Lys Arg Glu Glu Ile Ser Gly Val Lys Leu Glu Ser Ile Gly
            500                 505                 510
Thr Tyr Gln Ser Gly Arg Leu Val Pro Arg Gly Ser Pro Gly Ser Gly
        515                 520                 525
```

Tyr Ile Pro Glu Ala Pro Arg Asp Gly Gln Ala Tyr Val Arg Lys Asp
            530                 535                 540

Gly Glu Trp Val Leu Leu Ser Thr Phe Leu Gly Lys Pro Ile Pro Asn
545                 550                 555                 560

Pro Leu Leu Gly Leu Asp Ser Thr Gly His His His His His His
                565                 570                 575

<210> SEQ ID NO 12
<211> LENGTH: 574
<212> TYPE: PRT
<213> ORGANISM: Influenza A virus

<400> SEQUENCE: 12

Asp His Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asn Gly Val Lys
        35                  40                  45

Pro Leu Ile Leu Lys Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asp Ser Trp Ser Asp His Glu Ala Ser
        115                 120                 125

Leu Gly Val Ser Ser Ala Cys Pro Tyr Gln Gly Asn Ser Ser Phe Phe
130                 135                 140

Arg Asn Val Val Trp Leu Ile Lys Lys Gly Asn Ala Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Glu Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Ile Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Val Glu Tyr Gly
            260                 265                 270

Asn Cys Asn Thr Arg Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Lys Leu Val Leu Ala Thr Gly Leu Arg Asn Ser
305                 310                 315                 320

Pro Gln Arg Glu Arg Arg Arg Lys Arg Gly Leu Phe Gly Ala Ile Ala

```
              325                 330                 335
Gly Phe Ile Glu Gly Gly Trp Gln Gly Met Val Asp Gly Trp Tyr Gly
            340                 345                 350
Tyr His His Ser Asn Glu Gln Gly Ser Gly Tyr Ala Ala Asp Lys Glu
            355                 360                 365
Ser Thr Gln Lys Ala Ile Asp Gly Val Thr Asn Lys Val Asn Ser Ile
            370                 375                 380
Ile Asp Lys Met Asn Thr Gln Phe Glu Ala Val Gly Arg Glu Phe Asn
385                 390                 395                 400
Asn Leu Glu Arg Arg Ile Glu Asn Leu Asn Lys Lys Met Glu Asp Gly
            405                 410                 415
Phe Leu Asp Val Trp Thr Tyr Asn Ala Glu Leu Leu Val Leu Met Glu
            420                 425                 430
Asn Glu Arg Thr Leu Asp Phe His Asp Ser Asn Val Lys Asn Leu Tyr
            435                 440                 445
Asp Lys Val Arg Leu Gln Leu Arg Asp Asn Ala Lys Glu Leu Gly Asn
450                 455                 460
Gly Cys Phe Glu Phe Tyr His Lys Cys Asp Asn Glu Cys Met Glu Ser
465                 470                 475                 480
Val Arg Asn Gly Thr Tyr Asp Tyr Pro Gln Tyr Ser Glu Glu Ala Arg
            485                 490                 495
Leu Lys Arg Glu Glu Ile Ser Gly Val Lys Leu Glu Ser Ile Gly Thr
            500                 505                 510
Tyr Gln Ser Gly Arg Leu Val Pro Arg Gly Ser Pro Gly Ser Gly Tyr
            515                 520                 525
Ile Pro Glu Ala Pro Arg Asp Gly Gln Ala Tyr Val Arg Lys Asp Gly
            530                 535                 540
Glu Trp Val Leu Leu Ser Thr Phe Leu Gly Lys Pro Ile Pro Asn Pro
545                 550                 555                 560
Leu Leu Gly Leu Asp Ser Thr Gly His His His His His
            565                 570

<210> SEQ ID NO 13
<211> LENGTH: 574
<212> TYPE: PRT
<213> ORGANISM: Influenza A virus

<400> SEQUENCE: 13

Asp Gln Ile Cys Ile Gly Tyr His Ala Asn Asn Ser Thr Glu Gln Val
1               5                   10                  15
Asp Thr Ile Met Glu Lys Asn Val Thr Val Thr His Ala Gln Asp Ile
            20                  25                  30
Leu Glu Lys Thr His Asn Gly Lys Leu Cys Asp Leu Asp Gly Val Lys
            35                  40                  45
Pro Leu Ile Leu Arg Asp Cys Ser Val Ala Gly Trp Leu Leu Gly Asn
50                  55                  60
Pro Met Cys Asp Glu Phe Ile Asn Val Pro Glu Trp Ser Tyr Ile Val
65                  70                  75                  80
Glu Lys Ala Asn Pro Ala Asn Asp Leu Cys Tyr Pro Gly Asn Phe Asn
            85                  90                  95
Asp Tyr Glu Glu Leu Lys His Leu Leu Ser Arg Ile Asn His Phe Glu
            100                 105                 110
Lys Ile Gln Ile Ile Pro Lys Ser Ser Trp Ser Asp His Glu Ala Ser
            115                 120                 125
```

```
Ser Gly Val Ser Ser Ala Cys Pro Tyr Gln Gly Thr Pro Ser Phe Phe
    130                 135                 140

Arg Asn Val Val Trp Leu Ile Lys Lys Asn Asn Thr Tyr Pro Thr Ile
145                 150                 155                 160

Lys Arg Ser Tyr Asn Asn Thr Asn Gln Glu Asp Leu Leu Ile Leu Trp
                165                 170                 175

Gly Ile His His Ser Asn Asp Ala Ala Glu Gln Thr Lys Leu Tyr Gln
                180                 185                 190

Asn Pro Thr Thr Tyr Ile Ser Val Gly Thr Ser Thr Leu Asn Gln Arg
                195                 200                 205

Leu Val Pro Lys Ile Ala Thr Arg Ser Lys Val Asn Gly Gln Ser Gly
210                 215                 220

Arg Met Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Val Lys Ser Glu Val Glu Tyr Gly
                260                 265                 270

Asn Cys Asn Thr Lys Cys Gln Thr Pro Ile Gly Ala Ile Asn Ser Ser
                275                 280                 285

Met Pro Phe His Asn Ile His Pro Leu Thr Ile Gly Glu Cys Pro Lys
                290                 295                 300

Tyr Val Lys Ser Asn Lys Leu Val Leu Ala Thr Gly Leu Arg Asn Ser
305                 310                 315                 320

Pro Leu Arg Glu Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
                340                 345                 350

Tyr His His Ser Asn Glu Gln Gly Ser Gly Tyr Ala Ala Asp Lys Glu
                355                 360                 365

Ser Thr Gln Lys Ala Ile Asp Gly Val Thr Asn Lys Val Asn Ser Ile
    370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
                420                 425                 430

Asn Glu Arg Thr Leu Asp Phe His Asp Ser Asn Val Lys Asn Leu Tyr
                435                 440                 445

Asp Lys Val Arg Leu Gln Leu Arg Asp Asn Ala Lys Glu Leu Gly Asn
450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser Gly Val Lys Leu Glu Ser Ile Gly Thr
                500                 505                 510

Tyr Gln Ser Gly Arg Leu Val Pro Arg Gly Ser Pro Gly Ser Gly Tyr
                515                 520                 525

Ile Pro Glu Ala Pro Arg Asp Gly Gln Ala Tyr Val Arg Lys Asp Gly
                530                 535                 540

Glu Trp Val Leu Leu Ser Thr Phe Leu Gly Lys Pro Ile Pro Asn Pro
```

```
                545                 550                 555                 560
Leu Leu Gly Leu Asp Ser Thr Gly His His His His His
                565                 570

<210> SEQ ID NO 14
<211> LENGTH: 571
<212> TYPE: PRT
<213> ORGANISM: Influenza A virus

<400> SEQUENCE: 14

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asn Leu Asp Gly Val Lys
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Ser Glu Trp Ser Tyr Ile Val
65                  70                  75                  80

Glu Lys Ala Ser Pro Ala Asn Gly Leu Cys Tyr Pro Gly Asp Phe Asn
                85                  90                  95

Asp Tyr Glu Glu Leu Lys His Leu Leu Ser Arg Ile Asn His Leu Lys
            100                 105                 110

Lys Ile Lys Ile Ile Pro Lys Ser Tyr Trp Ser Asn His Glu Ala Ser
        115                 120                 125

Ser Gly Val Ser Ala Ala Cys Ser Tyr Leu Gly Glu Pro Ser Phe Phe
    130                 135                 140

Arg Asn Val Val Trp Leu Ile Lys Lys Asn Asn Thr Tyr Pro Pro Ile
145                 150                 155                 160

Lys Val Asn Tyr Thr Asn Thr Asn Gln Glu Asp Leu Leu Val Leu Trp
                165                 170                 175

Gly Ile His His Pro Asn Asp Glu Lys Glu Gln Ile Arg Ile Tyr Gln
            180                 185                 190

Asn Pro Asn Thr Ser Ile Ser Val Gly Thr Ser Thr Leu Asn Gln Arg
        195                 200                 205

Leu Val Pro Lys Ile Ala Thr Arg Pro Lys Val Asn Gly Gln Ser Gly
    210                 215                 220

Arg Met Glu Phe Phe Trp Thr Ile Leu Lys Pro Asn Asp Ser Ile Asn
225                 230                 235                 240

Phe Asp Ser Asn Gly Asn Phe Ile Ala Pro Glu Tyr Ala Tyr Lys Ile
                245                 250                 255

Ala Lys Lys Gly Asp Ser Val Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ala
305                 310                 315                 320

Pro Gln Thr Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350
```

```
Ser Asn Glu Gln Gly Ser Gly Tyr Ala Ala Asp Lys Ser Thr Gln
            355                 360                 365

Lys Ala Ile Asp Gly Ile Thr Asn Lys Val Asn Ser Ile Ile Asp Lys
    370                 375                 380

Met Asn Thr Gln Phe Glu Ile Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
                420                 425                 430

Thr Leu Asp Phe His Asp Ser Asn Val Lys Asn Leu Tyr Glu Lys Val
            435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Ser Arg
                485                 490                 495

Glu Glu Ile Ser Gly Val Lys Met Glu Ser Met Val Thr Tyr Gln Ser
            500                 505                 510

Gly Arg Leu Val Pro Arg Gly Ser Pro Gly Ser Gly Tyr Ile Pro Glu
    515                 520                 525

Ala Pro Arg Asp Gly Gln Ala Tyr Val Arg Lys Asp Gly Glu Trp Val
530                 535                 540

Leu Leu Ser Thr Phe Leu Gly Lys Pro Ile Pro Asn Pro Leu Leu Gly
545                 550                 555                 560

Leu Asp Ser Thr Gly His His His His His His
                565                 570

<210> SEQ ID NO 15
<211> LENGTH: 573
<212> TYPE: PRT
<213> ORGANISM: Influenza A virus

<400> SEQUENCE: 15

Asp Lys Ile Cys Ile Gly Tyr His Ala Asn Asn Ser Thr Thr Gln Val
1               5                   10                  15

Asp Thr Ile Leu Glu Lys Asn Val Thr Val Thr His Ser Val Glu Leu
            20                  25                  30

Leu Glu Asn Gln Lys Glu Glu Arg Phe Cys Lys Ile Leu Asn Lys Ala
        35                  40                  45

Pro Leu Asp Leu Arg Gly Cys Thr Ile Glu Gly Trp Ile Leu Gly Asn
    50                  55                  60

Pro Gln Cys Asp Leu Leu Leu Gly Asp Gln Ser Trp Ser Tyr Ile Val
65                  70                  75                  80

Glu Arg Pro Thr Ala Gln Asn Gly Ile Cys Tyr Pro Gly Ala Leu Asn
                85                  90                  95

Glu Val Glu Glu Leu Lys Ala Leu Ile Gly Ser Gly Glu Arg Val Glu
            100                 105                 110

Arg Phe Glu Met Phe Pro Lys Ser Thr Trp Thr Gly Val Asp Thr Ser
        115                 120                 125

Ser Gly Val Thr Lys Ala Cys Pro Tyr Asn Ser Gly Ser Ser Phe Tyr
    130                 135                 140

Arg Asn Leu Leu Trp Ile Ile Lys Thr Lys Ser Ala Ala Tyr Pro Val
145                 150                 155                 160
```

```
Ile Lys Gly Thr Tyr Asn Asn Thr Gly Ser Gln Pro Ile Leu Tyr Phe
            165                 170                 175

Trp Gly Val His His Pro Asp Thr Asn Glu Gln Asn Thr Leu Tyr
            180                 185                 190

Gly Ser Gly Asp Arg Tyr Val Arg Met Gly Thr Glu Ser Met Asn Phe
            195                 200                 205

Ala Lys Ser Pro Glu Ile Ala Ala Arg Pro Ala Val Asn Gly Gln Arg
            210                 215                 220

Gly Arg Ile Asp Tyr Tyr Trp Ser Val Leu Lys Pro Gly Glu Thr Leu
225                 230                 235                 240

Asn Val Glu Ser Asn Gly Asn Leu Ile Ala Pro Trp Tyr Ala Tyr Lys
            245                 250                 255

Phe Val Ser Thr Asn Asn Lys Gly Ala Ile Phe Lys Ser Asn Leu Pro
            260                 265                 270

Ile Glu Asn Cys Asp Ala Thr Cys Gln Thr Ile Ala Gly Val Leu Arg
            275                 280                 285

Thr Asn Lys Thr Phe Gln Asn Val Ser Pro Leu Trp Ile Gly Glu Cys
            290                 295                 300

Pro Lys Tyr Val Lys Ser Glu Ser Leu Arg Leu Ala Thr Gly Leu Arg
305                 310                 315                 320

Asn Val Pro Gln Ile Glu Thr Arg Gly Leu Phe Gly Ala Ile Ala Gly
            325                 330                 335

Phe Ile Glu Gly Gly Trp Thr Gly Met Ile Asp Gly Trp Tyr Gly Tyr
            340                 345                 350

His His Glu Asn Ser Gln Gly Ser Gly Tyr Ala Ala Asp Lys Glu Ser
            355                 360                 365

Thr Gln Lys Ala Ile Asp Gly Ile Thr Asn Lys Val Asn Ser Ile Ile
            370                 375                 380

Asp Lys Met Asn Thr Gln Phe Glu Ala Val Asp His Glu Phe Ser Asn
385                 390                 395                 400

Leu Glu Arg Arg Ile Asp Asn Leu Asn Lys Arg Met Glu Asp Gly Phe
            405                 410                 415

Leu Asp Val Trp Thr Tyr Asn Ala Glu Leu Leu Val Leu Leu Glu Asn
            420                 425                 430

Glu Arg Thr Leu Asp Leu His Asp Ala Asn Val Lys Asn Leu Tyr Glu
            435                 440                 445

Lys Val Lys Ser Gln Leu Arg Asp Asn Ala Asn Asp Leu Gly Asn Gly
            450                 455                 460

Cys Phe Glu Phe Trp His Lys Cys Asp Asn Glu Cys Ile Glu Ser Val
465                 470                 475                 480

Lys Asn Gly Thr Tyr Asp Tyr Pro Lys Tyr Gln Asp Glu Ser Lys Leu
            485                 490                 495

Asn Arg Gln Glu Ile Glu Ser Val Lys Leu Asp Asn Leu Gly Val Tyr
            500                 505                 510

Gln Ser Gly Arg Leu Val Pro Arg Gly Ser Pro Gly Ser Gly Tyr Ile
            515                 520                 525

Pro Glu Ala Pro Arg Asp Gly Gln Ala Tyr Val Arg Lys Asp Gly Glu
            530                 535                 540

Trp Val Leu Leu Ser Thr Phe Leu Gly Lys Pro Ile Pro Asn Pro Leu
545                 550                 555                 560

Leu Gly Leu Asp Ser Thr Gly His His His His His
            565                 570
```

```
<210> SEQ ID NO 16
<211> LENGTH: 567
<212> TYPE: PRT
<213> ORGANISM: Influenza A virus

<400> SEQUENCE: 16

Asp Lys Ile Cys Leu Gly His His Ala Val Ser Asn Gly Thr Lys Val
1               5                   10                  15

Asn Thr Leu Thr Glu Arg Gly Val Glu Val Val Asn Ala Thr Glu Thr
            20                  25                  30

Val Glu Arg Thr Asn Val Pro Arg Ile Cys Ser Lys Gly Lys Arg Thr
        35                  40                  45

Val Asp Leu Gly Gln Cys Gly Leu Leu Gly Thr Ile Thr Gly Pro Pro
    50                  55                  60

Gln Cys Asp Gln Phe Leu Glu Phe Ser Ala Asp Leu Ile Ile Glu Arg
65                  70                  75                  80

Arg Glu Gly Ser Asp Val Cys Tyr Pro Gly Lys Phe Val Asn Glu Glu
                85                  90                  95

Ala Leu Arg Gln Ile Leu Arg Glu Ser Gly Gly Ile Asp Lys Glu Thr
            100                 105                 110

Met Gly Phe Thr Tyr Ser Gly Ile Arg Thr Asn Gly Thr Thr Ser Ala
        115                 120                 125

Cys Arg Arg Ser Gly Ser Ser Phe Tyr Ala Glu Met Lys Trp Leu Leu
    130                 135                 140

Ser Asn Thr Asp Asn Ala Ala Phe Pro Gln Met Thr Lys Ser Tyr Lys
145                 150                 155                 160

Asn Thr Arg Lys Asp Pro Ala Leu Ile Ile Trp Gly Ile His His Ser
                165                 170                 175

Gly Ser Thr Thr Glu Gln Thr Lys Leu Tyr Gly Ser Gly Asn Lys Leu
            180                 185                 190

Ile Thr Val Gly Ser Ser Asn Tyr Gln Gln Ser Phe Val Pro Ser Pro
        195                 200                 205

Gly Ala Arg Pro Gln Val Asn Gly Gln Ser Gly Arg Ile Asp Phe His
    210                 215                 220

Trp Leu Ile Leu Asn Pro Asn Asp Thr Val Thr Phe Ser Phe Asn Gly
225                 230                 235                 240

Ala Phe Ile Ala Pro Asp Arg Ala Ser Phe Leu Arg Gly Lys Ser Met
                245                 250                 255

Gly Ile Gln Ser Glu Val Gln Val Asp Ala Asn Cys Glu Gly Asp Cys
            260                 265                 270

Tyr His Ser Gly Gly Thr Ile Ile Ser Asn Leu Pro Phe Gln Asn Ile
        275                 280                 285

Asn Ser Arg Ala Val Gly Lys Cys Pro Arg Tyr Val Lys Gln Glu Ser
    290                 295                 300

Leu Leu Leu Ala Thr Gly Met Lys Asn Val Pro Glu Ile Pro Lys Arg
305                 310                 315                 320

Arg Arg Arg Gly Leu Phe Gly Ala Ile Ala Gly Phe Ile Glu Asn Gly
                325                 330                 335

Trp Glu Gly Leu Ile Asp Gly Trp Tyr Gly Phe Arg His Gln Asn Ala
            340                 345                 350

Gln Gly Glu Gly Thr Ala Ala Asp Tyr Lys Ser Thr Gln Ser Ala Ile
        355                 360                 365

Asp Gln Ile Thr Gly Lys Leu Asn Arg Leu Ile Glu Lys Thr Asn Gln
    370                 375                 380
```

```
Gln Phe Glu Leu Ile Asp Asn Glu Phe Thr Glu Val Glu Arg Gln Ile
385                 390                 395                 400

Gly Asn Val Ile Asn Trp Thr Arg Asp Ser Met Thr Glu Val Trp Ser
                405                 410                 415

Tyr Asn Ala Glu Leu Leu Val Ala Met Glu Asn Gln His Thr Ile Asp
            420                 425                 430

Leu Ala Asp Ser Glu Met Asn Lys Leu Tyr Glu Arg Val Lys Arg Gln
        435                 440                 445

Leu Arg Glu Asn Ala Glu Glu Asp Gly Thr Gly Cys Phe Glu Ile Phe
    450                 455                 460

His Lys Cys Asp Asp Asp Cys Met Ala Ser Ile Arg Asn Asn Thr Tyr
465                 470                 475                 480

Asp His Ser Lys Tyr Arg Glu Glu Ala Ile Gln Asn Arg Ile Gln Ile
                485                 490                 495

Asp Pro Val Lys Leu Ser Ser Gly Tyr Lys Asp Ser Gly Arg Leu Val
            500                 505                 510

Pro Arg Gly Ser Pro Gly Ser Gly Tyr Ile Pro Glu Ala Pro Arg Asp
        515                 520                 525

Gly Gln Ala Tyr Val Arg Lys Asp Gly Glu Trp Val Leu Leu Ser Thr
    530                 535                 540

Phe Leu Gly Lys Pro Ile Pro Asn Pro Leu Leu Gly Leu Asp Ser Thr
545                 550                 555                 560

Gly His His His His His His
                565

<210> SEQ ID NO 17
<211> LENGTH: 572
<212> TYPE: PRT
<213> ORGANISM: Influenza A virus

<400> SEQUENCE: 17

Asp Arg Ile Cys Ile Gly Tyr Gln Ser Asn Asn Ser Thr Asp Thr Val
1               5                   10                  15

Asn Thr Leu Ile Glu Gln Lys Val Pro Val Thr Gln Thr Met Glu Leu
            20                  25                  30

Val Glu Thr Glu Lys His Pro Ala Tyr Cys Asn Thr Asp Leu Gly Ala
        35                  40                  45

Pro Leu Glu Leu Arg Asp Cys Lys Ile Glu Ala Val Ile Tyr Gly Asn
    50                  55                  60

Pro Lys Cys Asp Ile His Leu Lys Asp Gln Gly Trp Ser Tyr Ile Val
65                  70                  75                  80

Glu Arg Pro Ser Ala Pro Glu Gly Met Cys Tyr Pro Gly Ser Val Glu
                85                  90                  95

Asn Leu Glu Glu Leu Arg Phe Val Phe Ser Ser Ala Ala Ser Tyr Lys
            100                 105                 110

Arg Ile Arg Leu Phe Asp Tyr Ser Arg Trp Asn Val Thr Ser Ser Gly
        115                 120                 125

Thr Ser Lys Ala Cys Asn Ala Ser Thr Gly Gly Gln Ser Phe Tyr Arg
    130                 135                 140

Ser Ile Asn Trp Leu Thr Lys Lys Lys Pro Asp Thr Tyr Asp Phe Asn
145                 150                 155                 160

Glu Gly Thr Tyr Val Asn Asn Glu Asp Gly Asp Ile Ile Phe Leu Trp
                165                 170                 175

Gly Ile His His Pro Pro Asp Thr Lys Glu Gln Thr Thr Leu Tyr Lys
```

```
                180             185             190
Asn Ala Asn Thr Leu Ser Ser Val Thr Thr Asn Thr Ile Asn Arg Ser
            195                 200                 205
Phe Gln Pro Asn Ile Gly Pro Arg Pro Leu Val Arg Gly Gln Gln Gly
            210                 215                 220
Arg Met Asp Tyr Tyr Trp Gly Ile Leu Lys Arg Gly Glu Thr Leu Lys
225                 230                 235                 240
Ile Arg Thr Asn Gly Asn Leu Ile Ala Pro Glu Phe Gly Tyr Leu Leu
                245                 250                 255
Lys Gly Glu Ser His Gly Arg Thr Ile Gln Asn Glu Asp Ile Pro Ile
            260                 265                 270
Gly Asn Cys Tyr Thr Lys Cys Gln Thr Tyr Ala Gly Ala Ile Asn Ser
            275                 280                 285
Ser Lys Pro Phe Gln Asn Ala Ser Arg His Tyr Met Gly Glu Cys Pro
            290                 295                 300
Lys Tyr Val Lys Lys Ala Ser Leu Arg Leu Ala Val Gly Leu Arg Asn
305                 310                 315                 320
Thr Pro Ser Val Glu Pro Arg Gly Leu Phe Gly Ala Ile Ala Gly Phe
                325                 330                 335
Ile Glu Gly Gly Trp Ser Gly Met Ile Asp Gly Trp Tyr Gly Phe His
                340                 345                 350
His Ser Asn Ser Glu Gly Thr Gly Met Ala Ala Asp Gln Lys Ser Thr
            355                 360                 365
Gln Glu Ala Ile Asp Lys Ile Thr Asn Lys Val Asn Asn Ile Val Asp
            370                 375                 380
Lys Met Asn Arg Glu Phe Glu Val Val Asn His Glu Phe Ser Glu Val
385                 390                 395                 400
Glu Lys Arg Ile Asn Met Ile Asn Asp Lys Ile Asp Asp Gln Ile Glu
                405                 410                 415
Asp Leu Trp Ala Tyr Asn Ala Glu Leu Leu Val Leu Leu Glu Asn Gln
                420                 425                 430
Lys Thr Leu Asp Glu His Asp Ser Asn Val Lys Asn Leu Phe Asp Glu
            435                 440                 445
Val Lys Arg Arg Leu Ser Ala Asn Ala Ile Asp Ala Gly Asn Gly Cys
            450                 455                 460
Phe Asp Ile Leu His Lys Cys Asp Asn Glu Cys Met Glu Thr Ile Lys
465                 470                 475                 480
Asn Gly Thr Tyr Asp His Lys Glu Tyr Glu Glu Glu Ala Lys Leu Glu
                485                 490                 495
Arg Ser Lys Ile Asn Gly Val Lys Leu Glu Glu Asn Thr Thr Tyr Lys
            500                 505                 510
Ser Gly Arg Leu Val Pro Arg Gly Ser Pro Gly Ser Gly Tyr Ile Pro
            515                 520                 525
Glu Ala Pro Arg Asp Gly Gln Ala Tyr Val Arg Lys Asp Gly Glu Trp
            530                 535                 540
Val Leu Leu Ser Thr Phe Leu Gly Lys Pro Ile Pro Asn Pro Leu Leu
545                 550                 555                 560
Gly Leu Asp Ser Thr Gly His His His His His
                565                 570

<210> SEQ ID NO 18
<211> LENGTH: 565
<212> TYPE: PRT
<213> ORGANISM: Influenza A virus
```

<400> SEQUENCE: 18

| | | | | | | | | | | | | | | |
|---|---|---|---|---|---|---|---|---|---|---|---|---|---|---|
| Asp | Lys | Ile | Cys | Ile | Gly | Tyr | Gln | Ser | Thr | Asn | Ser | Thr | Glu | Thr | Val |
| 1 | | | | 5 | | | | | 10 | | | | | 15 | |
| Asp | Thr | Leu | Thr | Lys | Thr | Asn | Val | Pro | Val | Thr | Gln | Ala | Lys | Glu | Leu |
| | | | 20 | | | | | 25 | | | | | 30 | | |
| Leu | His | Thr | Glu | His | Asn | Gly | Met | Leu | Cys | Ala | Thr | Asn | Leu | Gly | His |
| | | | 35 | | | | | 40 | | | | | 45 | | |
| Pro | Leu | Ile | Leu | Asp | Thr | Cys | Thr | Ile | Glu | Gly | Leu | Ile | Tyr | Gly | Asn |
| | 50 | | | | | 55 | | | | | 60 | | | | |
| Pro | Ser | Cys | Asp | Leu | Leu | Leu | Gly | Gly | Arg | Glu | Trp | Ser | Tyr | Ile | Val |
| 65 | | | | | 70 | | | | | 75 | | | | | 80 |
| Glu | Arg | Pro | Ser | Ala | Val | Asn | Gly | Met | Cys | Tyr | Pro | Gly | Asn | Val | Glu |
| | | | | 85 | | | | | 90 | | | | | 95 | |
| Asn | Leu | Glu | Glu | Leu | Arg | Leu | Leu | Phe | Ser | Ser | Ala | Ser | Ser | Tyr | Gln |
| | | | 100 | | | | | 105 | | | | | 110 | | |
| Arg | Val | Gln | Ile | Phe | Pro | Asp | Thr | Ile | Trp | Asn | Val | Thr | Tyr | Ser | Gly |
| | | | 115 | | | | | 120 | | | | | 125 | | |
| Thr | Ser | Ser | Ala | Cys | Ser | Asn | Ser | Phe | Tyr | Arg | Ser | Met | Arg | Trp | Leu |
| | 130 | | | | | 135 | | | | | 140 | | | | |
| Thr | Gln | Lys | Asp | Asn | Thr | Tyr | Pro | Val | Gln | Asp | Ala | Gln | Tyr | Thr | Asn |
| 145 | | | | | 150 | | | | | 155 | | | | | 160 |
| Asn | Arg | Gly | Lys | Ser | Ile | Leu | Phe | Met | Trp | Gly | Ile | Asn | His | Pro | Pro |
| | | | | 165 | | | | | 170 | | | | | 175 | |
| Thr | Asp | Thr | Val | Gln | Thr | Asn | Leu | Tyr | Thr | Arg | Thr | Asp | Thr | Thr | Thr |
| | | | 180 | | | | | 185 | | | | | 190 | | |
| Ser | Val | Thr | Thr | Glu | Asp | Ile | Asn | Arg | Ala | Phe | Lys | Pro | Val | Ile | Gly |
| | | | 195 | | | | | 200 | | | | | 205 | | |
| Pro | Arg | Pro | Leu | Val | Asn | Gly | Leu | Gln | Gly | Arg | Ile | Asp | Tyr | Tyr | Trp |
| | 210 | | | | | 215 | | | | | 220 | | | | |
| Ser | Val | Leu | Lys | Pro | Gly | Gln | Thr | Leu | Arg | Val | Arg | Ser | Asn | Gly | Asn |
| 225 | | | | | 230 | | | | | 235 | | | | | 240 |
| Leu | Ile | Ala | Pro | Trp | Tyr | Gly | His | Ile | Leu | Ser | Gly | Glu | Ser | His | Gly |
| | | | | 245 | | | | | 250 | | | | | 255 | |
| Arg | Ile | Leu | Lys | Ser | Asp | Leu | Asn | Ser | Gly | Asn | Cys | Val | Val | Gln | Cys |
| | | | 260 | | | | | 265 | | | | | 270 | | |
| Gln | Thr | Glu | Arg | Gly | Gly | Leu | Asn | Thr | Thr | Leu | Pro | Phe | His | Asn | Val |
| | | | 275 | | | | | 280 | | | | | 285 | | |
| Ser | Lys | Tyr | Ala | Phe | Gly | Asn | Cys | Pro | Lys | Tyr | Val | Gly | Val | Lys | Ser |
| | 290 | | | | | 295 | | | | | 300 | | | | |
| Leu | Lys | Leu | Ala | Val | Gly | Met | Arg | Asn | Val | Pro | Ala | Arg | Ser | Ser | Arg |
| 305 | | | | | 310 | | | | | 315 | | | | | 320 |
| Gly | Leu | Phe | Gly | Ala | Ile | Ala | Gly | Phe | Ile | Glu | Gly | Gly | Trp | Pro | Gly |
| | | | | 325 | | | | | 330 | | | | | 335 | |
| Leu | Val | Ala | Gly | Trp | Tyr | Gly | Phe | Gln | His | Ser | Asn | Asp | Gln | Gly | Val |
| | | | 340 | | | | | 345 | | | | | 350 | | |
| Gly | Met | Ala | Ala | Asp | Arg | Asp | Ser | Thr | Gln | Lys | Ala | Ile | Asp | Lys | Ile |
| | | | 355 | | | | | 360 | | | | | 365 | | |
| Thr | Ser | Lys | Val | Asn | Asn | Ile | Val | Asp | Lys | Met | Asn | Lys | Gln | Tyr | Glu |
| | | | 370 | | | | | 375 | | | | | 380 | | |
| Ile | Ile | Asp | His | Glu | Phe | Ser | Glu | Ile | Glu | Thr | Arg | Leu | Asn | Met | Ile |
| 385 | | | | | 390 | | | | | 395 | | | | | 400 |
| Asn | Asn | Lys | Ile | Asp | Asp | Gln | Ile | Gln | Asp | Ile | Trp | Ala | Tyr | Asn | Ala |

```
            405                 410                 415
Glu Leu Val Leu Leu Glu Asn Gln Lys Thr Leu Asp Glu His Asp
            420                 425                 430

Ala Asn Val Asn Asn Leu Tyr Asn Lys Val Lys Arg Ala Leu Gly Ser
            435                 440             445

Asn Ala Met Glu Asp Gly Lys Gly Cys Phe Glu Leu Tyr His Lys Cys
        450                 455                 460

Asp Asp Arg Cys Met Glu Thr Ile Arg Asn Gly Thr Tyr Asn Arg Gly
465                 470                 475                 480

Lys Tyr Lys Glu Glu Ser Arg Leu Glu Arg Gln Lys Ile Glu Gly Val
                485                 490                 495

Lys Leu Glu Ser Glu Gly Thr Tyr Lys Ser Gly Arg Leu Val Pro Arg
            500                 505                 510

Gly Ser Pro Gly Ser Gly Tyr Ile Pro Glu Ala Pro Arg Asp Gly Gln
            515                 520                 525

Ala Tyr Val Arg Lys Asp Gly Glu Trp Val Leu Leu Ser Thr Phe Leu
        530                 535                 540

Gly Lys Pro Ile Pro Asn Pro Leu Leu Gly Leu Asp Ser Thr Gly His
545                 550                 555                 560

His His His His His
            565

<210> SEQ ID NO 19
<211> LENGTH: 583
<212> TYPE: PRT
<213> ORGANISM: Influenza A virus

<400> SEQUENCE: 19

Met Glu Thr Ile Ser Leu Ile Thr Ile Leu Leu Val Val Thr Ala Ser
1               5                   10                  15

Asn Ala Asp Lys Ile Cys Ile Gly His Gln Ser Thr Asn Ser Thr Glu
            20                  25                  30

Thr Val Asp Thr Leu Thr Glu Thr Asn Val Pro Val Thr His Ala Lys
        35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Val Tyr
65                  70                  75                  80

Gly Asn Pro Ser Cys Asp Leu Leu Leu Gly Gly Arg Glu Trp Ser Tyr
                85                  90                  95

Ile Val Glu Arg Ser Ser Ala Val Asn Gly Thr Cys Tyr Pro Gly Asn
            100                 105                 110

Val Glu Asn Leu Glu Glu Leu Arg Thr Leu Phe Ser Ser Ala Ser Ser
        115                 120                 125

Tyr Gln Arg Ile Gln Ile Phe Pro Asp Thr Thr Trp Asn Val Thr Tyr
    130                 135                 140

Thr Gly Thr Ser Arg Ala Cys Ser Gly Ser Phe Tyr Arg Ser Met Arg
145                 150                 155                 160

Trp Leu Thr Gln Lys Ser Gly Phe Tyr Pro Val Gln Asp Ala Gln Tyr
                165                 170                 175

Thr Asn Asn Arg Gly Lys Ser Ile Leu Phe Val Trp Gly Ile His His
            180                 185                 190

Pro Pro Thr Tyr Thr Glu Gln Thr Asn Leu Tyr Ile Arg Asn Asp Thr
        195                 200                 205
```

-continued

Thr Thr Ser Val Thr Thr Glu Asp Leu Asn Arg Thr Phe Lys Pro Val
210                215                220

Ile Gly Pro Arg Pro Leu Val Asn Gly Leu Gln Gly Arg Ile Asp Tyr
225                230                235                240

Tyr Trp Ser Val Leu Lys Pro Gly Gln Thr Leu Arg Val Arg Ser Asn
            245                250                255

Gly Asn Leu Ile Ala Pro Trp Tyr Gly His Val Leu Ser Gly Gly Ser
            260                265                270

His Gly Arg Ile Leu Lys Thr Asp Leu Lys Gly Asn Cys Val Val
        275                280                285

Gln Cys Gln Thr Glu Lys Gly Gly Leu Asn Ser Thr Leu Pro Phe His
290                295                300

Asn Ile Ser Lys Tyr Ala Phe Gly Thr Cys Pro Lys Tyr Val Arg Val
305                310                315                320

Asn Ser Leu Lys Leu Ala Val Gly Leu Arg Asn Val Pro Ala Arg Ser
            325                330                335

Ser Arg Gly Leu Phe Gly Ala Ile Ala Gly Phe Ile Glu Gly Gly Trp
            340                345                350

Pro Gly Leu Val Ala Gly Trp Tyr Gly Phe Gln His Ser Asn Asp Gln
            355                360                365

Gly Val Gly Met Ala Ala Asp Arg Asp Ser Thr Gln Lys Ala Ile Asp
370                375                380

Lys Ile Thr Ser Lys Val Asn Asn Ile Val Asp Lys Met Asn Lys Gln
385                390                395                400

Tyr Glu Ile Ile Asp His Glu Phe Ser Glu Val Glu Thr Arg Leu Asn
            405                410                415

Met Ile Asn Asn Lys Ile Asp Asp Gln Ile Gln Asp Val Trp Ala Tyr
            420                425                430

Asn Ala Glu Leu Leu Val Leu Leu Glu Asn Gln Lys Thr Leu Asp Glu
            435                440                445

His Asp Ala Asn Val Asn Asn Leu Tyr Asn Lys Val Lys Arg Ala Leu
450                455                460

Gly Ser Asn Ala Met Glu Asp Gly Lys Gly Cys Phe Glu Leu Tyr His
465                470                475                480

Lys Cys Asp Asp Gln Cys Met Glu Thr Ile Arg Asn Gly Thr Tyr Asn
            485                490                495

Arg Arg Lys Tyr Arg Glu Glu Ser Arg Leu Glu Arg Gln Lys Ile Glu
            500                505                510

Gly Val Lys Leu Glu Ser Glu Gly Thr Tyr Lys Ser Gly Arg Leu Val
            515                520                525

Pro Arg Gly Ser Pro Gly Ser Gly Tyr Ile Pro Glu Ala Pro Arg Asp
530                535                540

Gly Gln Ala Tyr Val Arg Lys Asp Gly Glu Trp Val Leu Leu Ser Thr
545                550                555                560

Phe Leu Gly Lys Pro Ile Pro Asn Pro Leu Leu Gly Leu Asp Ser Thr
            565                570                575

Gly His His His His His His
            580

<210> SEQ ID NO 20
<211> LENGTH: 366
<212> TYPE: DNA
<213> ORGANISM: Homo sapiens

<400> SEQUENCE: 20

```
gaagtgcagt tggtgcagtc tggaggaggc ttggtccagc ctgggggtc cctgagactc        60 gcctgtgtag tctctgggtt caccgtcacc agcaattata taacttgggt ccgccaggct       120
ccagggaagg gctggagtg gtctcagtt atttatagtc atggtcgcgc atattattca         180
gcctccgtga atggccgatt caccatctcc agacacactt ccaagaacac agtttatctt       240
gaaatgaaca gcctgagacc tgaggacacg gccgtctatt actgtgcggg cggggggccta     300 gtcggtggct acgacgaata tttctttgac tattggggcc agggaaccct ggccaccgtc      360
tcctca                                                                   366
```

<210> SEQ ID NO 21
<211> LENGTH: 122
<212> TYPE: PRT
<213> ORGANISM: Homo sapiens

<400> SEQUENCE: 21

```
Glu Val Gln Leu Val Gln Ser Gly Gly Gly Leu Val Gln Pro Gly Gly
1               5                   10                  15

Ser Leu Arg Leu Ala Cys Val Val Ser Gly Phe Thr Val Thr Ser Asn
            20                  25                  30

Tyr Ile Thr Trp Val Arg Gln Ala Pro Gly Lys Gly Leu Glu Trp Val
        35                  40                  45

Ser Val Ile Tyr Ser His Gly Arg Ala Tyr Tyr Ser Ala Ser Val Asn
    50                  55                  60

Gly Arg Phe Thr Ile Ser Arg His Thr Ser Lys Asn Thr Val Tyr Leu
65                  70                  75                  80

Glu Met Asn Ser Leu Arg Pro Glu Asp Thr Ala Val Tyr Tyr Cys Ala
                85                  90                  95

Gly Gly Gly Leu Val Gly Gly Tyr Asp Glu Tyr Phe Phe Asp Tyr Trp
            100                 105                 110

Gly Gln Gly Thr Leu Ala Thr Val Ser Ser
        115                 120
```

<210> SEQ ID NO 22
<211> LENGTH: 5
<212> TYPE: PRT
<213> ORGANISM: Homo sapiens

<400> SEQUENCE: 22

```
Ser Asn Tyr Ile Thr
1               5
```

<210> SEQ ID NO 23
<211> LENGTH: 16
<212> TYPE: PRT
<213> ORGANISM: Homo sapiens

<400> SEQUENCE: 23

```
Val Ile Tyr Ser His Gly Arg Ala Tyr Tyr Ser Ala Ser Val Asn Gly
1               5                   10                  15
```

<210> SEQ ID NO 24
<211> LENGTH: 14
<212> TYPE: PRT
<213> ORGANISM: Homo sapiens

<400> SEQUENCE: 24

```
Gly Gly Leu Val Gly Gly Tyr Asp Glu Tyr Phe Phe Asp Tyr
1               5                   10
```

<210> SEQ ID NO 25
<211> LENGTH: 6
<212> TYPE: PRT
<213> ORGANISM: Homo sapiens

<400> SEQUENCE: 25

Gly Phe Thr Val Thr Ser
1               5

<210> SEQ ID NO 26
<211> LENGTH: 9
<212> TYPE: PRT
<213> ORGANISM: Homo sapiens

<400> SEQUENCE: 26

Val Ile Tyr Ser His Gly Arg Ala Tyr
1               5

<210> SEQ ID NO 27
<211> LENGTH: 324
<212> TYPE: DNA
<213> ORGANISM: Homo sapiens

<400> SEQUENCE: 27

```
gaaactgtct tgacgcaatc tccaggcacc ttgtctttga ctccagggga aagagccacc      60
ctctcctgca gagtcggtca gagtgttagc ggcagccact tagcctggta ccaacagaaa     120
cctggccagg ctcccaggct cctcatctat ggtgcatcca gcagggccac tggcatccca     180
gacaggttcg gtggcagtgt gtctgggaca gacttcactc tcaccatcag cagactggag     240
cctgaagatt ctgcagttta ttactgtcag cagtatggtg actcacgata cacttttggc     300
caggggacca agctggagat caaa                                            324
```

<210> SEQ ID NO 28
<211> LENGTH: 108
<212> TYPE: PRT
<213> ORGANISM: Homo sapiens

<400> SEQUENCE: 28

Glu Thr Val Leu Thr Gln Ser Pro Gly Thr Leu Ser Leu Thr Pro Gly
1               5                   10                  15

Glu Arg Ala Thr Leu Ser Cys Arg Val Gly Gln Ser Val Ser Gly Ser
                20                  25                  30

His Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Gly
        50                  55                  60

Gly Ser Val Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Gly Asp Ser Arg
                85                  90                  95

Tyr Thr Phe Gly Gln Gly Thr Lys Leu Glu Ile Lys
            100                 105

<210> SEQ ID NO 29
<211> LENGTH: 12
<212> TYPE: PRT
<213> ORGANISM: Homo sapiens

<400> SEQUENCE: 29

```
Arg Val Gly Gln Ser Val Ser Gly Ser His Leu Ala
1               5                   10
```

<210> SEQ ID NO 30
<211> LENGTH: 7
<212> TYPE: PRT
<213> ORGANISM: Homo sapiens

<400> SEQUENCE: 30

```
Gly Ala Ser Ser Arg Ala Thr
1               5
```

<210> SEQ ID NO 31
<211> LENGTH: 9
<212> TYPE: PRT
<213> ORGANISM: Homo sapiens

<400> SEQUENCE: 31

```
Gln Gln Tyr Gly Asp Ser Arg Tyr Thr
1               5
```

<210> SEQ ID NO 32
<211> LENGTH: 381
<212> TYPE: DNA
<213> ORGANISM: Homo sapiens

<400> SEQUENCE: 32

```
caggtgcagc tacagcagtg gggcgcagga cttttgaaac cttcggagac cctgtccctc      60
acctgcactg tgtctggggg gtccctcact gattactctt ggaactggat ccgccagccc     120
ccagggaagg ggctggagtg gatcggtgac acccttcata atggctacac caactacaac     180
ccgtccctca gggtcgagt ttccatctca atagacacgt ccaagaacca ggtctcactc     240
aggctgacct ctgtgaccgc cgcggacacg gctctttatt actgtgcgag aggctcaggt     300
ggatatggtg gcttcgatta ttttggcaag ctccggacat gggacttctg gggccaggga     360
acgctggtca ccgtctcctc a                                               381
```

<210> SEQ ID NO 33
<211> LENGTH: 127
<212> TYPE: PRT
<213> ORGANISM: Homo sapiens

<400> SEQUENCE: 33

```
Gln Val Gln Leu Gln Gln Trp Gly Ala Gly Leu Leu Lys Pro Ser Glu
1               5                   10                  15
Thr Leu Ser Leu Thr Cys Thr Val Ser Gly Gly Ser Leu Thr Asp Tyr
            20                  25                  30
Ser Trp Asn Trp Ile Arg Gln Pro Pro Gly Lys Gly Leu Glu Trp Ile
        35                  40                  45
Gly Asp Thr Leu His Asn Gly Tyr Thr Asn Tyr Asn Pro Ser Leu Arg
    50                  55                  60
Gly Arg Val Ser Ile Ser Ile Asp Thr Ser Lys Asn Gln Val Ser Leu
65                  70                  75                  80
Arg Leu Thr Ser Val Thr Ala Ala Asp Thr Ala Leu Tyr Tyr Cys Ala
                85                  90                  95
Arg Gly Ser Gly Gly Tyr Gly Gly Phe Asp Tyr Phe Gly Lys Leu Arg
            100                 105                 110
Thr Trp Asp Phe Trp Gly Gln Gly Thr Leu Val Thr Val Ser Ser
        115                 120                 125
```

<210> SEQ ID NO 34
<211> LENGTH: 5
<212> TYPE: PRT
<213> ORGANISM: Homo sapiens

<400> SEQUENCE: 34

Asp Tyr Ser Trp Asn
1               5

<210> SEQ ID NO 35
<211> LENGTH: 16
<212> TYPE: PRT
<213> ORGANISM: Homo sapiens

<400> SEQUENCE: 35

Asp Thr Leu His Asn Gly Tyr Thr Asn Tyr Asn Pro Ser Leu Arg Gly
1               5                   10                  15

<210> SEQ ID NO 36
<211> LENGTH: 19
<212> TYPE: PRT
<213> ORGANISM: Homo sapiens

<400> SEQUENCE: 36

Gly Ser Gly Gly Tyr Gly Gly Phe Asp Tyr Phe Gly Lys Leu Arg Thr
1               5                   10                  15

Trp Asp Phe

<210> SEQ ID NO 37
<211> LENGTH: 6
<212> TYPE: PRT
<213> ORGANISM: Homo sapiens

<400> SEQUENCE: 37

Gly Gly Ser Leu Thr Asp
1               5

<210> SEQ ID NO 38
<211> LENGTH: 9
<212> TYPE: PRT
<213> ORGANISM: Homo sapiens

<400> SEQUENCE: 38

Asp Thr Leu His Asn Gly Tyr Thr Asn
1               5

<210> SEQ ID NO 39
<211> LENGTH: 321
<212> TYPE: DNA
<213> ORGANISM: Homo sapiens

<400> SEQUENCE: 39
gacattcagt tgacccagtc tccatcctcc ctgtctgcat ctgtgggaga cagagtcacc      60
atcacttgcc gggcaagtca gggcattaga aatgatttag ctggtatca gcaaaaacca     120 gggaacgccc ctaagcgcct gatcttggt gcatccagtt tgcaaagtgg ggtcccatca     180
aggttcagcg gcagtggatc tgggacagag ttcactctca caatcagcag cctgcagcct     240
gaggactttg caacttatta ctgtctacag cataatagtt acccgtacac ttttggccag     300
gggaccaagc tggagatcaa g                                               321

```
<210> SEQ ID NO 40
<211> LENGTH: 107
<212> TYPE: PRT
<213> ORGANISM: Homo sapiens

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Asn Ala Pro Lys Arg Leu Ile
        35                  40                  45

Phe Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 41
<211> LENGTH: 11
<212> TYPE: PRT
<213> ORGANISM: Homo sapiens

<400> SEQUENCE: 41

Arg Ala Ser Gln Gly Ile Arg Asn Asp Leu Gly
1               5                   10

<210> SEQ ID NO 42
<211> LENGTH: 7
<212> TYPE: PRT
<213> ORGANISM: Homo sapiens

<400> SEQUENCE: 42

Gly Ala Ser Ser Leu Gln Ser
1               5

<210> SEQ ID NO 43
<211> LENGTH: 9
<212> TYPE: PRT
<213> ORGANISM: Homo sapiens

<400> SEQUENCE: 43

Leu Gln His Asn Ser Tyr Pro Tyr Thr
1               5

<210> SEQ ID NO 44
<211> LENGTH: 354
<212> TYPE: DNA
<213> ORGANISM: Homo sapiens

<400> SEQUENCE: 44
caggtgcaac tggtgcagtc tggggctgag gtgaagaagc ctgggtcctc ggtgaaggtc      60
tcctgcaagg cttctggagg cagcttcagc aactatgcct tcagctgggt gcgacaggcc     120
cctggacaag gcttgagtg gatgggaggg accatccctc tacttggtac aacaaactac     180
gcacagaagt tccagggcag agtcacgatt tccgcggacc aattcacgag cacagcctac     240
atggagctgg gcagcctgag atctgaagac acggccgtgt attactgtac gagacggaaa     300
```

```
atgactacgg cttttgactc ctggggccag ggaaccctgg tcaccgtctc ctca        354
```

<210> SEQ ID NO 45
<211> LENGTH: 118
<212> TYPE: PRT
<213> ORGANISM: Homo sapiens

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Asn Tyr
            20                  25                  30

Ala Phe Ser Trp Val Arg Gln Ala Pro Gly Gln Gly Leu Glu Trp Met
        35                  40                  45

Gly Gly Thr Ile Pro Leu Leu Gly Thr Thr Asn Tyr Ala Gln Lys Phe
    50                  55                  60

Gln Gly Arg Val Thr Ile Ser Ala Asp Gln Phe Thr Ser Thr Ala Tyr
65                  70                  75                  80

Met Glu Leu Gly Ser Leu Arg Ser Glu Asp Thr Ala Val Tyr Tyr Cys
                85                  90                  95

Thr Arg Arg Lys Met Thr Thr Ala Phe Asp Ser Trp Gly Gln Gly Thr
            100                 105                 110

Leu Val Thr Val Ser Ser
        115

<210> SEQ ID NO 46
<211> LENGTH: 5
<212> TYPE: PRT
<213> ORGANISM: Homo sapiens

<400> SEQUENCE: 46

Asn Tyr Ala Phe Ser
1               5

<210> SEQ ID NO 47
<211> LENGTH: 17
<212> TYPE: PRT
<213> ORGANISM: Homo sapiens

<400> SEQUENCE: 47

Gly Thr Ile Pro Leu Leu Gly Thr Thr Asn Tyr Ala Gln Lys Phe Gln
1               5                   10                  15

Gly

<210> SEQ ID NO 48
<211> LENGTH: 9
<212> TYPE: PRT
<213> ORGANISM: Homo sapiens

<400> SEQUENCE: 48

Arg Lys Met Thr Thr Ala Phe Asp Ser
1               5

<210> SEQ ID NO 49
<211> LENGTH: 6
<212> TYPE: PRT
<213> ORGANISM: Homo sapiens

<400> SEQUENCE: 49

Gly Gly Ser Phe Ser Asn
1               5

<210> SEQ ID NO 50
<211> LENGTH: 10
<212> TYPE: PRT
<213> ORGANISM: Homo sapiens

<400> SEQUENCE: 50

Gly Thr Ile Pro Leu Leu Gly Thr Thr Asn
1               5                   10

<210> SEQ ID NO 51
<211> LENGTH: 354
<212> TYPE: DNA
<213> ORGANISM: Homo sapiens

<400> SEQUENCE: 51
cagcctgttc tgactcagcc accttctgca tcagcctccc tgggagcctc ggtcacactc      60
acctgcaccc tgagcagcgc ctacagtaat tataaagtgg actggtacca gcagagacca     120
gggaagggcc cccgctttgt gatgcgagtg ggcactggtg ggattgtggg atccaagggg     180
gatggcatcc ctgatcgctt ctcagtcttg ggctcaggcc tgaatcggta cctgaccatc     240
aagaacatcc aggaagagga tgagagtgac taccactgtg ggcagacca tggcagtggg      300 agcaacttcg tgtcccctta cgtattcggc ggagggacca agctgaccgt tcta            354

<210> SEQ ID NO 52
<211> LENGTH: 118
<212> TYPE: PRT
<213> ORGANISM: Homo sapiens

<400> SEQUENCE: 52

Gln Pro Val Leu Thr Gln Pro Pro Ser Ala Ser Ala Ser Leu Gly Ala
1               5                   10                  15

Ser Val Thr Leu Thr Cys Thr Leu Ser Ser Ala Tyr Ser Asn Tyr Lys
                20                  25                  30

Val Asp Trp Tyr Gln Gln Arg Pro Gly Lys Gly Pro Arg Phe Val Met
            35                  40                  45

Arg Val Gly Thr Gly Gly Ile Val Gly Ser Lys Gly Asp Gly Ile Pro
        50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser Gly Ser Asn Phe Val Ser Pro Tyr Val Phe Gly Gly Gly
            100                 105                 110

Thr Lys Leu Thr Val Leu
        115

<210> SEQ ID NO 53
<211> LENGTH: 12
<212> TYPE: PRT
<213> ORGANISM: Homo sapiens

<400> SEQUENCE: 53

Thr Leu Ser Ser Ala Tyr Ser Asn Tyr Lys Val Asp
1               5                   10

<210> SEQ ID NO 54
<211> LENGTH: 12
<212> TYPE: PRT

<210> SEQ ID NO 54
<211> LENGTH: 11
<212> TYPE: PRT
<213> ORGANISM: Homo sapiens

<400> SEQUENCE: 54

Val Gly Thr Gly Gly Ile Val Gly Ser Lys Gly Asp
1               5                   10

<210> SEQ ID NO 55
<211> LENGTH: 15
<212> TYPE: PRT
<213> ORGANISM: Homo sapiens

<400> SEQUENCE: 55

Gly Ala Asp His Gly Ser Gly Ser Asn Phe Val Ser Pro Tyr Val
1               5                   10                  15

<210> SEQ ID NO 56
<211> LENGTH: 369
<212> TYPE: DNA
<213> ORGANISM: Homo sapiens

<400> SEQUENCE: 56

```
caggtgcagc tggcgcagtc tggggctgag gtgaagaggc ctgggtcctc ggtgaaagtc      60
tcatgcacgg cttctggagg catcttcagg aagaatgcaa tcagctgggt gcgacaggcc     120
cctggacaag gccttgagtg gatgggaggg atcatcgcag tctttaacac agcaaattac     180
gcgcagaagt tcagggcag agtcaaaatt accgcagacg aatccgggaa tacagcctac      240
atggagctga gcagcctgag atctgacgac acggccgtgt attactgtgc gagtcaccca     300
aaatatttct atggttcggg gagttatccg gacttctggg gccagggaac cctggtcacc     360
gtctcgagc                                                             369
```

<210> SEQ ID NO 57
<211> LENGTH: 123
<212> TYPE: PRT
<213> ORGANISM: Homo sapiens

<400> SEQUENCE: 57

Gln Val Gln Leu Ala Gln Ser Gly Ala Glu Val Lys Arg Pro Gly Ser
1               5                   10                  15

Ser Val Lys Val Ser Cys Thr Ala Ser Gly Gly Ile Phe Arg Lys Asn
                20                  25                  30

Ala Ile Ser Trp Val Arg Gln Ala Pro Gly Gln Gly Leu Glu Trp Met
            35                  40                  45

Gly Gly Ile Ile Ala Val Phe Asn Thr Ala Asn Tyr Ala Gln Lys Phe
        50                  55                  60

Gln Gly Arg Val Lys Ile Thr Ala Asp Glu Ser Gly Asn Thr Ala Tyr
65                  70                  75                  80

Met Glu Leu Ser Ser Leu Arg Ser Asp Asp Thr Ala Val Tyr Tyr Cys
                85                  90                  95

Ala Ser His Pro Lys Tyr Phe Tyr Gly Ser Gly Ser Tyr Pro Asp Phe
            100                 105                 110

Trp Gly Gln Gly Thr Leu Val Thr Val Ser Ser
        115                 120

<210> SEQ ID NO 58
<211> LENGTH: 17
<212> TYPE: PRT
<213> ORGANISM: Homo sapiens

<400> SEQUENCE: 58

```
Gly Ile Ile Ala Val Phe Asn Thr Ala Asn Tyr Ala Gln Lys Phe Gln
1               5                   10                  15

Gly
```

<210> SEQ ID NO 59
<211> LENGTH: 14
<212> TYPE: PRT
<213> ORGANISM: Homo sapiens

<400> SEQUENCE: 59

```
His Pro Lys Tyr Phe Tyr Gly Ser Gly Ser Tyr Pro Asp Phe
1               5                   10
```

<210> SEQ ID NO 60
<211> LENGTH: 6
<212> TYPE: PRT
<213> ORGANISM: Homo sapiens

<400> SEQUENCE: 60

```
Gly Gly Ile Phe Arg Lys
1               5
```

<210> SEQ ID NO 61
<211> LENGTH: 10
<212> TYPE: PRT
<213> ORGANISM: Homo sapiens

<400> SEQUENCE: 61

```
Gly Ile Ile Ala Val Phe Asn Thr Ala Asn
1               5                   10
```

<210> SEQ ID NO 62
<211> LENGTH: 5
<212> TYPE: PRT
<213> ORGANISM: Homo sapiens

<400> SEQUENCE: 62

```
Lys Asn Ala Ile Ser
1               5
```

<210> SEQ ID NO 63
<211> LENGTH: 330
<212> TYPE: DNA
<213> ORGANISM: Homo sapiens

<400> SEQUENCE: 63

```
caatctgccc tgactcagcc tcgctcagtg tccgggtctc ctggacagtc agtcaccatc      60
tcctgcactg gaagcagcag tgatgttggt gcttctaact ctgtctcctg gtaccaacaa     120
cacccaggca aagcccccaa actcgttatt tatgatgtca ctgagcgacc ctcagggtc      180 cctcatcgct tctctggctc caagtctggc aacacggcct ccctgaccgt ctctgggctc     240
cagcctgagg acgaggctga ttatttctgc tgcgcatatg gaggcaaata tcttgtggtc     300
ttcggcggag ggaccaaggt gaccgtcctc                                      330
```

<210> SEQ ID NO 64
<211> LENGTH: 110
<212> TYPE: PRT
<213> ORGANISM: Homo sapiens

<400> SEQUENCE: 64

```
Gln Ser Ala Leu Thr Gln Pro Arg Ser Val Ser Gly Ser Pro Gly Gln
```

```
            1               5                  10                  15
Ser Val Thr Ile Ser Cys Thr Gly Ser Ser Ser Asp Val Gly Ala Ser
            20                  25                  30

Asn Ser Val Ser Trp Tyr Gln Gln His Pro Gly Lys Ala Pro Lys Leu
        35                  40                  45

Val Ile Tyr Asp Val Thr Glu Arg Pro Ser Gly Val Pro His Arg Phe
        50                  55                  60

Ser Gly Ser Lys Ser Gly Asn Thr Ala Ser Leu Thr Val Ser Gly Leu
65                  70                  75                  80

Gln Pro Glu Asp Glu Ala Asp Tyr Phe Cys Cys Ala Tyr Gly Gly Lys
                85                  90                  95

Tyr Leu Val Val Phe Gly Gly Gly Thr Lys Val Thr Val Leu
            100                 105                 110
```

<210> SEQ ID NO 65
<211> LENGTH: 14
<212> TYPE: PRT
<213> ORGANISM: Homo sapiens

<400> SEQUENCE: 65

```
Thr Gly Ser Ser Ser Asp Val Gly Ala Ser Asn Ser Val Ser
1               5                  10
```

<210> SEQ ID NO 66
<211> LENGTH: 7
<212> TYPE: PRT
<213> ORGANISM: Homo sapiens

<400> SEQUENCE: 66

```
Asp Val Thr Glu Arg Pro Ser
1               5
```

<210> SEQ ID NO 67
<211> LENGTH: 10
<212> TYPE: PRT
<213> ORGANISM: Homo sapiens

<400> SEQUENCE: 67

```
Cys Ala Tyr Gly Gly Lys Tyr Leu Val Val
1               5                  10
```

<210> SEQ ID NO 68
<211> LENGTH: 387
<212> TYPE: DNA
<213> ORGANISM: Homo sapiens

<400> SEQUENCE: 68

```
gaggtgctga tggtggagtc tgggggaggc ttggtccagc ctggggggtc cgtgagactc      60
tcctgtgtag cctctggatt cagtttcagt agtcattgga tgacctgggt ccgccaggct     120
ccagggaagg ggctggagtg ggtggccaac atagaggacg atggaggtga caagtactat     180
gtggactctg tgaagggccg attcattatc tccagagaca acgccaagaa ttcagtgtat     240
ctgcaaatga acagcctaag agccgaggac acggctgtgt atttctgtgc gagaggttcg     300
gggagctctg atagaagtga ttatgacccc cactactact actacttgga cgtctggggc     360
aaagggccca cggtcaccgt ctcctca                                         387
```

<210> SEQ ID NO 69
<211> LENGTH: 129
<212> TYPE: PRT

<213> ORGANISM: Homo sapiens

<400> SEQUENCE: 69

Glu Val Leu Met Val Glu Ser Gly Gly Gly Leu Val Gln Pro Gly Gly
1               5                   10                  15
Ser Val Arg Leu Ser Cys Val Ala Ser Gly Phe Ser Phe Ser Ser His
            20                  25                  30
Trp Met Thr Trp Val Arg Gln Ala Pro Gly Lys Gly Leu Glu Trp Val
        35                  40                  45
Ala Asn Ile Glu Asp Asp Gly Gly Asp Lys Tyr Tyr Val Asp Ser Val
    50                  55                  60
Lys Gly Arg Phe Ile Ile Ser Arg Asp Asn Ala Lys Asn Ser Val Tyr
65                  70                  75                  80
Leu Gln Met Asn Ser Leu Arg Ala Glu Asp Thr Ala Val Tyr Phe Cys
                85                  90                  95
Ala Arg Gly Ser Gly Ser Ser Asp Arg Ser Asp Tyr Asp Pro His Tyr
            100                 105                 110
Tyr Tyr Tyr Leu Asp Val Trp Gly Lys Gly Ala Thr Val Thr Val Ser
        115                 120                 125
Ser

<210> SEQ ID NO 70
<211> LENGTH: 5
<212> TYPE: PRT
<213> ORGANISM: Homo sapiens

<400> SEQUENCE: 70

Ser His Trp Met Thr
1               5

<210> SEQ ID NO 71
<211> LENGTH: 17
<212> TYPE: PRT
<213> ORGANISM: Homo sapiens

<400> SEQUENCE: 71

Asn Ile Glu Asp Asp Gly Gly Asp Lys Tyr Tyr Val Asp Ser Val Lys
1               5                   10                  15
Gly

<210> SEQ ID NO 72
<211> LENGTH: 20
<212> TYPE: PRT
<213> ORGANISM: Homo sapiens

<400> SEQUENCE: 72

Gly Ser Gly Ser Ser Asp Arg Ser Asp Tyr Asp Pro His Tyr Tyr Tyr
1               5                   10                  15
Tyr Leu Asp Val
            20

<210> SEQ ID NO 73
<211> LENGTH: 6
<212> TYPE: PRT
<213> ORGANISM: Homo sapiens

<400> SEQUENCE: 73

Gly Phe Ser Phe Ser Ser
1               5

<210> SEQ ID NO 74
<211> LENGTH: 10
<212> TYPE: PRT
<213> ORGANISM: Homo sapiens

<400> SEQUENCE: 74

Asn Ile Glu Asp Asp Gly Gly Asp Lys Tyr
1               5                   10

<210> SEQ ID NO 75
<211> LENGTH: 321
<212> TYPE: DNA
<213> ORGANISM: Homo sapiens

<400> SEQUENCE: 75

```
gacatccagc tgacccagtc tccatcttcc ctgtctgcat ctgtaggaga cagagtcacc     60
atcacttgcc gggcaagtca gagcattagt aggtatttaa attggtatca gcaaaaacca    120
gggaaagccc ctaagctcct gctgtttgct gcttctactt tgctagatgg ggtcccatca    180
agattcagtg gcagtggatc tgggacagat ttcactctca ccatcagcag tctgcaacct    240
gaagattttg caacttacta ctgtcaacgg aatcacagtc cctcgtggac gttcggccaa    300
gggaccaggg tggaaatcaa a                                              321
```

<210> SEQ ID NO 76
<211> LENGTH: 107
<212> TYPE: PRT
<213> ORGANISM: Homo sapiens

<400> SEQUENCE: 76

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Leu
        35                  40                  45

Phe Ala Ala Ser Thr Leu Leu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Asn His Ser Pro Ser Trp
                85                  90                  95

Thr Phe Gly Gln Gly Thr Arg Val Glu Ile Lys
            100                 105

<210> SEQ ID NO 77
<211> LENGTH: 11
<212> TYPE: PRT
<213> ORGANISM: Homo sapiens

<400> SEQUENCE: 77

Arg Ala Ser Gln Ser Ile Ser Arg Tyr Leu Asn
1               5                   10

<210> SEQ ID NO 78
<211> LENGTH: 7
<212> TYPE: PRT
<213> ORGANISM: Homo sapiens

<400> SEQUENCE: 78

Ala Ala Ser Thr Leu Leu Asp
1               5

<210> SEQ ID NO 79
<211> LENGTH: 9
<212> TYPE: PRT
<213> ORGANISM: Homo sapiens

<400> SEQUENCE: 79

Gln Arg Asn His Ser Pro Ser Trp Thr
1               5

<210> SEQ ID NO 80
<211> LENGTH: 372
<212> TYPE: DNA
<213> ORGANISM: Homo sapiens

<400> SEQUENCE: 80

```
caggtgcagc tgcaagagtc gggcccggga ctggtgaagc cttcggagac cctgtccctc      60
aactgcgctg tctctggagg ctccatcagt aattactact ggagctggat ccggcagccc     120
cccgggaagg gactggagtg gattggctat atctcttaca atgggaggcc caagtacaac     180
ccctccctca cgagtcgagt caccatatcc gtcgacacgt ccaaggacca gttctccctg     240
gagctgcgct ctgtgaccgc tgcggacacg gccctttatt actgtgcgag agaaacgcgg     300
ttcggggagt tattatctcc ctatgatgct tttgaaatct ggggccaagg gacaatggtc     360
accgtctcct ca                                                         372
```

<210> SEQ ID NO 81
<211> LENGTH: 124
<212> TYPE: PRT
<213> ORGANISM: Homo sapiens

<400> SEQUENCE: 81

Gln Val Gln Leu Gln Glu Ser Gly Pro Gly Leu Val Lys Pro Ser Glu
1               5                   10                  15

Thr Leu Ser Leu Asn Cys Ala Val Ser Gly Gly Ser Ile Ser Asn Tyr
                20                  25                  30

Tyr Trp Ser Trp Ile Arg Gln Pro Pro Gly Lys Gly Leu Glu Trp Ile
            35                  40                  45

Gly Tyr Ile Ser Tyr Asn Gly Arg Pro Lys Tyr Asn Pro Ser Leu Thr
        50                  55                  60

Ser Arg Val Thr Ile Ser Val Asp Thr Ser Lys Asp Gln Phe Ser Leu
65                  70                  75                  80

Glu Leu Arg Ser Val Thr Ala Ala Asp Thr Ala Leu Tyr Tyr Cys Ala
                85                  90                  95

Arg Glu Thr Arg Phe Gly Glu Leu Leu Ser Pro Tyr Asp Ala Phe Glu
            100                 105                 110

Ile Trp Gly Gln Gly Thr Met Val Thr Val Ser Ser
        115                 120

<210> SEQ ID NO 82
<211> LENGTH: 5
<212> TYPE: PRT
<213> ORGANISM: Homo sapiens

<400> SEQUENCE: 82

Asn Tyr Tyr Trp Ser
1               5

<210> SEQ ID NO 83
<211> LENGTH: 16
<212> TYPE: PRT
<213> ORGANISM: Homo sapiens

<400> SEQUENCE: 83

Tyr Ile Ser Tyr Asn Gly Arg Pro Lys Tyr Asn Pro Ser Leu Thr Ser
1               5                   10                  15

<210> SEQ ID NO 84
<211> LENGTH: 16
<212> TYPE: PRT
<213> ORGANISM: Homo sapiens

<400> SEQUENCE: 84

Glu Thr Arg Phe Gly Glu Leu Leu Ser Pro Tyr Asp Ala Phe Glu Ile
1               5                   10                  15

<210> SEQ ID NO 85
<211> LENGTH: 6
<212> TYPE: PRT
<213> ORGANISM: Homo sapiens

<400> SEQUENCE: 85

Gly Gly Ser Ile Ser Asn
1               5

<210> SEQ ID NO 86
<211> LENGTH: 9
<212> TYPE: PRT
<213> ORGANISM: Homo sapiens

<400> SEQUENCE: 86

Tyr Ile Ser Tyr Asn Gly Arg Pro Lys
1               5

<210> SEQ ID NO 87
<211> LENGTH: 321
<212> TYPE: DNA
<213> ORGANISM: Homo sapiens

<400> SEQUENCE: 87
gacatccaga tgacccagtc tccatcctcc ctgtctgcat ctgtaggaga cagagtcacc    60
atgacttgcc gggcaagtca gaacattaga agctatttaa attggtatca gcagagacca   120
gggacagccc ctaaactcct gatctatgct gcatccactt tacacagtgg ggtcccatca   180
aggttcagtg gcggtgggtc tgggacagat ttcactctca ccatcaataa tctgcaacct   240
gaagattttg catcttacta ctgtcaacag agttacgata accctcagac gttcggccaa   300
gggaccaagg tggaaatcaa a                                              321

<210> SEQ ID NO 88
<211> LENGTH: 107
<212> TYPE: PRT
<213> ORGANISM: Homo sapiens

<400> SEQUENCE: 88

Asp Ile Gln Met Thr Gln Ser Pro Ser Ser Leu Ser Ala Ser Val Gly
1               5                   10                  15

Asp Arg Val Thr Met Thr Cys Arg Ala Ser Gln Asn Ile Arg Ser Tyr
            20                  25                  30

Leu Asn Trp Tyr Gln Gln Arg Pro Gly Thr Ala Pro Lys Leu Leu Ile

```
            35                  40                  45
Tyr Ala Ala Ser Thr Leu His Ser Gly Val Pro Ser Arg Phe Ser Gly
         50                  55                  60

Gly Gly Ser Gly Thr Asp Phe Thr Leu Thr Ile Asn Asn Leu Gln Pro
 65                  70                  75                  80

Glu Asp Phe Ala Ser Tyr Tyr Cys Gln Gln Ser Tyr Asp Asn Pro Gln
                 85                  90                  95

Thr Phe Gly Gln Gly Thr Lys Val Glu Ile Lys
            100                 105
```

<210> SEQ ID NO 89
<211> LENGTH: 11
<212> TYPE: PRT
<213> ORGANISM: Homo sapiens

<400> SEQUENCE: 89

```
Arg Ala Ser Gln Asn Ile Arg Ser Tyr Leu Asn
 1               5                   10
```

<210> SEQ ID NO 90
<211> LENGTH: 7
<212> TYPE: PRT
<213> ORGANISM: Homo sapiens

<400> SEQUENCE: 90

```
Ala Ala Ser Thr Leu His Ser
 1               5
```

<210> SEQ ID NO 91
<211> LENGTH: 9
<212> TYPE: PRT
<213> ORGANISM: Homo sapiens

<400> SEQUENCE: 91

```
Gln Gln Ser Tyr Asp Asn Pro Gln Thr
 1               5
```

<210> SEQ ID NO 92
<211> LENGTH: 399
<212> TYPE: DNA
<213> ORGANISM: Homo sapiens

<400> SEQUENCE: 92

```
caggtgcagc tggtgcagtc tgggtctgag gtgaagaagc ctggggcctc agtgaaggtc      60
tcctgcaagg cttctggata caccttcacc aattatgaca tcaactggat tcgacaggcc     120
cctggtcaag acttgagtg gatgggctgg ataaatccca acagtggaac cacgggctct     180
gcacagaggt tccagggcag agtcaccata accgtggaca cctccataac cacagtctac     240
atggaactga gcagcctgag atctgacgac acggccattt actactgcgc gagaggccgt     300
gagctcctcc ggcttcaaca ttttttgact gactcccagt ccgagaggag ggactgcttc     360
gaccccctggg gccagggaac cctggtcacc gtctcctca                           399
```

<210> SEQ ID NO 93
<211> LENGTH: 133
<212> TYPE: PRT
<213> ORGANISM: Homo sapiens

<400> SEQUENCE: 93

```
Gln Val Gln Leu Val Gln Ser Gly Ser Glu Val Lys Lys Pro Gly Ala
 1               5                   10                  15
```

-continued

```
Ser Val Lys Val Ser Cys Lys Ala Ser Gly Tyr Thr Phe Thr Asn Tyr
            20                  25                  30

Asp Ile Asn Trp Ile Arg Gln Ala Pro Gly Gln Gly Leu Glu Trp Met
         35                  40                  45

Gly Trp Ile Asn Pro Asn Ser Gly Thr Thr Gly Ser Ala Gln Arg Phe
 50                  55                  60

Gln Gly Arg Val Thr Ile Thr Val Asp Thr Ser Ile Thr Thr Val Tyr
 65                  70                  75                  80

Met Glu Leu Ser Ser Leu Arg Ser Asp Asp Thr Ala Ile Tyr Tyr Cys
                 85                  90                  95

Ala Arg Gly Arg Glu Leu Leu Arg Leu Gln His Phe Leu Thr Asp Ser
             100                 105                 110

Gln Ser Glu Arg Arg Asp Cys Phe Asp Pro Trp Gly Gln Gly Thr Leu
         115                 120                 125

Val Thr Val Ser Ser
    130
```

<210> SEQ ID NO 94
<211> LENGTH: 5
<212> TYPE: PRT
<213> ORGANISM: Homo sapiens

<400> SEQUENCE: 94

```
Asn Tyr Asp Ile Asn
1               5
```

<210> SEQ ID NO 95
<211> LENGTH: 17
<212> TYPE: PRT
<213> ORGANISM: Homo sapiens

<400> SEQUENCE: 95

```
Trp Ile Asn Pro Asn Ser Gly Thr Thr Gly Ser Ala Gln Arg Phe Gln
1               5                  10                  15

Gly
```

<210> SEQ ID NO 96
<211> LENGTH: 24
<212> TYPE: PRT
<213> ORGANISM: Homo sapiens

<400> SEQUENCE: 96

```
Gly Arg Glu Leu Leu Arg Leu Gln His Phe Leu Thr Asp Ser Gln Ser
1               5                  10                  15

Glu Arg Arg Asp Cys Phe Asp Pro
            20
```

<210> SEQ ID NO 97
<211> LENGTH: 6
<212> TYPE: PRT
<213> ORGANISM: Homo sapiens

<400> SEQUENCE: 97

```
Gly Tyr Thr Phe Thr Asn
1               5
```

<210> SEQ ID NO 98
<211> LENGTH: 10
<212> TYPE: PRT
<213> ORGANISM: Homo sapiens

<400> SEQUENCE: 98

Trp Ile Asn Pro Asn Ser Gly Thr Thr Gly
1               5                   10

<210> SEQ ID NO 99
<211> LENGTH: 321
<212> TYPE: DNA
<213> ORGANISM: Homo sapiens

<400> SEQUENCE: 99
gatatccaga tgacccagtc tccttcctcc ctgtctgcat ctgtaggaga cagagtcacc    60
atcacttgcc gggcaaatca agacattggc atttatttaa attggtatca acagaatcca   120
gggaaagtcc ctaaactcct gctccatggt gcgtccagtt tgcagggcgg ggtcccatca   180
aggttcagtg ccagtggatc tgggacagat ttcactctca ccattcacag tctacaacct   240
gaagatttag caacctacta ctgtcaacag agtcgccgtc taccgtacac ttttggccag   300
gggaccaggg tggaactcaa a                                             321

<210> SEQ ID NO 100
<211> LENGTH: 107
<212> TYPE: PRT
<213> ORGANISM: Homo sapiens

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Asp Ile Gly Ile Tyr
            20                  25                  30

Leu Asn Trp Tyr Gln Gln Asn Pro Gly Lys Val Pro Lys Leu Leu Leu
        35                  40                  45

His Gly Ala Ser Ser Leu Gln Gly Gly Val Pro Ser Arg Phe Ser Ala
    50                  55                  60

Ser Gly Ser Gly Thr Asp Phe Thr Leu Thr Ile His Ser Leu Gln Pro
65                  70                  75                  80

Glu Asp Leu Ala Thr Tyr Tyr Cys Gln Gln Ser Arg Arg Leu Pro Tyr
                85                  90                  95

Thr Phe Gly Gln Gly Thr Arg Val Glu Leu Lys
            100                 105

<210> SEQ ID NO 101
<211> LENGTH: 11
<212> TYPE: PRT
<213> ORGANISM: Homo sapiens

<400> SEQUENCE: 101

Arg Ala Asn Gln Asp Ile Gly Ile Tyr Leu Asn
1               5                   10

<210> SEQ ID NO 102
<211> LENGTH: 7
<212> TYPE: PRT
<213> ORGANISM: Homo sapiens

<400> SEQUENCE: 102

Gly Ala Ser Ser Leu Gln Gly
1               5

<210> SEQ ID NO 103

```
<211> LENGTH: 9
<212> TYPE: PRT
<213> ORGANISM: Homo sapiens

<400> SEQUENCE: 103

Gln Gln Ser Arg Arg Leu Pro Tyr Thr
1               5

<210> SEQ ID NO 104
<211> LENGTH: 360
<212> TYPE: DNA
<213> ORGANISM: Homo sapiens

<400> SEQUENCE: 104
cagatcacct tgagggagtc tggtcctacg ctggtgaaac ccacacagac cctcacgctg      60
acctgcacct tctctgggtt ttcactcagc actaatggag tgaatgtggg ctggatccgt    120
cagcccccag gaaaggccct ggagtggctt gcactcattt actgggatga tgataagcgc    180
tacagtccgt ctctgaagag aaggctcacc atcaccaagg acacctccaa aaaccaagtg    240
gtccttacac tgaccaacat ggaccctgta gatacagcca catattactg tgcacacaga    300
cccgacttct atggtgactt cgagtactgg ggcccgggaa ccctggtcac cgtctcctca    360

<210> SEQ ID NO 105
<211> LENGTH: 120
<212> TYPE: PRT
<213> ORGANISM: Homo sapiens

<400> SEQUENCE: 105

Gln Ile Thr Leu Arg Glu Ser Gly Pro Thr Leu Val Lys Pro Thr Gln
1               5                   10                  15

Thr Leu Thr Leu Thr Cys Thr Phe Ser Gly Phe Ser Leu Ser Thr Asn
            20                  25                  30

Gly Val Asn Val Gly Trp Ile Arg Gln Pro Pro Gly Lys Ala Leu Glu
        35                  40                  45

Trp Leu Ala Leu Ile Tyr Trp Asp Asp Asp Lys Arg Tyr Ser Pro Ser
    50                  55                  60

Leu Lys Arg Arg Leu Thr Ile Thr Lys Asp Thr Ser Lys Asn Gln Val
65                  70                  75                  80

Val Leu Thr Leu Thr Asn Met Asp Pro Val Asp Thr Ala Thr Tyr Tyr
                85                  90                  95

Cys Ala His Arg Pro Asp Phe Tyr Gly Asp Phe Glu Tyr Trp Gly Pro
            100                 105                 110

Gly Thr Leu Val Thr Val Ser Ser
        115                 120

<210> SEQ ID NO 106
<211> LENGTH: 7
<212> TYPE: PRT
<213> ORGANISM: Homo sapiens

<400> SEQUENCE: 106

Thr Asn Gly Val Asn Val Gly
1               5

<210> SEQ ID NO 107
<211> LENGTH: 16
<212> TYPE: PRT
<213> ORGANISM: Homo sapiens

<400> SEQUENCE: 107
```

```
Leu Ile Tyr Trp Asp Asp Asp Lys Arg Tyr Ser Pro Ser Leu Lys Arg
1               5                   10                  15
```

<210> SEQ ID NO 108
<211> LENGTH: 10
<212> TYPE: PRT
<213> ORGANISM: Homo sapiens

<400> SEQUENCE: 108

```
Arg Pro Asp Phe Tyr Gly Asp Phe Glu Tyr
1               5                   10
```

<210> SEQ ID NO 109
<211> LENGTH: 8
<212> TYPE: PRT
<213> ORGANISM: Homo sapiens

<400> SEQUENCE: 109

```
Gly Phe Ser Leu Ser Thr Asn Gly
1               5
```

<210> SEQ ID NO 110
<211> LENGTH: 9
<212> TYPE: PRT
<213> ORGANISM: Homo sapiens

<400> SEQUENCE: 110

```
Leu Ile Tyr Trp Asp Asp Asp Lys Arg
1               5
```

<210> SEQ ID NO 111
<211> LENGTH: 330
<212> TYPE: PRT
<213> ORGANISM: Homo sapiens

<400> SEQUENCE: 111

```
Cys Ala Gly Thr Cys Thr Gly Cys Ala Cys Thr Gly Cys Thr Cys
1               5                   10                  15

Ala Gly Cys Cys Thr Gly Cys Cys Thr Cys Cys Gly Thr Gly Thr Cys
                20                  25                  30

Thr Gly Gly Gly Thr Cys Thr Cys Cys Gly Gly Ala Cys Ala Gly
                35                  40                  45

Thr Cys Gly Ala Thr Cys Ala Cys Cys Ala Thr Cys Thr Cys Cys Thr
    50                  55                  60

Gly Cys Ala Cys Thr Gly Gly Ala Ala Gly Cys Ala Gly Cys Ala Gly
65                  70                  75                  80

Thr Gly Ala Cys Ala Thr Thr Gly Gly Thr Gly Gly Thr Thr Ala Thr
                85                  90                  95

Ala Ala Cys Thr Ala Thr Gly Thr Cys Thr Cys Cys Thr Gly Gly Thr
                100                 105                 110

Ala Cys Cys Ala Ala Cys Ala Cys Ala Cys Cys Cys Ala Gly Gly
                115                 120                 125

Cys Ala Ala Gly Gly Cys Cys Cys Cys Ala Ala Ala Cys Thr Cys
        130                 135                 140

Ala Thr Gly Ala Thr Thr Thr Ala Thr Gly Gly Thr Gly Thr Cys Ala
145                 150                 155                 160

Ala Thr Ala Ala Thr Cys Gly Gly Cys Cys Thr Cys Ala Gly Gly
                165                 170                 175

Gly Gly Thr Thr Thr Cys Thr Ala Ala Thr Cys Gly Cys Thr Thr Cys
```

```
                    180                 185                 190
Thr Cys Thr Gly Gly Cys Thr Cys Cys Ala Ala Gly Thr Cys Thr Gly
            195                 200                 205
Gly Cys Ala Ala Cys Ala Cys Gly Gly Cys Cys Thr Cys Cys Cys Thr
            210                 215                 220
Gly Ala Cys Thr Ala Thr Cys Thr Cys Thr Gly Gly Cys Cys Thr Cys
225                 230                 235                 240
Cys Ala Gly Ala Cys Thr Gly Ala Cys Gly Ala Cys Gly Ala Gly Gly
                    245                 250                 255
Cys Thr Gly Ala Thr Thr Ala Thr Thr Ala Cys Thr Gly Cys Gly Gly
            260                 265                 270
Cys Thr Cys Ala Thr Ala Thr Ala Cys Ala Gly Gly Cys Ala Gly Thr
            275                 280                 285
Cys Cys Thr Cys Ala Thr Thr Ala Thr Gly Thr Cys Thr Thr Cys Gly
            290                 295                 300
Gly Ala Ala Cys Thr Gly Gly Ala Cys Cys Ala Ala Gly Gly Thr
305                 310                 315                 320
Cys Ala Cys Cys Gly Thr Cys Cys Thr Ala
                    325                 330

<210> SEQ ID NO 112
<211> LENGTH: 110
<212> TYPE: PRT
<213> ORGANISM: Homo sapiens

<400> SEQUENCE: 112

Gln Ser Ala Leu Thr Gln Pro Ala Ser Val Ser Gly Ser Pro Gly Gln
1               5                   10                  15
Ser Ile Thr Ile Ser Cys Thr Gly Ser Ser Ser Asp Ile Gly Gly Tyr
                20                  25                  30
Asn Tyr Val Ser Trp Tyr Gln Gln His Pro Gly Lys Ala Pro Lys Leu
            35                  40                  45
Met Ile Tyr Asp Val Asn Asn Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Thr Asp Asp Glu Ala Asp Tyr Tyr Cys Gly Ser Tyr Thr Gly Ser
                85                  90                  95
Pro His Tyr Val Phe Gly Thr Gly Thr Lys Val Thr Val Leu
                100                 105                 110

<210> SEQ ID NO 113
<211> LENGTH: 14
<212> TYPE: PRT
<213> ORGANISM: Homo sapiens

<400> SEQUENCE: 113

Thr Gly Ser Ser Ser Asp Ile Gly Gly Tyr Asn Tyr Val Ser
1               5                   10

<210> SEQ ID NO 114
<211> LENGTH: 7
<212> TYPE: PRT
<213> ORGANISM: Homo sapiens

<400> SEQUENCE: 114

Asp Val Asn Asn Arg Pro Ser
1               5
```

<210> SEQ ID NO 115
<211> LENGTH: 10
<212> TYPE: PRT
<213> ORGANISM: Homo sapiens

<400> SEQUENCE: 115

Gly Ser Tyr Thr Gly Ser Pro His Tyr Val
1               5                   10

<210> SEQ ID NO 116
<211> LENGTH: 363
<212> TYPE: DNA
<213> ORGANISM: Homo sapiens

<400> SEQUENCE: 116

```
caggtccaac tggtgcaatc tggggctgag gtgaggaagc ctgggtcctc ggtgaaggtc      60
tcctgcaagg cttctggagg ccccttcatg agttatgcta tcggctgggt gcgacaggcc     120
cctggacaag ggcttgagtg gatgggaggg atcaaccctg tgtttggtag accgcactac     180
gcacagaagt tccagggcag agtcaccatc gccacggacg actccacgaa gacatcgtac     240
atggaactga gtagcctgac gtctgaggac acgggcatgt attactgtgc gagtaggtat     300
agtaggtcgt ccccagggac ctttgagtcc tggggccagg gaaccctggt caccgtctcg     360
agc                                                                   363
```

<210> SEQ ID NO 117
<211> LENGTH: 121
<212> TYPE: PRT
<213> ORGANISM: Homo sapiens

<400> SEQUENCE: 117

Gln Val Gln Leu Val Gln Ser Gly Ala Glu Val Arg Lys Pro Gly Ser
1               5                   10                  15

Ser Val Lys Val Ser Cys Lys Ala Ser Gly Gly Pro Phe Met Ser Tyr
                20                  25                  30

Ala Ile Gly Trp Val Arg Gln Ala Pro Gly Gln Gly Leu Glu Trp Met
            35                  40                  45

Gly Gly Ile Asn Pro Val Phe Gly Arg Pro His Tyr Ala Gln Lys Phe
        50                  55                  60

Gln Gly Arg Val Thr Ile Ala Thr Asp Asp Ser Thr Lys Thr Ser Tyr
65                  70                  75                  80

Met Glu Leu Ser Ser Leu Thr Ser Glu Asp Thr Gly Met Tyr Tyr Cys
                85                  90                  95

Ala Ser Arg Tyr Ser Arg Ser Ser Pro Gly Thr Phe Glu Ser Trp Gly
                100                 105                 110

Gln Gly Thr Leu Val Thr Val Ser Ser
            115                 120

<210> SEQ ID NO 118
<211> LENGTH: 5
<212> TYPE: PRT
<213> ORGANISM: Homo sapiens

<400> SEQUENCE: 118

Ser Tyr Ala Ile Gly
1               5

<210> SEQ ID NO 119

<211> LENGTH: 17
<212> TYPE: PRT
<213> ORGANISM: Homo sapiens

<400> SEQUENCE: 119

Gly Ile Asn Pro Val Phe Gly Arg Pro His Tyr Ala Gln Lys Phe Gln
1               5                   10                  15
Gly

<210> SEQ ID NO 120
<211> LENGTH: 12
<212> TYPE: PRT
<213> ORGANISM: Homo sapiens

<400> SEQUENCE: 120

Arg Tyr Ser Arg Ser Ser Pro Gly Thr Phe Glu Ser
1               5                   10

<210> SEQ ID NO 121
<211> LENGTH: 6
<212> TYPE: PRT
<213> ORGANISM: Homo sapiens

<400> SEQUENCE: 121

Gly Gly Pro Phe Met Ser
1               5

<210> SEQ ID NO 122
<211> LENGTH: 10
<212> TYPE: PRT
<213> ORGANISM: Homo sapiens

<400> SEQUENCE: 122

Gly Ile Asn Pro Val Phe Gly Arg Pro His
1               5                   10

<210> SEQ ID NO 123
<211> LENGTH: 327
<212> TYPE: DNA
<213> ORGANISM: Homo sapiens

<400> SEQUENCE: 123
gaaatagtga tgacgcagtt tccagccacc ctgtctgtgt ctcccgggga acgagtcacc      60
ctctcctgta gggccagtca gagtgttagc aacaatttag cctggtacca gcaaaaacct    120
ggccagcctc ccaggctcct catctatgat gcatctacca gggccacggg tgtcccagcc    180
aagttcagtg gcactgggtc tggcacagag ttcactctca gcatcagcag cctgcagtcc    240
gaagattttg cagtttatta ctgtcagcag tatcacaact ggcctccctc gtacagtttt    300
ggcctgggga ccaagctgga gatcaaa                                        327

<210> SEQ ID NO 124
<211> LENGTH: 109
<212> TYPE: PRT
<213> ORGANISM: Homo sapiens

<400> SEQUENCE: 124

Glu Ile Val Met Thr Gln Phe Pro Ala Thr Leu Ser Val Ser Pro Gly
1               5                   10                  15

Glu Arg Val Thr Leu Ser Cys Arg Ala Ser Gln Ser Val Ser Asn Asn
            20                  25                  30

Leu Ala Trp Tyr Gln Gln Lys Pro Gly Gln Pro Pro Arg Leu Leu Ile

```
                35                  40                  45
Tyr Asp Ala Ser Thr Arg Ala Thr Gly Val Pro Ala Lys Phe Ser Gly
 50                  55                  60

Thr Gly Ser Gly Thr Glu Phe Thr Leu Ser Ile Ser Ser Leu Gln Ser
 65                  70                  75                  80

Glu Asp Phe Ala Val Tyr Tyr Cys Gln Gln Tyr His Asn Trp Pro Pro
                 85                  90                  95

Ser Tyr Ser Phe Gly Leu Gly Thr Lys Leu Glu Ile Lys
            100                 105

<210> SEQ ID NO 125
<211> LENGTH: 11
<212> TYPE: PRT
<213> ORGANISM: Homo sapiens

<400> SEQUENCE: 125

Arg Ala Ser Gln Ser Val Ser Asn Asn Leu Ala
 1               5                  10

<210> SEQ ID NO 126
<211> LENGTH: 7
<212> TYPE: PRT
<213> ORGANISM: Homo sapiens

<400> SEQUENCE: 126

Asp Ala Ser Thr Arg Ala Thr
 1               5

<210> SEQ ID NO 127
<211> LENGTH: 11
<212> TYPE: PRT
<213> ORGANISM: Homo sapiens

<400> SEQUENCE: 127

Gln Gln Tyr His Asn Trp Pro Pro Ser Tyr Ser
 1               5                  10

<210> SEQ ID NO 128
<211> LENGTH: 387
<212> TYPE: DNA
<213> ORGANISM: Homo sapiens

<400> SEQUENCE: 128
gaggtgcagc tggtggagtc tgggggagac ttggtacagc cagggcggtc cctgaaactc      60
tcctgcacag gttctggatt cacctttggt gattatggtg tgacctgggt ccgccaggct     120
ccagggaagg ggctggagtg ggtaggtttc attagaacca gaccttgggg tgggacagca     180
gataccgccg cgtctgtgaa aggcagattc actatttcaa gagatgattc caaaagtctc     240
gcctatctgc aaatgaacag cctgaaaacc gaggacacag ccgtgtatta ctgttgtaga     300
gatgcccctc caaatgtgga agtggcttct atgaccaact ggtacttcga tctctggggc     360
cgtggcaccc tggtcaccgt ctcctca                                         387

<210> SEQ ID NO 129
<211> LENGTH: 129
<212> TYPE: PRT
<213> ORGANISM: Homo sapiens

<400> SEQUENCE: 129

Glu Val Gln Leu Val Glu Ser Gly Gly Asp Leu Val Gln Pro Gly Arg
 1               5                  10                  15
```

Ser Leu Lys Leu Ser Cys Thr Gly Ser Gly Phe Thr Phe Gly Asp Tyr
            20                  25                  30

Gly Val Thr Trp Val Arg Gln Ala Pro Gly Lys Gly Leu Glu Trp Val
        35                  40                  45

Gly Phe Ile Arg Thr Arg Pro Trp Gly Gly Thr Ala Asp Thr Ala Ala
    50                  55                  60

Ser Val Lys Gly Arg Phe Thr Ile Ser Arg Asp Asp Ser Lys Ser Leu
65                  70                  75                  80

Ala Tyr Leu Gln Met Asn Ser Leu Lys Thr Glu Asp Thr Ala Val Tyr
                85                  90                  95

Tyr Cys Cys Arg Asp Ala Pro Pro Asn Val Glu Val Ala Ser Met Thr
            100                 105                 110

Asn Trp Tyr Phe Asp Leu Trp Gly Arg Gly Thr Leu Val Thr Val Ser
            115                 120                 125

Ser

<210> SEQ ID NO 130
<211> LENGTH: 5
<212> TYPE: PRT
<213> ORGANISM: Homo sapiens

<400> SEQUENCE: 130

Asp Tyr Gly Val Thr
1               5

<210> SEQ ID NO 131
<211> LENGTH: 19
<212> TYPE: PRT
<213> ORGANISM: Homo sapiens

<400> SEQUENCE: 131

Phe Ile Arg Thr Arg Pro Trp Gly Gly Thr Ala Asp Thr Ala Ala Ser
1               5                   10                  15

Val Lys Gly

<210> SEQ ID NO 132
<211> LENGTH: 18
<212> TYPE: PRT
<213> ORGANISM: Homo sapiens

<400> SEQUENCE: 132

Asp Ala Pro Pro Asn Val Glu Val Ala Ser Met Thr Asn Trp Tyr Phe
1               5                   10                  15

Asp Leu

<210> SEQ ID NO 133
<211> LENGTH: 6
<212> TYPE: PRT
<213> ORGANISM: Homo sapiens

<400> SEQUENCE: 133

Gly Phe Thr Phe Gly Asp
1               5

<210> SEQ ID NO 134
<211> LENGTH: 12
<212> TYPE: PRT
<213> ORGANISM: Homo sapiens

<400> SEQUENCE: 134

Phe Ile Arg Thr Arg Pro Trp Gly Gly Thr Ala Asp
1               5                   10

<210> SEQ ID NO 135
<211> LENGTH: 318
<212> TYPE: DNA
<213> ORGANISM: Homo sapiens

<400> SEQUENCE: 135
gacatccagc tgacccagtc tccatcctcc ctgtctgcat ctgtgggaga cagagtcacc      60
atcacttgcc gggcgagtca gggcattctc aattgtttag cctggtatca gcagaaaccg     120
gggaaagttc ctaacctcct gatgtatgct gcatccacat tgcagtcagg ggtcccatct     180
cggttcagcg gcagtggatt tgggacagat ttcactctca ccatcagcag cctgcagcct     240
gaagatgttg caacttatta ctgtcaaacg tatggcggtg tctctacttt cggcggaggg     300
accaaggtgg agatcaga                                                   318

<210> SEQ ID NO 136
<211> LENGTH: 106
<212> TYPE: PRT
<213> ORGANISM: Homo sapiens

<400> SEQUENCE: 136

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Leu Asn Cys
                20                  25                  30

Leu Ala Trp Tyr Gln Gln Lys Pro Gly Lys Val Pro Asn Leu Leu Met
            35                  40                  45

Tyr Ala Ala Ser Thr Leu Gln Ser Gly Val Pro Ser Arg Phe Ser Gly
        50                  55                  60

Ser Gly Phe Gly Thr Asp Phe Thr Leu Thr Ile Ser Ser Leu Gln Pro
65                  70                  75                  80

Glu Asp Val Ala Thr Tyr Tyr Cys Gln Thr Tyr Gly Gly Val Ser Thr
                85                  90                  95

Phe Gly Gly Gly Thr Lys Val Glu Ile Arg
            100                 105

<210> SEQ ID NO 137
<211> LENGTH: 11
<212> TYPE: PRT
<213> ORGANISM: Homo sapiens

<400> SEQUENCE: 137

Arg Ala Ser Gln Gly Ile Leu Asn Cys Leu Ala
1               5                   10

<210> SEQ ID NO 138
<211> LENGTH: 7
<212> TYPE: PRT
<213> ORGANISM: Homo sapiens

<400> SEQUENCE: 138

Ala Ala Ser Thr Leu Gln Ser
1               5

<210> SEQ ID NO 139
<211> LENGTH: 8
<212> TYPE: PRT

<210> SEQ ID NO 139 continued...

<213> ORGANISM: Homo sapiens

<400> SEQUENCE: 139

Gln Thr Tyr Gly Gly Val Ser Thr
1               5

<210> SEQ ID NO 140
<211> LENGTH: 372
<212> TYPE: DNA
<213> ORGANISM: Homo sapiens

<400> SEQUENCE: 140

```
caggtgcagc tgcaggagtc gggcccagga ctggtgaagc cttcggagac cttgtccctc      60
acctgcactg tctctggtgg ctccgtcagc agtgagactt actactggag ctggatccgg     120
cagcccccag ggaagggact agagtggatt ggatatatct attacattgg gaacaccgac     180
tacaggccct ccctcaagag tcgagtcacc atatcactgg acacgtccaa gaaccagttc     240
tccctgaagc tgagctctgt gaccgctgcg gacacggccg tttattactg tgcgagaggc     300
gcttattatg atagtagtgg ttacccggct tttatatatct ggggccaagg gacaatggtc     360
accgtctcct ca                                                         372
```

<210> SEQ ID NO 141
<211> LENGTH: 124
<212> TYPE: PRT
<213> ORGANISM: Homo sapiens

<400> SEQUENCE: 141

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Glu
            20                  25                  30

Thr Tyr Tyr Trp Ser Trp Ile Arg Gln Pro Pro Gly Lys Gly Leu Glu
        35                  40                  45

Trp Ile Gly Tyr Ile Tyr Tyr Ile Gly Asn Thr Asp Tyr Arg Pro Ser
    50                  55                  60

Leu Lys Ser Arg Val Thr Ile Ser Leu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ala Tyr Tyr Asp Ser Ser Gly Tyr Pro Ala Phe Tyr
            100                 105                 110

Ile Trp Gly Gln Gly Thr Met Val Thr Val Ser Ser
        115                 120

<210> SEQ ID NO 142
<211> LENGTH: 7
<212> TYPE: PRT
<213> ORGANISM: Homo sapiens

<400> SEQUENCE: 142

Ser Glu Thr Tyr Tyr Trp Ser
1               5

<210> SEQ ID NO 143
<211> LENGTH: 16
<212> TYPE: PRT
<213> ORGANISM: Homo sapiens

<400> SEQUENCE: 143

Tyr Ile Tyr Tyr Ile Gly Asn Thr Asp Tyr Arg Pro Ser Leu Lys Ser
1               5                   10                  15

<210> SEQ ID NO 144
<211> LENGTH: 14
<212> TYPE: PRT
<213> ORGANISM: Homo sapiens

<400> SEQUENCE: 144

Gly Ala Tyr Tyr Asp Ser Ser Gly Tyr Pro Ala Phe Tyr Ile
1               5                   10

<210> SEQ ID NO 145
<211> LENGTH: 8
<212> TYPE: PRT
<213> ORGANISM: Homo sapiens

<400> SEQUENCE: 145

Gly Gly Ser Val Ser Ser Glu Thr
1               5

<210> SEQ ID NO 146
<211> LENGTH: 9
<212> TYPE: PRT
<213> ORGANISM: Homo sapiens

<400> SEQUENCE: 146

Tyr Ile Tyr Tyr Ile Gly Asn Thr Asp
1               5

<210> SEQ ID NO 147
<211> LENGTH: 336
<212> TYPE: DNA
<213> ORGANISM: Homo sapiens

<400> SEQUENCE: 147
cagtctgtgc tgacgcagcc gccctcagtg tctggggccc cagggcagag ggtcaccatc      60
tcctgcactg ggagcagctc caacatcggg tcagattatg atgtgcactg gtacaagcaa     120
cttccaggaa cagcccccaa actcctcatc tttggtaaca gcaatcggcc ctcagggg tc     180 cctgaccgat tctctggctc caagtctggc acctcagcct ccctggccat cactgggctc     240
caggctgagg atgaggctga ttattactgc aatccctatg acagcagcct gagtggtttt     300
catgtcttcg gaagtgggac caaggtcacc gtccta                              336

<210> SEQ ID NO 148
<211> LENGTH: 112
<212> TYPE: PRT
<213> ORGANISM: Homo sapiens

<400> SEQUENCE: 148

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ser Asp
                20                  25                  30

Tyr Asp Val His Trp Tyr Lys Gln Leu Pro Gly Thr Ala Pro Lys Leu
            35                  40                  45

Leu Ile Phe Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Phe His Val Phe Gly Ser Gly Thr Lys Val Thr Val Leu
            100                 105                 110

<210> SEQ ID NO 149
<211> LENGTH: 14
<212> TYPE: PRT
<213> ORGANISM: Homo sapiens

<400> SEQUENCE: 149

Thr Gly Ser Ser Ser Asn Ile Gly Ser Asp Tyr Asp Val His
1               5                   10

<210> SEQ ID NO 150
<211> LENGTH: 7
<212> TYPE: PRT
<213> ORGANISM: Homo sapiens

<400> SEQUENCE: 150

Gly Asn Ser Asn Arg Pro Ser
1               5

<210> SEQ ID NO 151
<211> LENGTH: 12
<212> TYPE: PRT
<213> ORGANISM: Homo sapiens

<400> SEQUENCE: 151

Gln Ser Tyr Asp Ser Ser Leu Ser Gly Phe His Val
1               5                   10

<210> SEQ ID NO 152
<211> LENGTH: 354
<212> TYPE: DNA
<213> ORGANISM: Homo sapiens

<400> SEQUENCE: 152
caggtgcagc tggtgcagtc tggggctgac gtgaagaagc ctgggtcctc ggtgacggtc      60
tcctgcaagg cttctggagg cagcttcagc aactatggaa tcaactgggt gcgacaggcc     120
cctggacaag gcttgagtg gatgggggga atcatccctc tcattaatgc accgaactac     180
gcaccgaagt tccagggcag agtgacgatt accgcggaca tgttctcgaa tatagtctcc     240
ttgcagttga ccagcctgag aactgacgac acggccgtgt attattgtgc gagacgaaaa     300
atgactacgg ctattgacta ttggggccag ggaaccctgg tcaccgtctc ctca           354

<210> SEQ ID NO 153
<211> LENGTH: 118
<212> TYPE: PRT
<213> ORGANISM: Homo sapiens

<400> SEQUENCE: 153

Gln Val Gln Leu Val Gln Ser Gly Ala Asp Val Lys Lys Pro Gly Ser
1               5                   10                  15

Ser Val Thr Val Ser Cys Lys Ala Ser Gly Gly Ser Phe Ser Asn Tyr
            20                  25                  30

Gly Ile Asn Trp Val Arg Gln Ala Pro Gly Gln Gly Leu Glu Trp Met
        35                  40                  45

Gly Gly Ile Ile Pro Leu Ile Asn Ala Pro Asn Tyr Ala Pro Lys Phe
    50                  55                  60

```
Gln Gly Arg Val Thr Ile Thr Ala Asp Met Phe Ser Asn Ile Val Ser
 65                  70                  75                  80

Leu Gln Leu Thr Ser Leu Arg Thr Asp Asp Thr Ala Val Tyr Tyr Cys
                 85                  90                  95

Ala Arg Arg Lys Met Thr Thr Ala Ile Asp Tyr Trp Gly Gln Gly Thr
            100                 105                 110

Leu Val Thr Val Ser Ser
        115
```

<210> SEQ ID NO 154
<211> LENGTH: 5
<212> TYPE: PRT
<213> ORGANISM: Homo sapiens

<400> SEQUENCE: 154

```
Asn Tyr Gly Ile Asn
 1               5
```

<210> SEQ ID NO 155
<211> LENGTH: 17
<212> TYPE: PRT
<213> ORGANISM: Homo sapiens

<400> SEQUENCE: 155

```
Gly Ile Ile Pro Leu Ile Asn Ala Pro Asn Tyr Ala Pro Lys Phe Gln
 1               5                  10                  15

Gly
```

<210> SEQ ID NO 156
<211> LENGTH: 9
<212> TYPE: PRT
<213> ORGANISM: Homo sapiens

<400> SEQUENCE: 156

```
Arg Lys Met Thr Thr Ala Ile Asp Tyr
 1               5
```

<210> SEQ ID NO 157
<211> LENGTH: 12
<212> TYPE: PRT
<213> ORGANISM: Homo sapiens

<400> SEQUENCE: 157

```
Arg Ala Ser Gln Ser Val Ser Ser Ser Gln Leu Ala
 1               5                  10
```

<210> SEQ ID NO 158
<211> LENGTH: 10
<212> TYPE: PRT
<213> ORGANISM: Homo sapiens

<400> SEQUENCE: 158

```
Gly Ile Ile Pro Leu Ile Asn Ala Pro Asn
 1               5                  10
```

<210> SEQ ID NO 159
<211> LENGTH: 354
<212> TYPE: DNA
<213> ORGANISM: Homo sapiens

<400> SEQUENCE: 159

```
cagcctgttc tgactcagcc accttctgca tcagcctccc tgggagcctc ggtcacactc     60
```

```
acctgcaccc tgagcagcgc ctacagtaat tataaagtgg actggtacca gcagagacca        120
gggaagggcc cccgctttgt gatgcgagtg ggcactggtg ggattgtggg atccaagggg        180
gatggcatcc ctgatcgctt ctcagtcttg ggctcaggcc tgaatcggta cctgaccatc        240
aagaacatcc aggaagagga tgagagtgac taccactgtg gggcagacca tggcagtggg        300
agcaacttcg tgtcccctta cgtattcggc ggagggacca agctgaccgt ccta             354

<210> SEQ ID NO 160
<211> LENGTH: 354
<212> TYPE: DNA
<213> ORGANISM: Homo sapiens

<400> SEQUENCE: 160
caggtccagc tggtgcagtc tggggctgag gtgaagaagc cagggtcctc ggtgaaggtc         60
tcctgcaggg aatctggagg caccttcaac ggctacacta tcacctgggt gcgacaggcc        120
cctgggcaag gccttgagtg gatgggaggg atcatcccta tgatgggac agtcaactac        180 gcacagaagt tgcagggcag agtcaccatt accacggact atttcacgaa aacagcctac        240
atggatctga caatttaag atctgaagac acggccatgt attattgtgt gaaaatcaga        300
tatactgggc agcagctgct ctggggccag ggaaccctgg tcaccgtctc ctca             354

<210> SEQ ID NO 161
<211> LENGTH: 118
<212> TYPE: PRT
<213> ORGANISM: Homo sapiens

<400> SEQUENCE: 161

Gln Val Gln Leu Val Gln Ser Gly Ala Glu Val Lys Lys Pro Gly Ser
1               5                   10                  15

Ser Val Lys Val Ser Cys Arg Glu Ser Gly Gly Thr Phe Asn Gly Tyr
            20                  25                  30

Thr Ile Thr Trp Val Arg Gln Ala Pro Gly Gln Gly Leu Glu Trp Met
        35                  40                  45

Gly Gly Ile Ile Pro Met Met Gly Thr Val Asn Tyr Ala Gln Lys Leu
    50                  55                  60

Gln Gly Arg Val Thr Ile Thr Thr Asp Tyr Phe Thr Lys Thr Ala Tyr
65                  70                  75                  80

Met Asp Leu Asn Asn Leu Arg Ser Glu Asp Thr Ala Met Tyr Tyr Cys
                85                  90                  95

Val Lys Ile Arg Tyr Thr Gly Gln Gln Leu Leu Trp Gly Gln Gly Thr
            100                 105                 110

Leu Val Thr Val Ser Ser
        115

<210> SEQ ID NO 162
<211> LENGTH: 5
<212> TYPE: PRT
<213> ORGANISM: Homo sapiens

<400> SEQUENCE: 162

Gly Tyr Thr Ile Thr
1               5

<210> SEQ ID NO 163
<211> LENGTH: 17
<212> TYPE: PRT
<213> ORGANISM: Homo sapiens
```

<400> SEQUENCE: 163

Gly Ile Ile Pro Met Met Gly Thr Val Asn Tyr Ala Gln Lys Leu Gln
1               5                   10                  15

Gly

<210> SEQ ID NO 164
<211> LENGTH: 9
<212> TYPE: PRT
<213> ORGANISM: Homo sapiens

<400> SEQUENCE: 164

Ile Arg Tyr Thr Gly Gln Gln Leu Leu
1               5

<210> SEQ ID NO 165
<211> LENGTH: 6
<212> TYPE: PRT
<213> ORGANISM: Homo sapiens

<400> SEQUENCE: 165

Gly Gly Thr Phe Asn Gly
1               5

<210> SEQ ID NO 166
<211> LENGTH: 10
<212> TYPE: PRT
<213> ORGANISM: Homo sapiens

<400> SEQUENCE: 166

Gly Ile Ile Pro Met Met Gly Thr Val Asn
1               5                   10

<210> SEQ ID NO 167
<211> LENGTH: 321
<212> TYPE: DNA
<213> ORGANISM: Homo sapiens

<400> SEQUENCE: 167
gacatccaga tgacccagtc tccttccacc ctgtcggcat ctataggaga cagagtcacc      60
atcacttgcc gggccagtca gagtattgca agttggttgg cctggtatca gcaaaaacca     120
gggaaagccc ctaagctcct gatctatgag gcagttaatt tagaaagtgg ggtcccatca     180
aggttcagcg gcagtggatc tgggacagat ttcactctca ccatcagcag cctgcagccc     240
gatgattttg caacttattt ctgccaacat tatggtacta tttctcagac cttcggcgga     300
gggaccaagg tggagatcaa a                                               321

<210> SEQ ID NO 168
<211> LENGTH: 107
<212> TYPE: PRT
<213> ORGANISM: Homo sapiens

<400> SEQUENCE: 168

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ser Ile Ala Ser Trp
            20                  25                  30

Leu Ala Trp Tyr Gln Gln Lys Pro Gly Lys Ala Pro Lys Leu Leu Ile
        35                  40                  45

Tyr Glu Ala Val Asn Leu Glu Ser Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Asp Asp Phe Ala Thr Tyr Phe Cys Gln His Tyr Gly Thr Ile Ser Gln
                 85                  90                  95

Thr Phe Gly Gly Gly Thr Lys Val Glu Ile Lys
            100                 105
```

<210> SEQ ID NO 169
<211> LENGTH: 11
<212> TYPE: PRT
<213> ORGANISM: Homo sapiens

<400> SEQUENCE: 169

```
Arg Ala Ser Gln Ser Ile Ala Ser Trp Leu Ala
 1               5                   10
```

<210> SEQ ID NO 170
<211> LENGTH: 7
<212> TYPE: PRT
<213> ORGANISM: Homo sapiens

<400> SEQUENCE: 170

```
Glu Ala Val Asn Leu Glu Ser
 1               5
```

<210> SEQ ID NO 171
<211> LENGTH: 9
<212> TYPE: PRT
<213> ORGANISM: Homo sapiens

<400> SEQUENCE: 171

```
Gln His Tyr Gly Thr Ile Ser Gln Thr
 1               5
```

<210> SEQ ID NO 172
<211> LENGTH: 360
<212> TYPE: DNA
<213> ORGANISM: Homo sapiens

<400> SEQUENCE: 172

```
caggtccagc tggtgcaatc tgggagtgag gtgaagaagc ctgggacctc ggtgaaggtc      60
tcctgcacgg cctctggaag tgtcttcacc aattatggaa ttagttgggt gcgacaggcc     120
cctggacaag gcttgagtg gatgggaggg atcatccctc tctttggcgc agccaagtac      180
gcacagaaat tccagggcag agtcaccatc acagcggacg aatccacgaa cacagtctac     240
atggagctga gcaggctgac atctaaagac acggccatat atttctgtgc gaaggccccc     300
cgtgtctacg agtactactt tgatcagtgg ggccaggaa ccccagtcac cgtctcctca      360
```

<210> SEQ ID NO 173
<211> LENGTH: 120
<212> TYPE: PRT
<213> ORGANISM: Homo sapiens

<400> SEQUENCE: 173

```
Gln Val Gln Leu Val Gln Ser Gly Ser Glu Val Lys Lys Pro Gly Thr
 1               5                   10                  15

Ser Val Lys Val Ser Cys Thr Ala Ser Gly Ser Val Phe Thr Asn Tyr
             20                  25                  30

Gly Ile Ser Trp Val Arg Gln Ala Pro Gly Gln Gly Leu Glu Trp Met
```

```
                    35                  40                  45
Gly Gly Ile Ile Pro Leu Phe Gly Ala Ala Lys Tyr Ala Gln Lys Phe
         50                  55                  60

Gln Gly Arg Val Thr Ile Thr Ala Asp Glu Ser Thr Lys Thr Val Tyr
 65                  70                  75                  80

Met Glu Leu Ser Arg Leu Thr Ser Lys Asp Thr Ala Ile Tyr Phe Cys
                 85                  90                  95

Ala Lys Ala Pro Arg Val Tyr Glu Tyr Tyr Phe Asp Gln Trp Gly Gln
            100                 105                 110

Gly Thr Pro Val Thr Val Ser Ser
            115                 120

<210> SEQ ID NO 174
<211> LENGTH: 5
<212> TYPE: PRT
<213> ORGANISM: Homo sapiens

<400> SEQUENCE: 174

Asn Tyr Gly Ile Ser
1               5

<210> SEQ ID NO 175
<211> LENGTH: 17
<212> TYPE: PRT
<213> ORGANISM: Homo sapiens

<400> SEQUENCE: 175

Gly Ile Ile Pro Leu Phe Gly Ala Ala Lys Tyr Ala Gln Lys Phe Gln
1               5                   10                  15

Gly

<210> SEQ ID NO 176
<211> LENGTH: 11
<212> TYPE: PRT
<213> ORGANISM: Homo sapiens

<400> SEQUENCE: 176

Ala Pro Arg Val Tyr Glu Tyr Tyr Phe Asp Gln
1               5                   10

<210> SEQ ID NO 177
<211> LENGTH: 6
<212> TYPE: PRT
<213> ORGANISM: Homo sapiens

<400> SEQUENCE: 177

Gly Ser Val Phe Thr Asn
1               5

<210> SEQ ID NO 178
<211> LENGTH: 10
<212> TYPE: PRT
<213> ORGANISM: Homo sapiens

<400> SEQUENCE: 178

Gly Ile Ile Pro Leu Phe Gly Ala Ala Lys
1               5                   10

<210> SEQ ID NO 179
<211> LENGTH: 324
<212> TYPE: DNA
<213> ORGANISM: Homo sapiens
```

<400> SEQUENCE: 179

| | | | | | |
|---|---|---|---|---|---|
| gaaattgtgt tgacgcagtc tccaggcacc ctgtctttgt ctccagggga aagagccacc | | | | | 60 |
| ctctcctgca gggccagtca gagtgttagc agcagtcaat tagcctggta ccagcaaaaa | | | | | 120 |
| cctggccagg ctcccaggct catcatctat ggtgcgtcca ccagggccac tggcatccca | | | | | 180 |
| gacaggttca gtggaagtgg gtctgggaca gacttcactc tcaccatcgg cagactggag | | | | | 240 |
| cctgaagatt ttgcagtgtt tttctgtcag cagtatagta cctcacctcc gacgttcggc | | | | | 300 |
| caagggacca aggtggattt caaa | | | | | 324 |

<210> SEQ ID NO 180
<211> LENGTH: 108
<212> TYPE: PRT
<213> ORGANISM: Homo sapiens

<400> SEQUENCE: 180

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Gln Leu Ala Trp Tyr Gln Gln Lys Pro Gly Gln Ala Pro Arg Leu Ile
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Gly Arg Leu Glu
65                  70                  75                  80

Pro Glu Asp Phe Ala Val Phe Phe Cys Gln Gln Tyr Ser Thr Ser Pro
                85                  90                  95

Pro Thr Phe Gly Gln Gly Thr Lys Val Asp Phe Lys
            100                 105

<210> SEQ ID NO 181
<211> LENGTH: 7
<212> TYPE: PRT
<213> ORGANISM: Homo sapiens

<400> SEQUENCE: 181

Gly Ala Ser Thr Arg Ala Thr
1               5

<210> SEQ ID NO 182
<211> LENGTH: 9
<212> TYPE: PRT
<213> ORGANISM: Homo sapiens

<400> SEQUENCE: 182

Gln Gln Tyr Ser Thr Ser Pro Pro Thr
1               5

<210> SEQ ID NO 183
<211> LENGTH: 390
<212> TYPE: DNA
<213> ORGANISM: Homo sapiens

<400> SEQUENCE: 183

| | | | | | |
|---|---|---|---|---|---|
| caggtgcagc tgcagcagtg gggcgcagga ctgttgaagc cttcggagac cctgtccctc | | | | | 60 |
| acctgcgctg tctatggtgg gtccttcagt gtcagtggtt actactggag ctggatccgc | | | | | 120 |
| cagcccccag ggaggggcct ggagtggatt gggaaatca gtcatggtgg aagcaccaac | | | | | 180 |

```
tacaacccgt ccctcaagag tcgagtcacc atatcagtgg acacgaccaa gaaccagttc    240
tccctgagac tgagctctgt gaccgccgcg gacacggccg tctattactg tgcgagaggg    300
acagaccctg acacggaagt atattgtcgt gttggtaact gcgcggcctt tgactactgg    360
ggccagggaa gcctggtcac cgtctcctca                                     390
```

<210> SEQ ID NO 184
<211> LENGTH: 130
<212> TYPE: PRT
<213> ORGANISM: Homo sapiens

<400> SEQUENCE: 184

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Val Ser
            20                  25                  30

Gly Tyr Tyr Trp Ser Trp Ile Arg Gln Pro Pro Gly Arg Gly Leu Glu
        35                  40                  45

Trp Ile Gly Glu Ile Ser His Gly Gly Ser Thr Asn Tyr Asn Pro Ser
    50                  55                  60

Leu Lys Ser Arg Val Thr Ile Ser Val Asp Thr Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Gly Thr Asp Pro Asp Thr Glu Val Tyr Cys Arg Val Gly
            100                 105                 110

Asn Cys Ala Ala Phe Asp Tyr Trp Gly Gln Gly Ser Leu Val Thr Val
        115                 120                 125

Ser Ser
    130
```

<210> SEQ ID NO 185
<211> LENGTH: 7
<212> TYPE: PRT
<213> ORGANISM: Homo sapiens

<400> SEQUENCE: 185

```
Val Ser Gly Tyr Tyr Trp Ser
1               5
```

<210> SEQ ID NO 186
<211> LENGTH: 16
<212> TYPE: PRT
<213> ORGANISM: Homo sapiens

<400> SEQUENCE: 186

```
Glu Ile Ser His Gly Gly Ser Thr Asn Tyr Asn Pro Ser Leu Lys Ser
1               5                   10                  15
```

<210> SEQ ID NO 187
<211> LENGTH: 20
<212> TYPE: PRT
<213> ORGANISM: Homo sapiens

<400> SEQUENCE: 187

```
Gly Thr Asp Pro Asp Thr Glu Val Tyr Cys Arg Val Gly Asn Cys Ala
1               5                   10                  15

Ala Phe Asp Tyr
            20
```

<210> SEQ ID NO 188
<211> LENGTH: 8
<212> TYPE: PRT
<213> ORGANISM: Homo sapiens

<400> SEQUENCE: 188

Gly Gly Ser Phe Ser Val Ser Gly
1               5

<210> SEQ ID NO 189
<211> LENGTH: 9
<212> TYPE: PRT
<213> ORGANISM: Homo sapiens

<400> SEQUENCE: 189

Glu Ile Ser His Gly Gly Ser Thr Asn
1               5

<210> SEQ ID NO 190
<211> LENGTH: 327
<212> TYPE: DNA
<213> ORGANISM: Homo sapiens

<400> SEQUENCE: 190
gaaattatat tggcgcagtc tccaggcacc ctgtctttgt ctccagggga gagagccacc      60
ctctcctgca gggccagcca gtttgttagc accagatccc tggcctggta ccagcagaga     120
cctggccagg ctcccagact cctcatctat ggtgcatcca gcagggccac tggcatccca     180
gacaggttca gtggcagtgg gtctgggaca gacttcacgc tcaccatcag cagactggag     240
cctgaagatt ttgcagtgta ttactgtcag cactatggtt actcacctag gtacgctttt     300
ggccaggggt ccaaggttga gatcaaa                                         327

<210> SEQ ID NO 191
<211> LENGTH: 109
<212> TYPE: PRT
<213> ORGANISM: Homo sapiens

<400> SEQUENCE: 191

Glu Ile Ile Leu Ala Gln Ser Pro Gly Thr Leu Ser Leu Ser Pro Gly
1               5                   10                  15

Glu Arg Ala Thr Leu Ser Cys Arg Ala Ser Gln Phe Val Ser Thr Arg
                20                  25                  30

Ser Leu Ala Trp Tyr Gln Gln Arg Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Tyr Ser Pro
                85                  90                  95

Arg Tyr Ala Phe Gly Gln Gly Ser Lys Val Glu Ile Lys
            100                 105

<210> SEQ ID NO 192
<211> LENGTH: 12
<212> TYPE: PRT
<213> ORGANISM: Homo sapiens

<400> SEQUENCE: 192

```
Arg Ala Ser Gln Phe Val Ser Thr Arg Ser Leu Ala
1               5                   10
```

<210> SEQ ID NO 193
<211> LENGTH: 10
<212> TYPE: PRT
<213> ORGANISM: Homo sapiens

<400> SEQUENCE: 193

```
Gln His Tyr Gly Tyr Ser Pro Arg Tyr Ala
1               5                   10
```

<210> SEQ ID NO 194
<211> LENGTH: 384
<212> TYPE: DNA
<213> ORGANISM: Homo sapiens

<400> SEQUENCE: 194

```
caggtgcagc tccaacagtg gggctcagga ctgttgaagc cttcggagac cctgtccctc      60
acctgcgctg tctatggtgg gtccttcaga gatgactact ggacctggat tcgccagccc    120
ccaggcaagg ggctggagtg gattggggaa atcaatcata gtggaagaac caactacaac    180
ccgtccctca agagtcgagt caccatatca gtagacacgt ccctgaaaca gttctccttg    240
aaggtgattt ctgtgaccgc cgcggacacg gctgtttatt actgtgcgag agggacgagc    300
catgtttccc ggtattttga ttggttacca cccaccaact ggttcgaccc ctggggccag    360
ggaacccagg tcaccgtctc gagc                                           384
```

<210> SEQ ID NO 195
<211> LENGTH: 128
<212> TYPE: PRT
<213> ORGANISM: Homo sapiens

<400> SEQUENCE: 195

```
Gln Val Gln Leu Gln Gln Trp Gly Ser Gly Leu Leu Lys Pro Ser Glu
1               5                   10                  15

Thr Leu Ser Leu Thr Cys Ala Val Tyr Gly Gly Ser Phe Arg Asp Asp
            20                  25                  30

Tyr Trp Thr Trp Ile Arg Gln Pro Pro Gly Lys Gly Leu Glu Trp Ile
        35                  40                  45

Gly Glu Ile Asn His Ser Gly Arg Thr Asn Tyr Asn Pro Ser Leu Lys
    50                  55                  60

Ser Arg Val Thr Ile Ser Val Asp Thr Ser Leu Lys Gln Phe Ser Leu
65                  70                  75                  80

Lys Val Ile Ser Val Thr Ala Ala Asp Thr Ala Val Tyr Tyr Cys Ala
                85                  90                  95

Arg Gly Thr Ser His Val Ser Arg Tyr Phe Asp Trp Leu Pro Pro Thr
            100                 105                 110

Asn Trp Phe Asp Pro Trp Gly Gln Gly Thr Gln Val Thr Val Ser Ser
        115                 120                 125
```

<210> SEQ ID NO 196
<211> LENGTH: 5
<212> TYPE: PRT
<213> ORGANISM: Homo sapiens

<400> SEQUENCE: 196

```
Asp Asp Tyr Trp Thr
1               5
```

<210> SEQ ID NO 197
<211> LENGTH: 16
<212> TYPE: PRT
<213> ORGANISM: Homo sapiens

<400> SEQUENCE: 197

Glu Ile Asn His Ser Gly Arg Thr Asn Tyr Asn Pro Ser Leu Lys Ser
1               5                   10                  15

<210> SEQ ID NO 198
<211> LENGTH: 20
<212> TYPE: PRT
<213> ORGANISM: Homo sapiens

<400> SEQUENCE: 198

Gly Thr Ser His Val Ser Arg Tyr Phe Asp Trp Leu Pro Pro Thr Asn
1               5                   10                  15

Trp Phe Asp Pro
            20

<210> SEQ ID NO 199
<211> LENGTH: 6
<212> TYPE: PRT
<213> ORGANISM: Homo sapiens

<400> SEQUENCE: 199

Gly Gly Ser Phe Arg Asp
1               5

<210> SEQ ID NO 200
<211> LENGTH: 9
<212> TYPE: PRT
<213> ORGANISM: Homo sapiens

<400> SEQUENCE: 200

Glu Ile Asn His Ser Gly Arg Thr Asn
1               5

<210> SEQ ID NO 201
<211> LENGTH: 324
<212> TYPE: DNA
<213> ORGANISM: Homo sapiens

<400> SEQUENCE: 201
gacattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cgtcatgtat ggtgcagcca ccagggccac tggcatccca    180
gacaggttca gtggcagtgg gtctgggcca gacttcactc tcaccatcag cagactggag    240
cctgaagatt ttgcaatgta ttactgtcag cagtatggta actcaccgat caccttcggc    300
caagggacac gactggagat caaa                                           324

<210> SEQ ID NO 202
<211> LENGTH: 108
<212> TYPE: PRT
<213> ORGANISM: Homo sapiens

<400> SEQUENCE: 202

Asp Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Ala Pro Arg Leu Val
        35                  40                  45

Met Tyr Gly Ala Ala Thr Arg Ala Thr Gly Ile Pro Asp Arg Phe Ser
50                  55                  60

Gly Ser Gly Ser Gly Pro Asp Phe Thr Leu Thr Ile Ser Arg Leu Glu
65                  70                  75                  80

Pro Glu Asp Phe Ala Met Tyr Tyr Cys Gln Gln Tyr Gly Asn Ser Pro
                85                  90                  95

Ile Thr Phe Gly Gln Gly Thr Arg Leu Glu Ile Lys
            100                 105
```

<210> SEQ ID NO 203
<211> LENGTH: 12
<212> TYPE: PRT
<213> ORGANISM: Homo sapiens

<400> SEQUENCE: 203

```
Arg Ala Ser Gln Ser Val Ser Ser Ser Tyr Leu Ala
1               5                   10
```

<210> SEQ ID NO 204
<211> LENGTH: 7
<212> TYPE: PRT
<213> ORGANISM: Homo sapiens

<400> SEQUENCE: 204

```
Gly Ala Ala Thr Arg Ala Thr
1               5
```

<210> SEQ ID NO 205
<211> LENGTH: 9
<212> TYPE: PRT
<213> ORGANISM: Homo sapiens

<400> SEQUENCE: 205

```
Gln Gln Tyr Gly Asn Ser Pro Ile Thr
1               5
```

<210> SEQ ID NO 206
<211> LENGTH: 396
<212> TYPE: DNA
<213> ORGANISM: Homo sapiens

<400> SEQUENCE: 206

```
cagatcacct tgaaggagtc tggtcctaca ctggtgaaac ccacacagac cctcacactg      60
acctgcgtct ctctgggtt ctcactcagc attactggag tgcgtgtggg ctggatccgt     120
cagcccccag gaaaggccct ggagtggctt gcactcattt cttgggatga tgaaaagcac    180
tacagcccat ctctgcagag taggctcacc atcaccaagg acacctccaa aaaccaggtg    240
gtccttacaa tgaccaacct ggaccctgtc gacacagcca catattactg tgcacggtca    300
accgacaggg gccacgtctt acgatatttt ggctggatgt taccgggtga tgcatttgat    360
gtctggggcc aagggacaat ggtcaccgtc tcgagc                              396
```

<210> SEQ ID NO 207
<211> LENGTH: 132
<212> TYPE: PRT
<213> ORGANISM: Homo sapiens

<400> SEQUENCE: 207

Gln Ile Thr Leu Lys Glu Ser Gly Pro Thr Leu Val Lys Pro Thr Gln
1               5                   10                  15

Thr Leu Thr Leu Thr Cys Val Phe Ser Gly Phe Ser Leu Ser Ile Thr
            20                  25                  30

Gly Val Arg Val Gly Trp Ile Arg Gln Pro Pro Gly Lys Ala Leu Glu
        35                  40                  45

Trp Leu Ala Leu Ile Ser Trp Asp Asp Glu Lys His Tyr Ser Pro Ser
    50                  55                  60

Leu Gln Ser Arg Leu Thr Ile Thr Lys Asp Thr Ser Lys Asn Gln Val
65                  70                  75                  80

Val Leu Thr Met Thr Asn Leu Asp Pro Val Asp Thr Ala Thr Tyr Tyr
                85                  90                  95

Cys Ala Arg Ser Thr Asp Arg Gly His Val Leu Arg Tyr Phe Gly Trp
            100                 105                 110

Met Leu Pro Gly Asp Ala Phe Asp Val Trp Gly Gln Gly Thr Met Val
        115                 120                 125

Thr Val Ser Ser
    130

<210> SEQ ID NO 208
<211> LENGTH: 7
<212> TYPE: PRT
<213> ORGANISM: Homo sapiens

<400> SEQUENCE: 208

Ile Thr Gly Val Arg Val Gly
1               5

<210> SEQ ID NO 209
<211> LENGTH: 16
<212> TYPE: PRT
<213> ORGANISM: Homo sapiens

<400> SEQUENCE: 209

Leu Ile Ser Trp Asp Asp Glu Lys His Tyr Ser Pro Ser Leu Gln Ser
1               5                   10                  15

<210> SEQ ID NO 210
<211> LENGTH: 22
<212> TYPE: PRT
<213> ORGANISM: Homo sapiens

<400> SEQUENCE: 210

Ser Thr Asp Arg Gly His Val Leu Arg Tyr Phe Gly Trp Met Leu Pro
1               5                   10                  15

Gly Asp Ala Phe Asp Val
            20

<210> SEQ ID NO 211
<211> LENGTH: 8
<212> TYPE: PRT
<213> ORGANISM: Homo sapiens

<400> SEQUENCE: 211

Gly Phe Ser Leu Ser Ile Thr Gly
1               5

<210> SEQ ID NO 212
<211> LENGTH: 9

```
<212> TYPE: PRT
<213> ORGANISM: Homo sapiens

<400> SEQUENCE: 212

Leu Ile Ser Trp Asp Asp Glu Lys His
1               5

<210> SEQ ID NO 213
<211> LENGTH: 339
<212> TYPE: DNA
<213> ORGANISM: Homo sapiens

<400> SEQUENCE: 213
gacatcgtga tgacccagtc tccagacttc ctgcctgtgt ctctgggcga gagggccacc      60
atcaactgca gtccagcca gagagtttta tacagctcca acaataaaaa ctacttagct      120
tggtaccagc tgaaaccagg gcagcctcct aagttgatca tttattgggc atctacccgg     180
gaatccgggg tccctgaccg attcagtggc agcgggtctg ggacagaatt cactctcacc     240
atcagcagcc tgcaggctga agatgtggca gtttattact gtcaacaata ttatagtcgt    300
ccgtacactt ttggccaggg gaccaagctc gagatcaaa                           339

<210> SEQ ID NO 214
<211> LENGTH: 113
<212> TYPE: PRT
<213> ORGANISM: Homo sapiens

<400> SEQUENCE: 214

Asp Ile Val Met Thr Gln Ser Pro Asp Phe Leu Pro Val Ser Leu Gly
1               5                   10                  15

Glu Arg Ala Thr Ile Asn Cys Lys Ser Ser Gln Arg Val Leu Tyr Ser
            20                  25                  30

Ser Asn Asn Lys Asn Tyr Leu Ala Trp Tyr Gln Leu Lys Pro Gly Gln
        35                  40                  45

Pro Pro Lys Leu Ile Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Arg Pro Tyr Thr Phe Gly Gln Gly Thr Lys Leu Glu Ile
            100                 105                 110

Lys

<210> SEQ ID NO 215
<211> LENGTH: 17
<212> TYPE: PRT
<213> ORGANISM: Homo sapiens

<400> SEQUENCE: 215

Lys Ser Ser Gln Arg Val Leu Tyr Ser Ser Asn Asn Lys Asn Tyr Leu
1               5                   10                  15

Ala

<210> SEQ ID NO 216
<211> LENGTH: 7
<212> TYPE: PRT
<213> ORGANISM: Homo sapiens

<400> SEQUENCE: 216
```

Trp Ala Ser Thr Arg Glu Ser
1               5

<210> SEQ ID NO 217
<211> LENGTH: 9
<212> TYPE: PRT
<213> ORGANISM: Homo sapiens

<400> SEQUENCE: 217

Gln Gln Tyr Tyr Ser Arg Pro Tyr Thr
1               5

<210> SEQ ID NO 218
<211> LENGTH: 375
<212> TYPE: DNA
<213> ORGANISM: Homo sapiens

<400> SEQUENCE: 218

```
caggtgcagc tggtggagtc tgggggaggc gtggtccagc ctggggaggtc cctgagactc    60 tcctgtgcag cctctgaaat caccttcatt acctatgcta tgcactgggt ccgccaggcc   120
ccaggcaagg ggctggagtg gtggcactt atatcagatg atggaagcaa taaattctac   180
gcagactccg tgaagggccg attcaccatc tccagagaca attccaagaa cacgctgtat   240
ctgcaaatga acagcctgag agctgaggac acggctgctt attactgtgc gagagaaggg   300
gtttactttg attcggggac ttatagggc tactttgact actggggcca ggaaaccctg   360
gtcaccgtct cgagc                                                    375
```

<210> SEQ ID NO 219
<211> LENGTH: 125
<212> TYPE: PRT
<213> ORGANISM: Homo sapiens

<400> SEQUENCE: 219

Gln Val Gln Leu Val Glu Ser Gly Gly Gly Val Val Gln Pro Gly Arg
1               5                   10                  15

Ser Leu Arg Leu Ser Cys Ala Ala Ser Glu Ile Thr Phe Ile Thr Tyr
            20                  25                  30

Ala Met His Trp Val Arg Gln Ala Pro Gly Lys Gly Leu Glu Trp Val
        35                  40                  45

Ala Leu Ile Ser Asp Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Arg Glu Gly Val Tyr Phe Asp Ser Gly Thr Tyr Arg Gly Tyr Phe
            100                 105                 110

Asp Tyr Trp Gly Gln Gly Thr Leu Val Thr Val Ser Ser
        115                 120                 125

<210> SEQ ID NO 220
<211> LENGTH: 5
<212> TYPE: PRT
<213> ORGANISM: Homo sapiens

<400> SEQUENCE: 220

Thr Tyr Ala Met His
1               5

```
<210> SEQ ID NO 221
<211> LENGTH: 17
<212> TYPE: PRT
<213> ORGANISM: Homo sapiens

<400> SEQUENCE: 221

Leu Ile Ser Asp Asp Gly Ser Asn Lys Phe Tyr Ala Asp Ser Val Lys
1               5                   10                  15

Gly

<210> SEQ ID NO 222
<211> LENGTH: 16
<212> TYPE: PRT
<213> ORGANISM: Homo sapiens

<400> SEQUENCE: 222

Glu Gly Val Tyr Phe Asp Ser Gly Thr Tyr Arg Gly Tyr Phe Asp Tyr
1               5                   10                  15

<210> SEQ ID NO 223
<211> LENGTH: 6
<212> TYPE: PRT
<213> ORGANISM: Homo sapiens

<400> SEQUENCE: 223

Glu Ile Thr Phe Ile Thr
1               5

<210> SEQ ID NO 224
<211> LENGTH: 10
<212> TYPE: PRT
<213> ORGANISM: Homo sapiens

<400> SEQUENCE: 224

Leu Ile Ser Asp Asp Gly Ser Asn Lys Phe
1               5                   10

<210> SEQ ID NO 225
<211> LENGTH: 324
<212> TYPE: DNA
<213> ORGANISM: Homo sapiens

<400> SEQUENCE: 225
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagccact ggcctccgat caccttcggc     300
caagggacac gactggagat caaa                                            324

<210> SEQ ID NO 226
<211> LENGTH: 108
<212> TYPE: PRT
<213> ORGANISM: Homo sapiens

<400> SEQUENCE: 226

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
                20                  25                  30
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser His Trp Pro Pro
                85                  90                  95

Ile Thr Phe Gly Gln Gly Thr Arg Leu Glu Ile Lys
            100                 105

<210> SEQ ID NO 227
<211> LENGTH: 11
<212> TYPE: PRT
<213> ORGANISM: Homo sapiens

<400> SEQUENCE: 227

Arg Ala Ser Gln Ser Val Ser Ser Tyr Leu Ala
1               5                   10

<210> SEQ ID NO 228
<211> LENGTH: 7
<212> TYPE: PRT
<213> ORGANISM: Homo sapiens

<400> SEQUENCE: 228

Asp Ala Ser Asn Arg Ala Thr
1               5

<210> SEQ ID NO 229
<211> LENGTH: 10
<212> TYPE: PRT
<213> ORGANISM: Homo sapiens

<400> SEQUENCE: 229

Gln Gln Arg Ser His Trp Pro Pro Ile Thr
1               5                   10

<210> SEQ ID NO 230
<211> LENGTH: 363
<212> TYPE: DNA
<213> ORGANISM: Homo sapiens

<400> SEQUENCE: 230
caggtgcagc tggtacaatc tgggggaggc gtggtccagc ctggagggtc cctgagactc        60
tcctgtgcag cctctggatt caccttcagt agctacgcca tgcactgggt ccgccaggct       120
ccaggcaagg ggctggagtg ggtggctatt atatcatacg acggaaatga tcaatactat       180
acagactccg tgaagggccg attcaccatc tccagagaca gctccaaagt gtatctccaa       240
atgcacaggc tgagacctga ggacacggct gtttattact gtgcgaaaga atttgaaact       300
agtggttatt ttcatgggag ttttgactac tggggccagg gaatcctggt caccgtctcg       360
agc                                                                    363

<210> SEQ ID NO 231
<211> LENGTH: 121
<212> TYPE: PRT
<213> ORGANISM: Homo sapiens

<400> SEQUENCE: 231
```

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ile Ile Ser Tyr Asp Gly Asn Asp Gln Tyr Tyr Thr Asp Ser Val
    50                  55                  60

Lys Gly Arg Phe Thr Ile Ser Arg Asp Ser Lys Val Tyr Leu Gln
65                  70                  75                  80

Met His Arg Leu Arg Pro Glu Asp Thr Ala Val Tyr Tyr Cys Ala Lys
                85                  90                  95

Glu Phe Glu Thr Ser Gly Tyr Phe His Gly Ser Phe Asp Tyr Trp Gly
                100                 105                 110

Gln Gly Ile Leu Val Thr Val Ser Ser
            115                 120
```

<210> SEQ ID NO 232
<211> LENGTH: 5
<212> TYPE: PRT
<213> ORGANISM: Homo sapiens

<400> SEQUENCE: 232

```
Ser Tyr Ala Met His
1               5
```

<210> SEQ ID NO 233
<211> LENGTH: 17
<212> TYPE: PRT
<213> ORGANISM: Homo sapiens

<400> SEQUENCE: 233

```
Ile Ile Ser Tyr Asp Gly Asn Asp Gln Tyr Tyr Thr Asp Ser Val Lys
1               5                   10                  15

Gly
```

<210> SEQ ID NO 234
<211> LENGTH: 14
<212> TYPE: PRT
<213> ORGANISM: Homo sapiens

<400> SEQUENCE: 234

```
Glu Phe Glu Thr Ser Gly Tyr Phe His Gly Ser Phe Asp Tyr
1               5                   10
```

<210> SEQ ID NO 235
<211> LENGTH: 6
<212> TYPE: PRT
<213> ORGANISM: Homo sapiens

<400> SEQUENCE: 235

```
Gly Phe Thr Phe Ser Ser
1               5
```

<210> SEQ ID NO 236
<211> LENGTH: 10
<212> TYPE: PRT
<213> ORGANISM: Homo sapiens

<400> SEQUENCE: 236

Ile Ile Ser Tyr Asp Gly Asn Asp Gln Tyr
1               5                   10

<210> SEQ ID NO 237
<211> LENGTH: 330
<212> TYPE: DNA
<213> ORGANISM: Homo sapiens

<400> SEQUENCE: 237

```
cagtctgccc tgactcagcc tgcctccgtg tctgggtctc ctggacagtc gatcaccatc    60
tcctgcactg gaaccagcag tgacgttggt ggttataact atgtctcctg gtaccaacaa   120
cacccaggca aagcccccaa actcttgatt tatgaggtca ctaattggcc ctcaggggtt   180
tctaatcgct tctctggctc caagtctggc aacacggcct ccctgacaat ctctgggctc   240
caggctgagg acgaggctga ctattactgc agctcatatg cgggcagcag cacttgggtg   300
ttcggcggag ggaccagggt gaccgttcta                                    330
```

<210> SEQ ID NO 238
<211> LENGTH: 110
<212> TYPE: PRT
<213> ORGANISM: Homo sapiens

<400> SEQUENCE: 238

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Leu Ile Tyr Glu Val Thr Asn Trp Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Ser Thr Trp Val Phe Gly Gly Gly Thr Arg Val Thr Val Leu
            100                 105                 110

<210> SEQ ID NO 239
<211> LENGTH: 14
<212> TYPE: PRT
<213> ORGANISM: Homo sapiens

<400> SEQUENCE: 239

Thr Gly Thr Ser Ser Asp Val Gly Gly Tyr Asn Tyr Val Ser
1               5                   10

<210> SEQ ID NO 240
<211> LENGTH: 7
<212> TYPE: PRT
<213> ORGANISM: Homo sapiens

<400> SEQUENCE: 240

Glu Val Thr Asn Trp Pro Ser
1               5

<210> SEQ ID NO 241
<211> LENGTH: 10
<212> TYPE: PRT
<213> ORGANISM: Homo sapiens

<400> SEQUENCE: 241

Ser Ser Tyr Ala Gly Ser Ser Thr Trp Val
1               5                   10

<210> SEQ ID NO 242
<211> LENGTH: 378
<212> TYPE: DNA
<213> ORGANISM: Homo sapiens

<400> SEQUENCE: 242
caggtgcagc tgcaggagtc gggcccagga ctggtgaagc cttcggagac cctgtccctc     60
acctgcactg tctctggtgg ctccatcaat agttactact ggaactggat ccggcagccc    120
ccagggaagg gactggagtg gattggctat atctatcaca gtgggagcac caactacaac    180
ccctccctca agagtcgagt caccatttcg gtagacacgt ccaagaacca gttctccctg    240
cagctgagct ctgtgaccgc cgcagacacg gccgtgtatt actgtgcgag actccggacg    300
gactacggtg accccgactc ggtatactac tacggtatgg acgtctgggg ccaagggacc    360
acggtcaccg tctcgagc                                                  378

<210> SEQ ID NO 243
<211> LENGTH: 126
<212> TYPE: PRT
<213> ORGANISM: Homo sapiens

<400> SEQUENCE: 243

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Asn Trp Ile Arg Gln Pro Pro Gly Lys Gly Leu Glu Trp Ile
        35                  40                  45

Gly Tyr Ile Tyr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Gln Leu Ser Ser Val Thr Ala Ala Asp Thr Ala Val Tyr Tyr Cys Ala
                85                  90                  95

Arg Leu Arg Thr Asp Tyr Gly Asp Pro Asp Ser Val Tyr Tyr Tyr Gly
            100                 105                 110

Met Asp Val Trp Gly Gln Gly Thr Thr Val Thr Val Ser Ser
        115                 120                 125

<210> SEQ ID NO 244
<211> LENGTH: 5
<212> TYPE: PRT
<213> ORGANISM: Homo sapiens

<400> SEQUENCE: 244

Ser Tyr Tyr Trp Asn
1               5

<210> SEQ ID NO 245
<211> LENGTH: 16
<212> TYPE: PRT
<213> ORGANISM: Homo sapiens

<400> SEQUENCE: 245

```
Tyr Ile Tyr His Ser Gly Ser Thr Asn Tyr Asn Pro Ser Leu Lys Ser
1               5                   10                  15
```

<210> SEQ ID NO 246
<211> LENGTH: 18
<212> TYPE: PRT
<213> ORGANISM: Homo sapiens

<400> SEQUENCE: 246

```
Leu Arg Thr Asp Tyr Gly Asp Pro Asp Ser Val Tyr Tyr Tyr Gly Met
1               5                   10                  15

Asp Val
```

<210> SEQ ID NO 247
<211> LENGTH: 6
<212> TYPE: PRT
<213> ORGANISM: Homo sapiens

<400> SEQUENCE: 247

```
Gly Gly Ser Ile Asn Ser
1               5
```

<210> SEQ ID NO 248
<211> LENGTH: 9
<212> TYPE: PRT
<213> ORGANISM: Homo sapiens

<400> SEQUENCE: 248

```
Tyr Ile Tyr His Ser Gly Ser Thr Asn
1               5
```

<210> SEQ ID NO 249
<211> LENGTH: 324
<212> TYPE: DNA
<213> ORGANISM: Homo sapiens

<400> SEQUENCE: 249

```
tcctatgagc tgacacagcc accctcggtg tcagtgtccc caggacagac ggccaggatc      60
acctgctctg gagatgcatt gccaaagcaa aatgcttatt ggtaccagca gaagccaggc     120
caggcccctg tgctgctgat atataaagac agtgagaggc cctcagggat ccctgagcga     180
ttctctggct ccagctcagg gacaacagtc acgttgacca tcagtggagt ccaggcagag     240
gacgaggctg actattactg tcaatcagca gacagcagtg gtacttcttg ggtgttcggc     300
ggagggacca aactgaccgt tcta                                            324
```

<210> SEQ ID NO 250
<211> LENGTH: 108
<212> TYPE: PRT
<213> ORGANISM: Homo sapiens

<400> SEQUENCE: 250

```
Ser Tyr Glu Leu Thr Gln Pro Pro Ser Val Ser Val Pro Gly Gln
1               5                   10                  15

Thr Ala Arg Ile Thr Cys Ser Gly Asp Ala Leu Pro Lys Gln Asn Ala
            20                  25                  30

Tyr Trp Tyr Gln Gln Lys Pro Gly Gln Ala Pro Val Leu Leu Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
```

```
                65                  70                  75                  80
Asp Glu Ala Asp Tyr Tyr Cys Gln Ser Ala Asp Ser Ser Gly Thr Ser
                        85                  90                  95

Trp Val Phe Gly Gly Gly Thr Lys Leu Thr Val Leu
                100                 105
```

<210> SEQ ID NO 251
<211> LENGTH: 11
<212> TYPE: PRT
<213> ORGANISM: Homo sapiens

<400> SEQUENCE: 251

```
Ser Gly Asp Ala Leu Pro Lys Gln Asn Ala Tyr
1               5                   10
```

<210> SEQ ID NO 252
<211> LENGTH: 7
<212> TYPE: PRT
<213> ORGANISM: Homo sapiens

<400> SEQUENCE: 252

```
Lys Asp Ser Glu Arg Pro Ser
1               5
```

<210> SEQ ID NO 253
<211> LENGTH: 11
<212> TYPE: PRT
<213> ORGANISM: Homo sapiens

<400> SEQUENCE: 253

```
Gln Ser Ala Asp Ser Ser Gly Thr Ser Trp Val
1               5                   10
```

<210> SEQ ID NO 254
<211> LENGTH: 375
<212> TYPE: DNA
<213> ORGANISM: Homo sapiens

<400> SEQUENCE: 254

```
caggtgcagc tgcaggagtc gggcccagga ctggtgaagc cttcacagac cctgtccctc      60
acctgcactg tctctggtgg ctccatcagc agtggtaatt actactggaa ctgggtccgc     120
cagcacccag gaagggcct ggagtggatt gggtacatct attacagagg gagcaccttc     180
tacaacccgt ccctcaagag tcgagtgacc atatcaatag acacgtctaa gaaccagttc    240
tccctgaggc tgagctctgt gacggccgcg gacacggccg tgtattactg tgcgaaggat    300
acaaggtcga gcctagacaa ttaccagtac ggtatggacg tctggggcca agggaccacg    360
gtcaccgtct cgagc                                                     375
```

<210> SEQ ID NO 255
<211> LENGTH: 125
<212> TYPE: PRT
<213> ORGANISM: Homo sapiens

<400> SEQUENCE: 255

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asn Tyr Tyr Trp Asn Trp Val Arg Gln His Pro Gly Lys Gly Leu Glu
        35                  40                  45
```

```
Trp Ile Gly Tyr Ile Tyr Tyr Arg Gly Ser Thr Phe Tyr Asn Pro Ser
    50                  55                  60

Leu Lys Ser Arg Val Thr Ile Ser Ile Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Lys Asp Thr Arg Ser Ser Leu Asp Asn Tyr Gln Tyr Gly Met
                100                 105                 110

Asp Val Trp Gly Gln Gly Thr Thr Val Thr Val Ser Ser
            115                 120                 125

<210> SEQ ID NO 256
<211> LENGTH: 7
<212> TYPE: PRT
<213> ORGANISM: Homo sapiens

<400> SEQUENCE: 256

Ser Gly Asn Tyr Tyr Trp Asn
1               5

<210> SEQ ID NO 257
<211> LENGTH: 16
<212> TYPE: PRT
<213> ORGANISM: Homo sapiens

<400> SEQUENCE: 257

Tyr Ile Tyr Tyr Arg Gly Ser Thr Phe Tyr Asn Pro Ser Leu Lys Ser
1               5                   10                  15

<210> SEQ ID NO 258
<211> LENGTH: 15
<212> TYPE: PRT
<213> ORGANISM: Homo sapiens

<400> SEQUENCE: 258

Asp Thr Arg Ser Ser Leu Asp Asn Tyr Gln Tyr Gly Met Asp Val
1               5                   10                  15

<210> SEQ ID NO 259
<211> LENGTH: 8
<212> TYPE: PRT
<213> ORGANISM: Homo sapiens

<400> SEQUENCE: 259

Gly Gly Ser Ile Ser Ser Gly Asn
1               5

<210> SEQ ID NO 260
<211> LENGTH: 9
<212> TYPE: PRT
<213> ORGANISM: Homo sapiens

<400> SEQUENCE: 260

Tyr Ile Tyr Tyr Arg Gly Ser Thr Phe
1               5

<210> SEQ ID NO 261
<211> LENGTH: 330
<212> TYPE: DNA
<213> ORGANISM: Homo sapiens

<400> SEQUENCE: 261
```

```
cagactgtgg tgactcagga gccctcactg actgtgtccc caggagggac agtcactctc      60
acctgtgctt ccagcactgg agcagtcacc agtagttact ttccaaactg gttccagcag     120
aaacctggac aagcgcccag ccactgatta tatagtacaa ctatcagaca ctcctggacc     180
ccggcccgat tctcaggctc cctccttggg ggcaaagctg ccctgacact gtcaggtgtg     240
cagcctgagg acgaggctga ctattactgc ctgctctact ctggtggtga tccagtggct     300
ttcggcggag ggaccaaact gaccgttcta                                      330
```

<210> SEQ ID NO 262
<211> LENGTH: 110
<212> TYPE: PRT
<213> ORGANISM: Homo sapiens

<400> SEQUENCE: 262

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Ser
            20                  25                  30

Tyr Phe Pro Asn Trp Phe Gln Gln Lys Pro Gly Gln Ala Pro Arg Pro
        35                  40                  45

Leu Ile Tyr Ser Thr Thr Ile Arg His Ser Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Asp Tyr Tyr Cys Leu Leu Tyr Ser Gly Gly
                85                  90                  95

Asp Pro Val Ala Phe Gly Gly Gly Thr Lys Leu Thr Val Leu
            100                 105                 110

<210> SEQ ID NO 263
<211> LENGTH: 14
<212> TYPE: PRT
<213> ORGANISM: Homo sapiens

<400> SEQUENCE: 263

Ala Ser Ser Thr Gly Ala Val Thr Ser Ser Tyr Phe Pro Asn
1               5                   10

<210> SEQ ID NO 264
<211> LENGTH: 7
<212> TYPE: PRT
<213> ORGANISM: Homo sapiens

<400> SEQUENCE: 264

Ser Thr Thr Ile Arg His Ser
1               5

<210> SEQ ID NO 265
<211> LENGTH: 10
<212> TYPE: PRT
<213> ORGANISM: Homo sapiens

<400> SEQUENCE: 265

Leu Leu Tyr Ser Gly Gly Asp Pro Val Ala
1               5                   10

<210> SEQ ID NO 266
<211> LENGTH: 378
<212> TYPE: DNA
<213> ORGANISM: Homo sapiens

<400> SEQUENCE: 266

```
caggttcatc tggtgcagtc tggagctgag gtgaggaagc ctggggactc agtgaaggtc     60
tcctgtaaga cttctggtta caccttttcc acctatcctg tcgcctgggt gcgacaggtc    120
cccggacaag ggcttgagtg gatgggatgg atcagcactt acaatggaaa cacaaacttt    180
gcacagaact tccagggcag agtcaccctg accacagaca caaccacgaa cacagcctac    240
atggaagtga ggagcctgaa atttgacgac acggccgtct attactgtgc gagagtggaa    300
ggctcgtaca gggattttg gaataatcaa aacagattcg accctggggg ccagggaacc    360
ctggtcaccg tctcgagc                                                 378
```

<210> SEQ ID NO 267
<211> LENGTH: 126
<212> TYPE: PRT
<213> ORGANISM: Homo sapiens

<400> SEQUENCE: 267

```
Gln Val His Leu Val Gln Ser Gly Ala Glu Val Arg Lys Pro Gly Asp
1               5                   10                  15

Ser Val Lys Val Ser Cys Lys Thr Ser Gly Tyr Thr Phe Ser Thr Tyr
            20                  25                  30

Pro Val Ala Trp Val Arg Gln Val Pro Gly Gln Gly Leu Glu Trp Met
        35                  40                  45

Gly Trp Ile Ser Thr Tyr Asn Gly Asn Thr Asn Phe Ala Gln Asn Phe
    50                  55                  60

Gln Gly Arg Val Thr Leu Thr Thr Asp Thr Thr Thr Asn Thr Ala Tyr
65                  70                  75                  80

Met Glu Val Arg Ser Leu Lys Phe Asp Asp Thr Ala Val Tyr Tyr Cys
                85                  90                  95

Ala Arg Val Glu Gly Ser Tyr Arg Asp Phe Trp Asn Asn Gln Asn Arg
            100                 105                 110

Phe Asp Pro Trp Gly Gln Gly Thr Leu Val Thr Val Ser Ser
        115                 120                 125
```

<210> SEQ ID NO 268
<211> LENGTH: 5
<212> TYPE: PRT
<213> ORGANISM: Homo sapiens

<400> SEQUENCE: 268

```
Thr Tyr Pro Val Ala
1               5
```

<210> SEQ ID NO 269
<211> LENGTH: 17
<212> TYPE: PRT
<213> ORGANISM: Homo sapiens

<400> SEQUENCE: 269

```
Trp Ile Ser Thr Tyr Asn Gly Asn Thr Asn Phe Ala Gln Asn Phe Gln
1               5                   10                  15

Gly
```

<210> SEQ ID NO 270
<211> LENGTH: 17
<212> TYPE: PRT
<213> ORGANISM: Homo sapiens

```
<400> SEQUENCE: 270

Val Glu Gly Ser Tyr Arg Asp Phe Trp Asn Asn Gln Asn Arg Phe Asp
1               5                   10                  15

Pro

<210> SEQ ID NO 271
<211> LENGTH: 6
<212> TYPE: PRT
<213> ORGANISM: Homo sapiens

<400> SEQUENCE: 271

Gly Tyr Thr Phe Ser Thr
1               5

<210> SEQ ID NO 272
<211> LENGTH: 10
<212> TYPE: PRT
<213> ORGANISM: Homo sapiens

<400> SEQUENCE: 272

Trp Ile Ser Thr Tyr Asn Gly Asn Thr Asn
1               5                   10

<210> SEQ ID NO 273
<211> LENGTH: 318
<212> TYPE: DNA
<213> ORGANISM: Homo sapiens

<400> SEQUENCE: 273
tcctatgtac tgactcagcc accctcggtg tcagtggccc caggacagac ggccaggatt    60
tcctgtgggg gaagcaacat tggagggaaa agtgtgcact ggtaccagca aaagccaggc   120
caggcccctg tgctggtcgt ctatgatgat agcggccggc cctcagggat ccctgagcga   180
ttctctggct ccaactctgg ggacacggcc accctgacca tcagcagggt cgaagccggg   240
gatgaggccg actatttctg tcaggtgtgg gataatttcg ggggagtctt cggaactggg   300
accaaggtca ccgttcta                                                  318

<210> SEQ ID NO 274
<211> LENGTH: 106
<212> TYPE: PRT
<213> ORGANISM: Homo sapiens

<400> SEQUENCE: 274

Ser Tyr Val Leu Thr Gln Pro Pro Ser Val Ser Val Ala Pro Gly Gln
1               5                   10                  15

Thr Ala Arg Ile Ser Cys Gly Gly Ser Asn Ile Gly Gly Lys Ser Val
            20                  25                  30

His Trp Tyr Gln Gln Lys Pro Gly Gln Ala Pro Val Leu Val Val Tyr
        35                  40                  45

Asp Asp Ser Gly Arg Pro Ser Gly Ile Pro Glu Arg Phe Ser Gly Ser
    50                  55                  60

Asn Ser Gly Asp Thr Ala Thr Leu Thr Ile Ser Arg Val Glu Ala Gly
65                  70                  75                  80

Asp Glu Ala Asp Tyr Phe Cys Gln Val Trp Asp Asn Phe Gly Gly Val
                85                  90                  95

Phe Gly Thr Gly Thr Lys Val Thr Val Leu
            100                 105
```

```
<210> SEQ ID NO 275
<211> LENGTH: 11
<212> TYPE: PRT
<213> ORGANISM: Homo sapiens

<400> SEQUENCE: 275

Gly Gly Ser Asn Ile Gly Gly Lys Ser Val His
1               5                   10

<210> SEQ ID NO 276
<211> LENGTH: 7
<212> TYPE: PRT
<213> ORGANISM: Homo sapiens

<400> SEQUENCE: 276

Asp Asp Ser Gly Arg Pro Ser
1               5

<210> SEQ ID NO 277
<211> LENGTH: 9
<212> TYPE: PRT
<213> ORGANISM: Homo sapiens

<400> SEQUENCE: 277

Gln Val Trp Asp Asn Phe Gly Gly Val
1               5

<210> SEQ ID NO 278
<211> LENGTH: 369
<212> TYPE: DNA
<213> ORGANISM: Homo sapiens

<400> SEQUENCE: 278
caggtgcagc tgcaggagtc gggcccaggg ctggtgaagc cttcggagac cctgtccctc      60
acctgcactg tctctcgtgg ctccatcggt cattacttct ggagctggat ccggcagccc     120
ccagggaagg gactggagtg gattggttat atctcttaca gtgggagcac caagtacaac     180
ccctccctca ggagtcgagt caccatatca gtagacacgt ccaagaacca gttctccctg     240
aatctgaact ctgtcaccgc tacggacacg gccctatatt actgtgcgag agaggattac     300 gatatttttga ctggggcggg acccggtatg gaggtctggg ccaagggac cacggtcacc     360 gtctcgagc                                                             369

<210> SEQ ID NO 279
<211> LENGTH: 123
<212> TYPE: PRT
<213> ORGANISM: Homo sapiens

<400> SEQUENCE: 279

Gln Val Gln Leu Gln Glu Ser Gly Pro Gly Leu Val Lys Pro Ser Glu
1               5                   10                  15

Thr Leu Ser Leu Thr Cys Thr Val Ser Arg Gly Ser Ile Gly His Tyr
            20                  25                  30

Phe Trp Ser Trp Ile Arg Gln Pro Pro Gly Lys Gly Leu Glu Trp Ile
        35                  40                  45

Gly Tyr Ile Ser Tyr Ser Gly Ser Thr Lys Tyr Asn Pro Ser Leu Arg
    50                  55                  60

Ser Arg Val Thr Ile Ser Val Asp Thr Ser Lys Asn Gln Phe Ser Leu
65                  70                  75                  80

Asn Leu Asn Ser Val Thr Ala Thr Asp Thr Ala Leu Tyr Tyr Cys Ala
                85                  90                  95
```

Arg Glu Asp Tyr Asp Ile Leu Thr Gly Ala Gly Pro Gly Met Glu Val
            100                 105                 110

Trp Gly Gln Gly Thr Thr Val Thr Val Ser Ser
        115                 120

<210> SEQ ID NO 280
<211> LENGTH: 5
<212> TYPE: PRT
<213> ORGANISM: Homo sapiens

<400> SEQUENCE: 280

His Tyr Phe Trp Ser
1               5

<210> SEQ ID NO 281
<211> LENGTH: 16
<212> TYPE: PRT
<213> ORGANISM: Homo sapiens

<400> SEQUENCE: 281

Tyr Ile Ser Tyr Ser Gly Ser Thr Lys Tyr Asn Pro Ser Leu Arg Ser
1               5                   10                  15

<210> SEQ ID NO 282
<211> LENGTH: 15
<212> TYPE: PRT
<213> ORGANISM: Homo sapiens

<400> SEQUENCE: 282

Glu Asp Tyr Asp Ile Leu Thr Gly Ala Gly Pro Gly Met Glu Val
1               5                   10                  15

<210> SEQ ID NO 283
<211> LENGTH: 6
<212> TYPE: PRT
<213> ORGANISM: Homo sapiens

<400> SEQUENCE: 283

Arg Gly Ser Ile Gly His
1               5

<210> SEQ ID NO 284
<211> LENGTH: 9
<212> TYPE: PRT
<213> ORGANISM: Homo sapiens

<400> SEQUENCE: 284

Tyr Ile Ser Tyr Ser Gly Ser Thr Lys
1               5

<210> SEQ ID NO 285
<211> LENGTH: 333
<212> TYPE: DNA
<213> ORGANISM: Homo sapiens

<400> SEQUENCE: 285
cagtctatgt tgactcagcc accctcagcg tctgggaccc ccgggcagag ggtcaccatc        60
tcttgttctg ggagcagctc caacatcgga agtaatactg tcaactggtt caaacatctc       120
ccaggaacgg ccccccaaact cctcatctac agaaatgatc tgcggccctc agggggtccct     180 gaccgattct ctggctccaa gtctggcacc tcagcctccc tggccatcag tgggctccag       240
tctgaggatg aggctgatta ttactgtgca acatgggatg acagcctgaa tggttttttat      300 gtcttcggaa ctgggaccaa agtcaccgtt cta                        333

<210> SEQ ID NO 286
<211> LENGTH: 111
<212> TYPE: PRT
<213> ORGANISM: Homo sapiens

<400> SEQUENCE: 286

Gln Ser Met Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Phe Lys His Leu Pro Gly Thr Ala Pro Lys Leu Leu
        35                  40                  45

Ile Tyr Arg Asn Asp Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Asn Gly Phe Tyr Val Phe Gly Thr Gly Thr Lys Val Thr Val Leu
            100                 105                 110

<210> SEQ ID NO 287
<211> LENGTH: 13
<212> TYPE: PRT
<213> ORGANISM: Homo sapiens

<400> SEQUENCE: 287

Ser Gly Ser Ser Ser Asn Ile Gly Ser Asn Thr Val Asn
1               5                   10

<210> SEQ ID NO 288
<211> LENGTH: 7
<212> TYPE: PRT
<213> ORGANISM: Homo sapiens

<400> SEQUENCE: 288

Arg Asn Asp Leu Arg Pro Ser
1               5

<210> SEQ ID NO 289
<211> LENGTH: 12
<212> TYPE: PRT
<213> ORGANISM: Homo sapiens

<400> SEQUENCE: 289

Ala Thr Trp Asp Asp Ser Leu Asn Gly Phe Tyr Val
1               5                   10

<210> SEQ ID NO 290
<211> LENGTH: 384
<212> TYPE: DNA
<213> ORGANISM: Homo sapiens

<400> SEQUENCE: 290
caggtgcagc tacagcagtg gggcgcagga ctgttgaagc cttcggagac cctgtccctc    60
tcctgcgctg tctttggtgg gtccttcagt gattactact ggacctggat acgccagccc   120
ccagggaagg ggctggagtg gattggcgaa atcaaacata gtggaagaac caactacaac   180

```
ccgtcccttg agagtcgagt caccatatca gtggacacgt ccaagaacca gttttccctg    240
aaactgagtt ctgtgaccgc cgcggacacg gctatatatt attgtgcgag agggacagac    300
cctgacacgg agggatattg tcgtagtggt agctgctcgg cctttgactt ctggggccag    360
ggaaccctgg tcaccgtctc gagc                                           384
```

```
<210> SEQ ID NO 291
<211> LENGTH: 128
<212> TYPE: PRT
<213> ORGANISM: Homo sapiens

<400> SEQUENCE: 291
```

Gln Val Gln Leu Gln Gln Trp Gly Ala Gly Leu Leu Lys Pro Ser Glu
1               5                   10                  15

Thr Leu Ser Leu Ser Cys Ala Val Phe Gly Gly Ser Phe Ser Asp Tyr
            20                  25                  30

Tyr Trp Thr Trp Ile Arg Gln Pro Pro Gly Lys Gly Leu Glu Trp Ile
        35                  40                  45

Gly Glu Ile Lys His Ser Gly Arg Thr Asn Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg Gly Thr Asp Pro Asp Thr Glu Gly Tyr Cys Arg Ser Gly Ser Cys
            100                 105                 110

Ser Ala Phe Asp Phe Trp Gly Gln Gly Thr Leu Val Thr Val Ser Ser
        115                 120                 125

```
<210> SEQ ID NO 292
<211> LENGTH: 5
<212> TYPE: PRT
<213> ORGANISM: Homo sapiens

<400> SEQUENCE: 292
```

Asp Tyr Tyr Trp Thr
1               5

```
<210> SEQ ID NO 293
<211> LENGTH: 16
<212> TYPE: PRT
<213> ORGANISM: Homo sapiens

<400> SEQUENCE: 293
```

Glu Ile Lys His Ser Gly Arg Thr Asn Tyr Asn Pro Ser Leu Glu Ser
1               5                   10                  15

```
<210> SEQ ID NO 294
<211> LENGTH: 20
<212> TYPE: PRT
<213> ORGANISM: Homo sapiens

<400> SEQUENCE: 294
```

Gly Thr Asp Pro Asp Thr Glu Gly Tyr Cys Arg Ser Gly Ser Cys Ser
1               5                   10                  15

Ala Phe Asp Phe
            20

```
<210> SEQ ID NO 295
<211> LENGTH: 6
```

```
<212> TYPE: PRT
<213> ORGANISM: Homo sapiens

<400> SEQUENCE: 295

Gly Gly Ser Phe Ser Asp
1               5

<210> SEQ ID NO 296
<211> LENGTH: 9
<212> TYPE: PRT
<213> ORGANISM: Homo sapiens

<400> SEQUENCE: 296

Glu Ile Lys His Ser Gly Arg Thr Asn
1               5

<210> SEQ ID NO 297
<211> LENGTH: 327
<212> TYPE: DNA
<213> ORGANISM: Homo sapiens

<400> SEQUENCE: 297
gaaattgtgt tgacgcagtc tccaggcacc ctgtctttgt ctccagggga aagagccacc      60
ctctcctgca gggccagtca ctttgtgaac tacaggtcct tagcctggta ccagcagaca     120
cctggccagg ttcccaggct cctcatctat ggtgcgtcca ccaggccac tggcatccca      180 gacaggttca gtggcagtgg gtctgggaca gacttcactc tcaccatcag cagactggag     240
cctgaagatt ttgcagtgta tttctgtcag cagtatggtg gctcacctag gtacactttt     300
ggccagggga ccaggctgga gatcaaa                                         327

<210> SEQ ID NO 298
<211> LENGTH: 109
<212> TYPE: PRT
<213> ORGANISM: Homo sapiens

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Phe Val Asn Tyr Arg
                20                  25                  30

Ser Leu Ala Trp Tyr Gln Gln Thr Pro Gly Gln Val Pro Arg Leu Leu
            35                  40                  45

Ile Tyr Gly Ala Ser Thr Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Gly Gly Ser Pro
                85                  90                  95

Arg Tyr Thr Phe Gly Gln Gly Thr Arg Leu Glu Ile Lys
            100                 105

<210> SEQ ID NO 299
<211> LENGTH: 12
<212> TYPE: PRT
<213> ORGANISM: Homo sapiens

<400> SEQUENCE: 299

Arg Ala Ser His Phe Val Asn Tyr Arg Ser Leu Ala
1               5                   10
```

<210> SEQ ID NO 300
<211> LENGTH: 10
<212> TYPE: PRT
<213> ORGANISM: Homo sapiens

<400> SEQUENCE: 300

Gln Gln Tyr Gly Gly Ser Pro Arg Tyr Thr
1               5                   10

<210> SEQ ID NO 301
<211> LENGTH: 384
<212> TYPE: DNA
<213> ORGANISM: Homo sapiens

<400> SEQUENCE: 301

```
caggtgcagc tacagcagtg gggcgcagga ctgttgaagc cttcggagac cctgtccctc    60
acctgcggtg tctatggtgg gtccctcagt gattactact ggagctggat ccgccagccc   120
ccagggaagg ggctggagtg gattggagaa atcaatcata gtggaggcac caactacaat   180
ccgtccctca agagacgagt caccatatca gtagacacgt caaagaagca attctccctg   240
aagatgaact ctgtgaccgc cgcggacacg gctgtatatt actgtgcgag agggacagac   300
cctgacacgg aagtatattg tcgtgctggt aactgcgcgg cctttgactt ctggggccag   360
ggaaccctgg tcaccgtctc gagc                                          384
```

<210> SEQ ID NO 302
<211> LENGTH: 128
<212> TYPE: PRT
<213> ORGANISM: Homo sapiens

<400> SEQUENCE: 302

Gln Val Gln Leu Gln Gln Trp Gly Ala Gly Leu Leu Lys Pro Ser Glu
1               5                   10                  15

Thr Leu Ser Leu Thr Cys Gly Val Tyr Gly Gly Ser Leu Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Gly Thr Asn Tyr Asn Pro Ser Leu Lys
    50                  55                  60

Arg Arg Val Thr Ile Ser Val Asp Thr Ser Lys Lys Gln Phe Ser Leu
65                  70                  75                  80

Lys Met Asn Ser Val Thr Ala Ala Asp Thr Ala Val Tyr Tyr Cys Ala
                85                  90                  95

Arg Gly Thr Asp Pro Asp Thr Glu Val Tyr Cys Arg Ala Gly Asn Cys
            100                 105                 110

Ala Ala Phe Asp Phe Trp Gly Gln Gly Thr Leu Val Thr Val Ser Ser
        115                 120                 125

<210> SEQ ID NO 303
<211> LENGTH: 5
<212> TYPE: PRT
<213> ORGANISM: Homo sapiens

<400> SEQUENCE: 303

Asp Tyr Tyr Trp Ser
1               5

<210> SEQ ID NO 304
<211> LENGTH: 16

```
<212> TYPE: PRT
<213> ORGANISM: Homo sapiens

<400> SEQUENCE: 304

Glu Ile Asn His Ser Gly Gly Thr Asn Tyr Asn Pro Ser Leu Lys Arg
1               5                   10                  15

<210> SEQ ID NO 305
<211> LENGTH: 20
<212> TYPE: PRT
<213> ORGANISM: Homo sapiens

<400> SEQUENCE: 305

Gly Thr Asp Pro Asp Thr Glu Val Tyr Cys Arg Ala Gly Asn Cys Ala
1               5                   10                  15

Ala Phe Asp Phe
            20

<210> SEQ ID NO 306
<211> LENGTH: 6
<212> TYPE: PRT
<213> ORGANISM: Homo sapiens

<400> SEQUENCE: 306

Gly Gly Ser Leu Ser Asp
1               5

<210> SEQ ID NO 307
<211> LENGTH: 9
<212> TYPE: PRT
<213> ORGANISM: Homo sapiens

<400> SEQUENCE: 307

Glu Ile Asn His Ser Gly Gly Thr Asn
1               5

<210> SEQ ID NO 308
<211> LENGTH: 327
<212> TYPE: DNA
<213> ORGANISM: Homo sapiens

<400> SEQUENCE: 308
gaaattgtgt tgacgcagtc tccaggcacc ctgtctttgt ctccagggga gagagccacc      60
ctctcctgcc gggccagtca ctttgttata ggcagggctg tagcctggta ccagcagaaa     120
cctggccagg ctcccaggct cctcatctac ggtgcatcca gcagggccac tggcatcccg     180
gacaggttca gtggcagtgg gtctgggaca gacttcactc tcaccatcag cagactggag     240
actgaagatt ttgctgtgtt ttactgtcag cactatggta gctcacctag gtacgctttt     300
ggccagggga ccaagctgga gatcaaa                                         327

<210> SEQ ID NO 309
<211> LENGTH: 109
<212> TYPE: PRT
<213> ORGANISM: Homo sapiens

<400> SEQUENCE: 309

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Phe Val Ile Gly Arg
            20                  25                  30

Ala Val Ala Trp Tyr Gln Gln Lys Pro Gly Gln Ala Pro Arg Leu Leu
```

```
                35                  40                  45
Ile Tyr Gly Ala Ser Ser Arg Ala Thr Gly Ile Pro Asp Arg Phe Ser
             50                  55                  60
Gly Ser Gly Ser Gly Thr Asp Phe Thr Leu Thr Ile Ser Arg Leu Glu
 65                  70                  75                  80
Thr Glu Asp Phe Ala Val Phe Tyr Cys Gln His Tyr Gly Ser Ser Pro
                 85                  90                  95
Arg Tyr Ala Phe Gly Gln Gly Thr Lys Leu Glu Ile Lys
            100                 105
```

<210> SEQ ID NO 310
<211> LENGTH: 12
<212> TYPE: PRT
<213> ORGANISM: Homo sapiens

<400> SEQUENCE: 310

```
Arg Ala Ser His Phe Val Ile Gly Arg Ala Val Ala
 1               5                  10
```

<210> SEQ ID NO 311
<211> LENGTH: 11
<212> TYPE: PRT
<213> ORGANISM: Homo sapiens

<400> SEQUENCE: 311

```
Gln His Tyr Gly Ser Ser Pro Arg Tyr Ala Phe
 1               5                  10
```

<210> SEQ ID NO 312
<211> LENGTH: 384
<212> TYPE: DNA
<213> ORGANISM: Homo sapiens

<400> SEQUENCE: 312

```
caggtgcagc tgcaggagtc gggcccagga ctggtgaagc cttcacagac cctgtccctc      60
acctgcactg tctctggtga ctccattagt agtgttgatc actactggag ctggatccgc     120
caacacccag tgaagggcct ggagtggatt gggttcatgt attacagtgc gagcacctat     180
tacaacccgt ccctcaagag tcgagttacc atatcaacgg acacgtctaa gaaccagttc     240
tccctgaggc tgagttctgt gactgccgcg gacacggccg tatattactg tgcgagaggc     300
acttgtgctg gtgactgctc ccttcactac tactactacg gtttggacgt ctggggccaa     360
gggaggacgg tcaccgtctc gagc                                            384
```

<210> SEQ ID NO 313
<211> LENGTH: 128
<212> TYPE: PRT
<213> ORGANISM: Homo sapiens

<400> SEQUENCE: 313

```
Gln Val Gln Leu Gln Glu Ser Gly Pro Gly Leu Val Lys Pro Ser Gln
 1               5                  10                  15
Thr Leu Ser Leu Thr Cys Thr Val Ser Gly Asp Ser Ile Ser Ser Val
             20                  25                  30
Asp His Tyr Trp Ser Trp Ile Arg Gln His Pro Val Lys Gly Leu Glu
         35                  40                  45
Trp Ile Gly Phe Met Tyr Tyr Ser Ala Ser Thr Tyr Tyr Asn Pro Ser
     50                  55                  60
Leu Lys Ser Arg Val Thr Ile Ser Thr Asp Thr Ser Lys Asn Gln Phe
```

```
                65                  70                  75                  80
Ser Leu Arg Leu Ser Ser Val Thr Ala Ala Asp Thr Ala Val Tyr Tyr
                    85                  90                  95
Cys Ala Arg Gly Thr Cys Ala Gly Asp Cys Ser Leu His Tyr Tyr Tyr
               100                 105                 110
Tyr Gly Leu Asp Val Trp Gly Gln Gly Arg Thr Val Thr Val Ser Ser
           115                 120                 125
```

<210> SEQ ID NO 314
<211> LENGTH: 7
<212> TYPE: PRT
<213> ORGANISM: Homo sapiens

<400> SEQUENCE: 314

```
Ser Val Asp His Tyr Trp Ser
1               5
```

<210> SEQ ID NO 315
<211> LENGTH: 16
<212> TYPE: PRT
<213> ORGANISM: Homo sapiens

<400> SEQUENCE: 315

```
Phe Met Tyr Tyr Ser Ala Ser Thr Tyr Tyr Asn Pro Ser Leu Lys Ser
1               5                   10                  15
```

<210> SEQ ID NO 316
<211> LENGTH: 18
<212> TYPE: PRT
<213> ORGANISM: Homo sapiens

<400> SEQUENCE: 316

```
Gly Thr Cys Ala Gly Asp Cys Ser Leu His Tyr Tyr Tyr Gly Leu
1               5                   10                  15
Asp Val
```

<210> SEQ ID NO 317
<211> LENGTH: 8
<212> TYPE: PRT
<213> ORGANISM: Homo sapiens

<400> SEQUENCE: 317

```
Gly Asp Ser Ile Ser Ser Val Asp
1               5
```

<210> SEQ ID NO 318
<211> LENGTH: 9
<212> TYPE: PRT
<213> ORGANISM: Homo sapiens

<400> SEQUENCE: 318

```
Phe Met Tyr Tyr Ser Ala Ser Thr Tyr
1               5
```

<210> SEQ ID NO 319
<211> LENGTH: 321
<212> TYPE: DNA
<213> ORGANISM: Homo sapiens

<400> SEQUENCE: 319

```
gacatccaga tgacccagtc tccatcctcc ctgtctgcat ctgtaggaga cagagtcacc    60
atcacttgcc gggcaagtca gagcattagc agctatttaa attggtatca gcacaaacca   120
```
gggaaagccc ctaaggtcct gatgtatgct gtatccattt tgcaaagtgg ggtcccatca    180
aggttcagtg gcagtggatc tgggcagat ttcactctca ccatcagcag tctgcaacct    240
gaagattttg caacttacta ctgtcaacag agttacagtt ccccgctcac tttcggcgga    300
gggaccaagg tggagatcaa a    321

<210> SEQ ID NO 320
<211> LENGTH: 107
<212> TYPE: PRT
<213> ORGANISM: Homo sapiens

<400> SEQUENCE: 320

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln His Lys Pro Gly Lys Ala Pro Lys Val Leu Met
        35                  40                  45

Tyr Ala Val Ser Ile Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys
            100                 105

<210> SEQ ID NO 321
<211> LENGTH: 11
<212> TYPE: PRT
<213> ORGANISM: Homo sapiens

<400> SEQUENCE: 321

Arg Ala Ser Gln Ser Ile Ser Ser Tyr Leu Asn
1               5                   10

<210> SEQ ID NO 322
<211> LENGTH: 7
<212> TYPE: PRT
<213> ORGANISM: Homo sapiens

<400> SEQUENCE: 322

Ala Val Ser Ile Leu Gln Ser
1               5

<210> SEQ ID NO 323
<211> LENGTH: 9
<212> TYPE: PRT
<213> ORGANISM: Homo sapiens

<400> SEQUENCE: 323

Gln Gln Ser Tyr Ser Ser Pro Leu Thr
1               5

<210> SEQ ID NO 324
<211> LENGTH: 396
<212> TYPE: DNA
<213> ORGANISM: Homo sapiens

<400> SEQUENCE: 324

```
caggtgcagc tgcaggagtc gggcccagga ctggtgaagc cttcggagac cctgtccctc    60
acctgcactg tctctagtgg ccccatgagt gattattact ggagctggat ccggcagccc   120
ccagggaagg gactggagtg gattgggcat gtctctgtct ctcacggagg gaggaccaaa   180
tccaatccct ccgtcatgag tcagtcacc atttcagtag aaacgtccaa gaaccaattc    240
tccctgaaac tgacctccgt gaccgctgcg gacacggccg tttattactg tgcgagatta   300
aattactatg atagaagtgg ttatcattcg cctgacggcc cctcgaacaa ctggttcgac   360
cccctggggcc agggaaccct ggtcaccgtc tcgagc                             396
```

```
<210> SEQ ID NO 325
<211> LENGTH: 132
<212> TYPE: PRT
<213> ORGANISM: Homo sapiens

<400> SEQUENCE: 325
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Pro Met Ser Asp Tyr
            20                  25                  30

Tyr Trp Ser Trp Ile Arg Gln Pro Pro Gly Lys Gly Leu Glu Trp Ile
        35                  40                  45

Gly His Val Ser Val Ser His Gly Gly Arg Thr Lys Ser Asn Pro Ser
    50                  55                  60

Val Met Ser Arg Val Thr Ile Ser Val Glu Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Leu Asn Tyr Tyr Asp Arg Ser Gly Tyr His Ser Pro Asp
            100                 105                 110

Gly Pro Ser Asn Asn Trp Phe Asp Pro Trp Gly Gln Gly Thr Leu Val
        115                 120                 125

Thr Val Ser Ser
    130

```
<210> SEQ ID NO 326
<211> LENGTH: 18
<212> TYPE: PRT
<213> ORGANISM: Homo sapiens

<400> SEQUENCE: 326
```

His Val Ser Val Ser His Gly Gly Arg Thr Lys Ser Asn Pro Ser Val
1               5                   10                  15

Met Ser

```
<210> SEQ ID NO 327
<211> LENGTH: 22
<212> TYPE: PRT
<213> ORGANISM: Homo sapiens

<400> SEQUENCE: 327
```

Leu Asn Tyr Tyr Asp Arg Ser Gly Tyr His Ser Pro Asp Gly Pro Ser
1               5                   10                  15

Asn Asn Trp Phe Asp Pro
            20

```
<210> SEQ ID NO 328
<211> LENGTH: 6
```

```
<212> TYPE: PRT
<213> ORGANISM: Homo sapiens

<400> SEQUENCE: 328

Ser Gly Pro Met Ser Asp
1               5

<210> SEQ ID NO 329
<211> LENGTH: 11
<212> TYPE: PRT
<213> ORGANISM: Homo sapiens

<400> SEQUENCE: 329

His Val Ser Val Ser His Gly Gly Arg Thr Lys
1               5                   10

<210> SEQ ID NO 330
<211> LENGTH: 339
<212> TYPE: DNA
<213> ORGANISM: Homo sapiens

<400> SEQUENCE: 330
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg aatcagcggc agcgggtctg ggcagattt cactctcacc      240 atcagcagcc tgcaggctga agatgtggca gtttattact gtcagcagta ttttgctact     300
cctcggacgt tcggccaagg gaccaaggtg gaaatcaaa                            339

<210> SEQ ID NO 331
<211> LENGTH: 113
<212> TYPE: PRT
<213> ORGANISM: Homo sapiens

<400> SEQUENCE: 331

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Ile Ser Gly Ser Gly Ser Gly Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ala Thr Pro Arg Thr Phe Gly Gln Gly Thr Lys Val Glu Ile
                100                 105                 110

Lys

<210> SEQ ID NO 332
<211> LENGTH: 17
<212> TYPE: PRT
<213> ORGANISM: Homo sapiens

<400> SEQUENCE: 332

Lys Ser Ser Gln Ser Val Leu Tyr Ser Ser Asn Asn Lys Asn Tyr Leu
```

```
1               5                   10                  15
Ala

<210> SEQ ID NO 333
<211> LENGTH: 9
<212> TYPE: PRT
<213> ORGANISM: Homo sapiens

<400> SEQUENCE: 333

Gln Gln Tyr Phe Ala Thr Pro Arg Thr
1               5

<210> SEQ ID NO 334
<211> LENGTH: 366
<212> TYPE: DNA
<213> ORGANISM: Homo sapiens

<400> SEQUENCE: 334
caggtacagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccct  acagtggtga cacaaactat   180
gcacagaagt tcagggcag ggtcaccatg accagggaca cgtccatcac cacagcctac   240
atggagctga gcagcctgag atctgacgac acggccgtgt attactgtgc gagagattcc   300
ccctatagca gcagctggtc cttctttgac tactggggcc agggacccct ggtcaccgtc   360
tcgagc                                                              366

<210> SEQ ID NO 335
<211> LENGTH: 122
<212> TYPE: PRT
<213> ORGANISM: Homo sapiens

<400> SEQUENCE: 335

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Asp Thr Asn Tyr Ala Gln Lys Phe
        50                  55                  60

Gln Gly Arg Val Thr Met Thr Arg Asp Thr Ser Ile Thr Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Ser Pro Tyr Ser Ser Ser Trp Ser Phe Phe Asp Tyr Trp
            100                 105                 110

Gly Gln Gly Pro Leu Val Thr Val Ser Ser
        115                 120

<210> SEQ ID NO 336
<211> LENGTH: 5
<212> TYPE: PRT
<213> ORGANISM: Homo sapiens

<400> SEQUENCE: 336

Gly Tyr Tyr Met His
1               5
```

-continued

<210> SEQ ID NO 337
<211> LENGTH: 17
<212> TYPE: PRT
<213> ORGANISM: Homo sapiens

<400> SEQUENCE: 337

Trp Ile Asn Pro Asn Ser Gly Asp Thr Asn Tyr Ala Gln Lys Phe Gln
1               5                   10                  15

Gly

<210> SEQ ID NO 338
<211> LENGTH: 13
<212> TYPE: PRT
<213> ORGANISM: Homo sapiens

<400> SEQUENCE: 338

Asp Ser Pro Tyr Ser Ser Ser Trp Ser Phe Phe Asp Tyr
1               5                   10

<210> SEQ ID NO 339
<211> LENGTH: 6
<212> TYPE: PRT
<213> ORGANISM: Homo sapiens

<400> SEQUENCE: 339

Gly Tyr Thr Phe Thr Gly
1               5

<210> SEQ ID NO 340
<211> LENGTH: 10
<212> TYPE: PRT
<213> ORGANISM: Homo sapiens

<400> SEQUENCE: 340

Trp Ile Asn Pro Asn Ser Gly Asp Thr Asn
1               5                   10

<210> SEQ ID NO 341
<211> LENGTH: 339
<212> TYPE: DNA
<213> ORGANISM: Homo sapiens

<400> SEQUENCE: 341
gacatcgtga tgacccagtc tccagactcc ctggctgtgt ctctgggcga gagggccacc    60
atcaactgca gtccagcca gagtgtttta tacagctcca acaataagag ccacttagct    120
tggtaccagc agaaaccagg acagcctcct aagttgctca tttactgggc atctacccgg    180
gaatccgggg tccctgaccg attcagtggc agcgggtctg ggacagattt caccctcatc    240
atcagcagcc tgcaggctga ggatgtggca gtttattact gtcagcaata ttatttttct    300
cccctcactt tcggcggagg gaccaaggtg gagatcaaa                          339

<210> SEQ ID NO 342
<211> LENGTH: 113
<212> TYPE: PRT
<213> ORGANISM: Homo sapiens

<400> SEQUENCE: 342

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser

```
                 20                  25                  30

Ser Asn Asn Lys Ser His Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Ile
 65                  70                  75                  80

Ile Ser Ser Leu Gln Ala Glu Asp Val Ala Val Tyr Tyr Cys Gln Gln
                 85                  90                  95

Tyr Tyr Phe Ser Pro Leu Thr Phe Gly Gly Gly Thr Lys Val Glu Ile
            100                 105                 110

Lys
```

<210> SEQ ID NO 343
<211> LENGTH: 17
<212> TYPE: PRT
<213> ORGANISM: Homo sapiens

<400> SEQUENCE: 343

```
Lys Ser Ser Gln Ser Val Leu Tyr Ser Ser Asn Asn Lys Ser His Leu
 1               5                  10                  15

Ala
```

<210> SEQ ID NO 344
<211> LENGTH: 9
<212> TYPE: PRT
<213> ORGANISM: Homo sapiens

<400> SEQUENCE: 344

```
Gln Gln Tyr Tyr Phe Ser Pro Leu Thr
 1               5
```

<210> SEQ ID NO 345
<211> LENGTH: 369
<212> TYPE: DNA
<213> ORGANISM: Homo sapiens

<400> SEQUENCE: 345

```
caggtgcagc tgcaggagtc gggcccagga ctggtgaagc cttcggagac cctgtccctc      60
acctgcactg tctctggtgc ctccatcaat agtcactact ggagctggat ccggcagccc     120
ccagggaagg gactggagtg gattgggtat gtctattaca gtgggagcac cacctacaac     180
ccctccctca gagtcgagt caccttatca gtagatacgt ccaagaacca gttctccctg     240
aacctgagct ctgtgaccgc cgcagacacg gccttctatt actgtgcgag acatccctac     300
gatgttttga ctggttccgg ggactggttc gaccctgg gccagggaac cctggtcacc     360
gtctcgagc                                                             369
```

<210> SEQ ID NO 346
<211> LENGTH: 123
<212> TYPE: PRT
<213> ORGANISM: Homo sapiens

<400> SEQUENCE: 346

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Ala Ser Ile Asn Ser His
             20                  25                  30
```

```
Tyr Trp Ser Trp Ile Arg Gln Pro Gly Lys Gly Leu Glu Trp Ile
         35                  40                  45
Gly Tyr Val Tyr Tyr Ser Gly Ser Thr Thr Tyr Asn Pro Ser Leu Lys
 50                  55                  60
Ser Arg Val Thr Leu Ser Val Asp Thr Ser Lys Asn Gln Phe Ser Leu
 65                  70                  75                  80
Asn Leu Ser Ser Val Thr Ala Ala Asp Thr Ala Phe Tyr Tyr Cys Ala
                 85                  90                  95
Arg His Pro Tyr Asp Val Leu Thr Gly Ser Gly Asp Trp Phe Asp Pro
             100                 105                 110
Trp Gly Gln Gly Thr Leu Val Thr Val Ser Ser
            115                 120
```

<210> SEQ ID NO 347
<211> LENGTH: 5
<212> TYPE: PRT
<213> ORGANISM: Homo sapiens

<400> SEQUENCE: 347

```
Ser His Tyr Trp Ser
 1               5
```

<210> SEQ ID NO 348
<211> LENGTH: 16
<212> TYPE: PRT
<213> ORGANISM: Homo sapiens

<400> SEQUENCE: 348

```
Tyr Val Tyr Tyr Ser Gly Ser Thr Thr Tyr Asn Pro Ser Leu Lys Ser
 1               5                  10                  15
```

<210> SEQ ID NO 349
<211> LENGTH: 15
<212> TYPE: PRT
<213> ORGANISM: Homo sapiens

<400> SEQUENCE: 349

```
His Pro Tyr Asp Val Leu Thr Gly Ser Gly Asp Trp Phe Asp Pro
 1               5                  10                  15
```

<210> SEQ ID NO 350
<211> LENGTH: 7
<212> TYPE: PRT
<213> ORGANISM: Homo sapiens

<400> SEQUENCE: 350

```
Gly Ala Ser Ile Asn Ser His
 1               5
```

<210> SEQ ID NO 351
<211> LENGTH: 9
<212> TYPE: PRT
<213> ORGANISM: Homo sapiens

<400> SEQUENCE: 351

```
Tyr Val Tyr Tyr Ser Gly Ser Thr Thr
 1               5
```

<210> SEQ ID NO 352
<211> LENGTH: 324
<212> TYPE: DNA
<213> ORGANISM: Homo sapiens -continued

<400> SEQUENCE: 352

```
tcctatgttc tgactcaggc accctcggtg tcagtggccc caggacagac ggccaggatt    60
acctgtgggg gaaatgccat tggaagtaaa aaagttcact ggtaccagca caaggcaggc   120
caggcccctg tactcgtcgt ctatgatgat acagaccggc cctcaggat  ccctgagcga   180
ttctctggct ccaactcttg gagcacggcc accctgacca tcaacagggt cgaagccggg   240
gatgaggccg actattactg tcaggtgtgg gattttacca ttgatcatgt ggtcttcggc   300
ggagggacca agctgaccgt tcta                                           324
```

<210> SEQ ID NO 353
<211> LENGTH: 108
<212> TYPE: PRT
<213> ORGANISM: Homo sapiens

<400> SEQUENCE: 353

Ser Tyr Val Leu Thr Gln Ala Pro Ser Val Ser Val Ala Pro Gly Gln
1               5                   10                  15

Thr Ala Arg Ile Thr Cys Gly Gly Asn Ala Ile Gly Ser Lys Lys Val
            20                  25                  30

His Trp Tyr Gln His Lys Ala Gly Gln Ala Pro Val Leu Val Val Tyr
        35                  40                  45

Asp Asp Thr Asp Arg Pro Ser Gly Ile Pro Glu Arg Phe Ser Gly Ser
    50                  55                  60

Asn Ser Trp Ser Thr Ala Thr Leu Thr Ile Asn Arg Val Glu Ala Gly
65                  70                  75                  80

Asp Glu Ala Asp Tyr Tyr Cys Gln Val Trp Asp Phe Thr Ile Asp His
                85                  90                  95

Val Val Phe Gly Gly Gly Thr Lys Leu Thr Val Leu
            100                 105

<210> SEQ ID NO 354
<211> LENGTH: 11
<212> TYPE: PRT
<213> ORGANISM: Homo sapiens

<400> SEQUENCE: 354

Gly Gly Asn Ala Ile Gly Ser Lys Lys Val His
1               5                   10

<210> SEQ ID NO 355
<211> LENGTH: 7
<212> TYPE: PRT
<213> ORGANISM: Homo sapiens

<400> SEQUENCE: 355

Asp Asp Thr Asp Arg Pro Ser
1               5

<210> SEQ ID NO 356
<211> LENGTH: 11
<212> TYPE: PRT
<213> ORGANISM: Homo sapiens

<400> SEQUENCE: 356

Gln Val Trp Asp Phe Thr Ile Asp His Val Val
1               5                   10

<210> SEQ ID NO 357
<211> LENGTH: 387

```
<212> TYPE: DNA
<213> ORGANISM: Homo sapiens

<400> SEQUENCE: 357
gaggtgcaac tggttcagtc tggatcagag gtgaaaaagc ccggggagtc tctgaagatc      60
tcctgtaagg gttctggcta cagctttagc aactactgga tcggctgggt gcgccacatg     120
cccgggaaag gcctggaatg gatggggatc atttatcctg gtgactctga taccagatac     180
agcccgtcct tccaaggcca ggtcaccatg tcagccgaca gtccagcag caccgtctac     240
ctgcagtgga gcagcctgaa ggcctcggac accgccattt attattgtgc gagacggggc     300
ggacatagtt ttggatatgg gtcgggggggg gacacgcaca gtgaattcga ctcctggggc     360
cagggaaccc tggtcaccgt ctcgagc                                         387

<210> SEQ ID NO 358
<211> LENGTH: 129
<212> TYPE: PRT
<213> ORGANISM: Homo sapiens

<400> SEQUENCE: 358

Glu Val Gln Leu Val Gln Ser Gly Ser Glu Val Lys Lys Pro Gly Glu
1               5                   10                  15

Ser Leu Lys Ile Ser Cys Lys Gly Ser Gly Tyr Ser Phe Ser Asn Tyr
            20                  25                  30

Trp Ile Gly Trp Val Arg His Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Met Ser Ala Asp Lys Ser Ser Ser Thr Val Tyr
65                  70                  75                  80

Leu Gln Trp Ser Ser Leu Lys Ala Ser Asp Thr Ala Ile Tyr Tyr Cys
                85                  90                  95

Ala Arg Arg Gly Gly His Ser Phe Gly Tyr Gly Ser Gly Gly Asp Thr
            100                 105                 110

His Ser Glu Phe Asp Ser Trp Gly Gln Gly Thr Leu Val Thr Val Ser
        115                 120                 125

Ser

<210> SEQ ID NO 359
<211> LENGTH: 5
<212> TYPE: PRT
<213> ORGANISM: Homo sapiens

<400> SEQUENCE: 359

Asn Tyr Trp Ile Gly
1               5

<210> SEQ ID NO 360
<211> LENGTH: 17
<212> TYPE: PRT
<213> ORGANISM: Homo sapiens

<400> SEQUENCE: 360

Ile Ile Tyr Pro Gly Asp Ser Asp Thr Arg Tyr Ser Pro Ser Phe Gln
1               5                   10                  15

Gly

<210> SEQ ID NO 361
```

```
<211> LENGTH: 20
<212> TYPE: PRT
<213> ORGANISM: Homo sapiens

<400> SEQUENCE: 361

Arg Gly Gly His Ser Phe Gly Tyr Ser Gly Gly Asp Thr His Ser
1               5                   10                  15
Glu Phe Asp Ser
            20

<210> SEQ ID NO 362
<211> LENGTH: 6
<212> TYPE: PRT
<213> ORGANISM: Homo sapiens

<400> SEQUENCE: 362

Gly Tyr Ser Phe Ser Asn
1               5

<210> SEQ ID NO 363
<211> LENGTH: 10
<212> TYPE: PRT
<213> ORGANISM: Homo sapiens

<400> SEQUENCE: 363

Ile Ile Tyr Pro Gly Asp Ser Asp Thr Arg
1               5                   10

<210> SEQ ID NO 364
<211> LENGTH: 330
<212> TYPE: DNA
<213> ORGANISM: Homo sapiens

<400> SEQUENCE: 364
cagtctgtat tgacgcagtc gccctcagtg tctgcggccc caggacagaa ggtcaccatc      60
tcctgctctg gaagcgactc caacattggt gattattttg tatgttggta ccagcacctc     120
ccaggaaaac cccccaact  cctcatctat gaaaataata gcgaccctc  agggattcct     180
gaccgattct ctggctccaa gtctggcacg tcagccaccc tgggcatcac cggaatccag     240
accggggacg aggccgatta ctactgcgca acttgggatg cagcctgag  tgcttgggtg     300
ttcggcggag ggaccaagct gaccgttcta                                      330

<210> SEQ ID NO 365
<211> LENGTH: 110
<212> TYPE: PRT
<213> ORGANISM: Homo sapiens

<400> SEQUENCE: 365

Gln Ser Val Leu Thr Gln Ser Pro Ser Val Ser Ala Ala Pro Gly Gln
1               5                   10                  15
Lys Val Thr Ile Ser Cys Ser Gly Ser Asp Ser Asn Ile Gly Asp Tyr
            20                  25                  30
Phe Val Cys Trp Tyr Gln His Leu Pro Gly Lys Pro Gln Leu Leu
        35                  40                  45
Ile Tyr Glu Asn Asn Lys Arg Pro Ser Gly Ile Pro Arg Phe Ser
    50                  55                  60
Gly Ser Lys Ser Gly Thr Ser Ala Thr Leu Gly Ile Thr Gly Ile Gln
65                  70                  75                  80
Thr Gly Asp Glu Ala Asp Tyr Tyr Cys Ala Thr Trp Asp Gly Ser Leu
                85                  90                  95
```

Ser Ala Trp Val Phe Gly Gly Gly Thr Lys Leu Thr Val Leu
            100                 105                 110

<210> SEQ ID NO 366
<211> LENGTH: 13
<212> TYPE: PRT
<213> ORGANISM: Homo sapiens

<400> SEQUENCE: 366

Ser Gly Ser Asp Ser Asn Ile Gly Asp Tyr Phe Val Cys
1               5                   10

<210> SEQ ID NO 367
<211> LENGTH: 7
<212> TYPE: PRT
<213> ORGANISM: Homo sapiens

<400> SEQUENCE: 367

Glu Asn Asn Lys Arg Pro Ser
1               5

<210> SEQ ID NO 368
<211> LENGTH: 11
<212> TYPE: PRT
<213> ORGANISM: Homo sapiens

<400> SEQUENCE: 368

Ala Thr Trp Asp Gly Ser Leu Ser Ala Trp Val
1               5                   10

<210> SEQ ID NO 369
<211> LENGTH: 362
<212> TYPE: DNA
<213> ORGANISM: Homo sapiens

<400> SEQUENCE: 369
caggtccaag tggtgcagtc tggggctgag gtgaagaagc ctgggtcctc ggtgagggtc      60
tcctgccagg cttctggagg caccttcatg aattatgcta tcatttgggt gcgacgggcc     120
cctggacaag gccttgagtg gatgggaggg atcatccctg tctttcctac accaaactac     180
gcacagatgt tccagggcag agtcacgatt tccacggacg aatccaggag cacatccttc     240
ttggaactga ccaacctgag atatgaggac acggccgttt attactgtgc gagcgaattt     300
atcacggtgg taactccggc tttgacttct ggggccaggg aaccctggtc accgtctcga     360
gc                                                                    362

<210> SEQ ID NO 370
<211> LENGTH: 121
<212> TYPE: PRT
<213> ORGANISM: Homo sapiens

<400> SEQUENCE: 370

Gln Val Gln Val Val Gln Ser Gly Ala Glu Val Lys Lys Pro Gly Ser
1               5                   10                  15

Ser Val Arg Val Ser Cys Gln Ala Ser Gly Gly Thr Phe Met Asn Tyr
            20                  25                  30

Ala Ile Ile Trp Val Arg Arg Ala Pro Gly Gln Gly Leu Glu Trp Met
        35                  40                  45

Gly Gly Ile Ile Pro Val Phe Pro Thr Pro Asn Tyr Ala Gln Met Phe
    50                  55                  60

-continued

```
Gln Gly Arg Val Thr Ile Ser Thr Asp Glu Ser Arg Ser Thr Ser Phe
 65                  70                  75                  80

Leu Glu Leu Thr Asn Leu Arg Tyr Glu Asp Thr Ala Val Tyr Tyr Cys
                 85                  90                  95

Ala Arg Arg Ile Tyr His Gly Gly Asn Ser Gly Phe Asp Phe Trp Gly
            100                 105                 110

Gln Gly Thr Leu Val Thr Val Ser Ser
        115                 120
```

<210> SEQ ID NO 371
<211> LENGTH: 5
<212> TYPE: PRT
<213> ORGANISM: Homo sapiens

<400> SEQUENCE: 371

```
Asn Tyr Ala Ile Ile
1               5
```

<210> SEQ ID NO 372
<211> LENGTH: 17
<212> TYPE: PRT
<213> ORGANISM: Homo sapiens

<400> SEQUENCE: 372

```
Gly Ile Ile Pro Val Phe Pro Thr Pro Asn Tyr Ala Gln Met Phe Gln
1               5                   10                  15

Gly
```

<210> SEQ ID NO 373
<211> LENGTH: 12
<212> TYPE: PRT
<213> ORGANISM: Homo sapiens

<400> SEQUENCE: 373

```
Arg Ile Tyr His Gly Gly Asn Ser Gly Phe Asp Phe
1               5                   10
```

<210> SEQ ID NO 374
<211> LENGTH: 6
<212> TYPE: PRT
<213> ORGANISM: Homo sapiens

<400> SEQUENCE: 374

```
Gly Gly Thr Phe Met Asn
1               5
```

<210> SEQ ID NO 375
<211> LENGTH: 10
<212> TYPE: PRT
<213> ORGANISM: Homo sapiens

<400> SEQUENCE: 375

```
Gly Ile Ile Pro Val Phe Pro Thr Pro Asn
1               5                   10
```

<210> SEQ ID NO 376
<211> LENGTH: 327
<212> TYPE: DNA
<213> ORGANISM: Homo sapiens

<400> SEQUENCE: 376

```
gaaattgtgt tgacacagtc tccagccacc ctgtctttgt ctccagggga aagagccacc    60
```

```
ctctcctgca gggccagtca gagtgttggc aactacttag cctggtacca acagaaacct    120
ggccaggctc ccaggctcct catctatgat tcatccaaca gggcccctgg catcccagcc    180
aggttcagtg gcagtgggtc tgggacagac ttcactctca ccatcagcag cctcgcgcct    240
gaagattttg cagtttatta ctgtcagcag cgtagcaagt ggcctcccat gtacagtttt    300
ggccatggga ccaagctgga gatcaaa                                        327
```

<210> SEQ ID NO 377
<211> LENGTH: 109
<212> TYPE: PRT
<213> ORGANISM: Homo sapiens

<400> SEQUENCE: 377

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Asn Tyr
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Ala Pro
65                  70                  75                  80

Glu Asp Phe Ala Val Tyr Tyr Cys Gln Gln Arg Ser Lys Trp Pro Pro
                85                  90                  95

Met Tyr Ser Phe Gly His Gly Thr Lys Leu Glu Ile Lys
            100                 105

<210> SEQ ID NO 378
<211> LENGTH: 11
<212> TYPE: PRT
<213> ORGANISM: Homo sapiens

<400> SEQUENCE: 378

Arg Ala Ser Gln Ser Val Gly Asn Tyr Leu Ala
1               5                   10

<210> SEQ ID NO 379
<211> LENGTH: 7
<212> TYPE: PRT
<213> ORGANISM: Homo sapiens

<400> SEQUENCE: 379

Asp Ser Ser Asn Arg Ala Pro
1               5

<210> SEQ ID NO 380
<211> LENGTH: 11
<212> TYPE: PRT
<213> ORGANISM: Homo sapiens

<400> SEQUENCE: 380

Gln Gln Arg Ser Lys Trp Pro Pro Met Tyr Ser
1               5                   10

<210> SEQ ID NO 381
<211> LENGTH: 357
<212> TYPE: DNA
<213> ORGANISM: Homo sapiens

<400> SEQUENCE: 381

```
caggtccagg tggtgcagtc tgggactgag gtgaagaagc ctgggtcctc ggtgaaggtc    60
tcctgccaga cttctggagg caggttcatg agttatgcta tcacctgggt gcgacaggcc   120
cctggacaag gcttgagtg gatgggaggc atcgtccctg tcttcggaac agcaaactac   180
gctcagaagt tccagggcag agtcacgatc accacgacg attccacgcg cacagcctat   240
atggagttga gcagcctgag aagtgaggac acggccgttt attactgtgg gttccgatac   300
ggctctggtt acgggtttga ctcctggggc cagggaaccc tggtcaccgt ctcgagc     357
```

<210> SEQ ID NO 382
<211> LENGTH: 119
<212> TYPE: PRT
<213> ORGANISM: Homo sapiens

<400> SEQUENCE: 382

Gln Val Gln Val Val Gln Ser Gly Thr Glu Val Lys Lys Pro Gly Ser
1               5                   10                  15

Ser Val Lys Val Ser Cys Gln Thr Ser Gly Gly Arg Phe Met Ser Tyr
            20                  25                  30

Ala Ile Thr Trp Val Arg Gln Ala Pro Gly Gln Gly Leu Glu Trp Met
        35                  40                  45

Gly Gly Ile Val Pro Val Phe Gly Thr Ala Asn Tyr Ala Gln Lys Phe
    50                  55                  60

Gln Gly Arg Val Thr Ile Thr Thr Asp Asp Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Gly Phe Arg Tyr Gly Ser Gly Tyr Gly Phe Asp Ser Trp Gly Gln Gly
            100                 105                 110

Thr Leu Val Thr Val Ser Ser
        115

<210> SEQ ID NO 383
<211> LENGTH: 5
<212> TYPE: PRT
<213> ORGANISM: Homo sapiens

<400> SEQUENCE: 383

Ser Tyr Ala Ile Thr
1               5

<210> SEQ ID NO 384
<211> LENGTH: 17
<212> TYPE: PRT
<213> ORGANISM: Homo sapiens

<400> SEQUENCE: 384

Gly Ile Val Pro Val Phe Gly Thr Ala Asn Tyr Ala Gln Lys Phe Gln
1               5                   10                  15

Gly

<210> SEQ ID NO 385
<211> LENGTH: 10
<212> TYPE: PRT
<213> ORGANISM: Homo sapiens

<400> SEQUENCE: 385

Arg Tyr Gly Ser Gly Tyr Gly Phe Asp Ser
1               5                   10

<210> SEQ ID NO 386
<211> LENGTH: 6
<212> TYPE: PRT
<213> ORGANISM: Homo sapiens

<400> SEQUENCE: 386

Gly Gly Arg Phe Met Ser
1               5

<210> SEQ ID NO 387
<211> LENGTH: 10
<212> TYPE: PRT
<213> ORGANISM: Homo sapiens

<400> SEQUENCE: 387

Gly Ile Val Pro Val Phe Gly Thr Ala Asn
1               5                   10

<210> SEQ ID NO 388
<211> LENGTH: 324
<212> TYPE: DNA
<213> ORGANISM: Homo sapiens

<400> SEQUENCE: 388
gaaattgtat tgacgcagtc tccaggcacc ctgtctttgt ctccagggga aagagccacc      60
ctctcctgca gggccagtca gagtgttagt agcagctact tagcctggta tcagaagaaa     120
cctggccagg ctcccaggct cctcatctat ggtgcttcca ctagggccac tggcatcccg     180
gaccggttca ctggcagtgg gtctgggaca gacttcactc tcagcatcag tagactggag     240
cctgaagatt ttgcagtgta ttactgtcag cactttggta cctcagtctt cactttcggc     300
ggagggacca aggttgagat caaa                                            324

<210> SEQ ID NO 389
<211> LENGTH: 108
<212> TYPE: PRT
<213> ORGANISM: Homo sapiens

<400> SEQUENCE: 389

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Lys Lys Pro Gly Gln Ala Pro Arg Leu Leu
            35                  40                  45

Ile Tyr Gly Ala Ser Thr Arg Ala Thr Gly Ile Pro Asp Arg Phe Thr
        50                  55                  60

Gly Ser Gly Ser Gly Thr Asp Phe Thr Leu Ser Ile Ser Arg Leu Glu
65                  70                  75                  80

Pro Glu Asp Phe Ala Val Tyr Tyr Cys Gln His Phe Gly Thr Ser Val
                85                  90                  95

Phe Thr Phe Gly Gly Gly Thr Lys Val Glu Ile Lys
            100                 105

<210> SEQ ID NO 390
<211> LENGTH: 9
<212> TYPE: PRT
<213> ORGANISM: Homo sapiens

<400> SEQUENCE: 390

Gln His Phe Gly Thr Ser Val Phe Thr
1               5

<210> SEQ ID NO 391
<211> LENGTH: 360
<212> TYPE: DNA
<213> ORGANISM: Homo sapiens

<400> SEQUENCE: 391
caggtgcagc tggtgcagtc tggggctgat ctgaagaagc ctggggcctc agtgaaggtc    60
tcctgcaagg cttctggata caccttcacc gactactata ttcactgggt gcgacaggcc   120
cctggacaag ggcttgagtg gatgggatgg atcaaccctg aaagtggtga cacaaagtat   180
gcacagaagt ttcagggcag ggtcaccatg accagggaca cgtccatcac cacagcctac   240
atggagctgg gtaggctgag atccgacgac acggccgtgt attactgtgc gagagatgta   300
agtacgacct ggagctggtt cgccccctgg ggccagggaa ccctggtcac cgtctcgagc   360

<210> SEQ ID NO 392
<211> LENGTH: 120
<212> TYPE: PRT
<213> ORGANISM: Homo sapiens

<400> SEQUENCE: 392

Gln Val Gln Leu Val Gln Ser Gly Ala Asp Leu Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Glu Ser Gly Asp Thr Lys Tyr Ala Gln Lys Phe
    50                  55                  60

Gln Gly Arg Val Thr Met Thr Arg Asp Thr Ser Ile Thr Thr Ala Tyr
65                  70                  75                  80

Met Glu Leu Gly Arg Leu Arg Ser Asp Asp Thr Ala Val Tyr Tyr Cys
                85                  90                  95

Ala Arg Asp Val Ser Thr Thr Trp Ser Trp Phe Ala Pro Trp Gly Gln
            100                 105                 110

Gly Thr Leu Val Thr Val Ser Ser
        115                 120

<210> SEQ ID NO 393
<211> LENGTH: 5
<212> TYPE: PRT
<213> ORGANISM: Homo sapiens

<400> SEQUENCE: 393

Asp Tyr Tyr Ile His
1               5

<210> SEQ ID NO 394
<211> LENGTH: 17
<212> TYPE: PRT
<213> ORGANISM: Homo sapiens

<400> SEQUENCE: 394

Trp Ile Asn Pro Glu Ser Gly Asp Thr Lys Tyr Ala Gln Lys Phe Gln
1               5                   10                  15

Gly

<210> SEQ ID NO 395
<211> LENGTH: 11
<212> TYPE: PRT
<213> ORGANISM: Homo sapiens

<400> SEQUENCE: 395

Asp Val Ser Thr Thr Trp Ser Trp Phe Ala Pro
1               5                   10

<210> SEQ ID NO 396
<211> LENGTH: 6
<212> TYPE: PRT
<213> ORGANISM: Homo sapiens

<400> SEQUENCE: 396

Gly Tyr Thr Phe Thr Asp
1               5

<210> SEQ ID NO 397
<211> LENGTH: 10
<212> TYPE: PRT
<213> ORGANISM: Homo sapiens

<400> SEQUENCE: 397

Trp Ile Asn Pro Glu Ser Gly Asp Thr Lys
1               5                   10

<210> SEQ ID NO 398
<211> LENGTH: 339
<212> TYPE: DNA
<213> ORGANISM: Homo sapiens

<400> SEQUENCE: 398
gacatcgtga tgacccagtc tccagactcc ctggcagtgt ctctgggcga gagggccacc      60
atcaactgca ggtccagcca gagtattttc cacaactcca acaatgagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggcg gtttatttct gtcagcaata ttataatgct     300
ccgctcactt tcggcggagg gaccaaggtg gagatcaaa                            339

<210> SEQ ID NO 399
<211> LENGTH: 113
<212> TYPE: PRT
<213> ORGANISM: Homo sapiens

<400> SEQUENCE: 399

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Ile Phe His Asn
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Asn Ala Pro Leu Thr Phe Gly Gly Gly Thr Lys Val Glu Ile
                100                 105                 110

Lys

<210> SEQ ID NO 400
<211> LENGTH: 17
<212> TYPE: PRT
<213> ORGANISM: Homo sapiens

<400> SEQUENCE: 400

Arg Ser Ser Gln Ser Ile Phe His Asn Ser Asn Asn Glu Asn Tyr Leu
1               5                   10                  15

Ala

<210> SEQ ID NO 401
<211> LENGTH: 9
<212> TYPE: PRT
<213> ORGANISM: Homo sapiens

<400> SEQUENCE: 401

Gln Gln Tyr Tyr Asn Ala Pro Leu Thr
1               5

<210> SEQ ID NO 402
<211> LENGTH: 369
<212> TYPE: DNA
<213> ORGANISM: Homo sapiens

<400> SEQUENCE: 402
caggtgcagc tggtgcagtc tggggctgag gtgaagaggc ctgggtcctc ggtgaaggtc      60
tcatgcacgg cttctggagg catcttcagg aagaatgcaa tcagctgggt gcgacaggcc     120
cctggacaag gccttgagtg gatgggaggg atcatcgcag tctttaacac agcaaattac     180
gcgcagaagt tccagaacag agtcaaaatt accgcagacg agtcaggcaa tacgccctac     240
atggagctga gcagcctgac atctgacgac acggccgtgt attactgtgc gagtcaccca     300
aaatatttct atggttcggg gagttatccg gacttctggg gccagggaac cctggtcacc     360
gtctcgagc                                                              369

<210> SEQ ID NO 403
<211> LENGTH: 123
<212> TYPE: PRT
<213> ORGANISM: Homo sapiens

<400> SEQUENCE: 403

Gln Val Gln Leu Val Gln Ser Gly Ala Glu Val Lys Arg Pro Gly Ser
1               5                   10                  15

Ser Val Lys Val Ser Cys Thr Ala Ser Gly Gly Ile Phe Arg Lys Asn
                20                  25                  30

Ala Ile Ser Trp Val Arg Gln Ala Pro Gly Gln Gly Leu Glu Trp Met
            35                  40                  45

Gly Gly Ile Ile Ala Val Phe Asn Thr Ala Asn Tyr Ala Gln Lys Phe
        50                  55                  60

Gln Asn Arg Val Lys Ile Thr Ala Asp Glu Ser Gly Asn Thr Ala Tyr
65                  70                  75                  80

Met Glu Leu Ser Ser Leu Thr Ser Asp Asp Thr Ala Val Tyr Tyr Cys
                85                  90                  95

Ala Ser His Pro Lys Tyr Phe Tyr Gly Ser Gly Ser Tyr Pro Asp Phe

```
                      100                 105                 110
Trp Gly Gln Gly Thr Leu Val Thr Val Ser Ser
              115                 120

<210> SEQ ID NO 404
<211> LENGTH: 330
<212> TYPE: DNA
<213> ORGANISM: Homo sapiens

<400> SEQUENCE: 404
caatctgccc tgactcagcc tcgctcagtg tccgggtctc ctggacagtc aatcaccatc     60
tcctgtactg gtggcagcag tgatattggt gcttctaact ctgtctcctg gtaccaacaa    120
cacccaggca aagcccccaa actcgttatt tttgatgtca ctgagcgacc ctcaggggtc    180
ccgcatcggt tctctggctc caagtctggc aacacggcct ccctgaccgt ctctgggctc    240
cagcctgacg acgaggctga ttatttctgc tgcgcatatg gaggcaaata tcttgtggtc    300
ttcggcggag ggaccaaggt gaccgttcta                                     330

<210> SEQ ID NO 405
<211> LENGTH: 110
<212> TYPE: PRT
<213> ORGANISM: Homo sapiens

<400> SEQUENCE: 405

Gln Ser Ala Leu Thr Gln Pro Arg Ser Val Ser Gly Ser Pro Gly Gln
1               5                   10                  15

Ser Ile Thr Ile Ser Cys Thr Gly Gly Ser Ser Asp Ile Gly Ala Ser
            20                  25                  30

Asn Ser Val Ser Trp Tyr Gln Gln His Pro Gly Lys Ala Pro Lys Leu
        35                  40                  45

Val Ile Phe Asp Val Thr Glu Arg Pro Ser Gly Val Pro His Arg Phe
    50                  55                  60

Ser Gly Ser Lys Ser Gly Asn Thr Ala Ser Leu Thr Val Ser Gly Leu
65                  70                  75                  80

Gln Pro Asp Asp Glu Ala Asp Tyr Phe Cys Cys Ala Tyr Gly Gly Lys
                85                  90                  95

Tyr Leu Val Val Phe Gly Gly Gly Thr Lys Val Thr Val Leu
            100                 105                 110

<210> SEQ ID NO 406
<211> LENGTH: 14
<212> TYPE: PRT
<213> ORGANISM: Homo sapiens

<400> SEQUENCE: 406

Thr Gly Gly Ser Ser Asp Ile Gly Ala Ser Asn Ser Val Ser
1               5                   10

<210> SEQ ID NO 407
<211> LENGTH: 381
<212> TYPE: DNA
<213> ORGANISM: Homo sapiens

<400> SEQUENCE: 407
caggtgcagc tggtgcagtc tggggctgag gtgaagaaac ctggggcctc agtgaaggtc     60
tcctgcaagg cttctggata caccttcatc ggctatgata tgcactgggt gcgacaggcc    120
cctggacaag gcttgagtg gatgggatgg atcaacgcta aaagaggtgg cacaaactat    180
```

```
gcacaaaagt tcagggcag ggtcaccatg accagggaca cgtctatcag cacagcctac    240
atggagctga acagcctgag atctgacgac acggccgtgt attactgtgc gagagggtg    300 gggtcacgaa ctacgatttt tggagttctc aacccggaat ttgactactg gggccaggga   360
accctggtca ccgtctcgag c                                              381
```

<210> SEQ ID NO 408
<211> LENGTH: 127
<212> TYPE: PRT
<213> ORGANISM: Homo sapiens

<400> SEQUENCE: 408

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Gly Tyr
                20                  25                  30

Asp Met His Trp Val Arg Gln Ala Pro Gly Gln Gly Leu Glu Trp Met
            35                  40                  45

Gly Trp Ile Asn Ala Lys Arg Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Asn Ser Leu Arg Ser Asp Asp Thr Ala Val Tyr Tyr Cys
                85                  90                  95

Ala Arg Gly Val Gly Ser Arg Thr Thr Ile Phe Gly Val Leu Asn Pro
            100                 105                 110

Glu Phe Asp Tyr Trp Gly Gln Gly Thr Leu Val Thr Val Ser Ser
        115                 120                 125

<210> SEQ ID NO 409
<211> LENGTH: 5
<212> TYPE: PRT
<213> ORGANISM: Homo sapiens

<400> SEQUENCE: 409

Gly Tyr Asp Met His
1               5

<210> SEQ ID NO 410
<211> LENGTH: 17
<212> TYPE: PRT
<213> ORGANISM: Homo sapiens

<400> SEQUENCE: 410

Trp Ile Asn Ala Lys Arg Gly Gly Thr Asn Tyr Ala Gln Lys Phe Gln
1               5                   10                  15

Gly

<210> SEQ ID NO 411
<211> LENGTH: 18
<212> TYPE: PRT
<213> ORGANISM: Homo sapiens

<400> SEQUENCE: 411

Gly Val Gly Ser Arg Thr Thr Ile Phe Gly Val Leu Asn Pro Glu Phe
1               5                   10                  15

Asp Tyr

<210> SEQ ID NO 412

```
<211> LENGTH: 6
<212> TYPE: PRT
<213> ORGANISM: Homo sapiens

<400> SEQUENCE: 412

Gly Tyr Thr Phe Ile Gly
1               5

<210> SEQ ID NO 413
<211> LENGTH: 10
<212> TYPE: PRT
<213> ORGANISM: Homo sapiens

<400> SEQUENCE: 413

Trp Ile Asn Ala Lys Arg Gly Gly Thr Asn
1               5                   10

<210> SEQ ID NO 414
<211> LENGTH: 330
<212> TYPE: DNA
<213> ORGANISM: Homo sapiens

<400> SEQUENCE: 414
cagtctgccc tgactcagcc tccctccgcg tccgggtctc ctggacagtc agtcaccatc      60
tcctgcactg gatccagcag tgacgttggt ggttatgact atgtctcctg gtaccaacaa     120
cacccaggca aagcccccaa actcctgatt tatgaggtca ctaagcggcc ctcaggggtc     180
cctgatcgct tctctggctc caagtctggc aacacggcct ccctgaccgt ctctgggctc     240
caggctgagg atgaggctga ttattactgc agctcatatg cgggcaacta caatcatgtc     300
ttcggacctg ggaccaaggt caccgttcta                                      330

<210> SEQ ID NO 415
<211> LENGTH: 110
<212> TYPE: PRT
<213> ORGANISM: Homo sapiens

<400> SEQUENCE: 415

Gln Ser Ala Leu Thr Gln Pro Pro Ser Ala Ser Gly Ser Pro Gly Gln
1               5                   10                  15

Ser Val Thr Ile Ser Cys Thr Gly Ser Ser Ser Asp Val Gly Gly Tyr
            20                  25                  30

Asp Tyr Val Ser Trp Tyr Gln Gln His Pro Gly Lys Ala Pro Lys Leu
        35                  40                  45

Leu Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Asn
                85                  90                  95

Tyr Asn His Val Phe Gly Pro Gly Thr Lys Val Thr Val Leu
            100                 105                 110

<210> SEQ ID NO 416
<211> LENGTH: 14
<212> TYPE: PRT
<213> ORGANISM: Homo sapiens

<400> SEQUENCE: 416

Thr Gly Ser Ser Ser Asp Val Gly Gly Tyr Asp Tyr Val Ser
1               5                   10
```

<210> SEQ ID NO 417
<211> LENGTH: 7
<212> TYPE: PRT
<213> ORGANISM: Homo sapiens

<400> SEQUENCE: 417

Glu Val Thr Lys Arg Pro Ser
1               5

<210> SEQ ID NO 418
<211> LENGTH: 10
<212> TYPE: PRT
<213> ORGANISM: Homo sapiens

<400> SEQUENCE: 418

Ser Ser Tyr Ala Gly Asn Tyr Asn His Val
1               5                   10

<210> SEQ ID NO 419
<211> LENGTH: 354
<212> TYPE: DNA
<213> ORGANISM: Homo sapiens

<400> SEQUENCE: 419

```
caggtgcagc tggtgcagtc tggggctgag gtgaagaagc ctggggcctc agtgaaggtc      60
tcctgcaagg cttctggaca ccttcacc ggctactaca tacactgggt gcgacaggcc       120
cctggacaag gcttgagtg gatgggatgg atcaaccctg acagtggtgc caccagttct     180
gcacagaact ttcagggcag ggtcaccatg accggggaca cgtcctctag cacagcctac    240
atggagctga gtaggctgag ttttgacgac acggccgtct attactgtgc gagagtactg    300
tttaccagtc cttttgactt ctggggtgag ggaaccctgg tcaccgtctc gagc          354
```

<210> SEQ ID NO 420
<211> LENGTH: 118
<212> TYPE: PRT
<213> ORGANISM: Homo sapiens

<400> SEQUENCE: 420

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Gly Tyr
                20                  25                  30

Tyr Ile His Trp Val Arg Gln Ala Pro Gly Gln Gly Leu Glu Trp Met
            35                  40                  45

Gly Trp Ile Asn Pro Asp Ser Gly Ala Thr Ser Ser Ala Gln Asn Phe
        50                  55                  60

Gln Gly Arg Val Thr Met Thr Gly Asp Thr Ser Ser Ser Thr Ala Tyr
65                  70                  75                  80

Met Glu Leu Ser Arg Leu Ser Phe Asp Asp Thr Ala Val Tyr Tyr Cys
                85                  90                  95

Ala Arg Val Leu Phe Thr Ser Pro Phe Asp Phe Trp Gly Glu Gly Thr
            100                 105                 110

Leu Val Thr Val Ser Ser
            115

<210> SEQ ID NO 421
<211> LENGTH: 5
<212> TYPE: PRT

<213> ORGANISM: Homo sapiens

<400> SEQUENCE: 421

Gly Tyr Tyr Ile His
1               5

<210> SEQ ID NO 422
<211> LENGTH: 17
<212> TYPE: PRT
<213> ORGANISM: Homo sapiens

<400> SEQUENCE: 422

Trp Ile Asn Pro Asp Ser Gly Ala Thr Ser Ala Gln Asn Phe Gln
1               5                   10                  15

Gly

<210> SEQ ID NO 423
<211> LENGTH: 9
<212> TYPE: PRT
<213> ORGANISM: Homo sapiens

<400> SEQUENCE: 423

Val Leu Phe Thr Ser Pro Phe Asp Phe
1               5

<210> SEQ ID NO 424
<211> LENGTH: 6
<212> TYPE: PRT
<213> ORGANISM: Homo sapiens

<400> SEQUENCE: 424

Gly His Thr Phe Thr Gly
1               5

<210> SEQ ID NO 425
<211> LENGTH: 10
<212> TYPE: PRT
<213> ORGANISM: Homo sapiens

<400> SEQUENCE: 425

Trp Ile Asn Pro Asp Ser Gly Ala Thr Ser
1               5                   10

<210> SEQ ID NO 426
<211> LENGTH: 330
<212> TYPE: DNA
<213> ORGANISM: Homo sapiens

<400> SEQUENCE: 426
caggctgtgg tgactcagga gccctcactg gctgtgtccc caggagggac agtcactctc        60
acctgtggct ccagcactgg agctgtcacc aggggtcatt atccctattg gttccagcag       120
aagcctggcc aagcccccag ggcactcatt tatgatagtg caggcaacag acactcctgg       180
actcccgccc gattctcagg ctccctcctt gggggcaaag ctgccctgac cctttcgggt       240
gcgcagcctg aggatgaggc tgagtattac tgcttgctct cctatagtgg tgtctgggtg       300
ttcggcggag ggacgaagct gaccgttcta                                        330

<210> SEQ ID NO 427
<211> LENGTH: 110
<212> TYPE: PRT
<213> ORGANISM: Homo sapiens

<400> SEQUENCE: 427

Gln Ala Val Val Thr Gln Glu Pro Ser Leu Ala Val Ser Pro Gly Gly
1               5                   10                  15

Thr Val Thr Leu Thr Cys Gly Ser Ser Thr Gly Ala Val Thr Arg Gly
            20                  25                  30

His Tyr Pro Tyr Trp Phe Gln Lys Pro Gly Gln Ala Pro Arg Ala
        35                  40                  45

Leu Ile Tyr Asp Ser Ala Gly Asn Arg His Ser Trp Thr Pro Ala Arg
    50                  55                  60

Phe Ser Gly Ser Leu Leu Gly Gly Lys Ala Ala Leu Thr Leu Ser Gly
65                  70                  75                  80

Ala Gln Pro Glu Asp Glu Ala Glu Tyr Tyr Cys Leu Leu Ser Tyr Ser
                85                  90                  95

Gly Val Trp Val Phe Gly Gly Gly Thr Lys Leu Thr Val Leu
            100                 105                 110

<210> SEQ ID NO 428
<211> LENGTH: 14
<212> TYPE: PRT
<213> ORGANISM: Homo sapiens

<400> SEQUENCE: 428

Gly Ser Ser Thr Gly Ala Val Thr Arg Gly His Tyr Pro Tyr
1               5                   10

<210> SEQ ID NO 429
<211> LENGTH: 8
<212> TYPE: PRT
<213> ORGANISM: Homo sapiens

<400> SEQUENCE: 429

Asp Ser Ala Gly Asn Arg His Ser
1               5

<210> SEQ ID NO 430
<211> LENGTH: 9
<212> TYPE: PRT
<213> ORGANISM: Homo sapiens

<400> SEQUENCE: 430

Leu Leu Ser Tyr Ser Gly Val Trp Val
1               5

<210> SEQ ID NO 431
<211> LENGTH: 360
<212> TYPE: DNA
<213> ORGANISM: Homo sapiens

<400> SEQUENCE: 431
caggtccagc tggtgcaatc tgggagtgag gtgaagaagc ctgggacctc ggtgaaggtc     60
tcctgcacgg cctctggaag tgtcttcacc aattatggaa ttagttgggt gcgacaggcc    120
cctggacaag gcttgagtg gatgggaggg atcatccctc tctttggcgc agccaagtac    180
gcacagaaat tccagggcag agtcaccatc acagcggacg aatccacgaa gacagtctac    240
atggagctga gcaggctgac atctaaagac acggccatat atttctgtgc gaaggccccc    300
cgtgtctacg agtactactt tgatcagtgg ggccagggaa ccccagtcac cgtctcctca    360

<210> SEQ ID NO 432
<211> LENGTH: 327

```
<212> TYPE: DNA
<213> ORGANISM: Homo sapiens

<400> SEQUENCE: 432
gaaatagtga tgacgcagtt tccagccacc ctgtctgtgt ctcccgggga acgagtcacc      60
ctctcctgta gggccagtca gagtgttagc aacaatttag cctggtacca gcaaaaacct     120
ggccagcctc ccaggctcct catctatgat gcatctacca gggccacggg tgtcccagcc     180
aagttcagtg gcactgggtc tggcacagag ttcactctca gcatcagcag cctgcagtcc     240
gaagattttg cagtttatta ctgtcagcag tatcacaact ggcctccctc gtacagtttt     300
ggcctgggga ccaagctgga gatcaaa                                         327

<210> SEQ ID NO 433
<211> LENGTH: 351
<212> TYPE: DNA
<213> ORGANISM: Homo sapiens

<400> SEQUENCE: 433
caagagcagc tggtgcagtc tggggctgag gtgaagaagc ctggggcctc agtgaaggtc      60
tcctgcaagg cttctagaaa gtccttcatt ggctactatg tacactgggt gcgacaggcc     120
cctggacaag gcttgagtg gatgggatgg atcagccctg acagtgatgc cacaaagtac     180
gcacagaagt tcagggctc cgtcatcatg accagggaca cgtccgtcag cacagtgtac     240
atggagctga gtaggctgac atctgacgac acggcccttt attactgtct cctttttcga     300
ggtggaaact ccctctcctg gggccaggga accctggtca ccgtctcgag c              351

<210> SEQ ID NO 434
<211> LENGTH: 117
<212> TYPE: PRT
<213> ORGANISM: Homo sapiens

<400> SEQUENCE: 434

Gln Glu Gln Leu Val Gln Ser Gly Ala Glu Val Lys Lys Pro Gly Ala
1               5                   10                  15

Ser Val Lys Val Ser Cys Lys Ala Ser Arg Lys Ser Phe Ile Gly Tyr
                20                  25                  30

Tyr Val His Trp Val Arg Gln Ala Pro Gly Gln Gly Leu Glu Trp Met
            35                  40                  45

Gly Trp Ile Ser Pro Asp Ser Asp Ala Thr Lys Tyr Ala Gln Lys Phe
        50                  55                  60

Gln Gly Ser Val Ile Met Thr Arg Asp Thr Ser Val Ser Thr Val Tyr
65                  70                  75                  80

Met Glu Leu Ser Arg Leu Thr Ser Asp Asp Thr Ala Leu Tyr Tyr Cys
                85                  90                  95

Leu Leu Phe Arg Gly Gly Asn Ser Leu Ser Trp Gly Gln Gly Thr Leu
                100                 105                 110

Val Thr Val Ser Ser
        115

<210> SEQ ID NO 435
<211> LENGTH: 5
<212> TYPE: PRT
<213> ORGANISM: Homo sapiens

<400> SEQUENCE: 435

Gly Tyr Tyr Val His
1               5
```

<210> SEQ ID NO 436
<211> LENGTH: 17
<212> TYPE: PRT
<213> ORGANISM: Homo sapiens

<400> SEQUENCE: 436

Trp Ile Ser Pro Asp Ser Asp Ala Thr Lys Tyr Ala Gln Lys Phe Gln
1               5                   10                  15

Gly

<210> SEQ ID NO 437
<211> LENGTH: 8
<212> TYPE: PRT
<213> ORGANISM: Homo sapiens

<400> SEQUENCE: 437

Phe Arg Gly Gly Asn Ser Leu Ser
1               5

<210> SEQ ID NO 438
<211> LENGTH: 6
<212> TYPE: PRT
<213> ORGANISM: Homo sapiens

<400> SEQUENCE: 438

Arg Lys Ser Phe Ile Gly
1               5

<210> SEQ ID NO 439
<211> LENGTH: 10
<212> TYPE: PRT
<213> ORGANISM: Homo sapiens

<400> SEQUENCE: 439

Trp Ile Ser Pro Asp Ser Asp Ala Thr Lys
1               5                   10

<210> SEQ ID NO 440
<211> LENGTH: 327
<212> TYPE: DNA
<213> ORGANISM: Homo sapiens

<400> SEQUENCE: 440
caggctgtgg tgactcagga gccctcactg actgtgtccc caggagggac agtcaccctc      60
acctgtggct ccagcactgg acctgtcacc agtggtcatt atccctactg gttccagcag     120
aagcctggcc aagcccccag gacattgatt tctgctacat ccaacacaca ctcctggaca     180
cctgcccgct tctcaggctc cctccttggg ggcagagctg ccctgaccct ttcgggtgcg     240
cagcctgagg atgaggctga ctattattgc tttctctcct acagtggtgc ttgggtgttc     300
ggcggaggga ccacgctgac cgttcta                                         327

<210> SEQ ID NO 441
<211> LENGTH: 109
<212> TYPE: PRT
<213> ORGANISM: Homo sapiens

<400> SEQUENCE: 441

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Pro Val Thr Ser Gly

```
                    20                  25                  30

His Tyr Pro Tyr Trp Phe Gln Gln Lys Pro Gly Gln Ala Pro Arg Thr
            35                  40                  45

Leu Ile Ser Ala Thr Ser Asn Thr His Ser Trp Thr Pro Ala Arg Phe
        50                  55                  60

Ser Gly Ser Leu Leu Gly Gly Arg Ala Ala Leu Thr Leu Ser Gly Ala
65                  70                  75                  80

Gln Pro Glu Asp Glu Ala Asp Tyr Tyr Cys Phe Leu Ser Tyr Ser Gly
                85                  90                  95

Ala Trp Val Phe Gly Gly Gly Thr Thr Leu Thr Val Leu
            100                 105
```

<210> SEQ ID NO 442
<211> LENGTH: 14
<212> TYPE: PRT
<213> ORGANISM: Homo sapiens

<400> SEQUENCE: 442

```
Gly Ser Ser Thr Gly Pro Val Thr Ser Gly His Tyr Pro Tyr
1               5                   10
```

<210> SEQ ID NO 443
<211> LENGTH: 7
<212> TYPE: PRT
<213> ORGANISM: Homo sapiens

<400> SEQUENCE: 443

```
Ala Thr Ser Asn Thr His Ser
1               5
```

<210> SEQ ID NO 444
<211> LENGTH: 9
<212> TYPE: PRT
<213> ORGANISM: Homo sapiens

<400> SEQUENCE: 444

```
Phe Leu Ser Tyr Ser Gly Ala Trp Val
1               5
```

<210> SEQ ID NO 445
<211> LENGTH: 366
<212> TYPE: DNA
<213> ORGANISM: Homo sapiens

<400> SEQUENCE: 445

| | | | | | |
|---|---|---|---|---|---|
| gaggtgcagc | tggtggaatc | tgggggaggc | ttggtccagc | cggggggtc | cctgagactc | 60 |
| tcctgtgcag | cctctggatt | tatctttaga | aattactgga | tgagctgggt | ccggcaggct | 120 |
| ccagggaagg | ggctggagtg | ggtggccaac | ataaaacaag | atggaagaga | aagtactat | 180 |
| gtggactctc | tgaggggccg | agtcaacatc | tccagagaca | acgccgagaa | ctcattgtat | 240 |
| ctgcacatga | acagcctgag | agtcgaggac | acggctgttt | atttctgtgc | gagagctcgg | 300 |
| atggtggtgg | ttactggcga | tggttttgat | gtctggggcc | atgggacaat | ggtcaccgtc | 360 |
| tcgagc | | | | | | 366 |

<210> SEQ ID NO 446
<211> LENGTH: 122
<212> TYPE: PRT
<213> ORGANISM: Homo sapiens

<400> SEQUENCE: 446

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Arg Asn Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Arg Glu Lys Tyr Tyr Val Asp Ser Leu
50                  55                  60

Arg Gly Arg Val Asn Ile Ser Arg Asp Asn Ala Glu Asn Ser Leu Tyr
65                  70                  75                  80

Leu His Met Asn Ser Leu Arg Val Glu Asp Thr Ala Val Tyr Phe Cys
            85                  90                  95

Ala Arg Ala Arg Met Val Val Val Thr Gly Asp Gly Phe Asp Val Trp
            100                 105                 110

Gly His Gly Thr Met Val Thr Val Ser Ser
        115                 120

<210> SEQ ID NO 447
<211> LENGTH: 5
<212> TYPE: PRT
<213> ORGANISM: Homo sapiens

<400> SEQUENCE: 447

Asn Tyr Trp Met Ser
1               5

<210> SEQ ID NO 448
<211> LENGTH: 17
<212> TYPE: PRT
<213> ORGANISM: Homo sapiens

<400> SEQUENCE: 448

Asn Ile Lys Gln Asp Gly Arg Glu Lys Tyr Tyr Val Asp Ser Leu Arg
1               5                   10                  15

Gly

<210> SEQ ID NO 449
<211> LENGTH: 13
<212> TYPE: PRT
<213> ORGANISM: Homo sapiens

<400> SEQUENCE: 449

Ala Arg Met Val Val Val Thr Gly Asp Gly Phe Asp Val
1               5                   10

<210> SEQ ID NO 450
<211> LENGTH: 6
<212> TYPE: PRT
<213> ORGANISM: Homo sapiens

<400> SEQUENCE: 450

Gly Phe Ile Phe Arg Asn
1               5

<210> SEQ ID NO 451
<211> LENGTH: 10
<212> TYPE: PRT
<213> ORGANISM: Homo sapiens

<400> SEQUENCE: 451

Asn Ile Lys Gln Asp Gly Arg Glu Lys Tyr
1               5                   10

<210> SEQ ID NO 452
<211> LENGTH: 321
<212> TYPE: DNA
<213> ORGANISM: Homo sapiens

<400> SEQUENCE: 452

```
gacatccaga tgacccagtc tccatcctcc ctgtctgcat ctgtgggaga cagagtcacc      60
atcacttgcc gggcaagtca gaatattaag aggtatttca attggtatca gcagaaacca     120
gggaaagccc ctaagctcct gatctatgct gcatccaatt tagaaaatgg ggtcccatca     180
aggttcagtg gcagtggatc tgggacagat ttcactctca ccatcagcag tctgcaacct     240
gaggattttg cgacttatta ctgtcagcag agtttcagta atcgtggac attcggccaa      300
gggaccaacg tggacatcaa a                                               321
```

<210> SEQ ID NO 453
<211> LENGTH: 107
<212> TYPE: PRT
<213> ORGANISM: Homo sapiens

<400> SEQUENCE: 453

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Lys Arg Tyr
            20                  25                  30

Phe Asn Trp Tyr Gln Gln Lys Pro Gly Lys Ala Pro Lys Leu Leu Ile
        35                  40                  45

Tyr Ala Ala Ser Asn Leu Glu Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Lys Ser Trp
                85                  90                  95

Thr Phe Gly Gln Gly Thr Asn Val Asp Ile Lys
            100                 105

<210> SEQ ID NO 454
<211> LENGTH: 11
<212> TYPE: PRT
<213> ORGANISM: Homo sapiens

<400> SEQUENCE: 454

Arg Ala Ser Gln Asn Ile Lys Arg Tyr Phe Asn
1               5                   10

<210> SEQ ID NO 455
<211> LENGTH: 7
<212> TYPE: PRT
<213> ORGANISM: Homo sapiens

<400> SEQUENCE: 455

Ala Ala Ser Asn Leu Glu Asn
1               5

<210> SEQ ID NO 456
<211> LENGTH: 9
<212> TYPE: PRT
<213> ORGANISM: Homo sapiens

<400> SEQUENCE: 456

Gln Gln Ser Phe Ser Lys Ser Trp Thr
1               5

<210> SEQ ID NO 457
<211> LENGTH: 296
<212> TYPE: DNA
<213> ORGANISM: Influenza A virus

<400> SEQUENCE: 457
caggttcagc tggtgcagtc tggagctgag gtgaagaagc ctggggcctc agtgaaggtc    60
tcctgcaagg cttctggtta cacctttacc agctatggta tcagctgggt gcgacaggcc   120
cctggacaag gcttgagtg gatgggatgg atcagcgctt acaatggtaa cacaaactat    180
gcacagaagc tccagggcag agtcaccatg accacagaca catccacgag cacagcctac   240
atggagctga ggagcctgag atctgacgac acggccgtgt attactgtgc gagaga        296

<210> SEQ ID NO 458
<211> LENGTH: 296
<212> TYPE: DNA
<213> ORGANISM: Influenza A virus

<400> SEQUENCE: 458
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccta acagtggtgg cacaaactat    180
gcacagaagt tcagggcag ggtcaccatg accagggaca cgtccatcag cacagcctac   240
atggagctga gcaggctgag atctgacgac acggccgtgt attactgtgc gagaga        296

<210> SEQ ID NO 459
<211> LENGTH: 294
<212> TYPE: DNA
<213> ORGANISM: Influenza A virus

<400> SEQUENCE: 459
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccta acagtggtgg cacaaactat    180
gcacagaagt tcagggctg ggtcaccatg accagggaca cgtccatcag cacagcctac   240
atggagctga gcaggctgag atctgacgac acggccgtgt attactgtgc gaga          294

<210> SEQ ID NO 460
<211> LENGTH: 296
<212> TYPE: DNA
<213> ORGANISM: Influenza A virus

<400> SEQUENCE: 460
caggtgcagc tggtgcagtc tggggctgag gtgaagaagc ctgggtcctc ggtgaaggtc    60
tcctgcaagg cttctggagg cacctt cagc agctatgcta tcagctgggt gcgacaggcc   120
cctggacaag gcttgagtg gatgggaggg atcatcccta tctttggtac agcaaactac    180
gcacagaagt tccagggcag agtcacgatt accgcggacg aatccacgag cacagcctac   240
atggagctga gcagcctgag atctgaggac acggccgtgt attactgtgc gagaga        296

<210> SEQ ID NO 461
<211> LENGTH: 294
<212> TYPE: DNA
<213> ORGANISM: Influenza A virus

<400> SEQUENCE: 461
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accacggacg aatccacgag cacagcctac     240
atggagctga gcagcctgag atctgaggac acggccgtgt attactgtgc gaga            294

<210> SEQ ID NO 462
<211> LENGTH: 296
<212> TYPE: DNA
<213> ORGANISM: Influenza A virus

<400> SEQUENCE: 462
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggaca atccacgag cacagcctac      240 atggagctga gcagcctgag atctgaggac acggccgtgt attactgtgc gagaga          296

<210> SEQ ID NO 463
<211> LENGTH: 296
<212> TYPE: DNA
<213> ORGANISM: Influenza A virus

<400> SEQUENCE: 463
caggtccagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga          296

<210> SEQ ID NO 464
<211> LENGTH: 296
<212> TYPE: DNA
<213> ORGANISM: Influenza A virus

<400> SEQUENCE: 464
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag ggcttgagtg gatgggatgg atgaacccta cagtggtaa cacaggctat      180 gcacagaagt tccagggcag agtcaccatg accaggaaca cctccataag cacagcctac     240
atggagctga gcagcctgag atctgaggac acggccgtgt attactgtgc gagagg          296

<210> SEQ ID NO 465
<211> LENGTH: 297
<212> TYPE: DNA
<213> ORGANISM: Influenza A virus

<400> SEQUENCE: 465

-continued

```
cagatcacct tgaaggagtc tggtcctacg ctggtgaaac ccacacagac cctcacgctg 60
acctgcacct tctctgggtt ctcactcagc actagtggag tgggtgtggg ctggatccgt 120
cagcccccag gaaaggccct ggagtggctt gcactcattt attgggatga tgataagcgc 180
tacagcccat ctctgaagag caggctcacc atcaccaagg acacctccaa aaaccaggtg 240
gtccttacaa tgaccaacat ggaccctgtg gacacagcca catattactg tgcacgg 297

<210> SEQ ID NO 466
<211> LENGTH: 294
<212> TYPE: DNA
<213> ORGANISM: Influenza A virus
<400> SEQUENCE: 466
caggtgcagc tggtggagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gaga 294

<210> SEQ ID NO 467
<211> LENGTH: 296
<212> TYPE: DNA
<213> ORGANISM: Influenza A virus
<400> SEQUENCE: 467
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gagaga 296

<210> SEQ ID NO 468
<211> LENGTH: 296
<212> TYPE: DNA
<213> ORGANISM: Influenza A virus
<400> SEQUENCE: 468
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt attactgtgc gaaaga 296

<210> SEQ ID NO 469
<211> LENGTH: 296
<212> TYPE: DNA
<213> ORGANISM: Influenza A virus
<400> SEQUENCE: 469
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
 ctgcaaatga acagcctgag agccgaggac acggctgtgt attactgtgc gagaga 296

<210> SEQ ID NO 470
<211> LENGTH: 302
<212> TYPE: DNA
<213> ORGANISM: Influenza A virus

<400> SEQUENCE: 470
gaggtgcagc tggtggagtc tgggggaggc ttggtacagc cagggcggtc cctgagactc 60
tcctgtacag cttctggatt cacctttggt gattatgcta tgagctgggt ccgccaggct 120
ccagggaagg ggctggagtg ggtaggtttc attagaagca aagcttatgg tgggacaaca 180
gaatacgccg cgtctgtgaa aggcagattc accatctcaa gagatgattc caaaagcatc 240
gcctatctgc aaatgaacag cctgaaaacc gaggacacag ccgtgtatta ctgtactaga 300
ga 302

<210> SEQ ID NO 471
<211> LENGTH: 293
<212> TYPE: DNA
<213> ORGANISM: Influenza A virus

<400> SEQUENCE: 471
gaggtgcagc tggtggagtc tggaggaggc ttgatccagc ctggggggtc cctgagactc 60
tcctgtgcag cctctgggtt caccgtcagt agcaactaca tgagctgggt ccgccaggct 120
ccagggaagg ggctggagtg ggtctcagtt atttatagcg gtggtagcac atactacgca 180
gactccgtga agggccgatt caccatctcc agagacaatt ccaagaacac gctgtatctt 240
caaatgaaca gcctgagagc cgaggacacg gccgtgtatt actgtgcgag aga 293

<210> SEQ ID NO 472
<211> LENGTH: 296
<212> TYPE: DNA
<213> ORGANISM: Influenza A virus

<400> SEQUENCE: 472
caggtgcagc tggtgcagtc tggccatgag gtgaagcagc ctggggcctc agtgaaggtc 60
tcctgcaagg cttctggtta cagtttcacc acctatggta tgaattgggt gccacaggcc 120
cctggacaag ggcttgagtg gatgggatgg ttcaacacct acactgggaa cccaacatat 180
gcccagggct tcacaggacg gtttgtcttc tccatggaca cctctgccag cacagcatac 240
ctgcagatca gcagcctaaa ggctgaggac atggccatgt attactgtgc gagata 296

<210> SEQ ID NO 473
<211> LENGTH: 296
<212> TYPE: DNA
<213> ORGANISM: Influenza A virus

<400> SEQUENCE: 473
gaggtgcagc tggtggagtc tgggggaggc ttggtccagc ctggggggtc cctgagactc 60
tcctgtgcag cctctggatt cacctttagt agctattgga tgagctgggt ccgccaggct 120
ccagggaagg ggctggagtg ggtggccaac ataaagcaag atggaagtga gaaatactat 180
gtggactctg tgaagggccg attcaccatc tccagagaca acgccaagaa ctcactgtat 240
ctgcaaatga acagcctgag agccgaggac acggctgtgt attactgtgc gagaga 296

<210> SEQ ID NO 474

```
<211> LENGTH: 299
<212> TYPE: DNA
<213> ORGANISM: Influenza A virus

<400> SEQUENCE: 474
caggtgcagc tgcaggagtc g

```
acctgcgctg tctatggtgg gtccttcagt ggttactact ggagctggat ccgccagccc    120
ccagggaagg ggctggagtg gattggggaa atcaatcata gtggaagcac caactacaac    180
ccgtccctca agagtcgagt caccatatca gtagacacgt ccaagaacca gttctccctg    240
aagctgagct ctgtgaccgc cgcggacacg gccgtgtatt actg                    284
```

<210> SEQ ID NO 479
<211> LENGTH: 291
<212> TYPE: DNA
<213> ORGANISM: Influenza A virus

<400> SEQUENCE: 479

```
caggtgcagc tacagcagtg gggcgcagga ctgttgaagc cttcggagac cctgtccctc    60
acctgcgctg tctatggtgg gtccttcagt ggttactact ggagctggat ccgccagccc    120
ccagggaagg ggctggagtg gattggggaa atcattcata gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag a             291
```

<210> SEQ ID NO 480
<211> LENGTH: 299
<212> TYPE: DNA
<213> ORGANISM: Influenza A virus

<400> SEQUENCE: 480

```
cagctgcagc tgcaggagtc gggcccagga ctggtgaagc cttcggagac cctgtccctc    60
acctgcactg tctctggtgg ctccatcagc agtagtagtt actactgggg ctggatccgc    120
cagcccccag ggaaggggct ggagtggatt ggagtatct attatagtgg gagcacctac    180
tacaacccgt ccctcaagag tcgagtcacc atatccgtag acacgtccaa gaaccagttc    240
tccctgaagc tgagctctgt gaccgccgca gacacggctg tgtattactg tgcgagaca    299
```

<210> SEQ ID NO 481
<211> LENGTH: 297
<212> TYPE: DNA
<213> ORGANISM: Influenza A virus

<400> SEQUENCE: 481

```
gaggtgcagc tggtggagtc tgggggaggc ttagtaaaga ctggagggt ctctgagact     60 ctcctgtgca gcctctggat tcaccttcag tagctctgct atgcactggg tccaccaggc    120
tccaggaaag ggtttggagt gggtctcagt tattagtaca agtggtgata ccgtactcta    180
cacagactct gtgaagggct gattcaccat ctctagagac aatgcccaga ttcactgta    240 tctgcaaatg aacagcctga gagccgacga catggctgtg tattactgtg tgaaaga       297
```

<210> SEQ ID NO 482
<211> LENGTH: 288
<212> TYPE: DNA
<213> ORGANISM: Influenza A virus

<400> SEQUENCE: 482

```
caggtgcagc tgcaggagtc gggcccagga ctggtgaagc cttcggagac cctgtccctc    60
acctgcactg tctctggtgg ctccatcagt agttactact ggagctggat ccggcagccc    120
ccagggaagg gactggagtg gattgggtat atctattaca gtgggagcac caactacaac    180
ccctccctca agagtcgagt caccatatca gtagacacgt ccaagaacca attctccctg    240
```
aagctgagct ctgtgaccgc tgcggacacg gccgtgtatt actgtgcg 288

<210> SEQ ID NO 483
<211> LENGTH: 299
<212> TYPE: DNA
<213> ORGANISM: Influenza A virus

<400> SEQUENCE: 483
caggtgcagc tgcaggagtc gggcccagga ctggtgaagc cttcggagac cctgtccctc 60
acctgcactg tctctggtgg ctccgtcagc agtggtagtt actactggag ctggatccgg 120
cagcccccag ggaagggact ggagtggatt gggtatatct attacagtgg gagcaccaac 180
tacaacccct ccctcaagag tcgagtcacc atatcagtag acacgtccaa gaaccagttc 240
tccctgaagc tgagctctgt gaccgctgcg gacacggccg tgtattactg tgcgagaga 299

<210> SEQ ID NO 484
<211> LENGTH: 296
<212> TYPE: DNA
<213> ORGANISM: Influenza A virus

<400> SEQUENCE: 484
caggtgcagc tggtgcagtc tggccatgag gtgaagcagc tggggcctc agtgaaggtc 60 tcctgcaagg cttctggtta cagtttcacc acctatggta tgaattgggt gccacaggcc 120
cctggacaag ggcttgagtg gatgggatgg ttcaacacct acactgggaa cccaacatat 180
gcccagggct tcacaggacg gtttgtcttc tccatggaca cctctgccag cacagcatac 240
ctgcagatca gcagcctaaa ggctgaggac atggccatgt attactgtgc gagata 296

<210> SEQ ID NO 485
<211> LENGTH: 296
<212> TYPE: DNA
<213> ORGANISM: Influenza A virus

<400> SEQUENCE: 485
gaggtgcagc tggtgcagtc tggagcagag gtgaaaaagc ccggggagtc tctgaagatc 60
tcctgtaagg gttctggata cagctttacc agctactgga tcggctgggt gcgccagatg 120
cccgggaaag gcctggagtg gatggggatc atctatcctg gtgactctga taccagatac 180
agcccgtcct ccaaggcca ggtcaccatc tcagccgaca gtccatcag caccgcctac 240 ctgcagtgga gcagcctgaa ggcctcggac accgccatgt attactgtgc gagaca 296

<210> SEQ ID NO 486
<211> LENGTH: 287
<212> TYPE: DNA
<213> ORGANISM: Influenza A virus

<400> SEQUENCE: 486
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatagtt accctcc 287

<210> SEQ ID NO 487
<211> LENGTH: 287
<212> TYPE: DNA
<213> ORGANISM: Influenza A virus

<400> SEQUENCE: 487

```
gacatccaga tgacccagtc tccatcctcc ctgtctgcat ctgtaggaga cagagtcacc     60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccctcc                  287
```

<210> SEQ ID NO 488
<211> LENGTH: 287
<212> TYPE: DNA
<213> ORGANISM: Influenza A virus

<400> SEQUENCE: 488

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcc                  287
```

<210> SEQ ID NO 489
<211> LENGTH: 287
<212> TYPE: DNA
<213> ORGANISM: Influenza A virus

<400> SEQUENCE: 489

```
gacatccaga tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcc                  287
```

<210> SEQ ID NO 490
<211> LENGTH: 287
<212> TYPE: DNA
<213> ORGANISM: Influenza A virus

<400> SEQUENCE: 490

```
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attctcc                  287
```

<210> SEQ ID NO 491
<211> LENGTH: 302
<212> TYPE: DNA
<213> ORGANISM: Influenza A virus

<400> SEQUENCE: 491

```
gatgttgtga tgactcagtc tccactctcc ctgcccgtca cccttggaca gccggcctcc     60
atctcctgca ggtctagtca aagcctcgta cacagtgatg gaaacaccta cttgaattgg    120
```

| | |
|---|---|
| tttcagcaga ggccaggcca atctccaagg cgcctaattt ataaggtttc taaccgggac | 180 |
| tctggggtcc cagacagatt cagcggcagt gggtcaggca ctgatttcac actgaaaatc | 240 |
| agcagggtgg aggctgagga tgttggggtt tattactgca tgcaaggtac acactggcct | 300 |
| cc | 302 |

<210> SEQ ID NO 492
<211> LENGTH: 287
<212> TYPE: DNA
<213> ORGANISM: Influenza A virus

<400> SEQUENCE: 492

| | |
|---|---|
| gaaattgtgt tgacacagtc tccagccacc ctgtctttgt ctccagggga aagagccacc | 60 |
| ctctcctgca gggccagtca gagtgttagc agctacttag cctggtacca acagaaacct | 120 |
| ggccaggctc ccaggctcct catctatgat gcatccaaca gggccactgg catcccagcc | 180 |
| aggttcagtg gcagtgggtc tgggacagac ttcactctca ccatcagcag cctagagcct | 240 |
| gaagattttg cagtttatta ctgtcagcag cgtagcaact ggcctcc | 287 |

<210> SEQ ID NO 493
<211> LENGTH: 287
<212> TYPE: DNA
<213> ORGANISM: Influenza A virus

<400> SEQUENCE: 493

| | |
|---|---|
| gaaatagtga tgacgcagtc tccagccacc ctgtctgtgt ctccagggga aagagccacc | 60 |
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcag tataataact ggcctcc | 287 |

<210> SEQ ID NO 494
<211> LENGTH: 290
<212> TYPE: DNA
<213> ORGANISM: Influenza A virus

<400> SEQUENCE: 494

| | |
|---|---|
| gaaattgtgt tgacgcagtc tccaggcacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat ggtgcatcca gcagggccac tggcatccca | 180 |
| gacaggttca gtggcagtgg gtctgggaca gacttcactc tcaccatcag cagactggag | 240 |
| cctgaagatt ttgcagtgta ttactgtcag cagtatggta gctcacctcc | 290 |

<210> SEQ ID NO 495
<211> LENGTH: 305
<212> TYPE: DNA
<213> ORGANISM: Influenza A virus

<400> SEQUENCE: 495

| | |
|---|---|
| gacatcgtga tgacccagtc tccagactcc ctggctgtgt ctctgggcga gagggccacc | 60 |
| atcaactgca agtccagcca gagtgtttta tacagctcca acaataagaa ctacttagct | 120 |
| tggtaccagc agaaaccagg acagcctcct aagctgctca tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcagcaata ttatagtact | 300 | cctcc                                                              305

<210> SEQ ID NO 496
<211> LENGTH: 299
<212> TYPE: DNA
<213> ORGANISM: Influenza A virus

<400> SEQUENCE: 496
cagtctgtgc tgacgcagcc gccctcagtg tctggggccc cagggcagag ggtcaccatc    60
tcctgcactg ggagcagctc aacatcggg gcaggttatg atgtacactg gtaccagcag   120
cttccaggaa cagcccccaa actcctcatc tatggtaaca gcaatcggcc ctcagggggtc  180 cctgaccgat tctctggctc caagtctggc acctcagcct ccctggccat cactgggctc   240
caggctgagg atgaggctga ttattactgc cagtcctatg acagcagcct gagtggttc    299

<210> SEQ ID NO 497
<211> LENGTH: 296
<212> TYPE: DNA
<213> ORGANISM: Influenza A virus

<400> SEQUENCE: 497
cagtctgtgc tgactcagcc accctcagcg tctgggaccc ccgggcagag ggtcaccatc    60
tcttgttctg gaagcagctc aacatcgga agtaatactg taaactggta ccagcagctc   120
ccaggaacgg cccccaaact cctcatctat agtaataatc agcggccctc aggggtccct   180
gaccgattct ctggctccaa gtctggcacc tcagcctccc tggccatcag tgggctccag   240
tctgaggatg aggctgatta ttactgtgca gcatgggatg acagcctgaa tggtcc       296

<210> SEQ ID NO 498
<211> LENGTH: 296
<212> TYPE: DNA
<213> ORGANISM: Influenza A virus

<400> SEQUENCE: 498
cagtctgtgt tgacgcagcc gccctcagtg tctgcggccc caggacagaa ggtcaccatc    60
tcctgctctg gaagcagctc aacattggg aataattatg tatcctggta ccagcagctc   120
ccaggaacag cccccaaact cctcatctat gaaaataata gcgaccctc agggattcct   180 gaccgattct ctggctccaa gtctggcacg tcagccaccc tgggcatcac cggactccag   240
actggggacg aggccgatta ttactgcgga acatgggata gcagcctgag tgctgg       296

<210> SEQ ID NO 499
<211> LENGTH: 297
<212> TYPE: DNA
<213> ORGANISM: Influenza A virus

<400> SEQUENCE: 499
cagtctgccc tgactcagcc tcgctcagtg tccgggtctc ctggacagtc agtcaccatc    60
tcctgcactg gaaccagcag tgatgttggt ggttataact atgtctcctg gtaccaacag   120
cacccaggca aagcccccaa actcatgatt tatgatgtca gtaagcggcc ctcagggtc    180 cctgatcgct tctctggctc caagtctggc aacacggcct ccctgaccat ctctgggctc   240
caggctgagg atgaggctga ttattactgc tgctcatatg caggcagcta cactttc      297

<210> SEQ ID NO 500
<211> LENGTH: 297
<212> TYPE: DNA

<213> ORGANISM: Influenza A virus

<400> SEQUENCE: 500
cagtctgccc tgactcagcc tgcctccgtg tctgggtctc ctggacagtc gatcaccatc 60
tcctgcactg gaaccagcag tgacgttggt ggttataact atgtctcctg gtaccaacag 120
cacccaggca aagcccccaa actcatgatt tatgaggtca gtaatcggcc ctcaggggtt 180
tctaatcgct tctctggctc caagtctggc aacacggcct ccctgaccat ctctgggctc 240
caggctgagg acgaggctga ttattactgc agctcatata caagcagcag cactctc 297

<210> SEQ ID NO 501
<211> LENGTH: 297
<212> TYPE: DNA
<213> ORGANISM: Influenza A virus

<400> SEQUENCE: 501
cagtctgccc tgactcagcc tccctccgcg tccgggtctc ctggacagtc agtcaccatc 60
tcctgcactg gaaccagcag tgacgttggt ggttataact atgtctcctg gtaccaacag 120
cacccaggca aagcccccaa actcatgatt tatgaggtca gtaagcggcc ctcaggggtc 180
cctgatcgct tctctggctc caagtctggc aacacggcct ccctgaccgt ctctgggctc 240
caggctgagg atgaggctga ttattactgc agctcatatg caggcagcaa caatttc 297

<210> SEQ ID NO 502
<211> LENGTH: 284
<212> TYPE: DNA
<213> ORGANISM: Influenza A virus

<400> SEQUENCE: 502
tcctatgagc tgacacagct accctcggtg tcagtgtccc caggacagac agccaggatc 60
acctgctctg gagatgtact gggggaaaat tatgctgact ggtaccagca gaagccaggc 120
caggcccctg agttggtgat atacgaagat agtgagcggt accctggaat ccctgaacga 180
ttctctgggt ccacctcagg gaacacgacc accctgacca tcagcagggt cctgaccgaa 240
gacgaggctg actattactg tttgtctggg gatgaggaca atcc 284

<210> SEQ ID NO 503
<211> LENGTH: 282
<212> TYPE: DNA
<213> ORGANISM: Influenza A virus

<400> SEQUENCE: 503
tcctatgagc tgacacagcc accctcggtg tcagtgtccc caggacagac ggccaggatc 60
acctgctctg gagatgcatt gccaaagcaa tatgcttatt ggtaccagca gaagccaggc 120
caggcccctg tgctggtgat atataaagac agtgagaggc cctcagggat ccctgagcga 180
ttctctggct ccagctcagg gacaacagtc acgttgacca tcagtggagt ccaggcagaa 240
gacgaggctg actattactg tcaatcagca gacagcagtg gt 282

<210> SEQ ID NO 504
<211> LENGTH: 294
<212> TYPE: DNA
<213> ORGANISM: Influenza A virus

<400> SEQUENCE: 504
cagactgtgg tgactcagga gccctcactg actgtgtccc caggagggac agtcactctc 60
acctgtgctt ccagcactgg agcagtcacc agtggttact atccaaactg gttccagcag 120

| aaacctggac aagcacccag ggcactgatt tatagtacaa gcaacaaaca ctcctggacc | 180 |
| cctgcccggt tctcaggctc cctccttggg ggcaaagctg ccctgacact gtcaggtgtg | 240 |
| cagcctgagg acgaggctga gtattactgc ctgctctact atggtggtgc tcag | 294 |

<210> SEQ ID NO 505
<211> LENGTH: 294
<212> TYPE: DNA
<213> ORGANISM: Influenza A virus

<400> SEQUENCE: 505

| caggctgtgg tgactcagga gccctcactg actgtgtccc caggagggac agtcactctc | 60 |
| acctgtggct ccagcactgg agctgtcacc agtggtcatt atccctactg gttccagcag | 120 |
| aagcctggcc aagcccccag gacactgatt tatgatacaa gcaacaaaca ctcctggaca | 180 |
| cctgcccggt tctcaggctc cctccttggg ggcaaagctg ccctgaccct tcgggtgcg | 240 |
| cagcctgagg atgaggctga gtattactgc ttgctctcct atagtggtgc tcgg | 294 |

<210> SEQ ID NO 506
<211> LENGTH: 294
<212> TYPE: DNA
<213> ORGANISM: Influenza A virus

<400> SEQUENCE: 506

| caggctgtgg tgactcagga gccctcactg actgtgtccc caggagggac agtcactctc | 60 |
| acctgtggct ccagcactgg agctgtcacc agtggtcatt atccctactg gttccagcag | 120 |
| aagcctggcc aagcccccag gacactgatt tatgatacaa gcaacaaaca ctcctggaca | 180 |
| cctgcccggt tctcaggctc cctccttggg ggcaaagctg ccctgaccct tttgggtgcg | 240 |
| cagcctgagg atgaggctga gtattactgc ttgctctcct atagtggtgc tcgg | 294 |

<210> SEQ ID NO 507
<211> LENGTH: 317
<212> TYPE: DNA
<213> ORGANISM: Influenza A virus

<400> SEQUENCE: 507

| cagcctgtgc tgactcagcc accttctgca tcagcctccc tgggagcctc ggtcacactc | 60 |
| acctgcaccc tgagcagcgg ctacagtaat tataaagtgg actggtacca gcagagacca | 120 |
| gggaagggcc cccggtttgt gatgcgagtg ggcactggtg ggattgtggg atccaagggg | 180 |
| gatggcatcc ctgatcgctt ctcagtcttg ggctcaggcc tgaatcggta cctgaccatc | 240 |
| aagaacatcc aggaagagga tgagagtgac taccactgtg gggcagacca tggcagtggg | 300 |
| agcaacttcg tgtaacc | 317 |

<210> SEQ ID NO 508
<211> LENGTH: 317
<212> TYPE: DNA
<213> ORGANISM: Influenza A virus

<400> SEQUENCE: 508

| cagcctgtgc tgactcagcc accttctgca tcagcctccc tgggagcctc ggtcacactc | 60 |
| acctgcaccc tgagcagcgg ctacagtaat tataaagtgg actggtacca gcagagacca | 120 |
| gggaagggcc cccgatttgt gatgcgagtg ggcactggtg ggattgtggg atccaagggg | 180 |
| gatggcatcc ctgatcgctt ctcagtcttg ggctcaggcc tgaatcggta cctgaccatc | 240 |

```
aagaacatcc aggaagagga tgagagtgac taccactgtg gggcagacca tggcagtggg    300
agcaacttcg tgtaacc                                                   317
```

<210> SEQ ID NO 509
<211> LENGTH: 372
<212> TYPE: DNA
<213> ORGANISM: Homo sapiens

<400> SEQUENCE: 509

```
caggtgcaac tgcaggagtc gggcccagga ctggtgaagc cctcggagac cctgtccctc     60
acttgcgctg tctctggtgt ctccatcagc aatattgatt tctactgggg ctggatccgc    120
cagcccccag ggaaggggct agaatggatt ggcaatatct attatacggg gatcaccttc    180
tacaacccgt ccctcagcag tcgagtcgcc atatccattg acacctccaa gaaccagttc    240
tccctgactc tgacttctgt gaccgccgca gacacggcta tgtattactg tgcgagacat    300
tacggtgact ccgaggcaat aaacgatgcc tttgacatct ggggccaagg gacaatgctc    360
accgtctcga gc                                                        372
```

<210> SEQ ID NO 510
<211> LENGTH: 124
<212> TYPE: PRT
<213> ORGANISM: Homo sapiens

<400> SEQUENCE: 510

Gln Val Gln Leu Gln Glu Ser Gly Pro Gly Leu Val Lys Pro Ser Glu
1               5                   10                  15

Thr Leu Ser Leu Thr Cys Ala Val Ser Gly Val Ser Ile Ser Asn Ile
            20                  25                  30

Asp Phe Tyr Trp Gly Trp Ile Arg Gln Pro Pro Gly Lys Gly Leu Glu
        35                  40                  45

Trp Ile Gly Asn Ile Tyr Tyr Thr Gly Ile Thr Phe Tyr Asn Pro Ser
    50                  55                  60

Leu Ser Ser Arg Val Ala Ile Ser Ile Asp Thr Ser Lys Asn Gln Phe
65                  70                  75                  80

Ser Leu Thr Leu Thr Ser Val Thr Ala Ala Asp Thr Ala Met Tyr Tyr
                85                  90                  95

Cys Ala Arg His Tyr Gly Asp Ser Glu Ala Ile Asn Asp Ala Phe Asp
            100                 105                 110

Ile Trp Gly Gln Gly Thr Met Leu Thr Val Ser Ser
        115                 120

<210> SEQ ID NO 511
<211> LENGTH: 7
<212> TYPE: PRT
<213> ORGANISM: Homo sapiens

<400> SEQUENCE: 511

Asn Ile Asp Phe Tyr Trp Gly
1               5

<210> SEQ ID NO 512
<211> LENGTH: 16
<212> TYPE: PRT
<213> ORGANISM: Homo sapiens

<400> SEQUENCE: 512

Asn Ile Tyr Tyr Thr Gly Ile Thr Phe Tyr Asn Pro Ser Leu Ser Ser
1               5                   10                  15

<210> SEQ ID NO 513
<211> LENGTH: 14
<212> TYPE: PRT
<213> ORGANISM: Homo sapiens

<400> SEQUENCE: 513

His Tyr Gly Asp Ser Glu Ala Ile Asn Asp Ala Phe Asp Ile
1               5                   10

<210> SEQ ID NO 514
<211> LENGTH: 6
<212> TYPE: PRT
<213> ORGANISM: Homo sapiens

<400> SEQUENCE: 514

Gly Val Ser Ile Ser Asn
1               5

<210> SEQ ID NO 515
<211> LENGTH: 9
<212> TYPE: PRT
<213> ORGANISM: Homo sapiens

<400> SEQUENCE: 515

Asn Ile Tyr Tyr Thr Gly Ile Thr Phe
1               5

<210> SEQ ID NO 516
<211> LENGTH: 324
<212> TYPE: DNA
<213> ORGANISM: Homo sapiens

<400> SEQUENCE: 516
gagatagtga tgacgcagtc tccagccacc ctgtctgtgt ctccagggga aagagccacc      60
ctctcctgca gggccagtca gagtgttggc aatagtttag cctggtacca gcagagacct    120
ggccaggctc ccaggctcct catctacggt gcatccacca gggccactgg tatcccaccc    180
aggttcagtg gcagtgggtc tgggacagaa ttcactctca ccatcagcag cctgcagact    240
gaagattttg cagtttatta ctgtcaacaa tatattaact ggcgtccgct cagttttggc    300
ggagggacca aggtggagat caaa                                           324

<210> SEQ ID NO 517
<211> LENGTH: 11
<212> TYPE: PRT
<213> ORGANISM: Homo sapiens

<400> SEQUENCE: 517

Arg Ala Ser Gln Ser Val Gly Asn Ser Leu Ala
1               5                   10

<210> SEQ ID NO 518
<211> LENGTH: 10
<212> TYPE: PRT
<213> ORGANISM: Homo sapiens

<400> SEQUENCE: 518

Gln Gln Tyr Ile Asn Trp Arg Pro Leu Ser
1               5                   10

<210> SEQ ID NO 519
<211> LENGTH: 118

```
<212> TYPE: PRT
<213> ORGANISM: Homo sapiens

<400> SEQUENCE: 519

Gln Pro Val Leu Ser Gln Pro Pro Ala Ser Ala Ser Leu Gly Ala
1               5                   10                  15

Ser Val Thr Leu Thr Cys Thr Leu Ser Ser Gly Phe Asp Asn Tyr Gln
            20                  25                  30

Val Ala Trp Tyr Gln Gln Arg Pro Gly Lys Pro Arg Phe Val Met
        35                  40                  45

Arg Val Gly Asn Gly Gly Asn Val Ala Ser Lys Gly Asp Gly Ile Pro
    50                  55                  60

Asp Arg Phe Ser Val Ser Gly Ser Gly Leu Asn Arg Tyr Leu Thr Ile
65                  70                  75                  80

Lys Asn Ile Gln Glu Asp Asp Glu Ser Asp Tyr Tyr Cys Gly Ala Asp
                85                  90                  95

His Gly Ser Gly Asn Asn Phe Val Ser Pro Tyr Val Phe Gly Gly Gly
            100                 105                 110

Thr Lys Leu Thr Val Leu
        115

<210> SEQ ID NO 520
<211> LENGTH: 12
<212> TYPE: PRT
<213> ORGANISM: Homo sapiens

<400> SEQUENCE: 520

Thr Leu Ser Ser Gly Phe Asp Asn Tyr Gln Val Ala
1               5                   10

<210> SEQ ID NO 521
<211> LENGTH: 12
<212> TYPE: PRT
<213> ORGANISM: Homo sapiens

<400> SEQUENCE: 521

Val Gly Asn Gly Gly Asn Val Ala Ser Lys Gly Asp
1               5                   10

<210> SEQ ID NO 522
<211> LENGTH: 15
<212> TYPE: PRT
<213> ORGANISM: Homo sapiens

<400> SEQUENCE: 522

Gly Ala Asp His Gly Ser Gly Asn Asn Phe Val Ser Pro Tyr Val
1               5                   10                  15

<210> SEQ ID NO 523
<211> LENGTH: 354
<212> TYPE: DNA
<213> ORGANISM: Homo sapiens

<400> SEQUENCE: 523
cagcctgtgt tgagtcagcc accttctgca tcggcctccc tgggagcctc cgtcacactc      60
acctgcaccc tgagtagcgg cttcgataat tatcaagtgg cctggtacca gcagagacca     120
gggaagggcc ccgctttgt  gatgcgggtg ggcaatggtg gaatgtggc  ttccaagggg     180 gatggcattc ctgatcgttt ctcagtctcg ggctcaggcc tgaatcggta cctgaccatc     240
aagaacatcc aggaagacga tgagagtgac tattattgtg gggcagacca tggcagtggg     300
```

```
aacaacttcg tgtcccctta tgtgtttggc ggagggacca agctgaccgt tcta         354
```

<210> SEQ ID NO 524
<211> LENGTH: 108
<212> TYPE: PRT
<213> ORGANISM: Homo sapiens

<400> SEQUENCE: 524

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Asn Ser
            20                  25                  30

Leu Ala Trp Tyr Gln Gln Arg Pro Gly Gln Ala Pro Arg Leu Leu Ile
        35                  40                  45

Tyr Gly Ala Ser Thr Arg Ala Thr Gly Ile Pro Pro Arg Phe Ser Gly
    50                  55                  60

Ser Gly Ser Gly Thr Glu Phe Thr Leu Thr Ile Ser Ser Leu Gln Thr
65                  70                  75                  80

Glu Asp Phe Ala Val Tyr Tyr Cys Gln Gln Tyr Ile Asn Trp Arg Pro
                85                  90                  95

Leu Ser Phe Gly Gly Thr Lys Val Glu Ile Lys
            100                 105
```

<210> SEQ ID NO 525
<211> LENGTH: 11
<212> TYPE: PRT
<213> ORGANISM: Influenza A virus

<400> SEQUENCE: 525

```
Pro Gln Arg Glu Gly Gly Arg Arg Lys Arg
1               5                   10
```

<210> SEQ ID NO 526
<211> LENGTH: 6
<212> TYPE: PRT
<213> ORGANISM: Influenza A virus

<400> SEQUENCE: 526

```
Pro Gln Thr Glu Thr Arg
1               5
```